United States Patent

Chu et al.

[11] Patent Number: 5,599,816
[45] Date of Patent: Feb. 4, 1997

[54] QUINOLIZINONE TYPE COMPOUNDS

[75] Inventors: Daniel T. Chu, Santa Clara, Calif.; Qun Li, Gurnee, Ill.; Curt S. Cooper, Gurnee, Ill.; Anthony K. L. Fung, Gurnee, Ill.; Cheuk M. Lee; Jacob J. Plattner, both of Libertyville, Ill.; Zhenkun Ma, Gurnee, Ill.; Wei-Bo Wang, Park City, Ill.

[73] Assignee: Abbott Laboratories, Abbott Park, Ill.

[21] Appl. No.: 482,249

[22] Filed: Jun. 7, 1995

Related U.S. Application Data

[60] Division of Ser. No. 469,159, Jun. 6, 1995, which is a continuation-in-part of Ser. No. 316,319, Sep. 30, 1994, which is a continuation-in-part of Ser. No. 137,236, Oct. 14, 1992, abandoned, which is a continuation-in-part of Ser. No. 940,870, Oct. 27, 1992, abandoned, which is a continuation-in-part of Ser. No. 517,780, May 2, 1990, abandoned.

[51] Int. Cl.⁶ .................. A61K 31/495; A61K 31/535; A61K 31/505; A61K 31/44; C07D 498/02; C07D 487/00; C07D 455/02; C07D 471/02

[52] U.S. Cl. .................. 514/254; 514/230.5; 514/249; 514/253; 514/258; 514/300; 514/306; 514/291; 514/18; 514/19; 544/71; 544/105; 544/280; 544/333; 544/350; 544/362; 544/405; 544/8; 546/79; 546/80; 546/89; 546/92; 546/113; 546/138; 546/303; 546/341; 546/342; 546/344; 530/330; 530/331

[58] Field of Search .................. 546/138, 113, 546/303, 341, 342, 344; 514/306, 230.5, 249, 253, 258, 300, 254; 544/15, 71, 280, 105, 350, 333, 362, 405

[56] References Cited

U.S. PATENT DOCUMENTS 4,650,804  3/1987  Kitaura et al. .................. 514/306

*Primary Examiner*—Cecilia Tsang
*Attorney, Agent, or Firm*—Mona Anand; Thomas D. Brainard

[57] ABSTRACT

Antibacterial compounds having the formula

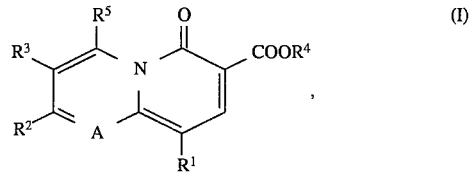

and the pharmaceutically acceptable salts, esters and amides thereof, selected preferred examples of which include those compounds wherein A is $=CR^6-$;

$R^1$ is cycloalkyl of from three to eight carbon atoms or substituted phenyl;

$R^2$ is selected from the group consisting of

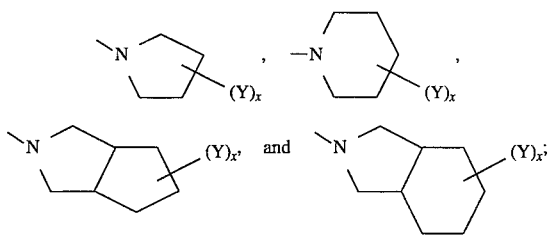

$R^3$ is halogen;

$R^4$ is hydrogen, loweralkyl, a pharmaceutically acceptable cation, or a prodrug ester group;

$R^5$ is hydrogen, loweralkyl, halo(loweralkyl), or $-NR^{13}R^{14}$; and $R^6$ is halogen, loweralkyl, halo(loweralkyl), hydroxy-substituted loweralkyl, loweralkoxy(loweralkyl), loweralkoxy, or amino(loweralkyl), as well as pharmaceutical compositions containing such compounds and the use of the same in the treatment of bacterial infections.

31 Claims, No Drawings

QUINOLIZINONE TYPE COMPOUNDS

This application is a divisional of prior application U.S. Ser. No. 08/469,159, filed on Jun. 6, 1995, which is a continuation-in-part of U.S. Ser. No. 08/316,319, filed Sep. 30, 1994, which is a continuation-in-part of U.S. Ser. No. 08/137,236, filed Oct. 14, 1993, now abandoned which is a continuation-in-part of U.S. Ser. No. 07/940,870, filed Oct. 27, 1992, now abandoned, which is a continution-in-part of U.S. Ser. No. 07/517,780, filed May 2, 1990, now abandoned.

TECHNICAL FIELD

The present invention relates to compounds having antimicrobial activity, pharmaceutical compositions containing such compounds, methods of treatment utilizing such compounds, and processes for their chemical synthesis. More particularly, this invention relates to novel 4-oxo-4H-quinolizine-3-carboxylic acid compounds which are highly effective in the treatment of microbial and especially bacterial infections, as well as compositions containing the same and the therapeutic use of such compounds.

BACKGROUND OF THE INVENTION

There is a continuing need for new antibacterial agents. Although many compounds are known which are useful in the treatment of Gram-positive and Gram-negative bacterial infections as well as other microbial infections, the widespread use of such compounds continues to give rise to resistant strains of microorganisms, i.e., strains of microorganisms against which a particular antibiotic or group of antibiotics, which was previously effective, is no longer useful. Also, known antibiotics may be effective against only certain strains of microorganisms or have limited activity against either Gram-positive or Gram-negative, aerobic or anaerobic organisms.

The therapeutic use of certain quinolizinone derivatives has been described previously. For example, Y. Kitaura et al., in U.S. Pat. No. 4,650,804, issued Mar. 17, 1987, have disclosed quinolizinone compounds having a tetrazolylcarbamoyl substituent which are useful for the treatment of allergic and ulcer diseases. J. V. Heck and E. D. Thorsett, in European Patent Application No. 0308019, published Mar. 22, 1989; have disclosed the use of certain 4-oxo-4H-quinolizine-3-carboxylic acids and derivatives thereof for treating bacterial infections. However, there remains an ongoing need for novel compounds which have improved antimicrobial potency and/or different spectra of activity.

SUMMARY OF THE INVENTION

In one aspect of the present invention are disclosed compounds represented by the following structural formula (I):

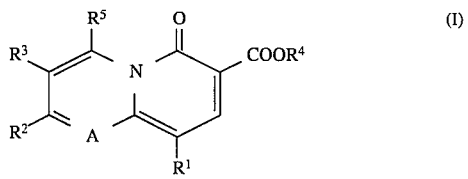

as well as the pharmaceutically acceptable salts, esters and amides thereof.

$R^1$ in formula (I) is selected from (a) loweralkyl, (b) loweralkenyl, (c) halo(lower-alkyl), (d) loweralkoxy, (e) cycloalkyl of from three to eight carbon atoms, (f) phenyl, (g) substituted phenyl, (h) halo, (i) cyano, (j) nitro, (k) bicycloalkyl, (l) loweralkynyl, (m) loweralkoxycarbonyl, (n) nitrogen-containing aromatic heterocycle, (o) halo-substituted nitrogen-containing aromatic heterocycle, (p) a 4-, 5- or 6-membered cyclic ether, and (q) —$NR^7R^8$. The radicals $R^7$ and $R^8$ are independently selected from hydrogen, loweralkyl and alkanoyl of from one to eight carbon atoms or, taken together with the nitrogen atom to which they are attached, $R^7$ and $R^8$ may form a 5-, 6- or 7-membered heterocycle, preferably in which the remainder of the ring atoms are carbon atoms.

$R^2$ in formula (I) is selected from (a) halogen, (b) loweralkyl, (c) loweralkenyl, (d) cycloalkyl of from three to eight carbons, (e) cycloalkenyl of from four to eight carbons, (f) loweralkoxy, (g) aryloxy, (h) aryl(loweralkyl)oxy, (i) aryl(loweralkyl), (j) cycloalkyl(loweralkyl), (k) amino, (l) (loweralkyl)amino, (m) aryl(loweralkyl)-amino, (n) hydroxy-substituted (loweralkyl)amino, (o) phenyl, (p) substituted phenyl, (q) bicyclic nitrogen-containing heterocycle, (r) nitrogen-containing aromatic heterocycle, (s) nitrogen-containing heterocycle having the formula

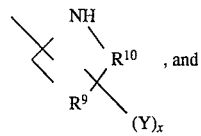

and (t) non-nitrogen-containing heterocycle having the formula

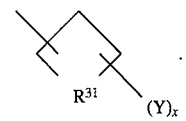

In subformula (Ia) above, x is zero, one, two or three, and $R^9$ is either (i) —$(CH_2)_m$— where m is one, two or three, or (ii) —$(CH_2)_nR^{13}(CH_2)_p$— where $R^{13}$ is selected from —S—, —O— and —NH—, $R^{10}$ is $CH_2$, or when $R^9$ is selected from option (i) may be O, S or N, n is one or two, and p is one or two. When present, the radical(s) Y is/are independently selected at each occurrence from the following:

(i) loweralkyl,
(ii) hydroxy,
(iii) halogen,
(iv) halo(loweralkyl),
(v) hydroxy-substituted loweralkyl,
(vi) loweralkenylamino,
(vii) loweralkylamino,
(viii) loweralkoxy,
(ix) (loweralkoxy)loweralkylamino,
(x) loweralkoxy(loweralkyl),
(xi) loweralkoxy(loweralkoxy)(loweralkyl),
(xii) hydroxy-substituted loweralkyl,
(xiii) imino,
(xiv) alkoxycarbonyl,
(xv) carbamoyl,
(xvi) aryl(loweralkyl),
(xvii) aminoxy
(xviii) amino(loweralkyl),
(xix) halo(loweralkyl)amino,
(xx) halo(loweralkyl)amino(loweralkyl), (xxi) thioloweralkoxy(loweralkyl), (xxii) aminothioloweralkoxy, (xxiii) cycloalkyl of from three to six carbon atoms, (xxiv) cycloalkyl(loweralkyl), (xxv) cycloalkylamino, (xxvi) phenyl, (xxvii) substituted phenyl, (xxviii) substituted phenyl(loweralkyl)

(xxix) nitrogen-containing aromatic heterocycle, (xxx) —$NR^{11}R^{12}$ where $R^{11}$ and $R^{12}$ are independently selected from hydrogen and loweralkyl or, when one of $R^{11}$ and $R^{12}$ is hydrogen, the other is alkanoyl of from one to eight carbon atoms, an alpha-amino acid, or a polypeptide residue of from two to five amino acids, and (xxxi) —$C(R^{21})(R^{22})NH_2$ where $R^{21}$ and $R^{22}$ are independently selected from among hydrogen, loweralkyl, hydroxy-substituted loweralkyl, amino(loweralkyl), loweralkoxy(loweralkyl), thioloweralkoxy(loweralkyl), cycloalkyl of from three to six carbon atoms, and loweralkyl substituted with nitrogen-containing aromatic heterocycle (or, taken together with the carbon atom to which they are attached, $R^{21}$ and $R^{22}$ form a ring structure selected from cycloalkyl of from three to six carbon atoms and nitrogen-containing heterocycle).

In subformula (Ib) above, x is zero, one, two or three, and $R^{31}$ is —$(CH_2)_q R^{32}$— where $R^{32}$ is selected from —S— and —O—, q is one, two or three, and the radical(s) Y is/are as defined above.

$R^3$ in formula (I) is selected from among hydrogen, halogen and loweralkoxy, while $R^4$ is selected from hydrogen, loweralkyl, a pharmaceutically acceptable cation, and a prodrug ester group.

$R^5$ in formula (I) is selected from (a) hydrogen, (b) halogen, (c) hydroxy, (d) loweralkyl, (e) halo(loweralkyl), (f) loweralkoxy, and (g) —$NR^{13}R^{14}$ where $R^{13}$ and $R^{14}$ are independently selected from among hydrogen, loweralkyl, hydroxy-substituted loweralkyl, loweralkoxy(loweralkyl), and alkanoyl of from one to eight carbon atoms.

A in formula (I) is =N— or =$CR^6$—, where $R^6$ is selected from (a) hydrogen, (b) halogen, (c) loweralkyl, (d) halo(loweralkyl), (e) hydroxy-substituted loweralkyl, (f) loweralkoxy(loweralkyl), (h) loweralkoxy, and (i) amino(loweralkyl).

Alternatively, taken together with the atoms to which they are attached, $R^1$ and $R^6$ may form a 6-membered saturated ring optionally containing an oxygen or a sulfur atom and optionally substituted with loweralkyl, so as to produce a tricyclic compound.

The compounds of the present invention are subject to the proviso that, if $R^5$ in formula (I) is hydrogen, A is =$CR^6$—, and $R^6$ is hydrogen, then $R^1$ may not be unsubstituted phenyl.

The above compounds of the invention are found to have a surprising degree of antimicrobial activity against a wide spectrum of Gram-positive and Gram-negative bacteria as well as enterobacteria. Susceptible organisms whose growth can be inhibited generally include both aerobic and anaerobic pathogens of the genera *Staphylococcus, Lactobacillus, Micrococcus, Enterococcus, Streptococcus, Sarcina, Escherichia, Enterobacter, Klebsiella, Pseudomonas, Acinobacter, Proteus, Providencia, Citrobacter, Nisseria, Bacillus, Bacteroides, Camphylobacter, Peptococcus, Clostridium, Salmonella, Shigella, Legionella, Serratia, Haemophilus, Brucella* and the like. It is therefore expected that the compounds of the present invention will be useful in the treatment and prevention of susceptible bacterial infections in both humans and lower animals. In addition, the compounds, by reason of their in vitro activity, may be used in scrub solutions for surface inhibition of bacterial growth.

Accordingly, in a further aspect of the present invention are disclosed pharmaceutical compositions which are useful in the treatment and prophylaxis of bacterial and/or fungal infection in humans and animals, comprising a compound of the invention in combination with a pharmaceutically acceptable carrier.

In yet another aspect of the present invention is disclosed a method of treating and/or preventing microbial infections in human or animal patients in need of such treatment, comprising the administration to such patients of a therapeutically effective amount of a compound of the invention in amounts and for such a period of time as are sufficient to produce the desired result.

In still another aspect of the present invention are disclosed synthetic schemes and processes which are useful in the preparation of the compounds of the invention, as well as synthetic (chemical) intermediates which can be utilized therein.

DETAILED DESCRIPTION OF THE INVENTION

Included among the compounds of the present invention are those in which A is =$CR^6$— and $R^6$ is selected from among halogen, loweralkyl, halo(loweralkyl), hydroxy-substituted loweralkyl, loweralkoxy(loweralkyl), loweralkoxy, or amino(loweralkyl). A sub-class of such compounds, particularly preferred and found to be surprisingly effective antibacterial agents, comprises those in which $R^6$ is methyl. In each case, more preferred compounds are those in which $R^3$ is halogen (especially fluoro); $R^5$ is hydrogen, loweralkyl, halo-(loweralkyl), or —$NR^{13}R^{14}$ (where $R^{13}$ and $R^{14}$ are as previously defined); $R^1$ is cycloalkyl of from three to eight carbon atoms or substituted phenyl; and/or $R^6$ is halogen, loweralkyl, or loweralkoxy.

The radical $R^2$ in the above compounds is preferably bicyclic nitrogen-containing heterocycle or a nitrogen-containing heterocycle of the formula

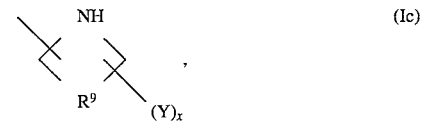

or, even more preferably, $R^2$ is selected from among radicals of the formulae

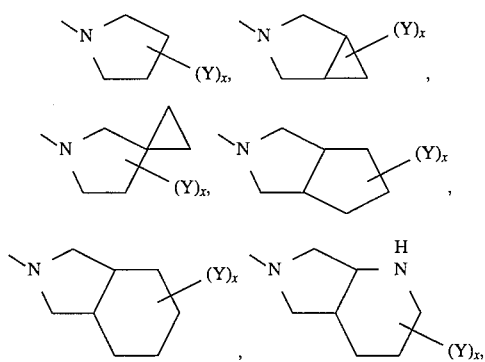

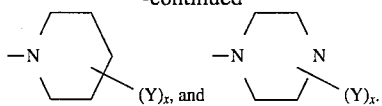

In these radicals $R^2$, x is preferably one or two, and Y is preferably either $-NR^{11}R^{12}$ or $-C(R^{21})(R^{22})NH_2$, where $R^{11}$, $R^{12}$, $R^{21}$ and $R^{22}$ are as defined above.

Especially preferred among the compounds of the present invention are those having the general formula

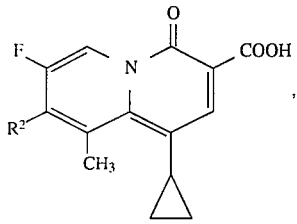

as well as the pharmaceutically acceptable salts, esters and amides thereof, in which $R^2$ is either bicyclic nitrogen-containing heterocycle or a nitrogen-containing heterocycle having the formula

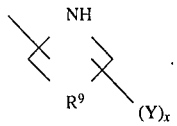

Of these, particularly preferred compounds are those in which $R^2$ is selected from among radicals having the formulae

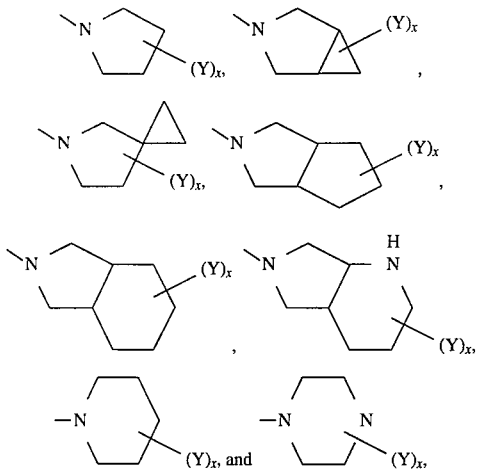

and especially those in which x is one or two and Y is $-NR^{11}R^{12}$ or $-C(R^{21})(R^{22})NH_2$.

Also included among the compounds of the present invention are those which have the general formula

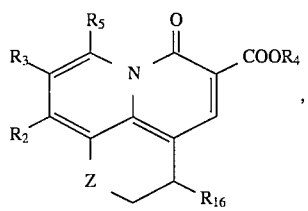

as well as the pharmaceutically acceptable salts, esters and amides thereof, in which Z is $-CH_2-$, $-O-$ or $-S-$; $R^{16}$ is loweralkyl; and $R^2$, $R^3$, $R^4$ and $R^5$ are as defined above. Preferred among such compounds are those in which Z is $-O-$ and $R^2$ is a nitrogen-containing heterocycle of the formula

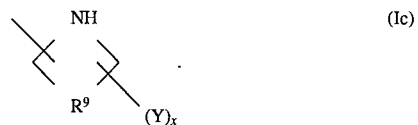

Particular compounds which are representative of the compounds of the present invention include the following:

3-fluoro-9-(4-fluorophenyl)-2-(4-methylpiperazin-1-yl)-6(H)-6-oxo-pyrido[1,2-a]pyrimidine-7-carboxylic acid;

9-(2,4-difluorophenyl)-3-fluoro-2-(4-methylpiperazin-1-yl)-6(H)-6-oxo-pyrido[1,2-a]pyrimidine-7-carboxylic acid;

3-fluoro-9-cyclopropyl-2-(4-methylpiperazin-1-yl)-6(H)-6-oxo-pyrido[1,2-a]pyrimidine-7-carboxylic acid;

8-(3-aminopyrrolidin-1-yl)-1-ethyl-4H-quinolizin-4-one-3-carboxylic acid;

2-(3-aminopyrrolidin-1-yl)-9-cyclopropyl-3-fluoro-6H-6-oxo-pyrido[1,2-a]pyrimidine-7-carboxylic acid;

2-(3-aminopyrrolidin-1-yl)-9-cyclopropyl-3-fluoro-6H-6-oxo-pyrido[1,2-a]pyrimidine-7-carboxylic acid;

9-(2,4-difluorophenyl)-3-fluoro-2-(4-methylpiperazin-1-yl)-6H-6-oxopyrido[1,2-a]pyrimidine-7-carboxylic acid;

2-(3-aminopyrrolidin-1-yl)-9-(2,4-difluorophenyl)-3-fluoro-6H-6-oxopyrido[1,2-a]pyrimidine-7-carboxylic acid;

2-(3-(N-t-butoxycarbonyl)aminopyrrolidin-1-yl)-9-(2,4-difluorophenyl)-3-fluoro-6H-6-oxopyrido[1,2-a]pyrimidine-7-carboxylic acid;

2-(3-aminopyrrolidin-1-yl)-9-(2,4-difluorophenyl)-3-fluoro-6H-6-oxopyrido[1,2-a]pyrimidine-7-carboxylic acid;

9-cyclopropyl-3-fluoro-2-(4-methylpiperazin-1-yl)-6H-6-oxo-pyrido[1,2-a]pyrimidine-7-carboxylic acid;

9-cyclopropyl-3-fluoro-2-(piperazin-1-yl)-6H-6-oxo-pyrido[1,2-a]pyrimidine-7-carboxylic acid;

9-cyclopropyl-3-fluoro-2-(morpholin-1-yl)-6H-6-oxo-pyrido[1,2-a]pyrimidine-7-carboxylic acid;

9-(2,4-difluorophenyl)-3-fluoro-2-(3-(N-(S)-norvalyl)aminopyrrolidin-1-yl)-6H-6-oxopyrido[1,2-a]pyrimidine-7-carboxylic acid;

2-(3-(N-(S)-alanyl)aminopyrrolidin-1-yl)-9-(2,4-difluorophenyl)-3-fluoro-6H-6-oxopyrido[1,2-a]pyrimidine-7-carboxylic acid;

2-(3-(N-(S)-alanyl-(S)-alanyl)aminopyrrolidin-1-yl)-9-(2,4-difluorophenyl)-3-fluoro-6H-6-oxopyrido[1,2-a] pyrimidine-7-carboxylic acid;

2-((2S,4S)-4-acetamido-2-methylpyrrolidin-1-yl)-9-(2,4-difluorophenyl)-3-fluoro-6H-6-oxopyrido[1,2-a]pyrimidine-7-carboxylic acid;

9-(2,4-difluorophenyl)-3-fluoro-2-(3-hydroxypyrrolin-1-yl)-6H-6-oxopyrido[1,2-a]pyrimidine-7-carboxylic acid;

2-((2S,4S)-4-amino-2-methylpyrrolidin-1-yl)-9-(2,4-difluorophenyl)-3-fluoro-6H-6-oxopyrido[1,2-a]pyrimidine-7-carboxylic acid;

8-(3-amino-1-pyrrolidinyl)-1-cyclopropyl-7-fluoro-9-methyl-4-oxo-4H-quinolizine-3-carboxylic acid;

8-(3-(aminomethyl)pyrrolidinyl)-1-cyclopropyl-7-fluoro-9-methyl-4-oxo-4H-quinolizine-3-carboxylic acid;

8-(2S,4S-4-amino-2-methylpyrrolidinyl)-1-cyclopropyl-7-fluoro-9-methyl-4-oxo-4H-quinolizine-3-carboxylic acid;

8-(3-aminoazetidinyl)-1-cyclopropyl-7-fluoro-9-methyl-4-oxo-4H-quinolizine-3-carboxylic acid;

8-(3(S)-aminopyrrolidinyl)-1-cyclopropyl-7-fluoro-9-methyl-4-oxo-4H-quinolizine-3-carboxylic acid;

1-cyclopropyl-7-fluoro-9-methyl-4-oxo-8-(3-methyl-1-piperazinyl)-4H-quinolizine-3-carboxylic acid;

1-cyclopropyl-7-fluoro-9-methyl-4-oxo-8-piperazinyl-4H-quinolizine-3-carboxylic acid;

1-cyclopropyl-7-fluoro-9-methyl-8-(2-((N-methyl)aminomethyl)-4-morpholinyl)-4-oxo-4H-quinolizine-3-carboxylic acid;

1-cyclopropyl-7-fluoro-9-methyl-4-oxo-8-(1,2,3,4-tetrahydro-2-isoquinolinyl)-4H-quinolizine-3-carboxylic acid;

1-cyclopropyl-7-fluoro-9-methyl-4-oxo-8-(4-amino-1-piperdinyl)-4H-quinolizine-3-carboxylic acid;

1-cyclopropyl-7-fluoro-9-methyl-4-oxo-8-(3-amino-1-piperdinyl)-4H-quinolizine-3-carboxylic acid;

1-cyclopropyl-7-fluoro-9-methyl-4-oxo-8-(4-(aminomethyl)-1-piperdinyl)-4H-quinolizine-3-carboxylic acid;

1-cyclopropyl-7-fluoro-9-methyl-4-oxo-8-(5-amino-1,2,3,4-tetrahydro-2-isoquinolinyl)-4H-quinolizine-3-carboxylic acid;

1-cyclopropyl-7-fluoro-9-methyl-4-oxo-8-(4-(1-pyrrolyl)-1-piperidinyl)-4H-quinolizine-3-carboxylic acid;

1-cyclopropyl-8-(cis-3,5-dimethyl-1-piperazinyl)-7-fluoro-9-methyl-4-oxo-4H-quinolizine-3-carboxylic acid;

1-cyclopropyl-8-(2,7-diaza-7-bicyclo[3.3.0]oct-2-yl)-7-fluoro-9-methyl-4-oxo-4H-quinolizine-3-carboxylic acid;

1-cyclopropyl-8-(2,8-diaza-8-bicyclo[4.3.0]nonyl)-7-fluoro-9-methyl-4-oxo-4H-quinolizine-3-carboxylic acid;

1-cyclopropyl-7-fluoro-9-methyl-4-oxo-8-(3(S)-(1-pyrrolyl)-1-pyrrolidinyl)-4H-quinolizine-3-carboxylic acid;

1-cyclopropyl-7-fluoro-8-(3-hydroxy-1-pyrrolidinyl)-9-methyl-4-oxo-4H-quinolizine-3-carboxylic acid;

1-cyclopropyl-7-fluoro-8-(4-methyl-1-piperazinyl)-9-methyl-4-oxo-4H-quinolizine-3-carboxylic acid;

1-cyclopropyl-9-chloro-7-fluoro-8-(3-amino-1-pyrrolidinyl)-4-oxo-4H-quinolizine-3-carboxylic acid;

8-(3-amino-1-pyrrolidinyl)-1-cyclopropyl-7,9-difluoro-4-oxo-4H-quinolizine-3-carboxylic acid;

8-(3-amino-1-pyrrolidinyl)-1-cyclopropyl-7-fluoro-9-methoxy-4-oxo-4H-quinolizine-3-carboxylic acid.

1cyclopropyl-8-(2,7-diaza-7-bicyclo[3.3.0]oct-2-yl)-7-fluoro-9-methyl-4-oxo-4H-quinolizine-3-carboxylic acid;

1-cyclopropyl-8-(2,8-diaza-8-bicyclo[4.3.0]nonyl)-7-fluoro-9-methyl-4-oxo-4H-quinolizine-3-carboxylic acid;

1-cyclopropyl-7-fluoro-9-methyl-4-oxo-8-(3(S)-(1-pyrrolyl)-1-pyrrolidinyl)-4H-quinolizine-3-carboxylic acid;

1-cyclopropyl-7-fluoro-8-(3-hydroxy-1-pyrrolidinyl)-9-methyl-4-oxo-4H-quinolizine-3-carboxylic acid;

1-cyclopropyl-7-fluoro-8-(4-methyl-1-piperazinyl)-9-methyl-4-oxo-4H-quinolizine-3-carboxylic acid;

1-cyclopropyl-9-chloro-7-fluoro-8-(3-amino-1-pyrrolidinyl)-4-oxo-4H-quinolizine-3-carboxylic acid;

8-(3-amino-1-pyrrolidinyl)-1-cyclopropyl-7,9-difluoro-4-oxo-4H-quinolizine-3-carboxylic acid;

8-(3-amino-1-pyrrolidinyl)-1-cyclopropyl-7-fluoro-9-methoxy-4-oxo-4H-quinolizine-3-carboxylic acid;

1-cyclopropyl-7-fluoro-9-methyl-8-(3(S)-methylamino-1-pyrrolidinyl)-4-oxo-4H-quinolizine-3-carboxylic acid;

1-cyclopropyl-7-fluoro-9-methyl-8-(3(S)-methylamino-1-pyrrolidinyl)-4-oxo-4H-quinolizine-3-carboxylic acid;

1-cyclopropyl-7-fluoro-9-methyl-8-(3(R)-amino-1-pyrrolidinyl)-4-oxo-4H-quinolizine-3-carboxylic acid;

(3S)-9-fluoro-3-methyl-10-(4-methyl-1-piperazinyl)-2H,3H,6H-6-oxo-pyrano[2.3.4-ij]quinolizine-5-carboxylic acid;

3(R)-9-fluoro-3-methyl-10-(4-methyl-1-piperazinyl)-2H,3H,6H-6-oxo-pyrano[2.3.4-ij]quinolizine-5-carboxylic acid;

9-fluoro-10-(1-morpholinyl)-2H,3H,6H-6-oxo-pyrano[2.3.4-ij]quinolizine-5-carboxylic acid;

(3S)-10-(3-amino-1-pyrrolidinyl)-9-fluoro-3-methyl-2H,3H,6H-6-oxo-pyrano[2.3.4-ij]quinolizine-5-carboxylic acid;

3(S)-10-(3-aminomethyl-1-pyrrolidinyl)-9-fluoro-3-methyl-2H,3H,6H-6-oxo-pyrano[2.3.4-ij]quinolizine-5-carboxylic acid;

3(S)-10-((2S,4S)-4-amino-2-methyl-1-pyrrolidinyl)-9-fluoro-3-methyl-2H,3H,6H-6-oxo-pyrano[2.3.4-ij]quinolizine-5-carboxylic acid;

3(S)-9-fluoro-10-(3-hydroxy-1-pyrrolidinyl)-3-methyl-2H,3H,6H-6-oxo-pyrano[2.3.4-ij]quinolizine-5-carboxylic acid;

9-fluoro-10-(4-methyl-1-piperazinyl)-2H,3H,6H-6-oxo-pyrano[2.3.4-ij]quinolizine-5-carboxylic acid;

8-(2,4-dimethyl-1-piperazinyl)-1-cyclopropyl-7-fluoro-9-methyl-4-oxo-4H-quinolizine-3-carboxylic acid;

8-(3-(methylamino)-1-piperazinyl)-1-cyclopropyl-7-fluoro-9-methyl-4-oxo-4H-quinolizine-3-carboxylic acid;

8-(3-(methylamino)-1-morpholinyl)-1-cyclopropyl-7-fluoro-9-methyl-4-oxo-4H-quinolizine-3-carboxylic acid;

8-(3-(S)-(methylamino)-1-pyrrolidinyl)-1-cyclopropyl-7-fluoro-9-methyl-4-oxo-4H-quinolizine-3-carboxylic acid;

8-(3-(S)-(1-(methylamino)methyl)-1-pyrrolidinyl)-1-cyclopropyl-7-fluoro-9-methyl-4-oxo-4H-quinolizine-3-carboxylic acid;

8-(3-(S)-(1-(ethylamino)methyl)-1-pyrrolidinyl)-1-cyclopropyl-7-fluoro-9-methyl-4-oxo-4H-quinolizine-3-carboxylic acid;

8-(octahydropyrrolo[3,4-c]pyrrol-1-yl)-1-cyclopropyl-7-fluoro-9-methyl-4-oxo-4H-quinolizine-3-carboxylic acid;

8-(octahydropyrrolo[3,4-c]pyridin-5-yl)-1-cyclopropyl-7-fluoro-9-methyl-4-oxo-4H-quinolizine-3-carboxylic acid;

8-(cis-4-amino-3-methylpyrrolidinyl)-1-cyclopropyl-7-fluoro-9-methyl-4-oxo-4H-quinolizine-3-carboxylic acid;

8-(trans-4-amino-3-methylpyrrolidinyl)-1-cyclopropyl-7-fluoro-9-methyl-4-oxo-4H-quinolizine-3-carboxylic acid;

8-(3-methyl-4-spirocyclopropylpyrrolidinyl)-1-cyclopropyl-7-fluoro-9-methyl-4-oxo-4H-quinolizine-3-carboxylic acid;

8-(2S,4S-4-amino-2-methylpyrrolidinyl)-1-cyclopropyl-7-fluoro-9-(fluoro)methyl-4-oxo-4H-quinolizine-3-carboxylic acid;

8-(3-dimethylaminopyrrolidinyl)-1-cyclopropyl-7-fluoro-9-methyl-4-oxo-4H-quinolizine-3-carboxylic acid;

(3R)-8-(3-dimethylaminopyrrolidinyl)-1-cyclopropyl-7-fluoro-9-methyl-4-oxo-4H-quinolizine-3-carboxylic acid;

(3R,1S)-8-(3-(1-aminoethyl)pyrrolidinyl)-1-cyclopropyl-7-fluoro-9-methyl-4-oxo-4H-quinolizine-3-carboxylic acid;

(3S,1R)-8-(3-(1-aminoethyl)pyrrolidinyl)-1-cyclopropyl-7-fluoro-9-methyl-4-oxo-4H-quinolizine-3-carboxylic acid;

(3R,1R)-8-(3-(1-aminoethyl)pyrrolidinyl)-1-cyclopropyl-7-fluoro-9-methyl-4-oxo-4H-quinolizine-3-carboxylic acid;

1-cyclopropyl-8-((R,S)-3-fluoropyrrloidine)-7-fluoro-9-methyl-4-oxo-4H-quinolizine-3-carboxylic acid;

8-(4-(1-piperidyl)-1-piperidyl)-1-cyclopropyl-7-fluoro-9-methyl-4-oxo-4H-quinolizine-3-carboxylic acid;

8-(4-(1-piperidyl)-1-piperidyl)-1-cyclopropyl-7-fluoro-9-methyl-4-oxo-4H-quinolizine-3-carboxylic acid;

8-(4-(2-pyridyl)-1-piperazinyl)-1-cyclopropyl-7-fluoro-9-methyl-4-oxo-4H-quinolizine-3-carboxylic acid;

8-((2-amino)thioethoxy)-1-cyclopropyl-7-fluoro-9-methyl-4-oxo-4H-quinolizine-3-carboxylic acid;

(3R,1S)-8-(3-(1-amino)propyl)pyrrolidinyl)-1-cyclopropyl-7-fluoro-9-methyl-4-oxo-4H-quinolizine-3-carboxylic acid;

(3R,1S)-8-(3-(1-(N-methyl)amino)propyl)pyrrolidinyl)-1-cyclopropyl-7-fluoro-9-methyl-4H-quinolizine-3-carboxylic acid;

(3R,1S)-8-(3-(1-amino-3-methylpropyl)pyrrolidinyl)-1-cyclopropyl-7-fluoro-9-methyl-4H-quinolizine-3-carboxylic acid;

8-(3-(1-aminocyclopropyl)pyrrolidinyl)-1-cyclopropyl-7-fluoro-9-methyl-4-oxo-4H-quinolizine-3-carboxylic acid;

(3R,1S)-8-(3-(1-amino-2-hydroxyethyl)pyrrolidinyl)-1-cyclopropyl-7-fluoro-9-methyl-4H-quinolizine-3-carboxylic acid;

(8-(3-(1-amino-1-methylethyl)pyrrolidinyl)-1-cyclopropyl-7-fluoro-9-methyl-4-oxo-4H-quinolizine-3-carboxylic acid;

8-(3-(1-aminobutyl)pyrrolidinyl)-1-cyclopropyl-7-fluoro-9-methyl-4-oxo-4H-quinolizine-3-carboxylic acid;

1-cyclopropyl-7-fluoro-9-methyl-4-oxo-8-(trans-4-trifluoromethyl-3-aminopyrrolidinyl)-4H-quinolizine-3-carboxylic acid;

1-cyclopropyl-7-fluoro-9-methyl-4-oxo-8-(trans-4-trifluoromethyl-3-aminomethylpyrrolidinyl)-4H-quinolizine-3-carboxylic acid;

3(S)-1-cyclopropyl-7-fluoro-9-methyl-4-oxo-8-(3-(N-(S)-norvalylamino)pyrrolidinyl)-4H-quinolizine-3-carboxylic acid;

3(S)-1-cyclopropyl-7-fluoro-9-methyl-4-oxo-8-(3-(N-(S)-alanylamino)pyrrolidinyl)-4H-quinolizine-3-carboxylic acid;

3(S)-1-cyclopropyl-7-fluoro-9-methyl-4-oxo-8-(3-(N-(S)-alanyl-(S)-alanylamino)pyrrolidinyl)-4H-quinolizine-3-carboxylic acid;

1-cyclopropyl-7-fluoro-6-methyl-4-oxo-8-(3-aminopyrrolidinyl)-4H-quinolizine-3-carboxylic acid;

1-cyclopropyl-7-fluoro-4H-8-(1-imidazolyl)-9-methyl-4-oxo-quinolizine-3-carboxylic acid;

8-(3-amino-1-pyrrolidinyl)-1-ethyl-7-fluoro-4H-4-oxo-9-methyl-quinolizine-3-carboxylic acid;

8-(3-amino-1-pyrrolidinyl)-1-cyclopropyl-9-ethyl-7-fluoro-4H-4-oxo-quinolizine-3-carboxylic acid;

1-cyclopropyl-7-fluoro-4H-9-methyl-4-oxo-8-(3-(1,2,3-triazol-1-yl)-1-pyrrolidinyl)quinolizine-3-carboxylic acid;

1-cyclopropyl-7-fluoro-4H-9-methyl-4-oxo-8-(cis-3-amino-4-methyl-1-pyrrolidinyl)quinolizine-3-carboxylic acid;

8-(2-aminoethyl)-1-cyclopropyl-7-fluoro-4H-9-methyl-4-oxo-quinolizine-3-carboxylic acid;

8-(3-(ethylaminomethyl)pyrrolidinyl)-1-cyclopropyl-7-fluoro-4H-9-methyl-4-oxo-quinolizine-3-carboxylic acid;

8-(3-(1-aminoethyl)pyrrolidinyl)-1-cyclopropyl-7-fluoro-4H-9-methyl-4-oxo-quinolizine-3-carboxylic acid;

1-cyclopropyl-7-fluoro-4H-9-methyl-8-(2-methyl-2,8-diaza-8-bicyclo[4.3.0]nonyl)-4-oxo-quinolizine-3-carboxylic acid;

1-cyclopropyl-7-fluoro-4H-8-((1S,4S)-2,5-diaza-bicyclo[2.2.1]heptan-2-yl)-9-methyl-4-oxoquinolizine-3-carboxylic acid;

1-cyclopropyl-7-fluoro-4H-9-methyl-4-oxo-8-(3-(2-pyridinyl)-1-pyrrolidinyl)-quinolizine-3-carboxylic acid;

8-((1R*,2S*,6R*)-2-amino-8-azabicyclo[4.3.0]nonan-8-yl))-1-cyclopropyl-7-fluoro-4H-9-methyl-4-oxo-quinolizine-3-carboxylic acid;

8-((1R*,2R*,6R*)-2-amino-8-azabicyclo[4.3.0]nonan-8-yl))-1-cyclopropyl-7-fluoro-4H-9-methyl-4-oxo-quinolizine-3-carboxylic acid;

8-((1a,5a,6a)-6-amino-3-azabicyclo[3.1.0]hexan-3-yl))-1-cyclopropyl-9-meth acid;

8-(trans-3-amino-4-fluoro-1-pyrrolidinyl))-1-cyclopropyl-9-methyl-7-fluoro-4H-4-oxo-quinolizine-3-carboxylic acid;

1-cyclopropyl-7-fluoro-4H-8-(1-homopiperazinyl))-9-methyl-4-oxo-quinolizine-3-carboxylic acid;

7,9-difluoro-4H-8-(4-methylpiperazinyl)-4-oxo-1-phenyl-quinolizine-3-carboxylic acid;

8-(spiro-1,3-dioxacyclopentane[2.3]-1-piperidinyl)-1-cyclopropyl-7-fluoro-4H-9-methyl-4-oxo-quinolizine-3-carboxylic acid;

8-(3-amino-4-methoxypyrrolidinyl)-1-cyclopropyl-7-fluoro-4H-9-methyl-4-oxo-quinolizine-3-carboxylic acid;

8-(4-amino-4-methylpyrrolidinyl)-1-cyclopropyl-7-fluoro-4H-9-methyl-4-oxo-quinolizine-3-carboxylic acid;

8-(4-(2-hydroxyethyl)piperidinyl)-1-cyclopropyl-7-fluoro-4H-9-methyl-4-oxo-quinolizine-3-carboxylic acid;

8-(4-(methoxymethyl)piperidinyl)-1-cyclopropyl-7-fluoro-4H-9-methyl-4-oxo-quinolizine-3-carboxylic acid;

8-(3-amino-3-methylpiperidinyl)-1-cyclopropyl-7-fluoro-4H-9-methyl-4-oxo-quinolizine-3-carboxylic acid;

8-(3-pyrrolylpiperidinyl)-1-cyclopropyl-7-fluoro-4H-9-methyl-4-oxo-quinolizine-3-carboxylic acid;

8-(3-aminopiperidinyl)-1-cyclopropyl-7-fluoro-4H-9-methyl-4-oxo-quinolizine-3-carboxylic acid;

8-(3-amino-3-methylpyrrolidinyl)-1-cyclopropyl-7-fluoro-4H-9-methyl-4-oxo-quinolizine-3-carboxylic acid;

8-(3-amino-4-(1',3'-dioxolanyl)pyrrolidinyl)-1-cyclopropyl-7-fluoro-4H-9-methyl-4-oxo-quinolizine-3-carboxylic acid;

8-(3-amino-4-hydroxy-pyrrolidinyl)-1-cyclopropyl-7-fluoro-4H-9-methyl-4-oxo-quinolizine-3-carboxylic acid;

8-(4-(1-(N-ethylamino)methyl)piperidinyl)-1-cyclopropyl-7-fluoro-4H-9-methyl-4-oxo-quinolizine-3-carboxylic acid;

1-cyclopropyl-7-fluoro-8-(3-hydroxy-4-methylaminopyrrolidinyl)-4H-9-methyl-4-oxo-quinolizine-3-carboxylic acid;

8-(3-aminomethylpiperidinyl)-1-cyclopropyl-7-fluoro-4H-9-methyl-4-oxo-quinolizine-3-carboxylic acid;

8-(2-aminomethyl-4-morpholinyl)-1-cyclopropyl-7-fluoro-4H-9-methyl-4-oxo-quinolizine-3-carboxylic acid;

8-(3-(1-(methylamino)methypiperidinyl)-1-cyclopropyl-7-fluoro-4H-9-methyl-4-oxo-quinolizine-3-carboxylic acid;

8-(3-(methyl(methylenedioxy)methyl)piperidinyl)-1-cyclopropyl-7-fluoro-4H-9-methyl-4-oxo-quinolizine-3-carboxylic acid;

8-(3-(S)-aminopiperidinyl)-1-cyclopropyl-7-fluoro-4H-9-methyl-4-oxo-quinolizine-3-carboxylic acid;

8-(3-(S)-(N-ethyl-N-methylamino)piperidinyl)-1-cyclopropyl-7-fluoro-4H-9-methyl-4-oxo-quinolizine-3-carboxylic acid;

1-cyclopropyl-8-(4-(2'-(N-methylamino)methyl-1',3'-dioxolanyl)piperidinyl)-7-fluoro-9-methyl-4-oxo-4H-quinolizine-3-carboxylic acid;

1-cyclopropyl-8-(3-aza-6-amino-6-methylbicyclo[3.3.0]octan-1-yl)-7-fluoro-9-methyl-4-oxo-4H-quinolizine-3-carboxylic acid;

1-cyclopropyl-8-(3-fluoromethylpiperidinyl)-7-fluoro-9-methyl-4-oxo-4H-quinolizine;

1-cyclopropyl-8-(4-(N,N-dimethyl)aminopiperidinyl)-7-fluoro-9-methyl-4-oxo-4H-quinolizine-3-carboxylic acid;

1-cyclopropyl-8-(6-amino-3-azabicyclo[3.3.0]octyl)-7-fluoro-9-methyl-4-oxo-4H-quinolizine-3-carboxylic acid;

1-cyclopropyl-8-((2-aza-4-(dimethylaminomethyl)bicyclo[4.3.0]non-2-yl)-7-fluoro-9-methyl-4-oxo-4H-quinolizine carboxylic acid;

1-cyclopropyl-8-(3-aza-6-(L-alanylamino)-6-methylbicyclo[3.3.0]octane)-7-fluoro-9-methyl-4-oxo-4H-quinolizine carboxylic acid;

(3R,1R)-8-(3-(1-(N-methyl)amino)propyl)pyrrolidinyl)-1-cyclopropyl-7-fluoro-9-methyl-4-oxo-4H-quinolizine-3-carboxylic acid;

(3R,1 S)-8-(3-(1-amino-2-methoxyethyl)pyrrolidinyl)-1-cyclopropyl-7-fluoro-9-methyl-4-oxo-4H-quinolizine-3-carboxylic acid;

8-(3-(S)-(acetylamino)pyrrolidinyl)-1-cyclopropyl-7-fluoro-4H-9-methyl-4-oxo-quinolizine-3-carboxylic acid;

8-(3-carbamoylpiperidinyl)-1-cyclopropyl-7-fluoro-4H-9-methyl-4-oxo-quinolizine-3-carboxylic acid;

8-(3-hydroxypiperidinyl)-1-cyclopropyl-7-fluoro-4H-9-methyl-4-oxo-quinolizine-3-carboxylic acid;

8-(3-hydroxymethylpiperidinyl)-1-cyclopropyl-7-fluoro-4H-9-methyl-4-oxo-quinolizine-3-carboxylic acid;

8-(3-(R)-hydroxypiperidinyl)-1-cyclopropyl-7-fluoro-4H-9-methyl-4-oxo-quinolizine-3-carboxylic acid;

(3R)-9-fluoro-3-methyl-10-(piperazin-1-yl)-2H, 3H, 6H-6-oxo-pyrano[2.3.4-ij]quinolizine-5-carboxylic acid;

1-cyclopropyl-8-(S,S-2,8-diaza-8-bicyclo[4.3.0]nonyl)-7-fluoro-4H-9-methyl-4-oxo-quinolizine-3-carboxylic acid;

1-cyclopropyl-8-(R,R-2,8-diaza-8-bicyclo[4.3.0]nonyl)-7-fluoro-4H-9-methyl-4-oxo-quinolizine-3-carboxylic acid;

1-cyclopropyl-8-(1-amino-3-aza-bicyclo[3.1.0]hexan-3-yl)-7-fluoro-4H-9-methyl-4-oxo-quinolizine-3-carboxylic acid;

8-(3-amino-3-fluoromethyl-1-pyrrolidinyl)-1-cyclopropyl-7-fluoro-4H-9-methyl-4-oxo-quinolizine-3-carboxylic acid;

8-(3-aminomethyl-3-fluoro-1-pyrrolidinyl)-1-cyclopropyl-7-fluoro-4H-9-methyl-4-oxo-quinolizine-3-carboxylic acid;

8-(3-(S)-hydroxy-1-pyrrolidinyl)-1-cyclopropyl-7-fluoro-4H-9-methyl-4-oxo-quinolizine-3-carboxylic acid;

8-(3-(R)-hydroxy-1-pyrrolidinyl)-1-cyclopropyl-7-fluoro-4H-9-methyl-4-oxo-quinolizine-3-carboxylic acid;

8-(1-amino-5-aza-spiro[2.4]heptan-5-yl)-1-cyclopropyl-7-fluoro-4H-9-methyl-4-oxo-quinolizine-3-carboxylic acid Diastereomer A;

8-(1-amino-5-aza-spiro[2.4]heptan-5-yl)-1-cyclopropyl-7-fluoro-4H-9-methyl-4-oxo-quinolizine-3-carboxylic acid Diastereomer B;

8-(3-(1-amino-2,2,2-trifluoroethyl)pyrrolidinyl)-1-cyclopropyl-7-fluoro-4H-9-methyl-4-oxo-quinolizine-3-carboxylic acid;

8-(3-(S*)-(1-(S*)-amino-2,2,2-trifluoroethyl)pyrrolidinyl)-1-cyclopropyl-7-fluoro-4H-9-methyl-4-oxo-quinolizine-3-carboxylic acid;

8-(3-aminoxypyrrolidinyl)-1-cyclopropyl-7-fluoro-4H-9-methyl-4-oxo-quinolizine-3-carboxylic acid;

8-(3-(R)-aminoxypyrrolidinyl)-1-cyclopropyl-7-fluoro-4H-9-methyl-4-oxo-quinolizine-3-carboxylic acid;

8-(3-(S)-aminoxypyrrolidinyl)-1-cyclopropyl-7-fluoro-4H-9-methyl-4-oxo-quinolizine-3-carboxylic acid;

8-(octahydropyrrolo[3,2-b]pyridin-1-yl)-1-cyclopropyl-7-fluoro-4H-9-methyl-4-oxo-quinolizine-3-carboxylic acid;

8-(trans-3-amino-4-fluoromethylpyrrodin-1-yl)-1-cyclopropyl-7-fluoro-4H-9-methyl-4-oxo-quinolizine-3-carboxylic acid;

8-(cis-3-amino-4-fluoromethylpyrrodin-1-yl)-1-cyclopropyl-7-fluoro-4H-9-methyl-4-oxo-quinolizine-3-carboxylic acid;

8-(8-amino-6-azaspiro[3.4]oct-6-yl)-1-cyclopropyl-7-fluoro-4H-9-methyl-4-oxo-quinolizine-3-carboxylic acid;

8-(2-aminomethyl-4-hydroxypyrrolidin-1-yl)-1-cyclopropyl-7-fluoro-4H-9-methyl-4-oxo-quinolizine-3-carboxylic acid;

8-(3-(R)-(aminomethyl)morpholin-1-yl)-1-cyclopropyl-7-fluoro-4H-9-methyl-4-oxo-qinolizine-3-carboxylic acid;

8-(3-(R)-(L-alanylamino)piperidinyl)-1-cyclopropyl-7-fluoro-4H-9-methyl-4-oxo-quinolizine-3-carboxylic acid;

8-(3-(5-aminooctahydroindol-1-yl)-1-cyclopropyl-7-fluoro-4H-9-methyl-4-oxo-quinolizine-3-carboxylic acid;

8-(3-(2-piperidyl)piperidin-1-yl)-1-cyclopropyl-7-fluoro-4H-9-methyl-4-oxo-quinolizine-3-carboxylic acid;

8-(5-amino-decahydroisoquinolin-2-yl)-1-cyclopropyl-7-fluoro-4H-9-methyl-4-oxo-quinolizine-3-carboxylic acid;

8-(2,7-diazabicyclo[3.3.0]oct-7-yl)-1-cyclopropyl-7-fluoro-4H-9-methyl-4-oxo-quinolizine-3-carboxylic acid;

8-(3,7-diazabicyclo[3.3.0]oct-3-yl)-1-cyclopropyl-7-fluoro-4H-9-methyl-4-oxo-quinolizine-3-carboxylic acid;

8-(3-carboxypyrrolidin-1-yl)-1-cyclopropyl-7-fluoro-4H-9-methyl-4-oxo-quinolizine-3-carboxylic acid;

8-(3-(2,2,2-trifluoroethyl)aminopyrrolidin-1-yl)-1-cyclopropyl-7-fluoro-4H-9-methyl-4-oxo-quinolizine-3-carboxylic acid;

8-(3-(2-fluoroethyl)aminopyrrolidin-1-yl)-1-cyclopropyl-7-fluoro-4H-9-methyl-4-oxo-quinolizine-3-carboxylic acid;

8-(3-((2-fluoroethyl)aminomethyl)pyrrolidin-1-yl)-1-cyclopropyl-7-fluoro-4H-9-methyl-4-oxo-quinolizine-3-carboxylic acid;

8-(3-(S)-(2-fluoroethyl)aminopyrrolidin-1-yl)-1-cyclopropyl-7-fluoro-4H-9-methyl-4-oxo-quinolizine-3-carboxylic acid;

8-(3-(R)-(2-fluoroethyl)aminopyrrolidin-1-yl)-1-cyclopropyl-7-fluoro-4H-9-methyl-4-oxo-quinolizine-3-carboxylic acid;

8-(3a-amino-octahydroisoindol-2-yl)-1-cyclopropyl-7-fluoro-4H-9-methyl-4-oxo-quinolizine-3-carboxylic acid;

8-(6-amino-2-aza-spiro[3.3]non-2-yl)-1-cyclopropyl-7-fluoro-4H-9-methyl-4-oxo-quinolizine-3-carboxylic acid (Isomer (I));

8-(3-amino-3-trifluoromethylpyrrolidin-1-yl)-1-cyclopropyl-7-fluoro-4H-9-methyl-4-oxo-quinolizine-3-carboxylic acid;

8-(3-(S)-hydroxymethylazetidin-1-yl)-1-cyclopropyl-7-fluoro-4H-9-methyl-4-oxo-quinolizine-3-carboxylic acid;

8-(3-aminomethyl-3-trifluoromethyl-pyrrolidin-1-yl)-1-cyclopropyl-7-fluoro-4H-9-methyl-4-oxo-quinolizine-3-carboxylic acid;

8-(octahydropyrrolo[3.4-c]pyrid-2-yl)-1-cyclopropyl-7-fluoro-4H-9-methyl-4-oxo-quinolizine-3-carboxylic acid;

8-(3-(cyclopropylamino)pyrrolidin-1-yl)-1-cyclopropyl-7-fluoro-4H-9-methyl-4-oxo-quinolizine-3-carboxylic acid;

8-(6-amino-2-aza-spiro[3.3]non-2-yl)-1-cyclopropyl-7-fluoro-4H-9-methyl-4-oxo-quinolizine-3-carboxylic acid (Isomer (II));

8-(2,7-diazabicyclo[3.3.0]oct-7-yl)-1-cyclopropyl-7-fluoro-4H-9-methyl-4-oxo-quinolizine-3-carboxylic acid Isomer A;

8-(2,7-diazabicyclo[3.3.0]oct-7-yl)-1-cyclopropyl-7-fluoro-4H-9-methyl-4-oxo-quinolizine-3-carboxylic acid Isomer B;

8-(3-(R)-(hydroxymethyl)pyrrolidin-1-yl)-1-cyclopropyl-7-fluoro-4H-9-methyl-4-oxo-quinolizine-3-carboxylic acid;

8-(3-(S)-(hydroxymethyl)pyrrolidin-1-yl)-1-cyclopropyl-7-fluoro-4H-9-methyl-4-oxo-quinolizine-3-carboxylic acid;

8-(2-(R)-(hydroxymethyl)pyrrolidin-1-yl)-1-cyclopropyl-7-fluoro-4H-9-methyl-4-oxo-quinolizine-3-carboxylic acid;

8-(2-(S)-(hydroxymethyl)pyrrolidin-1-yl)-1-cyclopropyl-7-fluoro-4H-9-methyl-4-oxo-quinolizine-3-carboxylic acid;

8-(2-(R)-aminomethyl-pyrrolidin-1-yl)-1-cyclopropyl-7-fluoro-4H-9-methyl-4-oxo-quinolizine-3-carboxylic acid;

8-(2-(S)-aminomethyl-pyrrolidin-1-yl)-1-cyclopropyl-7-fluoro-4H-9-methyl-4-oxo-quinolizine-3-carboxylic acid;

8-(3-(R)-(1-aminocyclopropyl)pyrrolidinyl))-1-cyclopropyl-7-fluoro-9-methyl-4-oxo-4H-quinolizine-3-carboxylic acid;

8-(3-(S)-(1-aminocyclopropyl)pyrrolidinyl))-1-cyclopropyl-7-fluoro-9-methyl-4-oxo-4H-quinolizine-3-carboxylic acid;

8-(3-(1-amino-1-cyclopropyl-methyl)pyrrolidinyl))-1-cyclopropyl-7-fluoro-9-methyl-4-oxo-4H-quinolizine-3-carboxylic acid;

8-(3-(R)-(pyrrolidin-2-(S)-yl)pyrrolidin-1-yl)-1-cyclopropyl-7-fluoro-9-methyl-4-oxo-4H-quinolizine-3-carboxylic acid;

8-(3-(aminomethyl)azetidin-1-yl)-1-cyclopropyl-7-fluoro-9-methyl-4-oxo-4H-quinolizine-3-carboxylic acid;

(8-(3-amino-4-methyl-piperidin-1-yl)-1-cyclopropyl-7-fluoro-9-methyl-4-oxo-4H-quinolizine-3-carboxylic acid; and 8-(3-(7-amino-5-azaspiro[2.4]heptan-5-yl)-1-cyclopropyl-7-fluoro-9-methyl-4-oxo-4H-quinolizine-3-carboxylic acid;

as well as the pharmaceutically acceptable salts, esters and amides thereof.

Preferred among the above representative compounds of the invention are the following:

8-(3-(aminomethyl)pyrrolidinyl)-1-cyclopropyl-7-fluoro-9-methyl-4-oxo-4H-quinolizine-3-carboxylic acid;

8-(3(S)-amino-1-pyrrolidinyl)-1-cyclopropyl-7-fluoro-9-methyl-4-oxo-4H-quinolizine-3-carboxylic acid;

8-(3-amino-1-pyrrolidinyl)-1-cyclopropyl-7-fluoro-9-methyl-4-oxo-4H-quinolizine-3-carboxylic acid;

(3R,1S)-8-(3-(1-amino)propyl)pyrrolidinyl)-1-cyclopropyl-7-fluoro-9-methyl-4-oxo-4H-quinolizine-3-carboxylic acid;

8-(3-(1-aminobutyl)pyrrolidinyl)-1-cyclopropyl-7-fluoro-9-methyl-4-oxo-4H-quinolizine-3-carboxylic acid;

(3R,1S)-8-(3-(1-amino-2-methoxyethyl)pyrrolidinyl)-1-cyclopropyl-7-fluoro-9-methyl-4-oxo-4H-quinolizine-3-carboxylic acid;

1-cyclopropyl-7-fluoro-9-methyl-4-oxo-8-(4-amino-1-piperdinyl)-4H-quinolizine-3-carboxylic acid;

1-cyclopropyl-7-fluoro-9-methyl-4-oxo-8-(4-(aminomethyl)-1-piperdinyl)-4H-quinolizine-3-carboxylic acid;

1-cyclopropyl-7-fluoro-9-methyl-4-oxo-8-(3-amino-1-piperdinyl)-4H-quinolizine-3-carboxylic acid;

8-(3-(S)-aminopiperidinyl)-1-cyclopropyl-7-fluoro-4H-9-methyl-4-oxo-quinolizine-3-carboxylic acid;

1-cyclopropyl-8-(3-aza-6-amino-6-methylbicyclo[3.3.0]octan-1-yl)-7-fluoro-9-methyl-4-oxo-4H-quinolizine-3-carboxylic acid;

1-cyclopropyl-8-(6-amino-3-azabicyclo[3.3.0]octyl)-7-fluoro-9-methyl-4-oxo-4H-quinolizine-3-carboxylic acid;

8-((1R*,2S*,6R*)-2-amino-8-azabicyclo[4.3.0]nonan-8-yl))-1-cyclopropyl-7-fluoro-4H-9-methyl-4-oxo-quinolizine-3-carboxylic acid;

8-((1R*,2R*,6R*)-2-amino-8-azabicyclo[4.3.0]nonan-8-yl))-1-cyclopropyl-7-fluoro-4H-9-methyl-4-oxo-quinolizine-3-carboxylic acid;

8-(3-(1-aminoethyl)pyrrolidinyl)-1-cyclopropyl-7-fluoro-4H-9-methyl-4-oxo-quinolizine-3-carboxylic acid;

(8-(3-(1-amino-1-methylethyl)pyrrolidinyl)-1-cyclopropyl-7-fluoro-9-methyl-4-oxo-4H-quinolizine-3-carboxylic acid;

(3R,1S)-8-(3-(1-(N-methyl)amino)propyl)pyrrolidinyl)-1-cyclopropyl-7-fluoro-9-methyl-4-oxo-4H-quinolizine-3-carboxylic acid;

8-(3-aminopiperidinyl)-1-cyclopropyl-7-fluoro-4H-9-methyl-4-oxo-quinolizine-3-carboxylic acid;

8-(3-(1-aminocyclopropyl)pyrrolidinyl)-1-cyclopropyl-7-fluoro-9-methyl-4-oxo-4H-quinolizine-3-carboxylic acid;

(3S,1R)-8-(3-(1-aminoethyl)pyrrolidinyl)-1-cyclopropyl-7-fluoro-9-methyl-4-oxo-4H-quinolizine-3-carboxylic acid;

(3R,1S)-8-(3-(1-aminoethyl)pyrrolidinyl)-1-cyclopropyl-7-fluoro-9-methyl-4-oxo-4H-quinolizine-3-carboxylic acid;

(3R,1R)-8-(3-(1-aminoethyl)pyrrolidinyl)-1-cyclopropyl-7-fluoro-9-methyl-4-oxo-4H-quinolizine-3-carboxylic acid;

1-cyclopropyl-8-(S,S-2,8-diaza-8-bicyclo[4.3.0]nonyl)-7-fluoro-4H-9-methyl-4-oxo-quinolizine-3-carboxylic acid;

1-cyclopropyl-8-(R,R-2,8-diaza-8-bicyclo[4.3.0]nonyl)-7-fluoro-4H-9-methyl-4-oxo-quinolizine-3-carboxylic acid;

1-cyclopropyl-8-(1-amino-3-aza-bicyclo[3.1.0]hexan-3-yl)-7-fluoro-4H-9-methyl-4-oxo-quinolizine-3-carboxylic acid;

8-(3-amino-3-fluoromethyl-1-pyrrolidinyl)-1-cyclopropyl-7-fluoro-4H-9-methyl-4-oxo-quinolizine-3-carboxylic acid;

8-(trans-3-amino-4-fluoromethylpyrrodin-1-yl)-1-cyclopropyl-7-fluoro-4H-9-methyl-4-oxo-quinolizine-3-carboxylic acid;

8-(cis-3-amino-4-fluoromethylpyrrodin-1-yl)-1-cyclopropyl-7-fluoro-4H-9-methyl-4-oxo-quinolizine-3-carboxylic acid;

8-(3-(S)-(2-fluoroethyl)aminopyrrolidin-1-yl)-1-cyclopropyl-7-fluoro-4H-9-methyl-4-oxo-quinolizine-3-carboxylic acid;

8-(3-(R)-(2-fluoroethyl)aminopyrrolidin-1-yl)-1-cyclopropyl-7-fluoro-4H-9-methyl-4-oxo-quinolizine-3-carboxylic acid;

8-(3-(R)-(hydroxymethyl)pyrrolidin-1-yl)-1-cyclopropyl-7-fluoro-4H-9-methyl-4-oxo-quinolizine-3-carboxylic acid;

8-(2-(R)-aminomethyl-pyrrolidin-1-yl)-1-cyclopropyl-7-fluoro-4H-9-methyl-4-oxo-quinolizine-3-carboxylic acid;

(8-(3-amino-4-methyl-piperidin-1-yl)-1-cyclopropyl-7-fluoro-9-methyl-4-oxo-4H-quinolizine-3-carboxylic acid; and 8-(3-(7-amino-5-azaspiro[2.4]heptan-5-yl)-1-cyclopropyl-7-fluoro-9-methyl-4acid;

as well as the pharmaceutically acceptable salts, esters and amides thereof.

Especially preferred among the representative compounds of the present invention are the following:

8-(3(S)-amino-1-pyrrolidinyl)-1-cyclopropyl-7-fluoro-9-methyl-4-oxo-4H-quinolizine-3-carboxylic acid;

8-(3-amino-1-pyrrolidinyl)-1-cyclopropyl-7-fluoro-9-methyl-4-oxo-4H-quinolizine-3-carboxylic acid;

(3R,1S)-8-(3-(1-amino-2-methoxyethyl)pyrrolidinyl)-1-cyclopropyl-7-fluoro-9-methyl-4-oxo-4H-quinolizine-3-carboxylic acid;

(8-(3-(1-amino-1-methylethyl)pyrrolidinyl)-1-cyclopropyl-7-fluoro-9-methyl-4-oxo-4H-quinolizine-3-carboxylic acid;

8-(3-(1-aminocyclopropyl)pyrrolidinyl)-1-cyclopropyl-7-fluoro-9-methyl-4-oxo-4H-quinolizine-3-carboxylic acid;

(3R,1S)-8-(3-(1-aminoethyl)pyrrolidinyl)-1-cyclopropyl-7-fluoro-9-methyl-4-oxo-4H-quinolizine-3-carboxylic acid;

1-cyclopropyl-8-(S,S-2,8-diaza-8-bicyclo[4.3.0]nonyl)-7-fluoro-4H-9-methyl-4-oxo-quinolizine-3-carboxylic acid;

1-cyclopropyl-8-(R,R-2,8-diaza-8-bicyclo[4.3.0]nonyl)-7-fluoro-4H-9-methyl-4-oxo-quinolizine-3-carboxylic acid;

1-cyclopropyl-8-(1-amino-3-aza-bicyclo[3.1.0]hexan-3-yl)-7-fluoro-4H-9-methyl-4-oxo-quinolizine-3-carboxylic acid;

8-(3-amino-3-fluoromethyl-1-pyrrolidinyl)-1-cyclopropyl-7-fluoro-4H-9-methyl-4-oxo-quinolizine-3-carboxylic acid;

8-(trans-3-amino-4-fluoromethylpyrrodin-1-yl)-1-cyclopropyl-7-fluoro-4H-9-methyl-4-oxo-quinolizine-3-carboxylic acid;

8-(cis-3-amino-4-fluoromethylpyrrodin-1-yl)-1-cyclopropyl-7-fluoro-4H-9-methyl-4-oxo-quinolizine-3-carboxylic acid;

8-(3-(S)-(2-fluoroethyl)aminopyrrolidin-1-yl)-1-cyclopropyl-7-fluoro-4H-9-methyl-4-oxo-quinolizine-3-carboxylic acid;

8-(3-(R)-(2-fluoroethyl)aminopyrrolidin-1-yl)-1-cyclopropyl-7-fluoro-4H-9-methyl-4-oxo-quinolizine-3-carboxylic acid;

8-(3-(R)-(hydroxymethyl)pyrrolidin-1-yl)-1-cyclopropyl-7-fluoro-4H-9-methyl-4-oxo-quinolizine-3-carboxylic acid;

8-(2-(R)-aminomethyl-pyrrolidin-1-yl)-1-cyclopropyl-7-fluoro-4H-9-methyl-4-oxo-quinolizine-3-carboxylic acid;

(8-(3-amino-4-methyl-piperidin-1-yl)-1-cyclopropyl-7-fluoro-9-methyl-4-oxo-4H-quinolizine-3-carboxylic acid; and 8-(3-(7-amino-5-azaspiro[2.4]heptan-5-yl)-1-cyclopropyl-7-fluoro-9-methyl-4-oxo-4H-quinolizine-3-carboxylic acid;

as well as the pharmaceutically acceptable salts: esters and amides thereof.

It will be observed above and elsewhere in the disclosure that numerous asymmetric centers may exist in the compounds of the present invention which will be found in the R or S configurations. Except where otherwise noted, the present invention contemplates the various stereoisomers and mixtures thereof.

A number of defined terms are used herein to designate particular elements of the present invention. When so used, the following meanings are intended:

The term "alkanoyl of from one to eight carbons" refers to a radical of the formula —C(O)R$^{15}$ where R$^{15}$ is hydrogen or an alkyl radical of from one to eight carbon atoms including, but not limited to, acetyl and pivaloyl.

The term "alkyl" refers to saturated, straight- or branched-chain hydrocarbon radicals containing between one and ten carbon atoms including, but not limited to, methyl, ethyl, propyl, isopropyl, n-butyl, tert-butyl and neopentyl.

The terms "alpha-amino acid" and "polypeptide residue" refer, respectively, to a single amino acid and two to five amino acids each joined by amide (peptide) bonds. The amino acids may be any of the naturally-occurring amino acids such as valine, phenylalanine and glycine or synthetic alpha-amino acids such as cyclohexylalanine, and further may be in either the L or D configuration or a mixture of the two isomers. Preferably, amino acid substituents are optically active and have the L configuration.

The term "amino(loweralkyl)" refers to a loweralkyl radical having appended thereto at least one amino substituent which in turn is optionally substituted with one or two loweralkyl radicals or an alpha-amino acid or polypeptide residue. Examples of amino(loweralkyl) groups include aminoethyl, aminomethyl and N,N-dimethylaminoethyl.

The term "aminooxy" refers to an amino group, optionally substituted once or twice with loweralkyl or halo(loweralkyl), which is appended to the rest of the molecule via an oxygen atom; (e.g. —O—NR'R" wherein R' and R" are hydrogen, loweralkyl or halo(loweralkyl).

The term "aminothioloweralkoxy" refers to a thioloweralkoxy radical having appended thereto an amino group, as for example aminothiomethoxy and 2-aminothioethoxy.

The term "aromatic group" refers to a C6-to-C10 cyclic radical which is aromatic according to Huckel's rule. Examples of aromatic groups include carbocyclic aromatic radicals such as phenyl and naphthyl as well as nitrogen-containing aromatic heterocyclic radicals, defined below.

The term "aryl(loweralkyl)" refers to a loweralkyl radical having appended thereto an aromatic hydrocarbon group, as for example benzyl and phenylethyl.

The term "aryl(loweralkyl)amino" refers to an amino radical having appended thereto an aryl(loweralkyl) group. Examples of aryl(loweralkyl)amino groups include benzylamino and phenylethylamino.

The term "aryl(loweralkyl)oxy" refers to an aryl(loweralkyl) radical which is joined to the rest of the molecule via an ether linkage (i.e., through an oxygen atom). Examples of aryl(loweralkyl)oxy radicals include benzyloxy and phenylethyloxy.

The term "aryloxy" refers to an aromatic hydrocarbon radical which is joined to the rest of the molecule via an ether linkage (i.e., through an oxygen atom), as for example phenoxy.

The term "bicycloalkyl" refers to a radical comprising a bridged, saturated or unsaturated hydrocarbon ring system having between five and nine carbon atoms in which two non-adjacent carbon atoms of a first ring are linked by an alkylene bridge of between one and three additional carbon atoms, the bicycloalkyl radical being optionally substituted with between one and three additional radicals selected from among aryl(loweralkyl), alkoxycarbonyl, loweralkyl, halo(loweralkyl), amino(loweralkyl), hydroxy-substituted loweralkyl, hydroxy, loweralkoxy, halogen, and amino, (loweralkyl)amino or alkanoylamino of from one to eight carbon atoms in which the amino group may be further substituted with alkanoyl of from one to eight carbons, an alpha-amino acid or a polypeptide. Examples of bicycloalkyl radicals include, but are not limited to, norbornyl, bicylo[2.2.1]hept-2-enyl and bicyclo[1.1.1]pentanyl.

The term "bicyclic nitrogen-containing heterocyclic group" refers to a radical comprising a bicyclic ring system in which the the rings are of the (a) fused, (b) bridged or (c) spiro form. Fused-ring bicyclic nitrogen-containing heterocyclic groups are those in which a first nitrogen-containing heterocycle or aromatic heterocycle has fused to it a second saturated or unsaturated carbocyclic or heterocyclic ring of between three and six atoms of which zero, one or two are heteratoms selected from S, O, and N. Both the first and the second ring may be optionally substituted with between one and three additional radicals A$^2$ independently selected from among loweralkyl, halo(loweralkyl), hydroxy-substituted loweralkyl, hydroxy, halogen, amino(loweralkyl), alkanoylamino of from one to eight carbons, phenyl and —NR$^{17}$R$^{18}$ where R$^{17}$ and R$^{18}$ are independently hydrogen or loweralkyl or, when one is hydrogen, the other is an alpha-amino acid or a polypeptide residue. Examples of fused-ring bicyclic nitrogen-containing heterocyclic radicals are those having 5:3, 5:4, 5:5, 5:6 and 6:5 ring systems and include, but are not limited to, radicals of the formulae

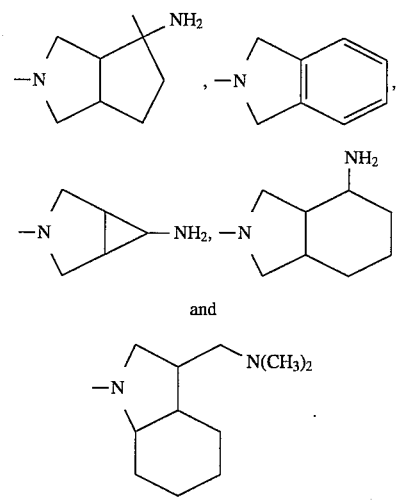

Bridged-ring bicyclic nitrogen-containing heterocyclic groups are those selected the formulae

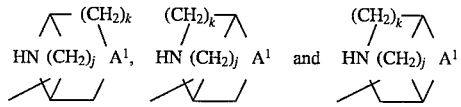

and unsaturated derivatives thereof, where j and k are independently one, two or three, and A$^1$ is a carbon atom or a heteroatom selected from S, O and N, optionally substituted at any position with between one and three additional radicals A$^2$ is as previously defined.

Spiro-ring bicyclic nitrogen-containing heterocyclic groups are those in which a first nitrogen-containing heterocycle or aromatic heterocycle to which is joined; by a single shared carbon atom, a second carbocyclic or heterocyclic ring of between three and six atoms of which zero, one or two are heteroatoms selected from S, O, and N. Either the first or the second ring may be substituted with between one and three additional radicals A², where A² is as previously defined. Examples of spiro-ting bicyclic nitrogen-containing heterocyclic radicals include, but are not limited to, those having the formulae

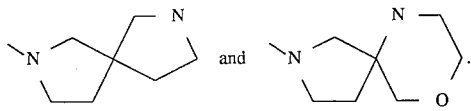

The term "cyclic ether" refers to a 4- to 6-membered monocyclic hydrocarbon radical containing an oxygen ring atom and joined to the rest of the molecule via any of the carbon atoms including, but not limited to, oxetane.

The term "cycloalkenyl of from four to eight carbons" refers to a mono-unsaturated monocyclic hydrocarbon radical having from four to eight carbon atoms in the ring, including, but not limited to, cyclobutenyl, cyclopentenyl, cyclohexenyl and cycloheptenyl, and optionally substituted with between one and three additionals radicals selected from among aryl(loweralkyl), alkoxycarbonyl, loweralkyl, halo(loweralkyl), amino(loweralkyl), hydroxy-substituted loweralkyl, hydroxy, loweralkoxy, halogen, amino, loweralkylamino, and amino, (loweralkyl)amino or alkanoylamino of from one to eight carbon atoms in which the amino group may be further substituted with alkanoyl of from one to eight carbons, an alpha-amino acid or a polypeptide.

The term "cycloalkyl of from three to eight carbons" refers to a saturated monocyclic hydrocarbon radical having from three to eight carbon atoms in the ring and optionally substituted with between one and three additional radicals selected from among aryl(loweralkyl), alkoxycarbonyl, loweralkyl, halo(loweralkyl),:amino(loweralkyl), hydroxy-substituted loweralkyl, hydroxy, loweralkoxy, halogen, and amino, (lowerallcyl)amino or alkanoylamino of from one to eight carbon atoms in which the amino group may be further substituted with alkanoyl of from one to eight carbons, an alpha-amino acid or a polypeptide. Examples of cycloalkyl radicals include, but are not limited to, cyclopropyl, cyclobutyl, cyclopentyl, cyclohexyl, cycloheptyl, 1-fluorocyclopropyl, 2-fluorocyclopropyl and 2-aminocyclopropyl.

The term "cycloalkyl(amino)" refers to an amino group substituted with at least one cycloalkyl group, typically having from three to eight carbons.

The term "cycloalkyl(loweralkyl)" refers to a loweralkyl radical having appended thereto a cycloalkyl radical of from three to eight carbon atoms, which cycloalkyl radical may be optionally substituted as described above.

The term "fused" as used herein refers to two cyclic groups having two adjacent ring atoms in common.

The terms "halo" and "halogen" refer to a monovalent radical selected from among chloro (Cl), bromo (Br), fluoro (F) and iodo (I).

The term "halo(loweralkyl)" refers to a loweralkyl radical having appended thereto between one and three halogen atoms. Examples of halo(loweralkyl) radicals include fluoromethyl, trifluoromethyl, 1-fluoroethyl, 2-fluoroethyl and 1,2-difluoroethyl.

The term "halo(loweralkyl)amino" refers to an amino group substituted with at least one halo(loweralkyl) group.

The term "halo(loweralkyl)amino(loweralkyl)" refers to an amino(loweralkyl) radical having appended thereto a halo(loweralkyl) group, as for example 2-fluoroethylaminomethyl.

The term "halo-substituted nitrogen-containing aromatic heterocycle" refers to a nitrogen-containing aromatic heterocycle radical having appended thereto between one and three halogen atoms including, but not limited to, 5-fluoro-2-pyrimidyl.

The term "hydroxy-substituted loweralkyl" refers to a loweralkyl radical having appended thereto between one and three hydroxyl groups, as for example hydroxymethyl and 2-hydroxyethyl.

The term "hydroxy-substituted (loweralkyl)amino" refers to a (loweralkyl)amino radical having appended thereto between one and three hydroxyl groups, as for example hydroxymethylamino and 2-hydroxyethylamino.

The term "imino" refers to a divalent radical of the formula =N—OH.

The term "loweralkenyl" refers to a straight- or branched-chain hydrocarbon radical containing between two and six carbon atoms and possessing at least one carbon-carbon double bond. Examples of loweralkenyl radicals include vinyl, allyl, 2- or 3-butenyl, 2-,3- or 4-pentenyl, 2-,3-,4- or 5-hexenyl and isomeric forms thereof.

The term "loweralkoxy" refers to a loweralkyl radical which is appended to the rest of the molecule via an ether linkage (i.e., through an oxygen atom), as for example methoxy, ethoxy, propoxy, tert-butoxy, pentyloxy, hexyloxy, isomeric forms thereof and the like.

The term "loweralkoxycarbonyl" refers to a radical of the formula —C(O)R²⁵ wherein R²⁵ is a loweralkoxy group, as for example ethoxycarbonyl and methoxycarbonyl.

The term "loweralkoxy(loweralkoxy)(loweralkyl)" refers to a loweralkoxy(loweralkyl) radical having appended thereto a loweralkoxy group, as for example methoxymethoxymethyl and ethoxymethoxymethyl.

The term "loweralkoxy(loweralkyl)" refers to a loweralkyl radical having appended thereto a loweralkoxy group and optionally substituted with an additional amino radical, as for example methoxyethyl, ethoxymethyl and 1-amino-2-methoxyethyl.

The term "loweralkyl" refers to an alkyl radical containing one to six carbon atoms including, but not limited to, methyl, ethyl, propyl, isopropyl, n-butyl, tert-butyl and neopentyl.

The term "(loweralkyl)amino" refers to an amino radical substituted with between one and three loweralkyl radicals including, but not limited to, methylamino, ethylamino, dimethylamino, propylamino and ethylmethylamino.

The term "loweralkynyl" refers to a straight- or branched-chain hydrocarbon radical containing between two and six carbon atoms and possessing at least one carbon-carbon triple bond. Examples of loweralkynyl radicals include ethynyl, 2-hexyn-1-yl, 3,3-dimethyl-1-butyn-1-yl and 3-methylbutyn-3-yl.

The term "nitrogen-containing aromatic heterocycle" refers to a monocyclic aromatic radical having from five to seven ring atoms of which one ring atom is nitrogen; zero, one or two ring atoms are additional heteroatoms independently selected from S, O and N; and the remaining ring atoms are carbon, the radical being joined to the rest of the molecule via any of the ring atoms. Examples of nitrogen-containing aromatic heterocycles include pyridine, pyrazine, pyrimidine, pyrrole, pyrazole, imidazole, thiazole, oxazole, isooxazole, thiadiazole, oxadiazole and substituted derivatives thereof.

The term "nitrogen-containing heterocycle" refers to a saturated or unsaturated monocyclic ring system radical having from four to seven ring atoms of which one is nitrogen; zero, one or two are additional heteroatoms independently selected from S, O and N; and the remainder are carbon, the radical being joined to the rest of the molecule via any of the ring atoms and being optionally substituted, either on a nitrogen or a carbon atom, by an additional radical selected from among aryl(loweralkyl), alkoxycarbonyl, loweralkyl, halo(loweralkyl), amino(loweralkyl), hydroxy-substituted loweralkyl, hydroxy, loweralkoxy, halogen, amino, loweralkylamino, and amino, (loweralkyl) amino or alkanoylamino of from one to eight carbon atoms in which the amino group may be further substituted with alkanoyl of from one to eight carbons, an alpha-amino acid or a polypeptide. Examples of nitrogen-containing heterocycles include pyrrolidine, dihydropylrole, isooxazolidine, oxazolidine, tetrhydropyridine, piperidine, piperazine, morpholine, thiomorpholine, aziridine and azetidine.

The term "pharmaceutically acceptable cation" refers to a positively-charged inorganic or organic ion that is generally considered suitable for human consumption. Examples of pharmaceutically acceptable cations are hydrogen, alkali metal (lithium, sodium and potassium), magnesium, calcium, ferrous, ferric, ammonium, alkylammonium, dialkylammonium, trialkylammonium, tetraalkylammonium, diethanolammmonium, triethanolammonium, and guanidinium ions, and protonated forms of lysine, procaine and choline. Cations may be interchanged by methods known in the art, such as ion exchange. Where compounds of the present invention are prepared in the carboxylic acid form (that is, where $R_4$ is hydrogen) addition of a base form of the cation, (such as a hydroxide or a free amine) will yield the appropriate cationic form.

By "pharmaceutically acceptable salts, esters and amides", as of the compounds of formula I, is meant those carboxylate salts, amino acid addition salts, esters and amides which are, within the scope of sound medical judgement, suitable for use in contact with the tissues of humans and lower animals without undue toxicity, irritation, allergic response and the like, commensurate with a reasonable benefit/risk ratio, and effective for their intended use, as well as the zwitterionic forms thereof.

Pharmaceutically acceptable salts are well known in the art. For example, S. M Berge et al. describe pharmaceutically acceptable salts in detail in *J. Pharmaceutical Sciences*, 66:1–19 (1977). Examples of pharmaceutically acceptable, nontoxic acid addition salts are salts of an amino group formed with inorganic acids such as hydrochloric acid, hydrobromic acid, phosphoric acid, surfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include nitrate, bisulfate, borate, formate, butyrate, valerate, 3-phenylpropionate, camphorate, adipate, benzoate, oleate, palmitate, stearate, laurate, lactate, fumarate, ascotbate, aspartate, nicotinate, p-toluenesulfonate, camphorsulfonate, methanesulfonate, 2-hydroxyethanesulfonate, gluconate, glucoheptonate, lactobionate, glycerophosphate, pectinate, lauryl surfate and the like or metal salts such as sodium, potassium, magnesium or calcium salts or amino salts such as ammonium, triethylamine salts and the like, all of which may be prepared according to conventional methods.

Examples of pharmaceutically acceptable, non-toxic esters of the present invention include C1-to-C6 alkyl esters and C5-to-C7 cycloalkyl esters, although C1-to-C4 alkyl esters are preferred. Esters of the compounds of formula I may be prepared according to conventional methods.

Examples of pharmaceutically acceptable, non-toxic amides of the present invention include amides derived from ammonia, primary C1-to-C6 alkyl amines and secondary C1-to-C6 dialkyl amines. In the case of secondary amines, the amine may also be in the form of a 5- or 6-membered heterocycle containing one nitrogen atom. Amides derived from ammonia, C1-to-C3 alkyl primary amides and C1-to-C2 dialkyl secondary amides are preferred. Amides of the compounds of formula I may be prepared according to conventional methods. It is intended that amides of the present invention include amino acid and peptide derivatives of the compounds of formula I as well.

As used herein, the term "pharmaceutically acceptable carrier" means a non-toxic, inert solid, semi-solid or liquid filler, diluent, encapsulating material or formulation auxiliary of any type. Some examples of the materials that can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, and preservatives can also be present in the composition, according to the judgement of the formulator.

The term "prodrug", as of the compounds of formula I, refers to derivative compounds that are rapidly transformed in vivo to yield the parent compound of the formula I, as for example by hydrolysis in blood. T. Higuchi and V. Stella provide a thorough discussion of the prodrug concept in "Pro-drugs as Novel Delivery Systems", Vol 14 of the A.C.S. Symposium Series, American Chemical Society (1975). Examples of esters useful as prodrugs for compounds containing carboxyl groups can be found on pages 14–21 of "Bioreversible Carriers in Drug Design: Theory and Application", edited by E. B. Roche, Pergamon Press:New York (1987). It is intended that these references, and any others cited throughout this specification, are incorporated herein by reference.

The term "prodrug ester group" refers to any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of prodrug ester groups can be found in the book "Pro-drugs as Novel Delivery Systems", by Higuchi and Stella, cited above.

The term "protecting group" is well-known in the art and refers to substituents on functional groups of compounds undergoing chemical transformation which prevent undesired reactions and degradations during a synthesis; see, for example, T. H. Greene, "Protective Groups in Organic Synthesis", John Whey & Sons, New York (1981).

The term "substituted phenyl" refers to a benzene ring having between one and five non-hydrogen substituents, each independently selected from among halogen, hydroxy, loweralkoxy, loweralkyl, hydroxy-substituted loweralkyl, amino, (loweralkyl)amino, amino(loweralkyl) and nitrogen-containing heterocycle. Examples of substituted phenyl radicals include 2-fluorophenyl, 4-fluorophenyl and 2,4-difluorophenyl.

The term "thioloweralkoxy" refers to a radical of the formula —$SR^{35}$ where $R^{35}$ is a loweralkyl group including, but not limited to, thiomethoxy and thioethoxy.

The term "thioloweralkoxy(loweralkyl)" refers to a loweralkyl radical having appended thereto a thioloweralkoxy group including, but not limited to, thiomethoxymethyl and thiomethoxyethyl.

According to the methods of treatment of the present invention, the compounds of the invention may be administered alone or in combination or in concurrent therapy with other agents. When utilizing the compounds of the present invention for antimicrobial therapy, the specific therapeutically effective dose level for any particular patient will depend upon a variety of factors including the disorder being treated and the severity of the disorder; activity of the particular compound used; the specific composition employed; the age, body weight, general health, sex and diet of the patient; the time of administration, route of administration, and rate of excretion of the specific compound employed; the duration of the treatment; drugs used in combination or coincidently with the specific compound employed; and like factors well known in the medical arts.

The total daily dose of the compounds of this invention administered to a host in single or in divided doses can be in amounts, as for example from 0.1 to 200 mg/kg body weight or more usually from 0.25 to 100 mg/kg body weight. Single dose compositions may contain such amounts or submultiples thereof as make up the daily dose.

According to the pharmaceutical compositions of the present invention, the compounds of the invention may be administered orally, parenterally, by inhalation spray, rectally, or topically in unit dosage formulations containing conventional nontoxic pharmaceutically acceptable carriers, adjuvants, diluents ancot vehicles as desired. The term "parenteral" as used herein includes subcutaneous injections, intravenous, intramuscular, intrastemal injection or infusion techniques.

Injectable preparations, as for example sterile injectable aqueous or oleaginous suspensions, may be formulated according to the known an using suitable dispersing or wetting agents and suspending agents. The sterile injectable preparation may also be a sterile injectable solution or suspension in a nontoxic parenterally acceptable diluent or solvent, as for example as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers such as polylactide-polyglycolide. Depending on the ratio of drug to polymer and the composition of the polymer, the rate of drug release can be controlled. Examples of other biodegradable polymers include polyorthoesters and polyanhydrides. Depot injectables can also be made by entrapping the drug in liposomes or microemulsions which are compatible with body tissues.

Suppositories for rectal or vaginal administration of the chug can be prepared by mixing the drug with a suitable nonirritating excipient such as cocoa butter and polyethylene glycol which are solid at ordinary temperature but will melt in the rectum or in the vagina and release the drug.

Solid dosage forms for oral administration may include capsules, tablets, pills, powders, prills and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Liquid dosage forms for oral administration may include pharmaceutically acceptable emulsions, microemulsions, solutions, suspensions, syrups and elixirs containing inert diluents commonly used in the an such as water. Such compositions may also comprise adjuvants, such as wetting agents; emulsifying and suspending agents; and sweetening, flavoring and perfuming agents.

If desired, the compounds of the present invention can be incorporated into slow release or targeted delivery systems such as polymer matrices, liposomes and microspheres. They may be sterilized, for example, by filtration through a bacteria-retaining filter, or by incorporating sterilizing agents in the form of sterile solid compositions which can dissolve in sterile water, or some other sterile injectable medium immediately before use.

The active compounds can also be in micro-encapsulated form with one or more excipients as noted above.

Dosage forms for topical or transdermal administration of a compound of this invention further include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons or substitutes therefor.

Transdermal patches have the added advantage of providing controlled delivery of a compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel.

A further possibility for delivery and/or utilization of the compounds of the present invention is by chemical conjugation of the compounds with other antibacterials such as beta-lactams. Similar dual-action conjugates (between beta-lactams and quinolones) are proposed in the published European patent application No. 597 303 of Dax et al. (published on May 18, 1994) and the published international patent application No. PCT/US92/08246 of White et al. (Publication No. WO 93/07154, published on Apr. 15, 1993). In the manner suggested by these references, a carbon-nitrogen bond or other covalent link may be formed between, for example, either an amino substituent at the C-8 position or a carboxylic acid group at the C-3 position of a compound of the present invention, and an alkyl or other group of a beta-lactam.

In general, the compounds of the present invention are synthesized according to reaction Schemes I through XVIII presented below, in which $R^1$ through $R^{16}$, A, X, Y and Z correspond to the groups defined in connection with formula (I), R is a loweralkyl group, X is a halogen atom, P is a protecting group and L is a suitable leaving group, as for example a halogen atom.

Certain abbreviations are used repeatedly in the specification which follows. These include: BOC for t-butoxycarbonyl; $(BOC)_2$ for di-t-butyl dicarbonate; CBZ for benzyloxycarbonyl; DMF for dimethyl formamide; DMSO for dimethyl sulfoxide; HRMS for high resolution mass spectroscopy; LAH for lithium aluminum hydride; LDA for lithium diethyl amide; RaNi for Raney Nickel; and THF for tetrahydrofuran.

For the preparation of the compounds of formula (I) which are alpha-amino acid or peptide derivatives of amine groups at $R^2$, the condensation of the amino group with amino acids and peptides may be effected in accordance with conventional condensation methods such as the azide method, the mixed acid anhydride method, the DCC (dicyclohexylcarbodiimide) method, the active ester method (p-nitrophenyl ester method, N-hydroxysuccinic acid imide ester method, cyanomethyl ester method and the like), the Woodward reagent K method, the DCC-HOBT (1-hydroxybenzotriazole) method and the like. Classical methods for amino acid condensation reactions are described in "Peptide Synthesis", Second Edition, M. Bodansky, Y. S. Klausnet and M. A. Ondetti (1976). It is contemplated that the amino acid coupling reaction could be carried out before or after the amino-containing group is incorporated into the compound by displacement of the 7-fluorine atom of the appropriate intermediate.

As in conventional peptide synthesis, branched chain amino and carboxyl groups at alpha and omega positions in amino acids may be protected and deprotected if necessary. The protecting groups for amino groups which can be used involve, for example, benzyloxycarbonyl (Z), o-chloro-benzyloxycarbonyl((2-Cl)Z), p-nitrobenzyloxycarbonyl (Z(NO2)), p-methoxybenzyloxycarbonyl (Z(OMe)), t-butoxycarbonyl (Boc), t-amyloxycarbonyl (Aoc), isoborneal-oxycarbonyl, adamantyloxycarbonyl (Adoc), 2-(4-biphenyl)-2-propyloxy carbonyl (Bpoc), 9-fluorenyl-methoxycarbonyl (Fmoc), methylsulfonylethoxy carbonyl (Msc), trifluoroacetyl, phthalyl, formyl, 2-nitrophenylsulfenyl (Nps), diphenylphosphinothioyl (Ppt) and dimethylphosphino-thioyl (Mpt).

The examples of protecting groups for carboxyl groups involve, for example, benzyl ester (OBzl), cyclohexyl ester, 4-nitrobenzyl ester (OBzlNO2), t-butyl ester (OtBu), 4-pyridylmethyl ester (OPic) and the like.

In the course of the synthesis of certain of the compounds of the present invention, specific amino acids having functional groups other than amino and carboxyl groups in the branched chain such as arginine, cysteine, serine and the like may be protected, if necessary, with suitable protecting groups. It is preferable that, for example, the guanidino group (NG) in arginine be protected with nitro, p-toluenesulfonyl (Tos), benzyloxycarbonyl (Z), adamantyloxycarbonyl (Adoc), p-methoxybenzenesulfonyl, 4-methoxy-2,6-dimethylbenzenesulfonyl (Mts) or the like; that the thiol group in cysteine be protected with benzyl, p-methoxybenzyl, triphenylmethyl, acetamidomethyl, ethylcarbamyl, 4-methylbenzyl (4-MeBzl), 2,4,6,-trimethylbenzyl (Tmb) or the like; and that the hydroxy group in serine may be protected with benzyl (Bzl), t-butyl, acetyl, tetrahydropyranyl (THP) or the like.

Scheme I

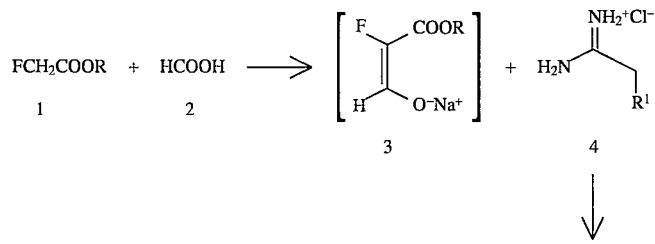

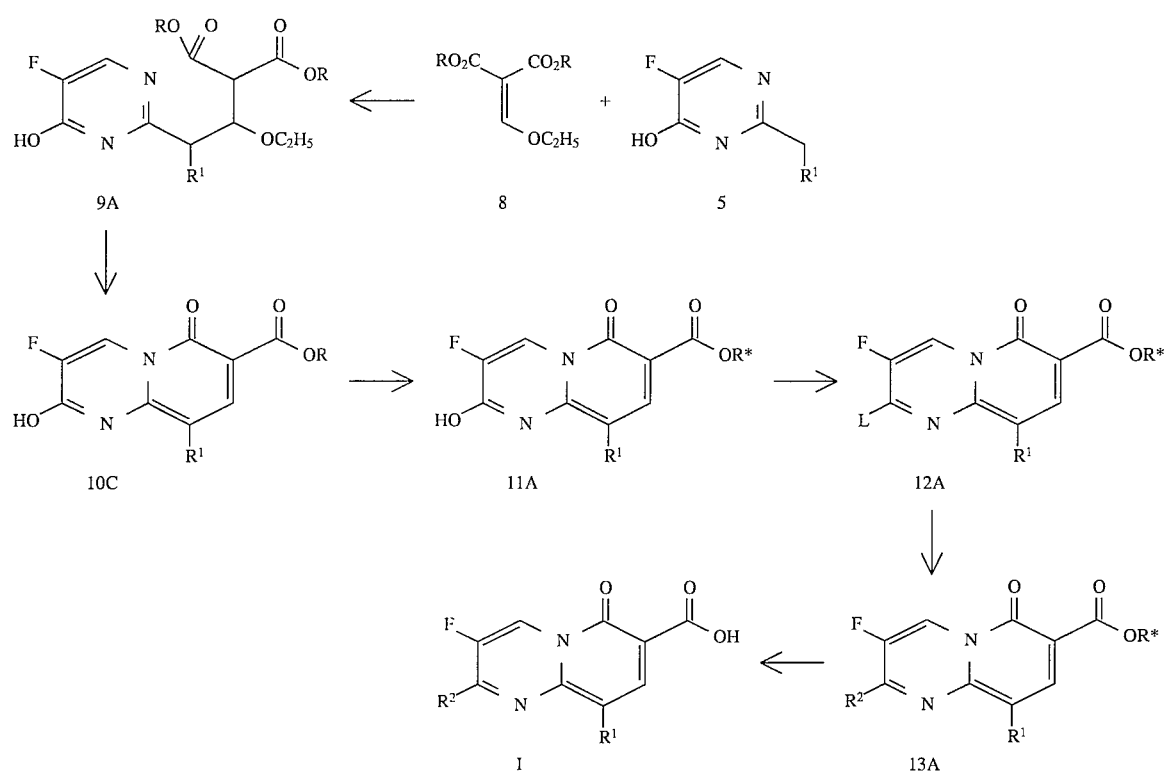
Scheme I
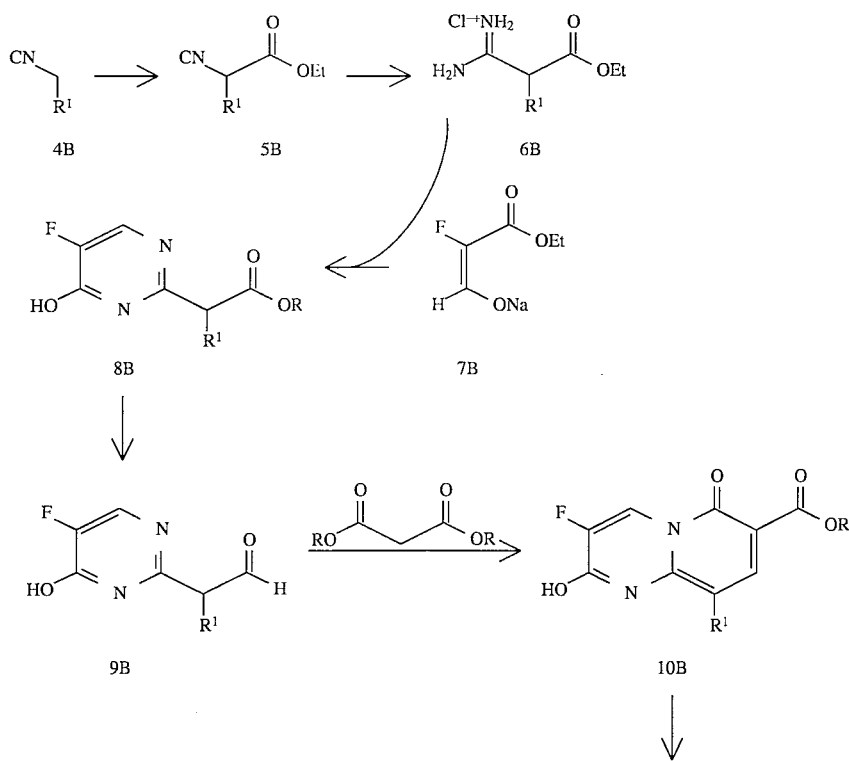
Scheme II

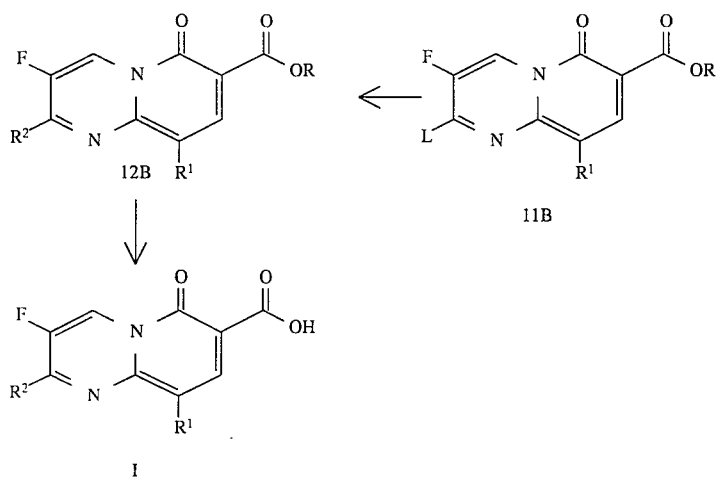
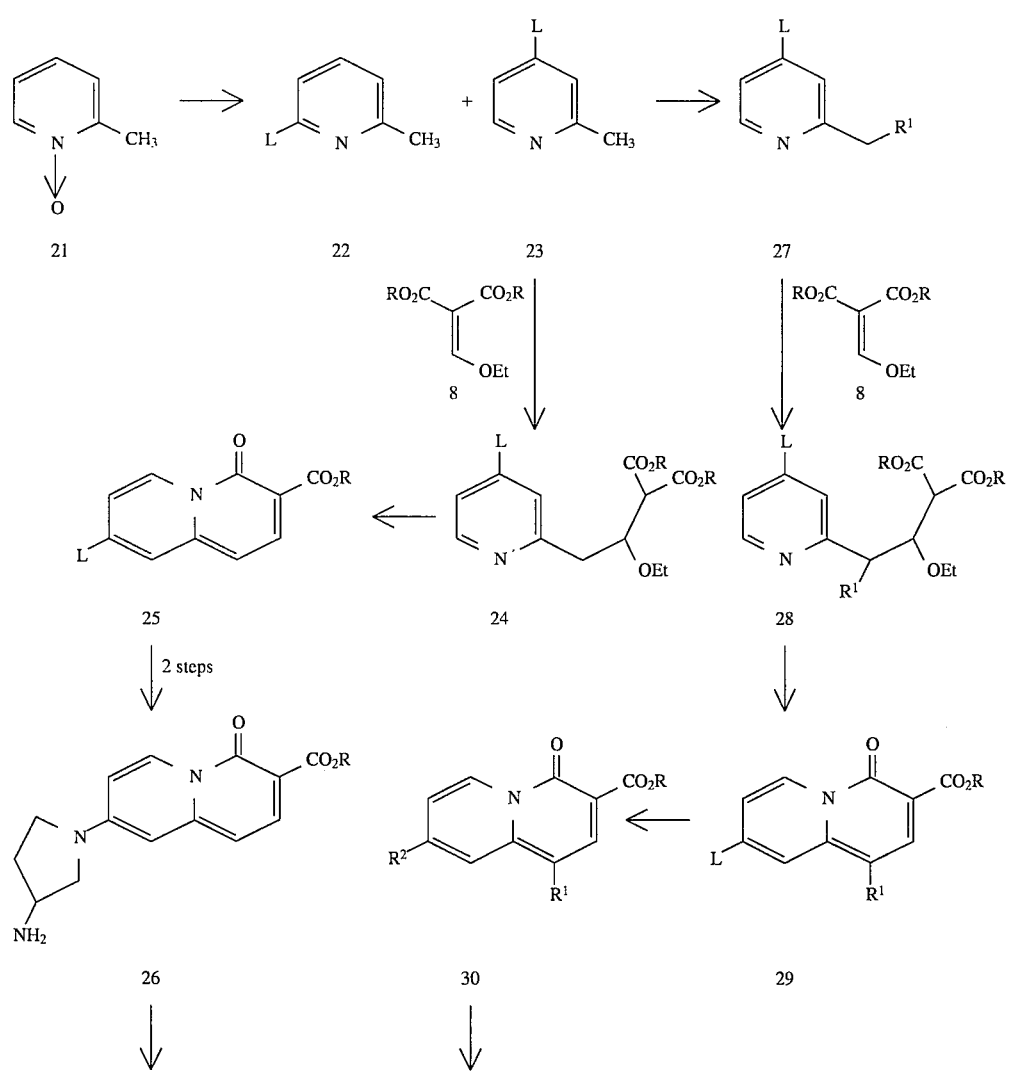

-continued
Scheme III
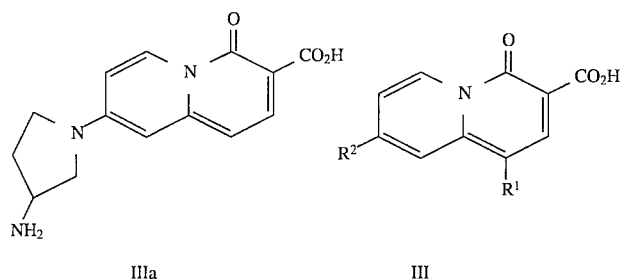
Scheme IVA
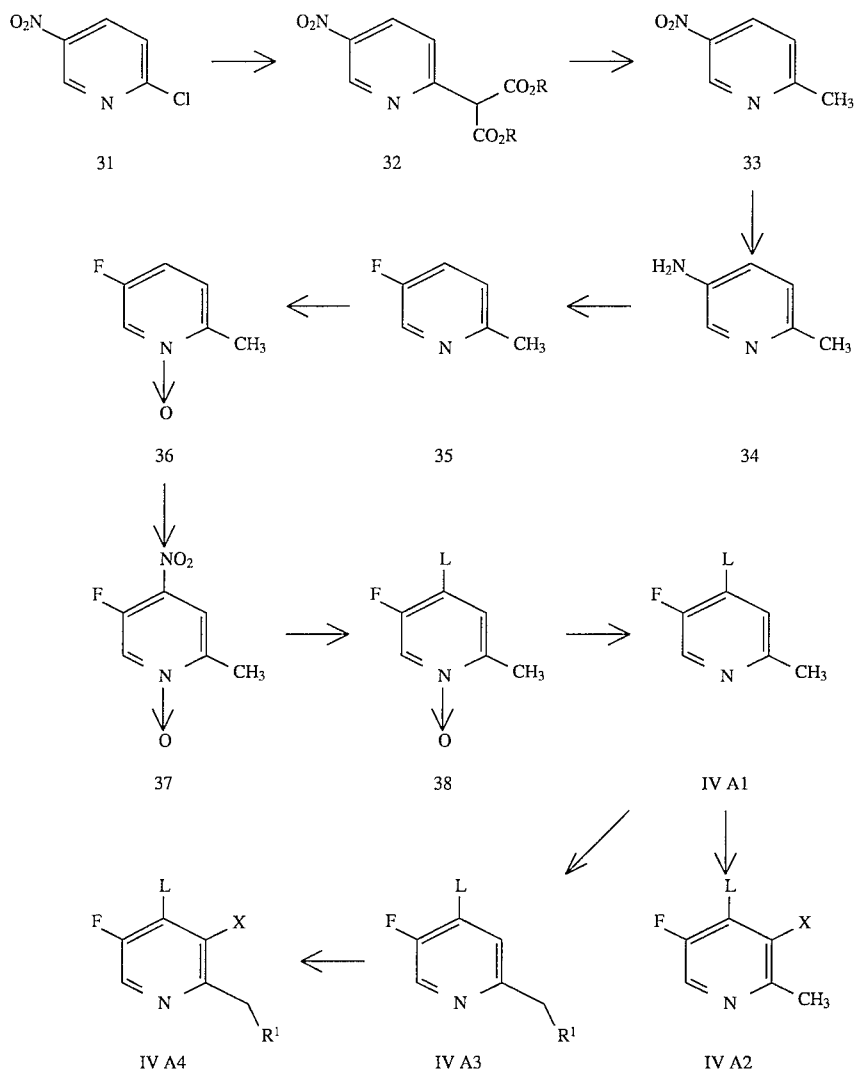

Scheme IVB
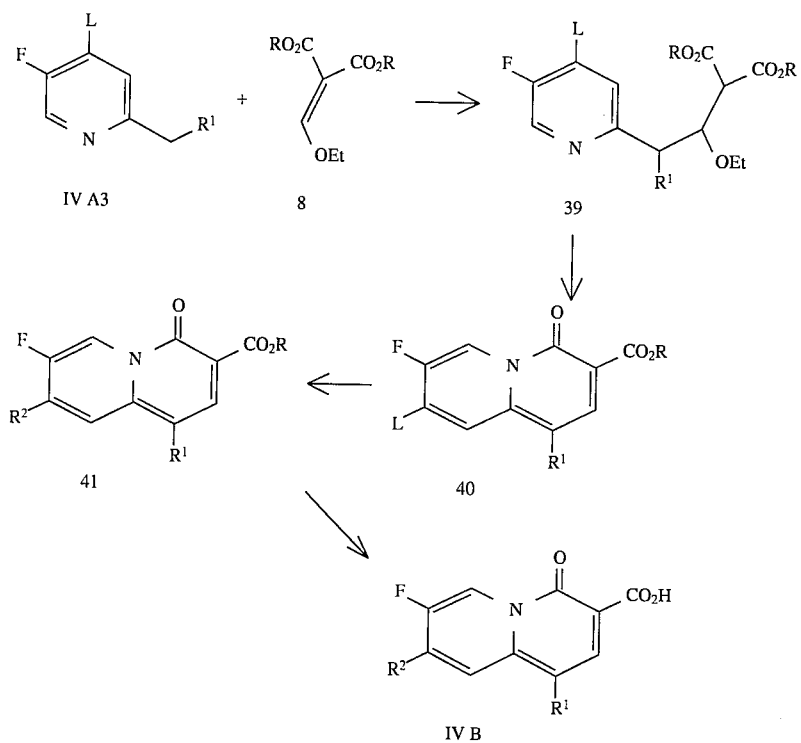
Scheme IVC
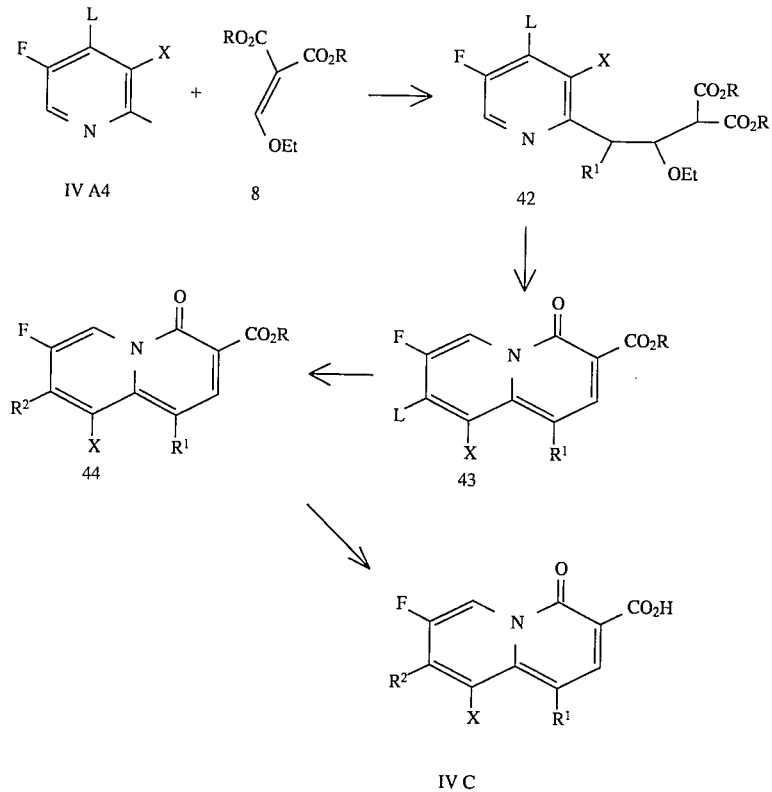

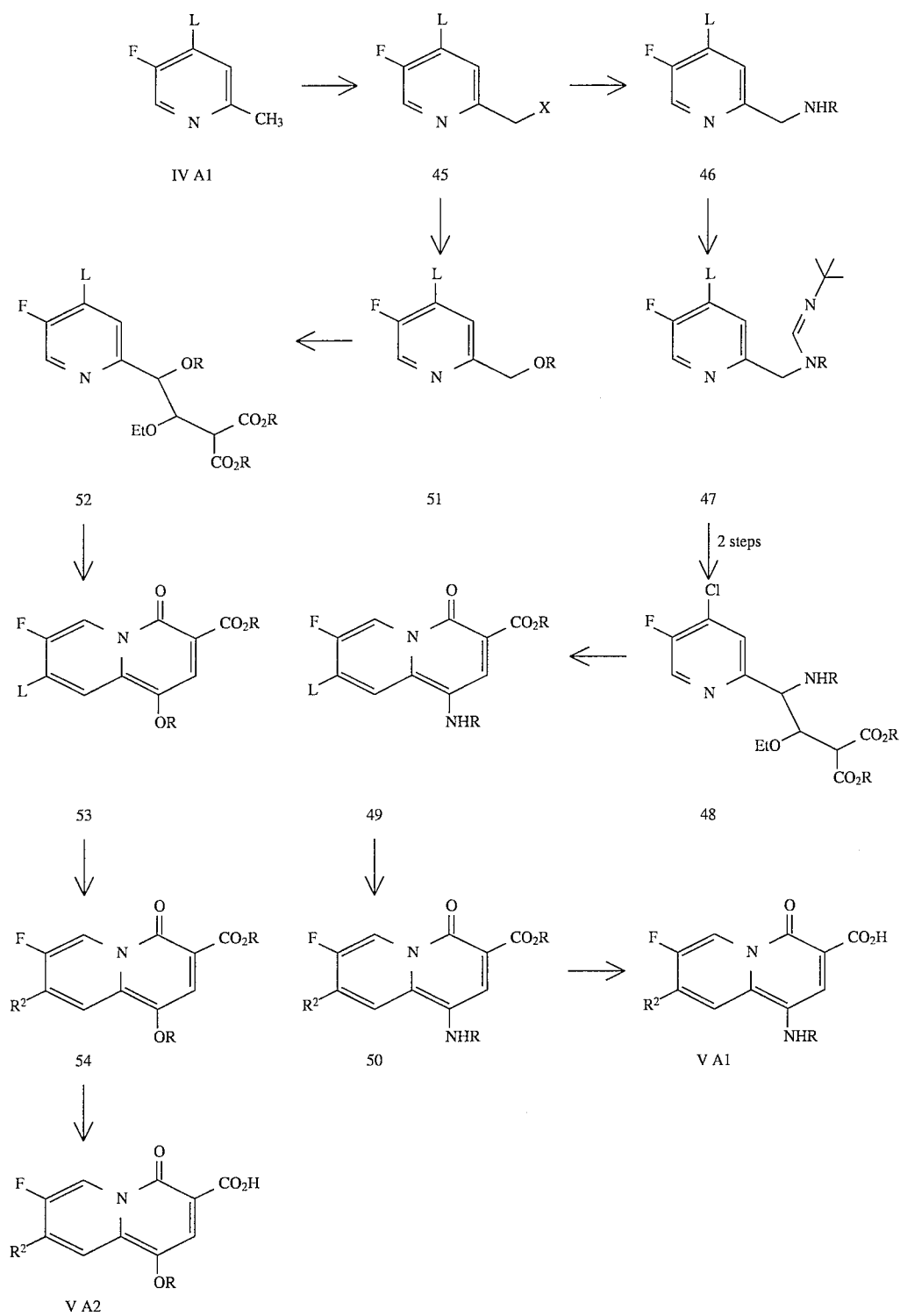

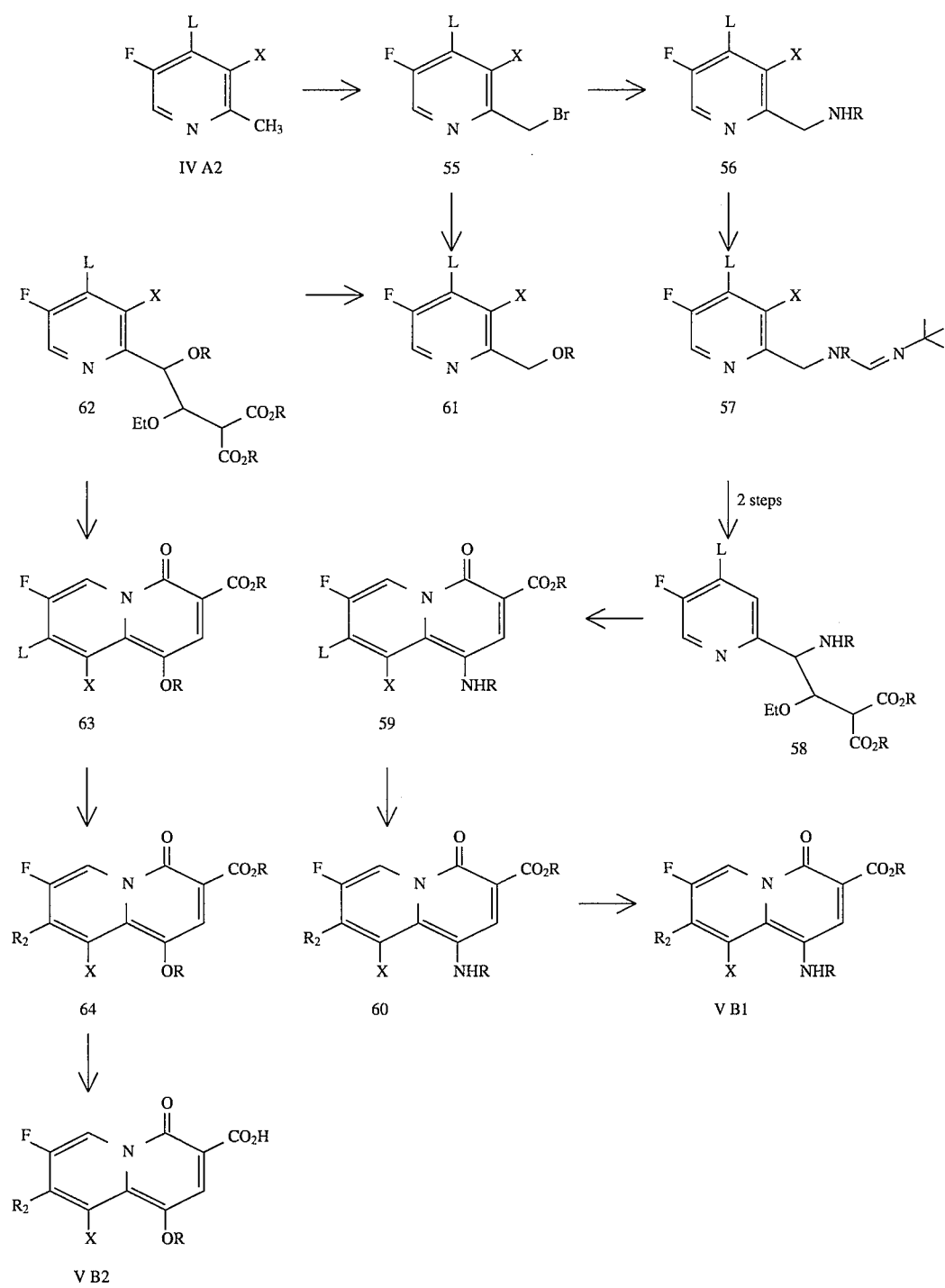

Scheme VI
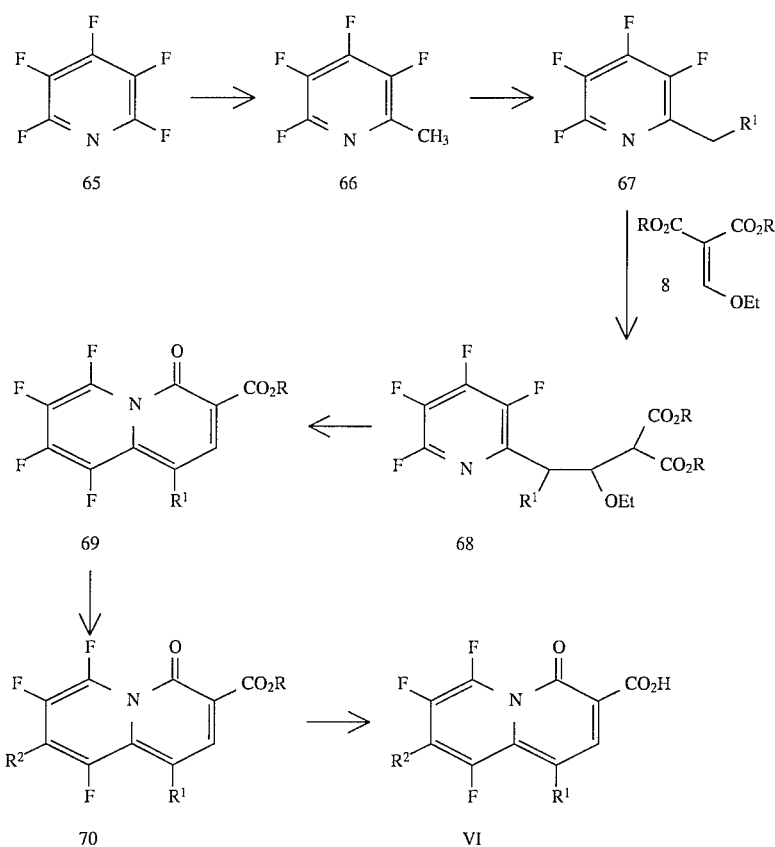
Scheme VII
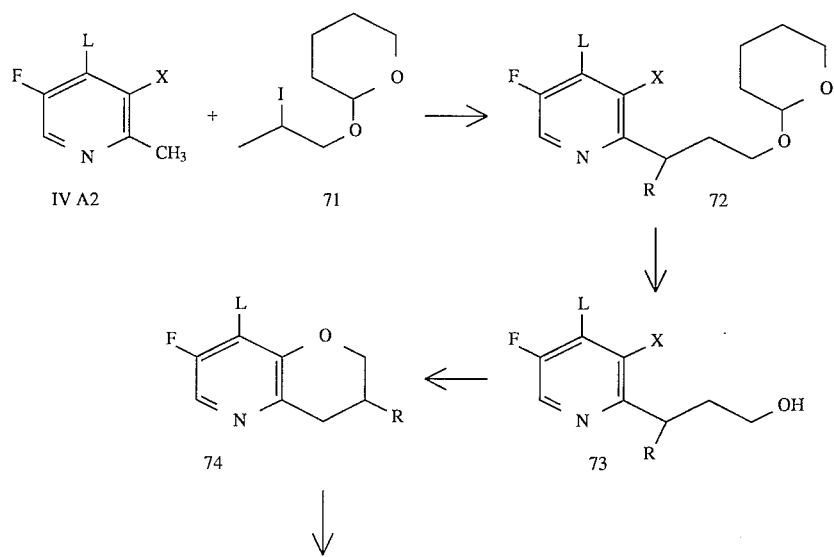

-continued
Scheme VII
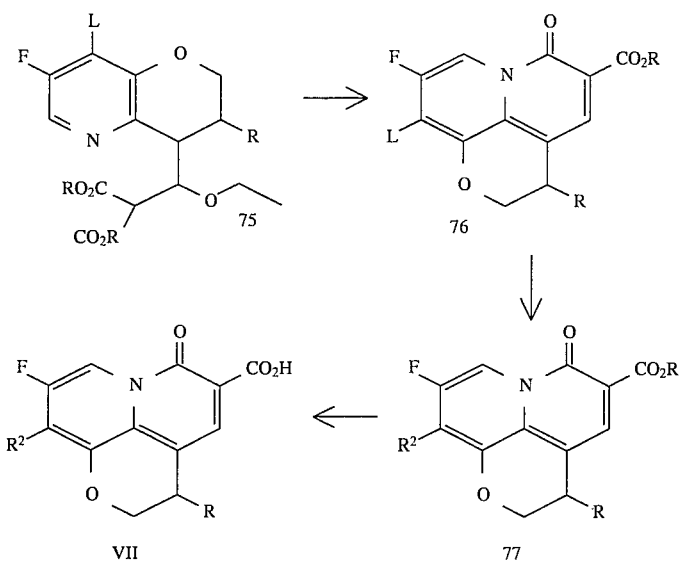
Scheme VIII
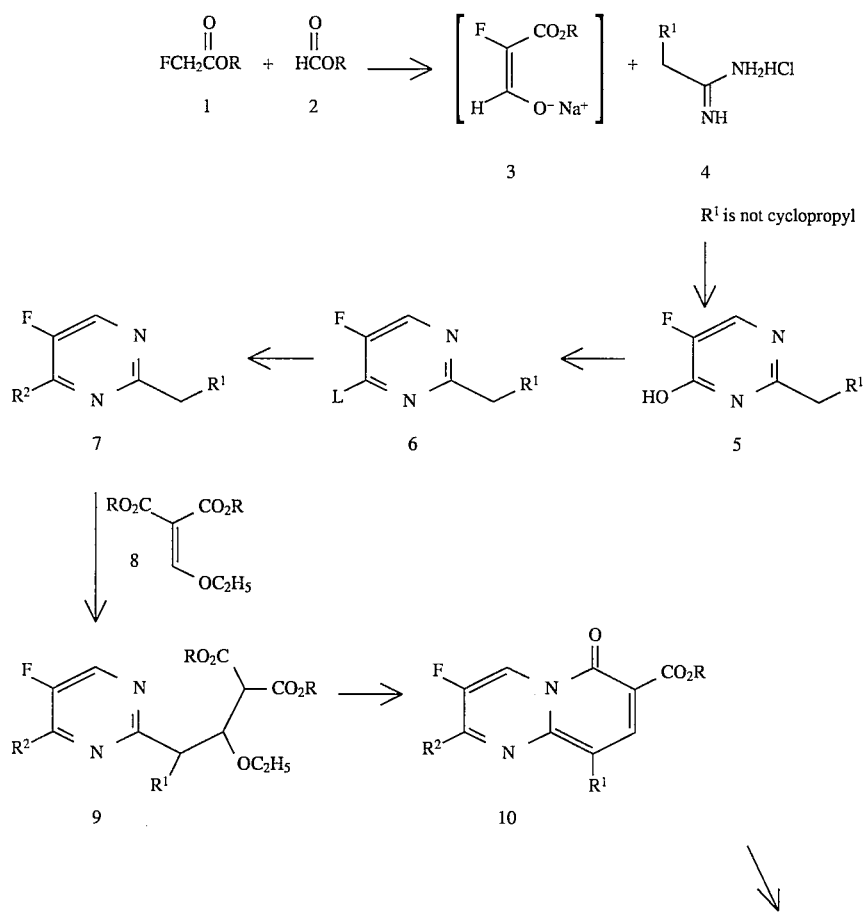

-continued
Scheme VIII
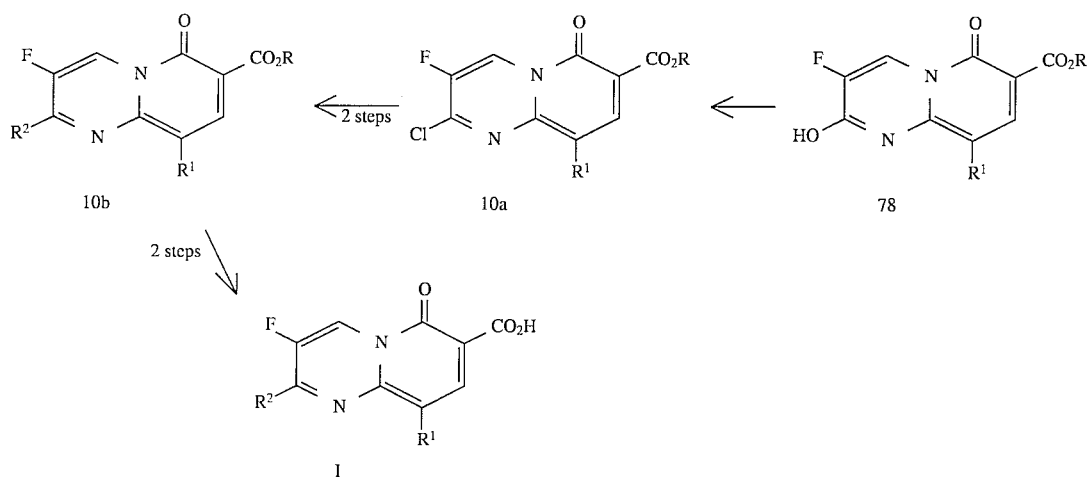
Scheme IX
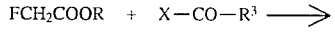
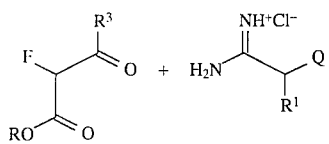
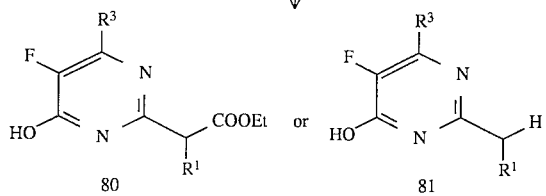
via Schemes I, II, or VIII
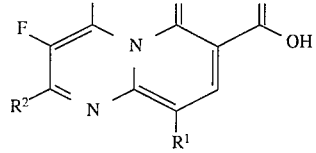
Scheme X
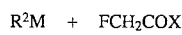
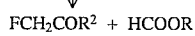
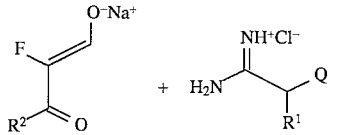
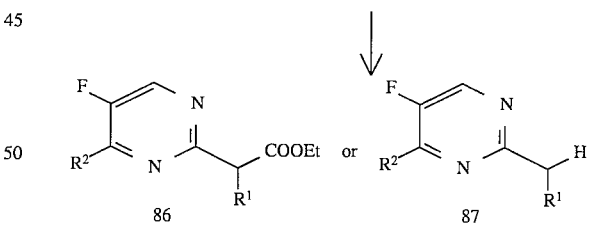
via Schemes II or VIII
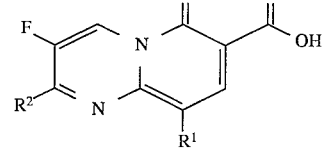

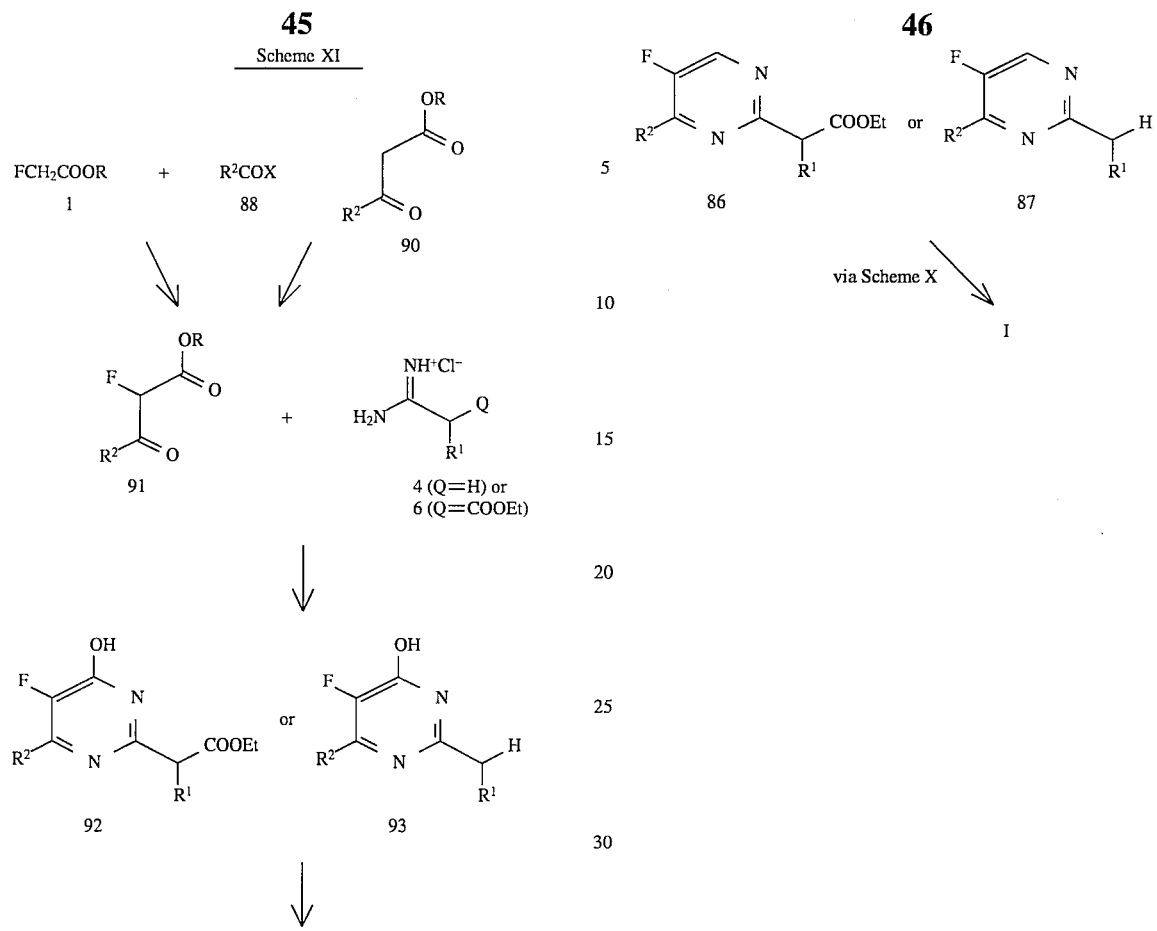
Scheme XI
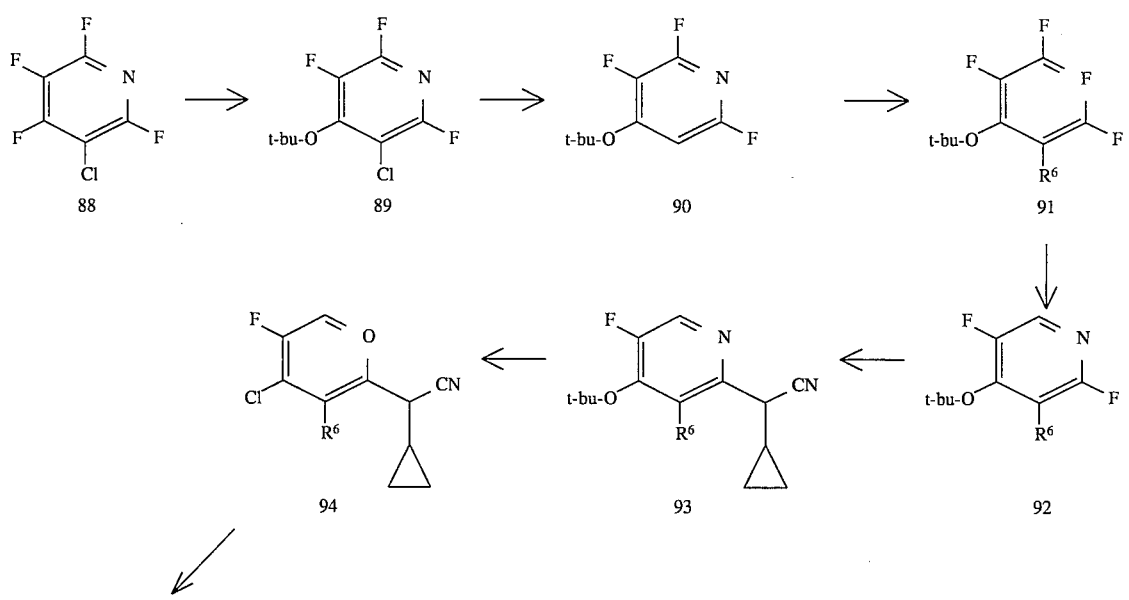
Scheme XII

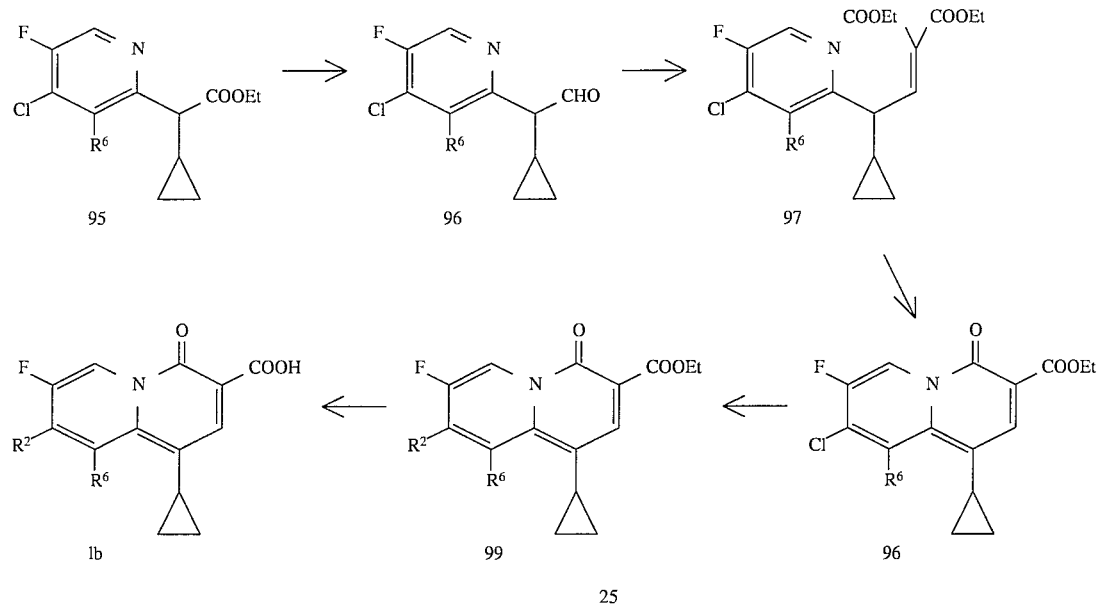
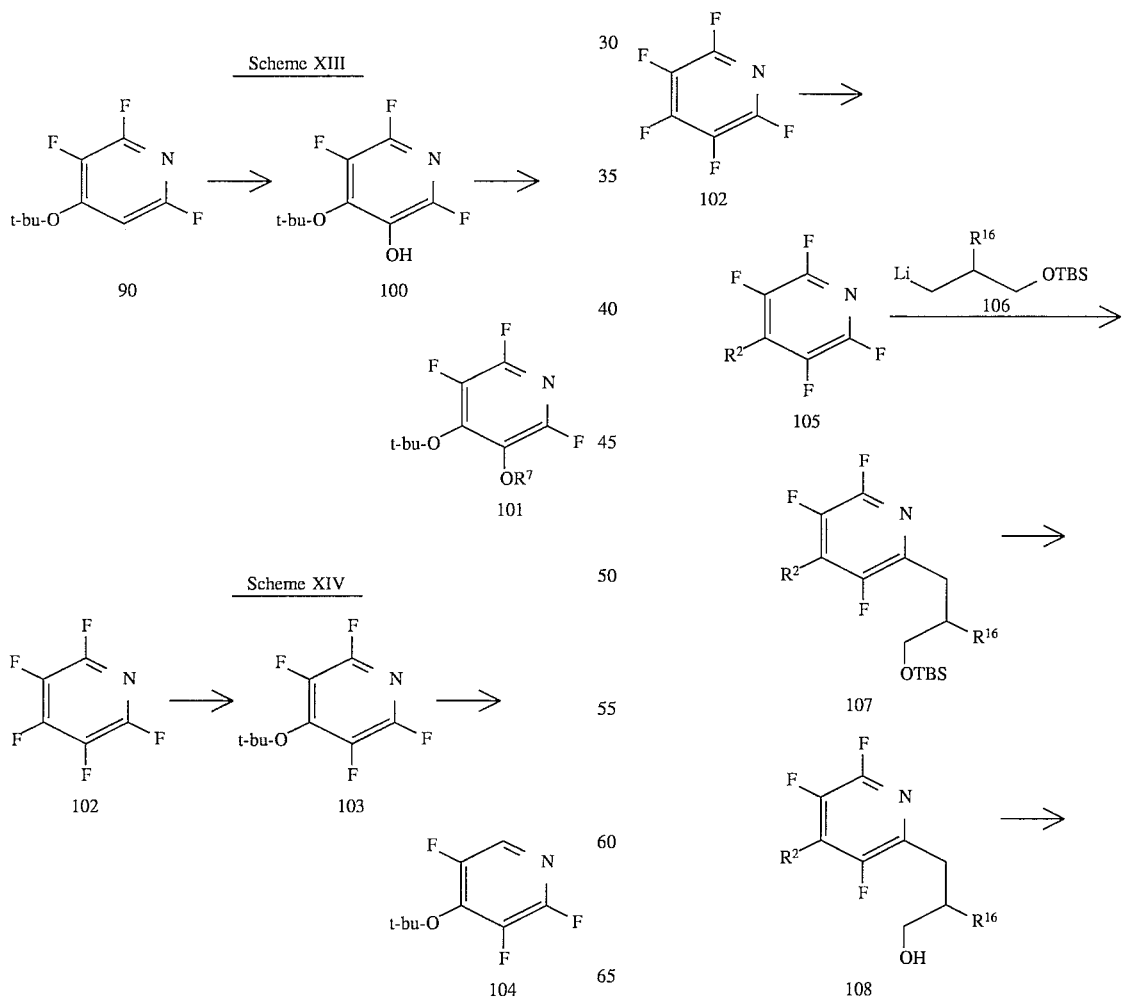

Scheme XV
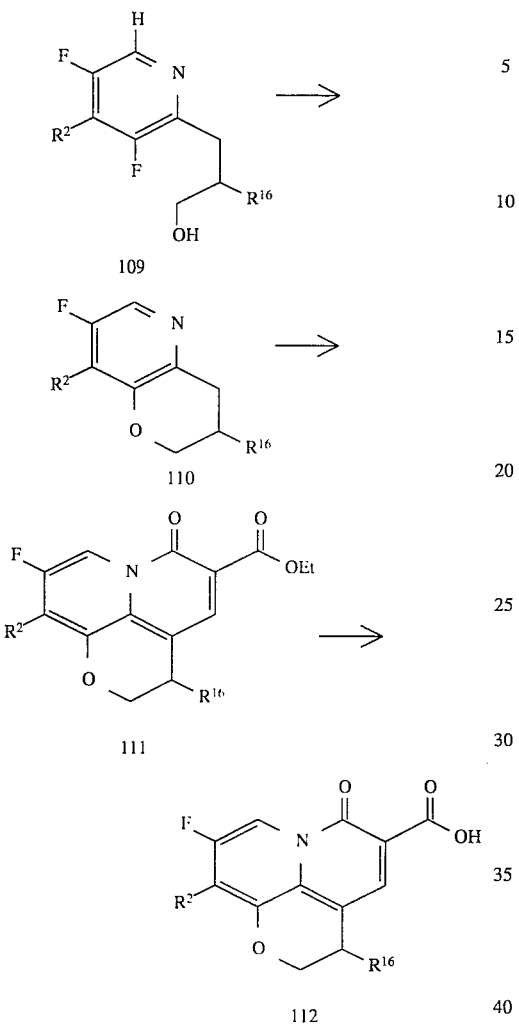
Scheme XVI
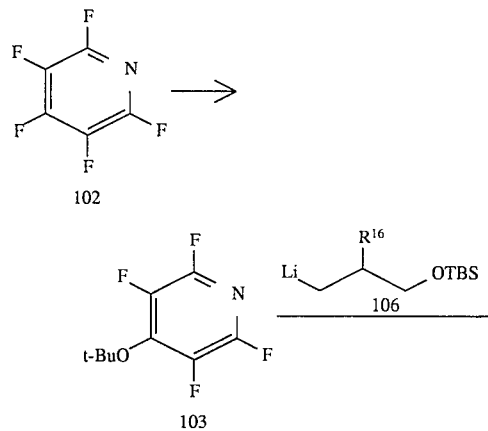
Scheme XVI -continued
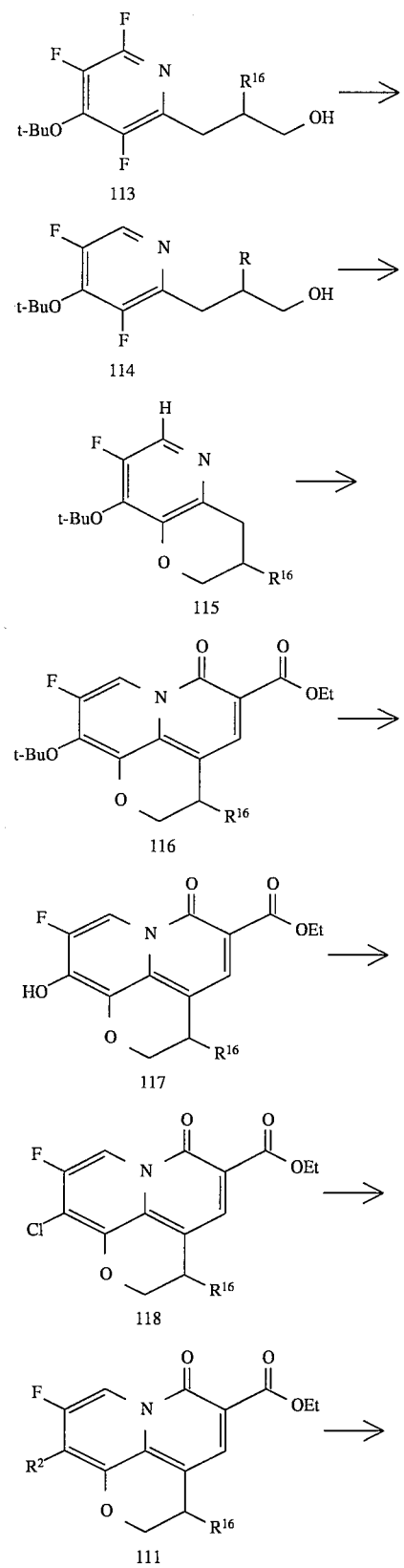

51
-continued
Scheme XVI

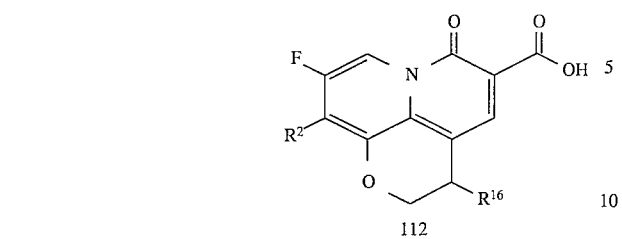
112

Scheme XVII

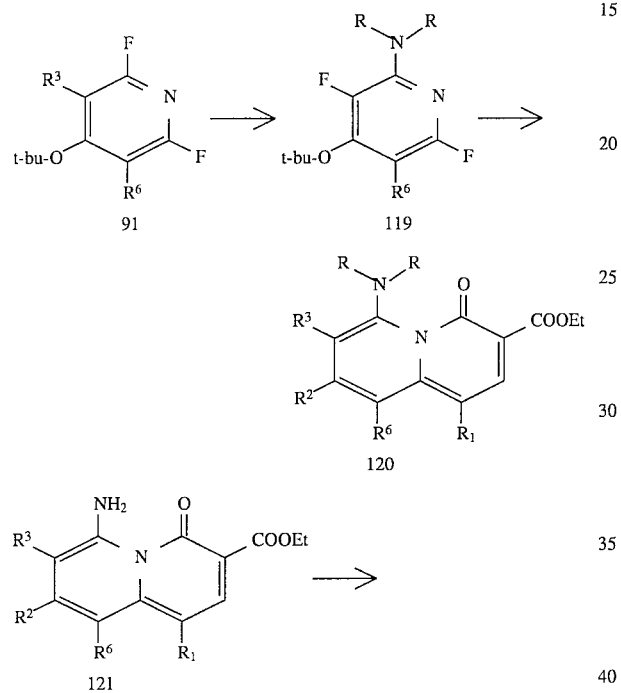

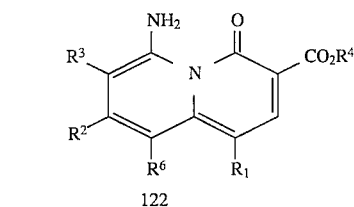
121

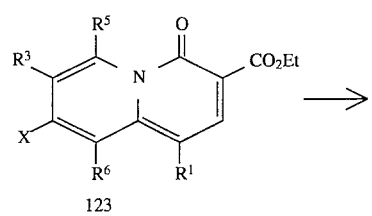
122

Scheme XVIII

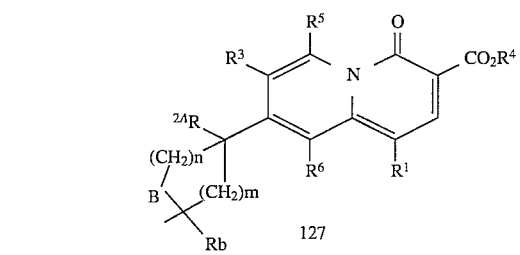
123

52
-continued
Scheme XVIII

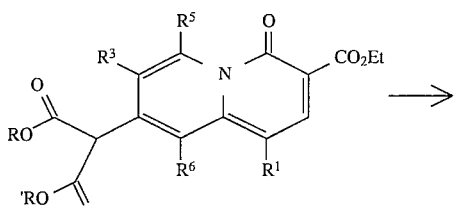
124

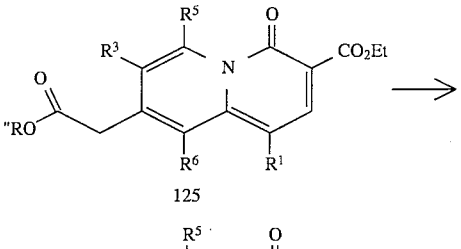
125

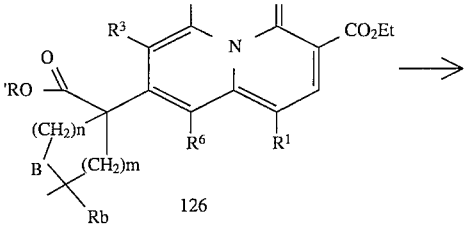
126

127

In accordance with reaction Scheme I, illustrated above, an alpha-halo acetate derivative of formula 1, such as ethyl 2-fluoroacetate, is condensed with a formate ester of formula 2 in the presence of a suitable base, as for example sodium ethoxide, in an inert solvent such as diethyl ether to to give an enolate compound of formula 3. Compounds of formula 3 are, in turn, converted to compounds of formula 5 by condensation with an amidine derivative of formula 4, in which $R^1$ is an electron withdrawing group such as phenyl, trifluoromethyl, cyano, perfluoroalkyl, vinyl, substituted vinyl, fluorine, nitro, acetylene, substituted acetylene, alkoxycarbonyl, or a nitrogen-containing aromatic heterocycle. Compounds of formula 5 are reacted with an alkoxymethylene malonate derivative of formula 8 in the presence of a suitable strong base, for example lithium diisopropylamide (LDA) or n-butyl lithium, preferably at a temperature below 0° C., and conveniently at −78° C. to afford the compounds of formula 9A.

The compounds of formula 9A are cyclized in the presence of a base, as for example DBU or piperidine, or in the presence of an acid, such as sulfuric acid, in a solvent such as toluene, THF, ethanol or chlorobenzene, or by heating the compound in a solvent, as for example xylene, diglyme, triglyme, suffolane or Dowtherm A® (a eutectic mixture of biphenyl and diphenyl ether) at a temperature greater than 120° C., to give the compounds of formula 10C. The esters 10C are converted into the esters 11A via transesterification with an alcohol suitable for selective hydrolysis, such as benzyl alcohol or 2-(trimethylsilyl)ethanol (TMSE), in the presence of a catalyst, as for example titanium tetraethoxide.

The 2-hydroxy compounds of formula 11A are convened to the corresponding halo-derivatives of formula 12A by treatment with a halogenating agent, for example phosphorous oxychloride to afford the chloro derivative, optionally in an inert solvent at a temperature between about 20° C. and 145° C., depending on the halogenating agent and the boiling point of the solvent if one is used, and conveniently at room temperature. The leaving group L in the compounds of formula 12A is then displaced by a nucleophile such as a nucleophilic amine, for example N-methylpiperazine or 2-methylpiperazine, to give the compounds of formula 13A. The reaction may be conducted at a temperature from about 20° C. to about 130° C. in a suitable organic solvent such as pyridine, methylene chloride, chloroform or 1-methyl-2-pyrrolidinone. It is desirable to carry out the reaction in the presence of an acid-acceptor such as triethylamine, potassium carbonate and the like, at a molar ratio of 1.0 to 2.0 moles of the acid acceptor per mole of compound of the formula 6. The amine can also be used as an acid acceptor in which case two or more equivalents of this reagent are used.

The benzyl ester group of compounds of formula 13A is then removed by hydrogenolysis when $R^*$ is benzyl, or with tetrabutylammonium fluoride when $R^*$ is TMSE, to afford a compound of formula I.

In accordance with Scheme II above, the substituted acetonitrile compounds of formula 4B, where $R^1$ is an alkyl, cycloalkyl, halo(loweralkyl) group or a (loweralkyl)amino group protected with a protecting group such as benzyloxycarbonyl, or may be an electron withdrawing group as described above for Scheme I, are reacted with diethyl carbonate and sodium hydride in an inert organic solvent, such as toluene, THF or the like, to give the substituted cyanoacetic acid ester of formula 5B. The cyano group of the compounds of formula 5B is then reacted with an inorganic acid, such as hydrochloric acid, in the presence of one equivalent of anhydrous alcohol, such as ethanol, followed by reaction with ammonia to give the substituted amidine ester of formula 6B, which is then condensed with an enolate compound of formula 7B, prepared in a-manner similar to compounds of formula 3 in Scheme I, in the presence of a suitable base, for example triethylamine, in a polar solvent such as methanol to give the substituted hydroxypyrimidine ester compounds of formula 8B. The ester function of the compounds of formula 8B is converted into an aldehyde function by reduction, for example with a hindered aluminum hydride, such as diisobutylaluminum hydride or LiAlH(O-t-butyl)$_3$, or with N,N-dimethyl-chloromethyleneiminium chloride in pyridine or diaminoaluminum hydride to produce a compound of formula 9B. This reaction may be conducted at a temperature below –20° C., and conveniently at –78° C. in the presence of a aprotic solvent such as hexane, toluene, methylene chloride or THF.

The aldehyde compounds of formula 9B are reacted with a malonic acid diester, such as diethyl malonate, dibenzyl malonate, t-butyl malonate or di-t-butyl malonate, in the presence of a suitable base such as piperidine and a catalytic amount of an acid, such as acetic acid or sulfuric acid, in a polar solvent, such as ethanol, to afford the pyridopyrimidine compounds of formula 10B. The compounds of formula 10B are reacted with a suitable halogenating agent such as phosphoryl chloride at room temperature to afford the compounds of formula 11B. The halo group is displaced as discussed in reaction Scheme I to afford the compounds of formula 12B, which are in turn convened into the compounds of formula I as described in Scheme I for the conversion of compounds of formula 10 into compounds of formula I.

According to reaction Scheme III illustrated above, 2-picoline-N-oxide is converted to a mixture of compounds of formulae 22 and 23 by treatment with a halogenating agent, for example phosphorus oxychloride, optionally in an inert solvent. The reaction may be run at a temperature between about 25° C. and 125° C., depending on the halogenating agent selected. When the halogenating agent is phosphorus oxychloride the reaction temperature is preferably between 60° C. and 120° C. A compound of formula 23 is, in turn, reacted with an alkoxymethylene malonate derivative of formula 8 in the presence of a suitably strong and hindered base, for example lithium diisopropylamide (LDA), preferably at a temperature below 0° C., and conveniently at –78° C. to afford the compounds of formula 24. Compounds of formula 24 are cyclized by heating the compound in a solvent with a boiling point greater than 120° C., for example xylene, diglyme, triglyme, sulfolane or Dowtherm A® (a eutectic mixture of biphenyl and diphenyl ether), to afford compounds of formula 25. The leaving group in the 8-position of the quinolizinone compound of formula 25 is then displaced using 3-aminopyrrolidine with the primary amino group protected, for example with t-butoxycarbonyl,. The protecting group is then removed to give the compounds of formula 26.

The esters of formula 26 are than converted to the carboxylic acids of formula III as described in Scheme 1 for the conversion of compounds of formula 10 to compounds of formula I.

Alternately, compounds of formula 23 are converted to compounds of formula 27, wherein $R^1$ is alkyl, cycloalkyl or carbocyclic aryl(loweralkyl), by treatment with an alkyl, cycloalkyl or carbocyclic aryl(loweralkyl) halide in the presence of a suitable base such as LDA. Compounds of formula 23 are converted to compounds of formula 27, wherein $R^1$ is a phenyl group as defined herein or an alkylamino group by conversion to the corresponding halomethyl compound and treatment of the halomethyl compound with an aryl metal compound such as phenyllithium as described above, or with an alkylamine such as methylamine as shown in reaction Scheme VA. The compounds of formula 27 are converted to the compounds of formula 29 by the sequence of reactions described above for the conversion of compounds of formula 25. The leaving group in the 8-position of the quinolizinone compound of formula 29 is then displaced, for example by a nucleophilic amine such as N-methylpiperazine or 2-methylpiperazine, to give the the compounds of formula 30. The reaction may be conducted at a temperature from about 20° C. to about 130° C. in a suitable organic solvent such as pyridine, methylene chloride, chloroform or 1-methyl-2-pyrrolidinone. It is desirable to carry out the reaction in the presence of an acid-acceptor such as triethylamine, potassium carbonate and the like, at a molar ratio of 1.0 to 2.0 moles of the acid acceptor per mole of compound of the formula29. The amine can also be used as an acid acceptor in which case two or more equivalents of this reagent are used.

In the case where $R^2$ is a phenyl group as defined herein, compounds of formula 30 are formed by coupling the compound of formula 29 with an aryl metal compound, for example phenyllithium, to replace the 8-leaving group with an unsubstituted phenyl group. The coupling reaction is carried in a reaction-inert solvent, i.e., a solvent which does not interfere with the coupling reaction of the aryl metal compound with a compound of formula29. Suitable reaction-inert solvents include ethers, for example diethyl ether, dimethoxyethane and tetrahydrofuran (THF). Co-solvents may be used with ethers if desired. These co-solvents may be benzene, toluene, tetramethylethyleneamine (TMEDA) and hexamethyl-phosphoramide (HMPA). The aryl metal compounds may be prepared by known methods. For example, they may be prepared by direct lithium-halogen exchange of the corresponding aryl halide using n-butyl-, sec-butyl- or t-butyl-lithium followed by transmetallation by a wide variety of salts by known methods such as described by E. Negishi in "Organometallics in Organic Sysnthesis", Vol. 1, page 104.

According to Scheme IV A illustrated above, a compound of formula 31 is treated with a malononic acid ester, for example diethyl malonate, in the presence of a suitable base such as sodium hydride in a polar nonprotic solvent such as an ether, for example diethyl ether or THF, to afford a compound of formula 32. Compounds of formula 32 are, in turn, decarboxylated, for example by heating them in strong mineral acid such as aqueous surfuric acid, to afford the compounds of formula 33. The nitro-compound of formula 33 is reduced to the corresponding amino-compound of formula 34. The nitro group may be reduced by catalytic hydrogenation using standard techniques or by any of a variety of known reducing agents such as using a metal, for example zinc, tin or iron, in the presence of a mineral acid, usually hydrochloric acid. The amino-compound of formula 34 is converted to the corresponding fluoro-compound of formula 35 by treatment with ethyl nitrite and tetrafluoroboric acid, followed by treatment with potassium fluoride. The compound of formula 35 is then converted into the corresponding N-oxide of formula 36 by oxidation, for example using peracetic acid. The reaction is carded out in the range from about 20° C. up to the reflux temperature of the solvent employed, preferably at about 50° C. The compound of formula 36 is nitrated to afford compounds of formula 37. The nitration reaction can be carried out using a variety of known nitrating agents, for example a mixture of nitric acid and surfuric acid or a mixture of sulfuric acid and potassium nitrate, or by using nitronium salts such as nitronium trifluoromethanesulfonate. The nitro compound of formula 37 is, in turn, converted to the corresponding halo compound of formula 38 by treatment with mineral acid at ambient or elevated temperature as desired. For example, the compound of formula 37 is treated with aqueous hydrochloric acid at a temperature of about 100°–120° C. to afford the compound of formula 38 wherein L is Cl. The compound of formula 38 is, in turn converted to the compound of formula IV A1 by reduction, for example using a metal such as iron or zinc in the presence of an acid such as acetic acid. The compound of formula IV A 1 is, in turn, converted to the compound of formula IV A2 by treatment with a suitable base, such as LDA, followed by treatment with a halogenating agent, for example N-chloro or N-bromo succinimide. Alternately, the compounds of formula IV A1 are converted to compounds of formula IV A3, wherein $R^1$ is alkyl, cycloalkyl or carbocyclic aryl(loweralkyl), by treatment with an alkyl, cycloalkyl or carbocyclic aryl(loweralkyl) halide in the presence of a suitable base such as LDA. The compounds of formula IV A3 are further treated with a a suitable base, such as LDA, followed by treatment with a halogenating agent, for example N-chloro or N-bromo succinimide to afford the compounds of formula IV A4. Compounds of formulae IV A1–IV A4 are key intermediates used in the synthesis of quinolizinone compounds.

According to Schemes IV B and IV C illustrated above, the compounds of formulae IV A3 and IV A4 are converted to the quinolizinone compounds of formula IV B and IV C, respectively, by the following series of reactions: (1) reaction with an alkoxymethylene malonate derivative of formula 8 in the presence of a suitably strong and hindered base, for example lithium diisopropylamide (LDA), preferably at a temperature below 0° C., and conveniently at −78° C., to afford the compounds of formulae 39 and 42, respectively (2) cyclization as discussed in reaction Scheme III, to afford the compounds of formulae 40 and 43, respectively (3) displacement of the leaving group in the 8-position as discussed in reaction Scheme III to afford the compounds of formulae 41 and 44, respectively and (4) hydrolysis or hydrogenolysis as discussed in reaction Scheme III of the carboxylic acid ester to the corresponding carboxylic acids of formulae IV B and IV C, respectively.

According to Scheme V A illustrated above, compounds of formula IV A 1 are treated with a halogenating agent under suitable conditions for generating halogen radicals, for example using N-bromo- or N-chlorosuccinimide in the presence of a free radical initiator such as AIBN to afford the compounds of formula 45. The halogen on the alpha carbon atom is then displaced by a nucleophile, for example an alkoxide to give the compounds of formula 51 or an amine to give the compounds of formula 46. The amine function is protected during synthesis by converting it to the corresponding formamidine function affording compounds of formula 47. Compounds of formula 47 are reacted with an alkoxymethylene malonate derivative of formula 8 in the presence of a suitably strong and hindered base, for example lithium diisopropylamide (LDA), preferably at a temperature below 0° C., and conveniently at −78° C. The formamidine group is then removed by reaction with hydrazine and acetic acid to afford the compounds of formula 48. The compounds of formula 48 are cyclized as discussed in reaction Scheme III, to afford the compounds of formula 49. The leaving group, L, is then displaced as discussed in reaction Scheme III to afford the compounds of formula 50. The compounds of formula 50 are, in turn, converted to the compounds of formula V A1 as discussed in reaction Scheme I.

The compounds of formula 51 are converted to the compounds of formula V A2 by the following series of reactions: (1) reaction with an alkoxymethylene malonate derivative of formula 8 in the presence of a suitably strong and hindered base, for example lithium diisopropylamide (LDA), preferably at a temperature below 0° C., and conveniently at −78° C., to afford the compounds of formula 52 (2) cyclization as discussed in reaction Scheme III, to afford the compounds of formula 53 (3) displacement of the leaving group in the 8-position as discussed in reaction Scheme III to afford the compounds of formula 54 and (4) conversion of the carboxylic acid ester to the corresponding carboxylic acids of formula V A2.

According to reaction Scheme V B illustrated above, compounds of formula IV A2 are converted to compounds of formulae V B1 and V B2 by the same procedures discussed in reaction Scheme V A for the conversion of compounds of formula IV A1 to compounds of formulae V A1 and V A2.

According to reaction Scheme VI illustrated above, perfluoroinated pyridine is converted to the compound of formula 66 by the procedures described in reaction Scheme IV A for the preparation of compounds of formula 33. Compounds of formula 66 are, in turn, converted to the compounds of formula VI A and VI B by the series of reactions discussed in reaction Scheme III for the conversion of compounds of formula 23 to compounds of formula III.

According to reaction Scheme VII illustrated above, compounds of formula IV A2 are reacted with a protected alcohol of formula 71, in the presence of a suitable base such as LDA, to afford compounds of formula 72. The hydroxy protecting group is preferably a THP (tetrahydopyranyl) ether group. The compounds of formula 72 are, in turn, deprotected by standard methods to afford the compounds of formula 73. The compounds of formula 73 are cyclized, in the presence of a suitable non-nucleophilic base such as sodium hydride, to afford the compounds of formula 74. The compounds of formula 74 are then converted to the compounds of formula 77 by the series of reactions described in reaction Scheme IV B for the conversion of the compounds of formula IV A3 to the compounds of formula IV B.

Compounds of formula I, wherein $R^2$ contains a free primary amino group are synthesized according to reaction Scheme VIII illustrated above. In accordance with reaction Scheme VIII, an alpha-halo acetate derivative of formula 1, such as ethyl 2-fluoroacetate, is condensed with a formate ester of formula 2, in the presence of a suitable base, for example sodium ethoxide, in an inert solvent such as diethyl ether to give an enolate compound of formula 3. Compounds of formula 3 are, in turn, converted to compounds of formula 5 by condensation with an amidine derivative of formula 4, in the presence of a suitable base, for example triethylamine, in a polar solvent such as methanol. The hydroxy-substituted compounds of formula 5 are converted to the corresponding halo-derivatives of formula 6 by treatment with a halogenating agent, for example phosphorus oxychloride to afford the chloro derivative, optionally in an inert solvent at a temperature between about 20° C. and 145° C., depending on the halogenating agent and the boiling point of the solvent if one is used. When phosphorus oxychloride is the halogenating agent, the reaction temperature is preferably between about 80° C. and 100° C. The leaving group in the 5-position of the pyrimidine ring of compounds of formula 6 is then displaced by a nucleophile such as a nucleophilic amine, for example N-methylpiperazine or 2-methylpiperazine, to give the the compounds of formula 7. The reaction may be conducted at a temperature from about 20° C. to about 130° C. in a suitable organic solvent such as pyridine, methylene chloride, chloroform or 1-methyl-2-pyrrolidinone. It is desirable to carry out the reaction in the presence of an acid-acceptor such as triethylamine, potassium carbonate and the like, at a molar ratio of 1.0 to 2.0 moles of the acid acceptor per mole of compound of the formula 6. The amine can also be used as an acid acceptor in which case two or more equivalents of this reagent are used.

The compounds of formula 7 are reacted with an alkoxymethylene malonate derivative of formula 8 in the presence of a suitably strong hindered base, for example lithium diisopropylamide (LDA), preferably at a temperature below 0° C., and conveniently at −78° C. to afford the compounds of formula 9. The compounds of formula 9 are cyclized in the presence of a suitable hindered base, for example DBU, in an aprotic solvent, such as toluene, THF or chlorobenzene to give the compounds of formula 10. The cyclization is carried out at a temperature in the range of about 30° C. to about 130° C., preferably at the reflux temperture of the reaction mixture. The compounds of formula 10 are hydrolyzed in the presence of a suitable base such as sodium or potasium hydroxide to afford the compounds of formula 78. The compounds of formula 78 are, in turn, chlorinated to afford the compounds of formula 10a using an appropriate chlorinating agent such as phosphorus oxychloride. The leaving group in the 8-position of the quinolizinone compound of formula 10a is then displaced using a nucleophilic amine such as 3-aminopyrrolidine (with the primary amino group protected, for example with t-butoxycarbonyl). The protecting group is then removed to give the compounds of formula 10b. The esters of formula 10b are then converted to the carboxylic acids of formula I. The conversion may be achieved by conventional hydrolysis or by converting a compound of formula 10b to the corresponding ester, via transesterification with an alcohol suitable for selective hydrolysis, such as benzyl alcohol or 2-(trimethylsilyl)ethanol (TMSE), in the presence of a catalyst, for example titanium tetraethoxide, and then, in turn, removing the alcohol group by hydrogenolysis when $R^*$ is benzyl or tetrabutylammonium fluoride when $R^*$ is TMSE to afford a compound of formula I.

Compounds of formula I where $R^3$ is loweralkyl or halo(loweralkyl) are synthesized according to reaction Scheme IX. In accordance with reaction Scheme IX illustrated above, an alpha-halo acetate derivative of formula 1, such as ethyl 2-fluoroacetate, is condensed with a compound of formula 78, where X may be a halogen or alkanoyl and R3 may be loweralkyl or halo(loweralkyl), for example acetyl chloride or ethyl trifluoroacetate, in the presence of a suitable base, for example sodium methoxide or sodium ethoxide, and in a suitable solvent, such as methanol, ethanol or ether, to give an alpha-fluoro beta-keto ester compound of formula 79. Compounds of formula 79 are then reacted with amidine compounds of formula 4 or formula 6, in which $R^1$ is an alkyl, halo(loweralkyl) or cycloalkyl group, or may be an electron withdrawing group such as phenyl, trifluoromethyl, cyano, perfluoroalkyl, vinyl, substituted vinyl, fluorine, nitro, acetylene, substituted acetylene, alkoxycarbonyl, or a nitrogen-containing aromatic heterocycle, in the presence of a suitable base, such as sodium methoxide or sodium ethoxide, in the presence of a suitable solvent, such as methanol or ethanol, to give compounds of formulae 81 or 80, respectively. Compounds of formula 80 may be substituted for compounds of formula 8B in Scheme II and convened via the reactions in that Scheme, described above, into compounds of formula I. Compounds of formula 81 may be substituted for compounds of formula 5 in Scheme I and converted into compounds of formula I via the reactions of Scheme I described above. Alternatively, the compounds of formula 81 may be substituted for compounds of formula 5 in Scheme VIII and convened via the reactions in that scheme, described above, into compounds of formula I.

Compounds of formula I where $R^2$ is loweralkyl, cycloalkyl, carbocyclic aryl(loweralkyl), cycloalkyl(loweralkyl), phenyl, nitrogen-containing aromatic heterocycle, or nitrogen-containing heterocycle are synthesized according to reaction Scheme X. In accordance with reaction Scheme X illustrated above, an organo-metallic derivative of formula 82, such as phenyl magnesium bromide, cyclopentyl magnesium bromide, or N-methylpiperidin-4-yl magnesium bromide is condensed with an alpha-haloacetate derivative of formula 83, where X may be a halogen or alkoxy group, such as ethyl 2-fluoroacetate or 2-fluoroacetyl chloride, in an anhydrous solvent, for example ether or THF, to produce the alpha-fluoro compounds of formula 84. Compounds of formula 84, may in turn be reacted with a formate ester of formula 2, in the presence of a suitable base, for example sodium ethoxide, in an inert solvent such as diethyl ether to give an enolate derivative of formula 85. The compounds of formula 85 are in turn converted to compounds of formula 86 or 87 by condensation with an amidine derivative of formula 4 or 6, in which $R^1$ is loweralkyl, halo(loweralkyl) or cycloalkyl, or is an electron withdrawing group such as phenyl, trifluoromethyl, cyano, perfluoroalkyl, vinyl, substituted vinyl, fluorine, nitro, acetylene, substituted acetylene, alkoxycarbonyl, or a nitrogen-containing aromatic heterocycle, in the presence of a suitable base, for example triethylamine, in a polar solvent such as methanol. Compounds of formula 87 may be substituted for compounds of formula 7 in Scheme VIII, and converted via the reactions in that scheme, described above, into compounds of formula I. Compounds of formula 86 may be substituted for compounds of formula 9B in Scheme II and, by reaction with a malonic acid diester as described for Scheme II above, convened directly into compounds of formula 12B and, thence, into compounds of formula I.

Alternatively, compounds of formula I, where $R^2$ is loweralkyl, cycloalkyl, carbocyclic aryl(loweralkyl), cycloalkyl(loweralkyl), phenyl, nitrogen-containing aromatic heterocycle, or nitrogen-containing heterocycle are synthesized according to reaction Scheme XI. An alpha-haloacetate derivative of formula 1 is condensed with an acid halide or ester derivative of formula 88, for example acetyl chloride, benzoyl chloride, isonicotinoyl chloride, or 2,6-dimethylisonicotinoyl chloride, in an anhydrous solvent, for example ether, THF, anhydrous methanol or an hydrous ethanol, in the presence of a suitable base, such as sodium methoxide or NaN(TMS)2, to produce the beta-ketoester derivative of formula 91, which is converted into compounds of formula 92 in the presence of a suitable base, such as sodium methoxide or sodium ethoxide, in the presence of a suitable solvent, such as methanol, ethanol or ether, to give the hydroxy-substituted compounds of formulae 92 or 93. These compounds, in turn, are converted into the corresponding halo- derivatives of formulae 94 and 95 under conditions as described for conversion of compounds of formula 5 to compounds of formula 6 in Scheme VIII. The compounds of formulae 94 and 95 are then reacted with reducing agents such as zinc in acetic acid or hydrogen in the presence of catalytic agents such as Ni, Pd, or Pt in suitable solvents such as ethanol or methanol to produce the compounds of formula 86 and 87, which are converted as described in Scheme X into compounds of formula I.

In addition, the non-fluorinated derivatives of formula 90, where R2 is as described above, may be converted to the beta-ketoester derivatives of formula 91 using a reagent such as N-fluoropyridinium triflate, N-fluorosulfonyl amide, cesium fluorooxysulfate, or acetyl hypofluoride.

In accordance with Scheme XII, which illustrates a process for preparing the desired compounds of formula Ib wherein $R^1$ is cyclopropyl, commercially available 3-chloro-2,4,5,6-tetrafluoropyridine (compound 88) is reacted with an alkali salt of t-butanol, such as for example, sodium t-butoxide or lithium t-butoxide, in a polar organic solvent such as THF, first at from 10° C. to −78° C. for 1–4 hours, then at room temperature for 2–72 hours, to give the compound of formula 89 (isolated from a mixture of products by chromatography). The compound of formula 89 is then reacted with hydrogen over a noble catalyst, such as Pd/C in a sodium acetate buffer, to remove the chlorine and give the compound of formula 90 (also isolated from a mixture of products by chromatography). In the instance where $R^6$ is alkyl, the compound of formula 90 is then reacted with a suitable alkyl halide, for example methyl halide or the like, in the presence of a suitably strong and hindered base, for example lithium diisopropylamide (LDA), preferably at a temperature below 0° C., and conveniently at −78° C. to afford the compounds of formula 91. In the instance where $R^6$ is haloalkyl, for example fluoroalkyl, the compound of formula 90 is first reacted with a suitably strong and hindered base, for example lithium diisopropylamide (LDA), preferably at a temperature below 0° C., and conveniently at −78° C. followed by reaction with formaldehyde to give the compound where $R^6$ is hydroxymethyl which is then reacted with diaminosulfur trifluoride (DAST) in a non-polar solvent such as methylene chloride to give the compound of formula 91. Alternately, when the $R^6$ group is to be a difluoromethyl, for example, the compound of formula 90 is first reacted with a suitably strong and hindered base, for example lithium diisopropylamide (LDA), preferably at a temperature below 0° C., and conveniently at −78° C. followed by reaction with DMF to form the intermediate compound wherein $R^6$ is CHO, and this intermediate is then reacted with DAST to prepare the compound of formula 91, wherein R6 is difluoromethyl. The compounds of formula 91 are then reacted with hydrazine under nitrogen at reflux temperature for 2–8 hours, and after removal of excess hydrazine the residue is dissolved in an organic solvent, such as methanol or benzene, for example, and air is then passed through the solution of the hydrazino product for 8–16 hours to give the compounds of formula 92. he compounds of formula 92 are then condensed with cyclopropyl acetonitrile in a polar organic solvent, such as THF, for example, in the presence of strong base, such as lithium diethylamide (LDA) or lithium diisopropylamide, at −78° C. for 1–4 hours and then at 0° C. for 1–4 hours or NaNH2 at −5° C. to −10° C. for 1 to 8 hours in order to prepare compounds of formula 93. The compounds of formula 93 are then reacted with trifluoroacetic acid under nitrogen for 1–4 hours at ambient temperature to removed the protecting t-butoxide group, and the unprotected material is then reacted with POCl3 in a suitable organic solvent, such as DMF or methylene chloride, for example, at ambient temperature for 8–24 hours in order to prepare the compounds of formula 94.

In an improved preparative method, regarded as a part of the present invention, the compounds of formula 89 may be converted directly to the compounds of formula 91 by treatment with a strong base, such as t-butyllithium or s-butyllithium, for example, in a polar solvent such as THF or the like for a period of from 0.5 to 3 hours, followed by reaction with methyl iodide at a temperature firstly below −50° C. then at ambient temperature for a period of from 4 to 20 hours. The compounds of formula 91 may then be converted to the compounds of formula 92 by treatment with a hydride reducing agent, such as LAH or sodium bis-(2-methoxyethoxy)aluminum hydride (Red-Al™), for example, at from 0° C. to ambient temperature for a period of from 8–24 hours. The resulting compounds of formula 93 are then reacted with POCl$_3$ in an organic solvent such as DMF or methylene chloride, for example, at ambient temperature for a period of from 6–20 hours in order to prepare directly the compounds of formula 94.

The cyano compounds of formula 94 are converted to esters of formula 95 by treatment with anhydrous ethanolic HCl followed by treatment with H$_2$O. The ester compounds of formula 95 are then reduced to the aldehyde compounds of formula 96 by reaction with lithium aluminum hydride in THF at reduced temperatures for 0.5–2 hours, followed by reaction with oxalyl chloride and DMSO in the presence of triethyl amine at −78° C. for 0.25–1.0 hours. The compounds of formula 96 are reacted with with a malonic acid diester, such as diethyl malonate, dibenzyl malonate, t-butyl malonate or di-t-butyl malonate, in the presence of a suitable base such as piperidine and a catalytic amount of an acid, such as acetic acid or sulfuric acid, in a polar solvent, such as ethanol, followed by isolation of the intermediate compounds of formula 97 with subsequent treatment thereof by heating in a polar, high-boiling solvent such as DMF or DMSO at reflux temperature or in Dowtherm A™ for a period of from 0.5 to 4 hours to form the pyridopyrimidine compounds of formula 98. The chloro group of the compounds 98 is displaced as discussed in reaction Scheme I to afford the compounds of formula 99, which are in turn converted into the compounds of formula Ib as described in Scheme I for the conversion of compounds of formula 13A into compounds of formula I.

In accordance with Scheme XIII, trifluoropyridine ether of formula 90 is reacted with a suitable strong base, for example, LDA, preferably at a temperature below 0° C. and conveniently at −78° C., in an inert solvent such as THF, for example. The anion thus generated is then reacted with an alkyl borate, such as, for example, trimethylborate or triethylborate, followed by oxidation with hydrogen peroxide in the presence of base such as sodium hydroxide in situ to give the compound of formula 100, wherein $R^7$ is lower alkyl. Compound 100 is then alkylated with a suitable alkylating agent, such as an alkyl iodide or alkyl sulfate, for example methyl sulfate or ethyl iodide or the like, in the presence of a base such as sodium hydroxide, barium hydroxide, potassium carbonate, lithium carbonate, or the like, in a polar solvent, such as acetone, ethanol, DMF, THF, or the like, within a temperature range of room temperature to reflux temperature of the solvent, to give the compound of formula 101. Alternately, compound 101 can be obtained by treating compound 100 with an alcohol of the formula $R^7OH$, wherein $R^7$ is as described above, triphenylphosphine and diethyldiazocarboxylate in a solvent such as THF at a temperature in the range of 0° C. to room temperature.

In accordance with Scheme XIV, commercially available pentafluoropyridine of formula 102, is reacted with an alkali metal salt of t-butanol, for example, sodium t-butoxide or potassium t-butoxide, in an anhydrous organic solvent such as THF, at a temperature in the range of −78° C. to room temperature, to give the compound of formula 103. Compound 103 is then reacted with hydrazine at a temperature in the range of room temperature to reflux temperature, and in a solvent such as methanol, iso-propanol, ether, or the like, followed by bubbling air through the solution of the intermediate in a solvent such as benzene of toluene, in the presence of a base such as sodium hydroxide to give to compound of formula 104.

In accordance with Scheme XV, the pentafluoropyridine of formula 102 is dissolved in a solvent, such as for example, THF or methylene chloride, and reacted with a cyclic amine of the formula $R^2H$, wherein $R^2$ is as defined above, or, when $R^2$ is substituted with a reactive group such as an amino group, a cyclic amine with suitably protected reactive substituents, in the presence of a suitable base, such as a tertiary amine, such as for example triethylamine, at a temperature in the range of 0° C. to room temperature. The reactant of formula 106, wherein $R^{16}$ is as defined above and TBS represents a tributylsilyl group, is generated from the corresponding iodide starting material by reaction with t-butyl lithium in ether at −78° C., and is reacted with compound 105 in a solvent such as THF or ether at −78° C. to give the compound of formula 107. The protecting TBS group is removed from compound 107 by reaction with tetrabutylammonium fluoride in THF at room temperature to give the compound of formula 108. The trifluoro compound 108 is converted into the difluoro compound 109 by reacting compound 108 with hydrazine at reflux temperature in a solvent such as ether, propanol, or methoxymethyl ether, followed by treatment of an intermediate hydrazino product with CuSO4 in a solvent such as methanol, ethanol, or toluene, or alternately by reaction with air in the presence of a base such as NaOH. The monocyclic compound 109 is then converted into the bicyclic compound of formula 110 by reaction with NaH at reflux temperature in a solvent such as dioxane or THF. Compound 110 is then treated with a strong base, such as LDA at −78° C., for example, and condensed with diethyl ethoxymethylenemalonate to give an intermediate product which is cyclized in the presence of a base such as DBU or piperidine/acetic acid, in a solvent such a ethanol or aqueous THF, at a temperature from room temperature to 60° C., to give the tricyclic ester of formula 111. The ester 111 is hydrolyzed to the acid of formula 112 with an alkali metal hydroxide in aqueous THF, for example. Any protecting groups remaining on the R2 or R16 groups may conveniently be removed at this point to give the desired compound of Formula I.

In accordance with Scheme XVI, an alternate method of preparing compounds 112 is given. Compound 103 (from Scheme XIV) is reacted with compound 106 (from Scheme XV) in a solvent such as THF or ether at −78° C. to give a TBS-protected intermediate compound, from which the TBS group is removed by reaction with tetrabutylammonium fluoride in THF at room temperature to give the compound of formula 113. The trifluoro compound 113 is converted into the difluoro compound 114 by reaction with hydrazine at reflux temperature in a solvent such as ether, propanol, or methoxymethyl ether, followed by treatment of an intermediate hydrazino product with CuSO4 in a solvent such as methanol, ethanol, or toluene, or alternately by reaction with air in the presence of a base such as NaOH. The monocyclic compound 114 is then converted into the bicyclic compound of formula 115 by reaction with NaH at reflux temperature in a solvent such as dioxane or THF. Compound 115 is then treated with a strong base, such as LDA at −78° C., for example, and condensed with diethyl ethoxymethylenemalonate to give an intermediate product which is cyclized in the presence of a base such as DBU or piperidine/acetic acid, in a solvent such a ethanol or aqueous THF, at a temperature from room temperature to 60° C., to give the tricyclic ester of formula 116. The protecting t-butoxy group is removed from compounds 116 by reaction with an acid, such as HCl or trifluoroacetic acid at room temperature, and optionally in a suitable solvent, such as methylene chloride or dioxane to give compound s 117. The free hydroxy group of compounds 117 is then reacted with POCl3/DMF in a suitable solvent such as methylene chloride at room temperature to give the chloro compounds of formula 118. Compounds 118 are reacted with a cyclic amine of the formula $R^2H$, wherein $R^2$ is as defined above, or, when $R^2$ is substituted with a reactive group such as an amino group, a cyclic amine with suitably protected reactive substituents, in the presence of a suitable base, such as a tertiary amine, such as for example triethylamine, in a suitable solven, such as acetonitrile or pyridine, at a reflux temperature to give the compounds 111. The ester group is hydrolyzed, and optional additional protecting groups removed, as described in Scheme XV.

In accordance with Scheme XVII are prepared desired compounds of Formula I wherein $R^5$ is amino Compounds of formula 91 are reacted with HN-P, wherein P are amino protecting groups, for example benzyl and p-methoxybenzyl groups, in a solvent such as ethanol or toluene, at elevated temperature to give compounds of formula 119. Compounds of formula 119 are treated according to the procedures as described in Schemes XII, XV and XVI above to provide compounds of formula 120. Deprotection of protected amino compounds of formula 120 by catalytic hydrogenation such as Pd-C in ethanol or methanol at room temperature, or by oxidation if R is p-methoxybenzyl with ammonium cerium nitrate, and the resulting compounds of formula 121 are hydrolyzed by a base such as LiOH or NaOH to give compounds of formula 122.

In accordance with Scheme XVIII are prepared compounds of Formula I wherein the $R^2$ group is a ring group attached via a carbon atom. Compounds of formula 123, wherein X is a leaving group such as chloride, bromide, iodide, fluoride or sulfonate, for example, is treated with an appropriately substituted malonate, wherein R, R' could be the same or different) are alkyl groups, such as diethyl and di-t-butyl malonate, in a polar solvent such as DMF, DMSO, or the like, in the presence of a strong base such as NaH, at a temperature between 0° to 60° C., to give compounds of formula 124. Decarboxylation of compounds of formula 124 under acidic conditions, such as trifluoroacetic acid and hydrogen chloride in a solvent such as methylene chloride, ethanol, water, or the like, followed by protection of the intermediate acid with an ester such as diphenylmethyl ester by treating with diphenyl diazomethane in a solvent such as methylene chloride or THF, gives the compounds of formula 125. Compounds of formula 125 are then cyclized to compounds of formula 126 by reaction with $Br(CH2)_nB(CH2)_mBr$ or $I(CH2)_nB(CH2)_mI$ or $R_b$ substituted iodide or bromide, for example, wherein B is $CH_2$, N, O or S, in the presence of a base such as NaH and in a solvent such as DMF, DMSO, or the like, at room temperature or elevated temperature. Alternately, conversion of compounds of formula 125 to the methylenyl intermediate by reacting with aqueous formaldehyde with a base such as sodium bicarbonate in a solvent such as DMF, followed by reacting with methanesulfonyl chloride and triethylamine. The methylenyl compound is then converted to compound 126 by cyclization or dipolar addition with a suitable reagent, such as trimethylsulfonium iodide or diazomethane for cyclopropyl compound, in a solvent such as DMF, DMSO, or the like at 0° to 60° C. in the presence of a suitable base such as NaH. Selective deprotection of the ester 'ROCO, such as using trifluoroacetic acid and anisol at room temperature for diphenylmethyl ester, followed by alkaline hydrolysis of the other ester provides the desired compounds of formula 127, and followed by Curtius rearrangement when 'R$_2$ is NH$_2$. In the compounds of formulas 126 and 127, n and m may be from 0–4, n+m=1–4, B may be $CH_2$, N, O or S; $R^b$ may be hydrogen, alkyl, amino, aminoalkyl, hydroxyl or alkoxyl groups, for example, or other substituents as described for substituent Y in subformula Ib above.

Representative of the chemical intermediates which are useful in the above syntheses, and which are regarded as a further aspect of the present invention, are the following compounds:

4-t-butoxy-3-chloro-2,5,6-trifluoropyridine;

4-t-butoxy-2,3,6-trifluoropyridine;

4-t-butoxy-2,3,6-trifluoro-5-methylpyridine;

4-t-butoxy-2,5-difluoro-3-methylpyridine;

2-(4-t-butoxy-5-fluoro-3-methyl-2-pyridinyl)cyclopropaneacetonitrile;

2-(4-chloro-5-fluoro-3-methyl-2-pyridinyl)cyclopropaneacetonitrile;

2-(4-chloro-5-fluoro-3-methyl-2-pyridinyl)cyclopropaneacetic acid;

ethyl 2-(4-chloro-5-fluoro-3-methyl-2-pyridinyl)cyclopropaneacetate;

2-(4-chloro-5-fluoro-3-methyl-2-pyridinyl)cyclopropaneacetaldehyde;

2-(4-chloro-5-fluoro-3-methyl-2-pyridinyl)cyclopropaneethanol;

2-(2-(4-chloro-5-fluoro-3-methyl-2-pyridinyl)-2-cyclopropylethylidinyl)-1,3-propanedicarboxylic acid, diethyl ester; and 8-chloro-1-cyclopropyl-7-fluoro-9-methyl-4-oxo-4h-quinolizine-3-carboxylic acid ethyl ester.

The foregoing may be better understood from the following examples, which are presented for the purpose of illustration and are not intended as a limitation upon the scope of the invention.

EXAMPLE 1

3-Fluoro-9-(4-fluorophenyl)-2-(4-methylpiperazin-1-yl)-6H-6oxo-pyrido[1,2-a]pyrimidine-7-carboxylic acid Step 1: 5-Fluoro-2-(4-fluorobenzyl)-4-hydroxypyrimidine Sodium hydride (4.36 g of 60% NaH in mineral oil, 107.6 mmol) was suspended, under a nitrogen atmosphere, in 125 mL of anhydrous diethyl ether in a 500 mL round-bottom flask fitted with a mechanical stirrer, a thermometer and a condenser. To this mixture, with vigorous stirring, was slowly added 6.28 mL (107.6 mmol) of anhydrous ethyl alcohol. After the evolution of gas ceased, a mixture of ethyl 2-fluoroacetate (10 mL, 102.5 mmol) and ethyl formate (12.5 mL, 153.7 mmol) was added, dropwise, to the ethoxide solution. The reaction mixture was cooled when necessary in order to maintain the reaction temperature between 18° C. and 20° C. The reaction mixture was stirred, under a nitrogen atmosphere, at 18°–20° C. for 4.75 hours. The solvent was removed under aspirator pressure, fresh anhydrous diethyl ether was added to the residue and the ether solution was concentrated under reduced pressure to afford, as a solid residue, the sodium enolate of ethyl 2-fluoro-3-oxo-2-propanecarboxylate, as described by E. Elkik and M. Imbeaux-Oudotte in *Bull Soc Chim*, 1165–1169, 1975. To this residue was added 20.3 g (107.6 mmol) of 4-fluorobenzylamidine hydrochloride, followed by 250 mL of methanol and 28.8 mL (205 mmol) of triethylamine (TEA). The reaction mixture was heated, with stirring, at reflux temperature for 16 hours and then concentrated in vacuo. The residue was triturated with hexane and the hexane was decanted. Water was added to the residue and the aqueous mixture was acidified with glacial acetic acid and extracted with 4×150 mL of methylene chloride. The combined organic extract was washed with 200 mL of water and concentrated in vacuo. The residue was recrystallized twice from ethyl acetate containing Norite® charcoal to afford the title compound, m.p. 169°–170° C.; MS DCI-NH$_3$ M/Z: 223 (M+H)$^+$; $^1$H NMR (DMSO-d6) d 3.87 (s, 2H), 7.14 (m, 2H), 7.33 (m, 2H), 7.98 (d, 1H). Analysis calculated for C$_{11}$H$_8$F$_2$N$_2$O: C, 59.46; H, 3.63; N, 12.61. Found: C, 59.08; H, 3.70; N, 12.57.

Step 2: 4-Chloro-5-fluoro-2-(4-fluorobenzyl)-pyrimidine

A mixture of 1.93 g (8.7 mmol) of 5-fluoro-2-(4-fluorobenzyl)-4-hydroxypyrimidine, from Step 1, and 15 mL of phosphorus oxychloride was heated in an oil bath at 90° C. for 1.5 hours and then concentrated in vacuo. The residue was triturated with 75 mL of ice water and the aqueous mixture was adjusted to pH 8–9 by the addition of solid sodium bicarbonate. The mixture was extracted with 3×70 mL of methylene chloride. The combined organic extracts were dried over anhydrous magnesium sulfate, filtered and concentrated in vacuo to a light brown residue. The residue was purified by flash chromatography on a 230–400 mesh silica gel column (4.8×14.6 cm) eluted with hexane:methylene chloride (1:1 v/v) to afford 1.94 g (90% yield) of the title compound; MS DCI-NH$_3$ M/Z: 241 (M+H)$^+$; $^1$H NMR (CDCl$_3$) d 4.22 (s, 2H), 7.00 (m, 2H), 7.30 (m, 2H), 8.48 (s, 1H).

Step 3: 5-Fluoro-2-(4-fluorobenzyl)-4-(4-methylpiperazin-1-yl)-pyrimidine

A mixture of 0.48 g (2 mmol) of 4-chloro-5-fluoro-2-(4-fluorobenzyl)-pyrimidine from Step 2 and 1.53 mL (14 mmol) of 4-methylpiperazine in 10 mL of methylene chloride was stirred at ambient temperature for 1.5 hours. The reaction mixture was concentrated in vacuo and the residue was dissolved in methylene chloride. The resultant solution was washed with 4×30 mL of water, dried over anhydrous magnesium sulfate, filtered and concentrated in vacuo to give 0.59 g (95% yield) of the title compound as an oil; $^1$H NMR (CDCl$_3$) d 2.32 (s, 3H), 2.47 (t, 4H), 3.78 (t, 4H), 3.99 (s, 2H), 6.97 (m, 2H), 7.29 (m, 2H), 7.97 (d, 1H). The product was carded on to the next step without purification.

Step 4: Diethyl 2-ethoxy-3-(4-fluorophenyl)-3-[5-fluoro-4-(4-methypiperazin-1-yl)pyrimidin-2-yl]-propane-1,1-dicarboxylate A solution of 0.35 mL (2.5 mmol) of diisopropylamine in 5 mL of anhydrous tetrahydrofuran (THF) was prepared under a nitrogen atmosphere and cooled in an ice/water bath. To this solution was added via syringe, 1.0 mL of a 2.5M solution of n-butyllithium (2.5 mmol) in hexane. The solution was stirred for 15 minutes at 0° C. and then cooled to –78° C. To the mixture at –78° C., was added a solution of 0.7 g (2.3 mmol) of 5-fluoro-2-(4-fluorobenzyl)-4-(4-methylpiperazin-1-yl)-pyrimidine, from Step 3, in 5 mL of anhydrous THF and a dark red-colored solution was formed. The solution was stirred at –78° C. for 1 hour and then 0.46 mL (2.3 mmol) of ethyl 2-carboethoxy-3-ethoxy-2-propenecarboxylate was added. Stirring was continued at –78° C. for 3 hours and the reaction mixture turned a light yellow color. The reaction mixture was poured into 30 mL of water, with 6 g of solid ammonium chloride. The aqueous mixture was extracted with 4×50 mL of methylene chloride. The combined organic extract was dried over magnesium sulfate, filtered and concentrated in vacuo. The residue was dissolved in 300 mL of methylene chloride. The resultant solution was washed with a 50 mL portion of water, followed by a 75 mL portion of water, dried over anhydrous magnesium sulfate, filtered and concentrated in vacuo to afford the title compound; MS DCI-NH$_3$ M/Z: 521 (M+H)$^+$; $^1$H NMR (CDCl$_3$) d 0.84 (2xt, 3H), 1.18 (t, 3H), 1.28 (t, 3H), 2.33 (s, 3H), 2.50 (m, 4H), 3.36–3.53 (m, 2H), 3.83 (s, 4H), 3.96–4.22 (m, 4H), 4.42 (t, 1H), 4.98 (dd, 1H), 6.95 (m, 2H), 7.48 (m, 2H), 7.99 (d, 1H).

Step 5: Ethyl 3-fluoro-9-(4-fluorophenyl)-2-(4-methylpiperazin-1-yl)-6H-6-oxo-pyrido[1,2-a]pyrimidine-7-carboxylate A solution of 0.57 g (1.1 mmol) of diethyl 2-ethoxy-3-(4-fluorophenyl)-3-[5-fluoro-4-(4-methypiperazin-1-ylpyrimidin-2-yl]-propane-1,1-dicarboxylate, from Step 4, and 0.2 mL of 1,8-diazabicyclo[5.4.0]undec-7-ene (DBU) in 200 mL of toluene was heated at reflux temperature, with stirring, for 20.5 hours. During the first 0.5 hours, 125 mL of toluene was removed via Dean Stark trap and 100 mL of fresh toluene was added through a dropping funnel. Water (75 mL) was added to the reaction mixture and stirring was continued at ambient temperature for 3 hours. The organic layer was separated and washed with 75 mL of water. The combined aqueous layers were extracted with 3×75 mL of toluene. The organic layers were all combined, dried over anhydrous magnesium sulfate, filtered and concentrated in vacuo. The residue (0.32 g) was purified on a 70–230 mesh silica gel column (2.4×43 cm) eluted with ethyl alcohol:chloroform (1:10 v/v) to afford 0.26 g (56% yield) of the title compound, m.p. 202°–204° C.; MS DCI-NH$_3$ M/Z: 429 (M+H)$^+$; $^1$H NMR (CDCl$_3$) d 1.40 (t, 3H), 2.33 (s, 3H), 2.51 (m, 4H), 3.93 (m, 4H), 4.40 (q, 2H), 7.08 (t, 2H), 7.50 (m, 2H), 8.43 (s, 1H), 9.20 (d, 1H).

Step 6: Benzyl 3-fluoro-9-(4-fluorophenyl)-2-(4-methylpiperazin-1-yl)-6H-6-oxo-pyrido[1,2-a]pyrimidine-7-carboxylate A mixture of 0.11 g (0.26 mmol) of ethyl 3-fluoro-9-(4-fluorophenyl)-2-(4-methylpiperazin-1-yl)-6H-6-oxo-pyrido[1,2-a]pyrimidine-7-carboxylate, from Step 5, 50 mL of dry benzyl alcohol and 0.05 mL of titanium tetraethoxide was heated, with stirring, at 100° C. for 22 hours. The benzyl alcohol was removed by distillation under reduced pressure and the residue was dissolved in 75 mL of methylene chloride. To this solution was added 5 mL of saturated aqueous lithium fluoride solution and the resultant mixture was stirred at ambient temperature for 20 minutes. The layers were separated and the organic layer was diluted with 75 mL of methylene chloride and washed with 20 mL of water. The aqueous layer was extracted with 25 mL of methylene chloride and the methylene chloride layer from this extraction was combined with the organic layer. The combined organic layers were dried over anhydrous magnesium sulfate, filtered and concentrated. The residue (0.18 g) was chromatographed on a 70–230 mesh silica gel column (1.8×34 cm) eluted with ethanol:chloroform (1:13 v/v) to afford 87 mg (67% yield) of the title compound; $^1$H NMR (CDCl$_3$) d 2.33 (s, 3H), 2.52 (m, 4H), 3.94 (m, 4H), 5.40 (s, 2H), 7.08 (s, 2H), 7.27 (m, 5H), 8.44 (s, 1H), 9.21 (d, 1H). The product was carded on to the next step without further purification.

Step 7: 3-Fluoro-9-(4-fluorophenyl)-2-(4-methylpiperazin-1-yl)-6H-6-oxo-pyrido[1,2-a]pyrimidine-7-carboxylic acid Benzyl 3-fluoro-9-(4-fluorophenyl)-2-(4-methylpiperazin-1-yl)-6H-6-oxo-pyrido[1,2-a]pyrimidine-7-carboxylate (87 mg, 0.177 mmol), from Step 6, was dissolved in 20 mL of ethyl acetate. To this solution was added 20 mg of 10% palladium on carbon and the resultant mixture was hydrogenated at ambient temperature, under 4 atmospheres of hydrogen, for approximately 19 hours. The catalyst was removed by filtration and washed with 400 mL of ethyl acetate The filtrate was concentrated in vacuo to give 65.2 mg of solid. The solid was purified by chromatography on a 70–230 mesh silica gel column (1.8×18.5 cm) eluted with chloroform:methanol:acetic acid:water (100:25:5:2.5 v/v/v/v). The fractions containing the desired product were combined and concentrated. Toluene was added to the residue and evaporated in vacuo. Chloroform was then added to the residue and evaporated in vacuo to afford the title compound as a yellow solid, m.p. 225°–230° C.; MS DCI-NH$_3$ M/Z: 401 (M+H)$^+$; $^1$H NMR (CDCl$_3$) d 1.68 (brs, 1H), 2.33 (s, 3H), 2.53 (brs, 4H), 3.98 (brs, 4H), 7.10 (t, 2H), 7.48 (m, 2H), 8.57 (s, 1H), 9.08 (d, 2H). Analysis calculated for $C_{20}H_{18}F_2N_4O_3+0.75H_2O$: C, 58.03; H, 4.75; N, 13.54. Found: C, 57.98; H, 4.32; N, 13.22.

EXAMPLE 2

3-Fluoro-9-(4-fluorophenyl)-2-(4-methylpiperazin-1-yl)-6H-6-oxo-pyrido[1,2-a]pyrimidine-7-carboxylic acid Step 1: Ethyl 3-fluoro-9-(4-fluorophenyl)-2-hydroxy-6H-6-oxo-pyrido[1,2-a]pyrimidine-7-carboxylate To a stirred solution of 0.87 g (2.05 mmol) of ethyl 3-fluoro-9-(4-fluorophenyl)-2-(4-methylpiperazin-1-yl)-6H-6-oxo-pyrido[1,2-a]pyrimidine-7-carboxylate, the product of Step 5 of Example 1, in 54 mL of THF/water (1:1) was added 6 mL of 1N aqueous sodium hydroxide solution. The reaction mixture was stirred at ambient temperature for 6 hours and then was allowed to stand overnight at ambient temperature. The solid was filtered and dried to give the title compound; $^1$H NMR (d$_6$-DMSO) d 1.23 (t, 3H), 4.15 (q, 2H), 7.17 (m, 2H), 7.52 (m, 2H), 7.91 (s, 1H), 8.77 (d, 1H).

Step 2: Ethyl 2-chloro-3-fluoro-9-(4-flourophenyl)-6H-6-oxo-pyrido[1,2-a]pyrimidine-7-carboxylate A mixture of 55.7 mg of ethyl 3-fluoro-9-(4-fluorophenyl)-2-hydroxy-6H-6-oxopyrido[1,2-a]pyrimidine-7-carboxylate from Step 1 and 0.5 mL of phosphorus oxychloride was stirred and heated at 90° C. for 1.25 hours. The mixture was evaporated under reduced pressure to yield the title compound which can be reacted with amines without purification. A pure sample of the title compound is obtained by treatment of the crude product with aqueous sodium bicarbonate solution and extracting the aqueous mixture with methylene chloride. The organic solution is concentrated and chromatographed on silica gel eluting with ethyl acetate.

Step 3: Ethyl 3-fluoro-9-(4-fluorophenyl)-2-(4-methylpiperazin-1-yl)-6H-6-oxo-pyrido[1,2-a]pyrimidine-7-carboxylate Following the procedures described in Step 3 of Example 1, ethyl 2-chloro-3-fluoro-9-(4-fluorophenyl)-6H-6-oxo-pyrido[1,2-a]pyrimidine-7-carboxylate from Step 2 is reacted with 4-methylpiperazine to afford the title compound.

Step 4: Benzyl 3-fluoro-9-(4-fluorophenyl)-2-(4-methylpiperazin-1-yl)-6H-6-oxo-pyrido[1,2-a]pyrimidine-7-carboxylate A mixture of 0.11 g (0.26 mmol) of ethyl 3-fluoro-9-(4-fluorophenyl)-2-(4-methylpiperazin-1-yl)-6H-6-oxo-pyrido[1,2-a]pyrimidine-7-carboxylate, from Step 3, 50 mL of dry benzyl alcohol and 0.05 mL of titanium tetraethoxide was heated, with stirring, at 100° C. for 22 hours. The benzyl alcohol was removed by distillation under reduced pressure and the residue was dissolved in 75 mL of methylene chloride. To this solution was added 5 mL of saturated aqueous lithium fluoride solution and the resultant mixture was stirred at ambient temperature for 20 minutes. The layers were separated and the organic layer was diluted with 75 mL of methylene chloride and washed with 20 mL of water. The aqueous layer was extracted with 25 mL of methylene chloride and the methylene chloride layer from this extraction was combined with the organic layer. The combined organic layers were dried over anhydrous magnesium sulfate, filtered and concentrated. The residue (0.18 g) was chromatographed on a 70–230 mesh silica gel column (1.8×34 cm) eluted with ethanol:chloroform (1:13 v/v) to afford 87 mg (67% yield) of the title compound; $^1$H NMR (CDCl$_3$) d 2.33 (s, 3H), 2.52 (m, 4H), 3.94 (m, 4H), 5.40 (s, 2H), 7.08 (s, 2H), 7.27 (m, 5H), 8.44 (s, 1H), 9.21 (d, 1H). The product was carried on to the next step without further purification.

Step 5: 3-Fluoro-9-(4-fluorophenyl)-2-(4-methylpiperazin-1-yl)-6H-6-oxo-pyrido[1,2-a]pyrimidine-7-carboxylic acid Benzyl 3-fluoro-9-(4-fluorophenyl)-2-(4-methylpiperazin-1-yl)-6H-6-oxo-pyrido[1,2-a]pyrimidine-7-carboxylate (87 mg, 0.177 mmol), from Step 4, was dissolved in 20 mL of ethyl acetate. To this solution was added 20 mg of 10% palladium on carbon and the resultant mixture was hydrogenated at ambient temperature, under 4 atmospheres of hydrogen, for approximately 19 hours. The catalyst was removed by filtration and washed with 400 mL of ethyl acetate The filtrate was concentrated in vacuo to give 65.2 mg of solid. The solid was purified by chromatography on a 70–230 mesh silica gel column (1.8×18.5 cm) eluted with chloroform:methanol:acetic acid:water (100:25:5:2.5 v/v/v/v). The fractions containing the desired product were combined and concentrated. Toluene was added to the residue and evaporated in vacuo. Chloroform was then added to the residue and evaporated in vacuo to afford the title compound as a yellow solid, m.p. 225°–230° C.; MS DCI-NH$_3$ M/Z: 401 (M+H)$^+$; $^1$H NMR (CDCl$_3$) d 1.68 (brs, 1H), 2.33 (s, 3H), 2.53 (brs, 4H), 3.98 (brs, 4H), 7.10 (t, 2H), 7.48 (m, 2H), 8.57 (s, 1H), 9.08 (d, 2H). Analysis calculated for C$_{20}$H$_{18}$F$_2$N$_4$O$_3$+0.75H$_2$O: C, 58.03; H, 4.75; N, 13.54. Found: C, 57.98; H, 4.32; N, 13.22.

EXAMPLES 3–38

By following the procedures described in Example 2 and using the appropriate amine, Examples 3–20, as disclosed in Table 1, may be prepared which have the general formula

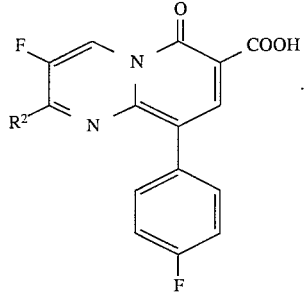

Likewise, Examples 21–38, as also disclosed in Table 1, may be prepared by using the appropriate amine and 2,4-difluorobenzylamidine instead of 4-fluoro-benzylamidine to produce the general formula

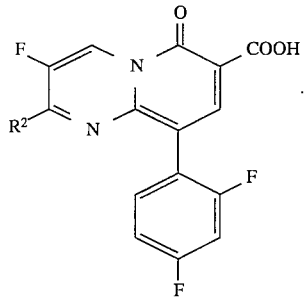

TABLE 1

| Example Nos. | R² | Example Nos. | R² |
|---|---|---|---|
| 3, 21 | piperazinyl-NH* | 12, 30 | morpholinyl (O) |
| 4, 22 | 2-methyl-3-amino-piperazinyl (CH₃, NH*) | 13, 31 | 3-(methylaminomethyl)morpholinyl (CH₂NH*CH₃, O) |
| 5, 23 | 4-ethylpiperazinyl | 14, 32 | pyrrolidinyl |
| 6, 24 | 3-(dimethylamino)piperazinyl (N(CH₃)₂) | 15, 33 | 3-aminopyrrolidinyl (NH₂*) |
| 7, 25 | 2,5-dimethyl-3-amino-piperazinyl (CH₃, NH*, CH₃) | 16, 34 | 3-amino-4-methylpyrrolidinyl (NH₂*, CH₃) |
| 8, 26 | 2-(fluoromethyl)-3-amino-piperazinyl (CH₂F, NH*) | 17, 35 | 3-amino-5-methylpyrrolidinyl (CH₃, NH₂*) |
| 9, 27 | 3-aminopiperidinyl (NH₂*) | 18, 36 | 3-amino-4-chloropyrrolidinyl (NH₂*, Cl) |
| 10, 28 | 4-aminopiperidinyl (NH₂*) | 19, 37 | 3-(aminomethyl)pyrrolidinyl (NH₂*) |
| 11, 29 | thiomorpholinyl (S) | 20, 38 | 3-((ethylamino)methyl)pyrrolidinyl (NH*ET) |

*The amines are protected and deprotected as described in Example 58

EXAMPLE 39

9-Cyclopropyl-3-fluoro-2-(4-methylpiperazin-1-yl)-6H-6-oxo-pyrido[1,2-a]pyrimidine-7-carboxylic acid Step 1: 2-Cyclopropyl-3-hydroxyacrylic acid A 1.1M solution of diethylzine (350 mL) in an oven-dried system under positive nitrogen atmosphere is coled in an ice bath. Vinyl acetic acid (17 mL, 200 mmol) is added dropwise with stirring, followed by 24 mL (300 mmol) of diiodomethane. The reaction mixture is stirred overnight at ambient temperature. The reaction mixture is then cautiously poured into 500 mL of 1N aqueous hydrochloric acid solution and the aqueous mixture is extracted with diethyl ether. The organic layer is dried over anhydrous sodium sulfate, filtered and concentrated. The residue is vacuum distilled to give cyclopropylacetic acid.

The cyclopropylacetic acid (15 g, 150 mmol) in a flask protected from moisture is cooled in an ice bath and 13.2 mL (180 mmol) of thionyl chloride is added dropwise with stirring. After the addition is complete, the reaction mixture is warmed to ambient temperature and then to 50° C. The reaction mixture is heated at 50° C. for 1 hour and then cooled in an ice bath. Absolute ethanol (26 mL, 450 mmol) is added dropwise with stirring to the reaction mixture. After the addition is complete, the reaction mixture is stirred at ambient temperature overnight. The reaction mixture is diluted with 500 mL of methylene chloride and then washed with 200 mL of 5% aqueous sodium bicarbonate solution. The organic layer is dried over anhydrous sodium sulfate, filtered and the ethyl ester of cyclopropylacetic acid is obtained by distillation.

2-Cyclopropyl-3-hydroxyacrylic acid (12.8 g, 100 mmol), from Step 1, is dissolved in 150 mL of dry dimethoxyethane in an oven-dried system under positive nitrogen atmosphere. The resultant solution is cooled in an ice bath and 4.4 g of 60% sodium hydride in mineral oil is added. The mixture is stirred for several hours at approximately 0° C. and then for several hours at ambient temperature. The reaction mixture is cooled in an ice bath and 8.9 mL (110 mmol) of ethyl formate in 90 mL of dry dimethoxyethane is added dropwise with stirring. After the addition is complete, the reaction mixture is stirred overnight at ambient temperature. The reaction mixture is then cautiously poured into 300 mL of saturated aqueous ammonium chloride solution and extracted with ethyl acetate. The ethyl acetate solution is dried over anhydrous sodium sulfate, filtered and concentrated in vacuo to afford the title compound.

Step 2: Ethyl 5-Cyclopropyl-2,6-dihydroxy-nicotinic acid

A solution of 11.5 (88 mmol) of monoethyl malonate monoamide in 25 mL of dry THF is cooled in an ice bath and is treated with 10.7 g (95 mmol) of potassium t-butoxide. The reaction mixture is stirred at 0°–5° C. for 1 hour. A solution of 12.5 g (80 mmol) of 2-cyclopropyl-3-hydroxy-acryllic acid, from Step 1, in 20 mL of dry THF is added dropwise with stirring. The reaction mixture is then warmed to ambient temperature and then heated at reflux overnight. The reaction mixture is poured into brine and is extracted with ethyl acetate. The organic layer is dried over anhydrous sodium sulfate, filtered and concentrated in vacuo to afford the title compound.

Step 3: Ethyl 5-cyclopropyl-2,6-dichloro-nicotinic acid

Ethyl 5-cyclopropyl-2,6-dihydroxy-nicotinic acid (15.6 g, 70 mmol) from Step 2, 1,2-dichloroethane (25 mL), anhydrous DMF (2 mL) and phosphoryl chloride (14.3 mL, 150 mmol) are combined in a system under positive nitrogen atmosphere, The reaction mixture is stirred at ambient temperature for 24 hours then diluted with 1,2-dichloroethane. The reaction mixture is then washed with 5% aqueous sodium bicarbonate solution and brine. The organic layer is dried over anhydrous sodium sulfate, filtered and concentrated in vacuo to afford the title compound.

Step 4: 2-Chloro-5-cyclopropyl-6-N-((4,5dimethoxy-2-nitro-phenyl)methoxycarbonyl)amino-nicotinic acid Ethyl 5-Cyclopropyl-2,6-dichloro-nicotinic acid (11.2 g, 50 mmol) from Step 3 is dissolved in 15 mL of anhydrous DMF. To this solution is added 25 mL of concentrated ammonium hydroxide and the reaction mixture is heated at reflux overnight. The reaction mixture is cooled to ambient temperature, diluted with water and extracted with 1,2-dichloroethane. The organic layer is dried over anhydrous sodium sulfate, filtered and concentrated in vacuo. The residue is dissolved in 250 mL of 1,2-dichloroethane and 200 mL of 10% aqueous sodium carbonate solution. The reaction mixture is cooled in an ice bath and 16.5 g (60 mmol) of 3,4-dimethoxy-6-nitrobenzylchloroformate is added. The reaction mixture is stirred at 0°–5° C. for 1 hour. The layers are separated and the aqueous layer is extracted with 1,2-dichloroethane. The combined organic layers are dried over anhydrous sodium sulfate, filtered and concentrated in vacuo.

Step 5: 2-Chloro-5-cyclopropyl-6-N-((4,5dimethoxy-2-nitro-phenyl)methoxycarbonyl)-N-(2-fluoroacetyl)amino-nicotinic acid 2-Chloro-5-cyclopropyl-6-N-((4,5dimethoxy-2-nitro-phenyl)methoxycarbonyl)amino-nicotinic acid (14.4 g, 30 mmol) from Step 4 is dissolved in 20 mL of dry THF in an oven-dried system under positive nitrogen atmosphere. The reaction mixture is cooled in an ice bath and 1.3 g of 60% sodium hydride in mineral oil is added. The reaction mixture is stired at 0°–5° C. for 1 hour and 3.2 g (33 mmol) of alpha-fluoroacetyl chloride in 5 mL of dry THF is added dropwise with stirring. After the addition is complete, the reaction mixture is slowly warmed to ambient temperature and stirred overnight at ambient temperature. The reaction mixture is then poured into brine and extracted with ethyl acetate. The ethyl acetate solution is dried over anhydrous sodium sulfate, filtered and concentrated in vacuo. to afford the title compound.

Step 6: 2-Chloro-5-cyclopropyl-6-N-((4,5dimethoxy-2-nitro-phenyl)methoxycarbonyl)-N-(2-fluoro-3-hydroxy-1-oxo-1-prop-2-enyl)amino-nicotinic acid Sodium hydride ()880 mg of 60% NaH in mineral oil) is suspended in 10 mL of dry THF. The suspension is cooled in an ice bath and 10.7 g (20 mmol) of 2-chloro-5-cyclopropyl-6-N-((4,5dimethoxy-2-nitro-phenyl)methoxycarbonyl)-N-(2-fluoroacetyl)amino-nicotinic acid, from Step 5, in 150 mL of dry THF is added dropwise with stirring. After the addition is complete, the reaction mixture is stirred at 0°–5° C. for 1 hour. Ethyl formate (1.78 mL, 22 mmol) in 25 mL of dry THF is added dropwise with stirring. After the addition is complete, the reaction is stirred overnight at ambient temperature and then poured into 10% aqueous ammonium chloride solution. The aqueous mixture is extracted with ethyl acetate. The organic layer is dried over anhydrous sodium sulfate, filtered and concentrated in vacuo to afford the title compound.

Step 7: Ethyl 9-Cyclopropyl-1-((4,5dimethoxy-2-nitro-phenyl)methoxycarbonyl)3-fluoro-2-hydroxy-6H-6-oxo-pyrido[1,2-a]pyrimidine-7-carboxylate A solution of 8.5 g (15 mmol) of 2-Chloro-5-cyclopropyl-6-N-((4,5dimethoxy-2-nitro-phenyl)methoxycarbonyl)-N-(2-fluoro-3-hydroxy-1-oxo-1-prop-2-enyl)amino-nicotinic acid, from Step 6, is dissolved in 200 mL of dioxane/water (1:1). To this solution is added 4.1 g (30 mmol) of potassium carbonate. The reaction mixture is heated at reflux with stirring overnight and then cooled to ambient temperature. The reaction mixture is then diluted with water and extracted with ethyl acetate. The organic layer is dried over anhydrous sodium sulfate, filtered and concentrated in vacuo to afford the title compound.

Step 8: Ethyl 9-cyclopropyl-3-fluoro-2-chloro-6H-6-oxo-pyrido[1,2-a]pyrimidine-7-carboxylate Ethyl 9-cyclopropyl-1-((4,5dimethoxy-2-nitro-phenyl)methoxy-carbonyl)3-fluoro-2-hydroxy-6H-6-oxo-pyrido[1,2-a]pyrimidine-7-carboxylate (5.3 g, 10 mmol) from Step 7 is dissolved in 75 mL of 2:1 dioxane:water and the resultant solution is illuminated with 320 nm light for 30 min. The reaction mixture is extracted with ethyl acetate. The organic layer is dried over anhydrous sodium sulfate, filtered and concentrated in vacuo. The residue is purified by silica gel chromatography to afford the product of Step 7 with the nitrogen protecting group removed. This product is dissolved in 1,2-dichloroethane and tretaed with phosphorous oxychloride at ambient temperature for 18 hours. The reaction mixture is diluted with 1,2-dichloroethane and is washed with saturated aqueous sodium bicarbonate solution and brine. The organic layer is dried over anhydrous sodium sulfate, filtered and concentrated in vacuo to afford crude title compound which is purified by recrystallization from ethyl alcohol.

Step 9: Ethyl 9-cyclopropyl-3-fluoro-2-(4-methylpiperazin-1-yl)-6H-6-oxo-pyrido[1,2-a]pyrimidine-7-carboxylic acid Following the procedures described in Step 3 of Example 1, ethyl 9-cyclopropyl-3-fluoro-2-chloro-6H-6-oxo-pyrido

[1,2-a]pyrimidine-7-carboxylate from Step 8 is reacted with 4-methylpiperazine to afford the title compound.
Step 10: 9-cyclopropyl-3-fluoro-2-(4-methylpiperazin-1-yl)-6H-6-oxo-pyrido[1,2-a]pyrimidine-7-carboxylic acid Following the procedures described in Steps 5–7 of Example 1, Ethyl 9-cyclopropyl-3-fluoro-2-(4-methylpiperazin-1-yl)-6H-6-oxo-pyrido[1,2-a]pyrimidine-7-carboxylic acid is converted to the title compound.

EXAMPLES 40–57

By following the procedures described in Example 39 and replacing 4-methylpiperazine in Step 4 with the appropriate amine, Examples 40–57 may be prepared as disclosed in Table 2 wherein the compounds have the general formula

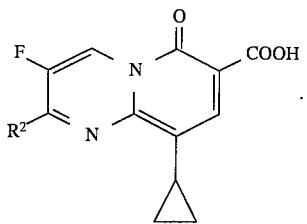

TABLE 2

| Example No. | R² | Example No. | R² |
|---|---|---|---|
| 40 | piperazine-NH* | 49 | morpholine (O) |
| 41 | 2-methylpiperazine-NH* | 50 | morpholine-CH₂NHCH₃* |
| 42 | 4-ethylpiperazine | 51 | pyrrolidine |
| 43 | 3,4-dimethylpiperazine (N-CH₃, CH₃) | 52 | 3-aminopyrrolidine NH₂* |
| 44 | 2,6-dimethylpiperazine-NH* (CH₃, CH₃) | 53 | 3-amino-4-methylpyrrolidine NH₂*, CH₃ |
| 45 | 2-(fluoromethyl)piperazine-NH* (CH₂F) | 54 | 3-amino-5-methylpyrrolidine CH₃, NH₂* |
| 46 | 3-aminopiperidine NH₂* | 55 | 3-amino-4-chloropyrrolidine NH₂*, Cl |
| 47 | 4-aminopiperidine NH₂* | 56 | 3-(aminomethyl)pyrrolidine NH₂* |
| 48 | thiomorpholine (S) | 57 | 3-(ethylaminomethyl)pyrrolidine NHET* |

*The amines are protected and deprotected as described in Example 58

EXAMPLE 58

8-(3-Amino-1-pyrrolidinyl)-4H-quinolizin-4-one-3-carboxylic acid hydrochloride Step 1: 4-Chloro-2-picoline To 34.5 mL (0.37 mol) of phosphorus oxychloride, under a nitrogen atmosphere, was added 20.0 g (0.19 mol) of 2-picoline-N-oxide (commercially available from Aldrich Chemical Company) in small portions. The reaction temperature slowly increased during the addition to ~60° C. After the addition was complete, the reaction mixture was a homogeneous dark red solution and the reaction temperature was 80° C. This solution was heated at 120° C. for 1.5 hours. The reaction mixture was concentrated under reduced pressure in order to remove most of the phosphorus oxychloride and the concentrate was poured into ice water. The aqueous mixture was allowed to stand for 2 hours at ambient temperature and then was extracted with diethyl ether. The ether extract was discarded. The aqueous layer was adjusted to pH 8.0 with potassium carbonate and then extracted with ethyl acetate. The organic extract was dried over anhydrous sodium sulfate, filtered and concentrated under reduced pressure. The liquid concentrate was distilled to afford 8.737 g of a mixture of the title compound and the isomeric 6-chloro-2-picoline as a clear colorless liquid, b.p. 70° C. (25 mm Hg). This product was combined with another sample of the same mixture prepared separately by the same procedure. The isomeric products were inseparable by distillation. The combined products (12.905 g) were dissolved in 750 mL of ethyl alcohol. To the resultant solution was added, dropwise, concentrated nitric acid solution until a white precipitate formed and the pH of the supernatant solution was 1. The precipitate was removed by filtration and dissolved in water. The resultant aqueous solution was adjusted to neutral pH with sodium bicarbonate and then extracted with methylene chloride. The organic extract was dried over anhydrous sodium sulfate, filtered and concentrated under reduced pressure to afford 7.487 g of the title compound. $^1$H NMR (CDCl$_3$) d 2.55 (s, 3H), 7.12 (dd, 1H, J=3 Hz, 6 Hz), 7.18 (d, 1H, J=3 Hz), 8.40 (d, 1H, J=6 Hz).

Step 2: Diethyl 2-ethoxy-3-(5-fluoropyridin-2-yl)-propane-1,1-dicarboxylate

Lithium diisopropylamide (LDA: 16 mL of a 1.5M solution in hexane) was added to 8 mL of dry THF, under a nitrogen atmosphere, and the resultant solution was cooled to −70° C. in a isopropyl alcohol/dry ice bath. To the cooled solution of LDA, was added dropwise, over a 30 minute period, a solution of 2.5 g (19.6 mmol) of 4-chloro-2-picoline, from Step 1, in 20 mL of dry THF. The solution turned a very dark red color. After stirring the dark red solution for 0.5 hours at −70° C., a solution of 4.04 mL (19.6 mmol) of ethoxymethylenemalonate in 18 mL of dry THF was added dropwise over a 30 minute period. The reaction solution turned from dark red to orange. After stirring for 0.5 hours at −70° C., the reaction solution was allowed to warm to −20° C. and was stirred at −20° C. for 1 hour. The reaction was quenched at −20° C. by the addition of 1.3 mL of glacial acetic acid and the cooling bath was removed. After 20 minutes the reaction solution was poured into 5% aqueous sodium bicarbonate solution. The aqueous mixture was extracted with methylene chloride and the organic extract was dried over anhydrous sodium sulfate, filtered and concentrated under reduced pressure. The residue (8.03 g) was purified by chromatography on a silica gel column (~120 g of SiO$_2$) eluted with 0.5% methanol in methylene chloride to afford 4.59 g (68% yield) of the title compound.

Step 3: Ethyl 8-chloro-4H-quinolizin-4-one-3-carboxylate 80 mL of Dowtherm A® in a 3-neck flask equipped with a thermometer, an addition funnel and an air-cooled condenser was heated to 235° C., under nitrogen, using a heating mantel. A solution of 4.26 g (12.4 mmol) of diethyl 2-ethoxy-3-(5-fluoropyridin-2-yl)-propane-1,1-dicarboxylate, from Step 2, in 45 mL of Dowtherm A® was added, dropwise over a 1.5 hours period, through the addition funnel to the heated stirring Dowtherm A®. After the addition was complete, the resultant solution was heated at ~200° C. for 1 hour and then was cooled to ambient temperature. The black-green-colored solution was then poured into 500 mL of hexane and a precipitate formed. The precipitate was collected by filtration, washed with 5×100 mL of hexane and dried to afford 1.487 g (48% yield) of the title compound.

Step 4: Ethyl 8-(3-(N-t-butoxycarbonyl)amino-1-pyrrolidinyl)-4H-quinolizin-4-one-3-carboxylate Ethyl 8-chloro-4H-quinolizin-4-one-3-carboxylate (1.0 g, 3.97 mmol), from Step 3, was dissolved in 20 mL of dry pyridine under a nitrogen atmosphere. To the resultant solution was added a solution of 1.85 g (9.92 mmol) of 3-(N-t-butoxycarbonylamino)pyrrolidine in 5 mL of dry pyridine and the reaction mixture was heated at 70° C. for 4.5 hours. The reaction mixture was then concentrated in vacuo in order to remove all of the pyridine. The dry residue (3.124 g) was purified by chromatography on silica gel eluted with 2% methanol in methylene chloride to afford 0.889 g (56% yield) of the title compound.

Step 5: 8-(3-Amino-1-pyrrolidinyl)-4H-quinolizin-4-one-3-carboxylic acid hydrochloride A solution of 0.889 g (2.2 mmol) of ethyl 8-(3-(N-t-butoxycarbonyl)amino-1-pyrrolidinyl)-4H-quinolizin-4-one-3-carboxylate, from Step 4, in 20 mL of trifluoroacetic acid (TFA) was stirred for 2 hours at ambient temperature. The TFA was evaporated in vacuo and the residue was dissolved in 200 mL of methanol. To the resultant solution was added 4.5 g of strongly basic ion exchange resin and the mixture was stirred at ambient temperature for 1 hour. The mixture was filtered and the filtrate was concentrated under reduced pressure to afford crude ethyl 8-(3-amino-1-pyrrolidinyl)-4H-quinolizin-4-one-3-carboxylate as a residue. The residue was dissolved in 5 mL of THF and 11 mL of a 1M aqueous solution of sodium hydroxide was added. The reaction mixture was heated at 60° C. for 1 hour and then the reaction temperature was increased to 85° C. in order to evaporate the THF. The concentrated reaction solution was diluted with 20 mL of water and the pH of the resultant solution was adjusted to 1–2 with concentrated hydrochloric acid. The aqueous solution was concentrated in vacuo. The residue was crystallized from ethyl alcohol:isopropyl alcohol:water (4:4:1 v/v/v) and recrystallized from ethyl alcohol/water to afford 0.388 g (57% yield) of the title compound, m.p.225°–230° C.; MS DCI-NH$_3$: 274 (M-Cl)$^+$ 90%, 230 ((M-Cl)-CO$_2$H)$^+$ base; IR (KBr): 3420 (OH), 1650 (C=O) cm$^{-1}$; $^1$H NMR (TFA) d 2.8–3.1 (m, 6H), 4.62 (m, 1H), 7.06 (s, 1H), 7.4 (d, 2H, J=9 Hz), 8.14 (d, 1H, J=9 Hz), 9.06 (d, 1H, J=9 Hz). Analysis calculated for C$_{14}$H$_{16}$ClN$_3$O$_3$+⅓H$_2$O: C, 53.21; H, 5.10; N, 13.30. Found: C, 53.58; H, 5.38; N, 13.30.

EXAMPLE 59

8-(3-(N-Norvalyl)amino-pyrrolidinyl)-4H-quinolizin-4-one-3-carboxylic acid

3-Amino-1-benzylpyrrolidine (I. Sumio and T. Matsuo, Japanese Kokai JP 5328161, published Mar. 16, 1978) is coupled to N-t-butoxycarbonyl norvaline (Boc-nVal) using conventional N-hydroxysuccinimide coupling procedures. The 1-benzyl group is removed by hydrogenolysis in methanol using palladium on carbon catalyst. The 3-(N-Boc-norvalyl)aminopyrrolidine is then reacted with ethyl 8-chloro-4H-quinolizin-4-one-3-carboxylate, the product of Step 3 of Example 58, as described in Step 4 of Example 58, replacing 3-(N-t-butoxycarbonylamino)pyrrolidine with 3-(N-Boc-norvalyl)aminopyrrolidine, to give 8-(3-(N-norvalyl)amino-pyrrolidinyl)-4H-quinolizin-4-one-3-carboxylic acid with the nitrogen of the amino acid protected with a Boc group. The Boc protecting group is removed by standard hydrolysis using trifluoroacetic acid and dilute aqueous hydrochloric acid.

Using the procedure outlined in Example 59, or any of the other conventional condensation methods listed above, other amino acid derivatives of the compounds of this invention having an amino group can be prepared. Examples of amino acids which can be coupled, either alone or in combination with one and other, include naturally occurring amino acids such as glycine, alanine, leucine, isoleucine, methionine, phenylalanine, valine, and the like, as well as synthetic amino acids such as cyclohexylalanine, cyclohexylglycine, aminopentanoic acid, and the like.

EXAMPLE 60

8-Chloro-4-H-quinolizin-4-one-3-carboxylic acid

Step 1: Ethyl 8-chloro-4H-quinolizin-4-one-3-carboxylate 35 mL of Dowtherm A® in a 3-neck flask equipped with a thermometer, an addition funnel and an air-cooled condenser was heated to 230°–235° C., under positive nitrogen pressure, using a heating mantel. A solution of 2.7 g (7.85 mmol) of diethyl 2-ethoxy-3-(5-fluoropyridin-2-yl)-propane-1,1-dicarboxylate, the product of Step 2 of Example 58, in 45 mL of Dowtherm A® was added, dropwise over a 1.5 hours period, through the addition funnel to the heated stirring Dowtherm A®. After the addition was complete, the resultant solution was heated at ~200° C. for 40 minutes and then was cooled to ambient temperature. The black-green-colored solution was then poured into 600 mL of hexane and a precipitate formed. The precipitate was collected by filtration, washed with 2×150 mL of hexane and dried to afford 1.15 g (58% yield) of the title compound, m.p. 153°–154° C.

Step 2: 8-Chloro-4-H-quinolizin-4-one-3-carboxylic acid

Ethyl 8-chloro-4H-quinolizin-4-one-3-carboxylate (125 mg, 0.5 mmol) was suspended in 5 mL of 0.5N aqueous sodium hydroxide solution. The reaction mixture was heated to 65° C. and 2 mL of THF was added. After the reaction mixture was stirred at 65° C. for 1 hour, the THF was distilled from the mixture. Stirring was continued for 2 hours at 65° C. and then the reaction mixture was allowed to cool to ambient temperature. The aqueous mixture was adjusted to pH 2 with 3 mL of 1.0N aqueous hydrochloric acid solution and diluted with 10 mL of water. The precipitate was collected by filtration, washed with 2×15 mL of water and dried in vacuo to afford 100 mg (89% yield) of the title compound, m.p. 229°–230° C. The product was recrystallized from ethyl alcohol and dried in vacuo to afford 50 mg (44.5% yield) of the title compound, m.p. 237°–238° C.; MS DCI-NH$_3$: 224 (M+H)$^+$, 241 (M+NH$_4$)$^+$; IR (KBr): 3430 (OH), 1740 (C=O) cm$^{-1}$; $^1$H NMR (CDCl$_3$) d 6.89 (d, 1H, J=6.9 Hz), 7.30 (dd, 1H, J=2.1 Hz, J=6.6 Hz), 7.71 (d, 1H, J=2.1 Hz), 8.64 (d, 1H, J=6.9 Hz), 9.25 (d, 1H, J=6.6 Hz). Analysis calculated for C$_{10}$H$_6$ClNO$_3$: C, 53.71; H, 2.70; N, 6.26. Found: C, 54.27; H, 2.86; N, 6.23.

EXAMPLE 61

8-(4-methylpiperazin-1-yl)-4H-quinolizin-4-one-3-carboxylic acid hydrochloride Step 1: Ethyl 8-(4-methylpiperazin-1-yl)-4H-quinolizin-4-one-3-carboxylate Ethyl 8-chloro-4H-quinolizin-4-one-3-carboxylate (755 mg, 3.0 mmol), the product of Step 3 of Example 58, was suspended in 12 mL of dry pyridine under a nitrogen atmosphere. To the resultant solution was added 6.0 mL (6.0 mmol) of N-methylpiperazine and the reaction mixture was heated at 70° C. for 8 hours. The reaction mixture was then concentrated in vacuo in order to remove all of the pyridine. The dry residue (3.124 g) was dissolved in 125 mL of methylene chloride and the methylene chloride solution was washed with 125 mL of saturated sodium chloride solution (brine). The aqueous layer was extracted with 125 mL of methylene chloride and the combined methylene chloride solutions were dried over anhydrous sodium sulfate, filtered and concentrated and dried in vacuo to afford 1.01 g of the title compound.

Step 2: 8-(4-methylpiperazin-1-yl)-4H-quinolizin-4-one-3-carboxylic acid hydrochloride A mixture of 0.865 g (2.75 mmol) of ethyl 8-(4-methylpiperazin-1-yl)-4H-quinolizin-4-one-3-carboxylate, from Step 1, in 12 mL of THF and 16.5 mL of a 0.5N aqueous solution of sodium hydroxide was heated, with stirring, at 75° C. for 8 hours. The THF was removed from the reaction mixture by distillation during the reaction. The concentrated reaction mixture was cooled to ambient temperature and adjusted to pH 2.0 with 10.5 mL of 1N aqueous hydrochloric acid solution. The aqueous solution was concentrated in vacuo to remove ~80% of the water and the concentrate was diluted with 50 mL of 95% ethyl alcohol. The solid was collected by filtration, washed with 2×5 mL of ethyl alcohol and dried in vacuo to afford the desired product. The product was recrystallized from ethyl alcohol/water (3:1 v/v) to afford 0.332 g (37% yield) of the title compound, m.p.257°–258° C.; MS DCI-NH$_3$: 288 (M-Cl)$^+$ 90%, 244 ((M-Cl)-CO$_2$H)$^+$ base, 270 (M-Cl-H$_2$O)$^+$; IR (KBr): 3420 (OH), 1645 (C=O) cm$^{-1}$; $^1$H NMR (TFA) d 3.20 (m, 3H), 3.52 (dd, 2H, J=10 Hz), 4.02 (m, 4H), 4.63 (d, 2H, J=12 Hz), 7.41 (m, 2H), 7.65 (d, 1H, J=7.5 Hz), 8.26 (d, 1H, J=9 Hz), 9.18 (d, 1H, J=7.5 Hz). Analysis calculated for C$_{15}$H$_{18}$ClN$_3$O$_3$+0.5H$_2$O: C, 54.14; H, 5.75; N, 12.62. Found: C, 54.23; H, 5.54; N, 12.64.

EXAMPLE 62

8-(3-Amino-1-pyrrolidinyl)-1-ethyl-4H-quinolizin-4-one-3-carboxylic acid hydrochloride Step 1: 4-Chloro-2-propyl-pyridine A 1.5M solution of LDA in hexane (100 mL, 150 mmol) was cooled to −60° C. in an isopropyl alcohol/dry ice bath. To the stirred LDA solution, under nitrogen, was added, dropwise over a 0.5 hours period, a solution of 17.466 g (137 mmol) of 4-chloro-2-picoline (the product of Step 1 of Example 58) in 80 mL of dry THF. The reaction mixture was stirred for 0.5 hours at −60° C. and then a solution of 10.95 mL (137 mmol) of ethyl iodide in 30 mL of dry THF was added, dropwise over a 20 minute period. After the reaction mixture was stirred at −60° C. for 0.5 hours, the cooling bath was allowed to slowly (1.5 hours) warm to −30° C. According to TLC analysis on silica gel eluted with 5% methanol in methylene chloride, the reaction had gone to completion.

The reaction mixture was poured into cold brine and the aqueous mixture was extracted with methylene chloride. The organic extract was dried over anhydrous sodium sulfate, filtered and concentrated in vacuo. The residue was distilled to afford 12.667 g (60% yield of the title compound, b.p. 77°–80° C. (10 mm Hg).

Step 2: Diethyl 2-ethoxy-3-[4-chloro-2-pyridyl]-pentane-1,1-dicarboxylate

A solution of 12.6 mL (89.9 mmol) of diisopropylamine in 20 mL of anhydrous tetrahydrofuran (THF) was prepared under a nitrogen atmosphere and cooled in an ice/water bath. To this solution was added, dropwise over a 30 minute period, 36 mL of a 2.5M solution of n-butyllithium (90 mmol) in hexane. The solution was stirred for 30 minutes at 0° C. and then cooled to −60° C. To the amine solution at −60° C., was added, dropwise over a 30 minute period, a solution of 12.66 g (81.9 mmol) of 4-chloro-2-propyl-pyridine, from Step 1, in 100 mL of anhydrous THF and a dark red-colored solution was formed. The solution was stirred at −60° C. for 0.5 hours and then 16.55 mL (81.9 mmol) of ethyl 2-carboethoxy-3-ethoxy-2-propenecarboxylate was added, dropwise over a 30 minute period. Stirring was continued at −60° C. for 0.5 hours and at −20° C. for 1.5 hours. The reaction mixture was poured into cold brine and the aqueous mixture was extracted with methylene chloride. The combined organic extract was dried over anhydrous sodium sulfate, filtered and concentrated in vacuo to afford 35.48 g of the title compound. The product was carried on to the next step without purification.

Step 3: Ethyl 8-chloro-1-ethyl-4H-quinolizin-4-one-3-carboxylate

A solution of 35.48 g (99.2 mmol) of diethyl 2-ethoxy-3-[4-chloro-2-pyridyl]-pentane-1,1-dicarboxylate, from Step 2, in 1 L of xylene was heated at 150° C., with stirring, for 24 hours and then concentrated in vacuo. The residue was washed with a mixture of hexane and cyclohexane to afford 14.867 g (54% yield) of the title compound as a green solid; MS DCI-NH$_3$ M/Z: 280 (M+H)$^+$, 246 (M-Cl)$^+$, 217 (MCl-Et)$^+$; $^1$H NMR (CDCl$_3$) d 1.31 (t, 3H, J=7.5 Hz), 1.43 (t, 3H, J=7.2 Hz), 2.78 (q, 2H, J=7.5 Hz), 4.43 (q, 2H, J=7.2 Hz), 7.10 (dd, 1H, J=2.4 Hz, 8.1 Hz), 7.70 (d, 1H, J=2.4 Hz), 8.32 (s, 1H), 9.40 (d, 1H, 8.1 Hz).

Step 4: Ethyl 8-(3-(N-t-butoxycarbonyl)amino-1-pyrrolidinyl)-1-ethyl-4H-quinolizin-4-one-3-carboxylate Ethyl 8-chloro-1-ethyl-4H-quinolizin-4-one-3-carboxylate (1.20 g, 4.3 mmol), from Step 3, was dissolved, under a nitrogen atmosphere, in 15 mL of dry pyridine. To the resultant solution was added 1.04 g (5.59 mmol) of 3-(N-t-butoxycarbonylaminopyrrolidine) and 1.8 mL (12.9 mmol) of dry triethylamine and the reaction mixture was heated at 60° C. for 12 hours. The reaction mixture was then concentrated in vacuo in order to remove all of the pyridine. Ethyl alcohol (4 mL) was added to the dry residue. The mixture was filtered to give 0.421 g of the desired product as a solid. The filtrate was concentrated and the residue purified by flash chromatography on silica gel eluted with 2% methanol in methylene chloride, followed by 5% methanol in methylene chloride to afford an additional 1.273 g of the desired product. The title compound was obtained in 92% yield (1.694 g) as a yellow solid and taken on to the next step.

Step 5: 8-(3-Amino-1-pyrrolidinyl)-1-ethyl-4H-quinolizin-4-one-3-carboxylic acid hydrocloride A solution of 1.694 g (3.94 mmol) of ethyl 8-(3-(N-t-butoxycarbonyl)-amino-1-pyrrolidinyl)-1-ethyl-4H-quinolizin-4-one-3-carboxylate, from Step 4, in 25 mL of trifluoroacetic acid (TFA) was stirred for 2 hours at ambient temperature. The TFA was evaporated in vacuo and the residue was dissolved in 200 mL of methanol. To the resultant solution was added 25 g of strongly basic ion exchange resin and the mixture was stirred at ambient temperature for 2 hours. The mixture was filtered and the filtrate was concentrated under reduced pressure to afford 1.146 g (88% yield) of ethyl 8-(3-amino-1-pyrrolidinyl)-1-ethyl-4H-quinolizin-4-one-3-carboxylate as a residue. The residue was dissolved in 6 mL of THF and 10.5 mL of a 1M aqueous solution of sodium hydroxide was added. The reaction mixture was heated at 60° C. for 2 hours and then the reaction temperature was increased to 90° C. for 2 hours, in order to evaporate the THF. The concentrated reaction solution was poured into water and the pH of the resultant solution was adjusted to ~2 with concentrated hydrochloric acid. The solid was filtered to afford 0.365 g (31% yield) of the title compound, m.p. 196°–198° C.; MS DCI-NH$_3$: 302 (M-Cl)$^+$ base, 258 ((M-Cl)-CO$_2$H)$^+$ 25%; IR (KBr): 3440 (OH), 2960, 1650 (C=O), 1500, 1360, 1280 cm$^-$; $^1$H NMR (TFA) d 1.41 (t, 3H, J=7.5 Hz), 2.39 (q, 2H, J=7.5), 2.70 (m, 3H), 4.0 (m, 3H), 4.53 (m, 1H), 6.93 (d, 1H, J=1.5 Hz), 7.33 (dd, 1H, J=9 Hz, 1.5 Hz), 7.93 (s, 1H), 9.08 (d, 1H, J=9 Hz). Analysis calculated for C$_{16}$H$_{20}$ClN$_3$O$_3$: C, 56.98; H, 5.97; N, 12.44. Found: C, 56.83; H, 6.00; N, 11.93.

EXAMPLE 63

8-(3-(Alanyl)amino-pyrrolidinyl)-1-ethyl-4H-quinolizin-4-one-3-carboxylic acid

3-Amino-1-benzylpyrrolidine (I. Sumio and T. Matsuo, Japanese Kokai JP 5328161, published Mar. 16, 1978) is coupled to N-t-butoxycarbonyl alanine (Boc-Ala) using conventional N-hydroxysuccinimide coupling procedures. The 1-benzyl group is removed by hydrogenolysis in methanol using palladium on carbon catalyst. The 3-(N-Boc-alanyl) aminopyrrolidine is then reacted with ethyl 8-chloro-1-ethyl-4H-quinolizin-4-one-3-carboxylate, the product of Step 3 of Example 62, as described in Step 4 of Example 62 replacing 3-(N-t-butoxycarbonylaminopyrrolidine) with 3-(N-Boc-alanyl)aminopyrrolidine, to give 8-(3-(N-alanyl) amino-pyrrolidinyl)-4H-quinolizin-4-one-3-carboxylic acid with the nitrogen of the amino acid protected with a Boc group. The Boc protecting group is removed by standard hydrolysis using trifluoroacetic acid and dilute aqueous hydrochloric acid.

Using the procedure outlined in Example 63, or any of the other conventional condensation methods listed above, other amino acid derivatives of the compounds of this invention having an amino group can be prepared. Examples of amino acids which can be coupled, either alone or in combination with one and other, include naturally occurring amino acids such as glycine, alanine, leucine, isoleucine, methionine, phenylalanine, valine, and the like, as well as synthetic amino acids such as cyclohexylalanine, cyclohexylglycine, aminopentanoic acid, and the like.

EXAMPLE 64

1-Ethyl-8-(3-methyl-1-piperazinyl)-4H-quinolizin-4-one-3-carboxylic acid hydrochloride Step 1: Ethyl 1-ethyl-8-(3-methyl-1-piperazinyl)-4H-quinolizin-4-one-3-carboxylate Ethyl 8-chloro-1-ethyl-4H-quinolizin-4-one-3-carboxylate (558 mg, 2.0 mmol), the product of Step 3 of Example 62, was dissolved in 10 mL of dry pyridine under a nitrogen atmosphere. To the resultant solution was added 600 mg (6.0 mmol) of 2-methylpiperazine and the stirred reaction mixture was heated at 65° C. for 3 hours. The reaction mixture was allowed to cool to ambient temperature and then concentrated in vacuo in order to remove all of the pyridine. The residue was dissolved in 60 mL of methylene chloride and the methylene chloride solution was washed with 60 mL of water. The aqueous layer was extracted with 2×60 mL of methylene chloride and the combined methylene chloride solutions were dried over anhydrous sodium sulfate, filtered and concentrated and dried in vacuo to afford 690 mg of the title compound. The product was carried on to the next step without purification.

Step 2: 1-Ethyl-8-(3-methyl-1-piperazinyl)-4H-quinolizin-4-one-3-carboxylic acid hydrochloride To a suspension of 0.686 g (2 mmol) of ethyl 1-ethyl-8-(3-methyl-1-piperazinyl)-4H-quinolizin-4-one-3-carboxylate, from Step 1, in 8 mL of THF was added 8.0 mL of a 1.0N aqueous sodium hydroxide solution and the reaction mixture was heated, with stirring, at 65° C. for 3 hours. The THF was removed from the reaction mixture by distillation during the reaction. The concentrated reaction mixture was cooled to ambient temperature and adjusted to pH 1–2 with 16 mL of 1N aqueous hydrochloric acid solution. The aqueous solution was concentrated in vacuo to remove the water and the residue was suspended in 10 mL of water. The solid was collected by filtration and dried in vacuo to afford the 385 mg (55% yield) of the title compound, m.p.>295° C.; MS DCI-NH$_3$: 316 (M-Cl)$^+$; IR (KBr): 3420 (OH), 1720 (C=O) cm$^{-1}$; $^1$H NMR (TFA) d 1.50 (t, 3H, J=7.5 Hz), 1.70 (d, 3H, J=6 Hz), 3.00 (q, 2H, J=7.5 Hz), 3.70–4.10 (m, 6H), 4.55 (m, 1H), 4.60 (m, 1H), 7.40 (d, 1H, J=3.0 Hz), 7.68 (dd, 1H, J=3.0 Hz, 8.4 Hz), 8.18 (s, 1H), 9.19 (d, 1H, J=8.4 Hz). Analysis calculated for $C_{17}H_{22}ClN_3O_3+H_2O$: C, 55.21; H, 6.54; N, 11.36. Found: C, 55.19; H, 6.07; N, 11.34.

EXAMPLE 65

1-Ethyl-8-(4-methylpiperazin-1-yl)-4H-quinolizin-4-one-3-carboxylic acid hydrochloride Step 1: Ethyl 1-ethyl-8-(4-methylpiperazin-1-yl)-4H-quinolizin-4-one-3-carboxylate Ethyl 8-chloro-1-ethyl-4H-quinolizin-4-one-3-carboxylate (279 mg, 1.0 mmol), the product of Step 3 of Example 62, was dissolved in 5 mL of dry pyridine under a nitrogen atmosphere. To the resultant solution was added 2 mL (2.0 mmol) of N-methylpiperazine and the stirred reaction mixture was heated at 85° C. for 2.5 hours. The reaction mixture was allowed to cool to ambient temperature and then concentrated in vacuo in order to remove all of the pyridine. The residue was dissolved in 50 mL of methylene chloride and the methylene chloride solution was washed with 50 mL of 5% aqueous sodium bicarbonate solution. The aqueous layer was extracted with 3×50 mL of methylene chloride and the combined methylene chloride solutions were dried over anhydrous sodium sulfate, filtered and concentrated and dried in vacuo to afford 343 mg of the title compound, m.p. 94°–96° C.; MS DCI-NH$_3$: 344 (M+H)$^+$.

Step 2: 1-Ethyl-8-(4-methylpiperazin-1-yl)-4H-quinolizin-4-one-3-carboxylic acid hydrochloride To a solution of 171 mg (0.5 mmol) of ethyl 1-ethyl-8-(4-methylpiperazin-1-yl)-4H-quinolizin-4-one-3-carboxylate, from Step 1, in 4 mL of THF was added 4.0 mL of a 1.0N aqueous sodium hydroxide solution and the reaction mixture was heated, with stirring, at 75° C. for 4.5 hours. The reaction mixture was cooled to ambient temperature and adjusted to pH 2 with 5 mL of 1N aqueous hydrochloric acid solution. The aqueous solution was concentrated in vacuo to ~5 mL and the solid was collected by filtration and dried in vacuo to afford 120 mg (68% yield) of the title compound, m.p. 293°–294° C. (dec); MS DCI-NH$_3$: 316 (M-Cl)$^+$ 90%, 272 ((M-Cl)-CO$_2$H)$^+$ base; IR (KBr): 3420 (OH), 1695 (C=O), 1640 (C=O) cm$^{-1}$; $^1$H NMR (TFA) d 1.47 (t, 3H, J=7.5 Hz), 3.00 (q, 2H, J=7.5 Hz), 3.23 (s, 3H), 3.55 (dd, 2H, J=9 Hz), 4.12 (m, 4H), 4.65 (d, 2H, J=15 Hz), 7.40 (s, 1H), 7.67 (d, 1H, J=9 Hz), 8.18 (s, 1H), 9.20 (d, 1H, J=7.5 Hz). Analysis calculated for $C_{17}H_{22}ClN_3O_3$: C, 56.59; H, 6.42; N, 11.64. Found: C, 56.86; H, 6.19; N, 11.60.

EXAMPLE 66

4-Chloro-5-fluoro-2-picoline

Step 1: 2-(5-Nitro-2-pyridyl)-1,3-propanedicarboxylate

Sodium hydride (20.2 g of NaH suspended in hexane, 0.504 mol) was suspended, under a nitrogen atmosphere, in 600 mL of anhydrous THF in a 3-neck 2 L round-bottom flask equiped with an addition funnel and a mechanical stirrer. The suspension was cooled to 0° C. in an ice bath. A solution of 71.8 mL (0.473 mol) of diethyl malonate in 60 mL of anhydrous THF was added dropwise to the sodium hydride suspension over a 1 hour period. After the addition and the evolution of hydrogen gas were complete, the reaction mixture was stirred for 20 min at 0° C. A solution of 50 g (0.3 15 mol) of 2-chloro-5-nitropyridine in 150 mL of anhydrous THF was added dropwise to the mixture, over a 25 min period. The ice bath was removed and the deep red-colored solution was stirred at ambient temperature for 48 hours. These procedures were repeated on the same scale. The two solutions containing the product were concentrated to ~500 mL and poured into a mixture of 1 L of 10% aqueous sodium bicarbonate solution and 1 L of brine. The aqueous mixture was extracted with 3×500 mL of methylene chloride. The combined organic extract was dried over anhydrous sodium sulfate, filtered and concentrated in vacuo to a solid residue. The residue was crystallized from ethyl alcohol and the crystals were washed with hexane to yield 140 g (79% yield) of the title compound as a bright yellow solid; MS DCI-NH$_3$ M/Z: 283 (M+H)$^+$ base, 253 ((M+H)-C$_2$H$_5$)$^+$ base; $^1$H NMR (CDCl$_3$) d 1.30 (t, 6H, J=7.5 Hz), 4.26 (q, 2H, J=6.0 Hz), 4.29 (q, 2H, J=6.0 Hz), 5.08 (s, 1H), 7.77 (dd, 1H, J=9.0 Hz, 0.6 Hz), 8.49 (dd, 1H, J=3.0 Hz, 9.0 Hz), 9.38 (dd, 1H, J=3.0 Hz, 9.0 Hz).

Step 2: 5-Nitro-2-picoline

A suspension of 102.0 g (0.361 mol) of 2-(5-nitro-2-pyridyl)-1,3-propanedicarboxylate, from Step 1, in 600 mL of 20% aqueous sulfuric acid solution was heated at 95° C. for 24 hours. The resultant solution was poured onto 1 kg of ice and the aqueous mixture was adjusted to a pH within the range pH 10–12 with 50% aqueous sodium hydroxide solution. The precipitate was filtered and dissolved in ethyl acetate. The ethyl acetate solution was dried over anhydrous sodium sulfate, filtered and concentrated to a solid residue. The residue was washed with hexane. The hexane was removed by filtration and the solid was dried to afford 45.86 g (92% yield) of the title compound; $^1$H NMR (CDCl$_3$) d 2.71 (s, 3H), 7.36 (d, 1H, J=9.0 Hz), 8.37 (dd, 1H, J=3.0 Hz, 9.0 Hz), 9.33 (d, 1H, J=3.0 Hz).

Step 3: 5-Amino-2-picoline

The product of Step 2, 5-nitro-2-picoline (45.86, 0.332 mol), was dissolved in 200 mL of methanol and 1.15 g of 10% palladium on carbon was added to the resultant solution. The reaction mixture was hydrogenated at ambient temperature under 4 atmospheres of hydrogen. The palladium catalyst was removed by filtration through a 45μ Millipore® filter and the filtrate was concentrated in vacuo to afford 33.96 g (95% yield) of the title compound as a tan solid; $^1$H NMR (CDCl$_3$) d 2.42 (s, 3H), 3.54 (brs, 2H), 6.91 (m, 2H), 8.00 (m, 1H).

Step 4: 5-Fluoro-2-picoline

A solution of 5-amino-2-picoline (20 g, 0.185 mol), from Step 3, in 105 mL of ethyl alcohol was cooled to 0° C. Tetrafluoroboric acid (55 mL of a 48% solution in water) was added to the cold 5-aminopicoline solution and the flask containing the resultant solution was weighed. Ethyl nitrite was bubbled through the cold solution until 13.88 g (0.185 mol) had been added. The addition took place over a 1.25 hours period. After the addition was complete the reaction solution was allowed to sit at 0° C. for 15 min, during which time, the excess ethyl nitrite evaporated from the solution. Diethyl ether (120 mL) was added to the reaction mixture to ensure complete precipitation of the tetrafluoroborate salt. After 30 minutes at 0° C., the mixture was filtered. The filter cake was washed with 200 mL of diethyl ether, followed by 300 mL of hexane. The solid was transferred to a 1 L beaker containing approximately 300 mL of hexane and 10.75 g (0.185 mol) of potassium fluoride. The mixture was heated to 40° C. over a 4.5 hours period. The orange-colored solid was converted to a black oily solid. The hexane was decanted and the residue was cooled to 0° C. The cold residue was triturated with approximately 200 mL of 50% sodium hydroxide. The mixture was combined with material obtained from duplicate runs of the preceeding procedures and the combined aqueous mixtures were steam distilled. The aqueous distillate collected between 92° C. and 100° C. was extracted with two portions of methylene chloride. The combined methylene chloride extract was dried over anhydrous sodium sulfate, filtered and added to the (hexane) distillate which was collected between 62° C. and 65° C. The product was carried on to the next step in solution.

Step 5: 5-Fluoro-2-picoline-N-oxide

To the solution of 5-fluoro-2-picoline obtained in Step 4, at 0° C., was added, with vigorous stirring, a cold solution of 40% peracetic acid (prepared by carefully adding 50 mL of 30% hydrogen peroxide solution to 150 mL of glacial acetic acid). The reaction mixture was heated at reflux temperature (50° C.) for 4 days and then poured into 600mL of ice water. The aqueous mixture was adjusted to pH 9 by the addition of potassium carbonate and then was stirred at ambient temperature for 4 hours. The aqueous solution was continuously extracted with methylene chloride for 24 hours and the methylene chloride extract was dried over anhydrous sodium sulfate, filtered and concentrated in vacuo to afford 30.8 g (22% yield) of the title compound; MS DCI-NH$_3$ M/Z: 128 (M+H)$^+$ base; $^1$H NMR (CDCl$_3$) d 2.48 (s, 3H), 7.00 (ddd, 1H), 7.22 (dd, 1H), 8.22 (dd, 1H).

Step 6: 5-Fluoro-4-nitro-2-picoline-N-oxide

The reaction was carried out in a flask vented to a gas scrubber containing aqueous sodium hydroxide solution. The product of Step 5, 5-fluoro-2-picoline-N-oxide (1.0 g, 7.86 mmol) was cooled to 0° C. and concentrated sulfuric acid (4.2 mL) was slowly added, with stirring. Solid potassium nitrate (1.27 g, 12.5 mmol) was then added to this mixture at 0° C., in small portions over a 45 minute period. The reaction mixture was allowed to warm to ambient temperature and was stirred at ambient temperature for 1 hour. Not all of the potassium nitrate had dissolved and the reaction mixture was heated at 50° C. for 0.5 hours and then at 100° C. for 18 hours. The homogeneous reaction solution was poured over ice and the resultant aqueous solution was adjusted to pH 9 with solid potassium carbonate. The aqueous solution was then extracted with 3×80 mL of methylene chloride. The combined organic extract was dried over anhydrous sodium sulfate, filtered and concentrated in vacuo to give 1.084 g (80% yield) of the title compound as a yellow solid, m.p. 107°–108° C.; MS DCI-NH$_3$ M/Z: 190 (M+NH$_4$)$^+$ 10%, 173 (M+H)$^+$ 30%, 157 (M-O)$^+$ 50%; $^1$H NMR (CDCl$_3$) d 2.48 (s, 3H), 8.05 (d, 1H, J=9.0 Hz), 8.31 (d, 1H, J=6.0 Hz).

Step 7: 4-Chloro-5-fluoro-2-picoline-N-oxide

The product of Step 6, 5-fluoro-4-nitro-2-picoline-N-oxide (3.56 g, 20.6 mmol) was dissolved in 30 mL of concentrated (37.5%) aqueous hydrochloric acid. The resultant solution was heated, with stirring, at 110° C. for 48 hours and then concentrated in vacuo. Water (30 mL) was added to the residue and the resultant aqueous solution was adjusted to pH 9–10 with sodium carbonate. The aqueous solution was then extracted with 3×50 mL of methylene chloride and the combined organic extract was dried over anhydrous sodium sulfate, filtered and concentrated in vacuo. The product was crystallized from hexane to afford 1.8 g (55% yield) of the title compound, m.p. 92°–93° C.; MS DCI-NH$_3$ M/Z: 179 (M+NH$_4$)$^+$ 30%, 162 (M+H)$^+$ base, 146 (M-O)$^+$ 60%; $^1$H NMR (CDCl$_3$) d 2.46 (s, 3H), 7.30 (d, 1H, J=9.0 Hz), 8.26 (d, 1H, J=4.5 Hz); IR (chloroform solution) 1605 (N-O), 1180 (C-F) cm$^{-1}$. Analysis calculated for C$_6$H$_5$ClFNO: C, 44.61; H, 3.12; N, 8.62. Found: C, 44.89; H, 3.25; N, 9.40.

Step 8: 4-Chloro-5-fluoro-2-picoline

4-Chloro-5-fluoro-2-picoline-N-oxide (12.43 g, 76.93 mmol), from Step 7, was dissolved in 52 mL of glacial acetic acid in a 3-necked flask equiped with a mechanical stirrer, a condenser and a thermometer. Iron powder (6.45 g, 115.5 mmol) was added to the solution at ambient temperature and the reaction mixture was carefully heated to 35°–40° C. After 10 min at 30° C., an exothermic reaction took place which caused the reaction temperature to rise to 120° C. and the reaction mixture became a very dark brown-colored solution. The flask was transferred to a cold water bath and the temperature of the solution brought down to ambient. The reaction mixture was then poured over ice. The resultant aqueous mixture was adjusted to pH 9 with potassium carbonate and steam distilled. The aqueous distillate collected at 92°–96° C. was extracted with three portions of methylene chloride. The combined organic extract was dried over anhydrous sodium sulfate, filtered and distilled to afford 15.91 g (71% yield) of the title compound, b.p. 138°–140° C.; MS GC-MS M/Z:146 (M+H)$^+$; $^1$H NMR (CDCl$_3$) d 2.53 (s, 3H), 7.23 (d, 1H, J=6.0 Hz), 8.37 (s, 1H).

EXAMPLE 67

3,4-Dichloro-5-fluoro-2-picoline

To 0.87 g (6 mmol) of 4-chloro-5-fluoro-2-picoline, the product of Example 66, in 20 mL of chloroform cooled to −45° C., is added 0.75 mL of t-butylhypochlorite. The reaction mixture is stirred at −45° C. for 2 hours and at 0° C. for 2 hours. The reaction mixture is then poured into water and the resultant aqueous mixture is extracted with methylene chloride. The organic solution is dried over anhydrous magnesium sulfate, filtered, concentrated under reduced pressure and distilled to afford the title compound.

EXAMPLE 68

3-Bromo-4-chloro-5-fluoro-2-picoline

4-Chloro-5-fluoro-2-picoline, the product of Example 66, is treated with bromine in fuming sulfuric acid containing 65% sulfur trioxide for 7 hours at 80° C. as described by L. van der Does and H. J. Hertog in Rec Trav Chim 81:864 (1965) to afford the title compound.

EXAMPLE 69

4-Chloro-3,5-difluoro-2-picoline

4-Chloro-5-fluoro-2-picoline is treated with 1.1 equivalents of acetyl hypofluorite as described by O. Lerman, et al. *J Org Chem*, 49:806–813 (1984) to afford the title compound.

EXAMPLE 70

4-Chloro-5-fluoro-2-propyl-pyridine

Diisopropylamine (924 µL, 6.59 mmol) was dissolved in 9 mL of dry THF and the resultant solution was cooled to 0° C. in an ice bath. n-Butyllithium (3.07 mL of a 2.05M solution in THF, 6.29 mmol) was added via syringe to the amine solution and the resultant solution was stirred for 30 minutes at 0° C. The lithium diisopropylamide (LDA) solution was then cooled to −50° C. in an isopropyl alcohol/dry ice bath. To the cold LDA solution was added, dropwise from an addition funnel, over a 15 min period, a solution of 4-chloro-5-fluoro-2-picoline (435 µL, 3.0 mmol), the product of Example 64, in 9 mL of THF. The reaction solution turned dark orange-brown in color. The reaction solution was stirred at a temperature in the range −50° C. to −45° C. for 5 hours and then was cooled over a 15 min period to −78° C. Ethyl iodide (792 µL, 9.9 mmol) was added in one portion and the reaction solution was stirred at −78° C. for 20 min. The reaction was then quenched by pouring the reaction solution into 60 mL of 10% aqueous ammonium chloride solution. The aqueous mixture was extracted with 2×50 mL of methylene chloride. The combined organic extract was dried over anhydrous sodium sulfate, filtered and concentrated in vacuo and the residue was distilledto afford the title compound, b.p. 80°–82° C. (12 mm Hg); MS DCI-NH$_3$ M/Z: 174 (M+H)$^+$ 40%; $^1$H NMR (CDCl$_3$) d 0.96 (t, 3H, J=7.5 Hz), 1.73 (spt, 2H, J=7.5 Hz), 2.73 (t, 2 H, J=7.5 Hz), 7.21 (d, 1H, J=6.0 Hz), 8.38 (s, 1H).

EXAMPLE 71

3,4- Dichloro-5-fluoro2-propyl-pyridine

By following the procedures described in Example 67 and replacing 4-chloro-5-fluoro-2-picoline (the product of Example 66) with 4-chloro-5-fluoro-2-propyl-pyridine (the product of Example 70), the title compound can be prepared.

EXAMPLE 72

3-Bromo-4-chloro-5-fluoro-2-propyl-pyridine

By following the procedures described in Example 68 and replacing 4-chloro-5-fluoro-2-picoline (the product of Example 66) with 4-chloro-5-fluoro-2-propyl-pyridine (the product of Example 70), the title compound can be prepared.

EXAMPLE 73

4-Chloro-3,5-difluoro-2-propyl-pyridine

By following the procedures described in Example 69 and replacing 4-chloro-5-fluoro-2-picoline (the product of Example 66) with 4-chloro-5-fluoro-2-propyl-pyridine (the product of Example 70), the title compound can be prepared.

EXAMPLE 74

1-Ethyl-7-fluoro-8-(4-methylpiperazin-1-yl)-4H-quinolizin-4-one-3-carboxylic acid hydrochloride By following the procedures described in Step 2 of Example 62 and in Example 65 and replacing 4-chloropicoline with 4-chloro-5-fluoro-picoline (the product of Example 66), the title compound can be prepared.

EXAMPLE 75

1-Ethyl-7-fluoro-8-(3-methyl-1-piperazinyl)-4H-quinolizin-4-one-3-carboxylic acid hydrochloride By following the procedures described in Step 2 of Example 62 and in Example 65 and replacing 4-chloropicoline with 4-chloro-5-fluoro-picoline (the product of Example 66), and replacing N-methylpiperazine with 2-methylpiperazine, the title compound can be prepared.

EXAMPLE 76

8-(3-Amino-1-pyrrolidinyl)-1-ethyl-7-fluoro-4H-quinolizin-4-one-3-carboxylic acid hydrochloride Following the procedures described in Example 62, replacing 4-chloropicoline with 4-chloro-5-picoline (the product of Example 66), the title compound is prepared.

EXAMPLE 77

9-Chloro-1-ethyl-7-fluoro-8-(4-methylpiperazin-1-yl)-4H-quinolizin-4-one-3-carboxylic acid hydrochloride Following the procedures described in Step 2 of Example 62 and in Example 65, replacing 4-chloropicoline with 3,4-dichloro-5-fluoro-picoline (the product of Example 67), the title compound is prepared.

EXAMPLE 78

9-Chloro-1-ethyl-7-fluoro-8-(3-methyl-1-piperazinyl)-4H-quinolizin-4-one-3-carboxylic acid hydrochloride Following the procedures described in Step 2 of Example 62 and in Example 65, replacing 4-chloropicoline with 3,4-dichloro-5-fluoropicoline (the product of Example 67), and replacing N-methylpiperazine with 2-methylpiperazine, the title compound is prepared.

EXAMPLE 79

8-(3-Amino-1-pyrrolidinyl)-9-chloro-1-ethyl-7-fluoro-4H-quinolizin-4-one-3-carboxylic acid hydrochloride Following the procedures described in Example 62, replacing 4-chloropicoline with 3,4-dichloro-5-fluoropicoline (the product of Example 67), the title compound is prepared.

EXAMPLE 80

9-Bromo-1-ethyl-7-fluoro-8-(4-methylpiperazin-1-yl)-
4H-quinolizin-4-one-3-carboxylic acid
hydrochloride Following the procedures described in Step 2 of Example 62 and in Example 65, replacing 4-chloropicoline with 3-bromo-4-chloro-5-fluoropicoline (the product of Example 68, the title compound is prepared.

EXAMPLE 81

9-Bromo-1-ethyl-7-fluoro-8-(3-methyl-1-piperazinyl)-
4H-quinolizin-4-one-3-carboxylic acid
hydrochloride Following the procedures described in Step 2 of Example 62 and in Example 65, replacing 4-chloropicoline with 3-bromo-4-chloro-5-fluoro-picoline (the product of Example 68), and replacing N-methylpiperazine with 2-methylpiperazine, the title compound is prepared.

EXAMPLE 82

8-(3-Amino-1-pyrrolidinyl)-9-bromo-1-ethyl-
7-fluoro-4H-quinolizin-4-one-3-carboxylic acid
hydrochloride Following the procedures described in Example 62, replacing 4-chloropicoline with 3-bromo-4-chloro-5-fluoropicoline (the product of Example 68), the title compound is prepared.

EXAMPLE 83

7,9-Difluoro-1-ethyl-8-(4-methylpiperazin-1-yl)-
4H-quinolizin-4-one-3-carboxylic acid
hydrochloride Following the procedures described in Step 2 of Example 62 and in Example 65, replacing 4-chloropicoline with 4-chloro-3,5-difluoropicoline (the product of Example 69), the title compound is prepared.

EXAMPLE 84

7,9-Difluoro-1-ethyl-8-(3-methyl-1-piperazinyl)-
4H-quinolizin-4-one-3-carboxylic acid
hydrochloride Following the procedures described in Step 2 of Example 62 and in Example 65, replacing 4-chloropicoline with 4-chloro-3,5-difluoropicoline (the product of Example 69), and replacing N-methylpiperazine with 2-methylpiperazine, the title compound is prepared.

EXAMPLE 85

8-(3-Amino-1-pyrrolidinyl)-7,9-difluoro-1-ethyl-
4H-quinolizin-4-one-3-carboxylic acid
hydrochloride Following the procedures described in Example 62, replacing 4-chloropicoline with 4-chloro-3,5-difluoropicoline (the product of Example 69), the title compound is prepared.

EXAMPLE 86

1-Cyclopropyl-7-fluoro-8-(4-methylpiperazin-1-yl)-
4H-quinolizin-4-one-3-carboxylic acid
hydrochloride Following the procedures described in Steps 1 and 2 of Example 62 and in Example 65, replacing 4-chloropicoline with 4-chloro-5-fluoropicoline (the product of Example 66), and replacing ethyl iodide with cyclopropyl iodide, the title compound is prepared.

EXAMPLE 87

1-Cyclopropyl-7-fluoro-8-(3-methyl-1-piperazinyl)-
4H-quinolizin-4-one-3-carboxylic acid
hydrochloride Following the procedures described in Steps 1 and 2 of Example 62, replacing 4-chloropicoline with 4-chloro-5-fluoropicoline (the product of Example 66) and replacing ethyl iodide with cyclopropyl iodide, and the procedures described in Example 65, replacing N-methylpiperazine with 2-methylpiperazine, the title compound is prepared.

EXAMPLE 88

8-(3-Amino-1-pyrrolidinyl)-1-cyclopropyl-7-fluoro-
4H-quinolizin-4-one-3-carboxylic acid
hydrochloride Following the procedures described in Example 62, replacing 4-chloropicoline with 4-chloro-5-fluoropicoline (the product of Example 66), and replacing ethyl iodide with cyclopropyl iodide, the title compound is prepared.

EXAMPLE 89

9-Chloro-1-cyclopropyl-7-fluoro-8-
(4-methylpiperazin-1-yl)-4H-quinolizin-
4-one-3-carboxylic acid hydrochloride Following the procedures described in Steps 1 and 2 of Example 62, replacing 4-chloropicoline with 3,4-dichloro-5-fluoropicoline (the product of Example 67) and replacing ethyl iodide with cyclopropyl iodide, and the procedures described in Example 65, the title compound is prepared.

EXAMPLE 90

9-Chloro-1-cyclopropyl-7-fluoro-8-(3-methyl-
1-piperazinyl-4H-quinolizin-4-one-3-carboxylic acid
hydrochloride Following the procedures described in Steps 1 and 2 of Example 62, replacing 4-chloropicoline with 3,4-dichloro-5-fluoropicoline (the product of Example 67) and replacing ethyl iodide with cyclopropyl iodide, and the procedures described in Example 65, replacing N-methylpiperazine with 2-methylpiperazine, the title compound is prepared.

EXAMPLE 91

8-(3-Amino-1-pyrrolidinyl)-9-chloro-1-cyclopropyl-
7-fluoro-4H-quinolizin-4-one-3-carboxylic acid
hydrochloride Following the procedures described in Example 62, replacing 4-chloropicoline with 3,4-dichloro-5-fluoropicoline (the product of Example 67) and replacing ethyl iodide with cyclopropyl iodide, the title compound is prepared.

EXAMPLE 92

9-Bromo-1-cyclopropyl-7-fluoro-
8-(4-methylpiperazin-1-yl)-4H-quinolizin-
4-one-3-carboxylic acid hydrochloride Following the procedures described in Steps 1 and 2 of Example 62, replacing 4-chloropicoline with 3-bromo-4-chloro-5-fluoropicoline (the product of Example 68) and replacing ethyl iodide with cyclopropyl iodide, and the procedures described in Example 65, the title compound is prepared.

EXAMPLE 93

9-Bromo-1-cyclopropyl-7-fluoro-8-(3-methyl-
1-piperazinyl)-4H-quinolizin-4-one-3-carboxylic
acid hydrochloride Following the procedures described in Steps 1 and 2 of Example 62, replacing 4-chloropicoline with 3-bromo-4-chloro-5-fluoropicoline (the product of Example 68) and replacing ethyl iodide with cyclopropyl iodide, and the procedures described in Example 65, replacing N-methylpiperazin with 2-methylpiperazine, the title compound is prepared.

EXAMPLE 94

8-(3-Amino-1-pyrrolidinyl)-9-bromo-1-cyclopropyl-
7-fluoro-4H-quinolizin-4-one-3-carboxylic acid
hydrochloride Following the procedures described in Example 62, replacing 4-chloropicoline with 3-bromo-4-chloro-5-fluoropicoline (the product of Example 68) and replacing ethyl iodide with cyclopropyl iodide, the title compound is prepared.

EXAMPLE 95

1-Cyclopropyl-7,9-difluoro-8-(4-methylpiperazin-
1-yl)-4H-quinolizin-4-one-3-carboxylic acid
hydrochloride Following the procedures described in Steps 1 and 2 of Example 62, replacing 4-chloropicoline with 4-chloro-3,5-difluoropicoline (the product of Example 69) and replacing ethyl iodide with cyclopropyl iodide, and the procedures described in Example 65, the title compound is prepared.

EXAMPLE 96

1-Cyclopropyl-7,9-difluoro-8-(3-methyl-
1-piperazinyl)-4H-quinolizin-4-one-3-carboxylic
acid hydrochloride Following the procedures described in Steps 1 and 2 of Example 62, replacing 4-chloropicoline with 4-chloro-3,5-difluoropicoline (the product of Example 69) and replacing ethyl iodide with cyclopropyl iodide, and the procedures described in Example 65, replacing N-methylpiperazine with 2-methylpiperazine, the title compound is prepared.

EXAMPLE 97

8-(3-Amino-1-pyrrolidinyl)-1-cyclopropyl-
7,9-difluoro-4H-quinolizin-4-one-3-carboxylic acid
hydrochloride Following the procedures described in Example 62, replacing 4-chloropicoline with 4-chloro-3,5-difluoropicoline (the product of Example 69) and replacing ethyl iodide with cyclopropyl iodide, the title compound is prepared.

EXAMPLE 98

7-Fluoro-1-methylamino-8-(4-methylpiperazin-
1-yl)-4H-quinolizin-4-one-3-carboxylic acid
hydrochloride Step 1: 4-Chloro-5-fluoro-alpha-bromo-2-picoline 4-Chloro-5-fluoro-2-picoline (2.9 g, 20 mmol), the product of Example 66, was dissolved in 50 mL of 1,2-dichloroethane in a dry flask. The resultant solution was heated, with stirring, to 75° C. and 4.09 (23 mmol) of N-bromosuccinimide was added, followed by 100 mG (0.7 mmol) of 2,2-azobisisobutyronitrile (AIBN), a free radical initiator. After the reaction mixture was stirred at 75° C. for 24 hours, it was diluted with 450 mL of methylene chloride and washed with 3×400 mL of water. The organic layer was separated and dried over anhydrous sodium sulfate, filtered and concentrated under reduced pressure. The residue was dried in vacuo to give 3.5 g (69% yield) of the title compound as an amber oil; $^1$H NMR (CDCl$_3$) d 4.50 (s, 2H), 7.54 (d, 1H), 8.44 (s, 1H).

Step 2: 4-Chloro-5-fluoro-2-(N-methylaminomethyl)-pyridine

4-Chloro-5-fluoro-alpha-bromo-2-picoline (1.37 g, 6.1 mmol), from Step 1 was dissolved in 15 mL of methanol in a pressure tube. Methylamine (3 mL of 40% aqueous solution) was added to the tube and the tube was sealed. The reaction mixture was stirred at ambient temperature for 26 hours and then the solvent was removed under reduced pressure. To the residue was added 50 mL of 10% aqueous sodium carbonate solution and the resultant aqueous mixture was extracted with 3×50 mL of methylene chloride. The organic combined extract was dried over anhydrous sodium sulfate, filtered and concentrated under reduced pressur. The residue was dried in vacuo to give 754 mg g (70% yield) of the title compound; MS DCI-NH$_3$ M/Z: 175 (M+H)$^+$ base; $^1$H NMR (CDCl$_3$) d 2.50 (s, 3H), 3.90 (s, 2H), 7.47 (d, 1H), 8.42 (s, 1H).

Step 3: N-(4chloro-5-fluoro-2-pyridyl)methyl-N-methyl-N-(2,2-dimethylethyl)-formamidine 4-Chloro-5-fluoro-2-(N-methylaminomethyl)-pyridine (650 mg, 3.72 mmol), from Step 2 was dissolved in 15 mL of toluene. To the resultant solution was added 2.3 mL (15 mmol) of N,N-dimethyl-N-(2,2-dimethylethyl)-formamide, followed by 40 mg (0.3 mmol) of ammonium sulfate. The reaction mixture was heated at reflux temperature, with stirring, for 28 hours and then allowed to cool to ambient temperature. The solvent was removed under reduced pressure and the residue dried in v acuo to give 560 mg (59% yield) of the title compound; MS DCI-NH$_3$ M/Z: 175 (M+H)$^+$ 73%, 203 ((M+H)-Cl-F)$^+$ base; $^1$H NMR (CDCl$_3$) d 1.17 (s, 3H), 1.19 (s, 9H), 2.83 (d, 2H), 4.47 (s, 1H), 7.43 (d, 1H, J=3 Hz), 8.40 (dd, 1H), J=3 Hz, 1.5 Hz).

Step 4: Diethyl 2-ethoxy-3-(5-fluoropyridin-2-yl)-3-[N-methyl-N-(2", 2"-dimethylethyl)methylamino]-propane-1,1-dicarboxylate Lithium diisopropylamide (LDA: 16 mL of a 1.5M solution in hexane) is added to 8 mL of dry THF, under a nitrogen atmosphere, and the resultant solution is cooled to −70° C. in a isopropyl alcohol/dry ice bath. To the cooled solution of LDA, is added dropwise, over a 30 minute period, a solution of 3.41 g (19.6 mmol) of N-(4-chloro-5-fluoro-2-pyridyl)methyl-N-methyl-N-(2,2-dimethylethyl)-formamidine, from Step 3, in 25 mL of dry THF. After stirring the solution for 0.5 hours at −70° C., a solution of 4.04 mL (19.6 mmol) of ethoxymethylenemalonate in 18 mL of dry THF is added dropwise over a 30 minute period. The reaction solution turns from dark red to orange. After stirring for 0.5 hours at −70° C., the reaction solution is allowed to warm to −20° C. and is stirred at −20° C. for 1 hour. The reaction is quenched at −20° C. by the addition of 1.3 mL of glacial acetic acid and the cooling bath is removed. After 20 minutes the reaction solution is poured into 5% aqueous sodium bicarbonate solution. The aqueous mixture is extracted with methylene chloride and the organic extract is dried over anhydrous sodium sulfate, filtered and concentrated under reduced pressure. The residue is purified by chromatography on a silica gel column to afford the title compound.

Step 5: Diethyl 2-ethoxy-3-(5-fluoropyridin-2-yl)-3-methylamino-propane-1,1-dicarboxylate A solution of 2 mmol (0.8 g) of diethyl 2-ethoxy-3-(5-fluoropyridin-2-yl)-3-[N-methyl-N-(2",2"-dimethylethyl) methylamino]-propane-1,1-dicarboxylate, from Step 4, 16 mmol of hydrazine and 6 mml of glacial acetic acid in 20 mL of 95% ethyl alcohol is heated at 50° C. under nitrogen for approximately 15 hours. Upon cooling, the solvent is removed in vacuo and the residue extracted with diethyl ether. The ether solution is washed with saturated aqueous sodium bicarbonate solution, dried over anhydrous sodium sulfate, and concentrated in vacuo to afford the title compound.

Step 6: Ethyl 8-chloro-7-fluoro-1-methylamino-4H-quinolizin-4-one-3-carboxylate 80 mL of Dowtherm A® in a 3-neck flask equipped with a thermometer, an addition funnel and an air-cooled condenser is heated to 235° C., under nitrogen, using a heating mantel. A solution of 3.9 g (12.4 mmol) of diethyl 2-ethoxy-3-(5-fluoropyridin-2-yl)-3-methylamino-propane-1,1-dicarboxylate, from Step 5, in 45 mL of Dowtherm A® is added, dropwise over a 1.5 hours period, through the addition funnel to the heated stirring Dowtherm A®. After the addition is complete, the resultant solution is heated at ~200° C. for 1 hour and then is cooled to ambient temperature. The solution is then poured into 500 mL of hexane and a precipitate forms. The precipitate is collected by filtration, washed with 5×100 mL of hexane and dried to afford the title compound.

Step 7: Ethyl 7-fluoro-1-methylamino-8-(4-methylpiperazin-1-yl)-4H-quinolizin-4-quinolizin -4-one 3-carboxylate Ethyl 8-chloro-7-fluoro-1-methylamino-4H-quinolizin-4-one-3-carboxylate (899 mg, 3.0 mmol), the product of Step 6, is suspended in 12 mL of dry pyridine under a nitrogen atmosphere. To the resultant solution is added 6.0 mL (6.0 mmol) of N-methylpiperazine and the reaction mixture is heated at 70° C. for 8 hours. The reaction mixture is then concentrated in vacuo in order to remove all of the pyridine. The dry residue is dissolved in 125 mL of methylene chloride and the methylene chloride solution is washed with 125 mL of brine. The aqueous layer is extracted with 125 mL of methylene chloride and the combined methylene chloride solutions are dried over anhydrous sodium surfate, filtered and concentrated and dried in vacuo to afford the title compound.

Step 8: 8-(4-methylpiperazin-1-yl)-4H-quinolizin-4-one-3-carboxylic acid hydrochloride A mixture of 1 g (2.75 mmol)of ethyl 7-fluoro-1-methylamino-8-(4-methylpiperazin-1-yl)-4H-quinolizin-4-one-3-carboxylate, from Step 7, in 12 mL of THF and 16.5 mL of a 0.5N aqueous solution of sodium hydroxide is heated, with stirring, at 75° C. for 8 hours. The THF is removed from the reaction mixture by distillation during the reaction. The concentrated reaction mixture is cooled to ambient temperature and adjusted to pH 2.0 with 10.5 mL of 1N aqueous hydrochloric acid solution. The aqueous solution is concentrated in vacuo to remove ~80% of the water and the concentrate is diluted with 50 mL of 95% ethyl alcohol. The solid is collected by filtration, washed with 2×5 mL of ethyl alcohol and dried in vacuo to afford the desired product.

EXAMPLES 99–116

By following the procedures described in Example 98 and replacing N-methylpiperazine in Step 7 with the appropriate amine as shown, Examples 99–116 are prepared as disclosed in Table 3 wherein the compounds have the general formula

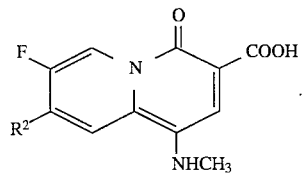

TABLE 3

| Example No. | $R^2$ | Example No. | $R^2$ |
|---|---|---|---|
| 99 | ⟨N-piperazinyl⟩-NH* | 108 | ⟨N-morpholinyl⟩-O |
| 100 | ⟨N-piperazinyl⟩(CH₃)-NH* | 109 | ⟨N-morpholinyl⟩(CH₂NHCH₃*)-O |

TABLE 3-continued

| Example No. | R² | Example No. | R² |
| --- | --- | --- | --- |
| 101 | 4-ethylpiperazin-1-yl | 110 | pyrrolidin-1-yl |
| 102 | 4-(2-(dimethylamino)propyl)piperazin-1-yl (approx.) — N-CH₂-CH(CH₃)-N(CH₃)₂ attached piperazine | 111 | 3-aminopyrrolidin-1-yl (NH₂*) |
| 103 | 3-methyl-4-(1-methylaminoethyl)piperazin-1-yl (NH*) | 112 | 3-amino-4-methylpyrrolidin-1-yl (NH₂*) |
| 104 | 3-(fluoromethyl)piperazin-1-yl (NH*) | 113 | 3-amino-4-methylpyrrolidin-1-yl (NH₂*) |
| 105 | 3-aminopiperidin-1-yl (NH₂*) | 114 | 3-amino-4-chloropyrrolidin-1-yl (NH₂*) |
| 106 | 4-aminopiperidin-1-yl (NH₂*) | 115 | 3-(aminomethyl)pyrrolidin-1-yl (NH₂*) |
| 107 | thiomorpholin-4-yl | 116 | 3-((ethylamino)methyl)pyrrolidin-1-yl (NHET*) |

*The amines are protected and deprotected as described in Example 58

EXAMPLE 117

7,9-Difluoro-1-methylamino-8-(4-methylpiperazin-1-yl)-4H-quinolizin-4-one-3-carboxylic acid hydrochloride By following the procedures described in Example 98 and replacing 4-chloro-5-fluoro-2-picoline (the product of Example 66) with 4-chloro-3,5-difluoro-2-picoline (the product of Example 69), the title compound is prepared.

EXAMPLES 118–135

By following the procedures described in Example 98, replacing 4-chloro-5-fluoro-2-picoline (the product of Example 66) with 4-chloro-3,5-difluoro-2-picoline (the product of Example 69) and replacing N-methylpiperazine with the appropriate amine as shown, Examples 118–135 are prepared as disclosed in Table 4 wherein the compounds have the general formula

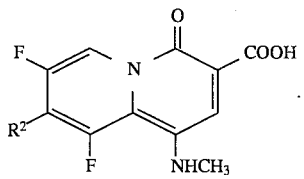

TABLE 4

| Example No. | R² | Example No. | R² |
|---|---|---|---|
| 118 | piperazinyl-NH* | 127 | morpholinyl (O) |
| 119 | piperazinyl with CH₃, NH* | 128 | morpholinyl with CH₂NHCH₃* |
| 120 | piperazinyl-N-ethyl | 128 | pyrrolidinyl |
| 121 | piperazinyl with N(CH₃)CH₃ | 130 | pyrrolidinyl-NH₂* |
| 122 | piperazinyl with two CH₃ and NH* | 131 | pyrrolidinyl with CH₃, NH₂* |
| 123 | piperazinyl with CH₂F, NH* | 132 | pyrrolidinyl with CH₃, NH₂* |
| 124 | piperidinyl-NH₂* | 133 | pyrrolidinyl with Cl, NH₂* |
| 125 | piperidinyl-NH₂* | 134 | pyrrolidinyl-CH₂NH₂* |
| 126 | thiomorpholinyl (S) | 135 | pyrrolidinyl-CH₂NHET* |

*The amines are protected and deprotected as described in Example 58

EXAMPLE 136

1-Ethyl-8-(4-methylpiperazin-1-yl)-6,7,9-trifluoro-4H-quinolizin-4-one-3-carboxylic acid hydrochloride Step 1: 3,4,5,6-Tertrafluoro-2-picoline 2,3,4,5,6-Pentafluoropyridine (commercially available from Aldrich Chemical Co.) is oxidized to the corresponding N-oxide following the procedures described in Step 6 of Example 66. The 2,3,4,5,6-pentafluoropyridine N-oxide is treated at ambient temperature with one equivalent of methylmagnesium iodide in diethyl ether as described by F. Binns and H. Suschitsky in *Chemical Communications*, 750–751 (1970) and *J Chem Soc (C)*, 1223–1231 (1771). The reaction mixture is treated with aqueous ammonium chloride and extracted with diethyl ether. The ether solution is dried over anhydrous magnesium sulfate, filtered and concentated under reduced pressure and the crude product is chromatographed on silica gel to afford 2-methyl-3,4,5,6-tetrafluoropyridine N-oxide (3,4,5,6-tetrafluoro-2-picoline). The N-oxide is then reduced to afford the title compound by the procedures described in Step 8 of Example 66.

Step 2: 2-Propyl-3,4,5,6-tetrafluoropyridine

A 1.5M solution of LDA in hexane (100 mL, 150 mmol) is cooled to –60° C. in an isopropyl alcohol/dry ice bath. To the stirred LDA solution, under nitrogen, is added, dropwise over a 0.5 hours period, a solution of 22.617 g (137 mmol) of 3,4,5,6-tetrafluoro-2-picoline, the product of Step 1, in 80 mL of dry THF. The reaction mixture is stirred for 0.5 hours at –60° C. and then a solution of 10.95 mL (137 mmol) of ethyl iodide in 30 mL of dry THF is added, dropwise over a 20 minute period. After the reaction mixture is stirred at −60° C. for 0.5 hours, the cooling bath is allowed to slowly (1.5 hours) warm to −30° C. The reaction mixture is poured into cold brine and the aqueous mixture is extracted with methylene chloride. The organic extract is dried over anhydrous sodium sulfate, filtered and concentrated in vacuo. The residue is distilled to afford the title compound.

Step 3: Diethyl 2-ethoxy-3-[3,4,5,6-tetrafluoro-2-pyridyl]-pentane-1,1-dicarboxylate A solution of 12.6 mL (89.9 mmol) of diisopropylamine in 20 mL of anhydrous tetrahydrofuran (THF) is prepared under a nitrogen atmosphere and cooled in an ice/water bath. To this solution is added, dropwise over a 30 minute period, 36 mL of a 2.5M solution of n-butyllithium (90 mmol) in hexane. The solution is stirred for 30 minutes at 0° C. and then cooled to −60° C. To the amine solution at −60° C., is added, dropwise over a 30 minute period, a solution of 15.82 g (81.9 mmol) of 2-propyl-3,4,5,6-tetrafluoropyridine, from Step 2, in 100 mL of anhydrous THF. The resultant solution is stirred at −60° C. for 0.5 hours and then 16.55 mL (81.9 mmol) of ethyl 2-carboethoxy-3-ethoxy-2-propenecarboxylate is added, dropwise over a 30 minute period. Stirring is continued at −60° C. for 0.5 hours and at −20° C. for 1.5 hours. The reaction mixture is poured into cold brine and the aqueous mixture is extracted with methylene chloride. The combined organic extract is dried over anhydrous sodium sulfate, filtered and concentrated in vacuo to afford 35.48 g of the title compound. The product is carried on to the next step without purification.

Step 4: Ethyl 1-ethyl-6,7,8,9-tetrafluoro-4-H-quinolizin-4-one-3-carboxylate

A solution of 40.61 g (99.2 mmol) of diethyl 2-ethoxy-3-[4-chloro-2-pyridyl]-pentane-1,1-dicarboxylate, from Step 3, in 1L of xylene is heated at 150° C., with stirring, for 24 hours and then concentrated in vacuo. The residue is washed with a mixture of hexane and cyclohexane to afford the title compound.

Step 5: Ethyl 1-ethyl-8-(4-methylpiperazin-1-yl)-6,7,9-trifluoro-4H-quinolizin-4-one-3-carboxylate Ethyl 8-chloro-1-ethyl-6,7,9-tetrafluoro-4H-quinolizin-4-one-3-carboxylate (317 mg, 1.0 mmol), from Step 4, is dissolved in 5 mL of dry pyridine under a nitrogen atmosphere. To the resultant solution is added 2 mL (2.0 mmol) of N-methylpiperazine and the stirred reaction mixture is heated at 85° C. for 2.5 hours. The reaction mixture is allowed to cool to ambient temperature and then concentrated in vacuo in order to remove all of the pyridine. The residue is dissolved in 50 mL of methylene chloride and the methylene chloride solution is washed with 50 mL of 5% aqueous sodium bicarbonate solution. The aqueous layer is extracted with 3×50 mL of methylene chloride and the combined methylene chloride solutions are dried over anhydrous sodium sulfate, filtered and concentrated and dried in vacuo to afford the title compound.

Step 6: 1-Ethyl-8-(4-methylpiperazin-1-yl)-6,7,9-trifluoro-4H-quinolizin-4-one-3-carboxylic acid hydrochloride To a solution of 199 mg (0.5 mmol) of ethyl 1-ethyl-8-(4-methylpiperazin-1-yl)-6,7,9-trifluoro-4H-quinolizin-4-one-3-carboxylate, from Step 5, in 4 mL of THF is added 4.0 mL of a 1.0N aqueous sodium hydroxide solution and the reaction mixture is heated, with stirring, at 75° C. for 4.5 hours. The reaction mixture is cooled to ambient temperature and adjusted to pH 2 with 5 mL of 1N aqueous hydrochloric acid solution. The aqueous solution is concentrated in vacuo to ~5 mL and the solid is collected by filtration and dried in vacuo to afford the title compound.

EXAMPLE 137

8-(3-Amino-1-1-pyrrolidinyl)-1-ethyl-6,7,9-trifluoro-4H-quinolizin-4-one-3-carboxylic acid hydrochloride Step 1: Ethyl 8-(3-(N-t-butoxycarbonyl)amino-1-pyrrolidinyl)-1-ethyl-6,7,9-trifluoro-4H-quinolizin-4-one-3-carboxylate Ethyl 6,7,8,9-tetrafluoro-1-ethyl-4H-quinolizin-4-one-3-carboxylate (1.26 g, 3.97 mmol), from Step 3 of Example 136, is dissolved in 20 mL of dry pyridine under a nitrogen atmosphere. To the resultant solution is added a solution of 1.85 g (9.92 mmol) of 3-(N-tbutoxycarbonylamino)pyrrolidine in 5 mL of dry pyridine and the reaction mixture is heated at 70° C. for 4.5 hours. The reaction mixture is then concentrated in vacuo in order to remove all of the pyridine. The dry residue (3.124 g) is purified by chromatography on silica gel to afford the title compound.

Step 2: 8-(3-Amino-1 -pyrrolidinyl)-1-ethyl-6,7,9-trifluoro-4H-quinolizin-4-one-3-carboxylic acid hydrochloride A solution of 1.11 g (2.2 mmol) of ethyl 8-(3-(N-t-butoxycarbonyl)amino-1-pyrrolidinyl)-1-ethyl-6,7,9-trifluoro-4H-quinolizin-4-one-3-carboxylate, from Step 1, in 20 mL of trifluoroacetic acid (TFA) is stirred for 2 hours at ambient temperature. The TFA is evaporated in vacuo and the residue is dissolved in 200 mL of methanol. To the resultant solution is added 4.5 g of strongly basic ion exchange resin and the mixture is stirred at ambient temperature for 1 hour. The mixture is filtered and the filtrate is concentrated under reduced pressure to afford crude ethyl 8-(3-amino-1-pyrrolidinyl)-1-ethyl-6,7,9-trifluoro-4H-quinolizin-4-one-3-carboxylate as a residue. The residue is dissolved in 5 mL of THF and 11 mL of a 1M aqueous solution of sodium hydroxide is added. The reaction mixture is heated at 60° C. for 1 hour and then the reaction temperature is increased to 85° C. in order to evaporate the THF. The concentrated reaction solution is diluted with 20 mL of water and the pH of the resultant solution is adjusted to 0 with concentrated hydrochloric acid. The aqueous solution is concentrated in vacuo. The residue is crystallized from ethyl alcohol:isopropyl alcohol:water (4:4:1 v/v/v) and recrystallized from ethyl alcohol/water to afford the title compound.

EXAMPLE 138

1-Ethyl-8-(3-(N-norvalyl)amino-pyrrolidinyl)-4H-quinolizin-4-one-3-carboxylic acid 3-Amino-1-benzylpyrrolidine (I. Sumio and T. Matsuo, Japanese Kokai JP 5328161, published Mar. 16, 1978) is coupled to N-t-butoxycarbonyl norvaline (Boc-nVal) using conventional N-hydroxysuccinimide coupling procedures. The 1-benzyl group is removed by hydrogenolysis in methanol using palladium on carbon catalyst. The 3-(N-Boc-norvalyl)aminopyrrolidine is then reacted with ethyl 6,7,8,9-tetrafluoro-1-ethyl-4H-quinolizin4-one-3-carboxylate, as described in Step 1 of Example 137, replacing 3-(N-t-butoxycarbonylamino)pyrrolidine with 3-(N-Boc-norvalyl)aminopyrrolidine, to give 1-ethyl-8-(3-(N-norvalyl)amino-pyrrolidinyl)-4H-quinolizin-4-one-3-carboxylic acid with the nitrogen of the amino acid protected with a Boc group. The Boc protecting group is removed by standard hydrolysis using trifluoroacetic acid and dilute aqueous hydrochloric acid.

Using the procedure outlined in Example 138, or any of the other conventional condensation methods listed above, other amino acid derivatives of the compounds of this invention having an amino group can be prepared. Examples of amino acids which can be coupled, either alone or in combination with one and other, include naturally occurring amino acids such as glycine, alanine, leucine, isoleucine, methionine, phenylalanine, valine, and the like, as well as synthetic amino acids such as cyclohexylalanine, cyclohexylglycine, aminopentanoic acid, and the like.

EXAMPLES 139–155

By following the procedures described in Example 136 or Example 137 and replacing N-methylpiperazine or 3-(N-t-butoxycarbonylamino)pyrrolidine with the appropriate amine as shown, Examples 139–155 are prepared as disclosed in Table 5 in which the compounds have the general formula

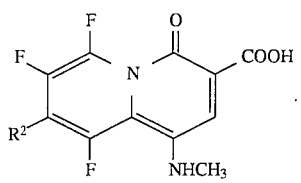

TABLE 5

| Example No. | $R^2$ | Example No. | $R^2$ |
|---|---|---|---|
| 139 | piperazinyl-CH2CH2-NH* | 148 | morpholinyl (N—CH2CH2—O) |
| 140 | piperazinyl-CH2CH(CH3)-NH* | 149 | morpholinyl-CH(CH2NHCH3*)—O |
| 141 | piperazinyl-CH2CH2-N(ethyl) | 150 | pyrrolidin-1-yl |
| 142 | piperazinyl-CH2CH(CH3)-N(CH3) | 151 | 3-amino-4-methylpyrrolidin-1-yl (NH2*, CH3) |
| 143 | piperazinyl-CH(CH3)CH(CH3)-NH* | 152 | 3-amino-5-methylpyrrolidin-1-yl (CH3, NH2*) |
| 144 | piperazinyl-CH(CH2F)-NH* | 153 | 3-amino-4-chloropyrrolidin-1-yl (NH2*, Cl) |
| 145 | 3-aminopiperidin-1-yl (NH2*) | 154 | 3-(aminomethyl)pyrrolidin-1-yl (CH2NH2*) |
| 146 | 4-aminopiperidin-1-yl (NH2*) | 155 | 3-(NHET*-methyl)pyrrolidin-1-yl |
| 147 | thiomorpholinyl (N—CH2CH2—S) | | |

*The amines are protected and deprotected as described in Example 58

EXAMPLE 156

11,12-Dihydro-7-fluoro-12-methyl-8-(4-methyl-1-piperazinyl)-4H-pyrano[i,j]quin-olizin-4-one-3-carboxylic acid

Step 1: 4-Chloro-3,5-difluoro-2-(1-(2-tetrahydropyranyl)oxy-2-propy)pyridine

A solution of 12.8 g (150 mmol) of 2-chloro-1-propanol is dissolved in 200 mL of acetone. To the resultant solution are added 40 g of anhydrous ferric chloride and 30 g (200 mmol) of sodium iodide. The reaction mixture is stirred at room temperature for 24 hours and then filtered to remove sodium chloride. The solvent is evaporated to afford the corresponding 2-iodo-1-propanol. The iodo alcohol is dissolved in 200 mL of methylene chloride and is treated with 20.5 mL (225 mmol) of 3,4-dihydro-2H-pyran and 50 mg of p-toluenesulfonic acid. The reaction mixture is stirtred at room temperature for several hours and then poured into 200 mL of 5% aqueous sodium bicarbonate solution. The aqueous mixture is extracted with methylene chloride. The methylene chloride solution is dried over anhydrous sodium sulfate, filtered and concentrated under reduced pressure to afford the THP-protected 2-iodo-1-propanol.

A solution of 4-chloro-3,5-difluoro-2-methylpyridine (16.5 g, 100 mmol) in 150 mL of dry THF under a positive nitrogen atmosphere is treated with 73 mL of 1.5M lithium diisopropylamine (LDA) at –78° C. After stirring at –78° C. for 30 minutes, a solution of 27.0 g (100 mmol) of the THP-protected 1-iodo-2-propanol in 150 mL of THF is added dropwise with stirring. The reaction mixture is stirred at –78° C. for several hours and then is slowly warmed to –20° C. The reaction is quenched by pouring the reaction mixture into 400 mL of saturated aqueous ammonium chloride solution. The aqueous layer is separated and extracted with methylene chloride. The combined organic layers are dried over anhydrous sodium surfate, filtered and concentrated under in vacuo to afford the title compound.

Step 2: 4-Chloro-3,5-difluoro-2-(1-hydroxy-2-propyl)pyridine

The product of Step 1 is dissolved in 200 mL of 2:1 THF:water and to this solution is added 6 mL of acetic acid. The reaction mixture is heated at 45° C. for approximately 5 hours. The THF is removed under reduced pressure and the aqueous reaction mixture is adjusted to a pH in the range of 8 to 9 with 10% sodium carbonate and is then extracted with methylene chloride. The organic layer is dried over anhydrous sodium sulfate, filtered and concentrated in vacuo to afford the title compound.

Step 3: 8-Chloro-3,4-dihydro-7-fluoro-3-methyl-2H-pyrano[3,2-b]pyridine

The product of Step 2 (15.5 g, 75 mmol) is dissolved in 100 mL of dry THF in an oven-dried system under positive nitrogen atmosphere. The reaction mixture is cooled in ice and 3.2 g (80 mmol) of 60% sodium hydride is added. The reaction mixture is warmed to room temperature and then heated at reflux temperature overnight with stirring. The reaction mixture is cooled to room temperature and poured into brine. The aqueous mixture is extracted with ethyl acetate. The organic layer is dried over anhydrous magnesium sulfate, filtered and concentrated in vacuo to afford the title compound.

Step 4: Diethyl 2-(8-chloro-3,4-dihydro-7-fluoro-3-methyl-2H-pyrano[3,2-b]pyridin-4-yl)-2-ethoxy1,1-ethanedicarboxylate Following the procedure described in Step 2 of Example 62, the product of Step 3 is treated with ethyl 2-carboethoxy-3-ethoxy-2-propenecarboxylate and LDA to afford the title compound.

Step 5: Ethyl 8-chloro-11,12-dihydro-7-fluoro-12-methyl-4H-pyrano[i,j]quin-olizin-4-one-3-carboxylate Following the procedures described in Step 3 of Example 62, the product of Step 4 is heated in refluxing Dowtherm A® to afford the desired cyclized product.

Step 6: Ethyl 11,12-dihydro-7-fluoro-12-methyl-8-(4-methyl-1-piperazinyl)-4H-pyrano[i,j]quin-olizin-4-one-3-carboxylate Following the procedures described in Step 1 of Example 65, the product of Step 5 is reacted with N-methylpiperazine to afford the title compound.

Step 7: 11,12-Dihydro-7-fluoro-12-methyl-8-(4-methyl-1-piperazinyl)-4H-pyrano[i,j]quin-olizin-4 -one-3-carboxylic acid Following the procedures described in Step 2 of Example 65, the tile compound is prepared.

EXAMPLE 157

2-(3-Aminopyrrolidin-1-yl)-9-cyclopropyl-3-fluoro-6H-6-oxo-pyrido[1,2-a]pyrimidine-7-carboxylic acid hydrochloride salt

Step 1: 2-Cyclopropyl-2-ethoxycarbonylacetamidine hydrochloride

Into a stirred solution of 38.72 g (0.253 mol) of ethyl 2-cyano-2-cyclopropylacetate (preparation described by R. W. J. Carney and J. Wojtkunski, *Org. Prep. Proced. Int.*, 5, 25 (1973)) in 17.7 mL (0.303 mol) of anhydrous ethanol under a dry $N_2$ atmosphere was introduced 10.0 g (0.274 mol) of gaseous hydrogen chloride with ice cooling. The mixture was allowed to warm to room temperature and stand for 72 hours. The reaction was diluted with 100 mL of anhydrous ethanol, 70 mL of ammonia in ethanol (4.17M) was added slowly at room temperature and the reaction was stirred for 3 hours. The reaction mixture was filtered to remove the ammonium chloride, and the solvent was removed to afford the title compound as a viscous off-white oil, which was taken directly to the next step.

Step 2: 2-Cyclopropyl-2-(5-fluoro-4-hydroxypyrimidin-2-yl)acetic acid methyl ester and 2-cyclopropyl-2-(5-fluoro-4-hydroxypyrimidin-2-yl)acetic acid ethyl ester A mixture of 0.253 mol of the compound from Step 1, 0.254 mol of the sodium salt of ethyl 2-fluoro-3-hydroxy-2-propenoate (prepared as described by E. Elkik and M. Imbeaux-Oudotte, *Bull. Soc. Chim. Fr.*, 5–6 pt2, 1165(1975))and 37.0 ml (0.265 mol) of triethylamine in 250 mL of anhydrous methanol was heated at reflux under a dry $N_2$ atmosphere for 17 hours. The solvent was removed, 200 mL of water added and the residue acidified to pH 5 with acetic acid. This mixture was then extracted with methylene chloride. The extract was washed with water, dried over anhydrous magnesium sulfate, and the solvent was removed by evaporation under vacuum to give a dark brown oil. The product was purified by column chromatography on silica gel eluting with 1:1 ethyl acetate:hexane to afford 22.8 g of the methyl ester title compound as a pale yellow viscous oil and 6.45 g of the ethyl ester title compound as a pale yellow viscous oil. Methyl ester: MS M/Z: 227 (M+H). NMR (CDCl$_3$): d 0.43 (1H, m), 0.52 (1H, m), 0.65 (1H, m), 0.77 (1H, m), 1.42 (1H, m), 2.97 (1H, d, J=10 Hz), 3.80 (3H, s), 7.88 (1H, d, J=3 Hz), 11.8 (1H, b). IR: (neat) 1740, 1690, 1615 cm$^{-1}$. Analysis calculated for $C_{10}H_{11}FN_2O_3 \cdot \frac{1}{4} H_2O$: C, 52.06; H, 5.02; N, 12.14. Found: C, 52.45; H, 4.94; N, 11.76.

Ethyl ester: MS M/Z: 258 (M+NH$_4$). NMR (CDCl$_3$): d 0.47 (1H, m), 0.54 (1H, m), 0.66 (1H, m), 0.74 (1H, m), 1.31 (3H, t, J=7 Hz), 1.34 (1H, m), 2.96 (1H, d, J=10 Hz), 4.27 (2H, m), 7.83 (1H, d, J=3 Hz), 11.0 (1H, b): IR: (neat) 1735, 1682, 1605 cm$^{-1}$. Analysis calculated for C$_{11}$H$_{13}$FN$_2$O$_3$.0.3 H$_2$O: C, 53.78 H, 5.58; N, 11.40. Found: C54.05; H 5.59; N, 11.11.

Step 3: 2-Cyclopropyl-2-(5-fluoro-4-hydroxypyrimidin-2-yl)acetaldehyde

To a solution of 4.960 g (21.9 mmol) of the methyl ester compound from Step 2 in 40 mL of toluene stirred at −70° C. under a dry N$_2$ atmosphere was added 46.0 mL of 1N diisobutylaluminum hydride in toluene (46 mmol). The reaction was stirred for 40 min and then quenched by the addition of 5 mL of acetic acid. The mixture was allowed to warm to room temperature, and the reaction was extracted with ethyl acetate. The extract was washed with water (3×), dried over anhydrous magnesium sulfate and concentrated under vacuum to afford 2.230 g of the title compound as a white solid. This compound was used directly in the next step.

MS M/Z: 214 (M+NH$_4$). NMR:(CDCl$_3$) d 0.48 (m, 2H), 0.91 (m, 2H), 1.35 (m, 1H0, 7.40 (d, 1H, J=10 Hz), 7.75 (d, 1H, J=4 Hz), 9.61 (br s, 1H), 13.64 (d, 1H, J=10 Hz). IR (KBr) 1695, 1660, 1635 cm$^{-1}$.

Step 4: 9-Cyclopropyl-3-fluoro-2-hydroxy-6H-6-oxo-pyridol[1,2-a]pyrimidine-7-carboxylic acid benzyl ester A 2.230 g (11.37 mmol) sample of the compound from Step 3 was dissolved in 100 mL of anhydrous ethanol. To this was added 3.5 mL (14.00 mmol) of dibenzyl malonate, 2.5 mL of piperidine and 0.25 mL of acetic acid. This reaction mixture under a dry N$_2$ atmosphere was heated under reflux conditions for 3 hours and stirred at room temperature overnight. The solvent was removed by evaporation, the residue was dissolved in methylene chloride which was washed with water and dried over anhydrous magnesium sulfate. The solvent was removed by evaporation under vacuum to give a yellow oil, which was purified by column chromatography on silica gel, eluting with 1:5:100 acetic acid:methanol:methylene chloride. Removal of the solvent afforded 1.800 g of the title compound as a pale yellow solid, mp 225.5°–226.5° C. MS M/Z 355 (M+H). NMR:(CDCl$_3$) d 0.64 (m, 2H), 1.08 (m, 2H), 1.62 (m, 1H), 5.37 (s, 2H), 7.35–7.48 (m, 5H), 8.28 (s, 1H), 9.00 (d, 1H, J=6 Hz). IR (KBr) 1720, 1700, 1690 cm$^{-1}$. Analysis calculated for C$_{19}$H$_{15}$FN$_2$O$_4$.¼ H$_2$O: C, 63.60; H, 4.35; N, 7.81. Found: C, 63.54; H, 4.08; N, 7.78.

Step 5: 2-Chloro-9-cyclopropyl-3-fluoro-6H-6-oxo-pyrido[1,2-a]pyrimidine-7-carboxylic acid benzyl ester A mixture of 0.200 g (0.564 mmol) of the compound from Step 4, 0.50 mL of DMF, 0.60 mL of phosphorous oxychloride and 10 mL of methylene chloride was stirred under a dry N$_2$ atmosphere at room temperature for 4 hours. Ice was added to react with the excess phosphorous oxychloride. The mixture was extracted with methylene chloride, which was washed with water, then the solvent was dried over anhydrous magnesium sulfate and the solvent was removed by evaporation under vacuum to yield the title compound as an orange residue. This compound was taken directly to the next step.

Step 6: 2-(3-(N-t-butoxycarbonyl)aminopyrrolidin-1-yl)-9-cyclopropyl-3-fluoro-6H-6-oxopyrido[1,2-a]pyrimidine-7-carboxylic acid benzyl ester The 0.564 mmol sample of the compound from the previous step was dissolved in 5 mL of dry methylene chloride and cooled to 0° C. To this solution was added 0.45 g of 3-(N-t-butoxycarbonyl)aminopyrrolidine, and the reaction mixture was stirred at room temperature overnight. The solvent was removed by evaporation under vacuum, and the product was purified by column chromatography on silica gel, eluting with 10% methanol in methylene chloride to afford 0.295 g of the title compound as a yellow solid, mp 159°–160° C. MS M/Z 523 (M+H). NMR:(CDCl$_3$) d 0.60 (m, 2H), 0.87 (m, 2H), 1.46 (s, 9H), 1.90–2.40 (m, 2H), 3.70–4.45 (m, 5H), 4.94 (br s, 1H), 5.37 (s, 2H), 7.29 (m, 1H), 7.37 (m, 2H), 7.50 (m, 2H), 7.99 (br s, 1H), 9.10 (d 1H, J=10 Hz). IR (KBr) 1715, 1685, 1660 cm$^{-1}$. Analysis calculated for C$_{28}$H$_{31}$FN$_4$O$_5$.½ H$_2$O: C, 63.44; H, 6.08; N, 10.57. Found: C, 63.39; H, 6.13; N, 10.83.

Step 7: 2-(3-(N-t-butoxycarbonyl)aminopyrrolidin-1-yl)-9-cyclopropyl-3-fluoro-6H-6-oxopyrido[1,2-a]pyrimidine-7-carboxylic acid To a 0.135 g (0.259 mmol) sample of the benzyl ester from Step 6 in 20 mL of methanol and 2 mL of THF was added 2.0 mL of 98% formic acid and 0.05 g of 10% Pd/C. This mixture was stirred under a dry N$_2$ atmosphere at room temperature for 37 min. The catalyst was removed by filtration, and the solvent was removed under vacuum. The crude product was purified by column chromatography on silica gel, eluting with 1:5:100 acetic acid:methanol:methylene chloride to afford the title compound as a yellow solid after removal of the solvent. This product was taken directly to the next step.

Step 8: 2-(3-Aminopyrrolidin-1-yl)-9-cyclopropyl-3-fluoro-6H-6-oxo-pyrido[1,2-a]pyrimidine-7-carboxylic acid hydrochloride salt The sample of the compound from the previous step was reacted with 10 mL of 4N HCl in dioxane under a dry N$_2$ atmosphere at room temperature 3 hours. The solvent was removed, the yellow solid was dissolved in distilled water. The yellow solution was filtered and freeze-dried to afford 0.0681 g of the title compound as a yellow solid, mp 234° C., (dec.). MS M/Z 333 (M—Cl). NMR: (CDCl$_3$) d 0.64 (m, 2H), 0.96 (m, 2H), 2.20–2.65 (m, 3H), 3.58–4.35 (m, 5H), 7.80 (d, 1H, J=10 Hz), 9.05 (br s, 1H), IR (KBr) 1665, 1620 cm$^{-1}$.

EXAMPLE 158

2-(3-Aminopyrrolidin-1-yl)-9-cyclopropyl-3-fluoro-6H-6-oxo-pyrido[1,2-a]pyrimidine-7-carboxylic acid Step 1: 9-Cyclopropyl-3-fluoro-2-hydroxy-6H-6-oxo-pyrido[1,2-a]pyrimidine-7-carboxylic acid t-butyl ester A 0.247 g (1.262 mmol) sample of 2-cyclopropyl-2-(5-fluoro-4-hydroxypyrimidin-2-yl)acetaldehyde, from Example 157 Step 3 above, was dissolved in 20 mL of ethanol, and 0.290 mL of ethyl t-butyl malonate, 0.5 mL of piperidine and 0.05 mL of acetic acid were added. The reaction was heated under a dry N$_2$ atmosphere at reflux for 25 hours, the solvents were removed by evaporation and the product was purified by column chromatography on silica gel, eluting with 1:10:100 acetic acid:methanol:methylene chloride. Removal of the solvent afforded 0.287 g of the title compound as a pale yellow solid, mp >265° C. MS M/Z 321 (M+H). NMR: (CDCl$_3$+CD$_3$OD) d 0.61 (m, 2H), 1.06 (m, 2H), 1.58 (s, 9H), 172 (m, 1H), 8.07 (s, 1H), 8.93 (d, 1H, J=6 Hz). IR (KBr)1720, 1525 cm-1.

Step 2: 2-Chloro-9-cyclopropyl-3-fluoro-6H-6-oxo-pyrido[1,2-a]pyrimidine-7-carboxylic acid t-butyl ester A mixture of 0.100 g (0.312 mmol) of the compound from Step 1, 0.29 mL of DMF, 0.33 mL of phosphorous oxychloride and 10 mL of methylene chloride was stirred under a dry $N_2$ atmosphere at room temperature for 1 hour. After workup as described in Example 157 Step 5. the title compound was obtained as a orange solution in methylene chloride. This compound was taken directly to the next step.

Step 3: 2-(3-(N-t-butoxycarbonyl)aminopyrrolidin-1-yl)-9-cyclopropyl-3-fluoro-6H-6-oxo-pyrido[1,2-a]pyrimidine-7-carboxylic acid t-butyl ester To the 0.312 mmol sample in methylene chloride from the previous step at room temperature was added several small portions of 3-(N-t-butoxycarbonyl)aminopyrrolidine until the color of the reaction turned from orange to light yellow. The solution was concentrated to leave a yellow residue. The product was purified by column chromatography on silica gel, eluting with 10:100 methanol: methylene chloride to afford 0.132 g of the title compound as a yellow solid after removal of the solvent. This compound was taken directly to the next step.

Step 4: 2-(3-aminopyrrolidin-1-yl)-9-cyclopropyl-3-fluoro-6H-6-oxo-pyrido[1,2-a]pyrimidine-7-carboxylic acid The boc-protected t-butyl ester from Step 4 was hydrolyzed by reacting the 0.132 g sample with 1 mL of 4N HCl in dioxane under a dry $N_2$ atmosphere. The solvent was removed, the yellow solid was dissolved in water and the solution adjusted to pH 7–8, and extracted with methylene chloride. The reaction was incomplete at this point, so the solid was redissolved in 5 mL of trifluoroacetic acid and the reaction stirred at room temperature overnight. The solvent was removed by evaporation. The residue was redissolved and extracted as above, then the product was purified by column chromatography on silica gel, eluting with 2:5:20:100 water:acetic acid:methanol:methylene chloride to afford 0.0515 g of the title compound as a yellow solid.

EXAMPLE 159

9-(2,4-Difluorophenyl)-3-fluoro-2-(4methylpiperazin-1-yl)-6H-6-oxopyridol[1,2-a]pyrimidine-7-carboxylic acid Step 1: 2-(2,4-Difluorophenyl)-acetamine hydrochloride Into a solution of 49.44 g (0.323 mol) of 2,4-difluorophenylacetonitrile (commercially available) in 20.8 mL (0.354 mol) of ethanol cooled to 0° C. in an ice bath and stirred under a dry $N_2$ atmosphere was added 14.61 g (0.400 mol) of gaseous HCl. After 20 min the reaction mixture solidified, this was then allowed to warm to room temperature and held at this temperature for 72 hours. To the mixture was then added 140 mL of ethanol, followed by 150 mL (0.42 mol) of 4.2M ammonia in ethanol. This mixture was stirred for an additional 3 hours at room temperature and filtered. The solvent was removed from the filtrate by evaporation to afford 65.7 g of the title compound as a white solid, mp 163°–164° C. NMR: (DMSO-d6) d 3.72 (s, 2H), 7.16 (m, 1H), 7.33 (m, 1H), 7.50 (m, 1H), 8.95 (broad, 4H). This compound was taken directly to the next step.

Step 2: 2-(2,4-Difluorobenzyl)-5-fluoro-4-hydroxypyrimidine

A mixture of 68.0 g (0.33 mol) of the compound from Step 1, 0.34 mol of the sodium salt of ethyl 2-fluoro-3-hydroxy-2-propenoate (prepared as described by E. Elkik and M. Imbeaux-Oudotte, *Bull. Soc. Chim. Fr.*, 5–6 pt 2, 1165 (1975)), 300 mL of anhydrous methanol and 50 mL of triethylamine was heated at reflux under a dry $N_2$ atmosphere for 23 hours. The solvent was removed by evaporation under vacuum, 200 mL of water added and the mixture acidified to pH 3–4 with 10% HCl. This mixture was then extracted with methylene chloride. The solvent was washed with water, dried over anhydrous magnesium sulfate, and the solvent was removed by evaporation under vacuum to give a dark oil which solidified upon standing. The sold was washed with ethyl acetate, ethyl acetate/hexane and hexane to afford 29.8 g of the title compound as a white solid, mp 155°–156° C. A second crop of 10.2 g of product was obtained from the filtrates after chromatography on silica gel, eluting with 2.5% methanol in methylene chloride. MS M/Z: 258 (M=$NH_4$), 241 (M+H). NMR: ($CDCl_3$) d 4.02 (s, 2H), 6.88 (m, 2H), 7.33 (m, 1H), 7.89 (d, 1H, J=3 Hz). IR (KBr): 1690, 1605 $cm^{-1}$. Analysis calculated for $C_{11}H_7F_3N_2O$: C, 55.00; H, 2.94; N, 11.67. Found: C, 54.63; H, 2.98; N, 11.50.

Step 3: 4-Chloro-2-(2,4-difluorobenzyl)-5-fluoropyrimidine

A mixture of 1.000 g (4.16 mmol) of the compound from Step 2, 3.40 mL (43.7 mmol) of DMF and 3.90 mL (43.7 mmol) of phosphorous oxychloride in 15 mL of methylene chloride was stirred under a dry $N_2$ atmosphere at ambient temperature for 2 hours, then quenched with water and ice. The mixture was then extracted with methylene chloride, which was washed with water, dried, filtered and concentrated to yield the title compound as a yellow oil. MS M/Z: 259 (M+H). NMR: ($CDCl_3$) d 4.27 (s, 2H), 6.83 (m, 2H), 7.27 (m, 1H), 8.48 (s, 1H). This compound was taken directly to the next step.

Step 4: 2-(2,4-Difluorobenzyl)-5-fluoro-4-(4-methylpiperazin-1-yl)pyrimidine

To the 4.16 mmol of the compound from Step 3 in 10 mL of methylene chloride was added 3 mL of N-methylpiperidine and the mixture was stirred under a dry $N_2$ atmosphere at room temperature for 1 hour. The solvent was removed by evaporation, and the product was purified by column chromatography on silica gel eluting with 5% methanol in methylene chloride. The solvent was removed by evaporation to afford 1.229 g of the title compound as a pale yellow oil, MS M/Z: 323 (M+H). NMR: ($CDCl_3$) d 2.32 (s, 3H), 2.46 (t, 4H, J=7 Hz), 3.75 (t, 4H, J=7 Hz), 4.05 (s, 2H), 6.80 (m, 2H), 7.25 (m, 1H), 7.99 (d, 1H, J=7 Hz). Analysis calculated for $C_{16}H_{17}F_3N_4$: C, 59.61; H, 5.32; N, 17.38. Found: C, 59.63; H, 5.31; N, 17.31.

Step 5: 3-(2,4-Difluorophenyl)-2-ethoxy-3-(5-fluoro-4-(4-methylpiperidin-1-yl)pyrimidin-2-yl)propane-1,1-dicarboxylic acid diethyl ester Following the procedure of Step 4 Example 1 the compound from Step 4 above (0.74 g, 2.3 mmol), 1.0 mL (2.5 mmol) of a 2.5M solution of n-butyllithium in hexane and 0.35 mL of diisopropylamine was reacted with 0.46 mL ethyl 2-carboethoxy-3-ethoxy-2-propenecarboxylate, to afford after work-up 1.22 g of the title compound as an oil. This material was further purified by column chromatography over silica gel, eluting with 5% ethanol in ethyl acetate to give 0.774 g of an oil; MS M/Z: 539 (M+H). NMR: ($CDCl_3$) d 0.87 (m, 3H), 1.22 (m, 6H), 2.34 (s, 3H), 2.50 (m, 4H), 3.52 (m, 2H), 3.81 (m, 4H), 4.16 (m, 5H), 4.82 (m, 1H), 4.99 (m, 1H), 6.78 (m, 2H), 7.59 (m, 1H), 8.01 (m, 1H).

Step 6: 9-(2,4-Difluorophenyl)-3-fluoro-2-(4-methylpiperazin-1-yl)-6H-6-oxopyrido[1,2-a]pyrimidine-7-carboxylic acid ethyl ester To a 1.847 g (3.43 mmol) sample of the compound from Step 5 dissolved in 40 mL of anhydrous ethanol was added 1.5 mL of piperidine and 0.05 mL of acetic acid, and the reaction was heated at reflux conditions under a dry $N_2$ atmosphere for 3 hours. The solvent was removed by evaporation to leave a yellow solid which was purified by column chromatography over silica gel, eluting with 0.5:10:100 28% aq. $NH_4OH$:methanol:methylene chloride to afford after removal of the solvent 1.282 g of the title compound as a yellow solid, mp 193°–195° C. MS M/Z: 447

(M+H). NMR: (CDCl$_3$) d 1.40 (t, 3H, J=7 Hz), 2.33 (s, 3H), 2.50 (m, 4H), 3.89 (m, 4H), 4.39 (q, 2H, J=7 Hz), 6.91 (m, 2H), 7.33 (m, 1H), 8.37 (s, 1H), 9.16 (d, 1H, J=10 Hz). IR (KBr): 1725, 1685, 1660 cm$^{-1}$. Analysis calculated for C$_{22}$H$_{21}$F$_3$N$_4$O$_3$.0.5 H$_2$O; C, 58.02; H, 4.87; N, 12.30. Found: C, 58.15; H, 4.70; N, 12.15.

Step 7: 9-(2,4-Difluorophenyl)-3-fluoro-2-(4-methylpiperazin-1-yl)-6H-6-oxopyrido[1,2-a]pyrimidine-7-carboxylic acid benzyl ester A mixture of a 1.166 g (2.61 mmol) sample of the ethyl ester compound from Step 1, 150 mL of dry benzyl alcohol and 0.5 mL of titanium tetramethoxide was heated under a dry N$_2$ atmosphere with stirring at reflux conditions for 17 hours. The solvent was removed by distillation at 100° C. under reduced pressure in a kugelrohr apparatus. The product was purified by column chromatography on silica gel, eluting with 0.5:10:100 28% aq. NH$_4$OH:methanol:methylene chloride to afford after removal of the solvent 0.895 g of the title compound as a yellow solid, mp 207°–208° C. MS M/Z: 509 (M+H). NMR: (CDCl$_3$) d 2.33 (s, 3H), 2.50 (m, 4H), 3.88 (m, 4H), 5.38 (s, 2H), 6.90 (m, 2H), 7.30–7.50 (m, 6H), 8.37 (s, 1H), 9.17 (d, 1H, J=10 Hz). IR (KBr): 1730, 1685, 1660 cm$^{-1}$.

Step 8: 9-( 2,4-Difluorophenyl)-3-fluoro-2-(4-methylpiperazin-1-yl)-6H-6-oxopyrido[1,2-a]pyrimidine-7-carboxylic acid A 0.300 g (0.590 mmol) sample of the benzyl ester from Step 7 was dissolved in 40 mL of dry methanol and 0.1 g of 10% Palladium on carbon was added. Four mL of 98% formic acid was added and the mixture stirred under a dry N$_2$ atmosphere for 20 min. The catalyst was removed by filtration through diatomaceous earth, and the solvent was removed under vacuum. The product was purified by column chromatography on silica gel, eluting with 1:10:100 acetic acid:methanol:methylene chloride give a yellow solid. This material was washed with pH 7.5 sodium bicarbonate solution, followed by water rinse to afford 0.178 g of the title compound as a yellow solid, mp 246°–248° C. (dec.). MS M/Z: 419 (M+H). NMR: (CDCl$_3$+CD$_3$OD) d 2.34 (s, 3H), 2.53 (m, 4H), 3.85–4.00 (m, 4H), 6.90 (m, 2H), 7.32 (m, 1H), 8.49 (s, 1H), 9.07 (d, 1H, J=9 Hz). IR (KBr): 1720, 1660 cm$^{-1}$. Analysis calculated for C$_{20}$H$_{17}$F$_3$N$_4$O$_3$: C, 57.42; H, 4.10; N, 13.39. Found: C, 57.21; H, 4.08; N, 13.21.

EXAMPLE 160

2-(3-(N-t-butoxycarbonyl)aminopyrrolidin-1-yl)-9-(2,4-difluorophenyl)-3-fluoro-6H-6-oxopyrido[1,2-a]pyrimidine-7-carboxylic acid Step 1. 3-(2,4-Difluorophenyl)-2-ethoxy-3-(5-fluoro-4-hydroxypyrimidin-2-yl)propane-1,1-dicarboxylic acid diethyl ester A 4.804 g (20.0 mmol) sample of 2-(2,4-Difluorobenzyl)-5-fluoro-4-hydroxypyrimidine (prepared as described in Step 2 Example 159 above) was dissolved in 150 mL of dry THF and cooled to −78° C. with stirring under a dry N$_2$ atmosphere. To this was slowly added 16.40 mL of 2.5N n-butyllithium in hexane, and the mixture was stirred for 30 min. Then 4.85 mL (24 mmol) of diethyl ethoxymethylenemalonate was added and the mixture stirred for an additional 30 min at −78° C. The reaction mixture was quenched with 10% HCl until the mixture was at pH 3, whereupon it was then extracted with ethyl acetate. This was dried over anhydrous magnesium surfate and the solvent was removed by evaporation under vacuum to afford the title compound as a yellow oil. This material was taken directly to the next step.

Step 2. 9-(2,4-Difluorophenyl)-3-fluoro-2-hydroxy-6H-6-oxopyrido[1,2-a]pyrimidine-7-carboxylic acid ethyl ester The compound from Step 1 was dissolved in 80 ml of ethanol, 2 mL of piperidine and 0.2 mL of acetic acid was added and the mixture heated at reflux (bath temperature at 90° C.) for 16 hours under a dry N$_2$ atmosphere. The solvent was removed by evaporation, and the residue was washed with methanol and methylene chloride to give 4.794 g of a pale yellow solid. The washings were concentrated and the residue was purified by column chromatography on silica gel, eluting with 2:10:100 acetic acid:methanol:methylene chloride to afford an additional 2.220 g of the title compound as a pale yellow solid, mp 239°–240° C. MS M/Z: 382 (M+NH$_4$), 365 (M+H). NMR:(DMSO-d$_6$) d 1.23 (t, 3H, J=7 Hz), 4.14 (q, 2H J=7 Hz), 7.08 (m, 1H), 7.21 (m, 1H), 7.40 (m, 1H), 7.83 (s, 1H), 8.74 (d, 1 H, J=8 Hz). IR (KBr) 1710, 1675, 1620 cm$^{-1}$.

Step 3. 9-(2,4-Difluorophenyl)-3-fluoro-2-hydroxy-6H-6-oxopyrido[1,2-a]pyrimidine-7-carboxylic acid benzyl ester To a 7.000 g sample of the ethyl ester compound from Step 2 dissolved in 200 mL of benzyl alcohol was added 0.70 mL of titanium tetraethoxide and the mixture heated with stirring at 100° C. for 2.5 hours under a dry N$_2$ atmosphere. The reaction was diluted with methylene chloride, then washed once with 1N HCl and three times with water, and the solvent was dried over anhydrous magnesium sulfate and removed by evaporation under vacuum to leave a yellow solid. This material was washed with ether and dried under vacuum to afford 6.655 g of the title compound as a yellow solid, mp 218°–219° C. MS M/Z 427 (M+H). NMR:(DMSO-d$_6$) d 5.26 (s, 2H), 7.15–7.45 (m, 8H), 8.00 (s, 1H), 9.00 (d, 1H, J=7 Hz). IR (KBr) 1710, 1675, 1620 cm$^{-1}$.

Step 4. 2-(3-(N-t-butoxycarbonyl)aminopyrrolidin-1-yl)-9-(2,4-difluorophenyl)-3-fluoro-6H-6-oxopyridol[1,2-a]pyrimidine-7-carboxylic acid benzyl ester A 1.200 g (2.815 mmol) sample of the compound from Step 3 was dissolved in 45 mL of methylene chloride and 2.50 mL of DMF and 2.95 mL of POCl$_3$ were added. The reaction was stirred under a dry N$_2$ atmosphere at room temperature for 2.5 hours, then quenched with ice and water. The mixture was extracted with methylene chloride, and the solvent was washed with water until the acidity of the rinse water was above pH 3. The solvent was then dried with magnesium sulfate and an excess of 2-(N-t-butoxycarbonylamino)pyrrolidine was added and allowed to react. The solution was then concentrated and the product was purified by column chromatography over silica gel eluting with 0.5:5:100 conc. ammonium hydroxide:methanol:methylene chloride. The solvent was removed to afford 1.579 g of the title compound as a light yellow crystalline solid, mp 103°–104° C. MS M/Z: 595 (M+H). NMR: (CDCl$_3$) d 1.45 (s, 9H), 1.85–2.30 (m, 2H), 3.42–4.35 (m, 5H), 4.65 (br s, 1H), 5.38 (s, 2H), 6.89 (m, 2H), 7.30–7.50 (m, 6H), 8.35 (s, 1H), 9.15 (d, 1H, J=9 Hz), 9.16 (d, 1H, J=9 Hz). IR (KBr): 1735, 1710, 1660 cm$^{-1}$.

Step 5. 2-(3-(N-t-butoxycarbonyl)aminopyrrolidin-1-yl)-9-(2,4-difluorophenyl)-3-fluoro-6H-6-oxopyrido[1,2-a]pyrimidine-7-carboxylic acid A 1.769 g sample of the compound from Example 160 Step 4 was dissolved in 80 mL of dry methanol, and the benzyl ester was removed by reacting with 4.0 mL of 98% formic acid in the presence of 0.200 g of 10% Pd/C under a dry N$_2$ atmosphere. After filtration and evaporation of the solvent, the product was purified by column chromatography on silica gel, eluting with 1:10:100 acetic acid:methanol:methylene chloride to afford, after removal of the solvent, 1.125 g of the title compound as a yellow solid, mp 209.5°–210.5° C. MS M/Z: 505 (M+H). NMR: (CDCl$_3$/CD$_3$OH) d 1.45 (s, 9H), 1.90–2.30 (m, 2H), 3.50–4.35 (m,5H) 6.91 (m, 2H), 7.32 (m, 1H), 8.44 (s, 1H), 9.03 (d, 1H, J=8 Hz), 9.04 (d, 1H, J=8 Hz). IR (KBr): 1714, 1662, 1620 cm$^{-1}$.

EXAMPLE 161

2-(3-Aminopyrrolidin-1-yl)-9-(2,4-difluorophenyl)-3-fluoro-6H-6-oxopyrido[1,2-a]pyrimidine-7-carboxylic acid A 0.100 g, (0.198 mmol) sample of 2-(3-(N-t-butoxycarbonyl)-aminopyrrolidin-1-yl)-9-(2,4-difluorophenyl)-3-fluoro-6H-6-oxopyrido[1,2-a]pyrimidine-7-carboxylic acid, from Example 160 Step 5, was dissolved in a small volume of 4N HCl in dioxane and stirred at room temperature for 3 hours under a dry N$_2$ atmosphere. The solvent was removed by evaporation under vacuum to yield a yellow solid, which was dissolved in water and neutralized to pH 7 with 5% sodium bicarbonate solution,. The resulting precipitate was filtered off, washed with water and dried to afford 0.075 g of the title compound as a yellow solid mp>250° C. MS M/Z: 405 (M+H). NMR: (DMSO) d 1.90–2.30 (m, 2H), 3.00–4.10 (m, 5H), 7.16 (m, 2H), 7.30 (m, 1H), 8.18 (s, 1H), 9.17 (d, 1H, J=8 Hz), 9.18 (d, 1H, J=8 Hz). IR (KBr): 1715, 1660 cm$^{-1}$. Analysis calculated for C$_{19}$H$_{15}$F$_3$N$_4$O$_3$.1.25 H$_2$O; C, 53.46; H, 4.07; N, 13.12. Found: C, 53.64; H, 3.70; N, 12.80.

EXAMPLE 162

2-(3-Aminopyrrolidin-1-yl)-9-(2,4-difluorophenyl)-3-fluoro-6H-6-oxopyridol[1,2-a]pyrimidine-7-carboxylic acid trifluoroacetic acid salt A 0.879 g (2.174 mmol) sample of 2-(3-aminopyrrolidin-1-yl)-9-(2,4-difluorophenyl)-3-fluoro-6H-6-oxopyrido[1,2-a]pyrimidine-7-carboxylic acid, from Example 161, was dissolved in 10 mL of trifluoroacetic acid, then the excess acid was removed by evaporation under vacuum. The yellow residue was dissolved in 600 mL of water with containing 1 mL of trifluoroacetic acid, the solution was filtered through sintered glass and freeze dried to afford 0.876 g of the title compound as a light yellow solid; mp 191°–192° C. (dec.);. MS M/Z: 405 (M+H). NMR (CD$_3$OH): ∂: 0:2.102.55 (m, 2H), 3.75–4.20 (m, 5H), 7.05 (m, 2H), 7.50 (m, 1H), 8.30 (s, 1H), 9.19 (d, 1H), J=8 Hz). IR (KBr): 1720, 1560, 1520 cm$^{-1}$. Analysis calculated for C$_{21}$H$_{16}$F$_6$N$_4$O$_5$.H$_2$O: C, 47.02; H, 3.38; N, 10.45. Found: C, 47.36; H, 3.07; N, 10.36.

EXAMPLE 163

9-Cyclopropyl-3-fluoro-2-(4-methylpiperazin-1-yl)-6H-6-oxo-pyrido[1,2-a]pyrimidine-7-carboxylic acid Step 1. 2-Chloro-9-cyclopropyl-3-fluoro-6H-6-oxo-pyrido[1,2-a]pyrimidine-7-carboxylic acid benzyl ester To a 0.100 g (0.282 mmol) sample of 9-cyclopropyl-3-fluoro-2-hydroxy-6H-6-oxo-pyrido[1,2-a]pyrimidine-7-carboxylic acid benzyl ester, prepared as described in Example 157 Step 4, was added 5 mL of methylene chloride, 0.275 mL of DMF and 0.33 mL of phosphorous oxychloride, and the reaction was stirred 5 hours at room temperature under a dry N$_2$ atmosphere. The solution was cooled to 0° C., and ice was added to destroy the excess phosphorous oxychloride. This mixture was then extracted with methylene chloride which was dried over anhydrous magnesium surfate The solvent was removed by evaporation under vacuum to afford the title compound as an orange solid. NMR (CDCl$_3$): d 4.27 (s, 2H), 6.83 (m, 2H), 7.27 (m, 2H), 8.48 (s, 1H). This material was taken directly to the next step.

Step 2. 9-Cyclopropyl-3-fluoro-2-(4-methylpiperazin-1-yl)-6H-6-oxo-pyrido[1,2-a]pyrimidine-7-carboxylic acid benzyl ester The compound from the previous step was dissolved in 2.5 mL of methylene chloride and 0.5 mL of N-methylpiperazine was added with cooling. The reaction was stirred at room temperature overnight. The solvent was removed by evaporation and the product was purified by column chromatography on silica gel, eluting with 10% methanol in methylene chloride. The solvent was removed to afford 0.107 g of the title compound as a yellow solid. Recrystallization from methanol gave yellow needles, mp 194°–195° C. MS M/Z 437 (M+H). NMR:(CDCl$_3$) d 0.62 (m, 2H), 0.88 (m, 2H), 2.12 (m, 1H), 2.57 (s, 3H), 2.59 (t, 4 H, J=7 Hz), 4.07 (t, 4H, J=7 Hz), 5.38 (s, 2H), 7.28 (m, 1H), 7.36 (m, 2H), 7.51 (m, 2H), 8.04 (s, 1H), 9.16 (d, 1H, J=10 Hz). IR (KBr): 1715, 1685, 1660 cm$^{-1}$. Analysis calculated for C$_{24}$H$_{25}$FN$_4$O$_3$.¼ H$_2$O: C, 65.37; H, 5.83; N, 12.70. Found: C, 65.21; H, 5.53; N 12.59.

Step 3. 9-Cyclopropyl-3-fluoro-2-(4-methylpiperazin-1-yl)-6H-6-oxo-pyrido[1,2-a]pyrimidine-7-carboxylic acid To a 0.050 g (0.115 mmol) sample of the benzyl ester compound from the previous step was added 10 mL of methanol, 1 mL of 98% formic acid and 0.04 g of 10% Pd/C, and the mixture was stirred under Argon for 30 min at room temperature. The solution was diluted with methylene chloride, filtered through diatomaceous earth and the solvent was removed to leave a yellow residue. The product was purified by column chromatography on silica gel, eluting with 1:10:100 acetic acid:methanol:methylene chloride. After removal of the solvent, 0.0345 g of the title compound was obtained as a yellow solid, mp 219°–220° C. MS M/Z 347 (M+H). NMR:(CDCl$_3$) d 0.67 (m, 2H), 0.95 (m, 2H), 2.18 (m, 1H), 2.39 (s, 3H), 2.65 (t, 4H, J=6 Hz), 4.13 (m, 4H), 8.11 (s, 1H), 9.02 (d, 1H), J=10 Hz). IR (KBr): 1720, 1660, 1620 cm$^{-1}$. Analysis calculated for C$_{17}$H$_{19}$FN$_4$O$_3$.0.6 CH$_3$COOH: C, 57.17; H, 5.64; N, 14.65. Found: C, 57.60; H, 5.79; N, 14.13.

EXAMPLE 164

9-Cyclopropyl-3-fluoro-2-(piperazin-1-yl)-6H-6-oxo-pyrido[1,2-a]pyrimidine-7-carboxylic acid Step 1. 2-Chloro-9-cyclopropyl-3-fluoro-6H-6-oxo-pyrido[1,2-a]pyrimidine-7-carboxylic acid t-butyl ester A mixture of 0.100 g (0.312 mmol) of 9-cyclopropyl-3-fluoro-2-hydroxy-6H-6-oxo-pyrido[1,2-a]pyrimidine-7-carboxylic acid t-butyl ester from Example 158 Step 1, 0.29 mL of DMF, 0.33 mL of phosphorous oxychloride and 10 mL of methylene chloride was stirred under a dry N$_2$ atmosphere at room temperature for 1 hour. After workup as described in Example 157 Step 5, the title compound was obtained as a orange solution in methylene chloride, which was taken directly to the next step.

Step 2. 9-Cyclopropyl-3-fluoro-2-(piperazin-1-yl)-6H-6-oxo-pyrido[1,2-a]pyrimidine-7-carboxylic acid t-butyl ester The sample from Step 1 in 5 mL of methylene chloride was added dropwise to a solution of 0.289 g piperazine in 10 mL of methylene chloride stirred under a dry N$_2$ atmosphere.

The resulting yellow solution was concentrated to give a yellow residue, which was purified by column chromatography on silica gel, eluting with 0.5:10:100 conc. ammonium hydroxide:methanol:methylene chloride, to afford after removal of the solvent 0.068 g of the title compound as a yellow solid. This material was taken directly to the next step.

Step 3. 9-Cyclopropyl-3-fluoro-2-(piperazin-1-yl)-6H-6-oxo-pyrido[1,2-a]pyrimidine-7-carboxylic acid The sample of the compound from the previous step was reacted with 10 mL of 4N HCl in dioxane under a dry $N_2$ atmosphere at room temperature overnight. The solvent was removed, the yellow solid was dissolved in distilled water, adjusted to pH 7–8 with saturated sodium carbonate solution, and the solution extracted with methylene chloride. The extracts were washed with water, dried, concentrated, and chromatographed on silica gel to afford 0.043 g of the title compound as a yellow solid, mp 198°–199° C. MS M/Z 333 (M+H). NMR:(CDCl$_3$) d 0.67 (m, 2H), 0.94 (m, 2H), 2.19 (m, 1H), 3.08 (t, 4H, J=6 Hz), 4.08 (m, 4H), 8.11 (s, 1H), 9.01 (d, 1H, J=10 Hz). IR (KBr): 1710, 1660 cm$^{-1}$. Analysis calculated for $C_{16}H_{17}FN_4O_3 \cdot 0.1\ H_2O$: C, 57.36; H, 5.20; N, 16.72. Found: C, 57.69; H, 5.22; N, 16.31.

EXAMPLE 165

9-Cyclopropyl-3-fluoro-2-(morpholin-1-yl)-6H-6-oxo-pyrido[1,2-a]pyrimidine-7-carboxylic acid Step 1. 9-Cyclopropyl-3-fluoro-2-(morpholin-1-yl)-6H-6-oxo-pyridol[1,2-a]pyrimidine-7-carboxylic acid benzyl ester To a 0.150 g (0.396 mmol) sample of 2-chloro-9-cyclopropyl-3-fluoro-6H-6-oxo-pyrido[1,2-a]pyrimidine-7-carboxylic acid benzyl ester, prepared as in Example 164 Step 1, dissolved in anhydrous methylene chloride and cooled to 0° C. and stirred under a dry $N_2$ atmosphere was added 0.042 mL (0.483 mmol) of morpholine dropwise. The color changed from orange to yellow, and the reaction was complete in 15 min. The solvent was removed by evaporation, and the product was purified by column chromatography on silica gel, eluting with 2:10:100 acetic acid:methanol:methylene chloride. The solvent was removed to afford the title compound as a yellow solid. This was taken directly to the next step. NMR:(CDCl$_3$) d 0.62 (m, 2H), 0.89 (m, 2H), 2.11 (m, 1H), 3.87 (t, 4H), J=6 Hz), 4.07 (t, 4H, J=6 Hz), 5.39 (s, 2H), 7.29 (m, 1H), 7.37 (m, 2H), 7.51 (m, 2H), 8.07 (s, 1H), 9:19 (d, 1H, J=10 Hz).

Step 2. 9-Cyclopropyl-3-fluoro-2-(morpholin-1-yl)-6H-6-oxo-pyrido[1,2-a]pyrimidine-7-carboxylic acid The benzyl ester product from the previous step was dissolved in 20 mL of anhydrous methanol and stirred with 0.020 g of 10% Pd/C catalyst under 1 atm. Hydrogen at room temperature for 5 hours. The catalyst was removed by filtration, and the solvent was removed under vacuum to afford 0.100 g of the title compound as a yellow solid, mp>260° C. MS M/Z 334 (M+H). NMR:(CDCl$_3$) d 0.68 (m, 2H), 0.95 (m, 2H), 2.19 (m, 1H), 3.90 (t, 4H, J=6 Hz), 4.10 (t, 4H, J=6 Hz)., 8.15 (s, 1H), 9.06 (d, 1H, J=10 Hz). IR 1720, 1660, 1620 cm$^{-1}$. Analysis calculated for $C_{16}H_{16}FN_3O_4 \cdot H_2O$: C, 54.70; H, 5.16; N, 11.96. Found: C, 55.01; H, 4.71; N, 11.62.

EXAMPLE 166

9-(2,4-Difluorophenyl)-3-fluoro-2-(3-(N-(S)-norvalyl) aminopyrrolidin-1-yl)-6H-6-oxopyrido [1,2-a]pyrimidine-7-carboxylic acid hydrochloride salt Step 1. 2-(3-Aminopyrrolidin-1-yl)-9-(2,4-difluorophenyl)-3-fluoro-6H-6-oxopyrido[1,2-a]pyrimidine-7-carboxylic acid benzyl ester.

A 1.579 g (2.655 mmol) sample of the 9-(2,4-difluorophenyl)-3-fluoro-2-(3-(N-t-butoxycarbonyl)aminopyrrolidin-1-yl)-6H-6-oxopyrido[1,2-a]pyrimidine-7-carboxylic acid benzyl ester, from Example 160 Step 4, was dissolved in 5 mL of trifluoroacetic acid and stirred at room temperature for 1 hour under a dry $N_2$ atmosphere. The solvent was removed by evaporation under vacuum to yield the deprotected title product as a yellow solid, which was taken directly to the next step. Mp 185°–186° C. NMR (CDCl$_3$): d 1.75–2.19 (m, 2H), 3.33–4.07 (m, 5H), 5.38 (s, 2H), 6.87 (m, 2H), 7.32 (m, 4H), 7.48 (m, 2H), 8.33 (s, 1H), 9.13 (apparent d, 1H, J=9 Hz).

Step 2. 2-(3-(N-(N-Benzyloxycarbonyl)norvalyl)aminopyrrolidin-1-yl)-9-(2,4-difluorphenyl)-3-fluoro-6H-6-oxopyrido[1,2-a]pyrimidine-7-carboxylic acid benzyl ester The sample from the previous step was suspended in 50 mL of THF and diisopropylethylamine was added with stirring at room temperature until a homogeneous solution resulted. Then 0.885 g (2.66 mmol) of the N-benzyloxycarbonyl protected (s)-norvaline succinamide was added and stirred at room temperature for 1 hour under a dry $N_2$ atmosphere. Another 0.050 g of the protected norvaline was added, and the solution was stirred for another 0.5 hours. The reaction was diluted with methylene chloride, washed with water (4×), and the organic solvent dried over anhydrous magnesium sulfate and removed by evaporation under vacuum. This product was purified by column chromatography on silica gel, eluting with 5% methanol in methylene chloride, to afford 1.678 g of the title compound as a yellow crystalline solid after removal of the solvent. Mp 103°–105° C. MS M/Z: 728 (M+H). NMR: (CDCl$_3$) d 0.90 (t, 3H, J=7 Hz), 1.39–2.30 (m, 6H), 3.30–4.40 (m, 5H), 4.85–5.40 (m, 5H), 6.75–7.40 (m, 13H), 8.15–8.80 (m, 2H). IR (KBr): 1700, 1660 cm$^{-1}$. Analysis calculated for $C_{39}H_{36}F_3N_5O_6 \cdot 0.25\ H_2O$: C, 63.97; H, 5.02; N, 9.56. Found: C, 64.19; H 5.11; N, 9.50.

Step 3. 9-(2,4-Difluorophenyl)-3-fluoro-2-(3-(N-(S)-norvalyl)aminopyrrolidin-1-yl)-6H-6-oxopyrido[1,2-a]pyrimidine-7-carboxylic acid hydrochloride salt A 1.515 g sample (2.0822 mmol) of the compound from the previous step was dissolved in 80 mL of methanol, and 4.0 mL of 98% formic acid and 0.2 g of 10% Pd/C was added. The mixture was stirred at room temperature for 1.7 hours under a dry $N_2$ atmosphere, filtered and concentrated to leave a yellow solid residue. This solid was dissolved in methanol and filtered through sintered glass, then the solvent was removed to leave a yellow solid. This solid was dissolved in 50 mL of methanol, 3 mL of conc. HCl was added and the solvent evaporated off. The residue was dissolved in 200 mL of water, filtered again through sintered glass, and the solution was freeze-dried to afford 0.969 g of the title product as a yellow solid, mp 192°–194° C. MS M/Z: 504 (M+H). NMR: (CD$_3$OD) d 0.96 (m, 3H), 1.90–2.35 (m, 6H), 3.50–4.60 (m, 5H), 7.02 (m, 2H), 7.48 (m, 1H), 8.22 (br s, 1H), 8.35 (br s, 2H), 9.09 (m, 1H). IR (KBr): 1710, 1665, 1610 cm$^{-1}$. Analysis calculated for $C_{24}H_{25}F_3N_5O_4 \cdot 2\ H_2O$:

C, 50.05; H, 5.07; N, 12.16. Found: C, 50.00; H, 4.56; N, 12.03.

EXAMPLE 167

2-(3-(N-(S)-Alanyl)aminopyrrolidin-1-yl)-9-(2,4-difluorophenyl)-3-fluoro-6H-6-oxopyridol[1,2a]pyrimidine-7-carboxylic acid hydrochloride Step 1. 2-(3-(N-(N-Benzyloxycarbonyl)alanyl)aminopyrrolidin-1-yl)-9-(2,4-difluorophenyl)-3-fluoro-6 H-6-oxopyrido[1,2-a]pyrimidine-7-carboxylic acid benzyl ester A 0.982 g (1.986 mmol) sample of 9-(2,4-difluorophenyl)-3-fluoro-2-(3-aminopyrrolidin-1-yl)-6H-6-oxopyrido[1,2-a]pyrimidine-7-carboxylic acid benzyl ester, prepared as described in Example 166 Step 1, was suspended in 40 mL of THF and 0.700 g (2.196 mmol) of the N-benzyloxycarbonyl protected (S)-alanine succinamide was added. The mixture was stirred at room temperature for 2 hour under a dry $N_2$ atmosphere. The reaction solvent was evaporated off, then the residue was dissolved in methylene chloride, which was washed with water (3×). The organic solvent was dried over anhydrous magnesium sulfate and removed by evaporation under vacuum. This product was purified by column chromatography on silica gel, eluting with 5% methanol in methylene chloride, to afford, after removal of the solvent, 1.318 g of the title compound as a yellow crystalline solid, mp 104°–107° C. MS M/Z 700 (M+H). NMR: (CDCl$_3$) d 1.43 (m, 3H), 1.95–2.30 (m, 2H), 3.40–4.40 (m, 5H), 4.75–5.35 (M, 5H), 6.77 (m, 2H), 7.10–7.40 (m, 1H), 8.18–8.40 (m, 2H). IR (KBr): 1720, 1660 cm$^{-1}$. Analysis calculated for $C_{37}H_{32}F_3N_5O_6 \cdot \frac{1}{2} H_2O$: C, 62.71; H, 4.69; N, 9.88. Found: C, 63.04; H, 4.49; N, 9.92

Step 2. 2-(3-(N-(S)-Alanyl)aminopyrrolidin-1-yl)-9-(2,4-difluorophenyl)-3-fluoro-6H-6-oxopyrido[1,2-a]pyrimidine-7-carboxylic acid hydrochloride A 1.262 g (1.804 mmol) sample of the compound from the previous step was suspended in 80 mL of methanol and 4.0 mL of 98% formic acid and 0.200 g of 10% Pd/C was added with stirring. The mixture was stirred at room temperature for 1.7 hours, then 40 ml of THF was added and the mixture stirred for 0.3 hours longer under a dry $N_2$ atmosphere, filtered and concentrated to leave a yellow solid residue. This was dissolved in 500 mL of water and 4 mL of conc. HCl was added, then the solution was filtered through sintered glass and freeze-dried to afford 0.877 g of the title compound as a yellow solid, mp 198°–200° C. (dec). MS M/Z 476 (M—Cl). NMR: (DMSO-d$_6$) d 1.33 (apparent t, 3H, J=7 Hz), 1.90–2.30 (m, 2H), 3.35–4.40 (m, 6H), 7.17 (m, 1H), 7.32 (m, 1H), 7.58 (m, 1H), 8.20 (d, 1H), 9.19 (m, 1H), 13.45 (br, 1H). IR (KBr): 1715, 1665, 1620 cm$^{-1}$. Analysis calculated for $C_{22}H_{21}ClF_3N_5O_4 \cdot 1.5 H_2O$; C, 49.03; H, 4.48; N, 12.99. Found: C, 49.18; H, 4.17; N, 12.53.

EXAMPLE 168

2-(3-(N-(S)-Alanyl-(S)-alanyl)aminopyrrolidin-1-yl)-9-(2,4-difluorophenyl)-3-fluoro-6H-6-oxopyrido[1,2-a]pyrimidine-7-carboxylic acid hydrochloride Step 1. 2-(3-(N-(N-Benzyloxycarbonyl)-(S)-alanyl-(S)-alanyl)aminopyrrolidin-1-yl)-9-(2,4-difluorophenyl)- 3-fluoro-6H-6-oxopyrido[1,2-a]pyrimidine-7-carboxylic acid benzyl ester A 0.905 g (1.830 mmol) sample of 9-(2,4-difluorophenyl)-3-fluoro-2-(3-aminopyrrolidin-1-yl)-6H-6-oxopyrido[1,2-a]pyrimidine-7-carboxylic acid benzyl ester, prepared as described in Example 166 Step 1, was suspended in 10 mL of DMF and 0.700 g (2.196 mmol) of the N-benzyloxycarbonyl protected (S)-alanyl-(S)-alanine. The mixture was stirred at 0° C. and 0.530 g of 1-ethyl-3-[3-dimethylaminopropyl]carbodiimide hydrochloride (EDAC) and 0.370 g of 1-hydroxybenzotriazole hydrate (HOBT) was added. The mixture was stirred for 30 min at 0° C., then at room temperature for 2 hours. The solvent was removed in a kugelrohr apparatus, then the residue was dissolved in methylene chloride, washed 2× with water, washed 2× with saturated sodium bicarbonate solution, then 2× again with water and dried over magnesium surfate. The solvent was removed by evaporation, and the product was purified by column chromatography on silica gel, eluting with 10% methanol in methylene chloride to afford 1.187 g of the title product as yellow crystals, mp 123°–126° C. MS M/Z 771 (M+H). NMR: (CDCl$_3$) d 1.37 (m, 6H), 1.92–2.18 (m, 2H), 3.58–4.48 (m, 5H), 4.76–5.00 (m, 2H), 5.30 (s, 2H), 5.32 (s, 2H), 6.80 (m, 2H), 7.10–7.45 (m, 1H), 8.23 and 8.30 (two s, 1H), 8.87 and 8.93 (two d, 1H, J=8 Hz). IR (KBr): 1720, 1660 cm$^{-1}$. Analysis calculated for $C_{40}H_{37}F_3N_6O_7 \cdot \frac{1}{2} H_2O$: C, 61.62; H, 4.91; N, 10.78. Found: C, 61.51; H, 4.71; N, 10.75.

Step 2. 2-(3-(N-(S)-Alanyl-(S)-alanyl)aminopyrrolidin-1-yl)-9-(2,4-difluorophenyl)-3-fluoro-6H-6-oxopyrido[1,2-a]pyrimidine-7-carboxylic acid hydrochloride A 1.131 g (1.467 mmol) sample of the compound from Step 1 was dissolved in 80 mL of methanol and 4.0 mL of 98% formic acid and 0.2 g of 10% Pd/C was added. The mixture was stirred 1 hour at room temperature under a dry $N_2$ atmosphere, filtered, and concentrated to leave a yellow residue. This was dissolved in 500 mL of distilled water and 3 mL of conc. HCl was added, then the solution was filtered though sintered glass, and freeze-dried to afford 0.729 g of the title compound as a pale yellow solid, mp 217°–219° C. (dec.) MS M/Z 547 (M-Cl). NMR: (DMSO-d$_6$) d 1.24 (m, 3H), 1.32 (d, 3H, J=7 Hz), 1.80–2.20 (m, 2H), 3.40–4.50 (m, 7H), 7.17 (m, 1H), 7.31 (m, 1H), 7.57 (m, 1H), 8.20 (br, 4H), 8.47 (m, 1H), 8.66 (m, 1H), 9.19 (m, 1H), 13.45 (br, 1H). IR (KBr): 1710, 1660, 1630 cm$^{-1}$.

EXAMPLE 169

2-((2S,4S)-4-Acetamido-2-methylpyrrolidin-1-yl)-9-(2,4-difluorophenyl)-3-fluoro-6H-6-oxopyrido[1,2-a]pyrimidine-7-carboxylic acid Step 1. 2-((2S,4S)-4-Acetamido-2-methylpyrrolidin-1-yl)-9-(2,4-D difluorophenyl)-3-fluoro-6H-6-oxopyrido[1,2-a]pyrimidine-7-carboxylic acid benzyl ester A 0.200 g (0.469 mmol) sample of 9-(2,4-difluorophenyl)-3-fluoro-2-hydroxy-6H-6-oxopyrido[1,2-a]pyrimidine-7-carboxylic acid benzyl ester, from Example 160 Step 3, was dissolved in 5 mL of methylene chloride and 0.42 mL of DMF and 0.49 mL of POCl$_3$ were added. The reaction was stirred under a dry $N_2$ atmosphere at room temperature for 3.5 hours, then quenched with ice and water. The mixture was extracted with methylene chloride, and the solvent was washed with water until the acidity of the rinse water was above pH 3. The solvent was then dried with magnesium sulfate and 0.120 g (0.656 mmol) of (2S,4S)-4-acetamido-2-methylpyrrolidine (prepared as described by Rosen, T., et al., *J. Med. Chem.*, 31, 1598–1611 (1988)) in 10 mL of methylene chloride and 2 mL of triethylamine was added and allowed to react. The solution was then concentrated and the product was purified by column chromatography over silica gel eluting with 1:10:100 acetic acid:methanol:methylene chloride. The solvent was removed to afford 0.205 g of the title compound as yellow crystals, mp 117°–119° C. [a]=–122.6° (25° C., D, c=0.05, CHCl$_3$). MS M/Z 551 (M+H). NMR: (CDCl$_3$) d 1.10 (d, 3H, J=7 Hz), 1.85–2.25 (m, 2H), 2.10 (s, 3H), 4.05 (m, 2H), 4.23 (m, 1H), 4.80 (m, 1H), 5.06 (d, 1H, J=13 Hz), 5.27 (d, 1H, J=13 Hz), 6.79 (m, 2H), 7.20–7.40 (m, 6H), 7.76 (br, 1H), 8.21 (s, 1H), 8.80 (d, 1H, J=9 Hz). IR (KBr): 1725, 1660 cm$^{-1}$. Analysis calculated for C$_{29}$H$_{25}$F$_3$N$_4$O$_4$.H$_2$O: C, 61.26; H, 4.79; N, 9.85. Found: C, 61.59; H, 4.37; N, 9.72.

Step 2. 2-((2S,4S)-4-Acetamido-2-methylpyrrolidin-1-yl)-9-(2,4-difluorophenyl)-3-fluoro-6H-6-oxopyrido[1,2-a]pyrimidine-7-carboxylic acid To a 0.198 g (0.359 mmol) sample of the compound from Step 1 in 20 mL of methanol was added 1 mL of 98% formic acid and 0.1 g of 10% Pd/C. The mixture was stirred at room temperature under a dry N$_2$ atmosphere for 1.25 hours. The mixture was filtered, and the filtrate concentrated to leave a yellow residue. The product was purified by column chromatography on silica gel, eluting with 1:10:100 acetic acid:methanol:methylene chloride to afford 0.126 g of the title compound as a yellow solid, after removal of the solvent, mp 163°–164° C. [a]=–50.2° (23° C., D, c=0.5, CHCl$_3$). MS M/Z 461 (M+H). NMR: (CDCl$_3$+CD$_3$OD) d 1.09 and 1.39 (two d, 3H, J=6 Hz), 1.92–2.15 (m, 2H), 2.00 (s, 3H), 3.97 (m, 1H), 4.16 (m, 1H), 4.32 (m, 1H), 4.72 (m, 1H), 6.90 (m, 2H), 7.25 (m, 1H), 8.17 and 8.31 (two s, 1H), 8.93 and 8.97 (two d, 1H, J=8 Hz). IR (KBr): 1720, 1660, 1035 cm$^{-1}$. Analysis calculated for C$_{22}$H$_{19}$F$_3$N$_4$O$_4$.H$_2$O: C, 55.23; H, 4.42; N, 11.71. Found: C, 55.25; H, 4.20; N, 11.21.

EXAMPLE 170

9-(2,4-Difluorophenyl)-3-fluoro-2-(3-hydroxypyrrolidin-1-yl)-6H-6-oxopyrido[1,2-a]pyrimidine-7-carboxylic acid Step 1. 9-(2,4-Difluorophenyl)-3-fluoro-2-(3-hydroxypyrrolidin-1-yl)-6H-6-oxopyrido[1,2-a]pyrimidine-7-carboxylic acid benzyl ester A 0.200 g (0.469 mmol) sample of 9-(2,4-difluorophenyl)-3-fluoro-2-hydroxy-6H-6-oxopyrido[1,2-a]pyrimidine-7-carboxylic acid benzyl ester, from Example 160 Step 3, was dissolved in 5 mL of methylene chloride and 0.42 mL of DMF and 0.49 mL of POCl$_3$ were added. The reaction was stirred under a dry N$_2$ atmosphere at room temperature for 3.5 hours, then quenched with ice and water. The mixture was extracted with methylene chloride, and the solvent was washed with water until the acidity of the rinse water was above pH 3. The solvent was then dried with magnesium sulfate and 0.1 mL of 3-pyrrolidinol was added and allowed to react. The solution was then concentrated and the product was purified by column chromatography over silica gel eluting with 1:10:100 acetic acid:methanol:methylene chloride. The solvent was removed to afford 0.183 g of the title compound as yellow crystals, mp 105°–107° C. MS M/Z 496 (M+H). NMR: (CDCl$_3$) d 2.00–2.16 (m, 2H), 3.55–3.68 (m, 2H), 3.96–4.16 (m, 2H), 4.18 and 4.55 (m, 1H), 5.36 and 5.38 (two s, 2H), 6.90 (m, 2H), 7.30–7.48 (m, 6H, 8.33 (s, 1H), 9.08 and 9.14 (two d, 1H, J=6 Hz). IR (KBr): 1725, 1690, 1660 cm$^{-1}$. Analysis calculated for C$_{26}$H$_{20}$F$_3$N$_3$O$_4$.¾ H$_2$O: C, 61.36; H, 4.26; N, 8.26. Found: C, 60.97; H, 3.67; N, 7.98.

Step 2. 9-(2,4-Difluorophenyl)-3-fluoro-2-(3-hydroxypyrrolidin-1-yl)-6H-6-oxopyrido[1,2-a]pyrimidine-7-carboxylic acid To a 0.166 g (0.334 mmol) sample of the compound from Step 1 in 20 mL of methanol and 15 mL of DMF was added 2 mL of 98% formic acid and 0.12 g of 10% Pd/C. The mixture was stirred at room temperature under a dry N$_2$ atmosphere for 1.33 hours. The mixture was filtered, and the tiltrate concentrated, removing the DMF in a kugelrohr apparatus, to leave a yellow residue. The product was purified by column chromatography on silica gel, eluting with 1:10:100 acetic acid:methanol:methylene chloride to afford 0.088 g of the title compound as a yellow solid, after removal of the solvent, mp 168°–170° C. (dec). MS M/Z 406 (M+H). NMR: d 2.00–2.15 (m, 2H), 3.55–3.70 (m, 2H), 3.97–4.12 (m, 2H), 4.50–4.60. (m, 1H), 6.93 (m, 2H), 7.35 (m, 1H), 8.43 (s, 1H), 9.01 and 9.04 (two d, 1H, J=4 Hz). IR (KBr): 1715, 1665, 1625 cm$^{-1}$. Analysis calculated for C$_{19}$H$_{14}$F$_3$N$_3$O$_4$.½ H$_2$O: C, 55.08; H, 3.65; N, 10.14. Found: C, 55.10; H, 3.53; N, 10.04.

EXAMPLE 171

2-((2S ,4S)-4-Amino-2-methylpyrrolidin-1-yl)-9-(2,4-difluorophenyl)-3-fluoro-6H-6-oxopyrido[1,2-a]pyrimidine-7-carboxylic acid hydrochloride Step 1. (2S, 4S)-4-acetamido-2-methylpyrrolidine A 6.000 g (24.760 mmol) sample of (2S, 4S)-4-acetamido-1-(t-butoxy-carbonyl)-2-methylpyrrolidine, prepared as described by Rosen, T., et al., *J. Med. Chem.*, 31, 1598–1611 (1988), was dissolved in 30 mL of 4N HCl in dioxane and stirred at room temperature for 24 hours to remove the boc group.. The solvent was removed by evaporation to give the hydrochloride salt of this compound as a white solid, which was taken directly to the next step.

Step 2. (2S, 4S)-4-acetamido-1-benzyl-2-methylpyrrolidine

This salt from the previous step was suspended in 27 mL of methylene chloride, 8.4 mL of triethylamine was added and the mixture stirred for 10 min. Next was added 3.2 mL (26.9 mmol) of benzyl bromide and the mixture heated at reflux for 5 hours. The mixture was diluted with methylene chloride, which was washed 3× with water, dried over magnesium surfate, and evaporated to leave the 1-benzyl protected compound as a white solid, which was taken directly to the next step.

Step 3. (2S, 4S)-4-amino- 1-benzyl-2-methylpyrrolidine hydrochloride

The acetyl group was removed from the compound from the previous step by heating at reflux for 6 hours in 6N HCl. Removal of the solvent gave the solid product which was taken directly to the next step.

Step 4. (2S, 4S)-1-benzyl-4-t-butoxycarbonylamino-2-methylpyrrolidine

The sample from the previous step was dissolved in 10 mL of water and 35 mL of methanol. To this solution stirred at 0° C. was added 5.2 mL of triethylamine and 4.21 g of di-t-butyl dicarbonate. The reaction was stirred for 2 hours at 0° C. and then at room temperature for 19 hours. The solvent was removed by evaporation, the residue dissolved in methylene chloride, which was washed with water and concentrated. The product was purified by column chromatography on silica gel, eluting with 0.5:5:100 conc. ammonium hydroxide:methanol:methylene chloride to give the title compound as a white solid after removal of the solvent. This material was taken directly to the next step.

117

Step 5. (2S, 4S)-4-t-butoxycarbonylamino-2-methylpyrrolidine

The sample from the previous step was dissolved in 150 mL of methanol, 0.90 g of 10% Pd/C was added and the mixture shaken under 4 atm of hydrogen at room temperature for 13 hours. The mixture was concentrated, the catalyst was removed by filtration, and the solvent removed to afford 3.081 g of the title compound as a white solid. MS M/Z 201 (M+H). NMR (CDCl$_3$): d 1.15 (d, 3H, J=6 Hz), 1.44 (s, (H), 1.54–1.63 (m, 2H, 1.75 (m, 1H), 2.64 (dd, 1H, J=5, J=12 Hz), 3.26 (m, 1H), 3.38 (dd, 1H, J=7, J=12 Hz), 4.12 (br, 1H), 4.63 (br, 1H). IR (KBr): 1685 cm$^{-1}$.

Step 6. 2-(2S,4S)-4-t-butoxycarbonylamino-2-methylpyrrolidin-1-yl)-9-(2.4-difluorophenyl) -3-fluoro-6H-6-oxopyrido[1,2-a]pyrimidine-7-carboxylic acid benzyl ester A 1.500 (3.518 mmol) sample of 9-(2,4-difluorophenyl)-3-fluoro-2-hydroxy-6H-6-oxopyrido[1,2-a]pyrimidine-7-carboxylic acid benzyl ester, from Example 160 Step 3, was dissolved in 40 mL of methylene chloride and 3.20 mL of DMF and 3.70 mL of POCl$_3$ were added. The reaction was stirred under a dry N$_2$ atmosphere at room temperature for 2.25 hours, then quenched with ice and water. The mixture was extracted with methylene chloride, and the solvent was washed with water until the acidity of the rinse water was above pH 3. The solvent was then dried with magnesium sulfate and 1.06 g (0.656 mmol) of (2S,4S)-4-t-butoxycarbonylamino-2-methylpyrrolidine, from Step 5 above, in 50 mL of methylene chloride and 7 mL of triethylamine was added and allowed to react. The solution was then concentrated and the product was purified by column chromatography over silica gel eluting with 0.5:10:100 conc. ammonium hydroxide:methanol:methylene chloride. The solvent was removed to afford 1.856 g of the title compound as yellow crystals, mp 106°–107° C. [a]=+13.4 (23°, D, c=0.5, CHCl$_3$). MS M/Z 609 (M+H). NMR: (CDCl$_3$) d 1.11 (two d, 3H, J=7 Hz), 1.45 and 1.55 (two s, 9H), 1.90–2.10 (m, 2H), 3.60–4.60 (m, 5H), 5.39 (s, 1H), 6.89 (m, 2H), 7.34–7.50 (m, 6H), 8.34 and 8.36 (two s, 1H), 9.16 and 9.19 (two d, 1H, J=9 Hz). IR (KBr): 1715, 1690, 1660 cm$^{-1}$. Analysis calculated for C$_{32}$H$_{31}$F$_3$N$_4$O$_5$.½ H$_2$O: C, 62.23; H, 5.22; N, 9.07. Found: C, 62.44; H, 5.20; N, 9.16.

Step 7. 2-((2S,4S)-4-Amino-2-methylpyrrolidin-1-yl)-9-(2,4-difluorophenyl)-3-fluoro-6H-6-oxopyrido[1,2-a]pyrimidine-7-carboxylic acid To a 1.814 g (2.981 mmol) sample of the compound from Step 6 dissolved in 80 mL of methanol and 10 mL of THF was added 8 mL of 98% formic acid and 1 g of 10% Pd/C. The mixture was stirred at room temperature under a dry N$_2$ atmosphere for 2.3 hours. The mixture was filtered, and the filtrate concentrated to leave a yellow residue. The product was purified by column chromatography on silica gel, eluting with 1:10:100 acetic acid:methanol:methylene chloride to afford 1.513 g of the title compound as a yellow solid, after removal of the solvent. The compound was taken directly to the next step.

Step 8. 2-((2S,4S)-4-Amino-2-methylpyrrolidin-1-yl)-9-(2.4-difluorophenyl)-3-fluoro-6H-6-oxopyrido[1,2-a]pyrimidine-7-carboxylic acid hydrochloride The 1.528 g sample of the compound from the previous step was dissolved in 20 mL of 4N HCl in dioxane and stirred at room temperature for 3.5 hours. The solvent was removed, the residue redissolved in 500 mL of water, 0.5. mL of conc. HCl was added, and the solution freeze-dried to afford 1.147 g of the title compound as a yellow solid, mp 204° C. (dec). [a]=+35.4° (22° C., D, c=0.5, CH$_3$OH). MS M/Z 419 (M—Cl). NMR: (CD$_3$OD) d and 1.41 (two d, 3H, J=7 Hz), 2.15–2.31 (m, 2H), 3.75–4.40 (m, 4H), 7.04 (m, 2H), 7.46 (m, 1H), 8.25 and 8.30 (two s, 1H), 9.11 and 9.21 (two d, 1H, J=9 Hz). IR (KBr): 1710, 1660, 1630 cm$^{-1}$. Analysis calculated for C$_{20}$H$_{18}$F$_{3Cl}$N$_4$O$_3$.H$_2$O: C, 50.80; H, 4.26; N, 11.85. Found: C, 50.98; H, 4.10; N, 11.85.

EXAMPLE 172

2-(3-Aminopyrrolidin-1-yl)-3-fluoro-9-(2,3,4,5,6-pentafluorophenyl)-6H-6-oxopyrido[1,2-a]pyrimidine-7-carboxylic acid hydrochloride salt Step 1. 2-(2,3,4,5,6-Pentafluorophenyl)-acetamidine hydrochloride Into a solution of 26.72 g (0.129 mol) of pentafluoroacetonitrile (commercially available) in 8.30 mL of anhydrous ethanol cooled to 0° C. and stirred under a dry N$_2$ atmosphere was introduced gaseous HCl, until the mixture solidified. The reaction was allowed to stand for 96 hours, then 60 mL of ethanol and 30.7 mL of 4.2N HCl in ethanol (0.124M) was added, and the slurry was stirred at room temperature for 2 hours. The mixture was faltered through sintered glass, and the filtrate was concentrated under vacuum to afford the title compound as a brownish solid, which was taken directly to the next step.

Step 2. 5-Fluoro-4-hydroxy-2-(2,3,4,5,6-pentafluorobenzyl)pyrimidine

A mixture of the compound (0.129 tool) from Step 1, 0.135 mol of the sodium salt of ethyl 2-fluoro-3-hydroxy-2-propenoate (prepared as described by E. Elkik and M. Imbeaux-Oudotte, *Bull. Soc. Chim. Fr.*, 5–6 pt 2, 1165 (1975)), 150 mL of anhydrous methanol and 25 mL of triethylamine was stirred under a dry N$_2$ atmosphere for 24 hours. The solvent was removed by evaporation under vacuum and the residue was dissolved in methylene chloride and washed (1×) with 10% HCl and (1×) with water, then dried over anhydrous magnesium sulfate, and the solvent was removed by evaporation under vacuum to give a dark oil which solidified upon standing. This solid was washed with 1:2 ethyl acetate:hexane to afford 4.843 g of the title compound as a white solid, mp 161°–162° C. The filtrate was concentrated and extracted with 1:4 ethyl acetate:hexane to leave a second crop of 4.454 g of product. Additional product was obtained by chromatography of the residue, for a total yield of 19.20 g of product. MS M/Z 312 (M+NH$_4$). NMR (CDCl$_3$): d 4.15 (apparent s, 2H), 7.80 (d, 1H, J=3 Hz), 13.38 (br s, 1H). IR (KBr): 3440, 1685, 1660, 1610 cm$^{-1}$.

Step 3. 2-Ethoxy-3-(5-fluoro-4-hydroxy-3-(2,3,4,5,6-pentafluorophenyl)propane-1,1-dicarboxylic acid diethyl ester The compound from Step 2 above (0.294 g, 1.00 mmol) was dissolved in 10 mL of THF and cooled to −78° C. with stirring, then 0.82 mL (2.05 mmol) of a 2.5M solution of n-butyllithium in hexane was added and the resulting yellow solution was stirred for 30 min. To this was added 0.243 mL (1.2 mmol) of ethyl 2-carboethoxy-3-ethoxy-2-propenecarboxylate with stirring for 15 min. The reaction was quenched with 10% HCl, allowed to warm to room temperature and extracted with ethyl acetate. The extract was washed (2×) with brine, and the solvent dried over magnesium sulfate and concentrated to afford the title compound as an oil, which was taken directly to the next step.

Step 4. 9-(2,3.4.5.6-pentafluorophenyl)-3-fluoro-2-hydroxy-6H-6-oxopyrido[1,2-a]pyrimidine-7-carboxylic acid ethyl ester The compound from Step 3 above was dissolved in 10 mL of ethanol, 0.2 mL of conc. sulfuric acid was added and the solution was heated at reflux for 18 hours. The solvent was removed and the residue washed with ether to afford 0.222 g of the title compound as a yellow solid, mp 235–236 C. MS M/Z 419 (M+H), 436 (M+NH$_4$). IR (KBr): 3440 (br), 1710, 1680, 1615 cm$^{-1}$. NMR (CDCl$_3$) d 1.38 (t, 3H, J=7 Hz), 4.37 (q, 2H, J=7 Hz), 8.23 (s, 1H), 9.05 (d, 1H, J=6 Hz).

Step 5. 3-Fluoro-2-hydroxy-9-(2.3,4.5.6-pentafluorophenyl)-6H-6-oxopyridol[1,2-a]pyrimidine-7-carboxylic acid benzyl ester A 1.000 g (2.391 mmol) sample of the compound from Step 4 was dissolved in 25 mL of benzyl alcohol, 0.09 mL of titanium tetraethoxide was added and the mixture was stirred at 90° C. for 20 hours. The reaction was diluted with methylene chloride, washed (1×) with 10% HCl and concentrated in a rotary evaporator. The crude product was purified in a kugelrohr apparatus to yield a yellow solid, which was washed with ether and dried to afford 0.457 g of the title compound, which was taken directly to the next step.

Step 6. 2-(3-(N-t-Butoxycarbonyl)aminopyrrolidin-1-yl)-3-fluoro-9-(2,3,4,5,6-pentafluorophenyl)-6H-6-oxopyrido[1,2-a]pyrimidine-7-carboxylic acid benzyl ester A 0.400 g (0.833 mmol) sample of the compound from Step 5 was dissolved in 10 mL of methylene chloride and 0.746 mL of DMF, and 0.870 mL of POCl$_3$ were added and stirred under a dry N$_2$ atmosphere at room temperature for 1.7 hours. The reaction was quenched with ice and the mixture extracted with methylene chloride which was washed (2×) with water. The organic layer was added to a stirred solution of 0.235 g (1.2 mmol) of 2-(N-t-butoxycarbonylamino)pyrrolidine in 4 mL of triethylamine. The solvent was removed by evaporation, and the product was purified by column chromatography on silica gel, eluting with 2.5:100 methanol:methylene chloride. Removal of the solvent afforded 0.353 g of the title product as a yellow crystalline solid, mp 107°–108° C. MZ M/Z 649 (M+H). NMR (CDCl$_3$) d 1.44 (s, 9H), 1.90–2.30 (m, 2H), 3.40–4.65 (m, 5H), 5.38 (s, 2H), 7.35 (m, 3H), 7.48 (m, 2H), 8.34 (s, 1H), 9.14 and 9.15 (two d, 1H, J=9 Hz).

Step 7. 2-(3-(N-t-Butoxycarbonyl)aminopyrrolidin-1-yl)-3-fluoro-9-(2,3,4,5,6-pentafluorophenyl)-6H-6-oxopyrido[1,2-a]pyrimidine-7-carboxylic acid A 0.335 g (0.516 mmol) sample of the compound from Step 6 was dissolved in 40 mL of dry methanol, and the benzyl ester was removed by reacting with 2.0 mL of 98% formic acid in the presence of 0.100 g of 10% Pd/C, stirring under a dry N$_2$ atmosphere for 0.0.25 hours. After filtration and evaporation of the solvent, the product was purified by column chromatography on silica gel, eluting with 1:15:100 acetic acid:methanol:methylene chloride to afford, after removal of the solvent, the title compound as a yellow solid, which was taken directly to the next step.

Step 8. 2-(3-Aminopyrrolidin-1-yl)-3-fluoro-9-(2,3,4,5,6-pentafluorophenyl)-6H-6-oxopyrido [1,2-a]pyrimidine-7-carboxylic acid hydrochloride salt The compound from the previous step was dissolved in 10 mL of 4N HCl in dioxane and stirred at room temperature for 0.7 hours, after which the solvent was removed under vacuum. The residue was dissolved in water which was filtered through sintered glass and freeze-dried to afford 0.232 g of the title compound as a yellow solid, mp 202°–204° C. MS M/Z 459 (M—Cl). NMR (CD$_3$OD): d 2.12–2.54 (m, 2H), 3.70–4.36 (m, 5H), 8.42 (s, 1H), 9.21 (d, 1H, J=9 Hz). IR (KBr): 1715, 1660, 1630 cm$^{-1}$. Analysis calculated for $C_{19}H_{12}F_6N_4O_3 \cdot HCl \cdot 0.5\ H_2O$: C, 45.30; H, 2.80; N, 11.12. Found: C, 45.46; H, 2,39; N, 10.57.

EXAMPLE 173

2-((2S, 4S)-4-(N-(S)-Alanyl-(S)-alany)amino-2-methylpyrrolidin-1-yl)-9-(2,4-difluorophenyl))-3-fluoro-6H-6-oxopyrido[1.2-a]pyrimidine-7-carboxylic acid hydrochloride Step 1. 2-((2S,4S)-4-amino-2-methylpyrrolidin-1-yl)-9-(2,4-difluorophenyl)-3-fluoro-6H-6-oxopyrido[1,2-a]pyrimidine-7-carboxylic acid benzyl ester Following the procedure described in Example 166 Step 1, replacing the boc-protected benzyl ester compound with a 2.345 mmol sample of 2-((2S,4S)-4-t-butoxycarbonylamino-2-methylpyrrolidin-1-yl)-9-(2,4-difluorophenyl)-3-fluoro-6H-6-oxopyrido[1,2-a]pyrimidine-7-carboxylic acid benzyl ester, from Example 171 Step 6, the boc protecting group was removed to afford 1.06 g of the title compound.

Step 2. 2-((2S, 4S)-4-(N-(N Benzoyloxycarbonyl)-(S)-alanyl-(S)-alanyl)amino-2-methylpyrrolidin-1-yl)-9-(2,4-difluorophenyl)-3-fluoro-6H-6-oxopyrido[1,2-a]pyrimidine-7-carboxylic acid benzyl ester Following the procedure of Example 168 Step 1, replacing the benzyl ester compound of that example with 1.06 g of the compound from Step 1 above, 0.98 g of the title compound was prepared.

Step 3. 2-((2S, 4S)-4-(N-(S)-Alanyl-(S)-alanyl)amino-2-methylpyrrolidin-1-yl)-9-(2,4-difluorophenyl)-3-fluoro-6H-6-oxopyrido[1,2-a]pyrimidine-7-carboxylic acid hydrochloride Following the procedure of Example 168 Step 2, replacing the boc-protected benzyl ester compound of that example with the compound from Step 2 above, 0.66 g of the title compound was prepared. Mp 198°–200° C. MS M/Z 561 (M—Cl). NMR (CD$_3$OD): d 1.14 and 1.40 (two d, 3H, J=7 Hz), 1.34 and 1.35 (two d, 3H, J=7 Hz), 1.50 and 1.51 (two d, 3H, J=7 Hz), 1.96–2.11 (m, 2H), 3.50–4.60 (m, 6H), 7.40 (m, 2H), 7.47 (m, 1H), 8.26 and 8.29 (two s, 1H), 9.12 and 9.16 (two d, 1H, J=9 Hz).

EXAMPLE 174

9-(2,4-Difluorophenyl)-3-fluoro-2-hydroxy-4-methyl-6H-6-oxopyrido[1,2-a]pyrimidine-7-carboxylic acid ethyl ester Step 1. 2-(2,4-Difluorobenzyl)-5-fluoro-4-hydroxy-6-methylpyrimidine A mixture of 8.6 g (0.0445 mmol) of 2-(2,4-difluorophenyl)-acetamidine hydrochloride, prepared as in Example 159 Step 1, and 6.1 g (0.0405 mmol) of ethyl 2-fluoro-3oxobutanoate (prepared as described by E. O. Bergmann, S. Cohen, and I. Shahak, *J. Chem. Soc.*, 3278_(1959)), in 30 mL of anhydrous methanol and 10.1 mL of a 2.5% solution of sodium methoxide was heated at reflux under a dry N$_2$ atmosphere for 16 hours. The solvent was removed by evaporation under vacuum, and the residue was washed with water, then 200 mL of water added and the mixture was acidified and the resulting precipitate was filtered off. The aqueous solution was then extracted (3×) with methylene chloride. The solvent was washed with water, dried over anhydrous magnesium sulfate, and the solvent was removed by evaporation under vacuum to give a dark solid. The solid was washed with ethyl ether and dried, then combined with the earlier precipitate which was recrystallized from methanol:ether to afford 4.51 g of the title compound. MS M/Z 272 (M+NH$_4$). NMR: (CDCl$_3$) d 2.22 (d, 3H, J=4 Hz), 3.92 (s, 2H), 6.92 (m, 2H), 7.30 (m, 1H).

Step 2. 3-(2,4-Difluorophenyl)-2-ethoxy-3-(5-fluoro-4-hydroxy-6-methylpyrimidin-2-yl) propane-1,1-dicarboxylic acid diethyl ester A 0.615 g (2.42 mmol) sample of the compound from Step 1 above was dissolved in THF and cooled to −78° C. with stirring under a dry N₂ atmosphere. To this was slowly added 1.98 mL of 2.5N n-butyllithium in hexane, and the mixture was stirred for 30 min. Then 0.586 mL (2.9 mmol) of diethyl ethoxymethylenemalonate was added at −78° C. and the mixture stirred for an additional 15 min at room temperature. The reaction mixture was quenched with 10% HCl until the mixture was about pH 3, whereupon it was then extracted with ethyl acetate. This was dried over anhydrous magnesium sulfate, and the solvent was removed by evaporation under vacuum to afford 1.6 g of the title compound as a yellow oil. This material was taken directly to the next step.

Step 3. 9-(2,4-Difluorophenyl)-3-fluoro-2-hydroxy-4-methyl-6H-6-oxopyrido[1,2-a]pyrimidine-7-carboxylic acid ethyl ester The compound from Step 2 was dissolved in toluene, 0.62 mL of DBU was added and the mixture heated at reflux in a flask equipped with a Dean-Stark condenser for 16 hours under a dry N₂ atmosphere. The mixture was removed from the heat and stirred with 70 mL of water for 2 hours. After separation, the organic phase was dried over magnesium sulfate, and the solvent was removed by evaporation. The residue was purified by column chromatography on silica gel, eluting with 1:5:100 acetic acid:methanol:methylene chloride to afford 0.175 g of the title compound as a yellow solid. MS M/Z: 379 (M+H). NMR:(DMSO-d₆) d 1.21 (t, 3H, J=7 Hz), 2.07 (d, 3H, J=4 Hz), 4.10 (q, 2H, J=7 Hz), 7.03 (m, 1H), 7.16 (m, 1H), 7.38 (m, 1H), 7.66 (s, 1H).

EXAMPLES 175–178

By following the procedures described in Example 174 and substituting the appropriate ester for ethyl 2-fluoro-3-oxobutyrate, Examples 175–178 may be prepared as disclosed in Table 6 (where R=ethyl and $R^1$=2,4-difluorophenyl).

TABLE 6

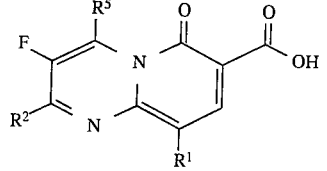

| Example No. | $R^5$ |
|---|---|
| 175 | —CH₂CH₂F |
| 176 | —CH₂F |
| 177 | —CHF₂ |
| 178 | —CF₃ |

EXAMPLES 179–195

By following the procedures described in Example 160 Steps 3, 4 and 5 and Example 161, and replacing 2-(N-t-butoxycarbonylamino)pyrrolidine in Step 4 with the appropriate N-methyl- or boc-protected amine, Examples 179–195 may be prepared as disclosed in Table 7 (where $R^1$=2,4-difluorophenyl).

TABLE 7

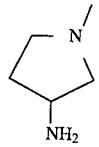

| Example No. | $R^2$ | $R^5$ |
|---|---|---|
| 179 | 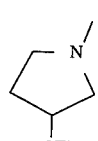 | —CH₃ |
| 180 | 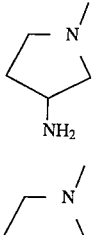 | —CH₃ |
| 182 | 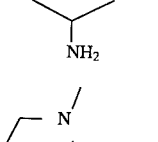 | —CH₂F |
| 183 | 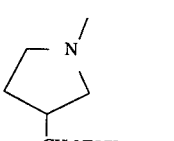 | —CF₃ |
| 184 | 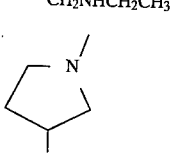 | —CH₃ |
| 185 | | —CH₂F |
| 186 | | —CHF₂ |

TABLE 7-continued

Structure: pyrido[1,2-a]pyrimidine with R⁵, R², F, N, carboxylic acid OH, R¹ substituents

| Example No. | R² | R⁵ |
|---|---|---|
| 187 | pyrrolidine-N— with CH₂NHCH₂CH₃ | $-CF_3$ |
| 188 | 2-methyl-4-amino-pyrrolidine-N— | $-CH_3$ |
| 189 | 2-methyl-4-amino-pyrrolidine-N— | $-CH_2F$ |
| 190 | 2-methyl-4-amino-pyrrolidine-N— | $-CHF_2$ |
| 191 | 2-methyl-4-amino-pyrrolidine-N— | $-CF_3$ |
| 192 | $CH_3-N$\_\_$N-$ (piperazine) | $-CH_3$ |
| 193 | $CH_3-N$\_\_$N-$ (piperazine) | $-CH_2F$ |
| 194 | $CH_3-N$\_\_$N-$ (piperazine) | $-CH_2F$ |
| 195 | $CH_3-N$\_\_$N-$ (piperazine) | $-CF_3$ |

EXAMPLES 196–240

By following the procedures described in Example 160 Steps 3, 4 and 5 and Example 161, replacing 2-(N-t-butoxycarbonylamino)pyrrolidine in Step 4 with the appropriate substituted or boc-protected amine and replacing 9-(2,4-difluoro-phenyl)-3-fluoro-2-hydroxy-6H-6-oxopyrido [1,2-a]pyrimidine-7-carboxylic acid benzyl ester with the compound containing the appropriate $R^1$ group (as described in Examples 2 and 39), Examples 196–240 may be prepared as disclosed in Table 8.1 to 8.3 in which: $R^1$ is 4-fluorophenyl (Table 8.1), 2,4-difluorophenyl (Table 8.2) or cyclopropyl (Table 8.3); and $R^5$ is hydrogen.

TABLE 8.1

Structure: pyrido[1,2-a]pyrimidine with R⁵, R², F, carboxylic acid OH, R¹ substituents $R^1$ = 4-fluorophenyl, $R^5$ = H:

| Example No. | R² |
|---|---|
| 196 | HO—N\_\_N— (4-hydroxypiperazine) |
| 197 | H₂N-cyclopropyl-fused-piperidine-N— |
| 198 | CH₃—N\_\_N— (bicyclic diazabicycle) |
| 199 | HN\_\_N— (bicyclic diazabicycle) |
| 200 | CH₃—N\_\_N— (bicyclic diazabicycle) |
| 201 | HN\_\_N— (bicyclic diazabicycle) |
| 202 | HN\_\_N— with CH₃, CH₃ (dimethylpiperazine) |
| 203 | NaSCSNH—pyrrolidine-N— |
| 204 | NH₂—, CH₂— substituted pyrrolidine-N— |
| 205 | NH₂, CH₃ substituted pyrrolidine-N— |
| 206 | CH₃NH—pyrrolidine-N— |

TABLE 8.1-continued
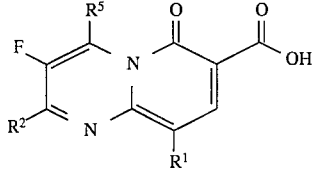
R¹ = 4-fluorophenyl, R⁵ = H:
| Example No. | R² |
|---|---|
| 207 | 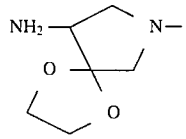 |
| 208 | 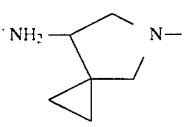 |
| 209 | 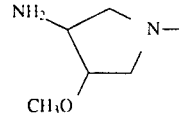 |
| 210 | 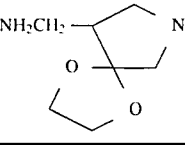 |
TABLE 8.2
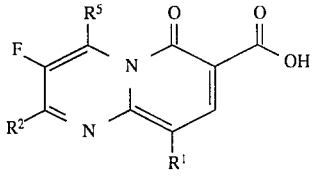
R¹ = 2,4-difluorophenyl, R⁵ = H:
| Example No. | R² |
|---|---|
| 211 | 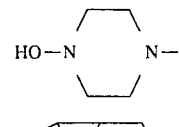 |
| 212 | 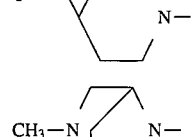 |
| 213 | 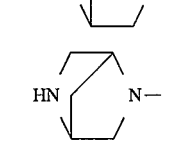 |
| 214 |  |
TABLE 8.2-continued
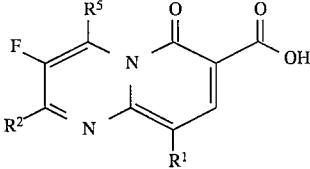
R¹ = 2,4-difluorophenyl, R⁵ = H:
| Example No. | R² |
|---|---|
| 215 | 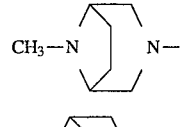 |
| 216 | 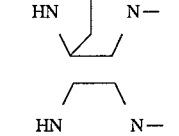 |
| 217 | 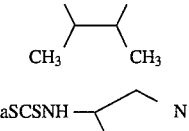 |
| 218 | 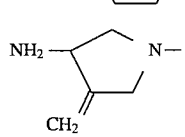 |
| 219 | 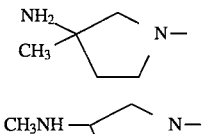 |
| 220 | 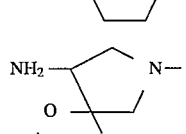 |
| 221 | 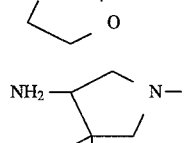 |
| 222 | 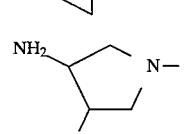 |
| 223 | 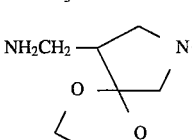 |
| 224 |  |
| 225 |  |

TABLE 8.3

Structure: pyrido-pyridine with R⁵, F, R² substituents and carboxylic acid

R¹ = cyclopropyl, R⁵ = H:

| Example No. | R² |
|---|---|
| 226 | HO—N⟨ ⟩N— (piperazine with N-OH) |
| 227 | H₂N-cyclopropane-fused piperidine—N— |
| 228 | CH₃—N⟨ ⟩N— (bridged diazabicycle) |
| 229 | HN⟨ ⟩N— (bridged diazabicycle) |
| 230 | CH₃—N⟨ ⟩N— (bridged diazabicycle) |
| 231 | HN⟨ ⟩N— (bridged diazabicycle) |
| 232 | HN⟨ ⟩N— with two CH₃ groups |
| 233 | NaSCSNH-pyrrolidine—N— |
| 234 | NH₂, CH₂ substituted pyrrolidine—N— |
| 235 | NH₂, CH₃ substituted pyrrolidine—N— |
| 236 | CH₃NH-pyrrolidine—N— |
| 237 | NH₂, dioxolane-fused pyrrolidine—N— |

TABLE 8.3-continued

R¹ = cyclopropyl, R⁵ = H:

| Example No. | R² |
|---|---|
| 238 | NH₂-spiro[cyclopropane-pyrrolidine]—N— |
| 239 | NH₂, CH₃O substituted pyrrolidine—N— |
| 240 | NH₂CH₂, dioxolane-fused pyrrolidine—N— |

EXAMPLES 241–250

By following the procedures of Example 157 Steps 2–8, replacing 2-cyclopropyl-2-ethoxycarbonylacetamidine hydrochloride in Step 2 with the compound containing the appropriate R¹ group (refer to compound 6B in Scheme II), and replacing the 3-(N-t-butoxycarbonyl)aminopyrrolidine in Step 6 with the appropriately protected amine, Examples 241–250 may be prepared as disclosed in Table 9, above, (in which R⁵ is hydrogen).

TABLE 9

Structure: pyrido-pyridine with R⁵, F, R² substituents and carboxylic acid, R¹

| Example No. | R² | R¹ |
|---|---|---|
| 241 | 3-aminopyrrolidin-1-yl (NH₂) | bicyclo[1.1.1]pentyl |
| 242 | 3-aminopyrrolidin-1-yl (NH₂) | C(CH₃)₃ (t-butyl) |
| 243 | 3-aminopyrrolidin-1-yl (NH₂) | C≡C-C(CH₃)₂ |

TABLE 9-continued

Structure: pyridine-fused pyridone with R5, F, R2, R1 substituents and carboxylic acid

| Example No. | R² | R¹ |
|---|---|---|
| 244 | 3-aminopyrrolidin-1-yl (NH₂ on pyrrolidine) | $F_3C-$ |
| 245 | 3-aminopyrrolidin-1-yl (NH₂ on pyrrolidine) | $FCH_2CH_2-$ |
| 246 | piperazin-1-yl (N—N) | bicyclobutyl |
| 247 | piperazin-1-yl | $-C(CH_3)_3$ |
| 248 | piperazin-1-yl | $-C(CH_3)_2$ (vinyl/alkene) |
| 249 | piperazin-1-yl | $F_3C-$ |
| 250 | piperazin-1-yl | $FCH_2CH_2-$ |

EXAMPLES 251–252

By following the procedures of Example 157, steps 2–8, replacing replacing 2-cyclopropyl-2-ethoxycarbonylacetamidine hydrochloride in Step 2 with 2-(N-benzoyloxycarbonyl-N-methylamino)-2-ethoxycarbonylacetamidine hydrochloride, and replacing the 3-(N-t-butoxycarbonyl) aminopyrrolidine in Step 6 with the appropriately protected amine, Examples 251–252 may be prepared as disclosed in Table 10 (in which R⁵=H).

TABLE 10

| Example No. | R² | R¹ |
|---|---|---|
| 251 | 3-aminopyrrolidin-1-yl (NH₂) | $CH_2NH-$ |
| 252 | piperazin-1-yl (HN—N) | $CH_3NH-$ |

EXAMPLES 253

8-(3-Amino-1-pyrrolidinyl)-1-cyclopropyl-7-fluoro-9-methyl-4-oxo-4H-quinolizine-3-carboxylic acid Step 253a. 4-t-Butoxy-3-chloro-2,5,6-trifluoropyridine To 250 mL of a THF solution containing 106 g (0.571 mmol) of a mixture of 4-chlorotetrafluoropyridine and 3-chloro-tetrahydropyridine (approx 70:30 ratio, from Aldrich Chemical Co.) at –78° C. was added a solution of 38.3 g (0.399 mmol) of sodium t-butoxide in 350 mL of THF, and the solution was stirred for 2 hours at –78° C. and at ambient temperature for 16 hours. The mixture was poured into 500 mL of hexane, and this mixture was filtered through celite and the filtrate concentrated. The residue was purified by flash chromatography, eluting first with hexane, then ethyl acetate:hexane (1:4), to separate the desired title product from the mixture of products. MS 238, 240 (M+H)⁺; 1H NMR (CDCl₃) ∂: 1.52 (d, J=2 Hz); ¹⁹F NMR (CDCl₃, CFCl₃ as reference) ∂: 73.75 (dd, J₁=14.2, J₂=23.2 Hz), 89.71 (dd, J₁14.2, J₂=21.98 Hz); 152.42 (apparent t, J=22 Hz).

Step 253b. 4-t-Butoxy-2,3,6-trifluoropyridine

To the product from Step 253a above (24.92 g, 0.104 mmol) in 100 mL of methanol was added 2.5 g of Pearlman's catalyst (Aldrich Chemical Co.), and the mixture was stirred at ambient temperature for 14 hours under and atmosphere of hydrogen. An additional 2.5 g of catalyst was added, and the mixture was stirred for another 22 hours. The mixture was filtered, the filtrate was concentrated, and the residue was extracted with hexane/ether. After filtration, the solvent was removed by evaporation, and the residue was purified by flash chromatography (ethyl acetate:hexane 1:16) to yield 12.05 g of the title product. MS 206 (M+H)⁺, 233 (M+18)⁺; 1H NMR (CDCl₃) ∂: 1.52 (s, 9H), 6.51 (m, 1H); $^{19}$F NMR (CDCl$_3$, CFCl$_3$ as reference) ∂: 72.60 (dd, J$_1$=14.3, J$_2$=21.0 Hz), 89.74 (dd, J$_1$=14.3, J$_2$=21.0 Hz), 164.68 (dt, J$_1$=4.2, J$_2$=21.0 Hz).

Step 253c. 4-t-Butoxy-2,3,6-trifluoro-5-methylpyridine

A freshly prepared solution of lithium diethylamide (LDA) (58.21 mmol) in 30 mL of THF at −78° C. was added to 10.0 g (48.74 mmol) of the product from Step 253b in 50 mL of THF at −78° C., and the reaction was stirred for 50 min. To the reaction mixture was added 4.3 mL (69.07 mmol) of methyl iodide, and the mixture was stirred at −78° C. for 1 hour and stirred at ambient temperature for 16 hours. The reaction was quenched with saturated NH$_4$Cl solution, extracted with hexane, and the extracts washed with water, dried over MgSO4 and concentrated to give the title product as a pale yellow oil, which was taken directly to the next step. MS (220) (M+H)$^+$; 1H NMR (CDCl$_3$) ∂: 1.47 (m, 9H), 2.12 (m, 3H). $^{19}$F NMR (CDCl$_3$, CFCl$_3$ as reference) ∂: 75.91 (dd apparent, J$_1$=15.0, J$_2$=22.1 Hz), 93.17 (dd apparent, J$_1$=15.0, J$_2$=22.1 Hz), 156.54 (m).

Step 253d. 4-t-Butoxy-2,5-difluoro-3-methylpyridine

A sample of the product from Step 253c above (48.74 mmol) and 13.5 mL of hydrazine monohydrate were dissolved in 150 mL of n-propanol. The reaction was stirred at reflux temperature under nitrogen for 4 hours. The volatiles were removed, and the residue was dissolved in methylene chloride, which was washed with water and dried over MgSO$_4$. The solvent was removed to give the intermediate hydrazine product as a yellow liquid, which was dissolved in 110 mL of methanol. To this was added 20 mL of 20% NaOH and air was passed through the solution for 16 hours. The solvents were removed at 30° C. under vacuum. The residue was dissolved in methylene chloride, which was washed with water and dried over MgSO$_4$. The solvent was removed and the crude product purified by flash chromatography, eluting with ethyl acetate:hexane 1:16 to give the title product as a colorless liquid after removal of the solvents. MS (202) (M+H)$^+$; 1H NMR (CDCl$_3$) ∂: 1.43 (d, 9H, J=1.5 Hz), 2.18 (d, 3H, J=1.5 Hz), 7.85 (br s, 1H); $^{19}$F NMR (CDCl$_3$, CFCl$_3$ as reference) ∂: 73.37 (d, J=24.5 Hz), 142.17 (d, J=24.5 Hz).

Step 253e. 2-(4-t-Butoxy-5-fluoro-3-methyl-2-pyridinyl)cyclopropaneacetonitrile

A sample of the product from Step 253d above (40.8 mmol) was dissolved in 50 mL of THF and cooled to −78° C. To this was added a freshly prepared solution of LDA (0.103 mmol) in 50 mL of THF at −78° C., and the reaction was stirred for 1 hour. The reaction was then stirred at 0° C. for 1 hour, quenched with saturated NH$_4$Cl solution and extracted with ether. The extracts were washed with saturated NaCl solution, dried over MgSO$_4$, and concentrated. The residue was purified by flash chromatography, eluting with 1:4 ethyl acetate:hexane, to yield 10.33 g of the title product after removal of the solvent. MS 263 (M+H)$^+$; 1H NMR (CDCl$_3$) ∂: 0.50 (m, 2H), 0.63 (m, 1H), 0.73 (m, 1H), 1.60 (m, 1H), 1.43 (d, 9H, J=2 Hz), 2.29 (s, 3H), 3.76 (d, 1H, J=8 Hz), 8.30 (d, 1H, J=3 Hz). IR (neat) 2240, 1580, 1470 cm$^{-1}$.

Step 253f. 2-(4-Chloro-5-fluoro-3-methyl-2-pyridinyl)cyclopropaneacetonitrile

A sample of the product from Step 253e above (5.21 g, 19.86 mmol) was dissolved in 50 mL of trifluoroacetic acid, the reaction was stirred under nitrogen for 1 hour at ambient temperature, and the material concentrated to dryness. The residue was dissolved in a mixture of 15.6 mL of DMF and 90 mL of methylene chloride. This solution was cooled in a water bath as 18.8 mL (19.86 mmol) of POCl$_3$ was added, then the reaction was stirred at ambient temperature for 16 hours. The reaction was quenched by pouring it into ice water, and the mixture was extracted with methylene chloride. The aqueous solution was adjusted to pH7 with NaOH and re-extracted with methylene chloride. The extracts were combined and washed with water, dried over MgSO$_4$ and concentrated. The residue was purified by flash chromatography with 1:4 ethyl acetate:hexane to give 3.26 g of the title product as a colorless liquid after removal of the solvents. MS 225, 227 (M+H)$^+$; 1H NMR (CDCl$_3$) ∂: 0.48 (m, 1H), 0.59 (m, 1H), 0.66 (m, 1H), 0.77 (m, 1H), 1.50 (m, 1H), 2.48 (s, 3H), 3.80 (d, 1H, J=8 Hz), 8.39 (s, 1H). IR (neat) 2240, 1570 1460 cm$^{-1}$.

Step 253g. Ethyl 2-(4-chloro-5-fluoro-3-methyl-2-pyridinyl)cyclopropaneacetate

A sample of the product from Step 253f above (3.26 g, 14.51 mmol) was dissolved in 10 mL of ethanol, and gaseous HCl was introduced until 4 g had been dissolved. The solution was heated to reflux, and 0.36 mL of water was added, then the mixture was stirred for 1 hour. The reaction was cooled, then poured into water, and the mixture was adjusted to pH7 with NaHCO$_3$. The mixture was then extracted with methylene chloride, which was washed with water, dried over MgSO$_4$ and concentrated. The residue was triturated with 1:4 ethyl acetate:hexane, and filtered. The filtrate was concentrated and the residue was purified by flash chromatography with 1:4 ethyl acetate:hexane to give 2.262 g of the title product after removal of the solvent. MS 272, 274 (M+H)$^+$; 1H NMR (CDCl$_3$) ∂: 0.12 (m, 1H), 0.38 (m, 1H), 0.53 (m, 1H), 0.76 (m, 1H), 1.20 (t, 3H, J=7 Hz), 1.67 (m, 1H), 2.40 (s, 3H), 3.23 (d, 1H, J=9 Hz), 4.16 (q, 2H, J=7 Hz), 8.36 (s, 1H).

Step 253h. 2-(4-Chloro-5-fluoro-3-methyl-2-pyridinyl)cyclopropane-acetaldehyde

A sample of the product from Step 253g above (1.73 g, 6.37 mmol) was dissolved in 10 mL of THF and stirred with water bath cooling and 3.2 mmol of LiAlH$_4$ (LAH) was added. The mixture was stirred at ambient temperature for 1 hour, then poured into water. This mixture was extracted with ether, the extracts were washed, dried and concentrated to give 1.48 g of a colorless oil. This oil was dissolved in 10 mL of methylene chloride and added to a solution of 3.8 mL (7.6 mmol) of oxalyl chloride and 1.1 mL of DMSO (15.5 mmol) in 15 mL of methylene chloride stirred at −78° C. The solution was stirred for 15 min, and 4.4 mL (31.6 mmol) of triethylamine was added. The stirring was continued at −78° C. for 5 min and at −10° C. for 10 min. The reaction was quenched with water, and extracted with methylene chloride. The extract was washed, dried and concentrated to give 1.49 g of the crude title product, which was taken directly to the next step without further purification. MS 228, 230 (M+H)$^+$; 1H NMR (CDCl$_3$) ∂: 0.25 (m, 1H), 0.35 (m, 1H), 0.60 (m, 1H), 0.75 (m, 1H), 1.53 (m, 1H), 2.38 (s, 3H), 3.19 (dd, 1H, J=3, J=9 Hz), 8.37 (s, 1H), 9.86 (d, 1H, J=3 Hz).

Step 253i. 8-Chloro-1-cyclopropyl-7-fluoro-9-methyl-4-oxo-4H-quinolizine-3-carboxylic acid ethyl ester A sample of the product from Step 253h above (6.37 mmol) was dissolved in 50 mL of ethanol, and to this were added 1.5 mL of piperidine, 1.5 mL of acetic acid, and 5 mL of diethyl malonate (32.9 mmol). The reaction was heated at reflux under nitrogen for 4 hours. The solvents were then removed, and the residue was dissolved in ether. The ether was washed with water and brine, then dried over MgSO$_4$ and concentrated. Purification in a kugelrohr apparatus gave 2.4 g of the crude condensation product. This intermediate product was dissolved in 20 ML of of Dowtherm A™, and this solution was added to 100 mL of Dowtherm A™ heated to 235° C. The reaction was then stirred at 220° C. for 45 min. After cooling, the product was separated from the solvent by flash chromatography, eluting with hexane to remove the solvent and then with 1:4 ethyl acetate hexane to remove the product. In this manner 1.065 g of the title product was obtained after removal of the solvent. MS 324, 326 (M+H)$^+$; 1H NMR (CDCl$_3$) $\partial$: 0.75 (m, 2H), 1.07 (m, 2H), 1.42 (t, 3H, J=7 Hz), 2.31 (m, 1H), 3.08 (s, 3H), 4.42 (q, 2H, J=7 Hz), 8.40 (s, 1H), 9.44 (d, 1H, J=6 Hz).

Step 253j. 8-(3-(N-BOC-amino)pyrrolidinyl)-1-cyclopropyl-7-fluoro-9-methyl-4-oxo-4H-quinolizine-3-carboxylic acid ethyl ester A sample of the product from Step 253i above (0.500 g, 1.544 mmol) was dissolved in 20 mL of anhydrous acetonitrile, and 0.600 g of sodium bicarbonate and 0.600 g (3.22 mmol) of 3(S)-(BOC-amino)pyrrolidine were added. The mixture was heated at reflux under nitrogen for 7 hours, then the solvent was removed and the residue was redissolved in methylene chloride. This solution was washed with water, 5% HCl, water, and concentrated. The residue was purified by flash chromatography, eluting with 100:10 methylene chloride:methanol, followed by 100:10:0.5 methylene chloride: methanol:NH$_4$OH. Removal of the solvent gave 0.778 g of the title product, which was taken directly to the next step.

Step 253k. 8-(3-(N-BOC-amino)pyrrolidinyl)-1-cyclopropyl-7-fluoro-9-methyl-4-oxo-4H-quinolizine-3-carboxylic acid A sample of the product from Step 253j above (0.778 g, 1.645 mmol) was dissolved in 20 mL of THF, 0.570 g of LiOH.H20 and 10 mL of water were added, and the mixture was stirred under nitrogen for 3 hours. The THF was removed under vacuum, and the residue was adjusted to a pH between 2 and 4 with 1N HCl. The solid was collected, and the filtrate was extracted with methylene chloride and washed and concentrated to give additional product. The combined solids were purified by flash chromatography eluting with 100:5:1 methylene chloride:methanol:acetic acid to yield 0.698 g of the title product after removal of the solvent. This material was taken directly to the next step.

Step 253l. 8-(3-aminopyrrolidinyl)-1-cyclopropyl-7-fluoro-9-methyl-4-oxo-4H-quinolizine-3-carboxylic acid hydrochloride A sample of the product from Step 253k above (0.697 g, 1.564 mmol) was dissolved in 17 mL of anhydrous methylene chloride, 5.0 mL of 4N HCl in dioxane was added, and the reaction was stirred for 1.75 hours. Ether was added, and the precipitate was collected by filtration and washed with ether. The solid was dissolved in water, filtered through a sintered glass funnel, and freeze-dried to give the title product as a yellow solid. mp 230°–232° C. (dec). MS 346 (M–Cl)$^+$; 1H NMR (DMSO) $\partial$: 0.58(m, 2H), 0.99 (m, 2H), 2.15 (m, 1H), 2.31 (m, 2H), 263 (s, 3H), 3.77 (m, 2H), 3.99–4.06 (m, 3H), 7.94 (s, 1H), 8.39 (br s, 3H), 9.10 (d, 1H, =11 Hz), 13.85 (br s); IR 3440, 1695, 1610 cm$^{-1}$.

EXAMPLE 254

8-(3-(aminomethyl)pyrrolidinyl)-1-cyclopropyl-7-fluoro-9-methyl-4-oxo-4H-quinolizine-3-carboxylic acid hydrochloride The 3-(BOC-amino)pyrrolidine of Step 253j above was replaced by 3-BOC-aminomethylpyrrolidine and the reaction product was carried forward as in Steps 253K and 253l, above, to prepare 0.085 g of the title compound. MS 360 (M–Cl)$^+$; 1H NMR (DMSO) $\partial$: 0.60 (m, 2H), 0.99 (m, 2H), 1.81 (m, 1H), 2.18 (m, 1H), 2.30 (m, 1H), 2.60 (s, 3H), 2.98 (m, 2H), 3.66–3.81 (m, 5H), 7.90 (s, 1H), 8.09 (br s, 3H), 9.06 (d, 1H, J=11 Hz), 13.85 (br s, 1H).

EXAMPLE 255

8-(2S,4S-4-amino-2-methylpyrrolidinyl)-1-cyclopropyl-7-fluoro-9-methyl-4-oxo-4H-quinolizine-3-carboxylic acid hydrochloride The 3-BOC-aminopyrrolidine of Step 253j above was replaced by (2S,4S)-4-(BOC-amino)-2-methylpyrrolidine and the reaction product was carried forward as in Steps 253K and 253l, above, to prepare 0.071 g of the title compound. MS 360 (M–Cl)$^+$; 1H NMR (DMSO) $\partial$: 0.51 (m, 1H), 0.63 (m, 1H), 0.90 (m, 1H), 1.09 (m, 1H), 1.17 (d, 3H, J=6 Hz), 2.01 (m, 1H), 2.40 (m, 2H), 2.64 (s, 3H), 3.40 (m, 1H), 3.98 (m, 1H), 4.31 (m, 1H), 4.61 (m, 1H), 8.00 (s, 1H), 9.17 (d, 1H, J=11 Hz).

EXAMPLE 256

8-(3-aminoazetidinyl)-1-cyclopropyl-7-fluoro-9-methyl-4-oxo-4H-quinolizine-3-carboxylic acid hydrochloride The 3-BOC-aminopyrrolidine of Step 253j above was replaced by 3-(BOC-amino)azetidine and the reaction product was carried forward as in Steps 253K and 253l, above, to prepare 0.094 g of the title compound. MS 332 (M–Cl)$^+$; 1H NMR (DMSO) $\partial$: 0.61 (m, 2H), 1.00 (m, 2H), 2.30 (m, 1H), 2.61 (s, 3H), 4.15 (m, 1H), 4.56 (m, 2H), 4.86 (m, 2H), 7.89 (s, 1H), 851 (br s, 3H), 9.13 (d, 1H, J=10 Hz).

EXAMPLE 257

8-(3(S)-aminopyrrolidinyl)-1-cyclopropyl-7-fluoro-9-methyl-4-oxo-4H-quinolizine-3-carboxylic acid hydrochloride The 3-BOC-aminopyrrolidine of Step 253j above was replaced by 3(S)-(BOC-amino)pyrrolidine and the reaction product was carried forward as in Steps 253K and 253l, above, to prepare 0.087 g of the title compound. MS 346 (M–Cl)$^+$; 1H NMR (DMSO) $\partial$: 0.59 (m, 2H), 0.99 (m, 2H), 2.14 (m, 1H), 2.31 (m, 2H), 2.63 (s, 3H), 3.76 (m, 2H), 398–4.07 (m, 3H), 7.94 (s, 1H), 8.36 (br s, 3H), 9.11 (d, 1H, J=11 Hz).

EXAMPLE 258

1-cyclopropyl-7-fluoro-9-methyl-4-oxo-8-(3-methyl-1-piperazinyl)-4H-quinolizine-3-carboxylic acid hydrochloride The 3-BOC-arninopyrrolidine of Step 253j above was replaced by 2-methylpiperazine (Aldrich Chemical Co.), and the reaction product was carded forward as in Steps 253K and 253l, above, to prepare 225 mg of the title compound. mp>300° C. IR (KBr): 3420, 1720, 1650 cm$^{-1}$. MS 360 (M–Cl)$^+$. $^1$H NMR (CD$_3$OD) $\partial$: 0.75 (m, 2H), 1.10 (m, 2H), 1.40 (d, 3H, J=7.5 Hz), 2.90 (s, 3H), 3.45 (m, 3H), 3.71 (m, 4H), 8.23 (s, 1H), 9.40 (d, 1H, J=12 Hz). Calc. for C$_{19}$H$_{23}$ClFN$_3$O$_3$.1.25 H$_2$O: C, 54.55; H, 6.14; N, 10.04; Found: C, 54.78; H, 5.78; N, 10.05.

EXAMPLE 259

1-cyclopropyl-7-fluoro-9-methyl-4-oxo-8-piperazinyl-4H-quinolizine-3-carboxylic acid hydrochloride The 3-BOC-aminopyrrolidine of Step 253j above was replaced by piperazine (Aldrich Chemical Co.), and the reaction product was carried forward as in Steps 253K and 253l, above, to prepare 75 mg of the title compound. mp=279°–280° C. IR (KBr): 3420, 1710, 1650, 1610 cm$^{-1}$. MS 346 (M–Cl)$^+$. $^1$H NMR (CD$_3$OD) ∂: 0.72 (m, 2H), 2.43 (m, 1H), 2.92 (s, 3H), 3.43 (m, 4H), 3.72 (m, 4H), 8.25 (s, 1H), 9.30 (d, 1H, J=12 Hz). Calc. for C$_{18}$H$_{21}$ClFN$_3$O$_3$.1.5 H$_2$O: C, 55.32; H, 5.67; N, 10.75; Found: C, 55.52; H, 5.49; N, 10.59.

EXAMPLE 260

1-cyclopropyl-7-fluoro-9-methyl-8-(2-((N-methyl)aminomethyl)-4-morpholinyl)-4-oxo-4H-quinolizine-3-carboxylic acid hydrochloride Step 260a. 1-N-benzyl-3-(chloromethyl)morpholine A mixture of 1.5 g (10 mmol) of N-benzyl-ethanolamine (Aldrich Chemical Co.) and 7.8 mL of epichlorohydrin was heated at 40° C. for 30 min. The reaction was cooled, and the excess epichlorohydrin was removed with a rotary evaporator. The residue was dried under vacuum, dissolved in 30 mL of conc. H$_2$SO$_4$, and the mixture heated at 150° C. for 30 min. The reaction was quenched by pouring onto ice, and the pH was adjusted with NaOH to pH 13. The basic solution was extracted with toulene (3×), and the extracts were dried over Na$_2$SO$_4$, filtered, and the solvent remove under vacuum. The residue was dried under vacuum to yield 193 mg of the title product.

Step 260b. 1-N-benzyl-3-((N-methylamino)methyl)-morpholine

A thick-walled glass tube was charged with 8.83 g of N-benzyl-3-(chloromethyl)morpholine, from step 260a above, dissolved in 15 mL of methanol. The tube and its contents were cooled and 25 mL of anhydrous methylamine was added. The tube was sealed and heated at 100° C. for 24 hours. The seal was broken, and the solvent was removed under vaccum. The residue was diluted with 100 mL of 10% Na$_2$CO$_3$, then extracted 3× with methylene chloride. The extract was dried over Na$_2$SO$_4$, filtered, and the solvent was removed on a rotary evaporator to yield 8.6 g of the title product.

Step 260 c. 1-N-benzyl-3-((N-BOC-N-methylamino)methyl)-morpholine

To a dry flask under positive N$_2$ atmosphere was added 8.6 g (39 mmol) of the 1-N-benzyl-3-((N-methylamino)methyl)-morpholine, from step 260b above, in 100 mL of dry methylene chloride. The solution was cooled in an ice bath and 8.6 mL (64.3 mmol) of triethylamine and 12.7 g (58.5 mmol) of di-t-butyldicarbonate was added. The reaction mixture was stirred at 0°–5° C. for 30 min, then warmed to room temperature and stirred for 72 hours. The reaction contents were diluted with 100 mL of methylene chloride, which was then washed with water and dried over Na$_2$SO$_4$. The solution was filtered, the solvent was removed on a rotary evaporator, and the residue dried under vacuum to afford 12.4 g of crude title product. The product was purified by column chromatography to yield 7.4 g of the title product as a colorless oil. Anal Calc. for C11H22N2O3: C, 67.47; H, 8.81;,N, 8.74; Found: C, 67.00; H, 8.53; N, 8.66.

Step 260d. 2-(N-BOC-N-methyl-aminomethyl)morpholine

A 1.10 g (3.43 mmol sample of 1-N-benzyl-3-((N-BOC-N-methylamino)methyl)-morpholine, from step 260c above, was dissolved in 100 mL of methanol. To this was added 500 mg of 20% Pd/C, and the mixture was stirred at room temperature under 4 atm of H$_2$ for 16 hours. The catalyst was removed by filtration, the solvent was removed with a rotary evaporator, and the residue was dried under vacuum to yield 794 mg of the title product as a colorless oil.

Step 260e. 1-cyclopropyl-7-fluoro-9-methyl-8-(2-((N-methyl)aminomethyl)-4-morpholinyl)-4-oxo-4H-quinolizine-3-carboxylic acid hydrochloride The 3-BOC-aminopyrrolidine of Step 253j above was replaced by 2-(N-BOC-N-methylaminomethyl)morpholine (from step 260d above)and the reaction product was carried forward as in Steps 253K and 253l, above, to prepare 280 mg of the title compound. mp=208°–210° C. IR (KBr): 3420, 1720, 1700, 1650 cm$^{-1}$. MS 390 (M–Cl)$^+$. $^1$H NMR (CD$_3$OD) ∂: 0.70 (m, 2H), 1.10 (m, 2H), 2.38 (m, 1H), 2.78 (s, 3H), 2.90 (s, 3H), 3.10–3.30 (m, 2H), 350–4.15 (m, 7H), 8.12 (s, 1H), 9.20 (d, 1H, J=14 Hz). Calc. for C$_{20}$H$_{25}$ClFN$_3$O$_4$.2H$_2$O: C, 52.01; H, 6.33; N, 9.10; Found: C, 51.90; H, 5.92; N, 9.09.

EXAMPLE 261

1-cyclopropyl-7-fluoro-9-methyl-4-oxo-8-(1,2,3,4-tetrahydro-2-isoquinolinyl)-4H-quinolizine-3-carboxylic acid The 3-BOC-aminopyrrolidine of Step 253j above was replaced by 1,2,3,4-tetrahydroisoquinoline (Aldrich Chemical Co.), and the reaction product was carded forward as in Steps 253K and 253l, above, to prepare 315 mg of the title compound. mp=214°–215° C. IR (KBr): 3420, 1730, 1680 cm$^{-1}$. MS 393 (M+H)$^+$. $^1$H NMR (CDCl$_3$) ∂: 0.70 (m, 2H), 1.08 (m, 2H), 2.30 (m, 1H), 2.85 (s, 3H),3.10 (dd, 2H, J=6 Hz), 3.75 (m, 2H), 4.60 (s, 2H), 7.28 (m, 4H), 8.40 (s, 1H), 9.22 (d, 1H, J=12 Hz). Calc. for C$_{23}$H$_{21}$FN$_2$O$_3$.1.25 H$_2$O: C, 66.58; H, 5.71; H, 6.75; Found: C, 66.56; H, 5.26; N, 6.62.

EXAMPLE 262

1-cyclopropyl-7-fluoro-9-methyl-4-oxo-8-(4-amino-1-piperdinyl)-4H-quinolizine-3-carboxylic acid hydrochloride Step 262a. N-benzyl-4-(N-hydroxyimino)piperidine A 3.78 g (20 mmol) sample of N-benzyl-4-oxo-piperidine (Aldrich Chemcial Co.) was dissolved in 50 mL of methanol. To this solution was added 4.16 g (60 mmol) of hydroxylamine hydrochloride and 5.2 g NaHCO3 (62 mmol) (Dissolved in 80 mL of water and added in 5 mL portions). The mixture was then stirred at room temperature for 18 hours. The mixture was filtered, and the solvent was removed from the filtrate on a rotary evaporator to give 3.05 g of the title product. mp 127°–128° C.

Step 262b. 1-N-benzyl-4-aminopiperidine

A 2.04 g (9.98 mmol) sample of the oxime from step 262a above was dissolved in 200 mL of methanol and reduced with 10 g of Raney nickel under 4 atmosphere of H$_2$ at room temperature for 4 hours. The catalyst was removed by filtration, and the solvent was removed on a rotary evaporator. The residue was dried under vacuum to yield 1.79 g of the title product. MS M/Z: 191 (M+H)$^+$.

Step 262c. 1-N-benzyl-4-BOC-aminopiperidine

In a dry system under $N_2$ pressure was introduced 1.78 g of the 1-N-benzyl-4aminopiperidine, from step 262b above, dissolved in 9 mL of dry methylene chloride. To this was added 1.6 mL (12 mmol) of triethylamine and 2.45 g (11.2 mmol) of di-t-butyldicarbonate. The reaction mixture was stirred at room temperature for 96 hours. The contents were diluted with 125 mL of methylene chloride and washed with water. The organic layer was dried over $Na_2SO_4$, filtered, and the solvent removed on a rotary evaporator. The residue was dried under vacuum to yield 2.45 g of the title product as an off-white solid. The crude product was purified by column chromatography on silica gel, eluting with 2% methanol in methylene chloride. Removal of the solvent gave 1.74 g of product, which was the recrystallized from ethanol, and dried under vacuum. mp. 121°–122° C. Anal. calc. for C17H25N2O2: C, 70.31; H, 9.02; N, 9.65; Found: C, 70.26; H, 9.02; N, 9.55.

Step 262d. 4-BOC-aminopiperidine

The benzyl group was removed from the product of step 262c by the procedure described for Example 260d above, to afford the title product.

Step 262e. 1-cyclopropyl-7-fluoro-9-methyl-4-oxo-8-(4-amino-1-piperdinyl)-4H-quinolizine-3-carboxylic acid hydrochloride The 3-BOC-aminopyrrolidine of Step 253j above was replaced by 4-(BOC-amino)methylpiperidine, from step 262d above, and the reaction product was carried forward as in Steps 253K and 253l, above, to prepare 480 mg of the title compound. mp=231°–232° C. IR (KBr): 3420, 1700, 1610 cm$^{-1}$. MS 360 (M–Cl)$^+$. $^1$H NMR (CD$_3$OD) ∂: 0.70 (m, 2H), 1.08 (m, 2H), 1.85 (m, 1H), 2.10 (m, 1H), 2.18 (m, 2H), 2.35 (m, 2H), 2.87 (s, 3H), 3.50 (m, 2H), 3.70 (m, 1H), 8.16 (s, 1H), 9.22 (d, 2H, J=9 Hz). Calc. for $C_{19}H_{23}ClFN_3O_3 \cdot 0.75$ H$_2$O: C, 55.75; H, 6.03; H, 10.26; Found: C, 55.70; H, 6.07; N, 10.36.

EXAMPLE 263

1-cyclopropyl-7-fluoro-9-methyl-4-oxo-8-(3-amino-1-piperdinyl)-4H-quinolizine-3-carboxylic acid hydrochloride The 3-BOC-aminopyrrolidine of Step 253j above was replaced by 3-amino-piperidine hydrochloride (Aldrich Chemical Co.), which was neutralized with triethylamine, and the reaction product was carried forward as in Steps 253K and 253l, above, to prepare 250 mg of the title compound. mp=222°–223° C. IR (KBr): 3400, 1700, 1680 cm$^{-1}$. MS 360 (M–Cl)$^+$. $^1$H NMR (CD$_3$OD) ∂: 0.70 (m, 2H, J=6 Hz), 1.10 (m, 2H, J=6 Hz), 1.70 (m,2H), 2.05 (m, 3H), 2.30 (m, 2H), 2.40 (m, 2H), 2.87 (s, 3H), 3.90 (m, 1H), 8.18 (s, 1H), 9.20 (d, 1H, J=9 Hz). Calc for $C_{19}H_{23}ClFN_3O_3 \cdot 2$ H$_2$O: C, 52.84; H, 6.30; H, 9.73; Found: C, 52.62; H, 6.62; N, 9.36.

EXAMPLE 264

1-cyclopropyl-7-fluoro-9-methyl-4-oxo-8-(4-(aminomethyl)-1-piperdinyl)-4H-quinolizine-3-carboxylic acid hydrochloride The 3-BOC-aminopyrrolidine of Step 253j above was replaced by 4(aminomethyl)piperidine (Aldrich Chemical Co.), and the reaction product was carried forward as in Steps 253K and 253l, above, to prepare 157 mg of the title compound. mp>300° C. IR (KBr): 3410, 1720, 1660 cm$^{-1}$. MS 374 (M–Cl)$^+$. $^1$H NMR (CD$_3$OD) ∂: 0.70 (m, 2H), 1.08 (m, 2H), 1.55 (m, 1H), 1.95 (m, 2H), 2.42 (m, 2H), 2.83 (s, 3H), 2.95 (m, 3H), 3.40 (m, 2H), 3.60 (m, 2H), 8.18 (s, 1H), 9.22 (d, 1H, J=9 Hz). Calc. for $C_{20}H_{25}ClFN_3O_3 \cdot 1.75$ H$_2$O: C, 54.42; H, 6.51; H, 9.52; Found: C, 53.92; H, 6.85; N, 9.73.

EXAMPLE 265

1-cyclopropyl-7-fluoro-9-methyl-4-oxo-8-(5-amino-1,2,3,4-tetrahydro-2-isoquinolinyl)-4H-quinolizine-3-carboxylic acid hydrochloride Step 265a. 5-amino-1,2,3,4-tetrahydroisoquinoline A 1.0 g (0.69 mmol) sample of 5-aminoisoquinoline (Aldrich Chemical Co.) was dissolved in 100 mL of methanol and reduced with 250 mg PtO$_2$ catalyst at 25° C. under 4 atmospheres of H$_2$ for 8 hours. The catalyst was removed by filtration, the solvent was removed on a rotary evaporator, and the residue was dried under vacuum to give 1.01 g of crude product. The material was crystallized from i-propanol and dried under vacuum, yield 602 mg. mp=153°–154° C. MS M/Z: 149 (M+H)$^+$, 166 (M+NH$_4$)$^+$.

Step 265b. 1-cyclopropyl-7-fluoro-9-methyl-4-oxo-8-(5-amino-1,2,3,4-tetrahydro-2-isoquinolinyl)-4H-quinolizine-3-carboxylic acid hydrochloride The 3-BOC-aminopyrrolidine of Step 253j above was replaced by 5-amino-1,2,3,4-tetrahydroisoquinoline, prepared in step 265a above, and the reaction product was carried forward as in Steps 253K and 253l, above, to prepare 507 mg of the title compound. mp=185°–187° C. IR (KBr): 3380, 1710, 1650 cm$^{-1}$. MS 408 (M–Cl)$^+$, 390 (M+NH$_4$–Cl)$^+$. $^1$H NMR (CD$_3$OD) ∂: 0.72 (m, 2H, J=6, J=3 Hz), 1.10 (m, 2H, J=3 Hz), 2.40 (m, 1H), 2.90 (s, 3H), 3.07 (m, 2H, J=7.5 Hz), 3.90 (dd, 2H, J=7.5, J=3 Hz), 4.74 (s 2H), 7.28 (m, 2H), 7.35 (m, 1H, J=9 Hz), 8.17 (s, 1H), 9.25 (d, 1H, J=12 Hz). Calc. for $C_{23}H_{23}ClFN_3O_3 \cdot 0.75$ H$_2$O: C, 60.39; H, 5.40; H, 9.19; Found: C, 60.38; H, 5.16; N, 9.10.

EXAMPLE 266

1-cyclopropyl-7-fluoro-9-methyl-4-oxo-8-(4-(1-pyrrolyl)-1-piperidinyl)-4H-quinolizine-3-carboxylic acid The 3-BOC-aminopyrrolidine of Step 253j above was replaced by 4-(1-pyrrrolyl)piperidine (prepared from N-benzyl-4-hydroxypiperidine by mesylation followed by displacing the mesyl group with pyrrole and removing the benzyl group), and the reaction product was carried forward as in Steps 253K and 253l, above, to prepare 386 mg of the title compound. mp=268°–269° C. IR (KBr): 3420, 1720, 1660 cm$^{-1}$. MS 427 (M+NH$_4$)$^+$, 410 (M+H)$^+$. $^1$H NMR (CD$_3$OD) ∂: 0.70 (m, 2H), 1.03 (m, 2H), 2.14 (m, 4H), 2.40 (m, 1H), 2.90 (s, 3H), 3.60 (m, 4H), 4.18 (m, 1H), 6.08 (dd, 2H, J=3 Hz), 6.84 (dd, 2H, J=3 Hz), 8.37 (s, 1H), 9.25 (d, 1H, J=12 Hz). Calc. for $C_{23}H_{24}FN_3O_3 \cdot 1.25$ H$_2$O: C, 63.95; H, 6.18; H, 9.73; Found: C, 63.60; H, 6.61; N, 9.43.

EXAMPLE 267

1-cyclopropyl-8-(cis-3,5-dimethyl-1-piperazinyl)-7-fluoro-9-methyl-4-oxo-4H-quinolizine-3-carboxylic acid hydrochloride The 3-BOC-aminopyrrolidine of Step 253j above was replaced by cis-3,5dimethylpiperazine (Aldrich Chemical Co.) and the reaction product was carried forward as in Steps 253j and 253k, above, to prepare 0.46 g of the title compound. IR (KBr): 3450, 1720, 1650, 1610 cm$^{-1}$. MS 374 (M−Cl)$^+$. $^1$H NMR (D$_6$DMSO) ∂: 0.70 (m, 2H), 1.04 (m, 2H), 1.30 (d, 6H, J=7 Hz), 2.41 (m, 1H), 2.80 (s, 3H), 3.40–3.65 (m, 6H), 8.03 (s, 1H), 9.26 (d, 1H, J=9Hz), 9.60 (br s, 1H). Calc. for C$_{20}$H$_{25}$ClFN$_3$O$_3$.0.75 H$_2$O: C, 56.74; H,6.31; N, 9.92; Found: C, 56.66; H, 6.21; N, 9.74.

EXAMPLE 268

1-cyclopropyl-8-(2,7-diazabicyclo[3.3.0]oct-2-yl)-
7-fluoro-9-methyl-4-oxo-4H-quinolizine-3-carboxylic
acid hydrochloride The 3-BOC-aminopyrrolidine of Step 253j above was replaced by 7-BOC-2,7-diaza[3.3.0]octane (prepared according to U.S. Pat. No. 5,071,999) and the reaction product was carried forward as in Steps 253j, k, and l, above, to prepare 0.34 g of the title compound. IR (KBr): 3400, 1700, 1650, 1605 cm$^{-1}$. MS 372 (M−Cl)$^+$. $^1$H NMR (D$_6$DMSO) ∂: 0.60 (m, 2H), 0.91 (m, 1H), 2.03–2.10 (m, 3H), 2.36 (m, 1H), 2.68 (s, 3H), 3.19 (m, 1H), 3.49 (m, 2H), 4.15 (m, 1H), 5.50 (m, 1H), 7.98 (s, 1H), 9.14 (d, 1H, J=10 Hz), 9.40 (br s, 1H). Calc. for C$_{20}$H$_{24}$Cl$_2$FN$_3$O$_3$: C, 54.06; H, 5.44; N, 9.46; Found: C, 53.86; H, 5.48; N, 9.63.

EXAMPLE 269

1-cyclopropyl-8-(2,8-diaza-8-bicyclo[4.3.0]nonyl)-
7-fluoro-9-methyl-4-oxo-4H-quinolizine-3-carboxylic
acid hydrochloride The 3-BOC-aminopyrrolidine of Step 253j above was replaced by 8-BOC-2,8-diaza[4.3.0]nonane (prepared according to U.S. Pat. No. 5,059,597), and the reaction product was carried forward as in Steps 253K and 253l, above, to prepare 0.50 g of the title compound. IR (KBr): 3400, 1690, 1650, 1600 cm$^{-1}$. MS 386 (M−Cl)$^+$. $^1$H NMR (D$_6$DMSO) ∂:0.56 (m, 1H), 0.62 (m, 1H), 0.93 (m, 1H), 1.07 (m, 1H), 1.60–1.80 (m, 4H), 2.28–2.32 (m, 2H), 2.67 (s, 3H), 2.72 (m, 1H), 2.94 (m, 1H), 3.70 (m, 2H), 3.91 (m, 1H), 4.03 (m, 1H), 4.35 (m, 1H), 7.93 (s, 1H), 8.90 (br s, 1H), 9.10 (d, 1H, J=11 Hz), 9.48 (br s, 1H), 13.85 (br s, 1h). Calc. for C$_{21}$H$_{26}$Cl$_2$FN$_3$O$_3$: C, 55.03; H, 5.72; N, 9.17; Found: C, 54.75; H, 5.82; N, 9.38.

EXAMPLE 270

1-cyclopropyl-7-fluoro-9-methyl-4-oxo-
8-(3(S)-(1-pyrrolyl)-1-pyrrolidinyl)-
4H-quinolizine-3-carboxylic acid A mixture of 25 mg 8-(3(S)-aminopyrrolidinyl)-1-cyclopropyl-7-fluoro-9-methyl-4-oxo-4H-quinolizine-3-carboxylic acid hydrochloride (from Example 257) and 40 mg of sodium acetate in 0.7 mL of ethyl acetate was heated to 100° C. To this solution was added 0.009 mL of dimethoxytetrahydrofuran dropwise, and the reaction was stirred at 110° C. for 5 min, then quenched by addition of water. The mixture was extracted twice with methylene chloride, and the extract was washed with water, dried over MgSO$_4$ and concentrated. The residue was purified by preparative TLC, eluting with 100:10 chloroform:methanol, to give 13.6 mg of the title product as a yellow solid after removal of the solvent. MS 395 (M−Cl)$^+$. $^1$H NMR (CDCl$_3$) ∂: 0.67 (m, 2H), 1.00 (m, 2H), 2.20 (m, 1H), 2.46 (m, 1H), 2.56 (m, 1H), 2.66 (s, 3H), 3.89 (m, 1H), 3.99 (m, 2H0, 4.15 (m, 1H), 4.86 (m, 1H), 6.23 (t, 2H, J=2 Hz), 6.79 (t, 2H, J=2 hz), 8.32 (s, 1H), 9.15 (d, 1H, J=10 Hz), 13.83 (br, 1H).

EXAMPLE 271

1-cyclopropyl-7-fluoro-8-(3-hydroxy-1-pyrrolidinyl)-
9-methyl-4-oxo-4H-quinolizine-3-carboxylic
acid hydrochloride The 3-BOC-aminopyrrolidine of Step 253j above was replaced by 3-hydroxypyrrolidine (Aldrich Chemical Co.), and the reaction product was carried forward as in Steps 253j and 253k above, to prepare 0.15 g of the title compound. IR (KBr): 3425, 1690, 1650, 1600 cm$^{-1}$. MS 346 (M+H)$^+$. $^1$H NMR (DMSO-d$_6$) ∂: 0.59 (m, 2H), 0.93 (m, 1H), 1.03 (m, 1H), 196–201 (m, 3H), 2.29 (m, 1H), 2.49 (s, 3H), 3.43 (m, 1H), 3.69 (m, 1H), 4.01 (m, 2H), 4.42 (m, 1H), 5.15 (d, 1H, J=3 Hz), 7.89 (s, 1H), 9.05 (d, 1H, J=11 Hz), 13.86 (br s, 1H). Calc. for C$_{18}$H$_{19}$FN$_2$O$_4$: C, 62.42; H, 5.53; N, 8.09; Found: C, 62.20; H, 5.55; N, 8.09.

EXAMPLE 272

1-cyclopropyl-7-fluoro-8-(4-methyl-1-piperazinyl)-
9-methyl-4-oxo-4H-quinolizine-3-carboxylic acid
hydrochloride The 3-BOC-aminopyrrolidine of Step 253j above was replaced by 1-methylpiperazine (Aldrich Chemical Co.), and the reaction product was carried forward as in Steps 253j and 253k, above, to prepare 0.15 g of the title compound. mp=210°–216° C. (dec). MS 360 (M−Cl)$^+$. $^1$H NMR (CDCl$_3$) ∂: 0.70 (m, 2H), 1.02 (m, 2H), 2.28 (m, 1H), 2.40 (s, 3H), 2.60 (m, 4H), 2.79 (s, 3H), 3.48 (m, 4H), 8.37 (s, 1H), 9.21 (d, 1H, J=9 Hz).

EXAMPLE 273

1-cyclopropyl-9-chloro-7-fluoro-8-(3-amino-
1-pyrrolidinyl)-4-oxo-4H-quinolizine-3-carboxylic
acid trifluoroacetic acid salt The 4-t-butoxy-2,3,6-trifluoro-5-methylpyridine of Step 253d above was replaced by 4-t-butoxy-3-chloro-2,5,6-trifluoropyridine (from step 253a above), and the methanol solvent was replace by benzene, and the reaction product was carried forward as in Steps 253d–l above, and the 4N HCl in dioxane of Step 253l was replaced with trifluoroacetic acid. to prepare 0.13 g of the title compound. MS 366 (M−CF$_3$CO$_2$)$^+$. $^1$H NMR (D$_6$-DMSO) ∂: 0.58 (m, 2H), 0.97 (m, 2H), 2.11 (m, 1H), 2.31 (m, 1H), 2.44 (m, 1H), 3.83 (m, 1H), 3.97 (m, 2H), 4.10 (m, 1H), 4.20 (m, 1H), 8.09 (s, 1H), 8.09 (br, 3H), 9.18 (d, 1H, J=11 Hz). Calc. for C$_{17}$H$_{17}$ClFN$_3$O$_3$:.CF$_3$COOH.0.5 H$_2$O: C, 46.69; H, 3.92; N, 8.60; Found: C, 46.62; H, 3.64; N, 8.45.

EXAMPLE 274

8-(3-amino-1-pyrrolidinyl)-1-cyclopropyl-
7,9-difluoro-4-oxo-4H-quinolizine-3-carboxylic acid
hydrochloride Step 274a. 4-t-butoxy-2,3,5,6-tetrafluoropyridine A 158.5 g (0.938 mmol) sample of pentafluoropyridine (Aldrich Chemical Co.) was dissolved in 600 mL of THF and cooled to −78° C. To this was added 88.29 g (0.919 mmol) of sodium-t-butoxide in 800 mL of THF over a 30 min period, with stirring and while maintaining the temperature at −78° C. The mixture was stirred for another 30 min at this temperature, then the temperature of the bath was raised to −20° C., and the reaction was stirred at this temperature for 64 hours. The reaction mixture was removed from the cold bath and diluted with 1.5 L of ether, then filtered through a diatomaceous earth filter aid. The solvent was removed under vacuum to leave a yellow oil. The oil was purified by vacuum distillation to afford 141.34 g of the title product.

Step274b. 4-t-butoxy-2,3,5-trifluoropyridine

A 20.0 g (0.089 mmol) sample of the product from step 274a above was dissolved in 100 mL of absolute ethanol, and 26.08 mL (0.538 mol) of hydrazine monohydrate was added. The reaction was stirred for 1 hour at room temperature and 1 hour at reflux. The solvent was removed under vacuum. The residue was dissolved in ether and washed with water and brine. The organic phase was dried over $MgSO_4$, and the solvent was removed under vacuum to yield a yellow solid. This material was dissolved in 120 mL of toluene, 60 mL of 20% sodium hydroxide was added, and air was bubbled through the stirred solution for 18 hours. To the reaction was added 100 mL of ether, and the organic phase was separated, washed with water and brine, and dried over $MgSO_4$. Removal of the solvent, and purification of the residue with flash chromatography on silica gel, eluting with 1:16 ethyl acetate:hexane, gave 14.6 g of the title product as a reddish liquid.

Step 274c. 8-(3-amino-1-pyrrolidinyl)-1-cyclopropyl-7,9-difluoro-4-oxo-4H-quinolizine-3-carboxylic acid hydrochloride Replacing the 4-t-butoxy-2,5-difluoro-3-methylpyridine of step 253c with the 4-t-butoxy-2,3,5-trifluoropyridine from step 274b above, and carrying the product forward according to the procedures of Steps 253e-l, 76 mg of the title compound was prepared. MS M/Z: 350 (M−Cl)$^+$. $^1$H NMR ($D_6$-DMSO) ∂: 0.65 (m, 2H), 0.90 (m, 2H), 2.15–2.30 (m, 3H, 3.95–4.00 (m, 3H), 4.18 (m, 2H), 7.81 (s, 1H), 8.46 (br, 3H), 9.17 (d, 1H, J=9 Hz).

EXAMPLE 275

8-(3-amino-1-pyrrolidinyl)-1-cyclopropyl-7-fluoro-9-methoxy-4-oxo-4H-quinolizine-3-carboxylic acid hydrochloride Step 275a. 4-t-butoxy-2,3,6-trifluoro-5-hydroxypyridine A 11.16 g (54.39 mmol) sample of 4-t-butoxy-2,3,6-trifluoropyridine, from Example 253 step b above, was dissoved in 50 mL of THF, and the solution was cooled to −78° C. To this solution was added LDA (65.6 mmol) with stirring for 30 min, during which a solid preciptated. To this mixture was added 7.5 mL of trimethoxyborane, with stirring for 25 min at −78° C. To this mixture was added 10 mL of acetic acid, and the mixture was stirred and allowed to warm to room temperature. Next was added 100 mL of 30% hydrogen peroxide and 100 mL of 2N sodium hydroxide while cooling in an ice bath. The mixture was then stirred at room temperature for 16 hours, and quenched with saturated $NH_4Cl$ solution. The mixture was extracted with ether, and the extract was washed with brine and dried over $MgSO_4$. The solvent was removed under vacuum, and the residue was purified by flash chromatography on silica gel, eluting with 1:8 ethyl acetate:hexane. Removal of the solvent gave 9.769 g of the title product as a colorless liquid.

Step 275b. 4-t-butoxy-2,3,6-trifluoro-5-methoxypyridine

To a solution of 237 mg (1.07 mmol) of 4-t-butoxy-2,3,6-trifluoro-5-hydroxypyridine, from step 275a above, in 3 mL of anhydrous THF was added 335 mg (1.277 mmol)of triphenyl phosphine and 0.060 mL (1.48 mmol) of methanol. To this solution was added 0.200 mL (1.270 mmol) of DEAD dropwise at room temperature. The reaction was complete in 10 min, so the solvents were removed under vacuum and the residue was purified by flash chromatography on silica gel, eluting with 1:16 ethyl acetate:hexane to give 215.6 mg of the title product as a colorless liquid after removal of the solvent.

Step 275c. 8-(3-amino-1-pyrrolidinyl)-1-cyclopropyl-7-fluoro-9-methoxy-4-oxo-4H-quinolizine-3-carboxylic acid hydrochloride Replacing the 4-t-butoxy-2,3,6-trifluoro-5-methylpyridine of Example 253 step c with the 4-t-butoxy-2,3,6-trifluoro-5-methoxypyridine of step 275b above and carrying the product forward according to the procedures of Steps 253d-l, 120 mg of the title compound was prepared. MS M/Z: 362 (M−Cl)$^+$. IR (KBr): 3440, 1799, 1650, 1610 cm$^{-1}$. $^1$H NMR ($D_6$-DMSO) ∂: 0.62 (m, 2H), 0.91 (m, 2H), 2.12 (m, 1H), 2.29 (m, 1H), 2.39 (m, 1H), 3.62 (s, 3H), 3.81 (m, 1H), 3.94 (m, 2H), 4.06 (m, 2H), 7.79 (s, 1H), 8.30 (br, 3H), 9.13 (d, 1H, J=10 Hz), 13.79 (br, 1H). Calc. for $C_{18}H_{20}FN_3O_4 \cdot 2HCl \cdot 0.5H_2O$: C, 48.77; H, 5.23; N, 9.48; Found: C, 48.65; H, 5.19; N, 9.56.

EXAMPLE 276

1-cyclopropyl-7-fluoro-9-methyl-8-(3(S)-methylamino-1-pyrrolidinyl)-4-oxo-4H-quinolizine-3-carboxylic acid hydrochloride Step 276a. 1-N-benzyl-3(S)-(BOC-amino)-pyrrolidine A 4.2 g sample of (3S)-3-BOC-aminopyrrolidine (TCI America) and 4.7 mL of triethylamine were dissolved in 75 mL of methylene chloride at room temperature. To this solution was added 2.95 mL of benzyl bromide dropwise, and the reaction was heated at reflux for 6 hours. After cooling, the solution was washed with water, and the solvent was dried and evaporated to give 5.10 g of the title product as a white solid.

Step 276b. 1-N-benzyl-3(S)-(methylamino)-pyrrolidine

The 5.10 g sample of 1-N-benzyl-3(S)-(BOC-amino)-pyrrolidine, from step 276a above, was dissolved in 25 mL of THF, and 55.6g of LiAlH4 (1.0M in THF) was added. The mixture was stirred and heated at reflux for 4 hours. The reaction was quenched with water, and the mixture was extracted with methylene chloride. The solvent was washed with water, dried over $MgSO_4$, and removed on a rotary evaporator to yield 2.43 g of the title product.

Step 276c. 1-N-benzyl-3(S)-(N-BOC-N-methylamino)-pyrrolidine

A 2.43 g sample of 1-N-benzyl-3(S)-(methylamino)-pyrrolidine, from step 276b above, was dissolved in 100 mL of a 4:1 methanol:water mixture, and 3.34 g of di-t-butyl dicarbonate was added in portions. The reaction was stirred at room temperature for 6 hours. The methanol was removed under vacuum, and the aqueous residue was extracted with methylene chloride. The solvent was washed with water, dried over $MgSO_4$ and removed under vacuum. The residue was purified by chromatography over silica gel, eluting wtih 100:5:0.5 methylene chloride:methanol:$NH_4OH$ to give 3.23 g of the title product.

Step 276d. 3(S)-(N-BOC-N-methylamino)-pyrrolidine

The product from step 276c was treated according to the procedure of Example 171 step 5 to remove the benzyl protecting group and afford 2.24 g of the title product as a white solid.

Step 276e. 1-cyclopropyl-7-fluoro-9-methyl-8-(3(S)-methylamino-1-pyrrolidinyl)-4-oxo-4H-quinolizine-3-carboxylic acid hydrochloride Following the procedure of Example 253 step j, replacing the 3-BOC-aminopyrrolidine of that example with the 3(S)-(N-BOC-N-methylamino)-pyrrolidine from step 276d above, and carrying the reaction product forward according to the procedures of Example 253 steps k and l, a 452 mg sample of the title product was obtained. MS: 360 (M–Cl)$^+$. IR (KBr): 3450, 1710, 1650, 1610 cm$^{-1}$. $^1$H NMR (d6-DMSO): 0.62 (m, 2H), 1.00 (m, 2H), 2.26 (m, 1H), 2.33 (m, 3H), 2.65 (s, 6H), 3.75 (m, 1H), 3.90 (m, 2H), 4.05 (m, 2H), 7.94 (s, 1H), 9.12 1H, J=10 Hz), 9.18 (br s, 2H), 13.86 (br s, 1H). Anal. Calc. for $C_{19}H_{22}FN_3O_3 \cdot HCl \cdot H_2O$: C, 55.14; H, 6.09; N, 10.15; Found: C, 55.29; H, 5.99; N, 10.18.

EXAMPLE 277

1-cyclopropyl-7-fluoro-9-methyl-8-(3(R)-amino-1-pyrrolidinyl)-4-oxo-4H-quinolizine-3-carboxylic acid hydrochloride Step 277a. 1-N-benzyl-3(R)-(BOC-amino)-pyrrolidine Following the procedure of Example 276 step a, replacing the (3S)-3-BOC-aminopyrrolidine of step 276a with (3R)-3-BOC-aminopyrrolidine (TCI America), the title compound was prepared.

Step 277b. 3(R)-(BOC-amino)pyrrolidine

The benzyl group was removed from the product of step 277a by the procedure of step 276d above, to give the title product.

Step 277c. 1-cyclopropyl-7-fluoro-9-methyl-8-(3(R)-amino-1-pyrrolidinyl)-4-oxo-4H-quinolizine-3-carboxylic acid hydrochloride Following the procedure of Example 253 step j, replacing the 3-(BOC-amino)pyrrolidine of that example with the 3(R)-(BOC-amino)-pyrrolidine from step 277b above, and carrying the reaction product forward according to the procedures of Example 253 steps k and l, a 452 mg sample of the title product was obtained. MS: 346 (M–Cl)$^+$. IR (KBr): 3440, 1700, 1650, 1610 cm$^{-1}$. $^1$H NMR (d6-DMSO): 0.59 (m, 2H), 1.00 (m, 2H), 2.15 (m, 1H), 2.31 (m, 2H), 2.63 (s, 3H), 3.76 (m, 2H), 4.00–4.07 (m, 3H), 8.40 (br, 3H), 9.10 (d, 1H, J=11 Hz) $C_{18}H_{20}FN_3O_3 \cdot HCl \cdot H_2O$: C, 54.07; H, 5.80; N, 10.51; Found: C, 54.19; H, 5.65; N, 10.37.

EXAMPLE 278

(3R)-9-fluoro-3-methyl-10-(4-methyl-1-piperazinyl)-2H,3H,6H-6-oxo-pyrano[2,3,4-ij]quinolizine-5-carboxylic acid hydrochloride Step 278a. (S)-1-bromo-2-methyl-3-(t-butyldimethylsilyloxy)propane To a 9.59 g (62.67 mmol) sample of (S)-(+)-3-bromo-2-methyl-1-propanol (Aldrich Chemical Co.) in 40 mL of DMF was added 4.27 g (62.720 mmol) of imidazole, and the solution was cooled to 0° C. To this cooled solution was added 9.45 g (62.69 mmol) of t-butyldimethylsilyl chloride, and the solution was stirred at room temperature for 16 hours. The reaction solution was poured into water, which was extracted with hexane. The organic layer was washed with water, satd. brine, dried over MgSO$_4$, and concentrated. The residue was distilled in a kugelrohr apparatus (0.2 mm Hg, 50° C.) to yield 15.00 g of the title product as a colorless liquid.

Step 278b. (S)-1-iodo-2-methyl-3-(t-butyldimethylsilyloxy) propane

A 15.00 g sample of the product from the preceeding step was dissolved in 100 mL of acetone, and 42.00 g (5 eq) of NaI was added. This mixture was heated at reflux under N$_2$ for 9 hours. The mixture was cooled, filtered, and the filtrate was concentrated. The residue was dissolved in hexane, and the solution was again filtered and concentrated to yield 16.62 g of a colorless liquid. This material was distilled in a kugelrohr apparatus (0.2 mm Hg, 60° C.) to give 16.479 g of the title product as a colorless liquid. MS: 315 (M+H)$^+$. 1H NMR (CDCl$_3$) ∂: 0.07 (s, 6H), 0.90 (s, 9H), 0.95 (d, 3H, J=7 Hz), 1.65 (m, 1H), 3.29 (m, 2H), 3.40 (m, 1H), 3.54 (m, 1H).

Step 278c. 1-(2,3,5,6-tetrafluoro-4-pyridyl)-4-methylpiperazine

A 25.10 g sample (0.148 mmol) of pentafluoropyridine (Aldrich Chemical Co.) and 23.0 mL (0.165 mmol) of triethylamine were dissolved in 150 mL of HPLC grade methylene chloride. To this solution 17.3 mL (0.156 mmol) of N-methylpiperazine were added slowly dropwise at 0° C. The solution was stirred for 16 hours at 0° C., then washed with water, dried over MgSO$_4$ and concentrated to give 36.95 g of the title product as a colorless oil, which solidifed upon standing. MS: 250 (M+H)$^+$. $^1$H NMR (CDCl$_3$) ∂: 2.36 (s, 3H), 2/53 (m, 4H), 3.52 (m, 4H).

Step 278d. (R)-2-methyl-3-(4-(4-methylpiperazinyl)-3.5.6-trifluoro-2-pyvridinyl)-1-propanol A 5.03 g (16.00 mmol) sample of (S)-1-iodo-2-methyl-3-(t-butyldimethylsilyloxy)propane, from step 278b above, was dissolved in 32 mL of ether and cooled to −78° C. To this solution was added 19.8 mL (33.66 mmol) of t-buthyl-lithium (1.7M in pentane), and the temperature was maintained at −78° C. while stirring for 40 min. The temperature was raised to 0° C., and stirring was continued for 30 min. This solution was designated the "lithium compound" and was utilized below. In a separate flask 3.99 g (16.01 mmol) of 1-(2,3,5,6-tetrafluoro-4-pyddyl)-4-methylpiperazine, from step 278c above, was dissolved in 50 mL of THF. To the latter solution at −78° C. was added via cannula the solution of the lithium compound. The reaction was stirred at −78° C. for 5 min and at room temperature for 30 min. The reaction was quenched by addition of satd. NH$_4$Cl, and extracted with ether. The extract was washed with satd. brine, dried over MgSO$_4$, and concentrated. The residue was dissolved in 30 mL of THF, and 16.5 mL of tetrabutlyammonium fluoride (1N in THF) was added. The mixture was stirred for 16 hours and concentrated. The residue was slurried with water and extracted with methylene chloride. The organic phase was washed with water, dried over MgSO$_4$, and concentrated. The residue was purified by flash chromatography on silica gel, eluting with 100:5:0.5 methylene chloride:methanol:NH$_4$OH to give 4.037 g of the title product as a colorless viscous oil. MS: 304 (M+H)$^+$. $^1$H NMR (CDCl$_3$) ∂: 0.95 (d, 3H, J=6.6 Hz), 2.11 (m, 1H), 2.35 (s, 3H), 2.53 (m, 4H), 2.63 (m, 1H), 2.71 (m, 1H), 3.37–3.50 (m, 6H). Anal calc for $C_{14}H_{20}F_3N_3O$: C, 55.44; H, 6.65; N, 13.72; Found: C, 55.10; H, 6.24; N, 13.72 [α]$_D$=+7.80° (26°, c=1.68, methylene chloride).

Step 278e. (R)-2-methyl-3-(4-(4-methylpiperazinyl)-3,5,-difluoro-2-pyridinyl)-1-propanol A 4.349 g (14.337 mmol) sample of 2-methyl-3-(4-(4-methylpiperazinyl)-3,5,6-trifluoro-2-pyridinyl)-1-propanol, from step 278d above, was dissolved in 20 mL of n-propanol, 3.50 mL (72.15 mmol) of hydrazine hydrate was added, and the reaction was heated at reflux under N$_2$ for 17 hours. Another 1.5 mL of hydrazine hydrate was added, and the reflux was continued for 15 hours. The solution was concentrated on a rotary evaporator, and the residue was slurried in water, then extracted with methylene chloride. The solvent was washed with water, dried over MgSO$_4$, and concentrated to give 4.60 g of the title product as a viscous oil. This intermediate hydrazino compound was dissolved in 300 mL of water, and a solution of 29.78 g of CuSO4 in 400 mL of water was added by pipet over a 15 min period. The reaction was then heated at reflux under N$_2$ for 50 min. The reaction was cooled to ambient temperature and the solution was made basic with NH$_4$OH. The solution was extracted with methylene chloride, which was washed with water, dried over MgSO$_4$ and concentrated. The residue was purified by flash chromatography on silica gel, eluting with 100:5:0:5 methylene chloride:methanol:NH$_4$OH, to give 3.605 g title product. MS: 286 (M+H)$^+$. $^1$H NMR (CDCl$_3$) ∂: 0.96 (d, 3H, J=6.6 Hz), 2.14 (m, 1H), 2.35 (s, 3H), 2.52 (m, 4H), 2.80 (m, 2H), 3.35–3.41 (m, 5H), 3.51 (m, 1H), 8.01 (d, 1H, J=3.3 Hz). Anal. calc. for C$_{14}$H$_{21}$F$_2$N$_3$O: C, 58.93; H, 7.42; N, 14.73; Found: C, 58.59; H, 7.22; N, 14.31.

Step 278f. 3(R)-7-fluoro-3-methyl-8-(4-methyl-1-piperazinyl)-2,3-dihydro-4H-pyranol[3,2-b]pyridine A 3.557 g (12.465 mmol) sample of 2-methyl-3-(4-(4-methylpiperazinyl)-3,5,-difluoro-2-pyridinyl)-1-propanol, from step 278e above, was dissolved in 30 mL of dioxane and added to a dispersion of 1.12 g (37.33 mmol) of NnH (50% dispersion) in 100 mL of dioxane. The mixture was heated at reflux for 19 hours, then concentrated to dryness. The residue was slurried with water, and extracted with ether. The extract was washed with satd. brine, dried over MgSO$_4$, and concentrated. The residue was purified by flash chromatography on silica gel, eluting with 100:5:0:5 methylene chloride:methanol:NH$_4$OH, to afford 2.299 g of the title product. MS: 266 (M+H)$^+$. $^1$H NMR (CDCl$_3$) ∂: 1.07 (d, 3H, J=6.6 Hz), 2.21 (m, 1H), 2.38 (s, 3H), 2.49 (m, 1H), 2.57 (m, 4H), 2.94 (m, 1H), 3.37 (m, 4H), 3.67 (dd, 1H, J=9.6, 10.3 Hz), 4.23 (m, 1H), 7.90 (d, 1H, J=3.3 Hz). Anal calc. for C$_{14}$H$_{20}$FN$_3$O: C, 63.38; H, 7.60; N, 15.84; Found: C, 63.58; H, 7.60; N, 15.84.

Step 278g. 3(R)-9-fluoro-3-methyl-10-(4-methyl-1-piperazinyl)-2H,3H,6H-6-oxo-pyranol[2,3,4-ij]quinolizine-5-carboxylic acid, ethyl ester A 132.7 mg (0.500 mmol) sample of 3(R)-7-fluoro-3-methyl-8-(4-methyl-1-piperazinyl)2,3-dihydro-4H-pyrano[3,2-b]pyridine, from step 278f above, was dissolved in 5 mL of THF and cooled to –78° C. To this solution was added 0.22 mL of n-butyl lithium (0.55 mmol, 2.5M in hexane), and the reaction was stirred at –78° C. for 30 min. To the reaction vessel was added 0.120 mL (0.594 mmol) of diethoxy ethoxymethylenemalonate, and the reaction was stirred for 5 min at –78° C. and at room temperature for 15 min. The solvent was removed, and the residue was dissolved in ethanol. To this was added 1.0 mL of piperidine and 0.2 mL of acetic acid, and the solution was heated at reflux for 16 hours. The solvents were removed, and the residue was dissolved in methylene chloride. This solution was washed with water, dried over MgSO$_4$, and concentrated. The residue was triturated with 50:50 ether:hexane, and the solid was isolated, and the filtrate purified by chromatography on silica gel, eluting with 100:5:0:5 methylene chloride:methanol:NH$_4$OH, to afford a total of 88.9 mg of the title product. MS: 390 (M+H)$^+$. IR 3440, 1710, 1630 cm$^{-1}$. $^1$H NMR (CDCl$_3$) ∂: 1.34 (d, 3H, J=7 Hz), 1.42 (t, 3H, J=7 hz), 2.37 (s, 3H), 2.56 (m, 4H), 3.12 (m, 1H), 3.55 (m, 4H), 4.02 (dd, 1H, J=11, 6 Hz), 4.28 (dd, 1H, J=11, 4 Hz), 4.41 (q, 2H, J=7 Hz), 8.03 (s, 1H), 9.06 (d, 1H, J=9 Hz). Anal calc. for C$_{20}$H$_{24}$FN$_3$O$_4$: C, 61.69; H, 6.21; N, 10.79; Found: C, 61.42; H, 5.89; N, 10.65. [α]$_D$=–37.14° (25° C., c=0.28, methylene chloride).

Step 278h. 3(R)-9-fluoro-3-methyl-10-(4-methyl-1-piperazinyl)-2H,3H,6H-6-oxo-pyrano[2,3,4-ij]quinolizine-5-carboxylic acid A 657 mg( 1.687 mmol) sample of 3(R)-9-fluoro-3-methyl-10-(4-methyl-1-piperazinyl)-2H,3H,6H-6-oxo-pyrano[2.3.4-ij]quinolizine-5-carboxylic acid, ethyl ester, from step 278g above, was dissolved in 6 mL of THF and 142 mg of LiOH.H$_2$O and 3 mL of water were added. The mixture was heated at 60° C. under N$_2$ for 80 min. The solvent was removed under reduced pressure, and the aqueous residue was diluted with additional water and extracted with methylene chloride. The aqueous solution was then neuralized to ph& with 10% HCl, and extracted with methylene chloride. The extract was washed with water, dried over MgSO$_4$ and concentrated to dryness. The residue was dissolved in methylene chloride, which was then filtered through a sintered glass funnel. The filtrate was concentrated to dryness, and the residue was triturated with 1:1 ether:hexane to give 494.2 mg of the title product as a yellow solid after drying. MS: 362 (M+1)$^+$. IR 3440, 1720, 1640, 1610 cm$_{-1}$. $^1$H NMR (CDCl$_3$) ∂: 1.37 (d, 3H, J=7 Hz), 2.39 (s, 3H), 2.60 (m, 4H), 3.19 (m, 1H), 3.61 (m, 4H), 4.06 (dd, 1H, J=6.3, 10.6 Hz), 4.34 (dd, 1H, J=3.6, 10.6 Hz), 8.15 (s, 1H), 8.94 (d, 1H, J=8.8 Hz), 13.86 (br, 1H). Anal calc. for C$_{18}$H$_{20}$FN$_3$O$_4$.0.5H$_2$O: C, 59.09; H, 5.65; N, 11.48; Found: C, 59.25; H, 5.59; N, 1139.

Step 278i. 3(R)-9-fluoro-3-methyl-10-(4-methyl-1-piperazinyl)-2H,3H, 6H-6-oxo-pyrano[2.3.4-ij]quinolizine-5-carboxylic acid hydrochloride A 200 mg sample of the free base from the previous step was dissolved in 15 mL of methylene chloride, and 0.75 mL of 1M HCl in ether was added. Additional ether was added to precipitate the product, which was collected by filtration. The solid was dissolved in water, and the solution was filtered through sintered glass. The filtrate was freeze-dried to give 213.1 mg of the title product as a yellow solid. MS: 362 (M–Cl)$^+$. IR 3440, 1700, 1637, 1603 cm$_{-1}$. $^1$H NMR (DMSO-d$_6$) ∂: 1.29 (d, 3H, j=7 Hz), 2.76 (s, 3H), 3.15–3.36 (m, 5H), 3.74 (m, 4H), 4.18 (dd, 1H, J=5.7, 10.7 Hz), 4.38 (dd, 1H, J=3.7, 10.7 Hz), 8.03 (s, 1H), 9.02 (d, 1H), J=8.8 Hz). Anal calc. for C$_{18}$H$_{20}$FN$_3$O$_4$.HCl.H$_2$O: C, 51.99; H, 5.57; N, 10.08; Found: C, 51.91; H, 5.33; N, 10.03. [α]$_D$= 24.2° (24° C., 0.33, methanol).

EXAMPLE 279

3(S)-9-fluoro-3-methyl-10-(4-methyl-1-piperazinyl)-2H,3H,6H-6-oxo-pyrano[2,3,4-ij]quinolizine-5-carboxylic acid hydrochloride Step 279a. 2(R)-3-(t-butyldimethylsilyl)oxy-2-methyl-1-propanol A 24.39 g (265 mmol) sample of (R)-(–)-methyl 3-hydroxy-2-methylpropionate (Aldrich Chemical Co.) and 15.46 g (227 mmol) of imidazole were dissolved in 120 mL of DMF. The solution was stirred at 0° C. under N$_2$ and 34.23 g (227 mmol) of t-butyldimethylsilyl chloride was added in several portions. The reaction was stirred at 0° C. for 1 hour and room temperature for 22 hours, then poured into water. The mixture was extracted with hexane, and the extract was washed with water, dried over MgSO$_4$, and concentrated to give 52.51 g of the protected intermediate. The intermediate was dissolved in 100 mL of THF and added via cannula to a flask containing 475 mL of DIBAL in 200 mL of THF at –78° C., then stirred for 15 min. The reaction was then warmed to 0° rapidly and stirred for 2 hours. The reaction was quenched by slowly pouring it into 1L of satd. Na$_2$SO$_4$. The mixture was filtered through a filter aid. The organic phase was separated and reserved. The aqueous phase was extracted with ether. The organic phases were combined, washed with satd. brine, dried over MgSO$_4$ and concentrated to give a yellow liquid. This material was distilled in a kugelrohr apparatus at 0.2 mmHg and 70° C. to yield 19.50 g of the title product. [α]$_D$=−8.12° (26° C., c=2.02, CH2Cl2). $^1$H NMR (CDCl$_3$) ∂: 0.07 (s, 6H), 0.84 (d, 3H, J=7 Hz), 0.90 (s, 9H), 1.94 (m, 1H), 2.81 (br, 1H), 3.54–3.62 (m, 3H), 3.74 (m, 1H).

Step 279b. 2(R)-3-(t-butyldimethylsilyl)oxy-1-iodo-2-methylpropane

A 19.50 g (95.41 mmol) sample of 2(R)-3-(t-butyldimethylsilyl)oxy-2-methyl-1-propanol, from step 279a above, was dissolved in 100 mL of methylene chloride and 26.6 mL (191 mmol) of triethylamine was added. The solution was cooled to 0° C., 11.0 mL (142 mmol) of methansulfonyl chloride was added, and the reaction was stirred for 1 hour. Stirring was discontinued, and the reaction was held at −20° C. for 16 hours. The reaction was quenched with 5% NaHCO3, then extracted with methylene chloride. The extract was washed with water, dried over MgSO$_4$ and concentrated. The residue was chromatographed of silica gel, eluting with melthylene chloride, and the solvent was removed to give 25.95 g of the mesylated intermediate. This intermediate was dissolved in 100 mL of acetone, and 55 g of NaI was added. The mixture was heated at reflux for 10 hours, then cooled, diluted with hexane, and filtered. The filtrate was concentrated, the residue redissolved and refiltered, and again concentrated. The residue was distilled in a kugekohr apparatus at 0.2 mmHg and 60° C. to yield 18.22 g of the title product. [α]$_D$=−9.39° (25° C., c=2.46, CH2Cl2). MS: 332 (M+18)$^+$, 315 (M+H)$^+$. $^1$H NMR (CDCl$_3$) ∂: 0.07 (s, 6H), 0.60 (s, 9H), 0.96 (d, 3H, J=7 Hz), 1.64 (m, 1H), 3.29 (m, 2H), 3.40 (m, 1H), 3.53 (m, 1H).

Step 279c. 3(S)-9-fluoro-3-methyl-10-(4-methyl-1-piperazinyl)-2H,3H,6H-6-oxo-pyranol[2.3.4-ij]quinolizine-5-carboxylic acid hydrochloride Following the procedure of Example 278d, substituting the 2(R)-3-(t-butyldimethylsilyl)oxy-1-iodo-2-methylpropane of step 279b above for the 2(S)-3-(t-butyldimethylsilyl)oxy-1-iodo-2-methylpropane of step 278d, and carrying the product forward according to Example 278 steps f–i, the title product was prepared. MS 362 (M−Cl)$^+$. IR (KBr): 3440, 1710, 1635, 1610 cm−1. $^1$H NMR (DMSO-d$_6$) ∂: 1.29 (d, 3H, J=7 Hz), 2.82 (s, 3H), 3.18 (m, 2H), 3.27 (m, 1H), 3.48 (m, 2H), 3.69 (m, 2H), 3.86 (m, 2H), 4.19 (dd, 1H, J=6, 11 Hz), 4.49 (dd, 1H, J=4, 11 Hz), 8.03 (s, 1H), 9.03 (d, 1H, J=9 Hz), 11.09 (br, 1H), 13.96 (br, 1H). Anal calc for C$_{18}$H$_{20}$FN$_3$O$_4$.HCl.1.5H$_2$O: C, 50.89; H, 5.69; N, 9.89; Found: C, 50.50; H, 5.46; N, 9.72.

EXAMPLE 280

9-fluoro-10-(1-morpholinyl)-2H,3H,6H-6-oxo-pyrano [2.3.4-ij]quinolizine-5-carboxylic acid Step 280a. 3-(t-butyldimethylsilyloxy)-1-iodopropane A mixture of 44.28 g (175 mmol) sample of 1-bromo-3-(t-butyldimethylsilyloxy)-propane (prepared according to Wilson and Zucker, *J. Org. Chem,* 33:2571 (1988)) and 100 g of NaI in 200 mL of acetone was heated at reflux for 20 hours, filtered and concentrated. The residue was dissolved in hexane, re-filtered and concentrated. The residue was distilled in a kugelrohr apparatus (0.2–0.3 mm Hg, 60° C.) to give 46.87 g of the title product. This material was distilled under reduced pressure, and the pure product coming over at 53°–57° C. and 0.3 mm Hg was collected. MS: 301 (M+H)$^+$. $^1$H NMR (CDCl$_3$) ∂: 0.70 (s, 6H), 0.90 (s, 9H), 1.99 (m, 2H), 3.28 (t, 2H, J=7 Hz), 3.66 (t, 2H, J=6 Hz).

Step 280b. 9-fluoro-10-(1-morpholinyl)-2H,3H,6H-6-oxo-pyrano[2.3.4-ij]quinolizine -5-carboxylic acid Following the procedure of Example 278d, replacing the (2S)-3-(t-butyldimethylsilyloxy)-1-iodo-2-methylpropane of that step with the 3-(t-butyldimethylsilyloxy)-1-iodopropane from step 280a above, and carrying the product forward according to the procedures of Examples 278d–h, 20 mg of the title product was obtained. MS: 335 (M+1)$^+$. IR (KBr): 3440, 1705, 1630, 1610 cm-1. $^1$H NMR (CDCl$_3$) ∂: 3.13 (t, 3H, J=5.5 Hz), 3.58 (m, 4H), 3.85 (m, 4H), 4.42 (t, 2H, J=5.5 Hz), 8.08 (s, 1H), 8.94 (d, 1H, J=8.8 Hz). Anal. Calc. for C$_{16}$H$_{15}$FN$_2$O$_4$·⅛H$_2$O: C, 57.10; H, 14.57; N, 8.32; Found: C, 57.07; H, 14.32; N, 8.23.

EXAMPLE 281

(3R)-10-(3-amino-1-pyrrolidinyl)-9-fluoro-3-methyl-2H,3H,6H-6-oxo-pyrano [2.3.4-ij]quinolizine-5carboxylic acid Step 281a. (2R)-3-(4-t-butoxy-3,5,6-trifluoro-2-pyridinyl)-2-methyl-1-propanol A 9.38 g (29.85 mmol) of (S)-1-iodo-2-methyl-3-(t-butyldimethylsilyloxy)-propane, from Step 278b above, was dissolved in 50 mL of ether and reacted with 36.9 mL (1.7M in pentane, 62.73 mmol) of t-butyl lithium at −78° C. for 40 min and at 0° C. for 30 min. This solution was cooled to −78° C. again and added to a stirred solution of 6.70 g (30.02 mmol) sample of 4-t-butoxy-2,3,5,6-tetrafluoropyridine, from Example 274a above, in 40 mL of ether at −78° C. The reaction was stirred for 5 min, the dry ice bath was removed, and the reaction was stirred at room temperature for 64 hours. The reaction was quenched with satd. NH4Cl, and the mixture was extracted with ether. The extract was washed wtih satd. brine, dried over MgSO$_4$ and concentrated. The residue was dissoved in 20 mL of THF, and 30 mL of a 1N solution of tetrabutylammonium fluoride was added. The reaction was stirred for 5 hours and concentrated. The residue was dissolved in ether, which was washed with water, brine, dried over MgSO$_4$, and concentrated to dryness. The residue was flash chromatographed on silica gel, eluting with 1:3 acetone:hexane to give 5.21 g of the title product as a colorless liquid after removal of the solvent. MS: 278 (M+H)$^+$. $^1$H NMR (CDCl$_3$) ∂: 0.93 (d, 3H, J–7 Hz), 1.44 (s, 9H), 1.83 (t, 1H, J=7 Hz), 2.15 (m, 1H), 2.67 (m, 1H), 2.8 (m, 1H, 3.50 (m, 2H). Anal. Calc. for C$_{13}$H$_{18}$F$_3$NO$_2$.¼H$_2$O: C, 55.41; H, 6.62; N, 4.97; Found: C, 55.17; H, 6.30; N, 4.61.

Step 281 b. (2R)-3-(4-t-butoxy-3,5-difluoro-2-pyridinyl)-2-methyl-1-propanol

Following the procedure of Example 274b, replacing the reactant from step 278a with (2S)-3-(4-t-butoxy-3,5,6-trifluoro-2-pyridinyl)-2-methyl-1-propanol, from step 281a above, 3.44 g of the title product was prepared. MS: 260 (M+H)$^+$. $^1$H NMR (CDCl$_3$) ∂: 00.93 (d, 3H, J=7 Hz), 1.42 (m, 9H), 2.16 (m, 1H), 2.86 (m, 2H), 2.96 (t, 1H, J=7 Hz), 3.40 (m, 1H), 3.53 (m, 1H), 8.21 (m, 1H). Anal. Calc. for C$_{13}$H$_{19}$F$_2$NO$_2$: C, 60.22; H, 7.39; N, 5.40; Found: C, 60.15; H 7.46; N, 5.22.

Step 281c. 3(R)-7-fluoro-3-methyl-8-(t-butyloxy)-2,3-dihydro-4H-pyrano[3,2-b]pyridine A 3.29 g (12.69 mmol) sample of (2R)-3-(4-t-butoxy-3,5-difluoro-2-pyridinyl)-2-methyl-1-propanol, from step 281b above, was dissolved in 100 mL of dioxane and added to a dispersion of 0.570 g (19.00 mmol) of NaH (80% dispersion) in 100 mL of dioxane. The mixture was heated at reflux for 4 hours, then concentrated to dryness. The residue was slurried with water, and extracted with ether. The extract was washed with satd. brine, dried over $MgSO_4$, and concentrated. The residue was purified by flash chromatography on silica gel, eluting with 1:2 ethyl acetete:hexane, to afford 2.722 g of the title product. MS: 240 $(M+H)^+$. $^1H$ NMR $(CDCl_3)$ ∂: 1.08 (d, 3H, J=6.5 Hz), 1.40 (d, 9H, J=1 Hz), 2.22 (m, 1H), 2.55 (m, 1H), 2.99 (m, 1H), 3.69 (dd, 1H, J=9, 10 Hz), 4.21 (m, 1H), 8.01 (d, 1H, J=1 Hz). Anal calc. for $C_{13}H_{18}FNO_2$: C, 66.25; H, 7.58; N, 5.85; Found: C, 66.35; H, 7.49; N, 6.04.

Step 281d. 3(R)-9-fluoro-10-hydroxy-3-methyl-2H,3H,6H-6-oxo-pyran[2.3.4-ij]quinolizine-5-carboxylic acid, ethyl ester A 400 mg (1.671 mmol) sample of 3(R)-7-fluoro-3-methyl-8-(t-butyloxy)-2,3-dihydro-4H-pyrano[3.2-b]pyridine, from step 281c above, was dissolved in 5 mL of THF and cooled to $-78°$ C. To this solution was added a solution of 0.80 mL of n-butyl lithium (2.0 mmol, 2.5M in hexane) and 0.28 mL of LDA (2.00 mmol) (prepared at $-78°$ C. and warmed to 0° C. for 15 min), and the reaction was stirred at $-78°$ C. for 30 min. To the reaction vessel was added 0.400 mL of diethoxy ethoxymethylenemalonate, and the reaction was stirred for 5 min at $-78°$ C. and at room temperature for 15 min. 1.7 mL of NNTMS2 (1N in THF) was added, the reaction was warmed to room temperature, then quenched with satd. NH4Cl. The mixture was extracted with ether, which was washed, dried over $MgSO_4$ and concentrated. The solvent was removed, and the residue was dissolved in 10 mL of ethanol. To this was added 0.5 mL of DBU and thereaction was refluxed for 2 hours, then concentrated to dryness. The residue was dissolved in methylene chloride, which was then washed with 10% citric acid, water, dried over $MgSO_4$, and concentrated. The residue was purified by chromatography on silica gel, eluting with 100:10 methylene chloride:methanol. To the residue of the desired fraction was added 3 mL of trifluoroacetic acid, and the mixture was concentrated immediately. The residue was washed with ether to leave 307.4 mg of the title product as a yellow solid. MS: 308 $(M+H)^+$. $^1H$ NMR $(DMSO-d_6)$ ∂: 1.25 (d, 3H, J=7 Hz), 1.27 (t, 3H, J=7 hz), 3.19 (m, 1H), 4.10 (dd, 1H, J=5, 10 Hz), 4.22 (q, 2H, J=7 Hz), 4.33 (dd, 1H, J=4, 10 Hz), 9.00 (d, 1H, J=8 Hz).

Step 281e. 3(R)-10-chloro-9-fluoro-3-methyl-2H,3H,6H-6-oxo-pyrano[2.3.4-ij]quinolizine-5-carboxylic acid, ethyl ester A 276.1 mg (0.899 mmol) sample of 3(R)-9-fluoro-10-hydroxy-3-methyl-2H,3H,6H-6-oxo-pyrano[2.3.4-ij]quinolizine-5-carboxylic acid, ethyl ester, from step 281d above, was dissolved in 5 mL of methylene chloride, and 0.71 mL (9.17 mmol) of DMF and 0.85 mL of $POCl_3$ (9.12 mmol) were added. The reaction was stirred for 15 hours and quenched with water and ice. The mixture was extracted with methylene chloride, and the extract was washed with water, dried over $MgSO_4$ and concentrated. The residue was purified by flash chromatography on silica gel, eluting with 10:1 methylene chloride:methanol to afford 180.6 mg of the title product as a yellow solid after removal of the solvent. MS: 326, 328 $(M+H)^+$. $^1H$ NMR $(CDCl_3)$ ∂: 1.40 (d, 3H, J=5 hz), 1.43 (t, 3H, 7 Hz), 3.22 (m, 1H), 4.21 (dd, 1H, J=6, 10 Hz), 4.45 (m, 3H), 8.25 (s, 1H), 9.09 (d, 1H, J=6 Hz).

Step 281f. 3(R)-10-(3-(N-BOC)amino-1-pyrrolidinyl)-9-fluoro-3-methyl-2H,3H,6H-6-oxo-pyrano[2.3.4-ij]quinolizine-5-carboxylic acid, ethyl ester A 130.9 mg (0.402 mmol) sample of 3(R)-10-chloro-9-fluoro-3-methyl-2H,3H,6H-6-oxo-pyrano[2.3.4-ij]quinolizine-5-carboxylic acid, ethyl ester, from step 281e above, was dissolved in 5 mL of acetonitrile. To this solution was added 0.24 mL of DBU and 120 mg (0.644 mmol) of 3-(N-BOX)aminopyrrolidine (TCI America, Inc.), and the reaction was heated at reflux for 8 hours. The solvent was removed, and the residue was dissolved in methylene chloride which was washed with water. The solvent was removed and the residue was purified by flash chromatography on silica gel, eluting with 100:10:0.5-methylene chloride:methanol:$NH_4OH$ to afford 187.6 mg of the title product as a yellow solid.

Step 281g. 3(R)-10-(3-(N-BOC)amino-1-pyrrolidinyl)-9-fluoro-3-methyl-2H,3H,6H-6-oxo-pyrano[2.3.4-ij]quinolizine-5-carboxylic acid A 187.6 mg (0.394 mmol) sample of 3(R)-10-(3-(N-BOC)amino-1-pyrrolidinyl)-9-fluoro-3-methyl-2H,3H,6H-6-oxo-pyrano[2.3.4-ij]quinolizine-5-carboxylic acid, ethyl ester, from step 281f above, was dissolved in 4 mL of THF and 70 mg of $LiOH.H_2O$ in 2 mL of water was added. The mixture was stirred under $N_2$ for 8 hours at 60° C. The pH was adjusted to 6.5 with 1N HCl, and the mixture was extracted wtih methylene chloride. The extract was washed with water, dried over $MgSO_4$ and concentrated. The residue was purified by flash chromatography on silica gel, eluting with 100:10:1 methylene chloride:methanol:acetic acid to afford 144 mg of the title product as a yellow solid. MS: 448 $(M+H)^+$. IR (KBr): 3440, 1710, 1640, 1610 $cm^{-1}$. $^1H$ NMR $(CDCl_3)$ ∂: 1.32 (d, 3H, J=7 Hz), 1.47 (s, 9H), 2.00 (m, 1H), 2.18 (m, 1H), 3.11 (m, 1H), 3.85 (m, 1H), 3/987 (m, 2H), 4.10–4.16 (m, 2H), 4.26 (m, 1H), 4.32 (m, 1H), 5.06 (m, 1H), 7.92 (s, 1H), 8.80 (d, 1H, j=10 Hz). Anal calc. for $C_{22}H_{16}FN_3O_6.H_2O$: C, 56.77; H, 6.06; N, 9.03; Found: C, 56.70; H, 5.80; N, 8.81.

Step 281h. 3(R)-10-(3-amino-1-pyrrolidinyl)-9-fluoro-3-methyl-2H,3H,6H-6-oxo-pyrano[2.3.4-ij]quinolizine-5-carboxylic acid hydrochloride A 115.7 mg (0.259 mmol) sample of 3(R)-10-(3-(N-BOC)amino-1-pyrrolidinyl)-9-fluoro-3-methyl-2H,3H,6H-6-oxo-pyrano[2.3.4-ij]quinolizine-5-carboxylic acid, from step 281g above, was dissolved in 3 mL of 4N HCl in dioxane, and the reaction was stirred for 1.5 hours at room temperature. The solution was concentrated to dryness, and the residue was dried in a vacuum. The residue was dissolved in water, filtered though sintered glass, and freeze-dried to give 97.3 mg of the title product as a yellow solid. MS: 348 $(M-Cl)^+$. IR (KBr): 3440, 1690, 1640, 1600 $cm^{-1}$. $^1H$ NMR $(DMSO-d_6)$ ∂: 1.27 (d, 3H, J=7 Hz)), 2.10 (m, 1H), 2.22 (m, 1H), 3.20 (m, 1H), 3.88 (m, 1H), 3.99 (m, 2H), 4.10–4.16 (m, 3H), 4.27 (m, 1H), 7.82 (s, 1H), 8.95 (d, 1H, J=10 Hz). Anal calc. for $C_{17}H_{18}FN_3O_4.0.5H_2O.2HCl$: C, 47.57; H, 4.93; N, 9.79; Found: C, 47.72; H, 4.81; N, 9.58.

Step 281i. 3(R)-10-(3-amino-1-pyrrolidinyl)-9-fluoro-3-methyl-2H,3H,6H-6-oxo-pyrano[2.3.4-ij]quinolizine-5-carboxylic acid A 50 mg sample of the hydrochloride salt from step 281h was dissolved in 5 mL of water, and satd. NaHCO3 was adde until the solution was pH 7. The solid (27.8 mg) was collected by filtration, and the filtrate was extracted with 10% methanol in methylene chloride and methylene chloride. The extract was washed, dried and concentrated to afford a second crop of product. MS: 348 $(M+H)^+$. IR (KBr): 3440, 1650, 1640, 1600 $cm^{31\ 1}$. $^1H$ NMR $(DMSO-d_6)$ ∂: 1.25 (d, 3H, J=7 Hz), 1.68 (m, 1H), 1.95 (m, 1H), 3.16 (m, 1H), 3.55 (m, 2H), 3.94–4.05 (m, 4H), 4.25 (m, 1H), 7.74 (s, 1H), 8.89 (d, 1H, J=11 Hz). Anal calc. for $C_{17}H_{18}FN_3O_4.1.5H_2O$: C, 54.54; H, 5.57; N, 11.23; Found: C, 54.78; H, 5.31; N, 11.05.

EXAMPLE 282

3(R)-10-(3-aminomethyl-1-pyrrolidinyl)-9-fluoro-3-methyl-2H,3H,6H-6-oxo-pyrano[2.3.4-ij]quinolizine-5-carboxylic acid hydrochloride Following the procedure of Example 281f, replacing the the 3-(BOC-amino)pyrrolidine of that step with 3-(BOC-amino)methylpyrrolidine (prepared according to EP Published application 0106489), and carrying the product forward according to steps 281g and h, 118 mg of the title compound was prepared. MS: 362 (M–Cl)$^+$. IR (KBr): 3440, 1640, 1600 cm$^{-1}$. $^1$H NMR (DMSO-d$_6$) $\partial$: 1.25 (d, 3H, J=7 Hz), 1.72 (m, 1H), 2.10 (m, 1H), 2.53 (m, 1H), 2.94 (m, 2H), 3.16 (m, 1H), 3.76 (m, 1H), 3.96 (m, 2H), 4.05 (m, 2H), 4.25 (m, 1H), 7.77 (s, 1H), 8.12 (br, 4H), 8.90 (d, 1H, J=10 Hz), 13.92 (br, 1H). Anal calc. for $C_{18}H_{26}FN_3O_4 \cdot 2HCl$: C, 49.78; H, 5.11; N, 9.68; Found: C, 49.90; H, 5.04; N, 9.74.

EXAMPLE 283

3(R)-10-((2S,4S)-4-amino-2-methyl-1-pyrrolidinyl)-9-fluoro-3-methyl-2H,3H,6H-6-oxo-pyrano[2.3.4-ij]quinolizine-5-carboxylic acid hydrochloride Following the procedure of Example 281f, replacing the the 3-(BOC-amino)pyrrolidine of that step with (2S,4S)-4-BOC-amino-2-methylpyrrolidine (from Example 171, step 5), and carrying the product forward according to steps 281g and h, 57 mg of the title compound was prepared. MS: 362 (M–Cl)$^+$. IR (KBr): 3440, 1700, 1635, 1610 cm$^{-1}$. $^1$H NMR (DMSO-d$_6$) $\partial$: 1.20 (d, 3H, J=6 Hz), 1.28 (d, 3H, J=7 Hz), 1.92 (m, 1H), 2.37 (m, 1H), 3.22 (m, 1H), 3.77 (m, 1H), 3.91 (m, 1H), 4.09 (m, 1H), 4.34 (m, 2H), 4.82 (m, 1H), 7.88 (s, 1H), 8.28 (br, 4H), 9.00 (d, 1H, J=10 Hz), 13.94 (br, 1H). Anal calc. for $C_{18}H_{26}FN_3O_4 \cdot 2HCl$: C, 49.78; H, 5.11; N, 9.68; Found: C, 49.78; H, 5.04; N, 9.73.

EXAMPLE 284

3(R)-9-fluoro-10-(3-hydroxy-1-pyrrolidinyl)-3-methyl-2H,3H,6H-6-oxo-pyrano[2.3.4-ij]quinolizine-5-carboxylic acid Following the procedure of Example 281f, replacing the the 3-(BOC-amino)pyrrolidine of that step with (3-hydroxypyrrolidine (Aldrich Chemical Co.), and carrying the product forward according to step 281g, 69 mg of the title compound was prepared. MS: 349 (M+H)$^+$. $^1$H NMR (DMSO-d$_6$) $\partial$: 1.24, 1.26 (two d, 3H, J=6 Hz), 1.80 (m, 2H), 3.16 (m, 1H), 3.69 (m, 1H), 3.92 (m, 1H), 4.06 (m, 3H), 4.26 (dd, 1H, J=10, 4 Hz), 4.36 (m, 1H), 5.09 (d, 1H, J=3 Hz), 7.76 (s, 1H), 8.90 (d, 1H, J=10 Hz), 13.94 (br, 1H). Anal calc. for $C_{17}H_{17}FN_2O_5$: C, 58.62; H, 4.92; N, 8.04; Found: C, 58.23; H, 4.91; N, 7.81.

EXAMPLE 285

9-fluoro-10-(4-methyl-1-piperazinyl)-2H,3H,6H-6-oxo-pyrano[2.3.4-ij]quinolizine-5-carboxylic acid hydrochloride Step 285a. 9-fluoro-10-(4-methyl-1-piperazinyl)-2H,3H,6H-6-oxo-pyrano[2.3.4-ij]quinolizine-5-carboxylic acid Following the procedure of Example 281f, replacing the the 3-(BOC-amino)pyrrolidine of that step with N-methylpiperazine (Aldrich Chemical Co.), and carrying the product forward according to step 281f and Example 278 step h, 69 mg of the title compound was prepared. MS: 348 (M+H)$^+$. $^1$H NMR (CDCl$_3$) $\partial$: 2.39 (s, 3H), 2.57 (m, 4H), 3.12 (t, 2H, J=6 Hz), 3.60 (m, 4H), 4.40 (t, 2H, J=6 Hz), 8.10 (s, 1H), 8.94 (d, 1H, J=9 Hz), 13.87 (s, 1H). Anal calc. for $C_{17}H_{18}FN_3O_4 \cdot 0.5H_2O$; C, 57.30; H, 5.37; N, 11.79; Found: C, 57.71; H, 5.23; N, 11.41.

Step 285b. 9-fluoro-10-(4-methyl-1-piperazinyl)-2H,3H,6H-6-oxo-pyrano[2.3.4-ij]-quinolizine-5-carboxylic acid hydrochloride Following the procedure of Example 278i, replacing the compound of step 278h with the 9-fluoro-10-(4-methyl-1-piperazinyl)-2H,3H,6H-6-oxo-pyrano[2.3.4-ij]quinolizine-5-carboxylic acid, from step 285a above, the title compound was prepared.

EXAMPLES 286–296

Following the procedures of Steps 253j, 253k and 253l (if required), above, replacing the 3-BOC-aminopyrrolidine of Step 253j with the reagent shown, the compounds of Examples 286–296 are prepared as shown in Table 11, below.

TABLE 11

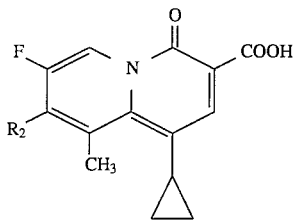

| Ex. No. | Reagent | R² |
|---|---|---|
| 286 | 1,3-dimethylpiperazine | 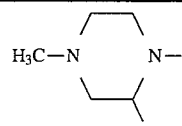 |

TABLE 11-continued
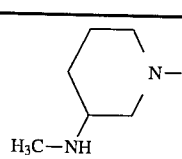
| Ex. No. | Reagent | R² |
|---|---|---|
| 287 | 3-(N—BOC—N-methyl)aminopiperidine | 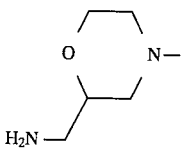 |
| 288 | 2-(N—BOC-aminomethyl)morpholine | 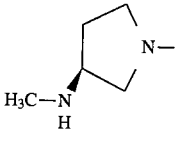 |
| 289 | 3(S)-(N—BOC—N-methylamino)-pyrrolidine | 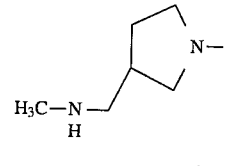 |
| 290 | 3-((N—BOC—N-methylamino)methyl)-pyrrolidine | 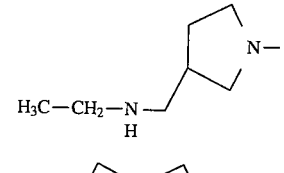 |
| 291 | 3-((N—BOC—N-ethylamino)methyl)-prrolidine | 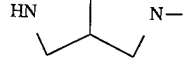 |
| 292 | 2-BOC-octahydropyrrolo[3,4-c]pyrrole | 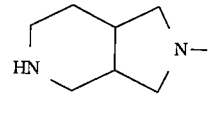 |
| 293 | 5-BOC-octahydropyrrolo[3,4-c]pyridine | 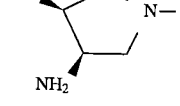 |
| 294 | cis-3-BOC-amino-4-methylpyrrolidine | 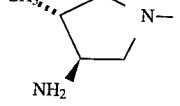 |
| 295 | trans-3-BOC-amino-4-methylpyrrolidine |  |

TABLE 11-continued

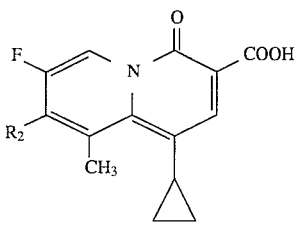

| Ex. No. | Reagent | R² |
|---|---|---|
| 296 | 7-amino-5-azaspiro[2.4]heptane | 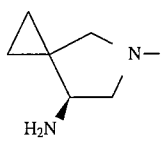 |

EXAMPLE 297

8-(2S,4S-4-amino-2-methylpyrrolidinyl)-1-cyclopropyl-7-fluoro-9-(fluoro)methyl-4-oxo-4H-quinolizine-3-carboxylic acid hydrochloride Following the procedure of Example 253c, reacting the product of Step 253b with LDA at −78° C., then adding formaldehyde and stirring until the reaction is complete, followed by reaction of the newly formed intermediate with diethylaminosulfur trifluoride (DAST) in methylene chloride to form the intermediate product 4-t-butoxy-2,3,6-trifluoro-5-(fluoro)methylpyridine, and carrying this product through the remaining steps as in Example 253d–1, the title compound is prepared.

EXAMPLE 298

8-(3-Dimethylaminopyrrolidinyl)-1-cyclopropyl-7-fluoro-9-methyl-4-oxo-4H-quinolizine-3-carboxylic acid, acetic acid salt A 81 mg sample of 8-chloro-1-cyclopropyl-7-fluoro-9-methyl-4-oxo-4H-quinolizine-3-carboxylic acid ethyl ester, from Example 253i above, was dissolved in 2.5 mL of dry pyridine under a nitrogen atmosphere. To this solution was added a solution of 114 g of 3-(dimethylamino)pyrrolidine in 2.5 mL of pyridine, and the reaction mixture was heated at 60° C. for 39 hours. The pyridine was removed under vacuum, and the residue was stirred with 1N NaOH in THF/water for at 60° C. for 6 hours. The solution was made acidic with acetic acid, and the product was extracted with chloroform. After drying over $MgSO_4$, the solvent was removed, and the residue was purified by chromatography on silica gel, eluting with 100:40:20:8 chloroform: methanol: acetic acid:water to give the title product. mp 165°–170° C. (dec.). MS 374 (M+H)⁺; ¹H NMR ($D_6$-DMSO) ∂: 0.53 (m, 2H), 0.82–1.08 (m, 2H), 1.75 (s, 3H), 2.22 (s, 6H), 2.08–2.33 (m, 2H), 2.74 (m, 2H), 3.44–3.94 (m, 5H), 8.01 (br s, 1H), 8.90 (br s, 1H).

EXAMPLE 299

(3R)-8-(3-Dimethylaminopyrrolidinyl)-1-cyclopropyl-7-fluoro-9-methyl-4-oxo-4H-quinolizine-3-carboxylic acid hydrochloride Following the procedure of Example 298, replacing the 3-(dimethylamino)pyrrolidine with (3R)-3-(dimethylamino)pyrrolidine, the title compound was prepared. mp 146°–148° C. MS 374 (M+H)⁺; ¹H NMR ($D_6$-DMSO) ∂: 0.64 (m, 2H), 1.02 (m, 2H), 2.23–243 (m, 3H), 2.66 (s, 3H), 2.83 (s, 6H), 3.78–4.17 (m, 5H), 7.95 (s, 1H), 9.12 (d, 1H, J=11 Hz), 11.14 (br s, 1H), 13.83 (br s, 1H).

EXAMPLE 300

(3R, 1S)-8-(3-(1-Aminoethyl)pyrrolidinyl)-1-cyclopropyl-7-fluoro-9-methyl-4-oxo-4-oxo-4H-quinolizine-3-carboxylic acid hydrochloride A sample of 8-chloro-1-cyclopropyl-7-fluoro-9-methyl-4-oxo-4H-quinolizine-3-carboxylic acid ethyl ester, from Example 253i above, was dissolved in anhydrous acetonitrile, reacted with (3R,1S)-3-(1-(t-butoxycarbonylamino)ethyl)pyrrolidine (prepared as described by Schroeder et at., *J. Heterocyclic Chem.*, 29:1481–1498 (1992)), and carried forward as described in Example 253k–1 to give the title product. mp 250°–255° C. (dec.). MS 374 (M+H)⁺; ¹H NMR ($D_6$-DMSO) ∂: 0.59 (m, 2H), 1.00 (m, 2H), 1.29 (d, 3H, J=6 Hz), 1.77 (m, 1H), 2.13 (m, 1H), 2.29 (m, 1H), 2.41 (m, 1H), 2.64 (s, 3H, 3.57 (s, 1H), 3.76 (m, 3H), 3.94 (m, 1H), 7.91 (s, 1H), 8.17 (brs, 3H), 9.07 (d, 1H, J=11 Hz), 13.83 (brs, 1H).

EXAMPLE 301

(3S, 1R)-8-(3-(1-Aminoethyl)pyrrolidinyl)-1-cyclopropyl-7-fluoro-9-methyl-4-oxo-4H-quinolizine-3-carboxylic acid hydrochloride A 0.44 g sample of 8-chloro-1-cyclopropyl-7-fluoro-9-methyl-4-oxo-4H-quinolizine-3-carboxylic acid ethyl ester, from Example 253i above, and 1.51 g of $NaHCO_3$ were dissolved in 40 mL of anhydrous acetonitrile, reacted with (3S,1R)-3-(1-(t-butoxycarbonylamino)ethyl)pyrrolidine (1.06 g, prepared as described by Schroeder et al., *J. Heterocyclic Chem.*, 29:1481–1498 (1992)), and carried forward as described in Example 253k–1 to give the title product. mp 235°–240° C. (dec.). MS 374 (M+H)⁺; ¹H NMR ($D_6$-DMSO) ∂: 0.59 (m, 2H), 1.00 (m, 2H), 1.29 (d, 3H, J=6 Hz), 1.76 (m, 1H), 2.13 (m, 1H), 2.28 (m, 1H), 2.41 (m, 1H), 2.63 (s, 3H), 3.30 (m, 1H), 3.74 (m, 3H), 3.94 (m, 1H), 7.90 (s, 1H), 8.16 (br s, 3H), 9.07 (d, 1H, J=11 Hz).

EXAMPLE 302

(3R,1R)-8-(3-(1-Aminoethyl)pyrrolidinyl)-1-cyclopropyl-7-fluoro-9-methyl-4-oxo-4H-quinolizine-3-carboxylic acid hydrochloride A 0.35 g sample of 8-chloro-1-cyclopropyl-7-fluoro-9-methyl-4-oxo-4H-quinolizine-3-carboxylic acid ethyl ester, from Example 253i above, and 0.73 g of sodium bicarbonate were dissolved in 24 mL of anhydrous acetonitrile, reacted with (3R, 1R)-3-(1-(t-butoxycarbonylamino)ethyl -pyrrolidine (0.51 g, prepared as described by Schroeder et al., *J. Heterocyclic Chem.*, 29:1481–1498 (1992)), and carried forward as described in Example 253k-1 to give the title product. mp 220°–222° C. MS 374 (M+H)$^+$; $^1$H NMR (D$_6$-DMSO) ∂: 0.61 (m, 2H), 0.94 (m, 1H), 1.07 (m, 1H), 1.28 (d, 3H, J=6 Hz), 1.82 (m, 1H) 2.27 (m, 2H), 2.46 (m, 1H), 2.62 (s, 3H), 3.57 (s, 1H), 3.92 (m, 1H), 7.90 (s, 1H), 8.17 (br s, 3H), 9.07 (d, 1H, J=11 Hz), 13.84 (brs, 1H).

EXAMPLE 303

1-cyclopropyl-8-((R,S)-3-fluoropyrrolidine)-7-fluoro-9-methyl-4-oxo-4H-quinolizine-3-carboxylic acid 303a. N-CBZ-(R,S)-3-hydroxypyrrolidine (R,S)-3-hydroxypyrrolidine (1.0 g, 0.011 mmol) was dissolved in ethyl acetate (50 mL) and to this solution at room temperature was added N-(benzyloxycarbonyl)succinimide (2.86 g, 0.011 mmol). The mixture was stirred overnight then partitioned between dilute aqueous HCl and ethyl acetate. The aqueous phase was extracted with ethyl acetate (2×). The organics were combined, dried (MgSO$_4$) and concentrated in vacuo. The crude product was purified by flash chromatography on silica gel (ethyl acetate-hexane) to give the desired compound as a clear oil, 2.1 g, 83%. MS (DCI/NH$_3$) m/z: 222 (M+H)$^+$, 239 (M+NH$_4$)$^4$ $^1$H NMR (CDCl$_3$) ∂: 1.85–2.10 (m, 2H), 3.37–3.65 (m, 4H), 4.44–455 (m, 1H), 5.15 (s,2H), 7.28–7.45 (m, 5H).

303b. N-CBZ-(R,S)-3-fluoropyrrolidine

The compound from step 303a above (32.01 gm, 9.10 mmole) was dissolved in anhydrous CH$_2$Cl$_2$ (40 mL) and cooled under nitrogen to −78° C. To the cold solution was added in one portion via syringe diethylaminosulfur trifluoride (DAST) (1.32 mL, 10.0 mmol), and the resulting solution was stirred overnight at room temperature. The product was isolated by concentrating the reaction mixture in vacuo with flash chromatography of the residue on silica gel(ethyl acetate-hexane) to give a clear oil, 1.53gm, 75%. MS (DCI/NH$_3$) m/z: 224 (M+H)$^+$, 241 (M+NH$_4$)$^+$ $^1$H NMR (CDCl$_3$) ∂: 1.83–2.15 (m, 1H), 216–2.35 (m, 1H), 3.43–3.90 (m, 4H), 5.21–5.24 (m, 2.5H) 5.28–5.36, (m, 0.5H), 7.28–7.5 (m5H).

303c. (R,S)-3-fluoropyrrolidine hydrochloride

The compound from step 303b above (1.53 g, 6.85 mmol) was dissolved in methanol (50 mL) to which was added 5% Pd/BaSO$_4$ (0.5g). The mixture was vacuum degassed (3×) then exposed to a low pressure atmosphere of hydrogen (balloon) at room temperature for 4 hours. The reaction was terminated by vacuum filtration to remove catalyst. The filtrate was cooled in an ice bath, then HCl gas was bubbled into the cold solution for one minute. The resulting solution was concentrated in vacuo, and the residue was triturated with ethyl acetate-ether. The solid was collected by vacuum filtration to give 0.659 g, 76%, of the hydrochloride as an off white solid. $^1$HNMR (CD$_3$OD) d: 2.1–2.46 (m, 2H), 3.33–3.65 (m, 4H), 5.43 (db.t, 1H, J$_{F,H}$=51 Hz).

303d. 1-cyclopropyl-8-((R,S)-3-fluoropyrrolidine)-7-fluoro-9-methyl-4-oxo-4H-quinolizine-3-carboxylic acid The N-boc-3-aminopyrrolidine of Example 253j above was replaced by the (R,S)-3-fluoro pyrrolidine hydrochloride of step 303c above (0.66 g, 5.24 mmol), and the reaction product was carried forward as previously described to give 0.326 g (65%) of the title compound as a bright yellow solid. mp 227.5°–230° C. (dec.). MS (DCI/NH$_3$) m/z: 349 (M+H)$^+$. $^1$H NMR(CDCl$_3$) d: 0.58–0.78 (cm, 2H), 0.85–0.98, (cm, 1H) 1.04–1.16 (cm, 1H), 2.03–2.53 (cm, 3H), 2.67 (s,3H), 3.60–3.86 (cm, 2H), 4.05–4.26 (cm, 2H), 5.43 (db.t, 1H, J$_{F,H}$=52 Hz), 7.26 (s, 1H), 8.26 (s, 1H), 8.26 (s, 1H), 9.08 (d, 1H, J=10.5 Hz), 13.8 (br.s., 1H). Calc. for C$_{18}$H$_{18}$N$_2$O$_3$F$_2$: % C, 62.05; H, 5.22; N, 8.04. Found: % C, 62.06; H 5.22; N, 7.86.

EXAMPLE 304

8-(4-(1-piperidyl)-1-piperidyl)-1-cyclopropyl-7-fluoro-9-methyl-4-oxo-4H-quinolizine-3-carboxylic acid A 70 mg sample of 8-chloro-1-cyclopropyl-7-fluoro-9-methyl-4-oxo-4H-quinolizine-3-carboxylic acid ethyl ester, from Example 253i above, was dissolved in 2 mL of anhydrous acetonitrile, reacted with 4-(1-piperidyl)piperidine (70 mg, 0.4 mmol, Aldrich Chem. Co.), and carried forward as described in Example 253j–k to give the title product. MS 428 (M+H)$^+$; $^1$H NMR (CDCl$_3$) ∂: 0.69 (m, 2H), 1.02 (m, 2H), 1.18 (m, 4H), 2.27 (n, 1H), 2.78 (s, 3H), 2.72 (m, 1H), 3.35 (m, 3H), 3.55 (m, 1H), 3.75 (m, 1H), 8.36 (s, 1H), 9.20 (d, 1H). Anal. Calcd for C$_{24}$H$_{30}$N$_3$O$_3$F.1.5 H$_2$O: C, 63.42; H, 7.32; N, 9.24; Found: C, 62.99; H, 7.04; N, 8.78.

EXAMPLE 305

8-(4-(1-piperidyl)-1-piperidyl)-1-cyclopropyl-7-fluoro-9-methyl-4-oxo-4H-quinolizine-3-carboxylic acid trifluoroacetic acid salt A 100 mg sample of 8-chloro-1-cyclopropyl-7-fluoro-9-methyl-4-oxo-4H-quinolizine-3-carboxylic acid ethyl ester, from Example 253i above, was dissolved in 3 mL of anhydrous acetonitrile, reacted with 4-(4-piperidyl)-piperidine (0.24 g, 0.93 mmol, obtained from Aldrich Chem. Co.), carried forward as described in Example 253j–k and converted to the TFA salt by the procedure of Example 162 to give the title product. MS 428 (M+H)$^+$; $^1$H NMR (CDCl$_3$) ∂: 0.69 (m, 2H), 1.03 (m, 2H), 1.70 (m, 2H), 1.87 (m, 2H), 1.98 (m, 2H), 2.14 (m, 2H), 2.27 (m, 1H), 2.77 (s, 3H), 2.91 (m, 2H), 3.33 (m, 2H), 3.54 (m, 4H), 8.37 (s, 1H), 9.21 (d, 1H). Anal. Calcd for C$_{24}$H$_{30}$N$_3$O$_5$F$_4$.1.5 H$_2$O: C, 54.93; H, 6.03; N, 7.39; Found: C, 54.97; H, 5.39; N, 7.24.

EXAMPLE 306

8-(4-(2-pyridyl)-1-piperazinyl)-1-cyclopropyl-7-fluoro-9-methyl-4-oxo-4H-quinolizine-3-carboxylic acid A 60 mg sample of 8-chloro-1-cyclopropyl-7-fluoro-9-methyl-4-oxo-4H-quinolizine-3-carboxylic acid ethyl ester, from Example 253i above, was dissolved in 2 mL of anhydrous acetonitrile, reacted with 4-(2-pyridyl)piperazine (63.5 mg, 0.39 mmol, Aldrich Chem. Co.), and carried forward as described in Example 253j-k to give the title product. MS 423 (M+H)+; 1H NMR (CDCl3) ∂: 0.71 (m, 2H), 1.05 (m, 2H), 2.30 (m, 1H), 2.86 (s, 3H), 3.59 (m, 4H), 3.78 (m, 4H), 6.76 (m, 2H), 7.57 (m, 1H), 8.25 (m, 1H), 8.40 (s, 1H), 8.25 (d, 1H), 13,83 (bs, 1H). Anal. Calcd for $C_{23}H_{23}N_4O_3F.1.5 H_2O$: C, 61.46; H, 5.83; N, 12.46; Found: C, 61.76; H, 5.54; N, 11.64.

EXAMPLE 307

8-((2-amino)thioethoxy)-1-cyclopropyl-7-fluoro-9-methyl-4-oxo-4H-quinolizine-3-carboxylic acid trifluoroacetic acid salt A 50 mg sample of 8-chloro-1-cyclopropyl-7-fluoro-9-methyl-4-oxo-4H-quinolizine-3-carboxylic acid ethyl ester, from Example 253i above, was dissolved in 2 mL of anhydrous acetonitrile, reacted with N-BOC-2-aminothiol (57.4 mg, 0.32 mmol, prepared by standard procedures from the unprotected compound obtained from Aldrich Chem. Co.), carried forward as described in Example 253j-k, deprotected as in step 253l, and converted to the TFA salt by the procedure of Example 162 to give the title product. MS 337 (M+H)+; 1H NMR (d6-DMSO) ∂: 0.74 (m, 2H), 1.08 (m, 2H), 3.04 (t, 2H), 3.16 (s, 3H), 3.33 (t, 2H), 8.27 (s, 1H), 9.32 (d, 1H), 13.8 (br, 1H).

EXAMPLE 308

(3R,1S)-8-(3-(1-amino)propyl)pyrrolidinyl)-1-cyclopropyl-7-fluoro-9-methyl-4-oxo-4H-quinolizine-3-carboxylic acid hydrochloride A 147 mg sample of 8-chloro-1-cyclopropyl-7-fluoro-9-methyl-4-oxo-4H-quinolizine-3-carboxylic acid ethyl ester, from Example 253i above, was dissolved in 3 mL of anhydrous acetonitrile, reacted with (3R,1S)-3-(1-BOC-amino)propyl)pyrrolidine (326 mg, 1.13 mmol, prepared as described by Hayakawa et al., U.S. Pat. No. 5,098,912, issued Mar. 24, 1992, using modifications for chiral products described by Plummer et al. *Tetr. Lett.* 34:7529-32 (1993)), and carried forward as described in Example 253j-l to give the title product. MS (high resolution) found: 388.2039; calc: 388.2036 (M+H)+; 1H NMR (D6-DMSO) ∂: 0.60 (m, 2H), 1.00 (t, 3H), 1.01 (m, 2H), 1.63 (m, 2H), 2.13 (m, 1H), 2.29 (m, 2H), 3.73 (m, 3H), 3.95 (m, 1H), 7.96 (s, 1H), 8.00 (b m, 2H), 9.08 (d, 1H), 13.83 (b s, 1H). Anal. Calcd for $C_{21}H_{27}N_3O_3FCl.0.5 H_2O$: C, 58.13; H, 6.74; N, 9.68; Found: C, 58.24; H, 6.51; N, 9.71.

EXAMPLE 309

(3R,1S)-8-(3-(1-(N-methy)amino)propyl) pyrrolidinyl)-1-cyclopropyl-7-fluoro-9-methyl-4-oxo-4H-quinolizine-3-carboxylic acid hydrochloride A 492.9 mg sample of 8-chloro-1-cyclopropyl-7-fluoro-9-methyl-4-oxo-4H-quinolizine-3-carboxylic acid ethyl ester, from Example 253i above, was dissolved in 8 mL of anhydrous acetonitrile, reacted with (3R,1S)-3-(1-(N-methyl)amino)propyl)pyrrolidine (501 mg, 3.53 mmol, prepared as described by Hayakawa et al., U.S. Pat. No. 5,098,912, issued Mar. 24, 1992, using modifications for chiral products described by Plummer et al. *Tetr. Lett.* 34:7529-32 (1993)), and carried forward as described in Example 253 j-l, omitting the deprotecting step, to give the title product. MS 402 (M+H)+; 1H NMR (D6-DMSO) ∂: 0.61 (m, 2H), 0.98 (t, 3H), 1.00 (m, 2H), 1.75 (m, 5H), 2.15 (m, 1H), 2.30 (m, 1H), 2.59 (s, 3H), 2.63 (s, 3H), 3.66 (m, 1H), 3.77 (m, 2H), 3.95 (m, 1H), 7.90 (s, 1H), 8.60 (bs, 2H), 9.08 (d, 1H), 13.83 (bs, 1H) Anal. Calcd for $C_{22}H_{29}N_3O_3FCl.H_2O$: C, 57.95; H, 6.85; N, 9.22; Found: C, 58.24; H, 6.58; N, 9.30.

EXAMPLE 310

(3R,1S)-8-(3-(1-amino-3-methylpropyl) pyrrolidinyl)-1-cyclopropyl-7-fluoro-9-methyl-4-oxo-4H-quinolizine-3-carboxylic acid hydrochloride A 171 mg sample of 8-chloro-1-cyclopropyl-7-fluoro-9-methyl-4-oxo-4H-quinolizine-3-carboxylic acid ethyl ester, from Example 253i above, was dissolved in 4 mL of anhydrous acetonitrile, reacted with (3R,1S)-3-(1-amino-3-methylpropyl)pyrrolidine (400 mg, 1.32 mmol, prepared as described by Plummer et al., *Tetr. Lett.* 34:7529-32 (1993)), and carried forward as described in Example 253j-l, omitting the deprotection reaction, to give the title product. MS (high resolution) found: 402.2174; calc: 402.2193 (M+H)+; 1H NMR (D6-DMSO) ∂: 0.60 (m, 2H), 0.95 (d, 3H), 1.06 (d, 3H), 1.75 (m, 1H), 2.13 (m, 1H), 229 (m, 2H), 2.50 (s, 3H), 3.66 (m, 3H), 3.78 (m, 1H), 3.97 (m, 1H), 7.88 (s, 1H), 908 (d, 1H), 13.82 (bs, 1H). Anal. Calcd for $C_{22}H_{29}N_3O_3FCl.0.75 H_2O$: C, 58.53; H, 6.81; N, 9.31; Found: C, 58.88; H, 6.70; N, 9.26.

EXAMPLE 311

8-(3-(1-aminocyclopropyl)pyrrolidinyl)-1-cyclopropyl-7-fluoro-9-methyl-4-oxo-4H-quinolizine3-carboxylic acid hydrochloride A 98 mg sample of 8-chloro-1-cyclopropyl-7-fluoro-9-methyl-4-oxo-4H-quinolizine-3-carboxylic acid ethyl ester, from Example 253i above, was dissolved in 2 mL of anhydrous acetonitrile, reacted with 1-(N-BOC-amino)cyclopropyl)pyrrolidine (172 mg, 0.76 mmol, prepared as described by Hayakawa et al., U.S. Pat. No. 5,098,912, issued Mar. 24, 1992), and carried forward as described in Example 253j-l to give the title product. MS (high resolution) found: 386.1893; calc: 386.1880 (M+H)+; 1H NMR (D6-DMSO) ∂: 0.60 (m, 2H), 0.91 (m, 5H), 1.04 (m, 1H), 1.67 (m, 1H), 2.04 (m, 1H), 2.29 (m, 2H), 2.61 (s, 3H), 370 (m, 3H), 3.93 (m, 1H), 7.90 (s, 1H), 8.43 (bs, 2H), 9.08 (d, 1H), 13.82 (s, 1H). Anal. Calcd for $C_{22}H_{29}N_3O_3FCl$: C, 59.55; H, 6.12; N, 9.80; Found: C, 59.78; H, 5.97; N, 9.69.

EXAMPLE 312

(3R,1S)-8-(3-(1-amino-2-hydroxyethyl) pyrrolidinyl)-1-cyclopropyl-7-fluoro-9-methyl-4-oxo-4H-quinolizine-3-carboxylic acid hydrochloride Step 312a. (S)-N-BOC-O-(methoxymethyl)serine methyl ester A 7 g (31.96 mmol) sample of ((S)-N-BOC-serine methyl ester (obtained from Aldrich) was dissolved in $CH_2Cl_2$ and cooled in an ice bath. To this stirred solution was added dropwise 2.83 g (35.16 mmol) of methoxymethyl chloride, followed by dropwise addition of 4.544 g (6.12 mL, 35.16 mmol) of diisopropylethylamine. After all reagents were added the reaction was stirred for 16 hours at room temperature. The solution was washed with 0.5% HCl, satd.

NaHCO$_3$, H$_2$O, and brine, dried over MgSO$_4$ and filtered. The solvent was removed to leave a yellow oil. The residue was purified by chromatography on silica gel, eluting with 15–20% ethyl acetate:hexane to afford 6 g of title product after removal of the solvent. MS 264 (M+H)$^+$; $^1$H NMR (CDCl$_3$) ∂: 1.47 (s, 9H), 3.31 (s, 3H), 3.74 (dd, 1H), 3.79 (s, 3H), 4.00 (dd, 1H), 4/45 (b M, 1H), 4.60 (s, 2H), 5.43 (b m, 1H).

Step 312b. 2-(BOC-amino)-3-(methoxymethoxy)-1-propanol

A solution of the compound from step 312a above (5.202 g, 19.78 mmol) in 15 mL of THF was added dropwise to a cooled (ice bath) suspension of 570 mg (14.84 mmol) of LAH in 15 mL of THF under N$_2$ atmosphere. The mixture was stirred for 1.5 hours, the reaction was quenched with water and 50% NaOH, filtered, and the filtrate evaporated to obtain the crude product. A yellow oil was obtained, which was purified by chromatography on silica gel, eluting with 35–40% ethyl acetate:hexane to give 3.475 g of the title product as a colorless oil. MS 236 (M+H)$^+$.

Step 312c. 2-(BOC-amino)-3-(methoxymethoxy)-1-propanal

To a solution of the compound from step 312b above (3.47 g, 14.77 mmol) in 7 mL of DMSO cooled to 0° C. was added dropwise 6.8 mL (48.74 mmol) of triethylamine. Pyridine.SO$_3$ complex (7.05 g, 44.31 mmol) was dissolved in 27 mL of DMSO and added to the first solution, and the reaction was stirred for one hour after the addition was complete. The solution was poured into 120 mL of cold brine, and the mixture was washed 3× with ethyl acetate. The extract was washed with water, dried over MgSO4, filtered and the solvent was removed under vacuum to give 6 g of a yellow oil, which was taken directly to the next step.

Step 312d. 4-(BOC-amino)-5-(methoxymethoxy)-2-pentenoic acid ethyl ester

To a solution of the compound from step 312c above (14.77 mmol) in 42 mL of CH$_2$Cl$_2$ and cooled in an ice bath was added dropwise 5.454 g (15.66 mmol) of (carboethoxymethylene)triphenylphosphorane in 56 mL of CH$_2$Cl$_2$. After addition was complete, the reaction was stirred for 16 hours at room temperature. The solvent was removed, and the residue purified by column chromatography on silica gel, eluting with 10% ethyl acetate:hexane, to give 2.763 g of a colorless oil. MS 304 (M+H)$^+$; $^1$H NMR (CDCl$_3$) ∂: 1.25 (t, 3H), 1.47 (s, 9H), 3.36 (s, 3H), 3.67 (dd, 1H), 3.73 (dd, 1H), 3.72 (m, 1H), 4.20 (q, 2H), 4.62 (s, 2H), 5.99 (dd, 1H), 6.93 (dd, 1H).

Step 312e. 4-(BOC-amino)-5-(methoxymethoxy)-3-(nitromethyl)-pentanoic acid ethyl ester To a solution of the compound from step 312d above (2.76 g, 9.71 mmol) in 8 mL of nitromethane cooled in an ice bath was added 7 mL (6.934 g, 45.55 mmol) of 1,8-diazabicyclo[5.4.0]undec-7-ene dropwise under N$_2$. The mixture was warmed to room temperature and stirred for 16 hours. The solution was diluted with CH$_2$Cl$_2$ and extracted with water, 10% HCl, 10% NaHCO$_3$, water and brine. The solution was dried over MgSO4, and the solvent was removed. The residue was chromatographed on silica gel, eluting with 10–15% ethyl acetate:hexane, and the solvent was removed to give 2.01 g of the title product as a white solid. MS 365 (M+H)$^+$; $^1$H NMR (CDCl$_3$) ∂: 1.27 (t, 3H), 1.47 (s, 9H), 2.46 (dd, 1H), 2.98 (br, 1H), 3.38 (s, 3H), 3.58 (ddd, 1H), 3.76 (dd, 1H), 3.97 (b m, 1H), 4.16 (q, 1H), 4.53 (dd, 1H), 4.62 (s, 2H), 4.67 (dd, 1H), 4.99 (b d, 1H).

Step 312f. 4-(BOC-amino)-5-(methoxymethoxy)-3-(aminomethyl)-pentanoic acid ethyl ester Two g of the compound from step 312e above was dissolved in 200 mL of ethanol and hydrogenated at 4 Atm over 4 g of Raney nickel catalyst for 24 hours. The catalyst was removed by filtration and the solvent was evaporated. The residue was taken directly to the next step.

Step 312g. N-BOC-2-(methoxymethoxy)-1-(5-oxo-3-pyrrolidinyl)-ethylamine

The residue from step 312f above was dissolved in 150 mL of ethanol and heated at reflux for 8 hours. The solvent was removed, the residue was chromatographed on silica gel, eluting with 4% methanol/methylene chloride. Removal of the solvent gave 1.36 g of title product. MS 289 (M+H)$^+$; $^1$H NMR (CDCl$_3$) δ: 1.47 (t, 3H), 2.17 (dd, 1H), 2.38 (dd, 1H), 2.78 (m, 1H), 3.31 (t, 1H), 3.46 (s, 3H), 3.46 (t, 1H), 3.59 (m, 2H), 3.81 (b t, 1H), 4.62 (s, 2H), 4.94 (br d, 1H), 5.43 (br, 1H).

Step 312h. N-BOC-2-(methoxymethoxy)-1-(5-thioxo-3-pyrrolidinyl)-ethylamine

A 500 mg (1.74 mmol) sample of the compound from step 312g above and 387 mg (0.957 mmol) of Lawesson's reagent were dissolved in 4 mL of THF and stirred under N$_2$ for 3 hours. The solvent was removed, and the residue was dissolved in CH$_2$Cl$_2$ and chromatographed on silica gel, eluting with 35% ethyl acetate:hexane. Removal of the solvent left 500 mg of product. MS 305 (M+H)$^+$; $^1$H NMR (CDCl$_3$) δ: 1.47 (s, 9H), 2.71 (dd, 1H), 2.89 (m, 1H), 3.00 (dd, 1H), 3.37 (s, 3H), 3.53 (dd, 2H), 3.66 (m, 2H), 3.83 (b m, 1H), 4.61 (s, 2H), 4.98 (b d, 1H).

Step 312i. N-BOC-2-(methoxymethoxy)-3-pyrrolidinyl)-ethylamine acetic acid salt

A 250 mg (0.825 mmol) sample of the compound from step 312h above and 1.57 g (6.6 mmol) of NiCl2.6H$_2$O were dissolved in 10 mL of a 1:1 mixture of methanol and THF, and the solution was cooled to −78° C. and stirred under N$_2$. A 749 mg (19.8 mmol) sample of NaBH$_4$ was added in portions, and the mixture was stirred for 2 hours. The solvents were removed under vacuum, and dissolved in 20% methanol in chloroform. The solution was filters and the solvent removed. The residue was chromatographed on silica gel, eluting with 1:1:1:1 n-butanol:ethyl acetate:H$_2$O:acetic acid to provide 349 mg of title product. MS 275 (M+H)$^+$; $^1$H NMR (D$_2$O) δ: 1.44 (s, 9H), 3.03 (m, 1H), 3.30 (m, 1H), 3.40 (s, 3H), 3.48 (m, 1H), 3.60 (t, 2H), 3.75 (m, 1H).

Step 312j. (3R,1S)-8-(3-(1-amino-2-hydroxyethyl)pyrrolidinyl)-1-cyclopropyl-7-fluoro-9-methyl-4-oxo-4H-quinolizine-3-carboxylic acid hydrochloride A 107 mg (0.33 mmol) sample of 8-chloro-1-cyclopropyl-7-fluoro-9-methyl-4-oxo-4H-quinolizine-3-carboxylic acid ethyl ester, from Example 253i above, was dissolved in 2.5 mL of anhydrous acetonitrile, reacted with the compound from step 3 12i above (0.825 mmol), and carded forward as described in Example 253j-1 to give 74 mg of the title product. $^1$H NMR (D$_6$-DMSO) δ: 0.60 (m, 2H), 0.94 (m, 1H), 1.05 (m, 1H), 1.78 (m, 1H), 2.05 (m, 1H), 2.19 (m, 2H), 2.60 (s, 3H), 3.57 (m, 1H), 3.73 (m, 3H), 3.92 (m, 1H), 5.41 (m, 1H), 7.91 (s, 1H), 9.09 (d, 1H), 13.83 (br s, 1H).

EXAMPLE 313

(8-(3-(1-amino-1-methylethyl)pyrrolidinyl)-1-cyclopropyl-7-fluoro-9-methyl-4-oxo-4H-quinolizine-3-carboxylic acid hydrochloride A 150 mg sample of 8-chloro-1-cyclopropyl-7-fluoro-9-methyl-4-oxo-4H-quinolizine-3-carboxylic acid ethyl ester, from Example 253i above, was dissolved in 2 mL of anhydrous acetonitrile, reacted with 1-amino-1-methylethyl)pyrrolidine (155 mg, 0.77 mmol, prepared by standard method from the free base described by Hayakawa et al., U.S. Pat. No. 5,098,912, issued Mar. 24, 1992), and carded forward as described in Example 253k-1 to give the title product. MS (high resolution) found: 388.2047; calc: 388.2036 (M+H)$^+$; $^1$H NMR (D$_6$-DMSO) δ:0.60 (m, 2H), 0.94 (m, 1H), 1.07 (m, 1H), 1.33 (s, 3H), 1.34 (s, 1H), 2.83 (m, 1H), 2.07 (m, 1H), 2.19 (m, 2H), 2.63 (s, 3H), 3.60 (b t, 1H), 3.68 (b t, 1H), 3.81 (m, 1H), 3.93 (m, 1H), 7.90 (s, 1H), 8.11 (b s, 1H), 9.08 (d, 1H), 13.83 (b s, 1Calcd for C$_{21}$H$_{27}$N$_3$O$_3$FCl.5 H$_2$O:C, 55.93; H, 6.71; N, 9.32; Found: C, 56.07; H, 6.71; N, 8.95.

EXAMPLE 314

8-(3-(1-aminobutyl)pyrrolidinyl)-1-cyclopropyl-7-fluoro-9-methyl-4-oxo-4H-quinolizine-3-carboxylic acid hydrochloride Step 314a. 4-(BOC-amino)-3-(nitromethyl)-heptanolic acid ethyl ester Following the procedure of Example 312 step b, substituting DL-N-BOC-norvaline methyl ester (prepared from norvaline by standard methods) for the compound of step 312a thereof, and carrying the product forward via the procedures of Example 312 steps c–e, the title compound was prepared.

Step 314b. 4-(BOC-amino)-3-(nitromethyl)-heptanol

Repeating the procedure of example 312 step b, substituting 4-(BOC-amino)-3-(nitromethyl)-heptanoic acid ethyl ester (1.3 g, 3.91 mmol), from step 314a above, for the compound of step 312a thereof, the title compound was prepared. MS 291 (M+H)$^+$; $^1$H NMR (CDCl$_3$) δ:0.93 (t, 3H), 1.45 (s, 9H), 1.48 (m, 5H), 1.77 (m, 1H), 2.53 (m, 1H), 3.79 (m, 3H), 4.33 (m, 1H), 4.38 (dd, 1H), 4.49 (dd, 1H).

Step 314c. 4-(BOC-amino)-(nitromethyl)-heptanol, O-mesityl ether

A 610 mg (2.03 mmol) sample of the compound from step 314c above was dissolved in 2 mL of CH$_2$Cl$_2$, and the solution was cooled to −10° C. To this was added dropwise 289 mg (0.195 mL, 2.52 mmol) of methanesulfonyl chloride and 319 mg (3.15 mmol) of triethylamine. The solution was stirred for 2 hours at 0°–10° C. The solution was diluted with CH$_2$Cl$_2$ and washed, once with water, once with 5% NaHCO$_3$, and once with brine. The solvent was dried over MgSO$_4$ and filtered, and the solvent was removed to give 720 mg of the title product as an oil.

Step 314d. 3-(1-(N-BOC-amino)butyl)pyrrolidine

The 720 mg sample of the product from step 314c was dissolved in 50 mL of methanol and hydrogenated over 360 mg of 10% Pd/C catalyst at 4 Atm and room temperature for 24 hours. MS 2243 (M+H)$^+$; $^1$H NMR (CD$_3$OD) 67 : (0.94 (t, 3H), 1.34 (m, 3H), 1.44 (s, 9H), 1.48 (m, 1H), 1.70 (m, 1H), 2.13 (m, 1H), 2.37 (q, 1H), 3.04 (m, 1H), 3.22 (m, 1H), 6.71 (b d, 1H).

Step 314f. 8-(3-(1-aminobutyl)pyrrolidinyl)-1-cyclopropyl-7-fluoro-9-methyl-4-oxo-4H-quinolizine-3-carboxylic acid hydrochloride A 238 mg sample of 8-chloro-1-cyclopropyl-7-fluoro-9-methyl-4-oxo-4H-quinolizine-3-carboxylic acid ethyl ester, from Example 253i above, was dissolved in 5 mL of anhydrous acetonitrile, reacted with 3-(1-(N-BOC-amino)butyl)pyrrolidine (620 mg, 1.83 mmol, prepared in step 314d above), and carried forward as described in Example 253j-1 to give the title product. MS (high resolution) found: 402.2199; calc: 402.2193 (M+H)$^+$; $^1$H NMR (D$_6$-DMSO) δ:0.60 (m, 2H), 0.89 (m, 4H), 1.05 (m, 1H), 1.49 (m, 5H), 1.17 (m, 1H), 2.14 (m, 1H), 2.27 (m, 1H), 2.62 (s, 3H), 3.77 (m, 4H), 3.94 (m, 1H), 7.89 (s, 1H), 8.54 (b m, 1H), 9.07 (d, 1H), 11.47 (br, 1H).

EXAMPLES 315–323

Following the procedures of Steps 253j, 253k and 253l above, replacing the 3-BOC-aminopyrrolidine of Step 253j with the reagent shown, the compounds of Examples 315–323 are prepared as shown in Table 12, below.

TABLE 12

| Ex. No. | Reagent | R$^2$ |
|---------|---------|-------|
| 315 | BOCNH-[pyrrolidine with CH$_3$S, H] | NH$_2$-[pyrrolidine with CH$_3$S, H] |
| 316 | BOC—NH-[pyrrolidine with CH$_3$S, H] | NH$_2$-[pyrrolidine with CH$_3$S, H] |

TABLE 12-continued
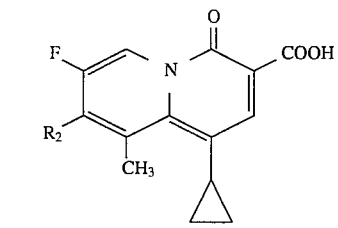
| Ex. No. | Reagent | R² |
|---|---|---|
| 317 | 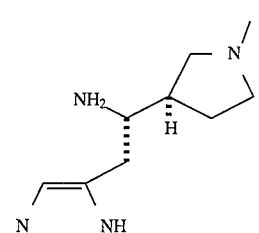 | 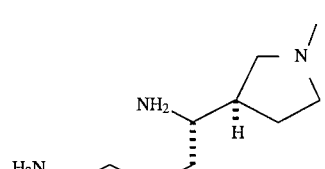 |
| 318 | 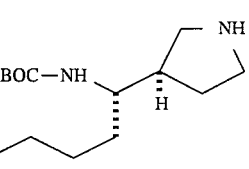 | 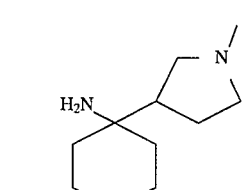 |
| 319 | 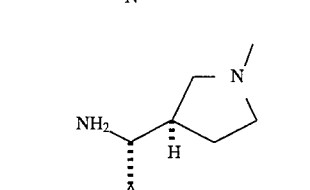 | 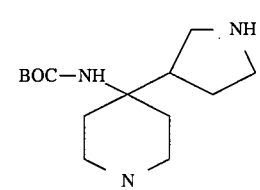 |
| 320 | 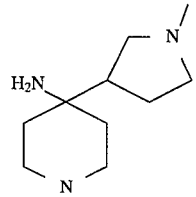 | 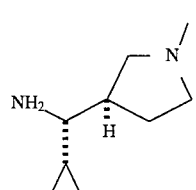 |
| 321 | 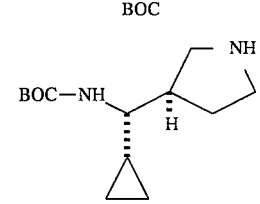 | 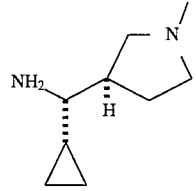 |
| 322 | 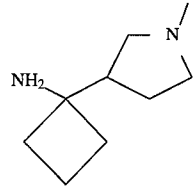 | 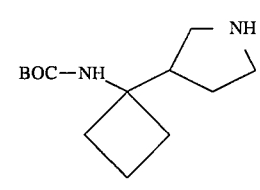 |

TABLE 12-continued

[Structure: quinolizine core with F, R₂, CH₃, cyclopropyl, COOH, and carbonyl substituents]

| Ex. No. | Reagent | R² |
|---|---|---|
| 323 | [BOC—NH-cyclohexyl-pyrrolidine-NH structure] | [NH₂-cyclohexyl-pyrrolidine-N structure] |

EXAMPLE 324

1-cyclopropyl-7-fluoro-9-methyl-4-oxo-8-(trans-4-trifluoromethyl-3-aminopyrrolidinyl)-4H-quinolizine-3-carboxylic acid hydrochloride Step 324a. trans-N-benzyl-4-trifluoromethyl-3-pyrrolidinecarboxylic acid ethyl ester Trifluoroacetic acid (3 mL, 1N in $CH_2Cl_2$) was added to a stirred solution of trans-ethyl trifluorocrotonate (4.969 g) and N-benzyl-N-methoxymethyl)trimethylsilylamine (7.00 g, prepared according to Chem. Pharm. Bull., 33:2762 (1985)) in 30 mL of $CH_2Cl_2$ at 0° C., and the mixture was stirred for 2 hours. After dilution with $CH_2Cl_2$, the solution was washed with satd. $NaHCO_3$ solution and water, dried over $MgSO_4$ and concentrated under vacuum to give a pale yellow liquid (8.75 g).

Step 324b. trans-N-benzyl-4-trifluoromethyl-3-pyrrolidinecarboxylic acid

A sample (4.739 g) of this liquid was hydrolyzed with 1.98 g of $LiOH.H_2O$ in $THF:H_2O$ (25 mL, 1.5:1) at 60° C. to give after workup 3.64 g of the intermediate as a solid.

Step 324c. trans-1-benzyl-3-(BOC-amino)-4-trifluoromethylpyrrolidine

A sample of the intermediate from 324b (3.64 g), diphenylphosphoryl azide (3.50 mL), t-butanol (40 mL), triethylamine (2.3 mL) and 40 mL of dioxane were mixed and heated at reflux under $N_2$ for 17 hours. The solvents were removed under vacuum. The residue was dissolved in $CH_2Cl_2$, washed with satd. $NaHCO_3$ solution and water, dried over $MgSO_4$ and concentrated under vacuum. The product was purified by chromatography on silica gel, eluting with 100:5:5 $CH_2Cl_2$:methanol: $NH_4OH$ to afford 1.77 g of the title compound.

Step 324d. trans-3-(BOC-amino)-4-trifluoromethylpyrrolidine

The compound from step 324c above (1.55 g) was hydrogenated in 50 mL of methanol over 0.45 g of 10% Pd/C catalyst under 4 Atm of $H_2$ for 3.5 days. The catalyst was removed by filtration, and the solvent was removed to afford the title compound as a white solid (1.09 g).

Step 324e. 1-cyclopropyl-7-fluoro-9-methyl-4-oxo-8-(trans-4-trifluoromethyl-3-aminopyrrolidinyl)-4H-quinolizine-3-carboxylic acid hydrochloride Following the procedure of Example 253 steps k and l, replacing the 3-BOC-aminopyrrolidine of Example 253j with the compound from step 325d above, the title compound was prepared (97 mg). MS: 414 (M+1)⁺; ¹H NMR ($D_6$-DMSO) δ: 0.63 (m, 2H), 1.01 (m, 2H), 2.39 (m, 1H), 2.70 (s, 3H), 3.59 (m, 1H), 3.81 (m, 2H), 4.11–4.25 (m, 3H), 8.01 (s, 1H). Anal. Calcd for $C_{19}H_{19}N_3O_3F_4.HCl.1.25 H_2O$:C, 48.31; H, 4.80; N, 8.90; Found: C, 48.45; H, 4.63; N, 8.53.

EXAMPLE 325

1-cyclopropyl-7-fluoro-9-methyl-4-oxo-8-(trans-4-trifluoromethyl-3-aminomethylpyrrolidinyl)-4H-quinolizine-3-carboxylic acid hydrochloride Step 325a. trans-1-benzyl-3-(hydroxymethyl)-4-trifluoromethylpyrroidine A sample of the compound from Example 324 step a above (4.02 g) was dissolved in 10 mL of THF, then LAH (8.0 mL, 1.0N in THF) was added, and the solution was stirred for 30 min at room temperature. The reaction was quenched, and the product was extracted to give 3.36 g of the title product after removal of the solvent.

Step 325b. trans-1-benzyl-3-(aminomethyl)-4-trifluoromethylpyrrolidine

The compound from step 325a above (3.36 g), triphenylphosphine, and phthalimide were dissolved in 50 mL of THF, and DEAD (2.05 mL) was added dropwise to the above solution at room temperature. The reaction was complete almost immediately, and the solvents were removed. The residue was dissolved in 50 mL of ethanol, 0.65 mL of $NH_2NH_2.H_2O$ was added, and the reaction was heated at reflux under $N_2$ for 3 hours. The solution was cooled to room temperature, 5 mL of conc. HCl was added, and the mixture was filtered. The filtrate was concentrated, and the residue was dissolved in 10% HCl and extracted (6×) with $CH_2Cl_2$. The aqueous layer was then adjusted to pH 11 with NaOH and extracted with $CH_2Cl_2$, which was washed with $H_2O$, dried over $MgSO_4$ and concentrated. The residue was dissolved in 7:25 $H_2O$:methanol, $(BOC)_2O$ was added, and the reaction stirred at room temperature for 30 min. The methanol was removed under vacuum, and the aqueous residue was extracted with $CH_2Cl_2$. The extract was washed with $H_2O$, dried over $MgSO_4$ and concentrated. The residue was purified by chromatography on silica gel, eluting with 1:4 ethyl acetate:hexane, to give the title compound as a white solid.

Step 325c. trans-3-(BOC-aminomethyl)-4-trifluoromethylpyrrolidine

The compound from step 325b above was hydrogenated according to the procedure of Example 324 step d to afford the title compound as a white solid.

Step 325d. 1-cyclopropyl-7-fluoro-9-methyl-4-oxo-8-(trans-4-trifluoromethyl-3-aminomethylidinyl)-4H-quinolizine-3-carboxylic acid hydrochloride Following the procedure of Example 253 step j above, substituting the compound from step 325c above for the 3-BOC-aminopyrrolidine thereof, and carrying the reaction product forward as in Example 253 steps k and l above, a 77 mg sample of the title product was prepared. MS: 428 $(M+1)^+$; $^1$H NMR ($D_6$-DMSO) δ: 0.63 (m, 2H), 1.02 (m, 2H), 2.36 (m, 1H), 2.69 (s, 3H), 2.80 (m, 1H), 3.08 (m, 2H), 3.69 (m, 1H), 3.83 (m, 1H), 3.94–4.06 (m, 3H), 7.99 (s, 1H), 9.17 (d, 1H, J=10 Hz). Anal. Calcd for $C_{20}H_{21}N_3O_3F_4 \cdot HCl \cdot H_2O$: C, 49.85; H, 5.02; N, 8.72; Found: C, 49.86; H, 5.10; N, 8.93.

EXAMPLE 326

3(S)-1-cyclopropyl-7-fluoro-9-methyl-4-oxo-8-(3-(N-(S)-norvalylamino)pyrrolidinyl-4H-quinolizine-3-carboxylic acid hydrochloride Following the procedure of Example 166, replacing the starting pyrido-pyrimidine material thereof with the product of Example 253 step j, the title compound was prepared. MS: 445 $(M+1)^+$; Anal. Calcd for $C_{23}H_{29}N_4O_4F \cdot 1.5HCl \cdot 0.75 H_2O$: C, 53.88; H, 6.29; N, 10.93; Found: C, 53.87; H, 6.10; N, 11.10.

EXAMPLE 327

3(S)-1-cyclopropyl-7-fluoro-9-methyl-4-oxo-8-(3-(N-(S)-alanylamino)pyrrolidinyl)-4H-quinolizine-3-carboxylic acid hydrochloride Following the procedure of Example 167, replacing the starting pyrido-pyrimidine material thereof with the product of Example 253 step j, 97 mg of the title compound was prepared. MS: 417 $(M+1)^+$; $^1$H NMR ($D_6$-DMSO) δ:0.60 (m,2H), 1.00 (m, 2H), 1.35 (d, 3H, J=7 Hz), 2.00 (m, 1H), 2.20–2.31 (m, 2H), 2.62 (s, 3H), 3.56 (m, 1H), 3.80 (m, 2H), 3.93–4.06 (m, 2H), 4.43 (m, 1H), 7.91 (s, 1H), 8.19 (br, 3H), 8.91 (d, 1H, J=6 Hz), 9.09 (d, 1H, J=10.5 Hz), 13.85 (br, 1H). Anal. Calcd for $C_{21}H_{25}N_4O_4F \cdot 2HCl$: C, 51.54; H, 5.56; Found: C, 51.50; H, 5.48.

EXAMPLE 328

3(S)-1-cyclopropyl-7-fluoro-9-methyl-4-oxo-8-(3-(N-(S)-alanyl-(S)-alanylamino)pyrrolidinyl)-4H-quinolizine-3-carboxylic acid hydrochloride Following the procedure of Example 168, replacing the starting pyrido-pyrimidine material thereof with the product of Example 253 step j, 680 mg of the title compound was prepared. MS: 488 $(M-Cl)^+$; $^1$H NMR ($D_6$-DMSO) δ:0.60 (m, 2H), 1.00 (m, 2H), 1.23 (d, 3H, J=7.5 Hz), 1.33 (d, 3H, J=7.0 Hz), 1.98 (m, 1H), 3.85–4.01 (m, 4H), 4.31-4.37 (m, 2H), 7.91 (s, 1H), 8.13 (br, 3H), 8.47 (d, 1H, J=6.0 Hz), 8.65 (d, 1H, J=7.5 Hz), 9.10 (d, 1H, J=10.5 Hz). Anal. Calcd for $C_{24}H_{30}N_5O_5F \cdot 3HCl \cdot 0.5 H_2O$:C, 46.18; H, 5.57; N, 11.22; Found: C, 46.34; H, 5.77; N, 11.52.

EXAMPLE 329

1-cyclopropyl-7-fluoro-6-methyl-4-oxo-8-(3-aminopyrrolidinyl)-4H-quinolizine-3-carboxylic acid hydrochloride Step 329a. 4-t-butoxy-3-chloro-2,5-difluoro-6-(trimethylsilylmethyl)pyridine To a stirred solution of 4-t-butoxy-3-chloro-trifluoropyridine (7.55 g, prepared as in Example 253 step a above) in 200 mL of THF at −78° C. was added trimethylsilylmethyl lithium (1.0M in pentane, 66 mL) dropwise, and the resulting solution was stirred for 1 hour. The reaction was quenched with satd NaCl solution, and the mixture was extracted with ether. The extract was washed with brine, dried over $MgSO_4$ and concentrated. The residue was purified by chromatography on silica gel, eluting with 1:32 ethyl acetate: hexane to give 6.26 g of title compound.

Step 329b. 4-t-butoxy-2,5-difluoro-6-(trimethylsilylmethyl)pyridine

The compound from step 329a above was dissolved in 100 mL of ethyl acetate, and 15 mL of triethylamine and 1.3 g of 10% Pd/C were added. The mixture was shaken under 4 Atm of $H_2$ for 24 hours. The catalyst was removed, and the filtrate was concentrated. The residue was purified with column chromatography on silica gel, eluting with 1:32 ethyl acetate:hexane to give 4.38 g of a colorless liquid.

Step 329c. 2,5-difluoro-4-t-butoxy-6-methylpyridine

A 1.00 g sample of the compound from step 329b above was dissolved in 10 mL of THF, $BH_4NF$ (1.0M in THF, 3.7 mL) was added, and the reaction was stirred at room temperature for 2.5 hours. The solvent was removed, and the residue was dissolved in ether, which was then washed with water, brine, and dried over MgSO4. Removal of the solvent and purification of the residue by chromatography on silica gel, eluting with 1:32 ethyl acetate:hexane, gave 0.68 g of the title compound as a colorless liquid.

Step 329d. 1-cyclopropyl-7-fluoro-6-methyl-4-oxo-8-(3-aminopyrrolidinyl)-4H-quinolizne-3-carboxylic acid hydrochloride Following the procedure of Example 253 step e, replacing the 3-methylpyridine compound thereof with the 6-methyl compound form step 329c above, and carrying the product forward according to steps 253e–l, a 31 mg sample of the title compound was prepared. MS: 346 $(M-Cl)^+$; $^1$H NMR ($D_6$-DMSO) δ: 0.53 (m, 2H), 0.99 (m, 2H), 1.87 (m, 1H), 2.20 (m, 1H), 2.34 (m, 1H), 2.87 (d, 3H, J=5.5 Hz), 3.76–4.02 (m, 5H), 6.92 (d, 1H, J=9 Hz), 7.72 (s, 1H), 8.38 (br, 3H). Anal. Calcd for $C_{18}H_{20}N_3O_3F \cdot HCl \cdot 1.5 H_2O$; C, 52.88; H, 5.92; N, 10.28; Found: C, 52.60; H, 5.98; N, 10.18.

EXAMPLE 330

1-cyclopropyl-7-fluoro-4H-8-(1-imidazolyl)-9-methyl-4-oxo-quinolizine-3-carboxylic acid hydrochloride Following the procedure of Example 253 step j, replacing the 3-t-BOC-aminopyrrolidine thereof with imidazole, and carrying the product forward as in Example 253 step k, the title compound was prepared. HRMS: $(M+H)^+$ calcd: 328.1097; found: 328.1110 $^1$H NMR ($CDCl_3$) δ: 0.90 (m, 2H), 1.18 (m, 2H), 2.40 (m, 1H), 2.83 (s, 3H), 7.15 (s, 1H), 7.39 (s, 1H), 7.71 (s, 1H), 8.66 (s, 1H), 9.43 (d, 1H, J=6 Hz).

EXAMPLE 331

8-(3-amino-1-pyrrolidinyl)-1-ethyl-7-fluoro-4H-4-oxo-9-methyl-quinolizine-3-carboxylic acid hydrochloride Following the procedure of Example 253 step e, replacing the cyclopropylacetonitrile compound thereof with propionitrile, and carrying the product forward as in Example 253 steps e–l, the title compound was prepared. MS: 334 (M–Cl)$^+$; $^1$H NMR (D$_6$-DMSO) δ:2.28 (m, 3H), 2.22 (m, 1H), 2.52 (m, 4H), 2.96 (m, 2H), 3.88–4.18 (m, 5H), 8.01 (s, 1H), 9.05 (d, 1H, J=10 Hz). Anal. Calcd for C$_{17}$H$_{20}$N$_3$O$_3$FCl.HCl1.5 H$_2$O:C, 51.45; H, 6.10; N, 10.59; Cl, 8.93; Found: C, 51.51; H, 5.90; N, 10.78; Cl, 8.91.

EXAMPLE 332

8-(3-amino-1-pyrrolidinyl)-1-cyclopropyl-9-ethyl-7-fluoro-4H-4-oxo-quinolizine-3-carboxylic acid hydrochloride Following the procedure of Example 253 step c, replacing the methyl iodide thereof with ethyl iodide, and carrying the product forward as in Example 253 steps 253d–l, the title compound was prepared. MS: 360 (M–Cl)$^+$; $^1$H NMR (D$_6$-DMSO) δ:0.52 (m, 2H), 0.87 (t, 3H, J=6 Hz), 0.98 (m, 2H), 2.20 (m, 2H), 2.33 (m, 1H), 3.20 (m, 2H), 3.65–3.96 (m, 5H), 7.95 (s, 1H), 8.43 (br, 3H), 9.07 (d, 1H, J=10.5 Hz), 13.83 (br, 1H). Anal. Calcd for C$_{19}$H$_{22}$N$_3$O$_3$F.1.25 HCl.1.5 H$_2$O: C, 53.95; H, 6.01; N, 9.93; Found: C, 53.82; H, 5.87; N, 10.18.

EXAMPLE 333

1-cyclopropyl-7-fluoro-4H-9-methyl-4-oxo-8-(3-(1,2,3-triazol-1-yl)-1-pyrrolidinyl)-quinolizine-3-carboxylic acid Step 333a. 1-benzyl-3-(1,2,3-triazol-1-yl)pyrrolidine A solution of 3-azido-1-benzylpyrrolidine (2.30 g) and trimethylsilylacetylene (8.0 mL) in 15 mL of toluene was heated at reflux for 18 hours. The solvents were removed to give an oily residue. The residue was dissolved in 20% HCl and heated at reflux for 16 hours. The solution was cooled, made basic with NaHCO$_3$, and extracted with methylene chloride. The organic layer was washed with water, dried over MgSO$_4$ and concentrated. The crude product was purified by chromatography on silica gel, eluting with CH$_2$Cl$_2$:methanol:NH$_4$OH 100:10:1.

Step 333b. 3-(1,2,3-triazol-1-yl)pyrrolidine

The compound from step 333a was dissolved in methanol and hydrolyzed by hydrogenation for 16 hours with a catalyst of 10% Pd/C. The mixture was filtered, and the solvent was removed to give 1.00 g of the product.

Step 333c. 1-cyclopropyl-7-fluoro-4H-9-methyl-4-oxo-8-(3-(1,2,3-triazol-1-ylpyrrolidinyl)-quinolizine-3-carboxylic acid Following the procedure of Example 253 step j, replacing the 3-BOC-aminopyrrolidine thereof with the compound from step 333b, and carrying the product forward as in Example 253 steps j & k, the title compound was prepared. mp 183°–186° C. MS: 398 (M–Cl)$^+$; $^1$H NMR (D$_6$-DMSO) δ: 0.61 (m, 2H), 0.99 (m, 2H), 2.31 (m, 1H), 2.56 (m, 2H), 2.62 (s, 3H), 3.84 (m, 1H), 3.99 (m, 1H), 4.10 (m, 1H), 4.36 (m, 1H), 5.46 (m, 1H), 7.80 (s, 1H), 7.92 (s, 1H), 8.32 (s, 1H), 9.11 (d, 1H, J=11 Hz). Anal. Calcd for C$_{20}$H$_{20}$N$_5$O$_3$F: C, 60.45; H, 5.07; N, 17.62; Found: C, 60.46; H, 5.20; N, 17.63.

EXAMPLE 334

1-cyclopropyl-7-fluoro-4H-9-methyl-4-oxo-8-(cis-3-amino-4-methyl-1-pyrrolidinyl)-quinolizine-3-carboxylic acid hydrochloride Following the procedure of Example 253 step j, replacing the 3-BOC-aminopyrrolidine thereof with cis-3-BOC-amino-4-methylpyrrolidine, and carrying the product forward as in Example 253 steps j–l, the title compound was prepared. MS: 360 (M–Cl)$^+$; $^1$H NMR (D$_6$-DMSO) δ:0.60 (m, 2H), 0.99 (m, 2H), 1.18 (d, 3H, J=7 Hz), 2.30 (m, 1H), 2.62 (s, 3H), 3.48–4.00 (m, 6H), 7.94 (s, 1H), 8.40 (m, 3H), 9.10 (d, 1H, J=10.5 Hz). Anal. Calc C$_{19}$H$_{22}$N$_3$O$_3$F.HCl.1.25 H$_2$O: C, 54.55; H, 6.14; N, 10.04; Found: C, 54.62; H, 6.10; N 10.08.

EXAMPLE 335

8-(2-aminomethyl)-1-cyclopropyl-7-fluoro-4H-9-methyl-4-oxo-quinolizine-3-carboxylic acid hydrochloride Following the procedure of Example 253 step j, replacing the 3-BOC-aminopyrrolidine thereof with 2-aminoethylamine, and carrying the product forward as in Example 253 steps j–l, the title compound was prepared. MS: 320 (M–Cl)$^+$; $^1$H NMR (D$_2$O) δ:0.60 (m, 2H), 1.02 (m, 2H), 2.02 (m, 1H), 2.64 (s, 3H), 3.40 (m, 2H), 3.99 (m, 2H), 7.40 (s, 1H), 8.80 (d, 1H, J=10.5 Hz). Anal. Calcd for C$_{16}$H$_{18}$N$_3$O$_3$F.HCl.0.85 H$_2$O: C, 51.78; H, 5.62; N, 11.32; Found: C, 51.79; H, 5.31; N, 11.15.

EXAMPLE 336

8-(3-(ethylaminomethyl)pyrrolidinyl)-1-cyclopropyl-7-fluoro-4H-9-methyl-4-oxo-quinolizine-3-carboxylic acid hydrochloride Following the procedure of Example 253 step j, replacing the 3-BOC-aminopyrrolidine thereof with 3-((N-BOC-N-ethyl)amino)methylpyrrolidine, and carrying the product forward as in Example 253 steps j–l, the title compound was prepared. MS: 388 (M–Cl)$^+$; $^1$H NMR (CD$_3$OD) δ:0.60–0.68 (m, 2H), 1.05 (m, 2H), 1.37 (m, 3H), 1.91 (m, 1H), 2.31 (m, 2H), 2.68 (s, 3H), 2.69 (m, 1H), 3.15 (m, 2H), 3.33 (m, 2H), 3.75–3.96 (m, 4H), 8.01 (s, 1H), 9.03 (d, 1H, J=10.5Hz). Anal. Calcd for C$_{21}$H$_{26}$N$_3$O$_3$F.1.25 HCl.H$_2$O: C, 55.92; H, 6.54; N, 9.32; Found: C, 56.18; H, 6.32; N, 9.27.

EXAMPLE 337

8-(3-(1-aminoethyl)pyrrolidinyl)-1-cyclopropyl-7-fluoro-4H-9-methyl-4-oxo-quinolizine-3-carboxylic acid hydrochloride Following the procedure of Example 253 step j, replacing the 3-BOC-aminopyrrolidine thereof with 3-(N-BOC-aminoethyl)pyrrolidine, and carrying the product forward as in Example 253 steps j–l, the title compound was prepared. MS: 374 (M–Cl)$^+$; Anal. Calcd for C$_{20}$H$_{24}$N$_3$O$_3$F.HCl.H$_2$O: C, 56.14; H, 6.36; Found: C, 56.27; H, 6.14.

EXAMPLE 338

1-cyclopropyl-7-fluoro-4H-9-methyl-8-(2-methyl-2,8-diaza-8-bicyclo[4,3,0]nonyl)-4-oxo-quinolizine-3-carboxylic acid hydrochloride Following the procedure of Example 253 step j, replacing the 3-BOC-aminopyrrolidine thereof with 2-methyl-2,8-diaza-bicyclo[4,3,0]nonane, and carrying the product forward as in Example 253 steps j–l, the title compound was prepared. MS: 400 (M–Cl)$^+$; $^1$H NMR (DMSO-d$_6$) δ:0.65 (m, 2H), 0.92 (m, 1H), 1.09 (m, 1H), 1.80–1.95 (m, 5H), 2.31 (m, 1H), 2.69 (s, 3H), 2.83 (m, 5H), 3.61–4.34 (m, 5H), 7.90 (s, 1H), 9.10 (d, 1H, J=10.5 Hz), Anal. Calcd for C$_{22}$H$_{26}$N$_3$O$_3$F.1.25 HCl.0.5 H$_2$O: C, 58.20; H, 6.27; N, 9.25; Found: C 58.09; H, 6.27; N, 9.25.

EXAMPLE 339

1-cyclopropyl-7-fluoro-4 H-8-((1S, 4S)-2,5-diaza-bicyclo[2,2,1]heptan-2-yl)-9-methyl-4-oxo-quinolizine-3-carboxlic acid hydrochloride Following the procedure of Example 253 step j, replacing the 3-BOC-aminopyrrolidine thereof with (1S,4S)-2,5-diaza-5-BOC-bicyclo[2,2,1]heptane (prepared according to J. Med Chem., 32:1598 (1988)), and carrying the product forward as in Example 253 steps j–l, the title compound was prepared. MS: 358 (M–Cl)$^+$; $^1$H NMR (DMSO-d$_6$) δ:0.59 (m, 1H), 0.93 (m, 1H), 1.06 (m, 1H), 2.05 (m, 1H), 2.31 (m, 2H), 2.59 (s, 3H), 3.45 (m, 2H), 3.61 (m, 1H), 4.09 (m, 1H), 4.51 (m, 1H), 4.96 (m, 1H), 7.97 (s, 1H), 9.07 (br, 1H), 9.20 (d, 1H, J=10.5 Hz), 9.54 (br, 1H). Anal. Calcd for C$_{19}$H$_2$O: N$_3$O$_3$F.1.5 HCl.1.0 H$_2$O: C 53.06; H, 5.51; N, 9.77; Found: C, 53.19; H, 5.37; N, 9.58.

EXAMPLE 340

1-cyclopropyl-7-fluoro-4H-9-methyl-4-oxo-8-(3-(2-pyridinyl)-1-pyrrolidinyl)-quinolizine-3-carboxylic acid hydrochloride Following the procedure of Example 253 step j, replacing the 3-BOC-aminopyrrolidine thereof with 3-(2-pyridinyl)pyrrolidine, and carrying the product forward as in Example 253 steps j–l, the title compound was prepared. MS: 408 (M–Cl)$^+$; $^1$H NMR (DMSO-d$_6$) δ:0.60 (m, 2H), 0.99 (m, 2H), 2.30–2.40 (m, 2H), 2.60 (m, 1H), 2.64 (s, 3H), 3.86–4.16 (m, 4H), 7.80 (m, 1H), 7.90 (s, 1H), 9.07 (d, 1H, J=11 Hz). Anal. Calcd for C$_{23}$H$_{23}$N$_3$O$_3$F .HCl.H$_2$O: C, 55.43; H, 5.26; N, 8.43; Found: C, 55.69; H, 4.97; N, 8.52.

EXAMPLE 341

8-((1R*,2S*,6R*)-2-amino-8-azabicyclo[4,3,0]nonan-8-yl))-1-cyclopropyl-7-fluoro-4H-9-methyl-4-oxo-quinolizine-3-carboxylic acid hydrochloride Step 341a. 1R*,2S*,6R*-2-BOC-amino-8-azabicyclo[4,3,0]nonane Two mL of 1.0N trifluoroacetic acid was added to a stirred solution of 2.o mL of cyclohexane and 4.92 g of N-benzyl-N-(methoxymethyl)-trimethylsilylmethylamine in 20 mL of methylene chloride at 0° C. The mixture was stirred at room temperature for 16 hours, then diluted with methylene chloride. The solution was washed with NaHCO$_3$ and water, then dried over MgSO4. Removal of the solvent left an oily residue. The residue was dissolved in 65 mL of methanol, after which were added 2.2 g of NH$_2$OH.HCl, 10 mL of 10% NaOH, and 6.5 mL of methylene chloride, and the reaction was heated at 60° C. for 3 hours. The solvents were removed, and the residue was dissolved in methylene chloride, which was washed with water, dried over MgSO$_4$ and concentrated to give an oil. The oil was dissolved in 50 mL of THF, 1.57 g of LAH were added, and the mixture was heated at reflux for 2 hours. The reaction was quenched with water, the solid was removed, and the filtrate was concentrated. The concentrate was dissolved in 40 mL of methanol and 10 mL of water. To this solution was added 5.0 g of (BOC)$_2$O and the reaction was stirred for 16 hours. The methanol was removed under vacuum, and the residue was extracted with methylene chloride. The extract was washed with water, dried over MgSO$_4$ and concentrated to give an oil. The oil was purified by chromatography on silica gel, eluting with 100:5:0.5 methylene chloride:methanol:NH$_4$OH to give 0.36 g of the 1R*,2S*,6R* isomer and 2.22 g of the 1R*,2R*,6R* isomer of the title compound. The 1R*,2S*,6R* isomer was stirred with 0.12 g of 10%Pd/C in 25 mL of methanol under 4 Atm of H$_2$ for 48 hours. The catalyst was filtered off, and the solvent was removed to give the title compound.

341b. 8-((1R*,2S*,6R*)-2-amino-8-azabicyclo[4.3.0]nonan-8-yl))-1-cyclopropyl-7-fluoro-4H-9-methyl-4-oxo-quinolizine-3-carboxylic acid hydrochloride Following the procedure of Example 253 step j, replacing the 3-BOC-aminopyrrolidine thereof with 1R*,2S*,6R*-2-BOC-amino-8-azabicyclo[4.3.0]nonane, prepared in step 341a above, and carrying the product forward as in Example 253 steps j–l, the title compound was prepared. MS: 400 (M–Cl)$^+$; $^1$H NMR (DMSO-d$_6$) δ: 0.63 (m, 2H), 0.94 (m, 1H), 1.05 (m, 1H), 1.42–1.62 (m, 4H), 1.97 (m, 1H), 2.31 (m, 2H), 2.62 (s, 3H), 2.67 (m, 1H), 3.19 (m, 1H), 3.54 (m, 1H), 3.82 (m, 1H), 4.00 (m, 2H), 7.89 (s, 1H), 8.18 (br, 3H), 9.06 (d, 1H, J=11 Hz). Anal. Calcd for C$_{22}$H$_{26}$N$_3$O$_3$F.1.25 HCl.1.5 H$_2$O: C, 55.55; H, 6.43; N, 8.83; Found: C, 55.40; H, 6.38; N, 8.72.

EXAMPLE 342

8-((1R*,2R*,6R*)-2-amino-8-azabicyclo[4.3.0]nonan-8-yl))-1-cyclopropyl-7-fluoro-4H-9-methyl-4-oxo-quinolizine-3-carboxylic acid hydrochloride Step 342a. 1R*,2R*,6R*-2-BOC-amino-8-azabicyclo[4,3,0]nonane Removing the N-benzyl group from the 1R*,2R*,6R*-isomer of Example 341 step a, the title compound was prepared.

Step 341 b. 8-((1R*,2R*,6R*)-2-amino-8-azabicyclo[4,3,0]nonan-8-yl))-1-cyclopyl-7-fluoro-4H-9-methyl-4-oxo-quinolizine-3-carboxylic acid hydrochloride Following the procedure of Example 253 step j, replacing the 3-BOC-aminopyrrolidine thereof with 1R*,2R*,6R*-2-BOC-amino-8-azabicyclo[4.3.0]nonane, prepared in step 342a above, and carrying the product forward as in Example 253 steps j–l, the title compound was prepared. MS: 400 (M–Cl)$^+$; $^1$H NMR (DMSO-d$_6$) δ: 0.53–0.61 (m, 2H), 0.95–1.06 (m, 2H), 1.30 (m,2H), 1.60 (m, 2H), 1.81 (m, 2H), 2.29 (m, 1H), 2.49 (m, 1H), 2.64 (2, 3H), 2.77 (m, 1H), 3.32–3.49 (m, 3H), 4.16 (m, 2H), 7.91 (s, 1H), 8.33 (br, 3H), 9.06 (d, 1H, J=10 Hz). Anal. Calcd for C$_{22}$H$_{26}$N$_3$O$_3$F.1.0

EXAMPLE 343

8-((1α,5α,6α)-6-amino-3-azabicyclo[3,1,0]hexan-3-yl))-1-cyclopropyl-9-methyl-7-fluoro-4H-4-oxo-quinolizine-3-carboxylic acid hydrochloride Following the procedure of Example 253 step j, replacing the 3-BOC-aminopyrrolidine thereof with 1α,2α,6α-2-BOC-amino-8-azabicyclo[4.3.0]hexane, prepared according to U.S. Pat. No. 5,298,629, and carrying the product forward as in Example 253 steps j-l, the title compound was prepared. MS: 358 (M–Cl)$^+$; $^1$H NMR (DMSO-d$_6$) δ: 0.61 (m, 2H), 1.01 (m, 2H), 2.12 (br s, 2H), 2.33 (m, 1H), 2.62 (s, 3H), 3.81 (m, 5H), 7.97 (s, 1H), 8.45 (br s, 3H), 9.11 (d, 1H, J=10.5 Hz), 13.83 (br, 1H). Anal. Calcd for C$_{19}$H$_{20}$N$_3$O$_3$F.1.5 HCl.0.5 H$_2$O: C, 54.19; H, 5.39; N, 9.98; Found: C, 54.43; H, 5.28; N, 9.87.

EXAMPLE 344

8-(trans-3-amino-4-fluoro-1-pyrrolidinyl))-1-cyclopropyl-9-methyl-7-fluoro-4H-4-oxo-quinolizine-3-carboxylic acid hydrochloride Step 344a. 1-CBZ-3,4-epoxy-pyrrolidine 1-CBZ-3-pyrroline (20 g) was dissolved in 200 mL of CH$_2$Cl$_2$. MCPBA (50–60% pure, 61.5 g) in 500 mL of CH$_2$Cl$_2$ was added to the above solution at 0° C., and the reaction was stirred at 45° C. for 18 hours. The reaction mixture was filtered, and the filtrate was treated with NaHSO$_3$ (ca. 5 g). The solution was then poured into 1 L of 1N NaOH, the mixture was shaken, and the organic phase was separated, washed with water, dried over MgSO$_4$ and concentrated. The residue was taken directly to the next step.

Step 344b. trans-3-azido-1-benzyloxycarboxy-4-hydroxy-pyrrolidine

The compound from step 344a above was dissolved in 250 mL of acetone. NaN3 (20.16 g) in 200 mL of water was added, and the reaction was stirred at 60° C. for 18 hours. The reaction mixture was poured into satd. NaCl solution, and the mixture was extracted (3×) with CH$_2$Cl$_2$. The extract was washed with water, dried over MgSO$_4$ and concentrated. The residue was purified by column chromatography on silica gel, eluting with 3% methanol in CH$_2$Cl$_2$ to yield 5.92 g of the product.

Step 344c. trans-azido-1-benzyloxycarboxy-4-fluoropyrrolidine

The compound from step 344b above was dissolved in 15 mL of CH$_2$Cl$_2$ and cooled to –78° C. DAST (0.82 mL) was added, and the reaction was stirred at room temperature for 16 hours. The solvent was removed, the residue dissolved in ethyl acetate, and the solution was washed with satd NaHCO$_3$, brine, and dried over mgso4. The solvent was removed, and the residue was purified by column chromatography on silica gel, eluting with 1% methanol in CH$_2$Cl$_2$ to yield 0.88 g of the tire compound. $^1$H NMR (CDCl$_3$) δ: 3.62 (m, 4H), 4.22 (br d, 1H, J=11 Hz), 4.99 (br d, 1H, J=51 Hz), 5.16 (s, 2H), 7.36 (m, 5H).

Step 344d. trans-3-(BOC-amino)-4-fluoropyrrolidine

The compound from step 344c was stirred with Raney Ni in methanol under 4 Atm H$_2$ for 9 hours. The catalyst was removed by filtration. The filtrate was concentrated, and the residue was treated with (BOC)$_2$O and the reaction was stirred for 16 hours. The methanol was removed under vacuum, and the residue was extracted with methylene chloride. The extract was washed with water, dried over MgSO$_4$ and concentrated. The residue was purified by chromatography on silica gel, eluting with 100:5:0.5 methylene chloride:methanol:NH$_4$OH to give the 1-benzyloxycarboxy compound. This protecting group was removed by hydrogenolysis over Pd/C under H$_2$ for 30 min. The catalyst was removed, and the filtrate was concentrated to give the title compound (331 mg). MS: 205 (M–Cl)$^+$; $^1$H NMR (CDCl$_3$) δ: 1.46 (s, (H), 2.67 (dd, J=4.5, 12 Hz, 1H), 3.04 (ddd, J=4.5, 14, 36 Hz, 1H), 3.18 (dd, J=14, 25 Hz, 1H), 3.44 (dd, J=7.5, 12 Hz, 1H), 4.08–4.12 (m, 1H), 4.49 (br s, 1H), 4.98 (br d, J=53 Hz, 1H).

Step 344e. 8-(trans-3-amino-4-fluoro-1-pyrrolidinyl))-1-cyclopropyl-9-methyl-7-fluoro-4H-4-oxo-quinolizine-3-carboxylic acid hydrochloride Following the procedure of Example 253 step j, replacing the 3-BOC-aminopyrrolidine thereof with the compound from step 344d above, and carrying the product forward as in Example 253 steps j-l, the title compound (44 mg) was prepared. MS: 354 (M–Cl)$^+$; HRMS: calc for C$_{18}$H$_{19}$N$_3$O$_3$F$_2$ (M_Cl)$^+$: 354.1473; found: 354.1480. $^1$H NMR (DMSO-d$_6$) δ: 0.62 (m, 2H), 1.00 (m, 2H), 2.35 (m, 1H), 2.58 (s, 3H), 3.77 (m, 1H), 3.93 (m, 1H), 4.11 (m, 1H), 4.31–4.41 (m, 1H), 5.50 (br d, J=51 Hz, 1H), 7.99 (s, 1H), 8.69 (br s, 3H), 9.16 (d, J=9 Hz, 1H), Anal. Calcd for C$_{18}$H$_{19}$N$_3$O$_3$F$_2$.1.3 HCl.2.0 H$_2$O C, 48.39; H, 5.48; N, 9.40; Found: C, 48.12; H, 5.58; N, 9.53.

EXAMPLE 345

1-cyclopropyl-7-fluoro-4H-8-(1-homopiperazinyl))-9-methyl-4-oxo-quinolizine-3-carboxylic acid, acetic acid salt Following the procedure of Example 298, replacing the 3-(dimethylamino)pyrrolidine thereof with the homopiperazine, the title compound was prepared. mp 195°–198° C. (dec.). MS: 360 (M+H)$^+$; $^1$H NMR (DMSO-d$_6$) δ: 0.55 (m, 2H), 0.98 (m, 2H), 1.83 (s, 6H), 2.26–2.38 (m, 2H), 2.69 (br s, 3H), 2.89 (m, 4H), 8.08 (br s, 1H), 9.04 (br s, 1H).

EXAMPLE 346

7,9-difluoro-4H-8-(4-methylpiperazinyl)-4-oxo-1-phenyl-quinolizine-3-carboxylic acid hydrochloride Step 346a. 1-(2,3,5,6-tetrafluoro-4-pyridinyl)-4-methylpiperazine To a cold solution of pentafluoropyridine (16.1 g, 95.2 mmol) and triethyl amine (11.1 g, 110 mmol) in 150 mL of CH$_2$Cl$_2$ a solution of N-methylpiperazine (10.0 g, 100 mmol) in 50 mL of CH$_2$Cl$_2$ was added dropwise. The solution was stirred for 2 hours, then stirred for 16 hours at room temperature. The solution was extracted with water and washed with brine, and the organic layer was dried over MgSO$_4$ and concentrated to give 23.25 g of the product. MS: 250 (M+H)$^+$; $^1$H NMR (CDCl$_3$) δ: 2.35 (s, 3H), 2.55 (m, 4H), 3.5 (m, 4H).

Step 346b. 1-(2-hydrazino-3,5,6-trifluoro-4-pyridinyl)-4-methylpiperazine

To a solution of the compound from step 346a above (23.24 g, 93.2 mmol) in 500 mL of ethanol was added 37.34 g (746 mmol) of hydrazine hydrate, and the reaction was heated at reflux for 16 hours. The solvent was removed, and the residue was dissolved in $CH_2Cl_2$. The solution was washed with water, dried over MgSO4, filtered and the solvent removed under vacuum. The residue was triturated with ether, and collected by filtration to obtain 17.42 g of light yellow solid. mp 174°–5° C. MS: 262 $(M+H)^+$; $^1H$ NMR $(CDCl_3)$ δ: 2.35 (s, 3H), 2.52 (m, 4H), 3.42 (m, 4H), 3.76 (s, 2H), 5.68 (s, 1H). Anal. Calcd for $C_{10}H_{14}N_5F_3$: C, 45.97; H, 5.40; N, 26.81; Found: C, 45.99; H, 5.34; N, 26.65.

Step 346c. 1-(2,3,5-trifluoro-4-pyridinyl)-4-methylpiperazine

A suspension of 17.36 g (66.4 mmol) of the compound from step 346b above in 200 mL of ethanol and 20 mL of 20% NaOH was stirred and air was bubbled through for 16 hours. The mixture was poured into brine, and this mixture was extracted with $CH_2Cl_2$. The extract was dried over MgSO4, filtered, and the solvent was removed to give 13.40 g of a solid. The residue was purified by chromatography on silica gel, eluting with ethyl acetate, to afford 11.54 g of pure title product. MS: 232 $(M+H)^+$; $^1H$ NMR $(CDCl_3)$ δ:2.34 (s, 3H), 2.52 (m, 4H), 3.46 (m, 4H), 7.66 (m, 1H). Anal. Calcd for $C_{10}H_{12}N_3F_3$: C, 51.94; H, 5.23; N, 18.18; Found: C, 51.63; H, 4.92; N, 17.73.

Step 346d. 2-(3,5-difluoro-4-(4-methylpiperazinyl)-2-pyridinyl)-phenylacetonitrile A solution of LDA (99.4 mmol, 66.3 mL, 1M in cyclohexane) in 50 mL of THF was prepared and cooled at –78° C. for 15 min. To this solution was added in a dropwise manner a solution of 8.87 g (75.7 mmol) of phenylacetonitrile in 35 mL of THF. The reaction was stirred at –78° C. for 15 min, then 0° C. for 30 min. The solution was then cooled to –60° C. and a solution of the compound from step 346c in 35 mL of THF was added dropwise. The reaction mixture was stirred for 1 hour at –60° C. and at 0° C. for 3 hours. The reaction contents were poured into excess $NH_4Cl$ solution, and the mixture was extracted with $CH_2Cl_2$. The extract was washed with brine, dried over $MgSO_4$ and filtered, and the solvent was removed. The residue was purified by chromatography on silica gel, eluting with 1:20 methanol:chloroform, to yield 10.24 g of the title compound. MS: 329 $(M+H)^+$; $^1H$ NMR $(CDCl_3)$ δ:2.35 (s, 3H), 2.52 (m, 4H), 3.41 (m, 4H), 5.43 (s, 1H), 7.35 (m, 3H), 7.45 (m, 2H), 8.13 (m, 1H). Anal. Calcd for $C_{18}H_{18}N_4F_2 \cdot 0.5 H_2O$: C, 64.95; H, 5.57; N, 16.83; Found: C, 62.51; H, 5.50; N, 16.96.

Step 346e. 1-(2-benzyl-3,5-difluoro-4-pyridinyl)-4-methylpiperazine

To a solution of the compound from step 346d above (8.55 g, 26 mmol) in 50 mL of ethanol was rapidly added 13.6 mL of conc. H2SO4. After an initial temperature rise, the solution was stirred at room temperature for 2 hr, then at reflux for 48 hours. The reaction solution was cooled and poured into $H_2$, adjusted to a basic pH with solid $K_2CO_3$ and extracted with $CH_2Cl_2$. The extract was dried over $MgSO_4$ and filtered, and the solvent was removed. The residue was purified by chromatography on silica gel, eluting with ethyl acetate to afford 3.57 g of the title compound. MS: 304 $(M+H)^+$; $^1H$ NMR $(CDCl_3)$ δ: 2.35 (s, 3H), 2.52 (m, 4H), 3.40 (m, 4H), 4.07 (m, 2H), 7.20 (m, 1H), 7.30 (m, 4H), 8.05 (m, 1H).

Step 346f. 4-(3,5-difluoro-4-(4-methylpiperazin-1-yl)-2-pyridinyl)-2-ethoxycarbonyl-4-phenyl-2-butenoic acid ethyl ester To 30 mL of THF cooled to –60° C. was slowly added 5.8 mL of butyl lithium (14.5 mmol, 2.5M in hexane), and the solution was stirred for 10 min. To this first solution was added dropwise a solution of 3.52 g (116 mmol) of the compound from step 346e above in 15 mL of THF. The reaction mixture was stirred for 10 min, then a solution of 3.4 mL (16.8 mmol) of diethyl ethoxymethylenemalonate in 15 mL of THF was added dropwise. The reaction was stirred for 0.5 hours at –60° C., then for 2 hours at room temperature. The reaction solution was poured into a 15% aq. $NH_4Cl$ solution, and the mixture was extracted with $CHCl_3$. The extract was dried over $MgSO_4$ and filtered, and the solvent was removed. The residue was purified by chromatography on silica gel, eluting with ethyl acetate to afford 4.09 g of the title compound. MS: 520 $(M+H)^+$; Anal. Calcd for $C_{27}H_{35}F_2N_3O_5$: C, 62.41; H, 6.79; N, 8.09; Found: C, 62.58; H, 6.63; N, 8.07.

Step 346g. 7,9-difluoro-4H-8-(4-methylpiperazinyl)-4-oxo-1-phenyl-quinolizine-3-carboxylic acid ethyl ester A 3.16 g (6.08 mmol) sample of the compound from step 346f above was dissolved in 20 mL of DMSO, and the solution was heated at reflux for 1 hour. The solution was poured into aq. 5 % $NaHCO_3$ solution, and the mixture was extracted with $CHCl_3$. The extract was washed with brine, dried over $MgSO_4$ and filtered, and the solvent was removed. The residue (2.23 g) was purified by chromatography on silica gel, eluting with 4:1:0.1 ethyl acetate:ethanol:TEA to yield 681 mg of the title compound. MS: 428 $(M+H)^+$; $^1H$ NMR $(CDCl_3)$ δ:1.40 (m, 3H), 2.40 (m, 2H), 2.58 (m, 5H), 3.10 (m, 2H), 4.38 (m, 2H), 7.40 (m, 6H), 8.12 (s, 1H), 9.30 (m, 1H).

Step 346h. 7,9-difluoro-4H-8-(4-methylpiperazinyl)-4-oxo-1-phenyl-quinolizine-3-carboxylic acid hydrochloride A solution of the compound from step 346g above (623 mg, 1.46 mmol) in 30 mL of THF was diluted with 15 mL of water. The suspension was cooled in an ice bath for 15 min, then $LiOH \cdot H_2O$ (183 mg, 4.37 mmol) was added, the reaction was stirred for 1 hour with cooling, then for 16 hours at room temperature. TLC showed the reaction to be incomplete, so an additional 123 mg of $LiOH \cdot H_2O$ was added, and the reaction was stirred for 24 hours. The reaction contents were poured into $H_2O$, and 1.3 mL of acetic acid were added. Solid $NaHCO_3$ was added until the solution was basic, and the mixture was extracted with $CHCl_3$ containing a small amount of DMF. The extract was dried over $MgSO_4$ and filtered, and the solvent was removed. Excess DMF was removed by co-distillation with toluene. The residue was suspended in water and carefully acidified with 0.5M HCl. The solution was frozen, and the water removed by freeze-drying. The solid was triturated with ether, collected by filtration, and dried for 48 hours at 50° C. in vacuum to yield 171 mg of the title compound. mp 230° C. (dec.). MS: 400 $(M+H)^+$; $^1H$ NMR $(DMSO-d_6)$ δ:2.73 (m, 3H), 2.80 (m, 4H), 3.70 (m, 4H), 7.40 (m, 6H), 7.93 (m, 1H), 9.33 (m, 1H), 11.0 (m, 1H). Anal. Calcd for $C_{21}H_{20}N_3O_3F_2 \cdot H_2O$: C, 55.57; H, 4.89; N, 9.26; Found: C, 55.89; H, 4.62; N, 8.99.

EXAMPLE 347

Scaled-Up Preparation of
8-(3(S)-aminopyrrolidinyl)-1-cyclopropyl-7-fluoro-4H-9-methyl-4-oxo-quinolizine-3-carboxylic acid hydrochloride Step 347a. 4-t-butoxy-3-chloro-2,5,6-trifluoropyridine A 927.55 g (5.0 mol) sample of 3-chloro-2,4,5,6-tetrafluoropyridine (from Fluorochem Ltd.) was dissolved in 4 L of anhydrous THF, and the solution was cooled to –10° C. To this solution was added 429 (5.36 mol) of lithium t-butoxide in portions over a 1-hr period, while maintaining the temperature between −5° C. to −10° C. The reaction was stirred for 2 hours at −10° C., the cooling bath was removed, and the solution was warmed to room temperature over a 3 hours period. The THF was removed under reduced pressure. The residue was dissolved in 6 L of ether, and the solution was washed with 4×1 L of water. The ether solution was dried over MgSO4, and the ether was removed under reduced pressure to give 1123.44 g of the crude product. The crude product was purified by chromatography, eluting with hexane. bp 43°–47° C./0.6 mm Hg.

Step 347b. 4-t-butoxy-3-methyl-2,5,6-trifluoropyridine

A 499 g (2.08 mol) sample of the compound from step 347a above was dissolved in 4 L of THF and cooled to −70° C. While maintaining a $N_2$ atmosphere, 1.6 L of sec-butyllithium (2.08 mol, 1.3M) was added, and the reaction mixture was stirred for 1 hour. Iodomethane (129.6 mL, 2.08 mol) was added rapidly dropwise, while maintaining the temperature below −50° C. The mixture was stirred while allowing the temperature to rise, and the stirring was continued for 16 hours. The reaction was quenched with 1 L of water while cooling with an ice bath, then 2 L of hexane were added, the phases mixed well, and the layers separated. The organic layer was concentrated on a rotary evaporator. The residue was dissolved in hexane, dried over MgSO4, filtered and concentrated to give 496 g of title compound, which was taken directly to the next step.

Step 347c. 4-t-butoxy-2,5-difluoro-3-methylpyridine

Lithium aluminum hydride (56.7 g, 1.42 mol) was added to 6 L of THF, and the suspension was stirred under $N_2$. The temperature was adjusted to 0° to −5° C., and 476.5 g (2.27 mol) of the compound from step 347b above (dissolved in 750 mL of THF) was added in a stream over a 15 min period. The mixture was stirred at room temperature for 16 hours, then 500 mL of hexane was added. The reaction was then quenched while maintaining an internal temperature of 10°–20° C. by adding 57 mL of $H_2O$, 57 mL of 15% NaOH solution, and 171 mL of $H_2O$, in that order. The mixture was filtered, and the filter cake was washed with THF and hexane. The filtrate was concentrated on a rotary evaporator with a bath temperature of 35° C. The residue was purified by column chromatography on silica gel, eluting with hexane and 5% ethyl acetate in hexane to afford 141 g of the title compound. Distillation at 80°–90° C. and 1 mm Hg gave 103.4 g of the pure product.

Step 347d. Alternate preparation of 4-t-butoxy-2,5-difluoro-3-methylpyridine

A 476.5 g (2.27 mmol) sample of the compound from step 347b above was dissolve in 6 L of THF and stirred under $N_2$. The temperature of the solution was adjusted to 0° to 5° C., and a solution of sodium bis-(2-methoxyethoxy)aluminum hydride in toluene (750 mL, 3.4M, 2.5 mol) was added rapidly dropwise over 1 hour. The reaction mixture was stirred at room temperature for 16 hours, and 500 mL of hexane was added. The reaction was then quenched while maintaining an internal temperature of <25° C. by careful addition of 500 mL of $H_2O$. The organic layer was decanted, and the solids were washed thoroughly with hexane. The solvents were combined and concentrated on a rotary evaporator, with a bath temperature of 55° C. The 440 g of crude product was twice purified by chromatography over silica gel, eluting with hexane and 3% ethyl acetate in hexane to give 137.5 of the pure title compound.

Step 347e. 2-(4-t-butoxy-5-fluoro-3-methyl-2-pyridinyl)-2-cyclopropylacetonitrile Diisopropylamine (445 mL, 3.18 mol) was dissolved in 1.5 L of anhydrous THF and stirred under $N_2$. The solution was cooled to −40° C., and n-butyllithium (1.274 L, 3.18 mole, 2.5M in hexane) was added at a rate such that the internal temperature was maintained at −40° to −20° C. The solution was warmed to −10° C., then cooled to −70° C. Cyclopropylacetonitrile (257 g, 3.17 mmol) was added dropwise to maintain the temperature below −68° C., then the solution was stirred for 35 min. A sample of 4-t-butoxy-2,5-difluoro-3-methylpyridine, from step 347c or 347d above, was dissolved in 1.2 L of anhydrous THF. To this solution was added in a dropwise manner the first solution containing the lithium salt of cyclopropylacetonitrile, at a rate that the internal temperature remained below −70° C. The solution was stirred at −78° C. for 1 hour, then allowed to warm to 0° C. The reaction was quenched by adding 1 L of satd aq. NH4Cl solution and 1L of $H_2O$. The organic layer was separated. The aqueous layer was extracted with ethyl acetate. The organic layers were combined, washed with brine, dried with MgSO4, and concentrated on a rotary evaporator to give an oil residue. The oil was distilled at 0.2 mm Hg at 25°–35° C. to remove low boiling impurities and residual cyclopropylacetonitrile. The residue was twice chromatographed on silica gel, eluting with 7% ethyl acetate in hexane to afford 646 g of pure title compound. MS: 263 $(M+H)^+$; $^1H$ NMR (CDCl$_3$) δ: 0.50 (m, 2H), 0.64 (m, 1H), 0.75 (m, 1H), 1.43 (d, J=1.5 Hz, 9H), 1.50 (m, 1H), 2.29 (s, 3H), 3.76 (d, J=7.5 Hz, 1H), 8.31 (s, 1H).

Step 347f. 2-(4-chloro-5-fluoro-3-methyl-2-pyridinyl)-2-cyclopropylacetonitrile

To a cooled (0° C.) solution of the compound from step 347e above (189.78 g, 0.72 mol) in 1.6 L of $CH_2Cl_2$ and 270 mL of DMF was added 300 mL (3.2 mol) of POCl$_3$, and the reaction was stirred for 12 hours. Another 25 mL (0.27 mol) of POCl$_3$ was added, and the reaction stirred for an additional 12 hours. The reaction mixture was then poured into $H_2O$, and this mixture was stirred for 1 hour. The organic material was extracted with $CH_2Cl_2$, which was washed with $H_2O$, sat aq NaHCO$_3$ solution, $H_2O$, dried over MgSO4, filtered and evaporated under vacuum to afford 129.3 g of the title compound as an oil. MS: 225,227 $(M+H)^+$, 191. $^1H$ NMR (CDCl$_3$) δ:0.48 (m, 1H), 0.58 (m, 1H), 0.66 (m, 1H), 0.77 (m, 1H), 1.50 (m, 1H), 2.49 (s, 3H), 3.80 (d, J=8 Hz, 1H), 8.39 (s, 1H).

Step 347g. 2-(4-chloro-5-fluoro-3-methyl-2-pyridinyl)-2-cyclopropylacetic acid, ethyl ester To 1 L of ethanol saturated with ca. 400 g HCl gas and stirred under $N_2$ and cooled to 0° C. was added a solution of 135.8 (0.6 mol) of the compound from step 347f in 90 mL of ethanol, and the reaction was stirred for 3 hours at 0° C. To this solution was added 90 mL of $H_2O$, and the reaction mixture was heated at 80° C. for 2 hours. The mixture was poured over ice to make a total volume of 4 L. The solution was neutralized with 50% NaOH to pH 8 while maintaining the temperature below 0° C. The solid was filtered off, redissolved in $CH_2Cl_2$, and the residual water layer removed. The organic layer was dried over MgSO$_4$ and evaporated to leave a tan solid (134.4 g). MS: 272 $(M+H)^+$; $^1H$ NMR (CDCl$_3$) δ:0.12 (m, 1H), 0.38 (m, 1H), 0.54 (m, 1H), 0.75 (m, 1H), 1.20 (t, J=7.5 Hz, 3H), 1.68 (m, 1H), 2.40 (s, 3H), 3.24 (d, J=9.3 Hz, 1H), 4.16 (q, J=7.5 Hz, 2H), 8.36 (s, 1H).

Step 347h. 2-(4-chloro-5-fluoro-3-methyl-2-pyridinyl)-2-cyclopropylethanol

A solution of the compound from step 347g above (130.72 g, 0.48 mol) in 530 mL of anhydrous THF was stirred under $N_2$ at −78° C. To this was added a solution of LiAlH$_4$ (480 mL, 1M in THF, 0.48 mol) dropwise while maintaining the temperature below −60° C. The reaction was stirred at −78°

C. for 2 hours. The reaction was quenched by addition of H₂O (16 mL), 15% NaOH (16 mL and H₂O (46 mL), and the mixture was stirred for 1 hour at room temperature. The solid was removed by filtration and washed with ether. The combined organic were washed with brine, dried over MgSO4, filtered and evaporated under vacuum to afford the title compound (108.6 g) as a white solid. MS: 230 (M+H)⁺, 196; ¹H NMR (CDCl₃) δ: 0.21 (m, 2H), 0.44 (m, 1H), 0.60 (m, 1H), 1.21 (m, 1H), 2.39 (s, 3H), 2.56 (m, 1H), 3.52 (br s, 1H), 4.02 (m, 2H), 8.31 (s, 1H).

Step 347i. 2-(4-chloro-5-fluoro-3-methyl-2-pyridinyl)-2-cyclopropylacetaldehyde

Anhydrous DMSO (80 mL, 1.14 mol) was dissolved in 900 mL of anhydrous $CH_2Cl_2$, and stirred under $N_2$. The solution was cooled to −78° C., and a solution of oxalyl chloride (2.0M, 284 mL, 0.569 mol) in $CH_2Cl_2$ was added over a 20 min period while holding the internal temperature below −60° C. and stirred for 35 min longer. The compound from step 346h (109 g, 0.475 mol) was dissolved in 400 mL of anhydrous $CH_2Cl_2$ and added dropwise to the first solution, while holding the internal temperature below −60° C. The reaction mixture was stirred for 30 min, and triethylamine (327 mL, 2.34 mol) was added dropwise over 10 min. The reaction was stirred as the internal temperature was raised to −10° C. The reaction was quenched with 500 mL of H₂O, and the organic layer was isolated, washed with H₂O, dried over MgSO₄ and evaporated to give 109.64 g of the title compound. MS: 228 (M+H)⁺; ¹H NMR (CDCl₃) δ:0.24 (m, 1H), 0.35 (m, 1H), 0.59 (s, 1H), 0.76 (m, 1H), 1.55 (m, 1H), 2.38 (s, 3H), 3.19 (dd, J=2.7, 9 Hz, 1H), 8.37 (s, 1H), 9.87 (d, J=2.7 Hz, 1H).

Step 347j. 4-(4-Chloro-5-fluoro-3-methyl-2-pyridinyl)-4-cyclopropyl-2-ethoxycarbonyl-2-butenoic acid ethyl ester The compound from step 347i above (109.68 g, 0.48 mol) was dissolved in 1.3 L of absolute ethanol and stirred under $N_2$. To this solution was added diethylmalonate (35 1 mL, 2.31 mol), piperidine (45.5 mL, 0.46 mol) and acetic acid (45.5 mL, 0.79 mol). The solution was heated at reflux for 8 hours and cooled to room temperature. The solvent was removed with a rotary evaporator, and the residue was dissolved in ethyl acetate. This solution was washed with water, brine, dried over MgSO₄ and concentrated to give an oily residue. The residue was distilled in a short-path distillation apparatus at 0.2 mm Hg and 25°–56° C. to remove excess diethyl malonate and volatile impurities. The residual oil was taken directly to the next step.

Step 347k. 8-chloro-1-cyclopropyl-7-fluoro-4H-9-methyl-4-oxo-quinolizine-3-carboxylic acid, ethyl ester The compound from step 347j above was dissolved in 400 mL of anhydrous DMSO and heated at reflux for 1 hour. The hot reaction mixture was slowly poured into rapidly stirred ice water (3 L). The product was filtered off and washed with water (3 L) and hexane (1.5 L). The product was dried in a vacuum oven for 16 hours to afford 105 g of the title compound as a yellow crystalline solid. MS: 324 (M+H)⁺; ¹H NMR (CDCl₃) δ:0.75 (m, 2H), 1.06 (m, 2H), 1.43 (t, 3H), 2.32 (m, 1H), 3.09 (s, 3H), 4.43 (q, 2H), 8.39 (s, 1H), 9.43 (dd, J=1, 6 Hz, 1H).

Step 347l. 8-(3(S)-(BOC-amino)pyrrolidinyl)-1-cyclopropyl-7-fluoro-4H-9-methyl-4-oxo-quinolizine-3-carboxylic acid, ethyl ester A 93.1 g (0.29 mmol) sample of the compound from step 347k above was dissolved in 1.24 L of acetonitrile, and 137 g (0.72 mol) of 3(S)-(BOC-amino)pyrrolidine and 113 g (1.45 mol) of NaHCO₃ were added. The mixture was heated at reflux under $N_2$ for 1 hour. The reaction mixture was cooled to 25° C., and 700 mL of H₂O were added. The mixture was extracted with ethyl acetate, and the solvent was washed with water, 1N HCl, water and brine. The solvent was dried over MgSO₄ and concentrated to a thick tar. MS: 474 (M+H)⁺; ¹H NMR (CDCl₃) δ: 0.60 (m, 2H)0.95 (m, 2H), 1.41 (t, 3H), 1.42 (m, 2H), 1.46 (s, 9H), 2.60 (s, 3H), 3.50 (m, 1H), 3.82 (m, 1H), 3.95 (m, 1H), 4.49 (q, 2H), 4.79 (br s, 1H), 8.2 (s, 1H), 9.25 (d, 1H).

Step 347m. 8-(3(S)-(BOC-amino)pyrrolidinyl)-1-cyclopropyl-7-fluoro-4H-9-methyl-4-oxo-quinolizine-3-carboxylic acid The material from step 347l above was dissolved in 900 mL of THF, and 550 mL of water and 107.5 g (2.56 mol) of LiOH.H₂O were added. The mixture was heated at reflux under $N_2$ for 1 hour. The mixture was diluted by pouting into a mixture of 1 L of THF and 0.5 L of water, with addition of ice to assist cooling. Conc. HCl was added with vigorous mixing to bring the acidity to pH 4, while holding the internal temperature below 15° C. The yellow precipitate was filtered off, then dissolved in $CH_2Cl_2$. The solution was washed with water until the washings tested neutral, then dried over MgSO₄ and concentrated. MS: 446 (M+H)⁺; ¹H NMR (CDCl₃) δ: 0.69 (m, 2H), 1.02 (m, 2H), 1.48 (s, 9H), 2.12 (m, 2H), 2.30 (m, 1H), 2.62 (s, 3H), 3.60 (m, 1H), 3.79 (m, 1H), 3.96 (m, 2H), 4.38 (br s, 1H), 5.11 (br s, 1H), 8.13 (s, 1H), 8.99 (d, 1H), 13.82 (s, 1H).

Step 347n. 8-(3(S)-amino)pyrrolidinyl)-1-cyclopropyl-7-fluoro-4H-9-methyl-4-oxo-quinolizine-3-carboxylic acid hydrochloride A 140 g sample of the compound from step 347m above was dissolved in 1.2 L of $CH_2Cl_2$, and 1.0 L of 1.0M HCl in acetic acid was added over 5 min. The mixture was stirred under $N_2$ for 1 hour at room temperature. The product was collected by filtration and washed with $CH_2Cl_2$ until colorless. The solid was dried in a vacuum oven (50° C., 10 mm Hg) for 48 hours. This material (307.45 g) was added to 3.8 L of absolute ethanol prewarmed to 70° C. To the mixture was added 1.23 L of H₂O, and the mixture was heated to boiling and stirred until all solid dissolved. Stirring was discontinued, seed crystals were added, and the solution allowed to cool to room temperature. The mixture was then cooled at 0° C. for 12 hours and at −25° C. with stirring for 2 hours. The product was filtered off and washed with chilled absolute ethanol. The solid was dried in vacuum for 48 hours to give the title product (261 g) as a yellow solid. MS: 346 (M−Cl)⁺; ¹H NMR (CD₃OD) δ: 0.69 (m, 2H), 1.06 (m, 2H), 2.26 (m, 2H), 2.52 (m, 1H), 2.73 (s, 3H), 3.88 (m, 2H), 4.05 (:m, 2H), 4.18 (m, 1H), 4.88 (br s, 1H), 8.03 (s, 1H), 9.02 (d, J=10.8 Hz, 1H).

EXAMPLE 348

8-(spiro-1,3-dioxacyclopentane[2,3]-1-piperidinyl)-1-cyclopropyl-7-fluoro-4H-9-methyl-4-oxo-quinolizine-3-carboxylic acid Step 348a. N-CBZ-3-hydroxypiperidine A sample of 3-hydroxypiperidine HCl (50.0 g) was dissolved in a small amount of water and the solution was cooled to 0° C. in an ice bath. The HCL was neutralized by slow addition of 363 mL of 1M NaOH. An additional 1.2 eq of 1 M NaOH was added quickly, and 52 mL of benzyl chloroformate in 20 mL of ether was added dropwise, then the solution was stirred for 4 hours at 0° C. The solution was diluted with 600 mL of water and extracted with methylene chloride. The organic extract was dried over Na₂SO₄, filtered, and taken to dryness to afford 89.2 g of the title compound.

Step 348b. N-CBZ-3-oxo-piperidine

A 30.0 g sample of N-CBZ-3-hydroxypiperidine, from step 348a above, was dissolved in 250 mL of DMSO, and the solution was cooled to 0° C. To this solution, stirred at 0°, was added 142 mL of diethylamine, and next was added dropwise a solution of 60.88 g of pyridine.SO$_3$ complex dissolved in 250 mL of DMSO. The cooling bath was removed, and the reaction mixture was stirred at room temperature for 20 hours. The reaction mixture was diluted with water, and the mixture was extracted with methylene chloride. The extract was dried over Na$_2$SO$_4$, filtered, and taken to dryness. The DMSO was distilled off under reduced pressure, and the residue purified by distillation in a kugelrohr apparatus to yield 26.53 g of the title compound.

Step 348c. spiro-1,3-dioxacyclopentane[2,3]piperidine

A 10.0 g sample of N-CBZ-3-oxo-piperidine, from step 348b above, was dissolved in 10 mL of toluene and 5.98 mL of ethylene glycol and 0.408 g of p-toluenesulfonic acid were added. The solution was stirred at 130° C. for 96 hours, then poured into 5% NaHCO3 solution. The mixture was extracted with methylene chloride, the extract was dried over Na$_2$SO$_4$, then the solvent was removed under vacuum and the residue was distilled in a kugelrohr apparatus to give 7.30 g of the title compound.

Step 348d. 8-(spiro-1,3-dioxacyclopentane[2,3]-1-piperidinyl)-1-cyclopropyl-7-fluoro-4H-9-yl-4-oxo-quinolizine-3-carboxylic acid Following the procedure of Example 253 step j, replacing the 3-BOC-aminopyrrolidine thereof with spiro-1,3-dioxacyclopentane[2.3]piperidine, from step 348c above, and carrying the product forward as in Example 253 steps j–k, the title compound was prepared (245 mg). mp 184°–187° C. MS: 403 (M+1)$^+$; $^1$H NMR (CDCl$_3$) δ: 0.69 (m, 2H), 1.03 (m, 2H), 1.88 (m, 2H), 1.99 (m, 2H), 2.28 (m, 1H), 2.82 (s, 3H), 3.35 (m, 4H), 3.97 (m, 4H), 8.36 (s, 1H), 9.20 (d, 1H, J=3 Hz), 13.91 (s, 1H). Anal. Calcd for C$_{21}$H$_{23}$N$_2$O$_5$F.0.5 H$_2$O: C, 61.31; H, 5.88; N, 6.81; Found: C, 61.41; H, 5.91; N, 6.62.

EXAMPLE 349

8-(3-amino-4-methoxypyrrolidinyl-1-cyclopropyl-7-fluoro-4H-9-methyl-4-oxo-quinolizine-3-carboxylic acid hydrochloride

Step 349a. N-CBZ-pyrroline

A 50.0 g sample of pyrroline (Aldrich) was dissolved in 868 mL of 1M NaOH, and the solution was cooled to 0° C. Benzyl chloroformate (103.29 mL) was dissolved in 100 mL of ether and added to the solution of pyrroline dropwise over a 1 hour period. The solution was stirred for 4 hours at 0° C., then diluted with 500 mL of water and extracted with methylene chloride. The extracts were combined, dried of Na$_2$SO$_4$, filtered, and evaporated to dryness to yield 144.6 g of the title compound.

Step 349b. N-CBZ-3,4-epoxy-pyrrolidine

In a dry system under N$_2$ a 15.0 g sample of N-CBZ-pyrroline, from step 349a above, was dissolved in 200 mL of methylene chloride, and the solution was cooled to 0° C. To this solution was added 46.3 g of m-chloroperbenzoic acid dissolved in 500 mL of methylene chloride dropwise over a 1 hour period. The reaction mixture was then heated at 45° C. for 18 hours, then recooled to 0° C. To the cool solution was added 3 g of sodium bisulfite, and the mixture was stirred for 1 hour and poured into 1 L of 1N NaOH. The organic layer was washed with water, dried over Na$_2$SO$_4$, filtered and evaporated to afford 14.5 g of the title compound.

Step 349C. N-CBZ-3-azido-4-hydroxy-pyrrolidine

A 16.18 g sample of N-CBZ-3,4-epoxy-pyrrolidine was dissolved in 145 mL of acetone. A 14.39 g sample of sodium azide was dissolved in 130 mL of water and added to the acetone solution. The reaction mixture was stirred at 60° C. for 16 hours, then poured into 400 mL of satd. NaCl solution. The quenched reaction mixture was extracted with methylene chloride, which was dried over Na$_2$SO$_4$, filtered and evaporated. The residue was purified by flash chromatography over silica gel to afford 21.40 g of the title compound.

Step 349d. N-CBZ-3-azido-4-methoxy-pyrrolidine

A 3.36 g sample of NaH was suspended in 60 mL of THF in a dry flask under N$_2$ and cooled to 0° C. A 20.0 g sample of N-CBZ-3-azido-4-hydroxy-pyrrolidine, from step 349c above, was dissolved in 200 mL of THF, and this solution was added dropwise to the suspension of NaH. The reaction mixture was stirred for 30 min at 0° C., 30 min at room temperature, and recooled to 0° C. To this solution was added dropwise a solution of 5.70 mL of methyl iodide in 60 mL of THF. The reaction mixture was stirred at 0° C. for 30 min and at room temperature for 23.5 hours. The reaction mixture was poured into 500 mL of 5% NH$_4$Cl solution, and the mixture was extracted with methylene chloride. The extract was dried over Na$_2$SO$_4$, filtered and evaporated. The residue was purified by flash chromatography over silica gel to afford 8.99 g of the title compound.

Step 349e. N-CBZ-3-amino-4-methoxy-pyrrolidine

A 8.98 g sample of N-CBZ-3-azido-4-methoxy-pyrrolidine, from step 349d above, was dissolved in 100 mL of methanol and hydrogenated at room temperature under 4 Atm of H$_2$ in the presence of 6.8 g of RaNi for 4 days in a sealed bomb. The catalyst was removed by filtration, and the methanol was evaporated. The residue was dissolved in methylene chloride, dried over Na$_2$SO$_4$, and filtered. The solvent was removed to yield 5.60 g of the title compound.

Step 349f. N-CBZ-3-(BOC-amino)-4-methoxy-pyrrolidine

A 5.60 g sample of N-CBZ-3-(BOC-amino)-4-methoxy-pyrrolidine was dissolved in 120 mL of methylene chloride in a dry flask under N$_2$ and cooled to 0° C. To this were added 6.61 mL of triethylamine and 7.76 g of di-t-butyl dicarbonate dissolved in 50 mL of methylene chloride (dropwise). The reaction mixture was stirred at )° C. fro 1 hour and at room temperature for 24 hours. The reaction was quenched by addition to water. The mixture was extracted with methylene chloride. The extract was dried over Na$_2$SO$_4$, filtered and evaporated to yield 6.88 g of crude product. The residue was purified by flash chromatography over silica gel to afford 1.97 g of pure title compound.

Step 349g. 3-(BOC-amino)-4-methoxy-pyrrolidine

A 1.97 g sample of N-CBZ-3-(BOC-amino)-4-methoxy-pyrrolidine, from step 349f above, was hydrogenated over 0.2 g of 10% Pd/C in 100 mL of methanol under 4 Atm of H$_2$ at room temperature for 24 hours. The catalyst was removed by filtration, the solvent was removed to yield 1.28 g of title compound.

Step 349h. 8-(3-amino-4-methoxypyrrolidinyl)-1-cyclopropyl-7-fluoro-4H-9-methyl-4-oxo-quinolizine-3-carboxylic acid hydrochloride Following the procedure of Example 253 step j, replacing the 3-BOC-aminopyrrolidine thereof with 3-(BOC-amino)-4-methoxypyrrolidine, from step 349g above, and carrying the product forward as in Example 253 steps j–l, the title compound was prepared (369 mg). MS: 376 (M+1)$^+$; $^1$H NMR (CD$_3$OD) δ: 0.71 (m, 2H), 1.88 (m, 2H), 2.30 (m, 1H), 2.74 (s, 3H), 3.51 (s, 3H), 3.84 (m, 2H), 3.98 (m, 1H), 4.24 (m, 3H), 8.02 (s, 1H), 9.02 (d, 1H, J=3.5 Hz). Anal. Calcd for $C_{19}H_{23}N_3O_4ClF.4\ H_2O$: C, 46.16; H, 6.46; N, 8.68; Found: C, 47.53; H, 6.06; N, 9.36.

EXAMPLE 350

8-(4-amino-4-methylpyrrolidinyl)-1-cyclopropyl-7-fluoro-4H-9-methyl-4-oxo-quinolizine-3-carboxylic acid hydrochloride Step 350a. N-CBZ-4-hydroxypiperidine A 35.43 g of 4-hydroxypiperidine was suspended in 420 mL of 1M NaOH, and cooled to 0° C. To this stirred solution was added 50.0 mL of benzyl chloroformate dissolved in 100 mL of ether dropwise over a 1 hour period. The reaction mixture was stirred for 3 hours, diluted with 200 mL of water, and extracted with methylene chloride. The extract was dried over $Na_2SO_4$, filtered and evaporated to afford the title compound.

Step 350b. N-CBZ-4-oxopipyridine

A 43.1 g sample of N-CBZ-4-hydroxypiperidine, from step 350a above, was dissolved in 370 mL of DMSO in a dry flask under $N_2$ and cooled to 0° C. To this solution was added 204 mL of triethyl amine, then a solution of 87.5 g of pyridine.$SO_3$ in 370 mL of DMSO was added dropwise over a period of 1 hour. The reaction was stirred for 24 hours at room temperature, then quenched by addition to 1 L of NaCl solution. The mixture was extracted with methylene chloride. The extract was dried over $Na_2SO_4$, filtered and evaporated. The residue was chromatographed of a silica gel column to afford 11.49 g of the title compound.

Step 350c. N-CBZ-4-hydroxy-4-methylpiperidine

A 58 mL sample of methyl magnesium bromide was placed into a dry flask under $N_2$ containing 450 mL of dry ether cooled to −20° C. A 25.00 g sample of N-CBZ-4-oxopiperidine, from step 350b above, was dissolved in 100 mL of dry ether and added to the reaction vessel dropwise over a 1 hour period. The reaction mixture was stirred for 1 hour, then warmed to room temperature over a 2.5-hour period. The reaction was quenched by dropwise addition of an excess of satd $NH_4Cl$ solution. The layers were separated, and the aqueous layer was extracted with ether. The organic layers were combined, dried over $Na_2SO_4$, filtered and evaporated. The residue was distilled in a kugelrohr apparatus to yield 44.3 g of the title compound.

Step 350d. N-CBZ-4-(acetylamino)-4-methylpiperidine

A solution of 270 mL of 90% sulfuric acid and 34 mL of acetonitrile was prepared and cooled to 0° C. A 44.3 g sample of N-CBZ-4-hydroxy-4-methylpiperidine, from step 350c above, dissolved in acetonitrile was added dropwise to the stirred solution in the reaction vessel over a 2 hours period. The reaction mixture was stirred an additional 45 min at 0° C. and 2.5 hours without cooling. The reaction mixture was poured over 1 kg of ice, and the mixture was adjusted to pH 12–13 with 50% NaOH. This mixture was extracted with ethyl acetate. The organic layers were combined, dried over $Na_2SO_4$, filtered and evaporated to give the title compound (10 1.5 g) as a white solid.

Step 3.50e. N-CBZ-4-amino-4-methylpiperidine

A 53 g sample of N-CBZ-4-(acetylamino)-4-methylpiperidine, from step 350e above, was dissolved in 202 mL of 12M HCl and heated at 115° C. for 90 hours. The reaction mixture was poured over 800 g of ice. This mixture was extracted with methylene chloride. The organic layers were combined, dried over $Na_2SO_4$, filtered and evaporated to give 37.6 g of the title compound.

Step 350f. N-CBZ-4-(BOC-amino)-4-methylpiperidine

In a dry flask under $N_2$ a 37.6 g sample of N-CBZ-4-amino-4-methylpiperidine, from step 350e above, was dissolved in 220 mL of $CCl_4$, 51.3 mL of triethylamine was added, and 52.2 g of di-t-butyl dicarbonate was added in small portions. The solution was stirred at 38° C. for 20 hours, then washed with water. The organic solvent was dried over $Na_2SO_4$, filtered and evaporated to give 23.71 g of title compound.

Step 350g. 4-(BOC-amino)-4-methylpiperidine

A 23.71 g sample of N-CBZ-4-(BOC-amino)-4-methylpiperidine, from step 350f above, was hydrogenated as described in Example 349g above to give 15.7 g of title compound.

350h.
8-(4-amino-4-methylpyrrolidinyl)-1-cyclopropyl-7-fluoro-4H-9-methyl-4-oxo-quinolizine-3-carboxylic acid hydrochloride Following the procedure of Example 253 step j, replacing the 3-BOC-aminopyrrolidine thereof with 4-(BOC-amino)-4-methylpyrrolidine (Aldrich) and carrying the product forward as in Example 253 steps j–l, the title compound was prepared (513 mg). mp 205°–207° C. MS: 374 $(M+1)^+$; $^1$H NMR $(CD_3OD)$ δ:0.71 (m, 2H), 1.08 (m, 2H), 1.54 (s, 3H), 2.00 (m, 4H), 2.38 (m, 1H), 2.87 (s, 3H), 3.60 (m, 4H), 8.20 (s, 1H), 9.27 (d, 1H, J=3 Hz). Anal. Calcd for $C_{20}H_{25}N_3O_3ClF.3\ H_2O$: C, 51.78; H, 6.73; N, 9.06; Found: C, 51.64; H, 6.39; N, 9.01.

EXAMPLE 351

8-(4-(2-hydroxyethyl)piperidinyl-1-cyclopropyl-7-fluoro-4H-9-methyl-4-oxo-quinolizine-3-carboxylic acid Following the procedure of Example 253 step j, replacing the 3-BOC-aminopyrrolidine thereof with 1-piperidineethanol, obtained from Aldrich, and carrying the product forward as in Example 253 steps j–k, the title compound was prepared (270 mg). MS: 389 $(M+1)^+$; $^1$H NMR $(CD_3OD)$ δ: 0.73 (m, 2H), 1.09 (m, 2H), 2.40 (m, 1H), 2.93 (s, 3H), 3.42 (m, 4H), 3.54 (m, 1H), 3.75 (m, 2H), 3.78 (m, 4H), 3.96 (m, 2H), 8.29 (s, 1H), 9.32 (d, 1H), J=3.3). Anal. Calcd for $C_{20}H_{24}N_3O_4F.2.5\ H_2O$: C, 55.29; H, 6.73; N, 9.67; Found: C, 55.08; H, 6.02; N, 9.56.

EXAMPLE 352

8-(4-(methoxymethyl)piperidinyl)-1-cyclopropyl-7-fluoro-4H-9-methyl-4-oxo-quinolizine-3-carboxylic acid Step 352a. N-CBZ-4-methoxymethoxypiperidine.

A 4.00 g sample of N-CBZ-4-hydroxypiperidine, prepared as in Example 350a above, was dissolved in 45 mL of methylene chloride, and 11.85 mL of diisopropylethylamine was added. To this solution was then added 3.87 mL of chloromethyl methyl ether dropwise over 10 min. The reaction mixture was stirred at room temperature for 17 hours, diluted with 50 mL of methylene chloride, and washed with 0.5M phosphoric acid, 5% $NaHCO_3$ and water. The solvent was dried over $Na_2SO_4$, filtered and evaporated to give 4.43 g of the title compound.

187

Step 352b. 4-methoxymethoxypiperidine

A 4.43 g sample of N-CBZ-4-methoxymethoxypiperidine, from step 352a above, was hydrogenated as described in Example 349g above to give 2.15 g of title compound.

Step 352c. 8-(4-(methoxymethyl)piperidinyl)-1-cyclopropyl-7-fluoro-4H-9-methyl-4-oxo-quinolizine-3-carboxylic acid Following the procedure of Example 253 step j, replacing the 3-BOC-aminopyrrolidine thereof with 4-methoxymethylpiperidine, from step 352b above, and carrying the product forward as in Example 253 steps j–k, the title compound was prepared (270 mg). mp 128°–130° C. MS: 405 (M+1)$^+$; $^1$H NMR (CD$_3$OD) δ:0.69 (m, 2H), 1.03 (m, 2H), 1.68 (m, 3H), 1.98 (m, 1H), 2.12 (m, 1H), 2.27 (m, 1H), 2.79 (s, 3H), 3.28 (m, 1H), 3.37 (m, 3H), 3.65 (m, 1H), 3.79 (m, 1H), 4.71 (m, 2H), 8.38 (s, 1H), 9.20 (d, 1H, J=12 Hz), 13.88 (s, 1H). Anal. Calcd for C$_{21}$H$_{25}$N$_2$O$_5$F.0.5 H$_2$O: C, 61.02; H, 6.11; N, 6.87; Found: C, 61.01; H, 6.34; N, 6.78.

EXAMPLE 353

8-(3-amino-3-methylpiperidinyl)-1-cyclpropyl-7-fluoro-4H-9-methyl-4-oxo-quinolizine-3-carboxylic acid hydrochloride Step 353a. N-benzyl-3-hydroxy-3-methylpiperidine To a dried system under N$_2$ was added 400 mL of dry ether and 32.2 mL of methyl magnesium bromide, and the solution was cooled to −30° C. To this solution was added dropwise a solution of 16.626 g of N-benzyl-3-piperidone (Aldrich) in 50 mL of dry ether. The reaction mixture was then stirred at room temperature for 4 hours. The reaction was quenched by dropwise addition of satd NH$_4$Cl solution with cooling until the suspended solid separated. An additional 300 mL of 10% NH$_4$Cl solution was then added, and the layers were separated. The aqueous layer was washed with ether, the organic solution and extracts were combined, dried over Na$_2$SO$_4$, filtered and evaporated. The residue was distilled in a kugelrohr apparatus to give 17.942 g of the title compound.

Step 353b. N-benzyl-3-(acetylamino)-3-methylpiperidine

A 21.961 g sample of N-benzyl-3-hydroxy-3-methylpiperidine, prepared as in step 353a above, was dissolved in 16.8 mL of acetonitrile and added dropwise over 1.5 hours to 134 mL of vigorously stirred 90% sulfuric acid cooled to 0° C. The reaction mixture was stirred for an additional 15 min at 0° C., and at room temperature for 6 hours. The reaction was quenched by pouring the reaction mixture over ice. This solution was adjusted to pH 12 with 50% NaOH solution and was then extracted with methylene chloride. The extract was dried over Na$_2$SO$_4$, filtered and evaporated to yield 19.2 of the title compound.

Step 353c. N-benzyl-3-amino-3-methylpiperidine

The sample of N-benzyl-3-(acetylamino)-3-methylpiperidine from the previous step was stirred with 100 mL of conc. HCl at 110° C. for 36 hours. The reaction mixture was poured over 800 g of ice. This mixture was extracted with methylene chloride. The organic layers were combined, dried over Na$_2$SO$_4$, filtered and evaporated to give the title compound.

Step 353d. N-benzyl-3-(BOC-amino)-3-methylpiperidine

The N-benzyl-3-amino-3-methylpiperidine of the previous step was reacted with di-t-butyl dicarbonate according to the procedure of Example 350f above, and the title compound was isolated.

188

Step 353e. 3-(BOC-amino)-3-methylpiperidine

A 3.32 g sample of N-benzyl-3-(BOC-amino)-3-methylpiperidine was hydrogenated according to the procedure of Example 350f above, and 2.50 g of the title compound was isolated.

Step 353f. 8-(3-amino-3-methylpiperidinyl)-1-cyclopropyl-7-fluoro-4H-9-methyl-4-oxo-quinolizine-3-carboxylic acid hydrochloride Following the procedure of Example 253 step j, replacing the 3-BOC-aminopyrrolidine thereof with 3-(BOC-amino)-3-methylpiperidine, from step 353e above, and carrying the product forward as in Example 253 steps j–l, the title compound was prepared (225 mg). MS: 373 (M+1)$^+$; $^1$H NMR (CD$_3$OD) δ: 0.69 (m, 2H), 1.05 (m, 2H), 1.53 (m, 3H), 1.80 (m, 1H), 2.23 (m, 2H), 2.86 (m, 3H), 3.23 (m, 2H), 3.41 (m, 2H), 3.72 (m, 2H), 8.68 (m, 2H). 8.15 (m, 1H), 9.01 (m, 1H), 13.64 (s, 1H). Anal. Calcd for C$_{20}$H$_{25}$N$_3$O$_3$ClF.H$_2$O: C, 56.14; H, 6.36; N, 9.82; Found: C, 55.73; H, 6.43; N, 9.48.

EXAMPLE 354

8-(3-pyrrolylpiperidinyl)-1-cyclopropyl-7-fluoro-4H-9-methyl-4-oxo-quinolizine-3-carboxylic acid Step 354a. N-CBZ-3-(methanesulformyloxy)piperidine A 4.0 g sample of N-CBZ-3-hydroxypiperidine (prepared from 3-hydroxypiperidine by standard methods) was dissolved in 25 mL of methylene chloride and cooled to 0° C. To this added 3.55 mL of triethylamine, then a solution of 1.77 mL of methanesulfonylchloride in 4 mL of methylene chloride was added dropwise. The reaction mixture was stirred at 0° C. for 15 min and at room temperature for 1.5 hours. The reaction was quenched by dilution with methylene chloride and extraction with 15% NaHCO$_3$ solution. The layers were separated, and the organic layer dried over Na$_2$SO$_4$, filtered and evaporated to give 5.02 g of the title compound.

Step 354b. N-CBZ-3-pyrrolylpiperidine

A 5.02 g sample of the N-CBZ-3-(methanesulfonyloxy)piperidine from step 354a above was dissolved in 8.89 g of pyrrole and heated at 100° C. for 20 hours. Excess pyrrole was removed under vacuum, and the residue was washed with 5% NaHCO$_3$ solution, water, dried over Na$_2$SO$_4$, filtered and taken to dryness. The residue was purified by flash chromatography on silica gel, eluting with 0–1% methanol in methylene chloride to afford 0.500 g of the title compound.

Step 354c. 3-pyrrolylpiperidine

A 612 mg sample of N-CBZ-3-pyrrolylpiperidine, from step 354b above, was hydrogenated according to the procedure of Example 350f above, and 500 mg of the title compound was isolated.

Step 354d. 8-(3-pyrrolylpiperidinyl)-1-cyclopropyl-7-fluoro-4H-9-methyl-4-oxo-quinolizine-3-carboxylic acid Following the procedure of Example 253 step j, replacing the 3-BOC-aminopyrrolidine thereof with 3-pyrrolylpiperidine, from step 354c above, and carrying the product forward as in Example 253 steps j–k, the title compound was prepared (157 mg). mp 182°–185° C. MS: 410 (M+1)$^+$; $^1$H NMR (CD$_3$OD) δ: 0.71 (m, 2H), 1.03 (m, 2H), 1.93 (m, 2H), 2.26 (m, 3H), 2.78 (s, 3H), 2.91–3.78 (m, 6H), 6.19 (m, 2H), 6.77 (m, 2H), 8.23 (s, 1H), 9.15 (d, 1H, J=12 Hz), 13.09 (s, 1H). Anal. Calcd for C$_{23}$H$_{24}$N$_3$O$_3$F.2.25 H$_2$O: C, 61.39; H, 5.83; N, 9.34; Found: C, 61.40; H, 5.63; N, 8.94.

EXAMPLE 355

8-(3-aminopiperidinyl)-1-cyclopropyl-7-fluoro-4H-9-methyl-4-oxo-quinolizine-3-carboxylic acid hydrochloride Step 355a. (R)-3-amino-2-piperidone A sample of D-omithine methyl ester hydrochloride was dissolved in 240 mL of methanol, and stirred with 75 g of an anion exchange resin in the OH⁻ form for 4 hours at room temperature. The suspension was filtered, and the filtrate was taken to dryness. The residue was distilled in a kugelrohr apparatus to yield 7.59 g of the title compound.

Step 355b. (R)-3-aminopiperidine

A 7.49 g sample of (R)-3-amino-2-piperidone, from step 355a above, was dissolved in 140 mL of THF, and the solution was cooled to 0° C. To this solution was carefully added in small portions 3.00 g of lithium aluminum hydride. The reaction mixture was stirred at room temperature for 2 hours. The reaction was quenched with water and NaOH, filtered, and the filter cake was extracted with THF. The solution was dried over $Na_2SO_4$, filtered, and evaporated to dryness. The residue was purified by distillation.

Step 355c. 8-(3-aminopiperidinyl)-1-cyclopropyl-7-fluoro-4H-9-methyl-4-oxo-quinolizine-3-acid hydrochloride Following the procedure of Example 253 step j, replacing the 3-BOC-aminopyrrolidine thereof with 3-aminopiperidine, from step 355b above, and carrying the product forward as in Example 253 steps j–l, the title compound was prepared (376 mg). MS: 360 (M+1)⁺; ¹H NMR (CD₃OD) δ: 0.71 (m, 2H),1.09 (m, 2H), 1.67–2.44 (m, 10H), 3.82 (d, 2H, J=12 Hz), 8.20 (s, 1H), 9.25 (d, 1H, J=9 Hz). Anal. Calcd for $C_{19}H_{23}N_3O_3ClF \cdot H_2O$: C, 55.14 H, 6.09; N, 10.15; Found: C, 55.50; H, 6.37; N, 9.26.

EXMAPLE 356

8-(3-amino-3-methylpyrrolidinyl)-1-cyclopropyl-7-fluoro-4H-9-methyl-4-oxo-quinolizine-3-carboxylic acid hydrochloride Following the procedure of Example 253 step j, replacing the 3-BOC-aminopyrrolidine thereof with 3-(BOC-amino)-3-methylpyrrolidine, and carrying the product forward as in Example 253 steps j–l, the title compound was prepared (255 mg). MS: 360 (M+1)⁺; ¹H NMR (CD₃OD) δ: 0.69 (m, 2H), 1.07 (m, 2H), 1.63 (s, 3H), 2.31 (m, 3H), 2.74 (s, 3H). 3.95 (m, 4H), 8.12 (s, 1H), 9.14 (d, 1H, J=9 Hz). Anal. Calcd for $C_{19}H_{23}N_3O_3ClF \cdot H_2O$: C, 55.14; H, 6.09; N, 10.15; Found: C, 55.08; H, 6.01; N, 9.77.

EXAMPLE 357

8-(3-amino-4-(1',3'-dioxolanyl)pyrrolidinyl)-1-cyclopropyl-7-fluoro-4H-9-methyl-4-oxo-quinolizine-3-carboxylic acid hydrochloride Step 357a. N-CBZ-3-amino- 4-hydroxy-pyrrolidine A 27.1 g sample of N-CBZ-3-azido-4-hydroxy-pyrrolidine, prepared as in step 349c above, was hydrogenated for 24 hours under the conditions of example 349e above, and 25.4 g of the title compound was obtained.

Step 357b. N-CBZ-3-(CBZ-amino)-4-hydroxy-pyrrolidine

A 25.4 g sample of N-CBZ-3-azido-4-hydroxy-pyrrolidine, from step 357a above, was dissolved in 129 mL of 1M NaOH, and the solution was cooled to 0° C. A 15.35 mL sample of benzyl chloroformate was dissolved in 20 mL of ethanol, and this solution was added dropwise to the vigorously stirred solution of the pyrrolidine over a 40 min period. The reaction mixture was stirred at 0° C. for 4 hours, then the reaction was quenched by pouring into 200 mL of water. This mixture was extracted with methylene chloride, which was dried over $Na_2SO_4$, filtered, and evaporated to dryness. The residue was purified by column chromatography on silica gel, eluting with 0.5–3.5% methanol in methylene chloride to yield 18.77 g of the title compound.

Step 357c. N-CBZ-3-(CBZ-amino)-4-pyrrolidinone

In a dry vessel under $N_2$ was place 385 mL of methylene chloride, and the solvent was cooled to 0° C. To this was added 17.32 mL of DMSO, then 21.89 mL of phenyl dichlorophosphate was added dropwise over a 30 min period. Next was added 34.03 mL of triethylamine over a 30 min period. To this solution was added a solution of N-CBZ-3-(CBZ-amino)-4-hydroxy-pyrrolidine, from step 357b above, in 100 mL of methylene chloride in a dropwise manner over a 45 min period. The reaction mixture was stirred at 0° C. for 1 hour and at room temperature for 20 hours. The reaction was quenched by pouring it into 20% NaCl solution. The mixture was extracted with methylene chloride, which was dried over $Na_2SO_4$, filtered, and evaporated to dryness. The excess DMSO was removed under vacuum with heating, and the residue was purified by column chromatography on silica gel, eluting with 0 to 1% methanol in methylene chloride to give 9.2 of the title compound.

Step 357d. N-CBZ-3-(CBZ-amino)-4-(1'-3-dioxolanylyl)pyrrolidine

A 0.932 g sample of N-CBZ-3-(CBZ-amino)-4-pyrrolidinone, from step 357c above, was dissolved in 17 mL of toluene and 0.353 mL of ethylene glycol and 24 mg of p-toluenesulfonic acid were added. The reaction mixture was stirred at 110° C. for 20 hours, then the reaction was quenched by addition of 5% NaHCO₃ solution. The mixture was extracted with methylene chloride, which was dried over $Na_2SO_4$, filtered, and evaporated to dryness. The residue was purified by column chromatography on silica gel, eluting with 2% methanol in methylene chloride to afford 578 mg of the title compound.

Step 357e. 3-amino-4-(1'-3-dioxolanylyl)pyrrolidine

A 2.68 g sample of N-CBZ-3-(CBZ-amino)-3-methylpiperidine was hydrogenated for 7 days according to the procedure of Example 350f above, and 937 mg of the title compound was isolated.

Step 357f. 8-(3-amino-4-(1',3'-dioxolanyl)pyrrolidinyl)-1-cyclopropyl-7-fluoro-4H-9-methyl-4-oxo-quinolizine-3-carboxylic acid hydrochloride Following the procedure of Example 253 step j, replacing the 3-BOC-aminopyrrolidine thereof with 3-amino-4-(1',3'-dioxolanyl)pyrrolidine, from step 357d above, and carrying the product forward as in Example 253 steps j–l, the title compound was prepared (324 mg). MS: 404 (M+1)⁺; ¹H NMR (CD₃OD) δ:0.69 (m, 2H), 1.06 (m, 2H), 2.33 (m, 1H), 2.75 (s, 3H), 3.88–4.02 (m, 4H), 4.16 (m, 4H), 4.21 (m, 1H), 8.16 (s, 1H), 9.21 (d, 1H, J=9 Hz). Anal. Calcd for $C_{20}H_{23}N_3O_5ClF \cdot H_2O \cdot HCl$: C, 48.59; H, 5.30; N, 8.50; Found: C, 48.80; H, 4.87; N, 8.52.

EXAMPLE 358

8-(3-amino-4-hydroxy-pyrrolidinyl)-1-cyclopropyl-7-fluoro-4H-9-methyl-4-oxo-quinolizine-3-carboxylic acid hydrochloride Step 358a. N-CBZ-3-azido-4-(methoxymethoxy)pyrrolidine A sample of N-CBZ-3-azido-4-hydroxypyrrolidine, prepared as in Example 349c above, was dissolved in 20 mL of methylene chloride, 5.02 mL of diisopropylethylamine was added, and 1.64 mL of methoxymethyl chloride was added dropwise over a 15 min period, with cooling as necessary to maintain the temperature at ambient. The reaction mixture was stirred at room temperature for 18 hours, then washed with 0.5M phosphoric acid, 5% NaHCO$_3$, dried over Na$_2$SO$_4$, filtered, and evaporated to dryness. The residue was purified by flash chromatography on silica gel, eluting with 0.5% methanol in methylene chloride to yield 1.58 g of the title compound.

Step 358b. N-CBZ-3-amino-4-(methoxymethoxy)pyrrolidine

A 2.23 g sample of N-CBZ-3-azido-4-(methoxymethoxy)pyrrolidine, prepared as in step 358a above, was dissolved in 200 mL of ethyl acetate and hydrogenated at room temperature under 4 Atm of H$_2$ in the presence of RaNi for 24 hours in a sealed bomb. The catalyst was removed by filtration, and the solvent was removed under vacuum to give the title product.

Step 358c. N-CBZ-3-(BOC-amino)-4-(methoxymethoxy)pyrrolidine

A 2.04 g sample of N-CBZ-3-amino-4-(methoxymethoxy)pyrrolidine, from step 358b above, was dissolved in 20 mL of methylene chloride, and the solution was cooled to 0° C. To this solution was added 2 mL of triethylamine, then 2.38 mL of di-t-butyl dicarbonate dissolved in 5 mL of methylene chloride. The reaction mixture was stirred for 30 min at 0° C., at room temperature for 24 hours, and at 40° C. for 8 hours, then quenched by pouring into 10% NaCl solution. The mixture was extracted with methylene chloride, which was dried over Na$_2$SO$_4$, filtered, and evaporated to dryness. The residue was purified by column chromatography on silica gel, eluting with 1% methanol in methylene chloride to give 1.35 g of the title compound.

Step 358d. 3-(BOC-amino)-4-(methoxymethoxy)pyrrolidine

A 1.35 g sample of N-CBZ-3-(BOC-amino)-4-(methoxymethoxy)pyrrolidine, from step 358c above, was hydrogenated for 12 days according to the procedure of Example 350f above, and 874 mg of the title compound was isolated.

Step 358e. 8-(3-amino-4-hydroxy-pyrrolidinyl)-1-cyclopropyl-7-fluoro-4H-9-methyl-4-oxo-quinolizine-3-carboxylic acid hydrochloride Following the procedure of Example 253 step j, replacing the 3-BOC-aminopyrrolidine thereof with 3-amino-4-hydroxypyrrolidine from step 358d above, and carrying the product forward as in Example 253 steps j–l, the title compound was prepared (125 mg). MS: 362 (M+1)$^+$; $^1$H NMR (CD$_3$OD) δ: 0.69 (m, 2H), 1.08 (m, 2H), 2.31 (m, 1H), 2.73 (s,3H), 3.69–4.53 (m, 7H), 8.08 (s, 1H), 9.10 (m, 2H). Anal. Calcd for C$_{18}$H$_{21}$N$_3$O$_4$ClF.1.5H$_2$O: C, 50.89; H, 5.69; N, 9.89; Found: C, 51.38; H, 5.65; N, 9.73.

EXAMPLE 359

8-(4-(1-(N-ethylamino)methyl)piperidinyl)-1-cyclopropyl-7-fluoro-4H-9-methyl-4-oxo-quinolizine-3-carboxylic acid hydrochloride Step 359a. 4-(N-B OC-N-ethylaminomethyl)pyridine A 4.00 g sample of 4-(N-ethylaminomethyl)pyridine (Aldrich) was dissolved in 50 mL of methylene chloride, and the solution was cooled to 0° C. To his solution was added 8.19 mL of triethylamine and then 8.01 g of di-t-butyl dicarbonate dissolved in 10 mL of methylene chloride was added dropwise. The reaction mixture was stirred for 1 hour at 0° C. and at room temperature for 30 min, then quenched by pouting into 10% NaCl solution. The mixture was extracted with methylene chloride, which was dried over Na$_2$SO$_4$, filtered, and evaporated to dryness. The residue was purified by flash chromatography on silica gel, eluting with 1% methanol in methylene chloride to yield 5.52 g of the title compound.

Step 359b. 4-(N-BOC-N-ethylaminomethyl)piperidine

A 5.50 g sample of 4-(N-BOC-N-ethylaminomethyl)pyridine, prepared as in step 359a above, was dissolved in 200 mL of ethyl acetate and hydrogenated at room temperature under 4 Atm of H$_2$ in the presence of RaNi for 24 hours in a sealed bomb. The catalyst was removed by filtration, and the solvent was removed under vacuum to give 1.80 g of the title product.

Step 359c. 8-(4-(1-(N-ethylamino)methyl)piperidinyl)-1-Cyclopropyl-7-fluoro-4H-9-methyl-4-oxo-quinolizine-3-carboxylic acid hydrochloride Following the procedure of Example 253 step j, replacing the 3-BOC-aminopyrrolidine thereof with 4-(N-BOC-N-ethylaminomethyl)piperidine, prepared in step 359b above, and carrying the product forward as in Example 253 steps j–l, the title compound was prepared (488 mg). MS: 402 (M+1)$^+$; $^1$H NMR (CD$_3$OD) δ: 0.69 (m, 2H), 1.07 (m, 2H), 1.36 (t, J=7.5 Hz, 3H), 1.91 (m, 4H), 2.36 (m, 1H), 2.84 (s, 3H), 2.97 (3.37 (m, 8H), 3.41 (m, 1H), 8.20 (s, 1H), 9.26 (d, J=9 Hz, 1H). Anal. Calcd for C$_{22}$H$_{29}$N$_3$O$_3$ClF.0.5H$_2$O: C, 59.12; H, 6.77; N, 9.40; Found: C, 58.74; H, 6.63; N, 9.28.

EXAMPLE 360

1-cyclopropyl-7-fluoro-8-(3-hydroxy-4-methylaminopyrrolidinyl)-4H-9-methyl-4-oxo-quinolizine-3-carboxylic acid hydrochloride Step 360a. N-CBZ-3-cyano-4-hydroxypyrrolidine A sample of N-CBZ-3,4-epoxypyrrolidine, prepared as in Example 349b above, was dissolved in 100 mL of ethanol and added to a solution of 9.88 g of MgSO$_4$ and 13.41 g of NaCN in 195 mL of water. The reaction mixture was stirred at 65° C. for 20 hours, cooled, filtered, and extracted with methylene chloride, which was dried over Na$_2$SO$_4$, filtered, and evaporated to dryness to afford 9.0 g of the title compound.

Step 360b. N-CBZ-3-aminomethyl-4-hydroxypyrrolidine

A 13.97 g sample of N-CBZ-3-cyano-4-hydroxypyrrolidine, prepared as in step 360a above, was dissolved in 210 mL of methanol containing 40 mL of triethylamine and hydrogenated at room temperature under 4 Atm of H$_2$ in the presence of RaNi for 24 hours in a sealed bomb. The catalyst was removed by filtration, and the solvent was removed under vacuum to give 14.38 g of the title product.

Step 360c. N-CBZ-3-(BOC-aminomethyl)-4-hydroxypyrrolidine

A 2.73 g sample of N-CBZ-3-aminomethyl-4-hydroxypyrrolidine, from step 360b above, was dissolved in 20 mL of methylene chloride, and the solution was cooled to 0° C. To this solution was added 2.86 g of di-t-butyl dicarbonate dissolved in 3 mL of methylene chloride, and the reaction mixture was stirred at 0° C. for 1 hour and at room temperature for 18 hours. The reaction was quenched by pouring into 250 mL of water, and the mixture was extracted with methylene chloride, which was dried over Na$_2$SO$_4$, faltered, and evaporated to dryness. The residue was purified by flash chromatography on silica gel to afford the title compound.

Step 360d. 3-hydroxy-4-methylaminopyrrolidine

A sample of N-CBZ-3-(BOC-aminomethyl)-4-hydroxy-pyrrolidine, from step 360c above, was hydrogenated over 10% Pd/C in 100 mL of methanol under 4 Atm of $H_2$ at room temperature for 24 hours. The catalyst was removed by filtration, the solvent was removed to yield 610 mg of title compound.

Step 360e. 1-cyclopropyl-7-fluoro-8-(3-hydroxy-4-methylaminopyrrolidinyl)-4H-9-methyl-4-oxo-quinolizine-3-carboxylic acid hydrochloride Following the procedure of Example 253 step j, replacing the 3-BOC-aminopyrrolidine thereof with 3-hydroxy-4-methylaminopyrrolidine, from step 360d above, and carrying the product forward as in Example 253 steps j–l, the title compound was prepared (540 mg). MS: 376 (M+1)$^+$; $^1$H NMR (CD$_3$OD) δ:0.68 (m, 3H), 0.99 (m, 2H), 2.29 (m, 1H), 2.70 (s, 3H), 3.55–4.58 (m, 9H), 8.09 (s, 1H), 9.02 (d, J=9 Hz, 1H). Anal. Calcd for $C_{19}H_{23}N_3O_4ClF.2H_2O$: C, 50.95; H, 6.08; N, 9.38; Found: C, 50.88; H, 5.77; N, 9.01.

EXAMPLE 361

8-(3-aminomethylpiperidinyl)-1-cyclopropyl-7-fluoro-4H-9-methyl-4-oxo-quinolizine-3-carboxylic acid hydrochloride Step 361a. 3-(N-BOC-aminomethyl)pyridine Under dry $N_2$, 15.69 g of di-t-butyldicarbonate was dissolved in 100 mL of $CH_2Cl_2$. The flask and contents were cooled in an ice bath, and to this was added a solution of 6.12 g of 3-(aminomethyl)pyridine in $CH_2Cl_2$ dropwise with stirring. The solution was stirred at 0°–5° C. for 30 min, then stirred at room temperature for 72 hours. The reaction was diluted with additional $CH_2Cl_2$ (100 mL), then washed with 250 mL of water. The water was back-extracted with $CH_2Cl_2$, and the organic layers were combined and dried over $Na_2SO_4$. The solution was filtered, and the solvent was removed on a rotary evaporator to give 13 g of title compound.

Step 361b. 3-(N-BOC-aminomethyl)piperidine

A 10.13 g sample of the compound from step 361a above was dissolved in 250 mL of methanol and reduced over 5 g of 5% Rh/C catalyst at room temperature under 4 Atm or $H_2$ for 18 hours. The catalyst was removed by filtration, and the solvent was removed under vacuum. The product was recrystallized from ethyl acetate, and dried under high vacuum to give 3.8 g of product. mp. 64°–65° C.

Step 361c. 8-(3-aminomethylpiperidinyl)-1-cyclopropyl-7-fluoro-4H-9-methyl-4-oxo-quinolizine-3-carboxylic acid hydrochloride Following the procedure of Example 253 step j, replacing the 3-BOC-aminopyrrolidine thereof with 3-(N-BOC-aminomethyl)piperidine, prepared in step 361b above, and carrying the product forward as in Example 253 steps j–l, the title compound was prepared (301 mg). mp 207°–208° C. MS: 374 (M+1)$^+$; $^1$H NMR (CD$_3$OD) δ: 0.70 (m, 2H), 1.05 (m, 2H), 1.45 (m, 2H), 1.90 (m, 2H), 2.10 (m, 2H), 2.35 (m, 1H), 2.84 (s, 3H), 3.00 (m, 2H), 3.20 (m, 1H), 3.30 (m, 2H), 8.09 (s, 1H), 8.32 (s, 1H), 9.17 (d, 1H, J=12 Hz). Anal. Calcd for $C_{20}H_{25}N_3O_3ClF.1.5H_2O$: C, 50.75; H, 6.18; N, 8.88; Found: C, 50.53; H, 6.20; N, 9.03.

EXAMPLE 362

8-(2-aminomethyl-4-morpholinyl)-1-cyclopropyl-7-fluoro-4H-9-methyl-4-oxo-quinolizine-3-carboxylic acid hydrochloride Step 362a. N-benzyl-2-chloromethylmorpholine A flask was charged with 1.5 g (10 mmol) of N-benzyl-ethanolamine, 7.8 mL of epichlorohydrin (71 mmol). The reaction mixture was heated at 40° C. for 30 min, then cooled to room temperature. The excess epichlorohydrin was removed under vacuum, and the residue was dissolved in 30 mL of conc. $H_2SO_4$. The solution was heated at 150° C. for 30 min and poured onto 50 g of ice. The solution was adjusted to pH 13 with NaOH, and the mixture was extracted with toluene. The solution was dried over $Na_2SO_4$, filtered, the solvent removed, and the product dried under vacuum to give 193 mg of the title compound. MS m/z: 226, 228 (M+H)$^+$.

Step 362b. 2-(N-benzyl-morpholinyl)-N-methylphthalimide

An oven-dried system under positive $N_2$ pressure was charged with 900 mg (4 mmol) of N-benzyl-3-chloromethylmorpholine dissolved in 20 mL of DMSO. To this was added 1.48 g (8 mmol) of potassium phthalimide. The reaction mixture was stirred at 100° C. for 96 hours, then cooled to room temperature and poured into 50 mL of water. The mixture was extracted with methylene chloride, the extract washed with water, and the organic layer was dried over $Na_2SO_4$. The solution was filtered, the solvent was removed under vacuum, and the product was dried under vacuum to give 1.18 g of the title compound. The material was recrystallized from ethanol, separated by filtration, and dried under vacuum to give 884 mg of pure title compound.

Step 362c. 4-benzyl-2-aminomethylmorpholine

A system under positive $N_2$ pressure was charged with 160 mg of 3-(N-benzyl-morpholinyl)-N-methylphthalimide, from step 362b above, suspended in 4 mL of ethanol. To this was added 50 μL of hydrazine hydrate, and the reaction mixture was stirred at room temperature for 3 hours and at 70° C. for 24 hours. The reaction mixture was cooled to room temperature and diluted with 10 mL of water. The mixture was filtered, and the aqueous layer was adjusted to pH 12 with NaOH and extracted with methylene chloride. The organic extract was dried over $Na_2SO_4$, filtered, and the solvent was removed and the product was dried under vacuum to give 72 mg of the title compound.

Step 362d. 4-benzyl-2-(BOC-aminomethyl)morpholine

An oven-dried system protected from moisture was charged with 198 mg of 1-benzyl3-aminomethylmorpholine, prepared as in step 362c above, dissolved in 2 mL of methylene chloride. To this solution was added 250 mg of di-t-butyl-dicarbonate. The reaction mixture was stirred at room temperature for 24 hours, diluted with 30 mL of methylene chloride, and dried over $Na_2SO_4$. The mixture was filtered, and the solvent was removed under vacuum. The residue was purified with preparative TLC on silica gel, developing with 9% methanol in methylene chloride and collecting the band at Rf=0.48. The product was removed from the silica gel with 300 mL of 10% methanol in methylene chloride, and the solvent was removed under vacuum to give 173 mg of the title compound. MS: 307 (M+1)$^+$.

Step 362e. 2-(BOC-aminomethyl)morpholine

A 50 mg sample of 4-benzyl-2-(BOC-aminomethyl)morpholine, from step 362d above, was dissolved in 5 mL of methanol and the benzyl group was removed by hydrogenation over under 4 Atm of $H_2$ over 25 mg of Pd/C at room temperature for 48 hours. The catalyst was filtered off, and the solvent was removed to give 33 mg of the title compound.

Step 362f. 8-(2-aminomethyl-4-morpholinyl)-1-cyclopropyl-7-fluoro-4H-9-methyl-4-oxo-quinolizine-3-Carboxylic acid hydrochloride Following the procedure of Example 253 step j, replacing the 3-BOC-aminopyrrolidine thereof with 2-(BOC-aminomethyl)morpholine, prepared as in step 362e above, and carrying the product forward as in Example 253 steps j–l, the title compound was prepared (287 mg). mp 209°–210° C. MS: 376 (M+1)$^+$, 393 (M+NH$_4$)$^+$; $^1$H NMR (CD$_3$OD) δ: 0.70 (dd 2H, J=4.5, 1.5 Hz), 1.09 (dd, 2H, J=1.5, 4.5 Hz), 2.38 (m, 1H), 2.88 (s, 3H), 3.05 (m, 2H), 3.20 (m, 2H), 3.40 (m, 2H), 3.50 (m, 2H), 3.90 (m, 2H), 4.10 (dd, 1H, J=1.5, 12 Hz), 8.03 (s, 1H), 8.15 (s, 1H), 9.23 (d, 1H, J=9 Hz), Anal. Calcd for C$_{19}$H$_{23}$N$_3$O$_4$ClF.2.25H$_2$O: C, 50.45; H, 6.13; N, 9.29; Found: C, 50.63; H, 6.17; N, 9.11.

EXAMPLE 363

8-(3-(1-(methylamino)methypiperidinyl)-1-cyclopropyl-7-fluoro-4H-9-methyl-4-oxo-quinolizine-3-carboxylic acid hydrochloride Step 363a. 3-(N-BOC-N-methylamino)methyl)pyridine To a dry flask under N$_2$ was added 84.7 mg (2.2 mmol) of NaH (minoil washed with dry hexane) and 2 mL of dry THF. The mixture was cooled in an ice bath and 416 mg of 3-(N-BOC-aminomethyl)piperidine, from Example 361b above, in 4 mL of dry THF was added dropwise. The mixture was stirred at 0°–5° C. for 1 hour after addition was complete, and 0.125 mL of methyl iodide was added. The mixture was stirred at 0°–5° C. for 30 min, then warmed to room temperature and stirred for 24 hours. The reaction was quenched by pouring it into 30 mL of said NaCl solution, and the mixture was extracted with 3×30 mL of methylene chloride. The organic extracts were combined, dried over Na$_2$SO$_4$, filtered and concentrated on a rotary evaporator to give 430 mg of title compound.

Step 363b. 3-(N-BOC-N-methylamino)methyl)piperidine

A 1.16 g sample of the compound from step 361a above was dissolved in 50 mL of methanol and reduced over 1.16 g of 5% Rh/C catalyst at room temperature under 4 Atm or H$_2$ for 18 hours. The catalyst was removed by filtration, and the solvent was removed under vacuum. The product was recrystallized from ethyl acetate, and dried under high vacuum to give 1.18 g of product. MS m/z: 229 (M+H)$^+$.

Step 363c. 8-(3-(1-(methylamino)methypiperidinyl)-1-cyclopropyl-7-fluoro-4H-9-methyl-4-oxo-quinolizine-3-carboxylic acid hydrochloride Following the procedure of Example 253 step j, replacing the 3-BOC-aminopyrrolidine thereof with 3-(N-BOC-N-methylamino)methyl)piperidine prepared according to step 363a above, and carrying the product forward as in Example 253 steps j–l, the title compound was prepared (535 mg). mp 246°–247° C. MS: 388 (M+1)$^+$; $^1$H NMR (CD$_3$OD) δ: 0.70 (dd, 2H, J=4.5 Hz), 1.07 (dd, 2H, J=7.8 Hz), 1.50 (m, 2H), 1.90 (m, 4H), 2.10 (m, 2H), 2.21 (m, 2.21 (m, 1H), 2.72 (s, 3H), 2.85 (s, 3H), 3.00 (m, 2H), 8.10 (s, 1H), 8.32 (s, 1H), 9.18 (d, 1H, J=9 Hz), Anal. Calcd for C$_{21}$H$_{27}$N$_3$O$_3$ClF.H$_2$O: C, 57.08; H, 6.61; N, 9.51; Found: C, 56.93; H, 6.68; N, 10.23.

EXAMPLE 364

8-(3-(methyl(methylenedioxy)methyl)piperidinyl)-1-cyclopropyl-7-fluoro-4H-9-methyl-4-oxo-quinolizine-3-carboxylic acid hydrochloride Following the procedure of Example 253 step j, replacing the 3-BOC-aminopyrrolidine thereof with 3-(methyl(methylenedioxy)methyl)piperidine prepared according to European Patent Application 342, 675, and carrying the product forward as in Example 253 steps j–k, the title compound was prepared (443 mg). mp 117°–118° C. MS: 419 (M+1)$^+$; $^1$H NMR (CDCl$_3$) δ:0.70 (m, 2H), 1.03 (m, 2H), 1.40 (m, 2H), 1.71 (m, 6H), 2.80 (s, 3H), 3.10 (dt, 1H, J=3, 12 Hz), 8.04 (dd, 2H, J=7.5 Hz), 8.32 (s, 1H), 9.18 (d, 1H, J=12 Hz); Anal. Calcd for C$_{22}$H$_{27}$N$_2$O$_5$F: C, 63.15; H, 6.50; N, 6.69; Found: C, 63.02; H, 6.42; N, 6.64.

EXAMPLE 365

8-(3-(S)-aminopiperidinyl)-1-cyclopropyl-7-fluoro-4H-9-methyl-4-oxo-quinolizine-3-carboxylic acid hydrochloride Following the procedure of Example 253 step j, replacing the 3-BOC-aminopyrrolidine thereof with 3-(S)-(N-BOC-amino)piperidine and carrying the product forward as in Example 253 steps j–l, the title compound was prepared (500 mg). mp 220°–221° C. MS: 360 (M+1) $^+$, 377 (M+NH$_4$)$^+$; $^1$H NMR (CD$_3$OD) δ:0.70 (m, 2H, J=6 Hz), 1.10 (m, 2H, J=6 Hz), 1.72 (m, 2H), 2.05 (m, 3H), 2.28 (m, 2H), 2.40 (m, 2H), 2.86 (s, 3H), 3.90 (m, 1H), 8.18 (s, 1H), 9.22 (d, 1H, J=9 Hz); Anal. Calcd for C$_{19}$H$_{23}$N$_2$O$_5$ClF.1.5 H$_2$O: C,53.97; H, 6.20; N, 9.94; Found: C, 54.28; H, 6.61; N, 8.85.

EXAMPLE 366

8-(3-(S)-(N-ethyl-N-methylamino)piperidinyl)-1-cyclopropyl-7-fluoro-4H-9-methyl-4-oxo-quinolizine-3-carboxylic acid Step 366a. (S)-3-acetylamino-1-benzylpyrrolidine To 1.30 g (7.38 mmol) of 3-amino-1-benzylpyrrolidine and 1.7 mL (12 mmol) of triethylamine in 25 mL of ethyl acetate stirred at room temperature was added 1.1 mL (12 mmol) of acetic anhydride, and the reaction was stirred for 1 hour. The solvent was removed, and the residue was treated with 1:1 20% K$_2$CO$_3$:brine, then extracted with methylene chloride. The organic extract was dried over Na$_2$SO$_4$, filtered, the solvent was removed under vacuum, and the residue was dried under high vacuum for 16 hours to give 1.71 g of the title compound. MS: 219 (M+1)$^+$; Anal. Calcd for C$_{13}$H$_{18}$N$_2$O: C,68.69; H, 8.42; N, 12.32; Found: C, 68.75; H, 8.00; N, 12.27.

Step 366b. (S)-3-ethylamino-1-benzylpyrrolidine

To 1.70 g (7.4 mmol) of the compound from step 366a above in 20 mL of THF was added 850 mg of lithium aluminum hydride, and the mixture was stirred at room temperature for 72 hours. The reaction was quenched with water and NaOH, stirred for 1 hour, filtered, and the filter cake was extracted with methylene chloride. The aqueous layers were extracted with methylene chloride, and the organic extracts were combined. The solution was dried over Na$_2$SO$_4$, filtered, and the solvent was removed under vacuum to give 1.71 g of the title compound. $^1$H NMR (CDCl$_3$) δ: 1.09 (t, 3H), 1.30–1.51 (m, 1H), 1.48–1.53 (m, 1H), 2.06–2.21 (m, 1H), 2.34 (dd, 1H), 2.58 (q, 2H), 2.47–2.68 (m, 2H), 2.77 (dd, 1H), 3.26–3.37 (m, 1H), 3.50 (s, 2H), 7.19–7.40 (m, 5H).

Step 366c. (S)-3-(N-BOC-N-ethylamino)-1-benzylpyrrolidine

To a 1.7 g sample of the compound from step 366b above dissolved in 3 mL of methylene chloride was added 1.94 g (8.9 mmol) of butoxycarbonyl anhydride, and the reaction was stirred for 16 hours. The solvent was removed under vacuum, and the residue was chromatographed on silica gel, eluting with 1; 1 hexane:ethyl acetate to give 1.8 g of the title compound. MS: 305 (M+1)+; 1H NMR (CDCl3) δ: 1.11 (t, 3H), 1.44 (s, 9H), 3.25 (q, 2H), 724–7.47 (m, 5H). Anal. Calcd for $C_{18}H_{28}N_2O_2$: C, 68.00; H, 9.35; N, 8.81; Found C, 68.05; H, 8.73; N, 8.85.

Step 366d. (S)-3-(N-ethyl-N-methylamino)-1-benzylpyrrolidine

To a 1.8 g (5.9 mmol) sample of the compound from step 366c above in 20 mL of THF was added 800 mg of LAH, and the reaction was stirred for 48 at reflux conditions. The reaction was cooled to room temperature, and 0.8 mL of water was added dropwise with stirring, followed by 0.8 mL of 15% NaOH similarly, and finally 2.4 mL of water, and the mixture was stirred for 2 hours at room temperature. The mixture was filtered, the filter cake washed with methylene chloride, the filtrate concentrated under vacuum to give the crude title product. This material was dissolved in acetic acid and filtered, methanol was added and the solvent removed, and the residue repeatedly dissolved in methanol and stripped. The residue was taken up in water, adjusted to pH 10–11 with $K_2CO_3$, saturated with NaCl, then this solution was extracted with 10% methanol in $CHCl_3$. The extract was dried over $Na_2SO_4$, filtered and the solvent was removed to give 603 mg of the title product. MS: 219 (M+1)+; 1H NMR (CDCl3) δ: 1.06 (t, 3H), 1.93–2.09 (m, 1H), 2.20 (s, 3H), 2.28–2.60 (br, 4H), 2.66–2.77 (m, 1H), 2.82 (dd, 1H), 2.96–3.14 (m, 1H), 3.60 (q, 2H), 7.18–7.41 (m, 5H).

Step 366e. (S)-3-(N-ethyl-N-methylamino)pyrrolidine

A 1.3 g sample of the compound from step 366d above was dissolved in 50 mL of acetic acid and 0.5 mL of HCl, 0.13 g of 10% Pd/C was added and the sample hydrogenated under 4 Atm of $H_2$. Additional amounts of catalyst and HCl were added before the reaction was complete. The solution was filtered, then the solvent was removed with repeated addition and removal of methanol. The residue was dissolved in water, which was adjusted to pH 10–11 with $K_2CO_3$, saturated with NaCl, and extracted repeatedly with 10% methanol in $CHCl_3$. The extract was dried over $Na_2SO_4$, filtered, and taken to dryness to give 603 mg of the title compound. HRMS (M+1)+: calc: 129.1936; found, 129.1392.

Step 366f. 8-(3-(S)-(N-ethyl-N-methylamino)piperidinyl)-1-cyclopropyl-7-fluoro-4H-9-methyl-4-oxo-quinolizine-3-carboxylic acid Following the procedure of Example 253 step j, replacing the 3-BOC-aminopyrrolidine thereof with (S)-3-(N-ethyl-N-methylamino)-pyrrolidine from step 366e above and carrying the product forward as in Example 253 steps j–k, the title compound was prepared. MS: 416 (M+1)+; 1H NMR (CDCl3) δ: 0.5–0.6M, 1H), 0.6–0.7 (m, 1H), 0.8–0.95 (m, 2H), 1.1 (t, 3H), 1.4 (t, 3H), 1.9–2.0 (m, 1H), 2.1–2.2 (m, 1H), 2.25 (s, 3H), 2.33 (s, 3H), 3.6–3.7 (m, 4H), 3.7–3.9 (m, 1H), 3.9–4.0 (m, 1H), 4.12 (dd, 1H), 4.4 (q, 2H), 8.13 (s, 1H), 9.25 (d, 2H).

EXAMPLE 367

1-cyclopropyl-8-(4-(2'-(N-methylamino)methyl-1',3'-dioxolanyl)piperidinyl)-7-fluoro-9-methyl-4-oxo-4H-quinolizine-3-carboxylic acid hydrochloride Step 367a. N-CBZ-4-(4'-bromomethyl-1',3'-dioxolanyl)piperidine, A 17.48 g sample of N-CBZ-4-oxopiperidine, prepared as in Example 350b above, was dissolved in 325 mL of toluene, and 16.40 mL of 3-bromo-1,2-propanediol and 713 mg of p-toluenesulfonic acid were added. The reaction mixture was heated at reflux (120°–125° C.) for 24 hours while collecting the water of reaction in a Dean-Stark trap. The reaction mixture was cooled to room temperature, then washed with 5% $NaHCO_3$ and water, dried over $Na_2SO_4$, filtered, and taken to dryness. The residue was purified by flash chromatography on silica gel, eluting with 0-to-1.5% methanol in methylene chloride to yield 26.5 g of the title compound.

Step 367b. N-CBZ-4-(4'-(methylaminomethyl)-1',3'-dioxolanyl)piperidine

A 7.29 g sample of N-CBZ-4-(4'-bromomethyl-1',3'-dioxolanyl)piperidine, from step 367a above, was heated with excess methylamine, and 3.427 g of the title compound was isolated and purified.

Step 367c. N-CBZ-4-(4'-(N-BOC-N-methylaminomethyl)-1',3'-dioxolanyl)piperidine

A 3.43 g sample of N-CBZ-4-(4'-(methylaminomethyl)-1',3'-dioxolanyl)piperidine, from step 367b above, was dissolved in 30 mL of methylene chloride, to which was added 2.98 mL of triethylamine followed by dropwise addition of 3.50 g of di-t-butyl dicarbonate in 20 mL of methylene chloride. The reaction mixture was stirred at 35° C. for 5 hours and at room temperature for 15 hours. The mixture was diluted with methylene chloride and washed with water. The extract was dried over $Na_2SO_4$, filtered, and taken to dryness to obtain 4.29 g of title compound.

Step 367d. 4-(4'-(N-BOC-N-methylaminomethyl)-1',3'-dioxolanyl)piperidine

A sample of N-CBZ-4-(4'-(N-BOC-N-methylaminomethyl)-1',3'-dioxolanyl)piperidine, from step 367c above, was hydrogenated over 10% Pd/C in 200 mL of methanol under 4 Atm of $H_2$ at room temperature for 24 hours. The catalyst was removed by filtration, and the solvent was removed to yield the title compound.

Step 367e. 1-cyclopropyl-8-(4-(2'-(N-methylamino)methyl-1',3'-dioxolanyl)piperidinyl)-7-fluoro-9-methyl-4-oxo-4H-quinolizine-3-carboxylic acid hydrochloride Following the procedure of Example 253 step j, replacing the 3-BOC-aminopyrrolidine thereof with 4-(4'-(N-BOC-N-methylaminomethyl)-1',3'-dioxolanyl)piperidine, prepared in step 367d above, and carrying the product forward as in Example 253 steps j–k, 199 mg of the title compound was prepared. IR (KBr) cm$^{-1}$: 3300 (br), 2850 (br), 1700(s), 1610 (m), 1530 (s), 790 (m). MS (CDI/NH3) m/z (M+H)+: 446 base. NMR (d6-DMSO): 9.18 (d, 1H), 8.00 (s, 1H), 3.69–4.57 (m, 4H), 2.95–3.25 (m, 5H), 2.76 (s, 3H), 2.48 (m, 3H), 2.40 (m, 1H), 1.88 (m, 4H), 1.02 (m, 2H), 0.65 (m, 2H). Anal. Calcd for $C_{23}H_{29}ClFN_3O_5$:.2 $H_2O$: C, 53.33; H, 6.42; N, 8.11; Found: C, 53.62; H, 6.38; N, 8.32.

EXAMPLE 368

1-cyclopropyl-8-(3-aza-6-amino-6-methylbicyclo[3,3,0]octan-1-yl)-7-fluoro-9-methyl-4-oxo-4H-quinolizine-3-carboxylic acid hydrochloride Step 368a. N-benzyl-3-aza-6-oxobicyclo[3,3,0]octane A 32.69 g sample of N-methoxymethyl-N-(trimethylsilylmethyl)-benzylamine was dissolved in 30 mL of methylene chloride, and the solution was cooled to 0° C. To this solution was added 9.5 mL of 2-cyclopentene-1-one and 1.75 mL of trifluoroacetic acid, and the reaction mixture was stirred at 0° C. for 0.5 hours and at room temperature for 24 hours. The reaction was quenched with water, and the mixture was extracted with methylene chloride, which was dried over $Na_2SO_4$, filtered, and taken to dryness to obtain 28.27 g of the title compound.

Step 368b. N-benzyl-3-aza-6-hydroxy-6-methylbicyclo[3,3,0]octane

In dry ether and under $N_2$, the compound from step 368a was reacted with methyl magnesium bromide at −30° C. Mter standard workup, the title compound was isolated.

Step 368c. N-benzyl-3-aza-6-(acetylamino)-6-methylbicyclo[3,3,0]octane

The compound of step 368b was reacted with acetonitrile in the presence of concentrated sulfuric acid. The reaction was quenched with water, and the product was extracted into methylene chloride, which was dried over $Na_2SO_4$, filtered, and taken to dryness to obtain the title compound.

Step 368d. N-benzyl-3-aza-6-amino-6-methylbicyclo[3,3,0]octane

The acetyl group was removed from the compound of step 368c by reaction with conc. HCl. The reaction mixture was made basic with NaOH, and the product was extracted into methylene chloride, which was dried over $Na_2SO_4$, filtered, and taken to dryness to obtain the title compound.

Step 368e. N-benzyl-3-aza-6-(BOC-amino)-6-methylbicyclo[3,3,0]octane

The compound from step 368d was reacted with di-t-butyl dicarbonate in the presence of triethylamine. The reaction was quenched with water, and the product was extracted into methylene chloride, which was dried over $Na_2SO_4$, filtered, and taken to dryness to obtain the title compound.

Step 368f. 3-aza-6-(BOC-amino)-6-methylbicyclo[3,3,0]octane

The benzyl group was removed from the compound of step 368f by hydrogenation in the presence of Pd/C. The catalyst was removed by filtration, and the product was obtained by evaporation of the solvent.

Step 368g. 1-cyclopropyl-8-(3-aza-6-amino-6-methylbicyclo[3,3,0]octan-1-yl)-7-fluoro-9-methyl-4-oxo-4H-quinolizine-3-carboxylic acid hydrochloride Following the procedure of Example 253 step j, replacing the 3-BOC-aminopyrrolidine thereof with 3-aza-6-(BOC-amino)-6-methylbicyclo[3,3,0]-octane, from step 369g above, and carrying the product forward as in Example 253 steps j–k, 418 mg of the tiff(compound was prepared. IR (KBr) $cm^{-1}$: 3340 (br), 2860 (br), 1700 (m), 1610 (m), 1430,(s), 1370 (m). MS (CDI/NH3) m/z $(M+H)^+$: 400 base. NMR ($CD_3OD$): 9.12 (m, 1H), 8.03 (s, 1H), 3.94 (m, 2H), 3.78 (m, 1H), 3.57 (m, 2H), 2.83 (m, 1H), 2.78 (m, 3H), 2.31 (m, 1H), 1.88 (m, 2H), 2.19 (m, 2H), 1.50 (s, 3H), 1.07 (m, 2H), 0.68 (m, 2H). Anal. Calcd for $C_{22}H_{27}ClFN_3O_3 \cdot 1.5 H_2O$ C,57.62; H, 6.37; N, 9.06; Found: C, 58.02; H, 6.64; N, 9.23.

EXAMPLE 369

1-cyclopropyl-8(3-fluoromethylpiperidinyl)-7-fluoro-9-methyl-4-oxo-4H-quinolizine Step 369a. N-BOC-3-hydroxymethylpiperidine A sample of 3-hydroxymethylpiperidine (2.0 g,17.4 mmol) was suspended in 60 mL of water and cooled to 0C. Sodium bicarbonate (2.63 g, 31 mmol) was added in one portion, then benzyl chloroformate (2.60 ml, 18.3 mmol) was added dropwise in 10 ml of diethyl ether. After stirring for 4 hours at 0C., the reaction was poured into 150 ml water and extracted with methylene chloride (3×100 ml). The combined organic layers were dried over sodium sulfate, then filtered and the filtrate evaporated to dryness to yield 3.74 g (86%).

Step 369b. N-BOC-3-fluoromethylpiperidine

This compound from step 369a (3.74 g, 15 mmol) was then dissolved in 10 ml of methylene chloride and added dropwise to a solution of diethylaminosulfur trifluoride (2.59 ml, 19.5 mmol) in 10 ml of methylene chloride at −78C. After the addition, the reaction was stirred at room temperature for 16 hours. 10 ml of water, then 30 ml of 1M sodium hydroxide was added dropwise to the reaction, then the product was extracted into methylene chloride (3×75 ml). The combined organic layers were dried over sodium sulfate, filtered, and the filtrate was evaporated to dryness. The product was purified by flash chromatography (100% methylene chloride) to yield 2.42 g (64%).

Step 369c. 3-fluoromethylpiperidine

The amine was deprotected under hydrogenation conditions in methanol using palladium on carbon (2 g). After 16 h at room temperature and 4 atm, the catalyst was filtered off and the filtrate concentrated to yield: 808 mg (68%) of the desired amine.

Step 369d. 1-cyclopropyl-8-(3-fluoromethylpiperidinyl)-7-fluoro-9-methyl-4-oxo-4H-quinolizine Following the procedure of Example 253 step j, replacing the 3-BOC-aminopyrrolidine thereof with 3-fluoromethylpiperidine, from step 369d above, and carrying the product forward as in Example 253 steps j–k, 198 mg of the title compound was prepared. IR (KBr) $cm^{-1}$: 2950 (br), 1650 (s), 1470 (s), 1440 (s), 1350 (m). MS (CDI/NH3) m/z $(M+H)^+$: 377 base. NMR ($CDCl_3$): 9.22 (d, 1H, J=9 Hz), 8.37 (s, 1H), 4.21–4.53 (m, 4H), 3.14–3.67 (m, 7H), 2.79 (s, 3H), 2.25 (m, 1H), 1.04 (m, 2H), 0.72 (m, 2H). Anal. Calcd for $C_{20}H_{22}F_2N_2O_3$: C, 63.82; H, 5.89; N, 7.44; Found: C, 63.35; H, 5.83; N, 6.85.

EXAMPLE 370

1-cyclopropyl-8-(4-(N,N-dimethyl)aminopiperidinyl)-7-fluoro-9-methyl-4-oxo-4H-quinolizine-3-carboxylic acid hydrochloride Step 370a. 4-(N,N-dimethyl)aminopiperidine 4-(N,N-dimethyl)aminopyridine (1.0 g, 8.2 mmol) was subjected to hydrogenation conditions in 100 ml methanol using Rhodium (50 mg) at room temperature and 4 atm for 72 hours. The catalyst was filtered off and the filtrate evaporated to yield 100% of the desired amine.

Step 370b. 1-cyclopropyl-8-(4-(N,N-dimethyl)aminopiperidinyl)-7-fluoro-9-methyl-4-oxo-4H-quinolizine-3-carboxylic acid hydrochloride Following the procedure of Example 253 step j, replacing the 3-BOC-aminopyrrolidine thereof with 4-(N,N-dimethyl)aminopiperidine, from step 370a above, and carrying the product forward as in Example 253 steps j–k, 345 mg of the title compound was prepared. IR (KBr) $cm^{-1}$: 2950 (br), 1710 (m), 1610 (m), 1470 (s), 1440 (s). MS (CDI/NH3) m/z $(M+H)^+$: 388 base. Anal. Calcd for $C_{21}H_{27}ClFN_3O_3$: C, 59.50; H, 6.42; N, 9.91; Found: C, 59.72; H, 6.69; N, 9.33.

EXAMPLE 371

1-cyclopropyl-8-(6-amino-3-azabicyclo[3,3,0]octyl)-7-fluoro-9-methyl-4-oxo-4H-quinolizine-3-carboxylic acid hydrochloride Step 371a. 3-aza-3-benzyl-6-(hydroxylimino)bicyclo[3,3,0]octane A 3.24 sample of 3-aza-6-oxobicyclo[3,3,0]octane, prepared as in Example 368a above, was dissolved in 40 mL of THF. Hydroxylamine hydrochloride (3.14 g) was dissolved in 60 mL of water and 4.05 g of NaHCO$_3$ was added to neutralize the salt. The neutral hydroxylamine solution was added to the THF solution, and the reaction mixture was stirred vigorously at room temperature for 18 hours. The THF was removed from the mixture under vacuum, and the aqueous solution was extracted with methylene chloride, which was dried over sodium sulfate, filtered and evaporated to dryness to yield 2.80 g of the title compound.

Step 371b. 3-aza-3-benzyl-6-aminobicyclo[3,3,0]octane

A 29.37 g sample of 3-aza-6-(hydroxylimino)bicyclo[3,3,0]octane, prepared as in step 371a above, was dissolved in 1 L of methanol and hydrogenated at 4 Atm of H$_2$ over 58.74 g of RaNi catalyst for 24 hours. The catalyst was filtered off, and the solvent was evaporated to afford the title compound.

Step 371c. 3-aza-3-benzyl-6-(BOC-amino)bicyclo[3,3,0]octane

A 2.63 g sample of 3-aza-3-benzyl-6-aminobicyclo[3,3,0]octane, from step 371b above, was dissolved in 25 mL of methylene chloride, 3.39 mL of triethylamine was added, and the solution was cooled to 0° C. A 3.98 g sample of di-t-butyl dicarbonate was dissolved in 6 mL of methylene chloride and added dropwise to the first solution. The reaction mixture was stirred 30 min at 0° C. and at room-temperature for 18 hours, the quenched by rapid addition to water. The mixture was extracted with methylene chloride, which was dried over sodium sulfate, filtered and evaporated to dryness. The residue was purified by column chromatography, eluting with 2% methanol in methylene chloride to afford the title compound.

Step 371d. 3-aza-6-(BOC-amino)bicyclo[3,3,0]octane

The compound from step 371c above was dissolved in 150 mL of methanol and hydrogenated for 23 hours at room temperature and 4 Atm of H$_2$ over 1.5 g of 10% Pd/C catalyst The catalyst was filtered off, and the solvent was evaporated to afford the title compound.

Step 371e. 1-cyclopropyl-8-(6-amino-3-azabicyclo[3,3,0]octyl)-7-fluoro-9-methyl-4-oxo-4H-quinolizine-3-carboxylic acid hydrochloride Following the procedure of Example 253 step j, replacing the 3-BOC-aminopyrrolidine thereof with 6-(BOC-amino)-3-azabicyclo[3,3,0]octane, from step 371d above, and carrying the product forward as in Example 253 steps j–k, 298 mg of the final compound was prepared. IR (KBr) cm$^{-1}$: 2900 (br), 1700 (m), 1610 (m), 1430 (s), 1380 (m). MS (CDI/NH3) m/z (M+H)$^+$: 386 base. NMR (CD$_3$OD): 9.04 (d, 1H, J=9 Hz), 7.97 (s, 1H), 3.92 (m, 2H), 3.78 (m, 2H), 3.57 (m, 1H), 3.15 (m, 1H), 3.04 (m, 1H), 2.76 (s, 3H), 2.29 (m, 1H), 1.69–2.21 (m, 3H), 1.08 (m, 2H), 0.67 (m, 2H). Anal. Calcd for C$_{21}$H$_{25}$ClFN$_3$O$_3$.1.5 H$_2$O. HCl: C, 51.97; H, 6.02; N, 8.66; Found: C, 52.07; H, 5.81; N, 8.48.

EXAMPLE 372

1-cyclopropyl-8-((2-aza-4-(dimethylaminomethyl)bicyclo[4,3,0] non-2-yl)-7-fluoro-9-methyl-4-oxo-4H-quinolizine carboxylic acid hydrochloride Step 372a. 2-aza-4-dimethylaminomethylbicyclo[3,3,0]nonane A 1 g sample of 3-dimethylaminomethylindole was hydrogenated over Pd/C in acetic acid/HCl, the catalyst removed by filtration, and the solvent diluted with water, adjusted to pH 11, and extracted with ethyl acetate. The solvent was dried and evaporated to afford the title compound.

Step 372b. 1-cyclopropyl-8-((2-aza-4-(dimethylaminomethyl)bicyclo[4,3,0]non-2-yl)-7-fluoro-9-methyl-4-oxo-4H-quinolizine carboxylic acid hydrochloride Following the procedure of Example 253 step j, replacing the 3-BOC-aminopyrrolidine thereof with 2-aza-4-(dimethylaminomethyl)bicyclo[4,3,0]-nonane, from step 372a above, and carrying the product forward as in Example 253 steps j–k, 354 mg of the final compound was prepared. IR (KBr) cm$^{-1}$: 3400 (br), 2950 (m), 2600 (br), 1720 (m), 1610 (m), 1430 (s), 1380 (m). MS (CDI/NH3) m/z (M+H)$^+$: 442 base. NMR (CDCl$_3$): 9.07 (d, 1H, J=9 Hz), 8.28 (s, 1H), 4.47 (m, 1H), 4.04 (m, 1H), 3.60 (m, 1H), 3.18 (m, 2H), 2.75 (s, 3H), 2.49 (m, 1H), 2.27 (m, 1H), 1.26 (m, 2H), 1.00–1.90 (m, 9H), 2.91 (s, 6H), 0.70 (m, 2H). Anal. Calcd for C$_{25}$H$_{33}$ClFN$_3$O$_3$.1.25 H$_2$O: C, 60.59; H, 7.73; N, 8.48; Found: C, 60.07; H, 7.71; N, 8.15.

EXAMPLE 323

1-cyclopropyl-8-(3-aza-6-(L-alanylamino)-6-methylbicyclo[3,3,0]octane)-7-fluoro-9-methyl-4-oxo-4H-quinolizine carboxylic acid hydrochloride A 50 mg sample of 1-cyclopropyl-8-(3-aza-6-(L-alanylamino)-6-methylbicyclo[3,3,0]octane)-7-fluoro-9-methyl-4-oxo-4H-quinolizine carboxylic acid hydrochloride, from Example 368, was dissolved in 3 mL of DMF, and the solution was cooled to 0° C. A 0.044 mL sample of diisopropylethylamine was added, followed by 35 mg of N-BOC-L-alanyl-N-hydroxysuccmimide, and the reaction was stirred at 0° C. for 20 min and at room temperature for 48 hours. The solution was poured into a large volume of water, and the product was filtered off and dried. IR (KBr) cm$^{-1}$: 2950 (br), 1680 (m), 1430 (s). MS (CDI/NH3) m/z (M+H)$^+$: 471 base. Anal. Calcd for C$_{25}$H$_{32}$ClFN$_4$O$_4$.H$_2$O: C, 57.19; H, 6.14; N, 10.67; Found: C, 57.16; H, 6.48; N, 9.90.

EXAMPLE 374

(3R, 1R)-8-(3-(1-(N-methyl)amino)propyl) pyrrolidinyl)-1-cyclopropyl-7-fluoro-9-methyl-4-oxo-4H-quinolizine-3-carboxylic acid hydrochloride A sample of 8-chloro-1-cyclopropyl-7-fluoro-9-methyl-4-oxo-4H-quinolizine-3-carboxylic acid ethyl ester, from Example 253i above, was dissolved in 8 mL of anhydrous acetonitrile, reacted with (3R, 1R)-3-(1-(N-methyl)amino) propyl)pyrrolidine (prepared as described by Hayakawa et al., U.S. Pat. No. 5,098,912, issued Mar. 24, 1992, using modifications for chiral products described by Plummer et al., *Tetr. Lett.* 34:7529–32 (1993)), and carded forward as described in Example 253 j-1, omitting the deprotecting step, to give the title product. MS 402 (M+H)$^+$; $^1$H NMR (D$_6$-DMSO) δ: 0.6–0.7 (m, 3H), 0.9 (t, 3H), 1–1.5 (m, 2H), 16–1.95 (m, 4H), 2.1–2.2 (m, 1H), 2.6–2.65 (m, 1H), 2.60 (s, 2H), 2.7 (s, 3H), 3.45–3.55 (m, 1H), 3.7–3.75 (m, 2H), 3.95–4 (m, 1H), 8.25 (s, 1H), 9.1 (d, 2H)

EXAMPLES 375–408

Following the procedures of Steps 253j, 253k and 253l above, replacing the 3-BOC-aminopyrrolidine of Step 253j with the appropriate unprotected or BOC-protected reagent, the compounds of Examples 375–412 are prepared as shown in Table 13, below.

TABLE 13
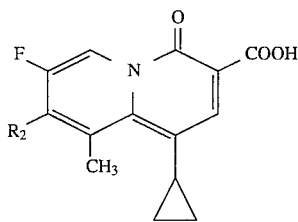
| Example # | R² |
|---|---|
| 375 | |
| 376 | |
| 377 | |
| 378 | |
| 379 | |
| 381 | |
| 382 | |
| 383 | |
| 384 | |
TABLE 13-continued
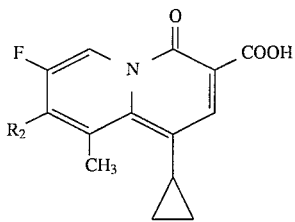
| Example # | R² |
|---|---|
| 385 | |
| 386 | |
| 387 | |
| 388 | |
| 389 | |
| 390 | |
| 391 | |
| 392 | |
| 393 | |
| 394 | |

TABLE 13-continued

[Structure: quinolizine core with F, R2, CH3, cyclopropyl, and COOH substituents]

| Example # | R² |
|---|---|
| 395 | [structure: F₃C-C(=O)- substituted pyrrolidinyl-N-methyl] |
| 396 | [structure: methylene pyrrolidinyl with H₂N] |
| 397 | [structure: dimethyl pyrrolidinyl with H₂N] |
| 398 | [structure: pyrrolinyl with H₂NCH₂-] |
| 399 | [structure: HO-N= pyrrolidinyl-N-methyl] |
| 400 | [structure: H₂N, SMe pyrrolidinyl] |
| 401 | [structure: H₂N cyclopenta-fused pyrrolinyl] |
| 402 | [structure: spiro HN-containing bicyclic pyrrolidinyl] |
| 403 | [structure: morpholine-like with NH, spiro pyrrolidinyl] |
| 404 | [structure: pyrazole-fused pyrrolidinyl] |
| 405 | [structure: H₂NCH₂, O pyrrolidinyl] |
| 406 | [structure: H₂NCH₂ cyclopenta-fused pyrrolidinyl] |
| 407 | [structure: vinyl-O pyrrolidinyl] |
| 408 | [structure: vinyl-S pyrrolidinyl] |
| 409 | [structure: H₂NCH₂ cyclopropane-fused pyrrolidinyl] |
| 410 | [structure: H₂N cyclopropyl-pyrrolidinyl] |
| 411 | [structure: HO-N= piperidinyl-N-methyl] |
| 412 | [structure: thiazoline-piperazinyl-N-methyl] |

EXAMPLE 413

(3R, 1S)-8-(3-(1-amino-2-methoxyethyl)pyrrolidinyl)-1-cyclopropyl-7-fluoro-9-methyl-4H-quinolizine-3-carboxylic acid hydrochloride Step 4 13a. (S)-N-BOC-O-(t-butyldimethylsilyl)serine methyl ester A 7 g (31.96 mmol) sample of ((S)-N-BOC-serine methyl ester (obtained from Aldrich) was dissolved in pyridine and cooled in an ice bath. To this stirred solution was added dropwise 5.54 g (36.76 mmol) of t-butyldimethylsilyl chloride (TBDMSC) dissolved in 40 mL of pyridine. After all reagents were added the reaction was stirred for 4 hours at room temperature. An additional 0.5 g of TBDMSC was added and the reaction was stirred for an additional 2 hours. To the mixture was then added 2.5 equivalents of imidazole in 14 mL of DMF, and the reaction was stirred for 2 hours. The solvents were removed under reduced pressure, and the residue was dissolved in ethyl acetate, which was washed with water and brine. The solvent was removed to give the title compound as a yellow oil. MS 334 (M+H)$^+$; $^1$H NMR (CDCl$_3$) δ:0.11 (s, 6H), 0.86 (s, 9H), 1.46 (s, 9H), 3.74 (s, 3H), 3.82 (dd, 1H). 4.04 (dd, 1H), 4.36 (m, 1H), 5.35 (br, 1H).

Step 413b. (S)-2-(BOC-amino)-3-(t-butyldimethylsilyloxy)-1-propanol

A solution of the compound from step 413a above (9.6 g, 28.83 mmol) in 44 mL of THF was added dropwise to a cooled (ice bath) suspension of 570 mg (14.84 mmol) of LAH in 15 mL of THF under N$_2$ atmosphere. The mixture was stirred for 1.5 hours, the reaction was quenched with water and 50% NaOH, filtered, and the filtrate evaporated to obtain the crude product. An oil was obtained, which was purified by chromatography on silica gel, eluting with 15–20% ethyl acetate:hexane to give 3.465 g of the title product as a colorless oil. MS 306 (M+H)$^+$; $^1$H NMR (CDCl$_3$) δ: 0.08(s, 6H), 0.90 (s, 9H), 1.45 (s, 9H), 2.68 (br, 1H), 3.68 (m, 2H), 3.81 (d, 2H), 3.85 (m, 1H), 5.15 (br, 1H).

Step 413c. (S)-2-(BOC-amino)-3-(t-butyldimethylsilyloxy)-1-propanol

To a solution of the compound from step 413b above (3.47 g, 11.36 mmol) in 6 mL of DMSO cooled to 0° C. was added dropwise 5.2 mL (37.49 mmol) of triethylamine. Pyridine.SO$_3$ complex (5.424 g, 34.08 mmol) was dissolved in 21 mL of DMSO and added to the first solution, and the reaction was stirred for 1.5 hours after the addition was complete. The solution was poured into 120 mL of cold brine, and the mixture was washed 3× with ethyl acetate. The extract was washed with water, dried over MgSO$_4$, filtered and the solvent was removed under vacuum to give 3.9 g of a yellow oil, which was taken directly to the next step.

Step 413d. (S)-4-(BOC-amino)-5-(t-butyldimethylsilyoxy)-2-pentenoic acid ethyl ester To a solution of the compound from step 413c above (11.36 mmol) in 24 mL of CH$_2$Cl$_2$ and cooled in an ice bath was added dropwise 3.958 g (11.36 mmol) of (carboethoxymethylene)triphenylphosphorane in 13 mL of CH$_2$Cl$_2$. After addition was complete, the reaction was stirred for 16 hours at room temperature. The solvent was removed, and the residue was purified by column chromatography on silica gel, eluting with 3–10% ethyl acetate:hexane, to give 3.93 g of a colorless oil. MS 374 (M+H)$^+$; $^1$H NMR (CDCl$_3$) δ: 0.05 (d, 6H), 0.88 (s, 9H), 1.27 (t, 3H), 1.46 (s, 9H), 3.72 (m, 2H), 4.19 (q, 2H), 4.36 (br, 1H), 5.98 (dd, 1H), 6.91 (dd, 1H).

Step 413e. (S)-4-(BOC-amino)-5-(t-butyldimethylsilyloxy)-3-(nitromethyl)-pentanoic acid ethyl ester To a solution of the compound from step 413d above (3.9 g, 10.46 mmol) in 6 mL of nitromethane cooled in an ice bath was added 1.56 mL (10.46 mmol) of 1,8-diazabicyclo[5.4.0]undec-7-ene dropwise under N$_2$. The mixture was warmed to room temperature and stirred for 16 hours. The solution was diluted with CH$_2$Cl$_2$ and extracted with water, 10% HCl, 10% NaHCO$_3$, water and brine. The solution was dried over MgSO4, and the solvent was removed. The residue was chromatographed on silica gel, eluting with 5–10% ethyl acetate:hexane, and the solvent was removed to give 3..6 g of the title product as a white solid. MS 435 (M+H)$^+$; $^1$H NMR (CDCl$_3$) δ: 0.09 (s, 6H), 0.91 (s, 9H), 1.28 (t, 3H), 1.45 (s, 9H), 2.45 (dd, 1H), 2.60 (dd, 1H), 2.93 (m, 1H), 3.68 (dd, 1H), 3.78 (dd, 1H), 3.84 (m, 1H), 4.15 (q, 2H), 4.52 (dd, 1H), 4.67 (dd, 1H), 4.84.

Step 413f. (S)-4-(BOC-amino)-5-(t-butyldimethylsilyloxy)-3-(aminomethyl)-pentanoic acid ethyl ester A 4.74 g sample of the compound from step 413e above was dissolved in 250 mL of ethanol and hydrogenated at 4 Atm over 14.2 g of Raney nickel catalyst for 24 hours. The catalyst was removed by filtration and the solvent was evaporated. The residue (mp 152°–154° C.) was taken directly to the next step.

Step 413g. (S)-4-(1-(BOC-amino)-2-(t-butyldimethylsilyloxy)ethyl)-2-oxo-4-pyrrolidine The residue from step 413f above was dissolved in 150 mL of ethanol and heated at reflux for 8 hours. The solvent was removed, the residue was chromatographed on silica gel, eluting with 4% methanol/methylene chloride. Removal of the solvent gave the title product.

Step 413h. (S)-4-(1-(BOC-amino)-2-(t-butyldimethylsilyloxy)ethyl)-1-benzyl-2-oxopyrrolidine A 200 mg (0.558 mg) sample of the compound from step 413g above was dissolved in 1 mL of THF and added dropwise to a 0° C. suspension of NaH (47 mg, 1.172 mmol) in 2 mL of THF, and the reaction mixture-was stirred for 1 hour. To this mixture was then added 124 mg of benzyl bromide, and the reaction was stirred at room temperature for 3 hours. The reaction was quenched with water, and .the mixture was extracted with ethyl acetate. The organic phase was acidified with citric acid solution, and the mixture was extracted with ethyl acetate. The solvent was washed with brine and dried over MgSO$_4$, filtered and evaporated. The residue was purified by column chromatography on silica gel, eluting with 30–35% ethyl acetate:hexane, to give 168 mg of the title compound. MS 449 (M+H)$^+$; $^1$H NMR (CDCl$_3$) δ: 0.03 (s, 6 H), 0.87 (s, 9H), 1.42 (s, 9H), 2.26 (dd, 1H), 2.52 (dd, 1H), 2.58 (m, 1H), 3.16 (br t, 1H), 3.27 (dd, 1H), 3.61 (br m, 3H), 4.28 (d, 1H), 4.59 (d, 1H), 4.70 (d, 1H), 7.23 (m, 2H), 7.32 (m, 3H).

Step 413i. (S)-4-(1-(BOC-amino)-2-hydroxyethyl)-1-benzyl-2-oxopyrrolidine

A 143 mg sample of the compound from step 4 13h above was dissolved in 1 mL of THF and reacted with 1 equivalent of tetra-n-butyl ammonium fluoride at room temperature for 1.5 hours. The solvent was removed, and the residue was dissolved in methylene chloride and purified by column chromatography on silica gel, eluting with 5% methanol in methylene chloride, to give 110 mg of the title compound. MS 335 (M+H)$^+$; $^1$H NMR (CDCl$_3$) δ: 1.42 (s, 9H), 2.28 (m, 1H), 2.59 (m, 3H), 3.15 (m, 1H), 3.31 (m, 1H), 3.61 (m, 2H), 3.70 (m, 1H), 4.30 (d, 1H), 4.58 (d, 1H), 4.78 (d, 1H), 7.23 (m, 2H), 7.32 (m, 3H).

Step 413j. (S)-4-(1-(BOC-amino)-2-methoxyethyl)-1-benzyl-2-oxopyrrolidine

A sample of the compound from step 413i above (7.34 mmol) was dissolved in 22 mL of THF and added to a suspension of 8.72 mg(16.148 mmol) of sodium methoxide in 40 mL of THF, and the reaction mixture was stirred at room temperature under nitrogen for 1 hour. To this solution was then added 3.958 g of methyl iodide in 5 mL of THF, and the reaction mixture was stirred for 16 hours. The solvents were removed under vacuum, and the residue was dissolved in ethyl acetate, which was washed with sodium thiosulfate and brine and dried over MgSO₄, filtered and evaporated. The residue was dissolved in methylene chloride and purified by column chromatography on silica gel, eluting with 5% methanol in methylene chloride, to give the title compound. MS 349 (M+H)⁺; ¹H NMR (CDCl₃) δ: 1.42 (s, 9H), 2.28 (dd, 1H), 2.56 (m, 3H), 3.14 (br t, 1H), 3.28 (dd, 1H), 3.30 (s, 3H), 3.37 (d, 2H), 3.71 (br, 1H), 4.24 (dd, 1H), 4.52 (dd, 1H), 4.80 (d, 1H), 7.23 (m, 2H), 7.31 (m, 3H).

Step 413k. (S)-4-(1-(BOC-amino)-2-methoxyethyl-1-benzyl-2-thioxopyrrolidine

A 50 mg (0.14 mmol) sample of the compound from step 413j above and 29 mg (0.07 mmol) of Lawesson's reagent were dissolved in 0.3 mL of THF and stirred under N₂ for 3 hours. The solvent was removed, and the residue was dissolved in CH₂Cl₂ and chromatographed on silica gel, eluting with 30% ethyl acetate:hexane. Removal of the solvent left 51 mg of product. MS 365 (M+H)⁺; ¹H NMR (CDCl₃) δ: 1.41 (s, 9H), 2.64 (dd, 1H), 2.87 (dd, 1H), 3.16 (dd, 1H), 3.29 (s, 3H), 3.36 (d,2H), 3.55 (m, 2H), 3.70 (m, 1H0, 4.70 (d, 1H), 4.83 (d, 1H), 5.21 (d, 1H), 7.33 (m, 5H).

Step 413l. (S)-3-(1-(BOC-amino)-2-methoxyethyl)-1-benzylpyrrolidine

A 45.7 mg (0.125 mmol) sample of the compound from step 413k above and 239 mg (1.0 mmol) of NiCl2.6H₂O were dissolved in 2 mL of a 1:1 mixture of methanol and THF, and the solution was cooled to −78° C. and stirred under N₂. A 114 mg (3.0 mmol) sample of NaBH₄ was added in portions, and the mixture was stirred for 2 hours. The solvents were removed under vacuum, and dissolved in 20% methanol in chloroform. The solution was filtered and the solvent removed. The residue was chromatographed on silica gel, eluting with 5% methanol in chloroform to provide 23 mg of title product. MS 335 (M+H)⁺; ¹H NMR (CDCl₃) δ: 1.45 (s, 9H), 2.01 (m, 1H), 2.37 (m, 1H), 2.49 (m, 2H), 2.61 (m, 1H), 2.71 (m, 1H), 3.32 (s, 3H), 3.35 (m, 2H), 3.44–3.67 (m, 4H), 7.23–7.33 (m, 5H).

Step 413m. (S)-3-(1-(BOC-amino)-2-methoxyethyl)-pyrrolidine

A 203 mg sample of the compound from step 413l above was dissolved in 25 mL of methanol and hydrogenated at 4 Atm over 50 mg of 10% Pd/C catalyst for 22 hours. The catalyst was removed by filtration and the solvent was evaporated to give 160 mg of the title compound as a viscous oil. MS 245 (M+H)⁺; ¹H NMR (CD₃OD) δ:1.43 (s, 9H), 1.92 (m, 1H), 2.24 (m, 1H), 2.43 (m, 1H), 2.75 (m, 1H), 2.90(m, 1H).

Step 413n. (3R, 1S)-8-(3-(1-amino-2-methoxyethyl)pyrrolidinyl)-1-cyclopropyl-7-fluoro-9-methyl-4-oxo-4H-quinolizine-3-carboxylic acid hydrochloride A 77 mg (0.238 mmol) sample of 8-chloro-1-cyclopropyl-7-fluoro-9-methyl-4-oxo-4H-quinolizine-3-carboxylic acid ethyl ester, from Example 253i above, was reacted with the (S)-3-(1-(BOC-amino)-2-methoxyethyl)-pyrrolidine from step 4 13m above and carded forward as described in Example 253 steps j–l, to give 62 mg of the title product. mp. 62°–64° C. HRMS calc: 404.1986; found: 404.1990 (M+H)⁺; ¹H NMR (D₆-DMSO) δ: 0.60 (m, 2H), 0.94, (m, 1H), 2.13 (m, 1H), 2.28 (m, 2H), 2.61 (s, 3H), 3.26 (s, 3H), 3.52 (m, 2H), 3.62 (dd, 1H), 3.71 (m, 2H), 3.91 (m, 1H), 7.91 (s, 1H), 8.10 (br, 2H), 9.08 (d, 1H).

EXAMPLE 414

8-(3-(S)-(acetylamino)pyrrolidinyl)-1-cyclopropyl-7-fluoro-4H-9-methyl-4-oxo-quinolizine-3-carboxylic acid To a 290 mg sample of 8-(3-(S)-aminopyrrolidinyl)-1-cyclopropyl-7-fluoro-9-methyl-4-oxo-4H-quinolizine-3-carboxylic acid, prepared from the HCl salt of Example 257 above, suspended in 4 mL of THF was added 0.342 mL of acetic anhydride dropwise with stirring. The reaction mixture was stirred for 3.5 hours, and the precipitate was separated by filtration dried under vacuum to give 196 mg of the title compound. mp. 116°–117° C. MS 388 (M+H)⁺; ¹H NMR (CDCl₃) δ: 0.65 (m, 1H), 0.80 (m, 1H), 1.00 (m, 1H), 1.10 (m, 1H), 2.03 (s, 3H), 2.20 (m, 2H), 2.35 (m, 1H), 2.60 (s, 3H), 3.73 (m, 2H), 4.10 (m, 2H), 4.60 (m, 1H), 7.48 (d, 1H, J=6 Hz), 7.75 (s, 1H), 8.83 (d, 1H, J=12 Hz), 13.95 (s, 1H). Analysis calculated for C₂₀H₂₂FN₃O₄.1.5 H₂O: C, 58.60; H, 6.02; N, 10.25. Found: C, 58.89; H, 5.85; N, 10.02.

EXAMPLE 415

8-(3-carbamoylpiperidinyl)-1-cyclopropyl-7-fluoro-4H-9-methyl-4-oxo-quinolizine-3-carboxylic acid Step 415a. 8-(3-carbamoylpiperidinyl)-1-cyclopropyl-7-fluoro-4H-9-methyl-4-oxo-quinolizine-3-carboxylic acid, ethyl ester A 971 mg sample of 8-chloro-1-cyclopropyl-7-fluoro-9-methyl-4-oxo-4H-quinolizine-3-carboxylic acid ethyl ester, prepared as in Example 253i above, was dissolved in 10 mL of DMF and placed in an oven-dried system under positive N₂ atmosphere. To this was added 1.15 g of nicotinamide (Aldrich) and 0.900 mL of triethylamine. The reaction mixture was heated at 55° C. with stirring for 24 hours. The reaction was quenched with water, and the mixture was extracted with methylene chloride. After washing with water, the organic solution was dried over Na₂SO₄ and filtered. The solvent was removed under vacuum to give the title compound as a yellow solid (1.138 g).

Step 415b. 8-(3-carbamoylpipefidinyl)-1-cyclopropyl-7-fluoro-4H-9-methyl-4-oxo-quinolizine-3-carboxylic acid A 442 mg sample of the compound from step 415a above was hydrolyzed with LiOH in THF/H₂O and the title product (308 mg) was isolated as described in Example 253 k. mp. 250°–251° C. MS 388 (M+H)⁺; ¹H NMR (CDCl₃) δ: 0.70 (m, 2H), 1.05 (m, 2H), 1.05 (m, 2H), 1.85 (m, 2H), 2.20 (m, 2H), 2.60 (m, 2H), 2.72 (s, 3H), 3.25–3.50 (m, 4H), 3.60 (m, 1H), 5.35 (s, 1H), 5.80 (s, 1H), 5.80 (s, 1H), 8.25 (s, 1H), 9.30 (d, 1H, J=14 Hz), 13.90 (s, 1H). Analysis calculated for C₂₀H₂₂FN₂O₄.0.75 H₂O: C, 59.92; H, 5.91; N; 10.48. Found: C, 60.18; H, 5.89; N, 10.62.

EXAMPLE 416

8-(3-hydroxypiperidinyl)-1-cyclopropyl-7-fluoro-4H-9-methyl-4-oxo-quinolizine-3-carboxylic acid A 2.0 g sample of 8-chloro-1-cyclopropyl-7-fluoro-9-methyl-4-oxo-4H-quinolizine-3-carboxylic acid ethyl ester, prepared as in Example 253i above, was dissolved in 25 mL of DMF and placed in an oven-dried system under positive N₂ atmosphere. To this was added 1.1 g of 3-hydroxypiperidine (Aldrich) and 1.8 mL of triethylamine. The reaction mixture was heated at 55° C. with stirring for 144 hours. The reaction was quenched with water, and the mixture was extracted with methylene chloride. After washing with water, the organic solution was dried over Na₂SO₄ and faltered. The solvent was removed under vacuum to give the intermediate ester compound as an oil (3 g). MS 389 (M+H)⁺. This ester was purified by chromatography on silica gel, after which the intermediate was hydrolyzed and the product isolated (1.34 g) as described in Example 415 above. mp. 232°–233° C. MS 361 (M+H)+; $^1$H NMR (CDCl$_3$) δ:0.70 (m, 2H), 1.03 (m, 2H), 1.75 (m, 2H), 1.90 (m, 1H), 2.08 (m, 2H), 2.28 (m, 1H), 2.81 (s, 3H), 3.25 (m, 2H, J=3, 9 Hz), 3.38 (m, 2H), 3.62 (d, 1H, J=12 Hz), 3.95 (s, 1H), 4.70 (br s, 1H), 8.32 (s, 1H), 9.20 (d, 1H, J=9 Hz), 14.90 (s, 1H). Analysis calculated for C$_{19}$H$_{21}$FN$_2$O$_4$.H$_2$O: C, 60.31; H, 6.13; N, 7.40. Found: C, 59.92; H, 5.79; N, 7.14.

EXAMPLE 417

8-(3-hydroxymethylpiperidinyl)-1-cyclopropyl-7-fluoro-4H-9-methyl-4-oxo-quinolizine-3-carboxylic acid A 0.971 g sample of 8-chloro-1-cyclopropyl-7-fluoro-9-methyl-4-oxo-4H-quinolizine-3-carboxylic acid ethyl ester, prepared as in Example 253i above, was dissolved in 10 mL of DMF and placed in an oven-dried system under positive N$_2$ atmosphere. To this was added 1.04 g of 3-piperidinemethanol (Aldrich) and 0.900 mL of triethylamine. The reaction mixture was heated at 55° C. with stirring for 72 hours. The reaction was quenched with water, and the mixture was extracted with methylene chloride. After washing with water, the organic solution was dried over Na$_2$SO$_4$ and filtered. The solvent was removed under vacuum to give the intermediate ester compound as an oil (1.25 g). MS 403 (M+H)+. This ester was purified by chromatography on silica gel, after which the intermediate was hydrolyzed and the product isolated (785 mg) as described in Example 415 above. mp. 133°–134° C. MS 375 (M+H)+; $^1$H NMR (CDCl$_3$) δ:0.70 (m, 2H), 1.03 (m, 2H), 1.30 (m, 1H), 1.58 (m, 2H), 1.75–2.08 (m, 3H), 2.13 (m, 1H), 2.90 (s, 3H), 3.15 (m, 1H, J=1.5, 9 Hz), 3.30 (m, 1H, J=1.5, 9 Hz), 3.50 (m, 1H), 3.60 (m, 1H), 3.70 (m, 2H), 8.30 (s, 1H), 9.15 (d, 1H<J=10 Hz), 13.92 (s, 1H). Analysis calculated for C$_{20}$H$_{23}$FN$_2$O$_4$.0.25 H$_2$O: C, 63.40; H, 7.39; N, 6.24. Found: C, 63.25; H, 7.29; N, 6.25.

EXAMPLE 418

8-(3-(R)-hydroxypiperidinyl)-1-cyclopropyl-7-fluoro-4H-9-methyl-4-oxo-quinolizine-3-carboxylic acid A 0.971 g sample of 8-chloro-1-cyclopropyl-7-fluoro-9-methyl-4-oxo-4H-quinolizine-3-carboxylic acid ethyl ester, prepared as in Example 253i above, was dissolved in 10 mL of DMF and placed in an oven-dried system under positive N$_2$ atmosphere. To this was added 1.23 g of 3-(R)-(+)-hydroxypiperidine (Aldrich) and 0.900 mL of diethylamine. The reaction mixture was heated at 55° C. with stirring for 72 hours. The reaction was quenched with water, and the mixture was extracted with methylene chloride. After washing with water, the organic solution was dried over Na$_2$SO$_4$ and filtered. The solvent was removed under vacuum to give the intermediate ester compound as an oil (1.56 g). This ester was purified by chromatography on silica gel, after which the intermediate was hydrolyzed and the product isolated (785 mg) as described in Example 415 above. mp. 192°–193° C. MS 361 (M+H)$^{30}$; $^1$H NMR (CDCl$_3$) δ: 0.70 (m, 2H), 1.02 (m, 2H), 1.75 (m, 2H), 1.90 (m, 1H), 2.05 (m, 1H), 2.28 (m, 1H), 2.80 (s, 3H), 3.20 (m, 2H, J=2, 9 Hz), 3.38 (m, 2H), 3.62 (dt, 1H, J=12, 1.5 Hz), 3.90 (m, 1H), 4.60 (br s, 1H), 8.34 (s, 1H), 9.20 (d, 1H, J=10 Hz), 13.85 (s, 1H). Analysis calculated for C$_{19}$H$_{21}$FN$_2$O$_4$.1.25 H$_2$O: C, 59.60; H, 6.19; N, 7.32. Found: C, 59.30; H, 5.94; N, 7.29.

EXAMPLE 419

(3R)-9-fluoro-3-methyl-10-(piperazin-1-yl)-2H, 3H, 6H -6-oxo-pyrano[2,3,4-ij]quinolizine-5-carboxylic acid hydrochloride Following the procedure of Example 281f, replacing the 3-(BOC-amino)pyrrolidine of that step with N-BOC-piperazine and carrying the product forward according to steps 281g and h, the title compound was prepared. MS 348 (M+H)+; $^1$H NMR (DMSO-d$_6$) δ:12.9 (d, J=7 Hz, 3H), 3.25 (m, 4H), 3.31 (m, 1H), 3.70 (m, 4H), 4.19 (dd, J=6, 11 Hz, 1H), 4.37 (dd, J=4, 11 Hz, 1H), 8.03 (s, 1H), 9.04 (d, J=9 Hz, 1H), 9.12 (br s, 2H). Analysis calculated for C$_{17}$H$_{18}$FN$_3$O$_4$.2.0 H$_2$O: C, 48.63; H, 5.52; N, 10.01. Found: C, 48.92; H, 5.57; N, 9.80.

EXAMPLE 420

1-cyclopropyl-8-(S,S-2,8-diaza-8-bicyclo[4,3,0] nonyl-7-fluoro-4H-9-methyl-4-oxo-quinolizine-3-carboxylic acid hydrochloride Step 420a. 6-(1-(S)-phenylethyl))-5,7-dihydro-6H-pyrrolo [3,4-b]pyridine-5,7-dione A 10 g sample of 2,3-pyridinedicarboxylic anhydride (Aldrich) was dissolved in 100 mL of anhydrous THF and cooled to 0° C. To this solution was added 8.70 mL of (S)-(–)-alpha-methylbenzylamine. The solution was warmed to room temperature and stirred for 30 minutes, then 11.96 g of 1,1'-carbonyldiimidazole was added. The reaction was stirred at room temperature under N$_2$ for 20 hours. The solvent was removed, and the residue was dissolved in methylene chloride. The solvent was washed with water and dried over MgSO$_4$. The solvent was removed under vacuum to give 15.344 g of the title compound.

Step 420b. 8-(1-(S)-phenylethyl-2,8-diazobicyclo[4,3,0] nonan-7,9-dione

A 15.344 g sample of the compound from step 420a above was hydrogenated in over Pd/C in 2-methoxyethanol at 4 atm H$_2$ and 100° C. for 22 hours. The catalyst and solvent were removed to give 10.12 g of the title compound.

Step 420c. 8-((1-(S)-phenylethyl)-2,8-diazobicyclo[4,3,0] nonane

A 10.12 g sample of the compound from step 420b was dissolved in 30 mL of THF, and this solution was added dropwise to a suspension of 3.13 g of LAH in 50 mL of anhydrous THF stirred at 0° C. under N$_2$. After addition was complete, the mixture was heated at reflux for 9 hours. The reaction was quenched at 0° C. by sequential addition of 25 mL of H$_2$O, 25 mL of 15% KOH and 25 mL of H$_2$O. The solids were removed by filtration, and the filtrate was extracted with ether. The extract was dried over MgSO$_4$, and the solvent was removed to give 7.98 g of the title compound.

Step 420d. 2-BOC-8-((1-(S)-phenylethyl)-2,8-diazobicyclo [4,3,0]nonane

A 7.98 g sample of the compound from step 40c above was dissolved in 75 mL of 2:1 methanol:H$_2$O. The solution was cooled to 0° C., and 7.94 g of di-t-butyl dicarbonate was added. The mixture was then warmed to room temperature and stirred for 1 hour. The organic solvent was removed under vacuum, and the residue was slurried with methylene chloride. The organic phase was separated, washed and dried. The solvent was removed, and the residue was purified by chromatography on silica gel, eluting with 100:5:0.5 methylene chloride:methanol:ammonium hydroxide, to give 4.6 g of the title compound as an oil. This material was separated into the 1,6-(R,R)- and 1,6-(S,S)-isomers by HPLC using a chiral support. The R,R-isomer had an $[\alpha]_D$ of +31.9° C. (23°, c=1.01, methanol); The S,S-isomer had an $[\alpha]_D$ of −84.6° C. (23°, c=1.04, methanol) (for additional information on assignment of isomers, refer to Poster #642, ICAAC 32nd Annual Meeting, 1994).

Step 420e. (S,S)-2-BOC-2,8-diazobicyclo[4,3,0]nonane

A 1.328 g sample of the S,S-isomer from step 420d above and 1.27 g of ammonium formate were dissolved in 40 mL of methanol. The flask was flushed with $N_2$, 130 mg of 10% Pd/C was added, and the reaction mixture was heated at reflux for 1.5 hours. The solution was cooled and filtered, then the solvent was removed. The residue was dissolved in methylene chloride and filtered again. The solvent was removed under vacuum to give the title compound (858 mg). $[\alpha]_D$ −70.8° C. (23°, c=1.30, methanol).

Step 420f. 1-cyclopropyl-8-(S,S-2,8-diaza-8-bicyclo[4,3,0]nonyl)-7-fluoro-4H-9-methyl-4-oxo-quinolizine-3-carboxylic acid hydrochloride Following the procedure of Example 253j, substituting 1,6-(S,S)-2-BOC-2,8-diazobicyclo[4,3,0]nonane from step 420e above, for the BOC-aminopyrrolidine thereof, and carrying the product forward as in steps 253k and l, the title compound was prepared. $[\alpha]_D$ −281.3° C (23°, c=0.52, methanol). MS 386 (M−Cl)$^+$; $^1$H NMR (DMSO-d$_6$) δ:0.56 (m, 1H), 0.62 (m, 1H), 0.92 (m, 1H), 1.07 (m, 1H), 1.61–1.81 (m, 4H), 2.30 (m, 1H), 2.56 (m, 1H), 2.67 (s, 3H), 2.92 (m, 1H), 3.25 (m, 1H), 3.69 (m, 2H), 3.90 (m, 1H), 4.06 (m, 1H), 4.35 (m, 1H), 7.92 (s, 1H), 9.02 (br, 1H), 9.09 (d, J=11 Hz, 1H), 9.59 (br, 1H). Analysis calculated for $C_{21}H_{24}FN_3O_3 \cdot HCl \cdot 1.25\ H_2O$: C, 56.76; H, 6.24; N, 9.45. Found: C, 56.73; H, 6.05; N, 9.44.

EXAMPLE 421

1-cyclopropyl-8-(R,R-2,8-diaza-8-bicyclo-[4,3,0]nonyyl)-7-fluoro-4H-9-methyl-4-oxo-quinolizine-3-carboxylic acid hydrochloride Step 421a. (R,R)-2-BOC-2,8-diazobicyclo[4,3,0]nonane Following the procedure of Example 420e above, a 1.864 g sample of the R,R-isomer from Example 420d above deprotected to give 1.219 g of the title product. $[\alpha]_D$ +73.6° C. (23°, c=1.15, methanol). Spectral data similar to the compound of Example 420e was obtained.

Step 421b. 1-cyclopropyl-8-(R,R-2,8-diaza-8-bicyclo[4,3,0]nonyl)-7-fluoro-4H-9-methyl-4-oxo-quinolizine-3-carboxylic acid hydrochloride Following the procedure of Example 253j, substituting (R,R)-2-BOC-2,8-diazobicyclo[4,3,0]nonane from step 421a above, for the BOC-aminopyrrolidine thereof, and carrying the product forward as in steps 253k and l, the title compound was prepared. $[\alpha]_D$ +275.1° C (23°, c=0.53, methanol). MS 386 (M−Cl)$^+$. $^1$H NMR (DMSO-d$_6$) δ: 0.56 (m, 1H), 0.62 (m, 1H), 0.92 (m, 1H), 1.08 (m, 1H), 1.63–1.81 (m, 4H), 2.31 (m, 1H), 2.56 (m, 1H), 2.68 (s, 3H), 2.91 (m, 1H), 3.25 (m, 1H), 3.69 (m, 2H), 3.90 (m, 1H), 4.06 (m, 1H), 4.35 (m, 1H), 7.92 (s, 1H), 9.02 (br, 1H), 9.09 (d, J=1 1 Hz, 1H), 9.60 (br, 1H). Analysis calculated for $C_{21}H_{24}FN_3O_3 \cdot HCl \cdot 1.5\ H_2O$: C, 56.19; H, 6.29; N, 9.36. Found: C, 56.19; H, 6.15; N, 9.44.

EXAMPLE 422

1-cyclopropyl-8-(1-amino-3-aza-bicyclo[3,1,0]hexan-3-yl)-7-fluoro-4H-9-methyl-4-oxo-quinolizine-3-carboxylic acid hydrochloride Step 422a. 1-cyclopropyl-8-(1-BOC-amino-3-aza-bicyclo[3,1,0]hexan-3-yl)-7-fluoro-4H-9-methyl-4-oxo-quinolizine-3-carboxylic acid, ethyl ester A 660 mg sample of 8-chloro-1-cyclopropyl-7-fluoro-9-methyl-4-oxo-4H-quinolizine-3-carboxylic acid ethyl ester, from Example 253i above, was placed in a flask, then 400 mg of 1-(BOC-amino)-3-azabicyclobicyclo[3,1,0]hexane, prepared according to U.S. Pat. No. 5,164,402, was dissolved in 15 mL of dry THF and added to the flask. Lastly 2.2 mL of triethylamine was added, and the solution was stirred at 5° C. for 26 hours. The reaction was cooled, quenched with 15 mL of $H_2O$, and the mixture was extracted with ethyl acetate. The organic extracts were dried over $MgSO_4$, and the solvent was removed under vacuum. The residue was purified by chromatography on silica gel, eluting with 3–5% methanol in methylene chloride, to give 350 mg of the title compound. MS 486 (M+H)$^+$. $^1$H NMR (CDCl$_3$) δ: 0.61 (m, 2H), 0.9–1.11 (m, 4H), 1.41 (t, J=7.5 Hz, 3H), 1.48 (s, 9H), 1.8 (br, 1H), 2.19 (m, 1H), 2.62 (s, 3H), 3.59 (d, J=10.5 Hz, 1H), 3.73 (d, J=10.5 Hz, 1H), 3.8 (br, 1H), 4.0 (br, 1H), 4.4 (q, J=7.5 Hz, 2H), 5.05 (br, 1H), 8.21 (s, 1H), 9.26 (d, J=10.5, 1H).

Step 422b. 1-cyclopropyl-8-(1-BOC-amino-3-aza-bicyclo[3,1,0]hexan-3-yl)-7-fluoro-4H-9-methyl-4-oxo-quinolizine-3-carboxylic acid Following the procedure of Example 253k, substituting the compound of step 422a for the starting material thereof, the title compound was prepared. MS 458 (M+H)$^+$. $^1$H NMR (CDCl$_3$) δ: 0.67 (m, 2H), 1.0 (m, 3H), 1.1 (m, 1H), 1.48 (s, 9H), 1.82 (br, 1H), 2.22 (m, 1H), 2.68 (s, 3H), 3.64 (d, J=10.5 Hz, 1H), 3.79 (d, J=10.5 Hz, 1H), 3.85 (br, 1H), 4.05 (br, 1H), 5.05 (br, 1H), 8.35 (s, 1H), 9.14 (d, J=10 Hz, 1H), 13.86 (br, 1H).

Step 422c. 1-cyclopropyl-8-(1-amino-3-aza-bicyclo[3,1,0]hexan-3-yl-7-fluoro-4H-9-methyl-4-oxo-quinolizine-3-carboxylic acid hydrochloride Following the procedure of Example 253l, substituting the compound of step 422b for the starting material thereof, the title compound was prepared. MS 358 (M+H)$^+$. $^1$H NMR (DMSO-d$_6$) δ: 0.62 (m, 2H), 0.98 (m, 3H), 1.31 (m, 1H), 2.04 (m, 1H), 2.37 (m, 1H), 2.63 (s, 3H), 3.62 (m, 1H), 3.8–4.0 (m, 3H), 8.01 (s, 1H), 8.81 (br, 2H), 9.16 (d, J=10, 1H), 13.82 (br, 1H). Analysis calculated for $C_{19}H_{21}FN_3O_3 \cdot HCl \cdot 1.5\ H_2O$: C, 54.22; H, 5.75; N, 9.98. Found: C, 54.10; H, 5.61; N, 9.86.

EXAMPLE 423

8-(3-amino-3-fluoromethyl-1-pyrrolidinyl)-1-cyclopropyl-7-fluoro-4H-9-methyl-4-oxo-quinolizine-3-carboxylic acid hydrochloride Step 423a. 2-fluoromethylpropenoic acid ethyl ester A 2.632 g (20 mmol) sample of 2-hydroxymethylpropenoic acid ethyl ester (prepared according to Villieras and Rambaud, *Synthesis*, 1982, 924) was dissolved in 35 mL of methylene chloride, and the solution was cooled to −78° C. To this solution was added 2.94 mL (22 mmol) of DAST, and the reaction mixture was stirred at −78° C. for 30 minutes and at room temperature for 1 hour. The reaction was quenched with $H_2O$ (35 mL), and the layers were separated. The organic solution was washed with brine, dried over $MgSO_4$, then the solvent was removed to give 2.343 g of the title compound. $^1$H NMR (CDCl$_3$) δ: 1.32 (t, J=7.5 Hz, 3H), 4.26 (q, J=7.5 Hz, 2H), 5.08 (d, J=46 Hz, 2H), 5.93 (m, 1H), 6.39 (m, 1H).

Step 423b. 1-benzyl-3-fluoromethyl-3-pyrrolidine carboxylic acid ethyl ester

A 739 mg (6 mmol) sample of the compound from step 423a and 1.327 g (6 mmol) of N-benzyl-N-(methoxymethyl)trimethylsilylmethylamine were dissolved in 4 mL of methylene chloride. This solution was cooled to 0° C., and 0.56 mL of 1N trifluoroacetic acid in methylene chloride was added slowly. The reaction mixture was stirred for 75 minutes at 0°–2° C. The solution was diluted with methylene chloride and washed with saturated NaHCO$_3$ solution and water, then dried over MgSO$_4$. The solvent was removed, and the residue was purified by chromatography on silica gel, eluting with 4:1 hexane:ethyl acetate, to obtain 875 mg of the title compound. MS 266 (M+H)$^+$. $^1$H NMR (CDCl$_3$) δ: 1.27 (t, J=7.5 Hz, 3H), 1.8 (m, 1H), 2.25 (m, 1H), 2.51 (m, 1H), 2.75 (m, 3H), 3.62 (s, 2H), 4.20 (q, J=7.5 Hz, 2H), 4.45 (q, J=8.7 Hz, 1H), 4.61 (q, J=8.7 Hz, 1H), 7.3 (m, 5H).

Step 423c. 3-fluoromethyl-3-pyrrolidine carboxylic acid ethyl ester

A 875 mg sample of the compound from step 423b above and 1.04 g of ammonium formate were dissolved in 30 mL of ethanol. The flask was flushed with N$_2$, 200 mg of Pd/C were added, and the mixture was heated at reflux for 15 minutes. The mixture was cooled, filter, and the solvent was removed to give 454 mg of the title compound. MS 176 (M+H)$^+$. $^1$H NMR (CDCl$_3$) δ: 1.29 (t, J=7.5, 3H), 1.8 (m, 1H), 2.15 (m, 1H), 2.95 (m, 2H), 3.08 (m, 1H), 3.32 (m, 1H), 4.2 (q, J=7.5 Hz, 2H), 4.48 (m, 1H), 4.63 (m, 1H).

Step 423d. 1-CBZ-3-fluoromethyl-3-pyrrolidine carboxylic acid ethyl ester

A 450 mg sample of the compound from step 423c above was dissolved in 4 mL of 1:1 dioxane:water, 324 mg of Na$_2$CO$_3$ was added, and the solution was cooled to 0° C. To this solution was added dropwise 0.44 mL of benzyloxycarbonyl chloride, and the reaction mixture was stirred at 0° C. for 45 minutes and at room temperature for 3 hours. The solution was diluted with ether, and the mixture was washed sequentially with water, saturated NaHCO$_3$, water and saturated brine. The ether layer was separated, and the solvent was removed. The residue was purified by chromatography on silica gel, eluting with 1:3 ethyl acetate:hexane to give 666 mg of the title compound. MS 3 10 (M+H)$^+$. $^1$H NMR (CDCl$_3$) δ: 1.28 (t, J=7.5 Hz, 3H), 2.05 (m, 1H), 2.32 (m, 1H), 3.55 (m, 3H), 3.84 (dd, J=3, 12 Hz, 1H), 4.22 (q, J=7.5 Hz, 2H), 4.48 (m, 1H), 4.61 (m, 1H), 5.14 (s, 2H), 7.35 (m, 5H).

Step 423e. 1-CBZ-3-fluoromethyl-3-pyrrolidinecarboxylic acid

A 550 mg sample of the compound from step 423d above was dissolved in 4 mL of THF, and the solution was cooled to 0° C. To this solution was added 173 mg of LiOH and 1 mL of H$_2$O. The reaction mixture was stirred at room temperature for 3 hours, then acidified by the addition of 1N HCl. The mixture was diluted with 40 mL of ethyl acetate, and the layers were separated. The organic solution was washed with water and saturated brine, and the solvent was removed. The residue was purified by chromatography on silica gel, eluting with 10% methanol in methylene chloride to give 251 mg of the title compound. MS 282 (M+H)$^+$. $^1$H NMR (CDCl$_3$) δ: 2.05 (m, 1H), 2.35 (m, 1H), 3.55 (m, 3H), 3.89 (m, 1H), 4.5 (m, 1H), 4.65 (m, 1H), 5.12 (s, 1H), 7.37 (m, 5H).

Step 423f. N-BOC-1-CBZ-3-fluoromethyl-3-pyrrolidineamine

A 715 mg sample of the compound from step 423e above was dried under vacuum and dissolved in 8 mL of distilled t-butanol. To this solution were added 0.71 mL of triethylamine and 0.81 mL of dppa, and the mixture was refluxed for 16 hours under a N$_2$ atmosphere. The reaction mixture was cooled and diluted with ether, and the mixture was washed with water, saturated NaHCO$_3$ and saturated brine. The solvent was removed, and the residue was purified by chromatography on silica gel, eluting with 1:4 ethyl acetate:hexane to give 587 mg of the title compound. MS 353 (M+H)$^+$. $^1$H NMR (CDCl$_3$) δ: 1.44 (s, 9H), 2.1 (m, 2H), 3.55 (m, 4H), 4.48 (m, 1H), 4.63 (m, 1H), 5.12 (s, 2H), 7.35 (m, 5H).

Step 423g. 3-(BOC-amino)-3-fluoromethylpyrrolidine

A 183 mg sample of the compound from step 423f above and 164 mg of ammonium formate were dissolved in 8 mL of ethanol. The flask was flushed with N$_2$, 50 mg of Pd/C were added, and the mixture was heated at reflux for 20 minutes. The mixture was cooled and filtered, and the solvent was removed to give 101 mg of the title compound. MS 219 (M+H)$^+$. $^1$H NMR (CDCl$_3$) δ: 1.45 (s, 9H), 1.6 (b, 1H), 1.92 (m, 2H), 2.95 (m, 2H), 3.1 (m, 2H), 4.5 (d, J=48 Hz, 1H), 4.75 (b, 1H).

Step 423h. 8-(3-(BOC-amino)-3-fluoromethyl-1-pyrrolidinyl)-1-cyclopropyl-7-fluoro-4H-9-methyl-4-oxo-quinolizine-3-carboxylic acid ethyl ester A 120 mg (0.37 mmol) sample of 8-chloro-1-cyclopropyl-7-fluoro-9-methyl-4-oxo-4H-quinolizine-3-carboxylic acid ethyl ester, from Example 253i above, was placed in a flask. To his flask was then added a solution of 95 mg of 3-(BOC-amino)-3-fluoromethylpyrrolidine, from step 423g above, dissolved in 3 mL of DMF, and 0.30 mL of triethylamine. The reaction mixture was heated at reflux for 16 hours, then the reaction was quenched with 4 mL of water. The mixture was cooled and extracted with ethyl acetate. The extract was dried over MgSO$_4$, and the solvent was removed. The residue was purified by chromatography on silica gel, eluting with 2–5% methanol in methylene chloride, to give 143 mg of the tile compound. MS 506 (M+H)$^+$. $^1$H NMR (CDCl$_3$) δ: 0.62 (m, 2H), 0.96 (m, 2H), 1.35 (m, 1H), 1.42 (t, J=7.5 Hz, 3H), 1.46 (s, 9H), 2.2 (m, 2H), 2.35 (m, 1H), 2.65 (s, 3H), 3.73 (m, 1H), 3.85 (b, 1H), 3.9 (m, 1H), 4.4 (q, J=7.5 Hz, 2H), 4.65 (d, J=48 Hz, 2H), 4.85 (b, 1H), 8.21 (s, 1H), 9.29 (d, J=10.5 Hz, 1H).

Step 423i. 8-(3-(BOC-amino)-3-fluoromethyl-1-pyrrolidinyl)-1-cyclopropyl-7-fluoro-4H-9-methyl-4-oxo-quinolizine-3-carboxylic acid Following the procedure of Example 253k, substituting 143 mg of the compound of step 423h for the starting material thereof, 115 mg of the title compound was prepared.

Step 423j. 8-(3-amino-3-fluoromethyl-1-pyrrolidinyl)-1-cyclopropyl-7-fluoro-4H-9-methyl-4-oxo-quinolizine-3-carboxylic acid hydrochloride Following the procedure of Example 253l, substituting 115 mg of the compound of step 423i for the starting material thereof, 95.5 mg of the title compound was prepared. MS 378 (M+H)$^+$. $^1$H NMR (DMSO-d$_6$) δ: 0.60 (m, 2H), 1.0 (m, 2H), 2.27 (m, 2H), 2.34 (m, 1H), 2.67 (s, 3H), 3.85 (m, 2H), 4.04 (m, 2H), 4.78 (d, J=46 Hz, 2H), 7.97 (s, 1H), 8.91 (b, 2H), 9.13 (d, J=10.5 Hz, 1H), 13.85 (b, 1H). Analysis calculated for C$_{19}$H$_{21}$F$_2$N$_3$O$_3$.2 HCl.0.5 H$_2$O: C, 49.68; H, 5.27; N, 9.15. Found: C, 49.66; H, 5.23; N, 8.91.

EXAMPLE 424

8-(3-aminomethyl-3-fluoro-1-pyrrolidinyl)-1-cyclopropyl-7-fluoro-4H-9-methyl-4-oxo-quinolizine-3-carboxylic acid Following the procedure of Example 253j, substituting 68 mg of 3-amino-3-fluoromethylpyrrolidine, prepared as in PCT patent application WO9414794, for the BOC-aminopyrrolidine thereof, and carrying the product forward as in step 253k, the title compound was prepared (note rearrangement of positions of F and amino groups on the pyrrolidine ring). MS 378 (M+H)$^+$. $^1$H NMR (DMSO-d$_6$) δ: 0.6 (m, 2H), 0.9 (m, 1H), 1.05 (m, 1H), 1.25 (m, 1H), 2.2–2.5 (m, 2H), 2.64 (s, 3H), 3.4 (m, 2H), 3.81 (m, 2H), 4.15 (m, 2H), 7.95 (s, 1H), 8.4 (b, 2H), 9.1 (d, J=10.5 Hz, 1H), 10.2 (s, 1H).

EXAMPLE 425

8-(3-(S)-hydroxy-1-pyrrolidinyl)-1-cyclopropyl-7-fluoro-4H-9-methyl-4-oxo-quinolizine-3-carboxylic acid Step 425a. (S)-1-BOC-3-pyrrolidinol A 9.8 g (55.2 mmol) sample of (S)-1-benzyl-3-pyrrolidinol was dissolved in 200 mL of ethanol, 1.96 g of 20% Pd/C was added, and the mixture was stirred under N$_2$. To this mixture was added 17.4 g of ammonium formate, and the reaction mixture was stirred for 10 minutes at an internal temperature of 70° C. The reaction mixture was removed for the bath and cooled until gas evolution subsided. The mixture was cooled, then diluted with methylene chloride. The solids were removed by filtration, and the filtrate was concentrated. The residue was suspended in 200 mL of methylene chloride, and 2.07 g of di-t-butyl dicarbonate was added with stirring and while holding the temperature at 19°–23° C. The mixture was stirred at room temperature for 16 hours. The organic solvent was removed under vacuum, and the residue was slurried with methylene chloride. The organic phase was separated, washed and dried. The solvent was removed, and the residue was purified by chromatography on silica gel to give 8.94 g of the title compound as a colorless oil.

Step 425a. 8-(3-(S)-hydroxy-1-pyrrolidinyl)-1-cyclopropyl-7-fluoro-4H-9-methyl-4-oxo-quinolizine-3-carboxylic acid Following the procedure of Example 253j, substituting (S)-1-BOC-3-pyrrolidinol, from step 425a above, for the BOC-aminopyrrolidine thereof, and carrying the product forward as in step 253k, the title compound was prepared. mp. 240° C. MS 347 (M+H)$^+$. $^1$H NMR (DMSO-d$_6$) δ: 0.6 (m, 2H), 0.95 (m, 1H), 1.05 (m, 1H), 2.0 (m, 2H), 2.3 (m, 1H), 2.6 (s, 3H), 3.4 (d, 1H), 3.7 (m, 1H), 4.0 (m, 2H), 4.4 (br s, 1H), 5.65 (d, 1H), 7.9 (s, 1H), 9.05 (d, 1H), 18.5 (s, 1H). Analysis-calculated for C$_{18}$H$_{19}$FN$_2$O$_4$: C, 62.42; H, 5.53; N, 8.09. Found: C, 62.34; H, 5.38; N, 7.99.

EXAMPLE 426

8-(3,(R)-hydroxy-1-pyrrolidinyl)-1-cyclopropyl-7-fluoro-4H-9-methyl-4-oxo-quinolizine-3-carboxylic acid Following the procedures of Example 425, replacing the (S)-1-benzyl-3-pyrrolidinol with (R)-1-benzyl-3-pyrrolidinol, the title compound was prepared. mp. 240° C. MS 347 (M+H)$^+$. $^1$H NMR (DMSO-d$_6$) δ: 0.6 (m, 2H), 0.95 (m, 1H), 1.05 (m, 1H), 2.0 (m, 2H), 2.3 (m, 1H), 2.6 (s, 3H), 3.4 (d, 1H), 3.7 (m, 1H), 4.05 (m, 2H), 4.45 (br s, 1H), 5.65 (d, 1H), 7.9 (s, 1H), 9.05 (d, 1H), 18.5 (s, 1H). Analysis calculated for C$_{18}$H$_{19}$FN$_2$O$_4$: C, 62.42; H, 5.53; N, 8.09. Found: C, 62.54; H, 5.56; N, 7.96.

EXAMPLE 427

8-(1-amino-5-aza-spiro[2,4]heptan-5-yl)-1-cyclopropyl-7-fluoro-4H-9-methyl-4-oxo-quinolizine-3-carboxylic acid hydrochloride Diasteromer A Step 427a. (5-(benzyl-amino)-5-aza-1-spiro[2,4]heptane acetic acid ethyl ester A 1.36 g (34 mmol) sample of NaH was suspended in 42 mL of stirred hexane. The hexane was then decanted to remove the mineral oil. To the residue was added 34 mL of DMSO and 7.9 g of trimethylsulfoxonium iodide in portions. The reaction was stirred at room temperature for 30 minutes, during which H$_2$ gas was released. To this mixture was then added 10 mL of DMSO containing 4.19 g (17 mmol) of 1-benzyl-3-ethoxycarbonylmethylenepyrrolidine, prepared as described in published European Application EP550016, and the reaction mixture was stirred for 1 hour at room temperature and 2 hours at 55° C. The reaction was quenched with 350 mL of water, and the mixture was extracted with methylene chloride. The extract was washed with water and brine, then dried, and the solvent was removed. The residue was chromatographed on silica gel, eluting with 22:88 ethyl acetate:hexane, which resolved and separated the two chiral diastereomers, which were designated as Diastereomers A and B.

Step 427b. (5-(BOC-amino)-5-aza-1-spiro[2,4]heptane acetic acid ethyl ester and (R)-(5-(BOC-amino)-5-aza-1-spiro [2,4]heptane acetic acid ethyl ester A 1.18 g sample of Diastereomer A from step 427a was dissolved in 25 mL of ethanol, and 240 mg of 20% Pd(OH)2/C and 1.1 g of di-t-butyl dicarbonate were added. The mixture was stirred under H$_2$ at room temperature for 23 hours, then filtered. The solvent was removed, and the residue was purified on silica gel, eluting with 15:85 ethyl acetate:hexane. MS 347 (M+H)$^+$.

Step 427c. (5-(BOC-amino)-5-aza-1-spiro[2,4]heptane acetic acid

A 0.49 g sample of the compound from step 427b above was dissolved in 4 mL of methanol, and 180 mg of NaOH in 2 mL of water was added. The mixture was stirred at room temperature for 3 hours, and the solvent was removed. Additional water was added and the solution was acidified with 2.3 mL of 2N HCl. The solution was extracted with methylene chloride, and the extract was dried and evaporated. The residue was 332 mg of a heavy oil, which was dried and taken to the next step.

Step 427d. 1-(benzyloxycarbonylamino-(5-(BOC-amino)-5-aza-spiro[2,4]heptane

A 1.455 g (6.03 mmol) sample of the compound from step 427c above, 30 mL of dioxane, 1.5 mL of DPPA, 0.9 mL of triethylamine and 1.0 mL of dry benzyl alcohol were placed in a flask, and the mixture was heated at 100° C. for 2 hours, at 110° C. for 17 hours and at 120° C. for 17 hours. The solvent was evaporated, and the residue was dissolved in methylene chloride. The solution was washed with NaHCO$_3$ solution, and the organic layer was washed, dried and evaporated. The residue was chromatographed on silica gel, eluting with 35:65 ethyl acetate:hexane, and an oil was obtained. MS 347 (M+H)$^+$.

Step 427e. 5-amino-1-(benzyloxycarbonyl)amino-5-aza-spiro[2,4]heptane

A 541 mg sample of the compound from step 427d was dissolved in 10 mL of anhydrous ethyl acetate, and 2.35 mL of 4M HCl in dioxane was added. The solution was stirred at room temperature for 24 hours. The solvent was removed, and the residue was triturated with 31.6 mL of 5% NaHCO$_3$ solution. The mixture was extracted with methylene chloride, then extracted with a 1:3 methanol:methylene chloride mixture. The extract was washed with brine and dried. The solvent was removed to give 0.384 g of the title compound, which was taken directly to the next step.

Step 427f. 8-(1-(benzyloxycarbonyl)amino-5-aza-spiro[2,4] heptan-5-yl)-1-cyclopropyl-7-fluoro-4H-9-methyl-4-oxo-quinolizine-3-carboxylic acid Following the procedure of Example 253j, substituting the compound from step 427e above, for the BOC-aminopyrrolidine thereof, and carrying the product forward as in step 253k, the title compound was prepared.

Step 427 g. 8-(1-amino-5-aza-spiro[2,4]heptan-5-yl-1-cyclopropyl-7-fluoro-4H-9-methyl-4-oxo-quinolizine-3-carboxylic acid hydrochloride Diastereomer A A 355 mg sample of the compound from step 427f was dissolved in a mixture of 20 mL of methanol and 8 mL of methylene chloride. To this was added 2 mL of formic acid, then the flask was flushed with $N_2$ and 142 mg of 10% Pd/C was added. The mixture was stirred at room temperature for 30 minutes. The mixture was diluted and filtered, and the filtrate was concentrated. The residue was dissolved in 2 mL of methanol, and 1.5 mL of 1N HCl in ether was added. Next 100 mL of ether was added, and the title compound was collected by filtration and dried. mp. 200° C. (dec). MS 372 $(M+H)^+$. $^1$H NMR (DMSO-$d_6$) δ: 0.6 (d, 2H), 1.0 (dd, 2H), 1.15 (t, 2H), 1.9 (m, 1H), 2.05 (m, 1H), 2.3 (m, 1H), 2.65 (s, 3H), 2.75 (m, 1H), 3.75 (m, 1H), 3.8 (m, 1H), 4.0 (m, 2H), 7.9 (s, 1H), 8.5 (br s, 2H), 9.1 (d, 1H). Analysis calculated for $C_{20}H_{22}FN_3O_3.HCl.2 H_2O$: C, 54.12; H, 6.13; N, 9.47. Found: C, 54.47; H, 5.79; N, 9.45.

EXAMPLE 428

8-(1-amino-5-aza-spiro[2,4]heptan-5-yl)-1-cyclopropyl-7-fluoro-4H-9-methyl-4-oxo-quinolizine-3-carboxylic acid hydrochloride Diastereomer B Following the procedures of Example 427b, substituting the Diastereomer B (5-(BOC-amino)-5-aza-1-spiro[2,4]heptane acetic acid ethyl ester, from step 427a, for the A isomer thereof, and carrying the product forward as in steps 427c–g, the title compound was prepared. mp. 200° C. (dec). MS 372 $(M+H)^+$. $^1$H NMR (DMSO-$d_6$) δ: 0.6 (d, 2H), 1.0 (t, 2H), 1.1 (t, 2H),1.15 (t, 1H), 2.15 (m, 2H), 2.3 (m, 1H), 2.6 (s, 3H), 2.8 (br m, 1H), 3.65 (m, 1H), 3.8 (m, 2H), 4.15 (m, 1H), 7.9 (s, 1H), 8.6 (br s, 2H), 9.1 (d, 1H) 13.85 (br s, 1H). Analysis calculated for $C_{20}H_{22}FN_3O_3.HCl.2 H_2O$: C, 54.12; H, 6.13; N, 9.47. Found: C, 54.21; H, 5.85; N, 9.38.

EXAMPLE 429

8-(3-(R*)-(1-(S*)-amino-2,2,2-trifluoroethyl) pyrrolidinyl)-1-cyclopropyl-7-fluoro-4H-9-methyl-4-oxo-quinolizine-3-carboxylic acid hydrochloride Step 429a. 1-benzyl-3-(1-hydroxy-2,2,2-trifluoroethylidene)-2-pyrrolidone A 1.2 g sample of NaH was suspended in 30 mL of dry THF, and this suspension was stirred at room temperature. To this was added 3.5 g of 1-benzyl-2-pyrrolidone (Aldrich), and the mixture was stirred at 65° C. To this mixture was next added 3.6 mL of ethyl trifluoroacetate in 10 mL of THF over a 25 minute period, and the reaction was heated at reflux for 3 hours. The reaction mixture was cooled, diluted with ether and neutralized with 1N HCl. The ether layer was separated, washed with brine, dried and taken to dryness. The residual oil was chromatographed on silica gel, eluting with 1:1 ethyl acetate:hexane to give 2.06 g of the title compound. MS 289 $(M+H)^+$.

Step 429b. 1-benzyl-3-(1-hydroxylimino-2,2,2-trifluoroethyl)-2-pyrrolidone

A 2.0 g sample of the compound from step 429a, 7.6 g of hydroxylamine HCl, 20 mL of pyridine and 40 mL of ethanol was heated at reflux for 4 hours. The solvents were removed under vacuum, and the residue was dissolved in methylene chloride. The solution was washed with water and brine, then dried and the solvent evaporated. The residue was azeotropically distilled with toluene to remove the pyridine to give after drying 1.30 g of title compound. MS 287 $(M+H)^+$.

Step 429c. 1-benzyl-3-(1-amino-2,2,2-trifluoroethyl)-2-pyrrolidine

A 1.3 g sample of the compound from step 429c was dissolved in 20 mL of THF, and 10 mL of 1M LAH in THF was added. The mixture was heated at reflux for 4 hours. The reaction was quenched while stirring under a $N_2$ atmosphere by the sequential addition of 0.4 mL $H_2O$, 0.4 mL of 15% NaOH and 1.2 mL of $H_2O$. The suspension was filtered, and the filtrate was washed with brine, dried and evaporated. The residue was then purified by chromatography on silica gel, eluting with 5:95 methanol:methylene chloride to give 943 mg of title compound. MS 259 $(M+H)^+$.

Step 429d. 1-benzyl-3-(1-(BOC-amino)-2,2,2-trifluoroethyl-2-pyrrolidine

A 0.94 g sample of the compound from step 429c was dissolved in 5 mL of methylene chloride, and 0.8 g of di-t-butyl dicarbonate in 1 mL of methylene chloride was added. The mixture was stirred at room temperature for 16 hours. Another 0.4 g of di-t-butyl dicarbonate was then added, and the reaction was stirred for 24 hours. The solvent was removed, and the residue was chromatographed on silica gel, eluting with 25:75 ethyl acetate :hexane. The product was resolved into two diastereomers by chromatography (they were arbitrarily assigned the relative stereochemistry 1S*,3R* and 1S*,3S*). Carrying the 1S*,3R* compound forward the title compound was prepared.

Step 429e. 3-(1-(BOC-amino)-2,2,2-trifluoroethyl)-2-pyrrolidine

A 1.49 g sample of the compound from step 429d was dissolved in 100 mL of methanol, 0.9 g of 10% Pd/C was added, and the mixture was hydrogenated under 4 atm of $H_2$ for 44 hours. The mixture was filtered, the filtrate was concentrated. The residue was triturated with acetonitrile, then filtered. The filtrate was concentrated to give 1.035 g of the title compound. MS 269 $(M+H)^+$.

Step 429f. 8-(3-(R*)-(1-(S*)-amino-2,2,2-trifluoroethyl)pyrrolidinyl)-1-cyclopropyl-7-fluoro-4H-9-methyl-4-oxo-quinolizine-3-carboxylic acid hydrochloride Following the procedure of Example 253j, substituting the compound from step 429e above, for the BOC-aminopyrrolidine thereof, and carrying the product forward as in step 253k, then removing the BOC-group by hydrolysis as in Example 253l, with 1N HCl in acetic acid. mp browned 160°–163° C., decomposed at 180°–183° C. MS 428 $(M+H)^+$. $^1$H NMR (DMSO-$d_6$) δ:0.6 (d, 2H), 0.9 (m, 1H), 1.1 (m, 1H), 1.9 (m, 1H), 2.3 (m, 1H), 2.6 (s, 3H), 2.75 (m, 1H), 3.7 (m, 2H), 4.0 (m, 2H), 4.4 (m, 1H), 7.9 (s, 1H), 9.1 (d, 1H), Analysis calculated for $C_{20}H_{21}F_4N_3O_3.HCl.2 H_2O$: C,48.05; H, 5.24; N, 8.41. Found: C, 48.45; H, 5.20; N, 8.50.

EXAMPLE 430

8-(3-(S*)-(1-(S*)-amino-2,2,2-trifluoroethyl) pyrrolidinyl)-1-cyclopropyl-7-fluoro-4H-9-methyl-4-oxo-quinolizine-3-carboxylic acid hydrochloride Carrying the 1S*,3S* compound from Example 429d above forward as in Examples 429e and 253j, k and l the title compound was prepared. mp browned 205° C., melted at 213° C. MS 428 (M+H)⁺. ¹H NMR (DMSO-d₆) δ: 0.6 (d, 2H), 1.0 (m, 2H), 2.0 (m, 1H), 2.3 (m, 1H), 2.65 (s, 3H), 2.75 (m, 1H), 3.75 (m, 2H), 4.0 (m, 2H), 4.4 (m, 1H), 7.9 (s, 1H), 9.1 (d, 1H). Analysis calculated for $C_{20}H_{21}F_4N_3O_3 \cdot HCl \cdot 2.5 H_2O$: C, 47.20; H, 5.34; N, 8.26. Found: C, 47.14; H, 4.91; N, 8.55.

EXAMPLE 431

8-(3-aminoxypyrrolidinyl)-1-cyclopropyl-
7-fluoro-4H-9-methyl-4-oxo-quinolizine-
3-carboxylic acid hydrochloride Step 431a. 1-BOC-3-pyrrolidinol To a solution of 3.25 g of 3-pyrrolidinol in 25 mL of methylene chloride was added, with cooling, 5 mL of methylene chloride containing 8.2 g of di-t-butyl dicarbonate, and the mixture was stirred for 4 hours. The volatiles were removed under vacuum, and the residue was chromatographed on silica gel, eluting with 7 % methanol in methylene chloride to give 7.64 g of the title compound.

Step 431b. N-(1-BOC-3-pyrrolidinoxy)phthalimide

To 50 mL of dry THF were added 5.17 g of the compound from 431a above, 9.7 g of triphenylphosphine, and 5.41 g of N-hydroxyphtahalimide. To this suspension, stirred and cooled to −20° C., was added 5.83 mL of DEAD, and the mixture was stirred for 1 hour at −20° C. The solution was quenched with water, then extracted with methylene chloride. The organic layer was dried and concentrated. The residue was chromatographed on silica gel, eluting with 40:60 ethyl acetate:hexane to give 7.60 g of the title compound.

Step 431c. (1-B OC-3-pyrrolidinoxy)amine

To a solution of 7.4 g of the compound from step 431b in 100 mL of methylene chloride was added 2.6 mL of hydrazine hydrate. The mixture was stirred at room temperature for 1 hour. The precipitate was removed by filtration, and the filtrate was washed with water, dried and evaporated to give 4.325 g of the title product as an oil.

Step 431d. 3-pyrrolidinoxyamine

A 4.318 g sample of the compound from step 431c was dissolved in 70 mL of dry methylene chloride, and 70 mL of 1M HCl in acetic acid was added. The mixture was stirred for 30 minutes at room temperature. The precipitate was collected by filtration, washed and dried to give 3.41 g of the tile compound.

Step 431e. 8-(3-aminoxypyrrolidinyl)-1-cyclopropyl-7-fluoro-4H-9-methyl-4-oxo-quinolizine-3-carboxylic acid ethyl ester A 0.25 g sample of the 3-pyrrolidinoxyamine from step 431d above and 1.06 mL of triethylamine were dissolved in 5 mL of dry THF, and the mixture was stirred at 55° C. for 7 hours. The reaction was quenched with water, and the mixture was extracted with ethyl acetate. The organic layer, wash washed with water, dried and evaporated. The residue was chromatographed on silica gel, eluting with 100:7;0.7 methylene chloride:methanol:NH4OH to give 224 mg of the title compound.

Step 431f. 8-(3-(BOC-aminoxy)pyrrolidinyl)-1-cyclopropyl-7-fluoro-4H-9-methyl-4-oxo-quinolizine-3-carboxylic acid ethyl ester A mixture of 224 mg of the compound from step 431e and 0.25 g of di-t-butyl dicarbonate were dissolved in 3 mL of methylene chloride, and the mixture was stirred for 4 days. The volatiles were removed, and the residue was taken directly to the next step.

Step 431g. 8-(3-(BOC-aminoxy)pyrrolidinyl)-1-Cyclopropyl-7-fluoro-4H-9-methyl-4-oxo-quinolizine4-carboxylic acid The material from the previous step, 4 mL of THF, 3 mL of water, 0.216 g of LiOH were combined, and the mixture was heated at 83° C. for 3 hours. The mixture was acidified with 1N HCl, and the precipitate was removed by filtration. The filtrate was washed with water and brine, then evaporated to give 245 mg of the title compound.

Step 431h. 8-(3-aminoxypyrrolidinyl)-1-cyclopropyl-7-fluoro-4H-9-methyl-4-oxo-quinolizine-3-carboxylic acid hydrochloride A 200 mg sample of the compound from step 431g was dissolved in 23 mL of dry methylene chloride and treated with 1N HCl in acetic acid at room temperature for 16 hours. The title compound was collected by filtration, washed with methylene chloride and dried. mp −158°−161° C. (dec). MS 362 (M+H)⁺. ¹H NMR (DMSO-d₆) δ: 0.6 (d, 2H), 0.9, (m, 1H), 1.05 (m, 1H), 2.3 (m, 3H), 2.6 (s, 3H), 3.65 (m, 1H), 3.75 (m, 1H), 4.0 (m, 1H), 4.2 (m, 1H), 5.0 (br s, 1H), 7.9 (s, 1H), 9.1 (d, 1H), 11.1 (br s, 2H). Analysis calculated for $C_{18}H_{20}FN_3O_4 \cdot HCl \cdot H_2O$: C, 51.99; H, 5.57; N, 10.10. Found: C, 51.84; H, 5.33; N, 9.95.

EXAMPLE 432

8-(3-(R)-aminoxypyrrolidinyl)-1-cyclopropyl-
7-fluoro-4H-9-methyl-4-oxo-quinolizine-
3-carboxylic acid hydrochloride Following the procedures of Example 432, except substituting (S)-1-BOC-3-pyrrolidinol for the racemic starting material thereof, the title compound was prepared. mp 160°−168° C. (dec). MS 362 (M+H)⁺. ¹H NMR (DMSO-d₆) δ: 0.6 (d, 2H), 0.9, (m, 1H), 1.05 (m, 1H), 2.3 (m, 3H), 2.6 (s, 3H), 3.65 (m, 1H), 3.8 (m, 1H), 4.0 (m, 1H), 4.15 (m, 1H), 4.95 (br s, 1H), 7.95 (s, 1H), 9.1 (d, 1H), 10.7 (br s, 2H). Analysis calculated for $C_{18}H_{20}FN_3O_4 \cdot HCl \cdot 0.75 H_2O$: C, 52.56; H, 5.51; N, 10.22. Found: C, 52.91; H, 5.57; N, 10.14.

EXAMPLE 433

8-(3-(S)-aminoxypyrrolidinyl)-1-cyclopropyl-
7-fluoro-4H-9-methyl-4-oxo-quinolizine-
3-carboxylic acid hydrochloride Following the procedures of Example 432, except substituting (R)-1-BOC-3-pyrrolidinol for the racemic starting material thereof, the title compound was prepared. mp 160°−168° C. (dec). MS 362 (M+H)⁺. ¹H NMR (DMSO-d₆) δ: 0.6 (d, 2H), 0.9, (m, 1H), 1.0 (m, 1H), 2.3 (m, 3H), 2.6 (s, 3H), 3.65 (m, 1H), 3.85 (br d, 1H), 4.0 (m, 1H), 4.15 (m, 1H), 4.95 (br s, 1H), 7.9 (s, 1H), 9.1 (d, 1H), 10.9 (br s, 2H). Analysis calculated for $C_{18}H_{20}FN_3O_4 \cdot HCl \cdot 0.75 H_2O$ : C, 52.56; H, 5.51; N, 10.22. Found: C, 52.98; H, 5.51; N, 10.16.

EXAMPLE 434

8-(octahydropyrrolo[3,2-b]pyridin-1-yl)-
1-cyclopropyl-7-fluoro-4H-9-methyl-
4-oxo-quinolizine-3-carboxylic acid hydrochloride Step 434a. 3-nitro-2-pyridineacetic acid ethyl ester A mixture of 25 g sample of diethyl malonate and 3 g of sodium was stirred at room temperature until the reaction was complete, then stirred at 120° C. for 30 minutes. The mixture became a thick suspension, and 50 mL of toluene was added, followed by 17.17 g of 2-chloro-3-nitropyridine.

The mixture was heated at reflux for 16 hours. The solvents were removed under vacuum, and the residue was dissolved in 50 mL of DMSO. To this solution was added 19.5 g of NaCl and 7.2 g of water, and the mixture was stirred at 160°–170° C. for 3 hours. The mixture was cooled and diluted with ethyl acetate. The layers were separated, and the organic layer was washed with water, brine and dried over MgSO$_4$. The solvent was removed, and the residue was chromatographed on silica gel to give 11.3 g of the title compound. $^1$H NMR (CDCl$_3$) δ: 8.8 (dd, 1H), 8.45 (dd, 1H), 7.5 (dd, 1H), 6.35 (s, 2H), 4.15 (q, 2H), 1.25 (t, 3H).

Step 434b. 1,3-dihydropyrrolo[3,2-b]pyridin-2-one

A 6 g sample of the compound from step 434a was dissolved in ethanol and hydrogenated at 4 atm over Pd/C for 2 hours. The mixture was filtered, and the filtrate was evaporated to give the 3-amino compound. This intermediate was dissolved in 60 mL of 2N HCl, and the solution was heated at reflux for 30 minutes. The mixture was neutralized with K$_2$CO3 to pH7–8, and the mixture was extracted with 4:1 methylene chloride:i-propanol. The extract was dried, and the solvent was removed to give the title compound. $^1$H NMR (CDCl$_3$) δ: 8.05 (m, 1H), 7.12 (m, 2H), 3.55 (s, 2H).

Step 434c. 4-(BOC-amino)-octahydropyrrolo[3,2-b]pyridin-2-one

A 2.8 g sample of the compound from step 434b was dissolved in 150 mL of acetic acid, and 1 g of PtO2 was added. The mixture was hydrogenated at 60 psi for 24 hours and at 2000 psi for 2 hours. The mixture was filtered, and the solvent was removed. The residue was dissolved in 10 mL of methanol, and 3 g NaHCO$_3$, 5 mL of water and 6 g of di-t-butyl dicarbonate were added sequentially. The mixture was stirred at room temperature for 4 hours. The mixture was diluted with methylene chloride, and the mixture was washed with water and brine. The solvent was dried and evaporated, and the residue was purified by chromatography on silica gel, eluting with 7:100 methanol:methylene chloride to give 3.1 g of the title compound.

Step 434d. 4-(BOC-amino)-octahydropyrrolo[3,2-b]pyridine

A 3.1 g sample of the compound from step 434c was dissolved in 20 mL of THF and heated with 2.6 g of Lawesson's Reagent at reflux for 2.5 hours. The solvent was removed, and the residue was chromatographed on silica gel. The intermediate product thus obtained was dissolved in 40 mL of methanol, and 30 g of 50% Raney Ni in water was added. The mixture was stirred at room temperature for 30 minutes, then filtered. The solvent was removed to give 2.5 g of the title compound. $^1$H NMR (CDCl$_3$) δ: 4.6–4.5 (m, 1H), 4.40 (m, 1H), 2.95–3.10 (m, 2H), 2.65–2.75 (m, 1H), 1.90–2.0 (m, 1H), 1.60–1.70 (m, 4H), 1.45 (s, 9H), 1.30–1.40 (m, 2H).

Step 434e. 8-(octahydropyrrolo[3,2-b]pyridin-1-yl-1-cyclopropyl-7-fluoro-4H-9-methyl-4-oxo-quinolizine-3-carboxylic acid hydrochloride Following the procedure of Example 253j, substituting the 4-(BOC-amino)-octahydropyrrolo[3,2-b]pyridine from step 434d for the BOC-amino-pyrrolidine thereof, and carrying the product forward as in steps 253k & l, the title compound was prepared. MS 386 (M+H)$^+$. $^1$H NMR (DMSO-d$_6$) δ: 9.20 (d, 1H), 8.0 (s, 1H), 4.5 (m, 1H), 4.40 (m, 1H), 3.95 (m, 1H), 3.20 (m, 1H), 2.90 (m, 1H), 2.70 (s, 3H), 2.4–2.6 (m, 3H), 2.10 (m, 1H), 1.90 (m, 2H), 1.50 (m, 2H), 0.9–1.10 (m, 2H), 0.60 (m, 2H).

EXAMPLE 435

8-(trans-3-amino-4-fluoromethylpyrrodin-1-yl)-1-cyclopropyl-7-fluoro-4H-9-methyl-4-oxo-quinolizine-3-carboxylic acid hydrochloride Step 435a. 4-fluoro-2-butenoic acid ethyl ester A 1.6 g sample of ethyl fluoroacetate was dissolved in methylene chloride, and the mixture was cooled to −78° C. To this solution was added 1 equivalent of DIBAL (1.0M in methylene chloride) during a 30 minute period. The reaction mixture was stirred for another 30 minutes, then the reaction mixture was warmed to room temperature and 1.1 equivalent of (triphenylphosphoran)ilidenylethyl acetate was added. The reaction mixture was stirred for 16 hours. The reaction was quenched by addition of methanol, and 5% citric acid solution. The mixture was extracted with methylene chloride, and the extract was dried and evaporated. The residue was distilled to yield a 3:1 mixture of the cis:trans isomers of the title compound.

Step 435b. 1-benzyl-3-fluoromethyl-2-pyrrolidineacetic acid ethyl ester

The compound (2.6 g, 20 mmol) from step 435a and 5 g of N-benzyl-N-(methoxymethyl)trimethylsilylamine were dissolved in 30 mL of dry methylene chloride. The solution was stirred at 0° C., and 1% trifluoroacetic acid was added dropwise. The mixture was then stirred for 1.5 hours at room temperature. The solvent was removed, and the residue chromatographed on silica gel to give cis- and trans isomers of the title compound.

Step 435c. trans-1-CBZ-3-fluoromethyl-2-pyrrolidineacetic acid ethyl ester

The trans compound from step 435b was dissolved in 20 mL of ethanol, and 10 equivalents of ammonium formate and 170 mg of 10% Pd/C. The reaction mixture was heated at reflux and stirred for 30 minutes. The mixture was filtered, and the filtrate was evaporated. The residue was dissolved in 10 mL of dioxane and 2.5 mL of water, and 20% Na$_2$CO$_3$ was added. The mixture was cooled to 0° C., and 1.5 equivalents of benzoyloxycarbonyl chloride was added slowly. The reaction was stirred for 30 minutes, then diluted with 100 mL of ether. The organic layer was separated, washed with brine and dried over MgSO$_4$. The solvent was removed, and the residue was chromatographed on silica gel to give 1.5 g of the title compound. $^1$H NMR (CDCl$_3$) δ:7.3–7.4 (m, 5H), 5.12 (s, 2H), 4.60 (m, 1H), 4.10–4.20 (q, 2H), 3.60–3.90 (m, 3H), 3.30–3.40 (m, 1H), 2.7–3.05 (m, 2H), 1.25 (t, 3H).

Step 435d. trans-2-(BOC-amino)-1-CBZ-3-fluoromethyl-pyrrolidine

A 1.5 g sample of the compound from step 435c was dissolved in 12 mL of THF. The solution was cooled to 0° C., and 4 equivalents of LiOH in 3 mL of water were added. The mixture was stirred a 0° C. for 2 hours, then diluted with water and acidified with 2N HCl to pH 2. The mixture was extracted with ether, and the extract was washed with brine and dried. The solvent was removed, and the residue was chromatographed on silica gel to give the intermediate acid. This compound was dissolved in 10 mL of anhydrous THF, and 1.1 equivalent of DPPA and 4 equivalents of triethylamine were added. The mixture was heated at reflux for 24 hours, then cooled. The solvent was removed, and the residue was chromatographed on silica gel. $^1$H NMR (CDCl$_3$) δ: 7.3–7.4 (m, 5H), 5.12 (s, 2H), 6.4–4.60 (m, 3H), 4.05–4.10 (m, 1H), 3.80–3.90 (m, 1H), 3.65–3.75 (m, 1H), 3.30–3.40 (m, 1H), 3.20 (m, 1H), 2.40–2.50 (m, 1H), 1.95 (s, 9H).

Step 435e. trans-2-(BOC-amino)-3-fluoromethyl-pyrrolidine

The compound from step 435d was hydrogenated with Pd/C in NMF and ethanol as in step 435c above, and the title compound was isolated.

Step 435f. 8-(trans-3-amino-4-fluoromethylpyrrodin-1-yl)-1-cyclopropyl-7-fluoro-4H-9-methyl-4-oxo-quinolizine-3-carboxylic acid hydrochloride Following the procedure of Example 253j, substituting the trans-2-(BOC-amino)-3-fluoromethyl-pyrrolidine from step 435c for the BOC-amino-pyrrolidine thereof, and carrying the product forward as in steps 253k & l, the title compound was prepared. MS 378 (M+H)$^+$. $^1$H NMR (DMSO-d$_6$) δ: 9.12 (d, 1H), 7.95 (s, 1H), 4.70–4.80 (m, 1H), 4.55–4.65 (m, 1H), 3.6–4.15 (m, 5H), 2.8–3.0 (m, 1H), 2.65 (s, 3H), 2.3–2.4 (m, 1H), 1.0 (m, 2H), 0.60 (m, 2H).

EXAMPLE 436

8-(cis-3-amino-4-fluoromethylpyrrodin-1-yl)-
1-cyclopropyl-7-fluoro-4H-9-methyl-
4-oxo-quinolizine-3-carboxylic acid hydrochloride Following the procedure of Example 435c, replacing the trans-isomer with the cis-isomer from step 435b, and carrying the product forward as in steps 435d–f, the title compound was prepared.

EXAMPLE 437

8-(8-amino-6-azaspiro[3,4]oct-6-yl-1-cyclopropyl-
7-fluoro-4H-9-methyl-4oxo-quinolizine-3-carboxylic
acid hydrochloride Step 437a. cyclobutylideneacetic acid ethyl ester A 5 g sample of cyclobutanone was mixed with 1.1 equivalent of (carboethhoxymethyl)triphenylphosphorane in 20 mL of toluene. The mixture was heated at reflux for 16 hours, then faltered, and the filtrate was distilled, with the title compound distilling at 186°–188° C.
Step 437b. 8-(8-amino-6-azaspiro[3,4]oct-6-yl-1-cyclopropyl-7-fluoro-4H-9-methyl-4-oxo-quinolizine-3-carboxylic acid hydrochloride Following the procedures of Example 435b, replacing the compound of step 435a with the cyclobutylideneacetic acid ethyl ester from step 437a above, and carrying the product forward according to steps 435c–f, the title compound was prepared. MS .386 (M+H)$^+$. $^1$H NMR (DMSO-d$_6$) δ: 9.10 (d, 1H), 7.92 (s, 1H), 6.1–4.25 (m, 2H), 3.9 (m, 1H), 3.65–3.80 (m, 2H), 2.62 (s, 3H), 2.25–2.40 (m, 1H), 1.85–2.20 (m, 3H), 0.9–1.1 (m, 2H), 0.6 (m, 2H).

EXAMPLE 438

8-(2-(R)-aminomethyl-4-(R)-hydroxypyrrolidin-1-yl-
1-cyclopropyl-7-fluoro-4H-9-methyl-
4-oxo-quinolizine-3-carboxylic acid
hydrochloride Step 438a. N-((1-BOC-4-(R)-(tributylsilyloxy)pyrrolidinyl)methyl)phthalimide A 4.5 g (14 mmol) sample of 1-BOC-2-(R)-hydroxymethyl-4-(R)-(tributylsilyloxy)pyrrolidine, 2.50 g (17 mmol) of phthalimide and 4.46 g (17 mmol) of triphenylphosphine were dissolved in 30 mL of THF at room temperature. To this solution was added 2.94 g (17 mmol) of DEAD in THF dropwise, and the mixture was stirred for 3 hours. The solvent was removed under vacuum, and the residue was dissolved in 1:1 ether:ethyl acetate. The solution was washed with water and brine and dried over MgSO$_4$. The solvent was removed, and the residue was chromatographed on silica gel to give the title compound.
Step 438b. N-((1-BOC-4-(R)-hydroxypyrrolidinyl)methylphthalimide A 4.60 g sample of the compound from step 438a was dissolved in 20 mL of THF. Tetrabutylammonium fluoride (1M in THF) was added dropwise while maintaining the solution at 0° C., the reaction was stirred at room temperature for 30 minutes. The mixture was diluted with ethyl acetate, then washed with water, brine and dried. The solvent was removed to give the title compound.
Step 438c. N-((4-(R)-hydroxypyrrolidinyl)methyl)phthalimide A 2 g sample of the compound from step 438b was dissolved in 10 mL of methylene chloride, and 4N HCl in dioxane was added. The mixture was stirred for 4 hours, and the product was collected by filtration.
Step 438d. N-((1-CBZ-4-(R)-hydroxypyrrolidinyl)methyl)phthalimide The compound from step 438c was dissolved in 10 mL of dioxane, and 3 g of Na$_2$CO$_3$ was added. The mixture was stirred at 0° C. for 30 minutes, then 1.1 equivalent of benzyl chloroformate was added dropwise. The reaction was stirred for 1 hour, and ethyl acetate was added. The water layer was separated, and the organic layer was washed and dried. The solvent was removed to give the title compound.
Step 438e. 2-(R)-aminomethyl-1-CBZ-4-(R)-hydroxypyrrolidine The compound from step 438d was dissolved in 20 mL of ethanol, and 1.2 equivalents of hydrazine hydrate was added. The mixture was heated at reflux for 2 hours, 6N HCl was added, and the mixture was filtered. The filtrate was concentrated to give the title compound.
Step 438f. 2-(R)-(BOC-amino)methyl-1-CBZ-4-(R)-hydroxypyrrolidine The compound of step 438e was treated with di-t-butyl dicarbonate and NaHCO$_3$ in methanol/water as described above, to give the title compound.
Step 438g. 2-(R)-(BOC-amino)methyl-4-(R)-hydroxypyrrolidine The compound of step 438f was treated with ammonium formate and Pd/C using the procedure described above to five the title compound.
Step 438h. 8-(2-(R)-aminomethyl-4-(R)-hydroxypyrrodin-1-yl)-1-cyclopropyl-7-fluoro-4H-9-methyl-4-oxo-quinolizine-3-carboxylic acid hydrochloride Following the procedures of Example 435b, replacing the compound of step 435a with the 2-(BOC-amino)methyl-4-hydroxypyrrolidine from step 438g above, and carrying the product forward according to steps 435c–f, the title compound was prepared. MS 376 (M+H)$^+$. $^1$H NMR (DMSO-d$_6$) δ: 9.20 (d, 1H), 8.0 (s, 1H), 5.58 (m, 1H), 4.60 (m, 1H), 4.40 (m, 1H), 3.88 (m, 1H), 2.95 (m, 2H), 2.70 (s, 3H), 2.40 (m, 2H), 1.90 (m, 1H), 0.90–1.10 (m, 2H), 0.60 (m, 2H).

EXAMPLE 439

8-(3-(R)-(aminomethyl)morpholin-1-yl)-
1-cyclopropyl-7-fluoro-4H-9-methyl-
4-oxo-quinolizine-3-carboxylic acid hydrochloride Step 439a. 1-benzyl-3-(R)chloromethyl)morpholine A 1.53 mL (10.8 mmol) sample of N-benzylethanolamine and 5.0 g (54 mmol) of (R)-(−)-epichlorohydrin were combined and heated at 40° C. for 40 minutes, then the excess epichlorohydrin was removed by distillation. The residue was dissolved in 2 mL of conc. H$_2$SO4, and the mixture was heated at 140° C. for 35 minutes. The reaction was quenched by pouring it onto ice, and the pH was adjusted with 20% NaOH to pH 10–12. The mixture was extracted with methylene chloride, and the solvent was dried, filtered and concentrated to give the title compound (0.97 1 g). MS 226 (M+H)$^+$.
Step 439b. (R)-N-((1-benzylmorpholin-3-yl)methylphthalimide A 971 mg sample of the compound from step 439a was dissolved in 20 mL of DMSO and 1.59 g of phthalimide was added. The reaction mixture was heated at 100° C. for 72 hours. The reaction was quenched by pouring it into 250 mL of water. The mixture was extracted with methylene chloride, which was washed, dried and concentrated to give 1.65 g of the title compound.

Step 439c. (R)-1-benzyl-3-(aminomethylmorpholine

A 1.45 g sample of the compound from step 439b was dissolved in 30 mL of ethanol, 0.627 mL of hydrazine hydrate was added, and the mixture was stirred at room temperature for 18 hours. To this solution was added 13.2 mL of 1N HCl, and the mixture was heated at 70° C. for 6 hours. The reaction was quenched by the addition of water and filtered. The filtrate was adjusted to pH 12 with 20% NaOH and extracted with methylene chloride. The extract was dried, filtered and concentrated to give 667 mg of the title compound. MS 207 (M+H)$^+$.

Step 439d. (R)-1-benzyl-3-(BOC-aminomethylmorpholine

The compound from step 439c (667 mg) was dissolved in 10 mL of methylene chloride, and the solution was cooled to 0° C. To this solution was added 0.90 1 mL of triethylamine, then 0.812 g of di-t-butyl dicarbonate in 4 mL of methylene chloride (dropwise). The reaction mixture was then stirred at room temperature for 20 hours. The solvent was removed, and the residue was purified by chromatography on silica gel to give 691 mg of the title compound.

Step 439e. (R)-3-(BOC-aminomethyl)morpholine

The compound from step 439d was hydrogenated in methanol over Pd/C at 4 atm at room temperature for 24 hours. The mixture was filtered, and the solvent was evaporated to give 435 mg of the title compound.

Step 439f. 8-(3-(R)-(aminomethyl)morpholin-1-yl)-1-cyclopropyl-7-fluoro-4H-9-methyl-4-oxo-quinolizine-3-carboxylic acid hydrochloride Following the procedures of Example 435b, replacing the compound of step 435a with the (R)-3-(BOC-aminomethyl)morpholine from step 439c above, and carrying the product forward according to steps 435c–f, the title compound was prepared. MS 376 (M+H)$^+$. $^1$H NMR (DMSO-d$_6$) δ: 0.66 (m, 2H), 1.04 (m, 2H), 2.41 (m, 1H), 2.79 (s, 3H), 2.90 (m, 1H), 3.08 (m, 1H), 3.26 (m, 2H), 3.47 (m, 1H), 3.57 (m, 1H), 3.75 (m, 1H), 3.96 (m, 1H), 4.04 (m, 1H), 8.01 (br s, 2H), 8.05 (s, 1H), 9.25 (d, J=9 Hz, 1H).

EXAMPLE 440

8-(3-(R)-(L-alanylamino)piperidinyl)-1-cyclopropyl-7-fluoro-4H-9-methyl-4-oxo-quinolizine-3-carboxylic acid hydrochloride Step 440a. 8-(3-(R)-(BOC-L-alanylamino)piperidinyl)-1-cyclopropyl-7-fluoro-4H-9-methyl-4-oxo-quinolizine-3-carboxylic acid hydrochloride A 0.50 g sample of 8-(3-(R)-aminopiperidinyl)-1-cyclopropyl-7-fluoro-4H-9-methyl-4-oxo-quinolizine-3-carboxylic acid hydrochloride, from Example 355 above, was dissolved in 15 mL of DMF, and the solution was cooled to 0° C. To this solution was added dropwise 0.484 mL of diisopropylethylamine, and the mixture was stirred for 10 minutes. To this solution was added 0.380 g of BOC-L-alanyl-N-hydroxy succinimide, the reaction was stirred for 20 minutes, then held without stirring at 4° C. for 16 hours. This solution was poured into 150 mL of 1N HCl, and the precipitate was collected and dried to yield 0.755 g of the title compound.

Step 4401b. 8-(3-(R)-(L-alanylamino)piperidinyl)-1-cyclopropyl-7-fluoro-4H-9-methyl-4-oxo-quinolizine-3-carboxylic acid hydrochloride The compound from step 440a was stirred in 12 mL of 4N HCl in dioxane at room temperature for 70 minutes. The solvent was removed, and the residue was triturated with ether. The solid was collected and dried, then redissolved in ethanol, which was refiltered and dried to give 0.353 g of the title compound. MS 431 (M+H)$^+$. $^1$H NMR (DMSO-d$_6$) δ: 0.66 (m, 2H), 1.03 (m, 2H), 1.37 (d, 3H, J=7.5 Hz), 1.5–2.0 (m, 5H), 2.40 (m, 1H), 2.78 (s, 3H), 3.12 (m, 1H), 3.64 (m, 2H), 3.87 (m, 2H), 8.42 (d, 1H, J=7.5 Hz), 9.22 (d, 1H, J=7.5 Hz), 13.86 (s, 1H). Analysis calculated .1.5H$_2$O: C, 53.49; H, 6.12; N, 11.34. Found: C, 53.25; H, 6.15; N, 11.34.

EXAMPLE 441

8-(3-(5-aminooctahydroindol-1-yl-1-cyclopropyl-7-fluoro-4H-9-methyl-4-oxo-quinolizine-3-carboxylic acid hydrochloride 441a. 5-aminooctahydroindole A 1.0 g sample of 5-aminoindole was hydrogenated at 4 atm H$_2$ in 50 mL of acetic acid over 2 g of Pt2O at room temperature for 90 hours. The solution was filtered, and the solvent was removed.

441b. 8-3-(5-aminooctahydroindol-1-yl), 1-cyclopropyl-7-fluoro-4H-9-methyl-4-oxo-quinolizine-3-carboxylic acid ethyl ester Following the procedure of Example 253j, substituting the 5-aminooctahydroindole from step 441a for the BOC-amino-pyrrolidine thereof, the title compound was prepared.

441c. 8-(3-(5-aminooctrahydroindol-1-yl-1-cyclopropyl-7-fluoro-4H-9-methyl-4-ox quinolizine-3-carboxylic acid hydrochloride The compound was from step 441b was treated with di-t-butyl dicarbonate in the presence of triethylamine. The resulting intermediate was treated with LiOH to hydrolyze the ester. The carboxylic acid compound was deprotected with HCl in dioxane, and the title compound was isolated (0.136 g). MS 400 (M+H)$^+$. $^1$H NMR (DMSO-d$_6$) δ: 0.64 (m, 2H), 1.09 (m, 2H), 1.35 –3.04 (m, 11H), 2.12 (m, 1H, 2.66 (s, 3H), 4.07 (m, 2H), 4.28 (m, 2H), 8.04 (s, 1H), 9.18 (d, J=10.5, 1H), 13.86 (s, 1H). Analysis calculated for C$_{22}$H$_{27}$ClFN$_3$O$_3$.2H$_2$O: C, 55.99; H, 6.41; N, 8.90. Found: C, 56.08; H, 6.45; N, 8.40.

EXAMPLE 442

8-(3-(2-piperidyl)piperidin-1-yl)-1-cyclopropyl-7-fluoro-4H-9-methyl-4-oxo-quinolizine-3-carboxylic acid hydrochloride Step 442a. 1-Boc-2-(3-pyridylpiperidine Anabasine (0.300 g, Aldrich) was treated with di-t-butyl dicarbonate and triethylamine in methylene chloride for 5 hours. The reaction was quenched with water, and the mixture was extracted with methylene chloride. The extract was washed, dried and concentrated. The residue was purified by chromatography on silica gel to give 0.36 g of the title compound.

Step 442b. 1-BOC-2-(3-piperidyl)piperidine

The compound of step 442a was dissolved in 25 mL of acetic acid and hydrogenated under 4 atm of $H_2$ over 0.36 g Pt2O for 17 hours. The mixture was filter, the solvent was removed, and the title compound was dried under vacuum.

Step 442c. 8-(3-(2-piperidyl)piperidin-1-yl-1-cyclopropyl-7-fluoro-4H-9-methyl-4-oxo-quinolizine-3-carboxylic acid hydrochloride Following the procedure of Example 253j, substituting the 1-BOC-2-(3-piperidyl)piperidine from step 442b for the BOC-amino-pyrrolidine thereof, and carrying the product forward as in steps 253k & l, the title compound was prepared. MS 465 (M+H)$^+$. $^1$H NMR (DMSO-d$_6$) δ: 0.72 (m, 2H), 1.07 (m, 2H), 1.52 (m, 2H), 1.79 (m, 3H), 1.97 (m, 3H), 2.28 (m, 2H), 2.38 (m, 1H), 2.82 (m, 3H), 2.92 (m, 2H), 3.22 (m, 2H), 3.42 (m, 2H), 3.87 (m, 2H), 8.04 (s, 1H), 9.05 (m, 1H), 9.45 (m, 1H). Analysis calculated for $C_{24}H_{32}ClFN_3O_3$: C, 62.13; H, 6.73; N, 9.06. Found: C, 61.49; H, 6.68; N, 8.91.

EXAMPLE 443

8-(5-amino-decahydroisoquinolin-2-yl)-1-cyclopropyl-7-fluoro-4H-9-methyl-4-oxo-quinolizine-3-carboxylic acid hydrochloride Step 443a. 5-amino-decahydroisoquinoline A 2 g sample of 5-aminoisoquinoline (Aldrich) was dissolved in 100 mL of methanol and hydrogenated at 4 atm of $H_2$ at room temperature for 6 days over 0.9 g of 5% Rh/C. The mixture was filtered, and the solvent was removed to give the title compound.

Step 443b. 8-(5-amino-decahydroisoquinolin-2-yl)-1-cyclopropyl-7-fluoro-4H-9-methyl-4-oxo-quinolizine-3-carboxylic acid hydrochloride Following the procedure of Example 253j, substituting the 5-amino-decahydroisoquinoline from step 442b for the BOC-amino-pyrrolidine thereof, the condensed ester was produced. This compound was treated with di-t-butyl dicarbonate in the presence of triethylamine. The resulting intermediate was treated with LiOH to hydrolyze the ester. The carboxylic acid compound was aleprotected with HCl in dioxane, and the title compound was isolated. MS 414 (M+H)$^+$. $^1$H NMR (DMSO-d$_6$) δ: 0.67 (m, 2H), 1.03, m, 2H), 1.30–2.25 (m, 11H), 2.40 (m, 1H), 2.76 (s, 3H), 3.45–3.70 (m, 4H), 9.00 (m, 1H), 9.00 (m, 1H), 9.20 (m, 1H). Analysis calculated for $C_{23}H_{28}FN_3O_3 \cdot HCl \cdot H_2O$: C, 59.03; H, 6.46; N, 8.98. Found: C, 58.91; H, 6.77; N, 9.37.

EXAMPLE 444

8-(2,7-diazabicyclo[3,3,0]oct-7-yl)-1-cyclopropyl-7-fluoro-4H-9-methyl-4-oxo-quinolizine-3-carboxylic acid hydrochloride Step 444a. 7-BOC-2-CBZ-2,7-diazabicyclo[3,3,0]octane A 1.06 g sample of 7-BOC-2,7-diazabicyclo[3,3,0]octane (prepared as in Example 268) was dissolved in 12 mL of 1N NaOH, and the solution was cooled to 0° C. To this solution was added 1.43 mL of benzyl chloroformate in 10 mL of ether over a 10 minute period, and the mixture was stirred under $N_2$ for 4 hours. The mixture was extracted with methylene chloride, and the extract was washed, dried and concentrated to give the title compound (0.40 g).

Step 444b. 2-CBZ-2,7-diazabicyclo[3,3,0]octane

The compound from step 444a was dissolved in ethyl acetate and treated with 4N HCl in dioxane to remove the BOC group. The solvent was removed, and the residue was dissolved in 5% NaHCO$_3$. The mixture was washed with ethyl acetate, and the aqueous phase extracted with 1:3 i-propyl alcohol:methylene chloride. The extract was washed with brine, dried and concentrated to give 0.600 g of the title compound.

Step 444c. 8-(2,7-diazabicyclo[3,3,0]oct-7-yl)-1-cyclopropyl-7-fluoro-4H-9-methyl-4-oxo-quinolizine-)-1-cyclopropyl-7-fluoro-4H-9-methyl-4-oxo-quinolizine-3-carboxylic acid hydrochloride Following the procedure of Example 253j, substituting the 2-CBZ-2,7-diazabicyclo[3,3,0]octane from step 444b for the BOC-amino-pyrrolidine thereof, the condensed ester was produced. The ester was hydrolyzed according to the procedure of Example 253k, then the CBZ group was removed by hydrogenation over Pd/C, followed by formation and isolation of the salt according to the procedure of Step 253l. MS 372 (M+H)$^+$. $^1$H NMR (DMSO-d$_6$) δ: 0.62 (m, 2H), 1.00 (m, 2H), 1.98 (m, 1H), 2.18 (m, 1H), 2.35 (m 1H), 2.69 (s, 3H), 3.12 (m, 1H), 3.27 (m, 1H), 3.7 1 (m, 2H), 3.93 (m, 1H), 4.05 (m, 1H), 4.31 (m, 1H), 8.00 (s, 1H), 9.17 (d, J=12 Hz, 1H). Analysis calculated for $C_{20}H_{22}FN_3O_3 \cdot HCl \cdot H_2O$ : C, 56.40; H, 5.92; N, 9.87. Found: C, 56.57; H, 6.00; N, 9.69.

EXMAPLE 445

8-(3,7-diazabicyclo[3,3,0]oct-3-yl)-1-cyclopropyl-7-fluoro-4H-9-methyl-4-oxo-quinolizine-3-carboxylic acid hydrochloride Step 445a. 3,7-dibenzyl-2,4-dioxo-3,7-diazabicyclo[3,3,0]octane A 1.80 g (10 mmol) sample of N-benzylmaleimide and 2.38 g (10 mmol) of N-methoxymethyl-N-trimethylsilylmethyl-benzylamine were dissolved in methylene chloride, and the solution was cooled to 0° C. To this solution was added 1.00 mL (1.0 mmol) of 1.0N TFA in methylene chloride dropwise over 5 minutes. The reaction was stirred for 3 hours, then another 238 mg of the amine reagent was added and the mixture was stirred at room temperature for 1 hour. The mixture was diluted with 50 mL of methylene chloride and the solution was washed with 5% NaHCO$_3$ and brine. The solution was dried and concentrated to give the title compound as a whim solid.

Step 445b. 3-benzyl-2,4-dioxo-3,7-diazabicyclo[3,3,0]octane

The compound from step 445a (3.00 g, 9.38 mmol) was dissolved in 50 mL of methanol, 500 mg of 10% Pd/C was added, and the mixture was flushed with $N_2$. To this mixture was added 2.96 g (46.87 mmol) of ammonium formate, and the reaction was stirred at 70° C. under $N_2$ for 1.25 hours. The mixture was diluted with methylene chloride and filtered. The filtrate was washed with water and concentrated. The residue was redissolved in methylene chloride, rewashed, filtered, and the solvent was removed to give 2.37 g of the title compound.

Step 445c. 3-benzyl-3,7-diazabicyclo[3,3,0]octane

A 1.2 g (30.0 mmol) sample of LAH was suspended in ether under $N_2$ at room temperature. A solution of the compound from step 445b (2.3 g, 10 mmol) in methylene chloride was added dropwise over 10 minutes while cooling the vessel in a −10° C. bath, and the mixture was stirred for 2 hours. The reaction was quenched by the sequential dropwise addition of 1.2 mL water, 1.2 mL 15% NaOH and 3.6 mL of water. The mixture was filtered, and the filtrate was concentrated to give 1.77 g of the title compound.

Step 445e. 3-benzyl-7-BOC-3,7-diazabicyclo[3,3,0]octane

A 1.77 g of the compound from step 445c was dissolved in a 4:1 mixture of methanol: water, and 2.29 g of di-t-butyl dicarbonate was added. The mixture was stirred at room temperature for 1.5 hours, and the solvents were removed. The residue was dissolved in methylene chloride, and the solution was washed with 5% NaHCCO3, brine, dried and concentrated. The residue was chromatographed on silica gel to give 1.68 g of the title compound.

Step 445e. 3-BOC-3,7-diazabicyclo[3,3,0]octane

The compound from step 445d was treated with ammonium formate and 10% Pd/C as in step 445b for 30 minutes, and the title compound was isolated in a similar manner.

Step 445f. 8-(3,7-diazabicyclo[3,3,0]oct-3-yl-1-cyclopropyl-7-fluoro-4H-9-methyl-4-oxo-quinolizine-3-carboxylic acid hydrochloride Following the procedure of Example 253j, substituting the 3-BOC-3,7-diazabicyclo[3,3,0]octane from step 445e for the BOC-amino-pyrrolidine thereof, and carrying the product forward according to steps 253k&l, the title compound (552 mg) was obtained MS 372 (M+H)$^+$. $^1$H NMR (DMSO-d$_6$) δ: 0.6i (m, 2H), 0.99 (m, 2H), 2.33 (m, 1H), 2.67 (s, 3H), 3.12 (m, 4H), 3.43 (m, 2H), 3.70 (m, 2H), 3.85 (m, 2H), 7.96 (s, 1H) 9.12 (d, J=10 Hz, 1H), 13.86 (br s, 1H). Analysis calculated for C$_{20}$H$_{22}$FN$_3$O$_3$.HCl.H$_2$O: C, 56.40; H, 5.92; N, 9.87. Found: C, 56.59; H, 5.80; N, 9.81.

EXAMPLE 446

8-(3-carboxypyrrolidin-1-yl)-1-cyclopropyl-7-fluoro-4H-9-methyl-4-oxo-quinolizine-3-carboxylic acid hydrochloride Step 446a. 1-benzylpyrrolidine-3-carboxylic acid methyl ester 4.3 g of methyl acrylate and 13.09 g of N-methoxymethyl-N-trimethylsilylmethylbenzylamine were dissolved in 100 mL of methylene chloride, and the solution was cooled to 0° C. To this solution was added 5.00 mL of 1.0N TFA in methylene chloride over a 10 minute period, and the reaction was stirred at room temperature for 16 hours. The mixture was washed with 5% NaHCO$_3$ and brine, then concentrated. The residue was chromatographed on silica gel to give 7.20 g of the title compound.

Step 446b. 1-benzylpyrrolidine-3-carboxylamide

The compound (2.02 g) from step 446a was dissolved in 50 mL of methanol, NH3 was bubbled in until the solution was saturated, and the solution was stirred under balloon pressure for 4 days. Additional NH3 was added, and the mixture stirred for 2 more days. The solvent was removed to give the title compound (1.60 g).

Step 446c. 3-carbamoyl-pyrrolidine

The compound (1.6 g) from step 446b was treated with ammonium formate and 10% Pd/C according to the procedure of step 445b for 1.75 hours, and the title compound was isolated in a similar manner (200 mg).

Step 446d. 8-(3-carboxylpyrrolidin-1-yl)-1-cyclopropyl-7-fluoro-4H-9-methyl-4-oxo-quinolizine-3-carboxylic acid Following the procedure of Example 253j, substituting the 3-carbamoyl-pyrrolidine (1.90 g) from step 446c for the BOC-amino-pyrrolidine thereof, and carrying the product forward as in step 253k the title compound was prepared (44 mg). MS 375 (M+H)$^+$. $^1$H NMR (DMSO-d$_6$) δ:0.60 (m, 2H), 0.98 (m, 2H), 2.20 (m, 3H), 3.16 (m, 1H), 3.77 (m, 2H), 3.88 (m, 2H), 7.91 (s, 1H), 9.07 (d, J=10 Hz, 1H). Analysis calculated for C$_{19}$H$_{18}$FN$_2$O$_5$.HCl.0.5H$_2$O: C, 59.53; H, 5.26; N, 7.31. Found: C, 59.35; H, 5.06; N, 7.19.

EXAMPLE 447

8-(3-(2,2,2-trifluoroethyl)aminopyrrolidin-1-yl)-1-cyclopropyl-7-fluoro-4H-9-methyl-4-oxo-quinolizine-3-carboxylic acid hydrochloride 447a. 1-benzyl-3-(2,2,2-trifluoroeacetyl)aminopyrrolidine A 3.52 g sample of N-benzyl-3-aminopyrrolidine (prepared as in *J. Med. Chem.*, 33:2521, 1990) was dissolved in 300 mL of methylene chloride, and the solution was cooled to 0° C. and flushed with N$_2$. To this solution was added 4.85 mL of pyridine, then 8.45 mL of trifluoroacetic anhydride (dropwise over 10 minutes). The mixture was stirred at 0° C. for 10 minutes and at room temperature for 20 minutes. The reaction mixture was washed with 5% NaHCO$_3$ and brine, then filtered and concentrated to give 5.76 g of the title compound.

447b. 1-benzyl-3-(2,2,2-trifluoroethyl)aminopyrrolidine

A 2.64 g sample of the compound from step 447a was added dropwise to a suspension of 1.11 g of LAH in ether stirred under N$_2$ at 0° C. After one hour, the reaction was stirred at room temperature for 6 hours. The reaction was quenched by sequential addition of 1.2 mL of water, 1.2 mL of 15% NaOH and 2.4 mL of water. The mixture was filtered, and the filtrate was concentrated to give 2.39 of the title compound.

447c. 1-benzyl-3-(N-BOC-N-(2,2,2-trifluoroethyl)aminopyrrolidine

A 2.36 g sample of the compound from step 447b was treated with di-t-butyl dicarbonate in the THF/water, and the compound was isolated as in previous examples (e.g., Ex. 445e). Yield 1.81 g of the title compound.

447d. 3-(N-BOC-N-(2,2,2-trifluoroethyl)aminopyrrolidine

A 2.80 g sample of the compound from step 447c was treated with ammonium formate and 10% Pd/C according to the procedure of step 445b for 1.75 hours, and the title compound was isolated (1.09 g).

447e. 8-(3-(N-BOC-N-(2,2,2-trifluoroethyl)amino)pyrrolidin-1-yl)-1-cyclopropyl-7-fluoro-4H-9-methyl-4-oxo-quinolizine-3-carboxylic acid hydrochloride Following the procedure of Example 253j, substituting the 3-(N-BOC-N-(2,2,2-trifluoroethyl)aminopyrrolidine (0.646 g) from step 447d for the BOC-amino-pyrrolidine thereof, and carrying the product forward as in steps 253k&l the title compound was prepared (493 mg). MS 428 (M+H)$^+$. $^1$H NMR (DMSO-d$_6$) δ: 0.60 (m, 2H), 1.93 (m, 1H), 2.10 (m, 1H), 2.29 (m, 1H), 2.60 (s, 3H), 3.54 (m, 2H), 3.75 (m, 1H), 3.91 (m, 2H), 7.89 (s, 1H), 9.06 (d, 1H, J=10 Hz). Analysis calculated for C$_{20}$H$_{20}$F$_4$N$_3$O$_3$.HCl.0.25 H$_2$O: C, 55.62; H, 5.02; N, 9.73. Found: C, 55.72; H, 4.83; N, 9.62.

EXAMPLE 448

8-(3-(2-fluoromethyl)aminopyrrolidin-1-yl)-
1-cyclopropyl-7-fluoro-4H-9-methyl-
4-oxo-quinolizine-3-carboxylic acid hydrochloride

448a. 1-benzyl-3-(N-BOC-N-(2-fluoroethyl)amino)pyrrolidine

A 3.52 g (2.00 mmol) sample of N-benzyl-3-aminopyrrolidine (prepared as in *J. Med. Chem.*, 33:2521, 1990) and 340 mg of NaHCO$_3$ were dissolved in 5 mL of acetonitrile. This solution was flushed with N$_2$ and 0.140 mL of 1-bromo-2-fluoroethane (Aldrich) was added. The reaction was stirred at 50° C. under N$_2$ for 48 hours and at 70° C. for 1.5 hours. This mixture was cooled, and then were added 5 mL of water, 5 mL of methanol and 873 mg of di-t-butyl dicarbonate. This reaction mixture was stirred for 7 hours, then diluted with methylene chloride. This mixture was washed with 5% NaHCO$_3$ and brine. The organic layer was dried and concentrated to give the title compound.

448b. 3-(N-BOC-N-(2-fluoroethyl)amino)pyrrolidine

A 225 mg sample of the compound from step 448a was treated with ammonium formate and 10% Pd/C according to the procedure of step 445b for 1 hour, and the title compound was isolated (190 mg).

448b. 8-(3-(2-fluoroethyl)aminopyrrolidin-1-yl)-1-cyclopropyl-7-fluoro-4H-9-methyl-4-oxo-quinolizine-3-carboxylic acid hydrochloride Following the procedure of Example 253j, substituting the 3-(N-BOC-N-(2-fluoroethyl)amino)pyrrolidine (0.245 g) from step 448b for the BOC-amino-pyrrolidine thereof, and carrying the product forward as in steps 253k&l the title compound was prepared (76 mg). MS 392 (M+H)$^+$. $^1$H NMR (DMSO-d$_6$) δ: 0.61 (m, 2H), 1.00 (m, 2H), 2.33 (m, 3H), 3.38 (s, 3H), 3.54 (m, 1H), 3.50 (m, 1H), 3.80 (m, 1H), 4.00 (m, 4H), 4.62 (m, 1H), 4.87 (m, 1H), 7.95 (s, 1H), 9.13 (d, 1H, J=10 Hz), 13.85 (br s, 1H). Analysis calculated for C$_{20}$H$_{23}$F$_2$N$_3$O$_3$.HCl.H$_2$O: C, 53.87; H, 5.88; N, 9.42. Found: C, 53.75; H, 5.61; N, 9.45.

EXAMPLE 449

8-(3-((2-fluoroethyl)aminomethyl)pyrrolidin-1-yl)-
1-cyclopropyl-7-fluoro-4-oxo-quinolizine-
3-carboxylic acid hydrochloride Following the procedures of Example 448a–b, substituting 1-benzyl-3-(BOC-amino)methylpyrrolidine (prepared according to *J. Med. Chem.*, 1981:1320), then substituting that product for the BOC-amino-pyrrolidine forward following the procedure of Example 352j of Example 253j, and following the procedure of 253j and carrying the product forward as in steps 253k&l the title compound was prepared (85 mg). MS 406 (M+H)$^+$. $^1$H NMR (DMSO-d$_6$) δ: 0.60 (m, 2H), 1.01 (m, 2H), 1.84 (m, 1H), 2.20 (m, 1H), 2.29 (m, 1H), 2.62 (s, 3H), 2.68 (m, 1H), 3.16 (m, 2H), 3.78 (m, 4H), 4.80 (m, 2H), 7.91 (s, 1H), 9.08 (d, 1H, J=10 Hz). Analysis calculated for C$_{20}$H$_{25}$F$_2$N$_3$O$_3$.HCl.H$_2$O: C, 54.84; H, 6.14; N, 9.14. Found: C, 54.23; H, 5.87; N, 8.95.

EXAMPLE 450

8-(3-(S)-(2-fluoroethyl)aminopyrrolidin-1-yl)-
1-cyclopropyl-7-fluoro-4H-9-methyl-
4-oxo-quinolizine-3-carboxylic acid hydrochloride Following the procedures of Example 448, beginning with the (S)-N-benzyl-3-aminopyrrolidine, the title compound (553 mg) was prepared. MS 392 (M+H)$^+$. $^1$H NMR (DMSO-d$_6$) δ: 0.62 (m, 2H), 1.00 (m, 2H), 2.32 (m, 3H), 2.64 (s, 1H), 3.40 (m, 1H), 3.48 (m, 1H), 3.80 (m, 1H), 4.01 (m, 4H), 4.83 (m, 2H). 7.93 (s, 1H), 9.10 (d, 1H, J=10 Hz), 13.85 (br s, 1H). Analysis calculated for C$_{20}$H$_{23}$F$_2$N$_3$O$_3$.HCl.H$_2$O: C, 53.87; H, 5.88; N, 9.42. Found: C, 53.88; H, 5.75; N, 9.30.

EXAMPLE 451

8-(3-(R)-(2-fluoroethyl)aminopyrrolidin-1-yl)-
1-cyclopropyl-7-fluoro-4H-9-methyl-
4-oxo-quinolizine-3-carboxylic acid hydrochloride Following the procedures of Example 448, beginning with the (R)-N-benzyl-3-aminopyrrolidine, the title compound (601 mg) was prepared. MS 392 (M+H)$^+$. $^1$H NMR (DMSO-d$_6$) δ: 0.61 (m, 2H), 1.00 (m, 2H), 2.32 (m, 3H), 2.64 (s, 3H), 3.40 (m, 1H), 3.48 (m, 1H), 3.80 (m, 1H), 4.00 (m, 4H), 4.83 (m, 2H), 7.94 (s, 1H), 9.11 (d, 1H, J=10 Hz). Analysis calculated for C$_{20}$H$_{23}$F$_2$N$_3$O$_3$.HCl.H$_2$O: C, 53.87; H, 5.88; N, 9.42. Found: C, 53.75; H, 5.61; N, 9.45.

EXAMPLE 452

8-(3a-amino-octahydroisoindol-2-yl)-
1-cyclopropyl-7-fluoro-4H-9-methyl-
4-oxo-quinolizine-3-carboxylic acid hydrochloride Step 452a. 2-benzyl-3a-nitro-octahydroisoindole A 1.27 g (10.0 mmol) sample of 1-nitro-1-cyclohexene (Aldrich) and 2.38 g (10.0 mmol) of N-benzyl-N-(methoxymethyl)-trimethylsilylmethylamine were dissolved in methylene chloride, and the solution was flushed with N$_2$ and cooled to 0° C. To this solution was added 10 mL of methylene chloride containing 1N TFA over a 10 minute period, and the mixture was stirred at 0° C. for 0.5 hour and at room temperature for 15 hours. An additional 479 mg (2 mmol) of N-benzyl-N-(methoxymethyl)-trimethylsilylmethylamine were added, and the solution was stirred for 5 hours. The mixture was washed with 5% NaHCO$_3$ and brine, dried and concentrated to give 2.935 g of the title compound.

Step 452b. 2-benzyl-3a-amino-octahydroisoindole

A 520 mg sample of the compound from step 452a was dissolved in 30 and treated with ammonium formate and 10% Pd/C according to the procedure of step 445b for 1 hour, and the title compound was isolated (550 mg).

Step 452c. 8-(3a-amino-octahydroisoindol-2-yl)-1-cyclopropyl-7-fluoro-4H-9-methyl-4-oxo-quinolizine-3-carboxylic acid hydrochloride Following the procedure of Example 253j, substituting the 2-benzyl-3a-aminooctahydroisoindole (0.550 g) from step 448b for the BOC-amino-pyrrolidine thereof, then reacting the product with di-t-butyl dicarbonate in methanol, and carrying the BOC-protected product forward as in steps 253k&l the title compound was prepared (66 mg). MS 400 (M+H)$^+$. $^1$H NMR (DMSO-d$_6$) δ: 0.61 (m, 2H), 1.00 (m, 2H), 2.33 (m, 3H), 3.38 (s, 3H), 3.54 (m, 1H), 3.50 (m, 1H), 3.80 (m, 1H), 4.00 (m, 4H), 4.62 (m, 1H), 4.87 (m, 1H), 7.95 (s, 1H), 9.13 (d, 1H, J=10 Hz), 13.85 (br s, 1H). Analysis calculated for $C_{22}H_{26}FN_3O_3 \cdot HCl \cdot 2H_2O$: C, 55.99; H, 6.62; N, 8.90. Found: C, 55.56; H, 6.30; N, 8.95.

EXAMPLE 453

8-(6-amino-2-aza-spiro[3,3]non-2-yl)-
1-cyclopropyl-7-fluoro-4H-9-methyl-
4-oxo-quinolizine-3-carboxylic acid hydrochloride
(Isomer (I))

Step 453a. 1-(2-bromoethyl)-2-oxo-cyclopentanecarboxylic acid

A 4.68 g (30 mmol) sample of 2-oxo-cyclopentanecarboxylic acid and 28.18 g (150 mmol) of 1,2-dibromoethane were dissolved in 100 mL of acetone. 20.73 g (150 mmol) of K2CO3 were added and the mixture was heated at reflux for 4 hours. The mixture was filtered and concentrated. The residue was chromatographed on silica gel to give 4.52 g of the title compound.

Step 453b. 2-aza-2-benzyl-spiro[3,3]nonan-1,6-dione

A 4.07 g sample of the compound from step 453a and 4.98 g of benzylamine were dissolved in 50 mL of toluene, and the mixture was heated at reflux for 8 hours in the presence of 14 g of 4 Å, molecular sieves. To this mixture was added 36.6 mL of 2M HCl, and the mixture was stirred at room temperature for 1 hour. The mixture was filtered, and the organic layer was separated and washed with 2M HCl, dried and concentrated. The residue was chromatographed on silica gel to give 1.69 g of the title compound.

Step 453c. 2-aza-2-benzyl-spiro[3,3]nonan-6-ol

A 1.18 g (4.85 mmol) sample of the compound from step 453b was dissolved in 15 mL of dry THF, and 14.6 mL (14.55 mmol) of LAH (1M in ether) was added dropwise. The mixture was heated at reflux for 2 hours, then the reaction was quenched by the sequential dropwise addition of 0.55 mL water, 0.55 mL of 15% NaOH and 1.65 mL of water. The mixture was stirred for 1 hour and filtered. The filtrate was dried and concentrated to give 1.13 g of the title compound.

Step 453d. 2-aza-2-benzyl-spiro[3,3]nonan-6-one

A 1.13 g sample of the compound from step 453c was dissolved in 35 mL of acetone, the solution was cooled to 0° C.m and 0.25 mL of $H_2SO4$ was added. To this mixture was added Jones reagent dropwise, and the reaction was stirred at room temperature for 4 hours. Isopropanol was added, the acetone was removed under reduced pressure, and 6.5 mL of 6M NaOH was added. The mixture was filter, and the filtrate was washed with water and brine, dried and concentrated to give 845 mg of the title compound.

Step 453e. 6-amino-2-aza-2-benzyl-spiro[3,3]nonane

A 845 mg sample of the compound from step 453d, 173 mg of NaBH3CN and 2.84 g of ammonium acetate were dissolved in 120 mL of absolute methanol, and the mixture was stirred at room temperature for 16 hours. The mixture was concentrated, and 200 mL of methylene chloride were added. The solution was filtered, and the filtrate was washed with 5% NaHCO3, brine, dried and concentrated to give 853 mg of the title compound.

Step 453f. 6-(BOC-amino)-2-aza-2-benzyl-spiro[3,3]nonane

A 847 mg sample of the compound from step 453e was dissolved in 24 mL of methanol and 6 mL of water, and 1.61 g of di-t-butyl dicarbonate was added. The mixture was stirred at room temperature under $N_2$ for 3 hours. The mixture was concentrated, and the residue was dissolved in methylene chloride. The solution was washed with 5% NaHCO3, dried and concentrated to give 1.40 g of the title compound.

Step 453g. 6-(BOC-amino)-2-aza-spiro[3.3]nonane

A 138 mg sample of the compound from step 453f was dissolved in 30 and treated with ammonium formate and 10% Pd/C according to the procedure of step 445b for 1 hour, and the title compound was isolated (105 mg).

Step 453h. 8-(6-amino-2-aza-spiro[3,3]non-2-yl)-1-cyclopropyl-7-fluoro-4H-9-methyl-4-oxo-quinolizine-3-carboxylic acid hydrochloride Following the procedure of Example 253j, substituting the 6-(BOC-amino)-2-aza-2-benzyl-spiro[3,3]nonane (138 mg) from step 453g for the BOC-amino-pyrrolidine thereof, and carrying the product forward as in steps 253k&l the title compound was prepared (57 mg). Stereoisomers were separated by HPLC. Isomer (I): MS 400 (M+H)$^+$. $^1$H NMR (DMSO-d$_6$) δ: 0.62 (m, 2H), 1.00 (m, 2H), 1.65–2.35 (m, 11H), 2.63 (s, 3H), 3.47 (m, 1H), 3.58 (m, 1H), 3.81 (m, 2H), 3.92 (m, 1H), 4.62 (m, 1H), 7.93 (s, 1H), 9.09 (d, 1H, J=10 Hz). Analysis calculated for $C_{22}H_{26}FN_3O_3 \cdot HCl \cdot 1.5H_2O$: C, 57.08; H, 6.53; N, 9.08. Found: C, 56.85; H, 6.41; N, 8.84.

EXAMPLE 454

8-(3-amino-3-trifluoromethylpyrrolidin-1-yl)-
1-cyclopropyl-7-fluoro-4H-9-methyl-
4-oxo-quinolizine-3-carboxylic acid hydrochloride 454a. 1-benzyl-3-trifluoromethylpyrrolidine-3-carboxylic acid A 2.48 g sample of 2-(trifluoromethyl)acrylic acid was dissolved in 40 mL of dry methylene chloride, and a solution of 4.75 g of N-benzyl-N-(methoxymethyl)trimethylsilyl-methylamine in 20 mL of dry methylene chloride was added dropwise under $N_2$ at 0° C. To this mixture was added 2 mL of trifluoroacetic acid, and the mixture was stirred for 2 hours at room temperature. The product was removed by filtration, washed and dried to give the title product.

454b.
1-benzyl-3-(BOC-amino)-3-trifluoromethylpyrrolidine

A mixture of 1.42 g of the compound from step 454a, 1.71 g of diphenylphosphoryl azide, 12.3 g of t-butanol and 0.627 g of trimethyl amine was heated at reflux under $N_2$ for 24 hours. The mixture was concentrated to dryness, and the residue was dissolved in methylene chloride. The solution was washed with satd. NaHCO$_3$ and water, then concentrated. The residue was chromatographed on silica gel to give 1.73 g of the title compound.

454c. 3-(BOC-amino)-3-trifluoromethylpyrrolidine

A 413 mg sample of the compound from step 447c was treated with ammonium formate and 10% Pd/C according to the procedure of step 445b for 2 hours, and the title compound was isolated (282 mg).

454d. 8-(3-amino-3-trifluoromethylpyrrolidin-1-yl)-
1-cyclopropyl-7-fluoro-4H-9-methyl-
4-oxo-quinolizine-3-carboxylic acid hydrochloride Following the procedure of Example 253j, substituting the 3-(BOC-amino)-3-trifluoromethylpyrrolidine (227 mg) from step 453g for the BOC-amino-pyrrolidine thereof, and carrying the product forward as in steps 253k&l the title compound was prepared (79 mg). MS 414 (M+H)$^+$. $^1$H NMR (DMSO-d$_6$) δ: 0.62 (m, 2H), 1.02 (m, 2H), 2.19 (m, 1H), 2.35 (m, 2H), 2.65 (m, 3H), 3.78 (m, 2H), 4.19 (m, 2H), 7.97 (s, 1H), 9.08 (d, 1H, J=10 Hz).

EXAMPLE 455

8-(3-(S)-hydroxymethylazetidin-1-yl)-
1-cyclopropyl-7-fluoro-4H-9-methyl-
4-oxo-quinolizine-3-carboxylic acid Following the procedure of Example 253j, substituting 3-(S)-hydroxymethylazetidine (540 mg) for the BOC-amino-pyrrolidine thereof, and carrying the product forward as in step 253k the title compound was prepared (102 mg). MS 347 (M+H)$^+$. $^1$H NMR (DMSO-d$_6$) δ: 0.59 (m, 2H), 0.86 (m, 1H), 1.04 (m, 1H), 2.26 (m, 2H), 2.60 (s, 3H), 3.61 (m, 1H), 3.77 (m, 1H), 4.23 (m, 1H), 4.58 (m, 1H), 4.91 (m, 1H), 5.06 (m, 1H), 7.86 (s, 1H), 9.04 (d, 1H, J=10 Hz). Analysis calculated for $C_{18}H_{19}FN_2O_4 \cdot 0.25H_2O$: C, 61.62; H, 5.60; N, 7.98. Found: C, 61.71; H, 5.55; N, 7.81.

EXAMPLE 456

8-(3-aminomethyl)-3-trifluoromethyl-pyrrolidin-
1-yl-1-cyclopropyl-7-fluoro-4H-9-methyl-
4-oxo-quinolizine-3-carboxylic acid hydrochloride 456a. 1-benzyl-3-trifluoromethylpyrrolidine-
3-carboxylic acid 2-(Trifluoromethyl)acrylic acid (2.48 g, 20 mmol) was dissolved in 30 mL of dry methylene chloride, a solution of 4.75 g (20 mmol) of N-benzyl-N-(methoxymethyl)trimethylsilylmethylamine in 20 mL of dry methylene chloride was added dropwise under N$_2$ at 0° C. To this solution was added 2 mL of TFA, and the solution was stirred for 2 hours at room temperature. The white precipitate was collected, washed and dried to give 3.22 g of the title compound.

456b.
1-benzyl-3-trifluoromethylpyrrolidine-3-methanol

The compound from step 456a (2.32 g) was dissolved in 60 mL of dry THF, 1.12 eq of LAH (1N in dry THF) was added, and the reaction was stirred under N$_2$ for 3 hours. The reaction was quenched by the sequential dropwise addition of 0.35 mL water, 0.35 mL of 15% NaOH and 1.3 mL of water, then the mixture was stirred for 1 hour and filtered. The filtrate was dried and concentrated to give 2.2 g of the title compound.

456c. 1-benzyl-3-trifluoromethyl-
3-(toluenesulfonyloxymethyl)pyrrolidine

The compound from step 456b (1.61 g) was dissolved in dry pyridine, and the solution was cooled to 0° C. To this was added 1.458 g of p-toluenesulfonyl chloride in 4 mL of dry pyridine, and the reaction was stirred at 0.C. for 4 days. The mixture was diluted with 300 mL of methylene chloride, then washed with water and brine and dried. Removal of the solvent gave 2.81 g of the title compound.

456d.
1-benzyl-3-trifluoromethyl-3-(azidomethyl)pyrrolidine

The compound (2.43 g) from step 456c was dissolved in acetonitrile, then reacted with tetrabutylammonium azide at 80° C. for 16 hours. The mixture was diluted with methylene chloride, then washed with water and brine and dried. Removal of the solvent gave 0.751 g of the title compound.

456e. 1-benzyl-3-(BOC-aminomethyl)-
3-trifluoromethyl-pyrrolidine

The compound from step 456c (284 mg) and di-t-butyl dicarbonate (262 mg) were dissolved in anhydrous acetic acid and added to a suspension of Pd/C (29 mg) in 10 mL of dry acetic acid. The reaction was stirred at room temperature under N$_2$ for 4 hours, then filtered The filtrate was washed with 5% NaHCO$_3$ and brine, then dried and concentrated. The residue was purified by chromatography on silica gel to give 172 mg of the title compound.

456f.
3-(BOC-aminomethyl)-3-trifluoromethyl-pyrrolidine

A 330 mg sample of the compound from step 447c was treated with ammonium formate and 10% Pd/C according to the procedure of step 445b for 2 hours, and the title compound was isolated (222 mg).

456f.
8-(3-aminomethyl)-3-trifluoromethyl-pyrrolidin-
1-yl)-1-cyclopropyl-7-fluoro-4H-9-methyl-
4-oxo-quinolizine-3-carboxylic acid hydrochloride Following the procedure of Example 253j, substituting 3-(BOC-aminomethyl)-3-trifluoromethyl-pyrrolidine from step 456f (182 mg) for the BOC-amino-pyrrolidine thereof, and carrying the product forward as in steps 253k&l the title compound was prepared (47 mg). MS 428 (M+H)$^+$. $^1$H NMR (DMSO-d$_6$) δ: 0.63 (m, 2H), 1.02 (m, 2H), 2.32 (m, 3H), 2.55 (m, 1H), 2.68 (s, 3H), 3.85 (m, 2H), 3.98 (m, 2H), 7.99 (s, 1H), 9.16 (d, 1H, J=12 Hz). Analysis calculated for $C_{20}H_{21}F_4N_3O_3 \cdot HCl \cdot 1.75H_2O$: C, 48.49; H, 5.19; N, 8.48. Found: C, 48.48; H, 4.99; N, 8.49.

EXAMPLE 457

8-(octahydropyrrolo[3,4-c]pyrid-2-yl)-
1-cyclopropyl-7-fluoro-4H-9-methyl-
4-oxo-quinolizine-3-carboxylic acid hydrochloride 457a. N-benzyl-3,4-pyrrolidinedicarboxylic acid
diethyl ester Diethyl glutaconate (7.44 g, 40 mmol) was dissolved in 60 mL of dry methylene chloride, and a solution of 9.52 g (40 mmol) of N-benzyl-N-(methoxymethyl)trimethylsilylmethylamine in 20 mL of dry methylene chloride was added dropwise under N$_2$ at 0° C. To this solution was added 2 mL of 1N TFA in methylene chloride, and the solution was stirred for 2 hours at room temperature. The solution was washed with 5% NaHCO$_3$ and brine, then dried and concentrated to give 12.48 g of the title compound.

457b.
2-benzyl-4,6-dioxooctahydropyrrolo[3,4-c]pyridine

A solution of 9.00 mmol of Na in liquid NH3 was prepared at −78° C. To this was added 15 mg of FeCl3, and the reaction mixture was warmed to −40° C. To this solution, stirred under N$_2$, a cooled (−40° C.) solution of the compound (957 mg) from step 457a in THF was added over a 10 minute period, and the reaction mixture was stirred at −33° C. for 3 hours. Ammonium chloride (1.5 g) was added with stirring, then the mixture was warmed to room temperature and the excess ammonia was evaporated. To this was added 60 mL of water, and the mixture was extracted with methylene chloride. The extract was washed with brine, dried and concentrated. The residue was chromatographed on silica gel to give 425 mg of the title compound.

457c. 2,5-dibenzyl-4,6-dioxooctahydropyrrolo[3,4-c]pyridine

To a mixture of 905 mg of K2CO3 and 400 mg of the compound from step 457b in 5 mL of DMF was added 308 mg of benzyl bromide, and the reaction mixture was stirred at room temperature under N$_2$ for 6.5 hours. The mixture was diluted with ethyl acetate, which was washed With water and brine, dried and concentrated to give 610 mg of the title compound.

457d. 5-benzyl-4,6-dioxoctahydropyrrolo[3,4-c]pyridine

A 700 mg sample of the compound from step 447c was treated with ammonium formate and 10% Pd/C according to the procedure of step 445b for 2 hours, and the title compound was isolated (540 mg).

457e. 5-benzyl-octahydropyrrolo[3,4-c]pyridine

A suspension of 266 mg of LAH in 10 mL of ether was stirred at 10° C. under N$_2$. To this suspension was added 540 mg of the compound from step 457d dissolved in 10 mL of methylene chloride. The mixture was stirred under N$_2$ for 1.5 hours. The reaction was quenched by the sequential dropwise addition of 0.3 mL water, 0.3 mL of 15% NaOH and 0.6 mL of water, then the mixture was stirred for 1 hour and filtered. The filtrate was dried and concentrated to give 389 mg of the title compound.

Step 457f. 8-(octahydropyrrolo[3,4-c]pyrid-2-yl)-1-cyclopropyl-7-fluoro-4H-9-methyl-4-oxo-quinolizine-3-carboxylic acid hydrochloride Following the procedure of Example 253j, substituting 5-benzyl-octahydropyrrolo[3,4-c]pyridine from step 457e (330 mg) for the BOC-amino-pyrrolidine thereof, and carrying the product forward as in steps 253k&l the title compound was prepared (22 mg). MS 386 (M+H)$^+$. $^1$H NMR (DMSO-d$_6$) δ: 0.60 (m, 2H), 0.98 (m, 2H), 1.78 (m, 1H), 1.89 (m 1H), 2.27 (m, 1H), 2.61 (s, 3H), 2.50–2.75 (m, 3H), 3.00 (m, 1H), 3.17 (m, 2H), 3.65–4.00 (m, 4H), 7.90 (s, 1H), 9.08 (d, 1H, J=10 Hz).

EXAMPLE 458

8-(3-(cyclopropylamino)pyrrolidin-1-yl)-1-cyclopropyl-7-fluoro-4H-9-methyl-4-oxo-quinolizine-3-carboxylic acid hydrochloride

458a. 1-benzyl-3-(cyclopropylmethyl)aminopyrrolidine

A sample (1.75 g 10 mmol) of 1-benzyl-3-pyrrolidinone was dissolved in methylene chloride, and 1.44 g of anhydrous MgSO$_4$ was added. The mixture was stirred under N$_2$ at 0° C., and 634 mg of cyclopropylamine was added dropwise. The mixture was stirred at room temperature for 5 hours, then 10 mL of methanol followed by 534 mg of NaBH4 in small portions was added. The mixture was stirred for 1 hour, then diluted with methylene chloride. The solution was washed with 5% NaHCO$_3$ and brine, dried and concentrated to give 2.12 g of the title compound.

458b. 1-benzyl-3-(N-BOC-N-(cyclopropylmethyl)amino)pyrrolidine

The compound from step 458 was treated with di-t-butyl dicarbonate in acetonitrile for 2 hours, and the title compound (2.11) g was obtained after extraction of the compound and chromatography on silica gel.

458c. 1-benzyl-3-(N-BOC-N-(cyclopropylmethyl)amino)pyrrolidine

A 2.11 g sample of the compound from step 458b was treated with ammonium formate and 10% Pd/C according to the procedure of step 445b for 2 hours, and the title compound was isolated (1.92 mg).

458d. 8-(3-(cyclopropylamino)pyrrolidin-1-yl)-1-cyclopropyl-7-fluoro-4H-9-methyl-4-oxo-quinolizine-3-carboxylic acid hydrochloride Following the procedure of Example 253j, substituting 1-benzyl-3-(N-BOC-N-(cyclopropylmethyl)amino)pyrrolidine from step 458c (1.13 g) for the BOC-amino-pyrrolidine thereof, and carrying the product forward as in steps 253k&l the title compound was prepared. MS 386 (M+H)$^+$. $^1$H NMR (DMSO-d$_6$) δ:0.60 (m, 2H), 0.81 (m, 2H), 1.00 (m, 4H), 2.34 (m, 3H), 2.64 (s, 3H), 2.83 (m, 1H), 3.30 (m, 1H), 4.06 (m, 4H), 7.93 (s, 1H), 9.11 (d, 1H, J=10 Hz).

EXAMPLE 459

8-(6-amino-2-aza-spiro-[3,3]non-2-yl)-1-cyclopropyl-7-fluoro-4H-9-methyl-4-oxo-quinolizine-3-carboxylic acid hydrochloride (Isomer (II))

The second stereoisomer (Isomer II) from Example 453 was also obtained by HPLC. Isomer (II): MS 400 (M+H)$^+$. $^1$H NMR (DMSO-d$_6$) δ:0.62 (m, 2H), 1.00 (m, 2H), 1.60–1.95 (m, 6H), 2.30 (m, 2H), 2.60 (s, 3H), 3.47 (m, 1H), 3.52 (m, 1H), 3.85 (m, 4H), 7.90 (s, 1H), 9.09 (d, 1H, J=10 Hz). Analysis calculated for C$_{22}$H$_{26}$FN$_3$O$_3$.HCl.H$_2$O: C, 58.21; H, 6.44; N, 9.26. Found: C, 58.00; H, 6.29; N, 8.86.

EXAMPLE 460

8-(2,7-diazabicyclo[3,3,0]oct-7-yl-1-cyclopropyl-7-fluoro-4H-9-methyl-4-oxo-3-carboxylic acid hydrochloride Isomer A 7-BOC-2-CBZ-2,7-diazabicyclo[3,3,0]octane was prepared according to the procedure of Example 444. This compound was separated by HPLC into two stereoisomers. Isomer A was carried forward according to the procedures of steps 444b and 444c to give the title compound (194 mg). MS 372 (M+H)$^+$. $^1$H NMR (DMSO-d$_6$) δ: 0.62 (m, 2H), 1.00 (m, 2H), 1.98 (m, 1H), 2.18 (m, 1H), 2.35 (m, 1H), 2.69 (s, 3H), 3.12 (m, 1H), 3.27 (m, 1H), 3.71 (m, 2H), 3.93 (m, 1H), 4.05 (m, 1H), 4.31 (m, 1H), 8.00 (s, 1H), 9.17 (d, J=11 Hz, 1H). Analysis calculated for C$_{20}$H$_{22}$FN$_3$O$_3$.HCl.1.75 H$_2$O : C, 55.66; H, 6.08; N, 9.56. Found: C, 54.68; H, 5.73; N, 9.54.

EXAMPLE 461

8-(2,7-diazabicyclo[3,3,0]oct-7-yl)-1-cyclopropyl-7-fluoro-4H-9-methyl-4-oxo-quinolizine-3-carboxylic acid hydrochloride Isomer B 7-BOC-2-CBZ-2,7-diazabicyclo[3,3,0]octane was prepared according to the procedure of Example 444. This compound was separated by HPLC into two stereoisomers. Isomer B was carried forward according to the procedures of steps 444b and 444c to give the title compound (263 mg). MS 372 (M+H)$^+$. $^1$H NMR (DMSO-d$_6$) δ: 0.62 (m, 2H), 1.00 (m, 2H), 1.98 (m, 1H), 2.18 (m, 1H), 2.36 (m, 1H), 2.69 (s, 3H), 3.13 (m, 1H), 3.28 (m, 1H), 3.71 (m, 2H), 3.91 (m, 1H), 4.04 (m, 1H), 4.31 (m, 1H), 8.00 (s, 1H), 9.17 (d, J=11 Hz, 1H). Analysis calculated for C$_{20}$H$_{22}$FN$_3$O$_3$·HCl·1.5 H$_2$O: C, 55.24; H, 6.03; N, 9.66. Found: C, 55.37; H, 5.79; N, 9.59.

EXAMPLE 462

8-(3-(R)-(hydroxymethyl)pyrrolidin-1-yl)-1-cyclopropyl-7-fluoro-4H-9-methyl-4-oxo-3quinolizine-3-carboxylic acid hydrochloride Step 462a. 1-(1-(R)-phenylethyl)pyrrolidine-3-(R)-methanol A 2.61 g (10 mmol) sample of 5-oxo-1-(1-(R)-phenylethyl-3-(R)-pyrrolidine carboxylic acid ethyl ester (prepared as described by D. R. Johnson et at., *J. Heterocyclic Chem.*, 29:1481 (1992)) and 0.95 g of LAH were suspended in 20 mL of dry THF, and the reaction mixture was stirred at room temperature for 16 hours. The reaction was quenched by the sequential addition of water, 15% NaOH and water. The mixture was extracted with ether, which was washed, dried and concentrated to give the title compound (1.8 g) as an oil. MS 206 (M+H)$^+$. $^1$H NMR (CDCl$_3$) δ: 1.4 (d, 3H), 1.6–1.7 and 1.9–2.01 (m, 3H), 2.2–2.5 (m, 3H), 2.55–2.65 (tt, 1H), 3.13–3.2 (1, 1H), 3.5–3.57 (dd, 1H), 3.7–3.76 (dd, 1H), 7.2–7.32 (m, 5H).

Step 462b. 3-(R)-pyrrolidinemethanol

A sample of the compound from step 462a was dissolved in methanol, 10% Pd/C was added, and the mixture was hydrogenated at 4 atm H$_2$ for 16 hours at room temperature. The solution was filtered, and the solvent was removed. The residue was taken directly to the next step.

462c. 8-(3-(R)-(hydroxymethyl)pyrrolidin-1-yl)-1-cyclopropyl-7-fluoro-4H-9-methyl-4oxo-4H-quinolizine-3-carboxylic acid hydrochloride Following the procedure of Example 253j, substituting 3-(R)-pyrrolidinemethanol from step 462b for the BOC-amino-pyrrolidine thereof, and carrying the product forward as in steps 253k&l the title compound was prepared. MS 361 (M+H)$^+$. $^1$H NMR (DMSO-d$_6$) δ: 0.6–0.75 (m, 2H), 0.9–1.05 (m, 2H), 1.85–1.95 (m, 1H), 2.1–2.2 (m, 2H), 2.45 (m, 1H), 2.6 (s, 3H), 3.7–4.03 (m, 6H), 8.15 (s, 1H), 9.02 (d, 1H, J=12 Hz).

EXAMPLE 463

8-(3-(S)-(hydroxymethylpyrrolidin-1-yl-1-cyclopropyl-7-fluoro-4H-9-methyl-4-oxo-quinolizine-3-carboxylic acid hydrochloride Step 463a. 1-(1-(R)-phenylethyl)pyrrolidine-3-(S)-methanol A 2.61 g (10 mmol) sample of 5-oxo-1-(1-(R)-phenylethyl-3-(S)-pyrrolidine carboxylic acid ethyl ester (prepared as described by D. R. Johnson et al., *J. Heterocyclic Chem.*, 29:1481 (1992)) and 0.95 g of LAH were suspended in 20 mL of dry THF, and the reaction mixture was stirred at room temperature for 16 hours. The reaction was quenched by the sequential addition of water, 15% NaOH and water. The mixture was extracted with ether, which was washed, dried and concentrated to give the title compound as an oil. MS 206 (M+H)$^+$. $^1$H NMR (CDCl$_3$) δ: 1.39 (d, 3H), 1.7–1.8 and 1.94–2.07 (m, 3H), 2.2–2.46 (m, 3H), 2.97–3.05 (tt, 1H), 3.12–3.2 (1, 1H), 3.45–3.53 (dd, 1H), 3.6–3.65 (dd, 1H), 7.2–7.35 (m, 5H).

Step 462b. 3-(S)-pyrrolidinemethanol

A sample of the compound from step 462a was dissolved in methanol, 10% Pd/C was added, and the mixture was hydrogenated at 4 atm H$_2$ for 16 hours at room temperature. The solution was filtered, and the solvent was removed. The residue was taken directly to the next step.

463c. 8-(3-(S)-(hydroxymethyl)pyrrolidin-1-yl)-1-cyclopropyl-7-fluoro-4H-9-methyl-4H-quinolizine-3-carboxylic acid hydrochloride Following the procedure of Example 253j, substituting 3-(R)-pyrrolidinemethanol from step 463b for the BOC-amino-pyrrolidine thereof, and carrying the product forward as in steps 253k&l the title compound was prepared. MS 361 (M+H)$^+$. $^1$H NMR (DMSO-d$_6$) δ: 0.6–0.75 (m, 2H), 0.9–1.05 (m, 2H), 1.85–1.9 (m, 1H), 2.15–2.2 (m, 2H), 2.55–2.6 (s, 1H), 2.65 (s, 3H), 3.65–3.85 (m, 6H), 8.19 (s, 1H), 9.08 (d, 2H).

EXAMPLE 464

8-(2-(R)-(hydroxymethyl)pyrrolidin-1-yl)-1-cyclopropyl-7-fluoro-4H-9-methyl-4-oxo-quinolizine-3-carboxylic acid hydrochloride Following the procedure of Example 253j, substituting 2-(R)-pyrrolidinemethanol (Aldrich) for the BOC-aminopyrrolidine thereof, and carrying the product forward as in steps 253k&l the title compound was prepared. $^1$H NMR (DMSO-d$_6$) δ:0.5–1.1 (m, 2H), 1.9–2.2 (m, 5H), 2.68 (s, 3H), 3.22 (s, 1H), 3.62 (m, 1H), 4.0 (m, 2H), 4.55 (m, 1H), 7.95 (s, 1H), 9.0 (d, 2H).

EXAMPLE 465

8-(2-(S)-(hydroxymethyl)pyrrolidin-1-yl)-1-cyclopropyl-7-fluoro-4H-9-methyl-4-oxo-quinolizine-3-carboxylic acid hydrochloride Following the procedure of Example 253j, substituting 2-(S)-pyrrolidinemethanol (Aldrich) for the BOC-aminopyrrolidine thereof, and carrying the product forward as in steps 253k&l the title compound was prepared. $^1$H NMR (DMSO-d$_6$) δ: 0.5–1.2 (m, 4H), 1.8–2.0 (m, 5H), 2.67 (s, 3H), 3.22 (m, 1H), 3.65 (m, 1H), 4.0 (m, 2H), 4.57 (m, 1H), 7.9 (s, 1H), 9.0 (d, 2H).

EXAMPLE 466

8-(2-(R)-aminomethyl-pyrrolidin-1-yl)-1-cyclopropyl-7-fluoro-4H-9-methyl-4-oxo-quinolizine-3-carboxylic acid hydrochloride Following the procedure of Example 253j, substituting 2-(R)-BOC-aminomethyl)pyrrolidine (prepared as described in JP87-236335) for the BOC-aminopyrrolidine thereof, and carrying the product forward as in steps 253k&l the title compound was prepared. MS 360 (M+H)+. 1H NMR (DMSO-$d_6$) δ: 0.61 (m, 2H), 0.92 (m, 1H), 1.10 (m, 1H), 1.87 (m, 2H), 2.06 (m, 1H), 2.64 (s, 3H), 2.84 (m, 1H), 2.94 (m, 1H), 3.92 (m, 1H), 4.53 (m, 1H), 8.00 (s, 1H), 9.18 (d, 1H). HRMS (M+H)+: calculated for $C_{19}H_{23}FN_3O_3$: 360.1723; found: 360.1713.

EXAMPLE 467

8-(2-(S)-aminomethyl-pyrrolidin-1-yl)-
1-cyclopropyl-7-fluoro-4H-9-methyl-
4-oxo-quinolizine-3-carboxylic acid hydrochloride Following the procedure of Example 253j, substituting 2-(S)-(BOC-aminomethyl)pyrrolidine (prepared as described in JP87-236335) for the BOC-aminopyrrolidine thereof, and carrying the product forward as in steps 253k&l the title compound was prepared. MS: 360 (M+H)+. 1H NMR (DMSO-$d_6$) δ: 0.60 (m, 2H), 0.92 (m, 1H), 1.09 (m, 1H), 1.87 (m, 2H), 2.06 (m, 1H), 2.26 (m, 1H), 2.35 (m, 1H), 2.64 (s, 3H), 2.84 (m, 1H), 2.97 (m, 1H), 3.91 (m, 1H), 4.54 (m, 1H), 8.01 (s, 1H), 9.16 (d, 1H), 13.84 (b, 1H). HRMS (M+H)+: calculated for $C_{19}H_{23}FN_3O_3$: 360.1723; found: 360.1730.

EXAMPLE 468

8-(3-(R)-(1-aminocyclopropyl)pyrrolidinyl)-
1-cyclopropyl-7-fluoro-9-methyl-4-oxo-
4H-quinolizine-3-carboxylic acid hydrochloride

468a. 4-(R)-(1-(BOC-amino)cyclopropyl)pyrrolidin-2-thione and 4-(S)-(1-(BOC-amino)cyclopropyl)pyrrolidin-2-thione A sample of 4-(1-(BOC-amino)cyclopropyl)-pyrrolidin-2-one (4.3 g, 17.92 mmol, prepared as described by Hayakawa et al., U.S. Pat. No. 5,098,912, issued Mar. 24, 1992) and 3.987 g of Lawesson's Reagent were suspended in 41 mL of THF, and the reaction mixture was stirred under $N_2$ for 3 hours at room temperature. The solvent was removed, and the residue was dissolved in 1% methanol in methylene chloride and purified by chromatography on silica gel to give 3.773 g of the title compound. MS: 257 (M+H)+. This compound was subjected to chiral HPLC to separate the R and S isomers.

468b. 3-(R)-(1-(BOC-amino)cyclopropylpyrrolidine

A sample of the (R)-isomer (203 mg) from step 468a and 1.51 g of $NiCL_2 \cdot 6H_2O$ were dissolved in 10 mL of 1:1 methanol:THF, and the solution was cooled in an ice bath. To this was added 720 mg of NaBH4 in portions, and the reaction mixture was stirred at room temperature for 2 hours. The solvent was removed, and the residue was purified by chromatography on silica gel to give the title compound.

468c. 8-(3-(R)-1-aminocyclopropyl)pyrrolidinyl)-1-cyclopropyl-7-fluoro-9-methyl-4-oxo-4H-quinolizine-3-carboxylic acid hydrochloride Following the procedure of Example 253j, substituting 3-(R)-(1-(BOC-amino)cyclopropyl)pyrrolidine from step 468b for the BOC-amino-pyrrolidine thereof, and carrying the product forward as in steps 253k&l the title compound was prepared. The spectroscopic data were similar to the racemic mixture of Example 311 above.

EXAMPLE 469

8-(3-(S)-(1-aminocyclopropyl)pyrrolidinyl)-
1-cyclopropyl-7-fluoro-9-methyl-4-oxo-
4H-quinolizine-3-carboxylic acid hydrochloride

469a. 3-(S)-(1-(BOC-amino)cyclopropyl)pyrrolidine

A sample of the (S)-isomer (194 mg) from Example 468a above and 1.46 g of $NiCL_2 \cdot 6H_2O$ were dissolved in 10 mL of 1:1 methanol:THF, and the solution was cooled in an ice bath. To this was added 690 mg of NaBH4 in portions, and the reaction mixture was stirred at room temperature for 2 hours. The solvent was removed, and the residue was purified by chromatography on silica gel to give the title compound.

469b. 8-(3-(S)-(1-aminocyclopropyl)pyrrolidinyl)-1-cyclopropyl-7-fluoro-9-methyl-4-oxo-4H-quinolizine-3-carboxylic acid hydrochloride Following the procedure of Example 253j, substituting 3-(S)-(1-(BOC-amino)cyclopropyl)pyrrolidine from step 468b for the BOC-amino-pyrrolidine thereof, and carrying the product forward as in steps 253k&l the title compound was prepared. The spectroscopic data were similar to the racemic mixture of Example 311 above.

EXAMPLE 470

8-(3-(1-amino-1-cyclopropyl-methyl)pyrrolidinyl)-
1-cyclopropyl-7-fluoro-9-methyl-4-oxo-
4H-quinolizine-3-carboxylic acid hydrochloride

470a. 1-cyclopropyl-prop-2-ene-1-one

A sample (5 g, 59 mmol) of 1-cyclopropyl methyl ketone (Aldrich) was dissolved in 59 mL of THF, and the solution was heated at reflux under $N_2$, then cooled. Another solution 7.97 g of formalin and 19.57 g of N-methylpyridinium trifluoroacetate was prepared. Half of the second solution was added to the cooled first solution, and this mixture was then heated at reflux for half an hour. The reaction mixture was then cooled, the second half of the second solution was added, and the reaction mixture heated at reflux for 7 hours. The mixture was cooled, and ether (100 mL) was added slowly with stirring, and a gummy precipitate was obtained. The gum was triturated with ethers. The ether solutions were combined and extracted with aqueous $NaHCO_3$. The ether solution was dried, filtered and concentrated. The residue was triturated with ether, and the ether solution was again dried, filtered and concentrated to give 4.60 g of the title compound.

470b. (1-benzyl-pyrroldin-3-yl)-cyclopropyl-methanone

A 2 g sample of the compound from step 470a and 4.94 g of N-benzyl-N-(methoxymethyl)-trimethylsilylmethylamine were dissolved in methylene chloride, and the solution was cooled in an ice bath. To this solution was added 2.1 mL of TFA (1N in methylene chloride), and the reaction mixture was stirred at room temperature for 2 hours. The mixture was diluted with methylene chloride, and the solution was washed with $NaHCO_3$, water and brine, then concentrated. The residue was purified by chromatography on silica gel to give 2.037 g of the title compound.

470c.
1-(1-benzyl-pyrroldin-3-yl)-1-cyclopropyl-methylamine

A 1 g sample of the compound from step 470b, 3.37 g of ammonium acetate and 274 mg of NaBH$_3$CN were dissolved in 15 mL of methanol, 1.2 g of 4 Å molecular sieves were added, and the mixture was stirred at room temperature under N$_2$ for 16 hours. The mixture was filtered, the sieves washed with methanol, the wash and filtrate combined, and concentrated. The residue was dissolved in 100 mL of methylene chloride, and 30 mL of 15% NaOH was added. The organic phase and a second wash of the aqueous phase were combined and washed with water and brine, then dried over MgSO$_4$. The solvent was removed, and the residue was chromatographed on silica gel to give 460 mg of the title compound.

470d. N-BOC-1-(1-benzyl-pyrroldin-3-yl)-1-cyclopropyl-methylamine

The compound from step 470c was treated with di-t-butyl dicarbonate in methylene chloride and triethylamine for 2 hours, and the title compound (640 mg) was obtained after chromatography on silica gel.

470e.
3-(1-(BOC-amino)-1-cyclopropyl-methyl)pyrrolidine

A sample (548 mg) of the compound from step 470d was dissolved in methanol, 140 mg of 10% Pd/C was added, and the mixture was hydrogenated at 4 arm H$_2$ for 42 hours at room temperature. The solution was filtered, and the solvent was removed to give 140 mg of the title compound.

470f.
8-(3-(1-amino-1-cyclopropyl-methyl)pyrrolidinyl)-1-cyclopropyl-7-fluoro-9-methyl-4-oxo-4H-quinolizine-3-carboxylic acid hydrochloride Following the procedure of Example 253j, substituting 3-(1-(BOC-amino)-1-cyclopropyl-methyl)pyrrolidine from step 470e for the BOC-amino-pyrrolidine thereof, and carrying the product forward as in steps 253k&l the title compound was prepared. $^1$H NMR (DMSO-d$_6$) δ: 0.46 (m, 1H), 0.62 (m, 4H), 0.92 (m, 1H), 1.03 (m, 2H), 1.82 (m, 1H), 2.27 (m, 3H), 2.61 (s, 3H), 3.74 (m, 2H), 3.89 (m, 2H), 7.90 (s, 1H), 9.07 (d, 1H), 13.83 (br s, 1H). HRMS (M+H)$^+$: calculated for C$_{22}$H$_{27}$FN$_3$O$_3$: 400.2036; found: 400.2030.

EXAMPLE 471

8-(3-(R)-pyrrolidin-2-(S)-yl)pyrrolidin-1-yl)-1-cyclopropyl-7-fluoro-9-methyl-4-oxo-4H-quinolizine-3-carboxylic acid hydrochloride

471a.
3-(R)-(1-BOC-2-(S)-pyrrolidinyl)-4-nitrobutanol

A 7.5 g sample of ethyl 3-(R)-(1-BOC-2-(S)-pyrrolidinyl)-4-nitrobutanoate (prepared according to the procedure of Hayakawa et al., U.S. Pat. No. 5,098,912, issued Mar. 24, 1992) was dissolved in 35 mL of ether and treated with 0.76 g of LAH. After careful quenching of the excess reagents, the title compound was extracted and purified by chromatography (4.5 g).

471a.
3-(R)-(1-BOC-2-(S)-pyrrolidinyl)-4-nitrobutanyl methylsulfonyl ether

A 3.5 g sample of the alcohol from step 471a above was dissolved in 25 mL of methylene chloride and treated with methanesulfonyl chloride an TEA at 0° C. for 2 hours. The reaction mixture was washed with NaHCO$_3$ solution and water, and the solvent was removed. The residue was chromatographed on silica gel to give 3 g of the title compound.

471c. 3-(R)-(1-BOC-pyrrolidin-2-(S)-yl)pyrrolidine

The ether compound from step 471a was treated by hydrogenation at 4 atm H$_2$ over Pd/C in methanol to give the title compound.

471d. 8-(3-(R)-(pyrrolidin-2-(S)-yl)pyrrolidin-1-yl)-1-cyclopropyl-7-fluoro-9-methyl-4-oxo-4H-quinolizine-3-carboxylic acid hydrochloride Following the procedure of Example 253j, substituting 3-(R)-(1-BOC-pyrrolidin-2-(S)-yl)pyrrolidine from step 471c for the BOC-amino-pyrrolidine thereof, and carrying the product forward as in steps 253k&l the title compound was prepared. MS 400 (M+H)$^+$. $^1$H NMR (DMSO-d$_6$) δ:0.58–0.62 (m, 2H), 0.9–1.1 (m, 2H), 1.68–2.8 (m, 8H), 2.5 (s, 3H), 3.1–3.8 (m, 7H), 7.9 (s, 1H), 9.08 (dd, 2H).

EXAMPLE 472

8-(3-(aminomethyl)azetidin-1-yl)-1-cyclopropyl-7-fluoro-9-methyl-4-oxo-4H-quinolizine-3-carboxylic acid hydrochloride

472a.
3-(BOC-aminomethyl)-1-diphenylmethyl-azetidine

A sample (0.6 g) of 3-aminomethyl-1-diphenylmethyl-azetidine (prepared according to Anderson and Lok, J. Org. Chem., 37:3393–5 (1972)) was treated with di-t-butyl dicarbonate in methylene chloride and triethylamine for 2 hours, and the title compound (450 mg) was obtained after chromatography on silica gel.

472b. 3-(BOC-aminomethyl)-azetidine

A sample of the compound from step 473a was treated with 4 atm of H$_2$ in the presence of Pd/C in methanol at room temperature. The mixture was filtered, and the solvent was removed to give the title compound.

472c.
8-(3-(aminomethyl)azetidin-1-yl)-1-cyclopropyl-7-fluoro-9-methyl-4-oxo-4H-quinolizine-3-carboxylic acid hydrochloride Following the procedure of Example 253j, substituting 3-(BOC-aminomethyl)-azetidine from step 472b for the BOC-amino-pyrrolidine thereof, and carrying the product forward as in steps 253k&l the title compound was prepared. MS 346 (M+H)$^+$. $^1$H NMR (DMSO-d$_6$) δ: 0.61 (m, 2H), 0.98 (m, 2H), 2.16 (m, 1H), 2.60 (s, 3H), 3.01 (m, 1H), 3.76 (m, 1H), 4.41 (m, 2H), 4.69 (m, 2H), 7.88 (s, 1H), 9.10 (d, 1H).

EXAMPLE 473

6-amino-8-(3-aminopyrrolidinyl)-1-cyclopropyl-7-fluoro-4H-9-methyl-4-oxo-quinolizine-3-carboxylic acid hydrochloride Step 473a-a: 4-t-Butoxy-6-dibenzylamino-2,5-difluoro-3-methylpyridine 4-t-Butoxy-2,5,6-trifluoro-3-methylpyridine from Step 253c above is reacted with dibenzylamine in ethanol at reflux temperature. Solvent is removed, and the residue is dissolved in methylene chloride and washed with water. The product is purified by column chromatography.

Step 473b: 6-dibenzylamino-8-(3-aminopyrrolidinyl)-1-cyclopropyl-7-fluoro-4H-9-methyl-4-oxo-quinolizine-3-carboxylic acid hydrochloride Following the procedure of Example 253e, replacing 4-t-butoxy-2,5-difluoro-3-methylpyridine with 4-t-butoxy-6-dibenzylamino-2,5-difluoro-3-methylpyridine from Step 473a above, and carrying the product forward as in Example 253 steps e-l, the title compound is prepared.

Step 473c: 6-amino-8-(3-aminopyrrolidinyl)-1-cyclopropyl-7-fluoro-4H-9-methyl-4-oxo-quinolizine-3-carboxylic acid hydrochloride A sample from Step 473d above is heated with ammonium formate in the presence of 10% Pd-C in ethanol. After the completion of the reaction, the mixture is filtered and the filtrate is concentrated and treated with HCl in ether to give the title compound.

EXAMPLE 474

6-amino-8-(7-amino-5-azaspiro[2,4]heptan-5-yl)-1-cyclopropyl-7-fluoro-4H-9-methyl-4-oxo-quinolizine-3-carboxylic acid hydrochloride Following the procedures of Example 473, replacing 3-BOC-aminopyrrolidine with 7-BOC-amino-5-azaspiro[2,4]heptane (prepared according to the procedures as described in J. Med. Chem. 1994, 37, 3344), and carrying the product forward the title compound is prepared.

EXAMPLE 475

6-amino-8-(2,8-diaza-8-bicyclo[4,3,0]nonyl)-1-cyclopropyl-7-fluoro-4H-9-methyl-4-oxo-quinolizine-3-carboxylic acid hydrochloride Following the procedures of Example 473, replacing 3-BOC-aminopyrrolidine with 2,8-diazabicyclo[4,3,0]nonane (prepared according to U.S. Pat. No. 5,059,597), and carrying the product forward the title compound is prepared.

EXAMPLE 476

6-amino-8-(3,5-cis-dimethylpiperazin-1-yl)-1-cyclopropyl-7,9-difluoro-4H-4-oxo-quinolizine-3-carboxylic acid hydrochloride Following the procedure of Example 473a, replacing 4-t-butoxy-2,5,6-trifluoro-3-methylpyridine with 4-t-butoxy-2,3,5,6-tertafluoropyridine from Example 274b above, and carrying the product forward as in Example 473b–c, replacing 3-BOC-aminopyrrolidine with 3,5-cis-dimethylpiperazine and carrying the product forward the title compound is prepared.

EXAMPLE 477

8-(1-amino-1-cyclopropyl)-1-cyclopropyl-7-fluoro-9-methyl-4H-4-oxo-quinolizine-3-carboxylic acid hydrochloride Step 477a: 1-cyclopropyl-8-(diphenylmethoxycarbonylmethyl)-7-fluoro-9-methyl-4-oxo-4H-quinolizine-3-carboxylic acid ethyl ester To a suspension of NaH in DMF with ice bath cooling is added di-t-butyl malonate. After the addition, 8-chloro-1-cyclopropyl-7-fluoro-9-methyl-4-oxo-4H-quinolizine-3-carboxylic acid ethyl ester from Example 253i above is added. The reaction is then heated to 50° to 60° C., and the mixture is poured into water and acidified. The product is extracted into methylene chloride and dried over MgSO$_4$. The residue, after removal of the solvent, is dissolved in methylene chloride and trifluoroacetic acid at room temperature. The solvent is removed under vacuum, and the product is treated with diphenyldiazomethane in methylene chloride and methanol. When the reaction is finished, the solvents are removed under vacuum, and the product is purified by column chromatography to give the title compound.

Step 477b: 1-cyclopropyl-8-(1-diphenylmethoxycarbony-1-vinyl)-7-fluoro-9-methyl-4-oxo-4H-quinolizine-3-carboxylic acid ethyl ester The product from Step 477a is heated with 35% formaldehyde in DMF in the presence sodium bicarbonate. When the reaction is complete, the product is extracted into methylene chloride, washed with water and dried over MgSO$_4$. The solvent is removed, and the residue is dissolved methylene chloride. Triethylamine is added, followed by methanesulfonyl chloride with ice bath cooling. After the addition, the reaction is stirred at room temperature, then poured into water and acidified. The mixture is extracted with ethylene chloride, and the solvent is removed to give the crude product, which is purified by column chromatography.

Step 477c: 1-cyclopropyl-8-(1-diphenylmethoxycarbony-1-cyclopropyl)-7-fluoro-9-methyl-4-oxo-4H-quinolizine-3-carboxylic acid ethyl ester Trimethylsulfonium iodide is added to a stirred solution of NaH in DMSO at 0° C. and the resulting solution is stirred at room temperature. The product from Step 477b above is added and mixture is stirred at 50° C. The mixture is quenched with water, and the product is extracted to give the title compound.

Step 477d: 1-cyclopropyl-8-(1-hydroxycarbonyl-1-cyclopropyl-7-fluoro-9-methyl-4-oxo-4H-quinolizine-3-carboxylic acid ethyl ester The product from Step 477d is dissolved in the mixture of anisol and trifluoroacedic acid and is stirred at room temperature. The solvents are removed and residue is purified by a column chromatography to give the title compound.

Step 477e: 1-cyclopropyl-8-(1-Bocamino-1-cyclopropyl)-7-fluoro-9-methyl-4-oxo-4H-quinolizine-3-carboxylic acid ethyl ester A sample of the product from Step 477d is heated with diphenylphosphoryl azide, t-butanol, triethylamine and dioxane. The solvents is removed under vacuum. The residue is dissolved in methylene chloride, washed with water and dried over MgSO$_4$ and concentrated under vacuum. The title compound is purified by chromatography on silica gel.

Step 477f: 1-cyclopropyl-8-(1-amino-1-cyclopropyl)-7-fluoro-9-methyl-4-oxo-4H-quinolizine-3-carboxylic acid hydrochloride

EXAMPLE 478

3(R)-10-(1-amino-1-cyclopropyl)-9-fluoro-
3-methyl-2H,3H,6H-6-oxo-pyrano
[2,3,4-ij]quinolizine-5-carboxylic acid
hydrochloride Follow the procedures as described in Example 477, replacing 8-chloro-1-cyclopropyl-7-fluoro-9-methyl-4-oxo-4H-quinolizine-3-carboxylic acid ethyl ester with 3(R)-10-chloro-9-fluoro-3-methyl-2H,3H,6H-6-oxo-pyrano[2,3,4-ij] quinolizine-5-carboxylic acid ethyl ester from Example 281e to give the title compound.

EXAMPLE 479

8-(1-amino-1-cyclopropyl)-1-cyclopropyl-
7-fluoro-9-methoxy-4H-4-oxo-quinolizine-3-carboxylic
acid hydrochloride Follow the procedures as described in Example 477, replacing 8-chloro-1-cyclopropyl-7-fluoro-9-methyl-4-oxo-4H-quinolizine-3-carboxylic acid ethyl ester with 8-chloro-1-cyclopropyl-7-fluoro-9-methoxy-4H-4-oxo-quinolizine-3-carboxylic acid ethyl ester from Example 275 to give the title compound.

EXAMPLE 480

8-(1-aminomethyl-1-cyclopropyl)-1-cyclopropyl-
7-fluoro-9-methyl-4H-4-oxo-quinolizine-3-carboxylic
acid hydrochloride Step 480a: 8-(1-cyano-1-cyclopropyl)-1-cyclopropyl-7-fluoro-9-methyl-4H-4-oxo-quinolizine-3-carboxylic acid ethyl ester The product from Example 477d is treated with oxalyl chloride in methylene chloride followed by quenching with aqueous ammonia. Aqueous work up gives the amide, which is treated with POCl$_3$ at room temperature to give the title compound.

Step 480b: 8-(1-Bocaminomethyl-1-cyclopropyl)-1-cyclopropyl-7-fluoro-9-methyl-4H-4-oxo-quinolizine-3-carboxylic acid ethyl ester The product from Step 480a is treated with Raney Ni in ethanol under hydrogen. The residue after removal of the solvent is reacted with d-t-butyl dicarbonate in the mixture of methanol and water. Reaction is extracted into methylene chloride, washed with water and dried over MgSO$_4$ and concentrated trader vacuum. The title compound is purified by chromatography on silica gel.

Step 480c: 8-(1-aminomethyl-1-cyclopropyl)-1-cyclopropyl-7-fluoro-9-methyl-4H-4-oxo-quinolizine-3-carboxylic acid hydrochloride The product from Step 480b is treated by procedures as described in Example 253 k–1 to give the title compound.

EXAMPLES 481–565

Following the procedures of Steps 253j, 253k and 253l above, replacing the 3-BOC-aminopyrrolidine of Step 253j with the appropriate unprotected or BOC-protected reagent, the compounds of Examples 481–565 are prepared as shown in Table 13A, below. In those cases wherein specific chiral isomers are indicated, the examples are to be understood as also representing the opposite stereoisomers and diastereomers thereof.

TABLE 13A

[Structure shown with F, R$_2$, CH$_3$, COOH, and cyclopropyl substituents on a quinolizine core]

| Example # | R$^2$ |
|---|---|
| 481 | [3-(N-methylamino)pyrrolidin-1-yl] |
| 482 | [3-(N-(2-methoxyethyl)amino)pyrrolidin-1-yl] |
| 482 | [3-(N-allylamino)pyrrolidin-1-yl] |
| 484 | [3-((N-methylaminomethyl))pyrrolidin-1-yl] |
| 485 | [3-((N-carboxymethylamino)methyl)pyrrolidin-1-yl] |
| 486 | [3-((N-carbamoylmethylamino)methyl)pyrrolidin-1-yl] |
| 487 | [3-(2-aminoethyl)pyrrolidin-1-yl] |
| 488 | [3-aminoazetidin-1-yl] |
| 489 | [3-(2-aminoethyl)azetidin-1-yl] |
| 490 | [3-(hydroxymethyl)azetidin-1-yl] |

TABLE 13A-continued
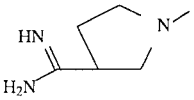
| Example # | R² |
|---|---|
| 491 | 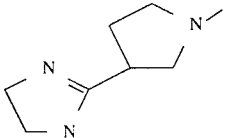 |
| 492 | 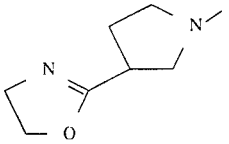 |
| 493 | 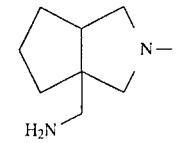 |
| 494 | 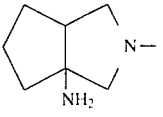 |
| 495 | 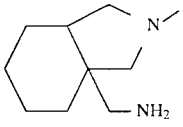 |
| 496 | 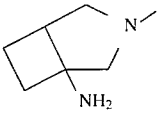 |
| 497 | 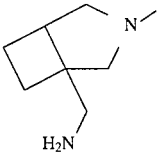 |
| 498 | 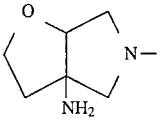 |
| 499 | 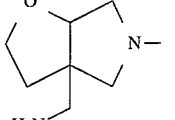 |
TABLE 13A-continued
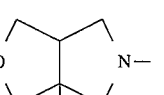
| Example # | R² |
|---|---|
| 500 | 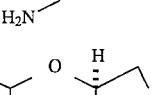 |
| 501 | 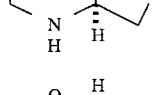 |
| 502 | 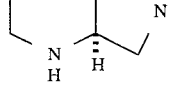 |
| 503 | 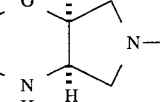 |
| 504 | 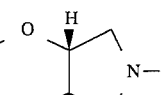 |
| 505 | 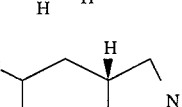 |
| 506 | 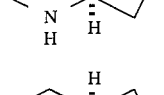 |
| 507 | 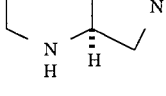 |
| 508 |  |

TABLE 13A-continued
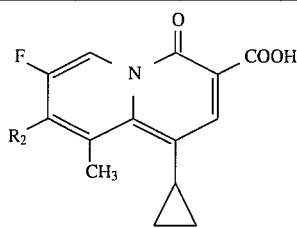
| Example # | R² |
|---|---|
| 509 | |
| 510 | |
| 511 | |
| 512 | |
| 513 | |
| 514 | |
| 515 | |
| 516 | |
TABLE 13A-continued
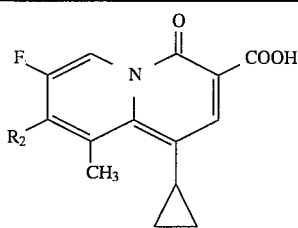
| Example # | R² |
|---|---|
| 517 | |
| 518 | |
| 519 | |
| 520 | |
| 521 | |
| 522 | |
| 523 | |
| 524 | |
| 525 | |
| 526 | |

TABLE 13A-continued
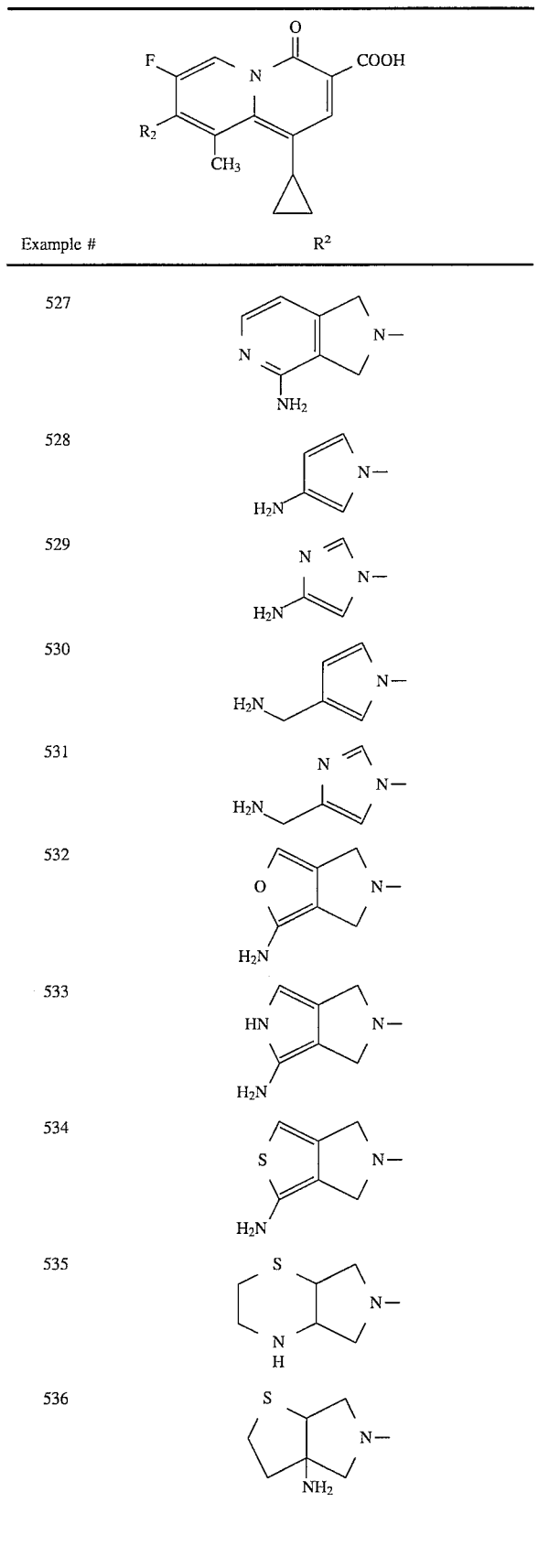
| Example # | R² |
|---|---|
| 527 | |
| 528 | |
| 529 | |
| 530 | |
| 531 | |
| 532 | |
| 533 | |
| 534 | |
| 535 | |
| 536 | |
TABLE 13A-continued
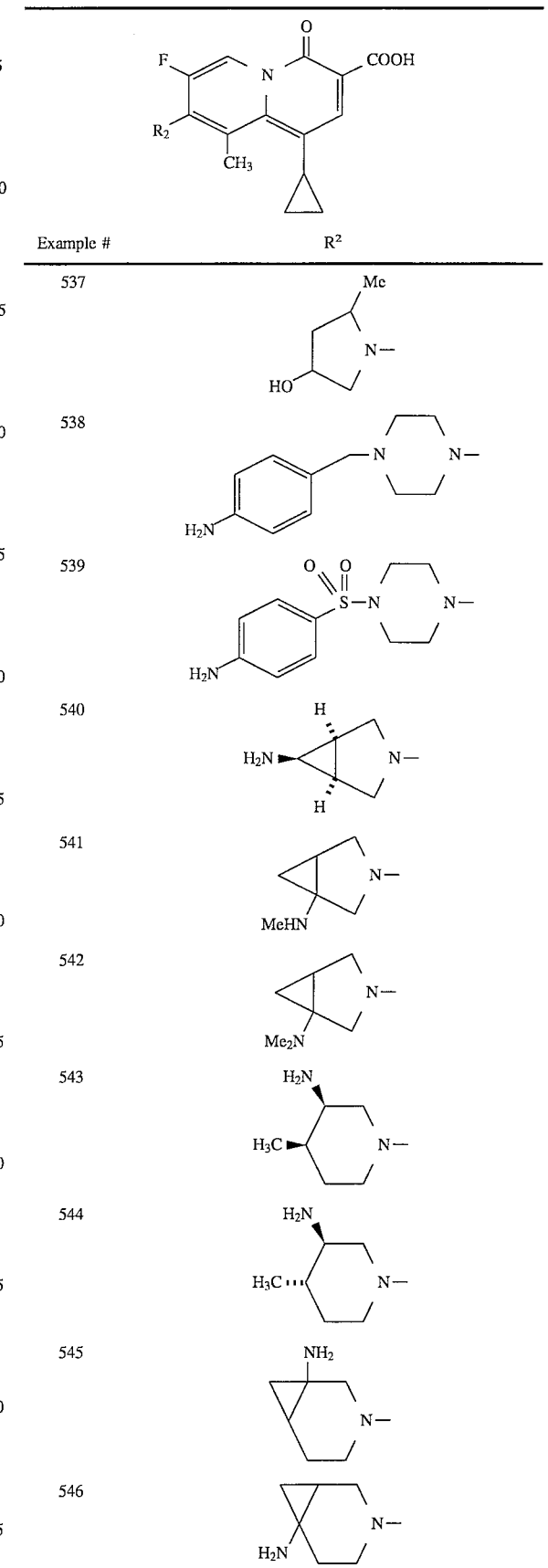
| Example # | R² |
|---|---|
| 537 | |
| 538 | |
| 539 | |
| 540 | |
| 541 | |
| 542 | |
| 543 | |
| 544 | |
| 545 | |
| 546 | |

TABLE 13A-continued
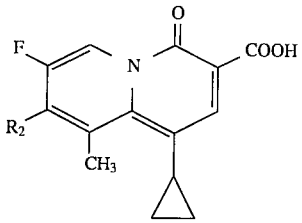
| Example # | R² |
|---|---|
| 547 | 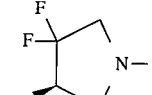 |
| 548 | 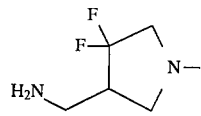 |
| 549 | 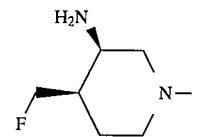 |
| 550 | 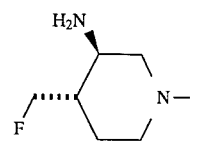 |
| 551 | 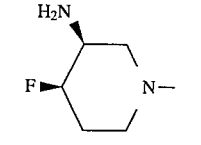 |
| 552 | 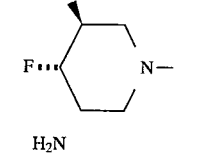 |
| 553 | 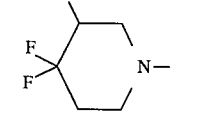 |
| 554 | 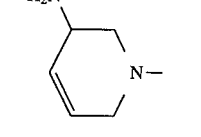 |
| 555 | 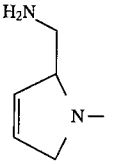 |
TABLE 13A-continued
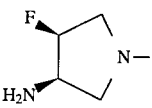
| Example # | R² |
|---|---|
| 556 | 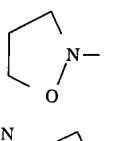 |
| 557 | 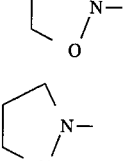 |
| 558 | 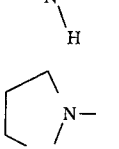 |
| 559 | 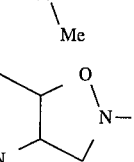 |
| 560 | 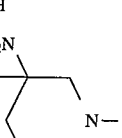 |
| 561 | 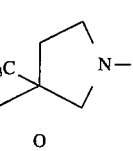 |
| 562 | 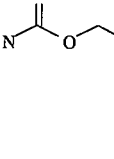 |
| 563 | 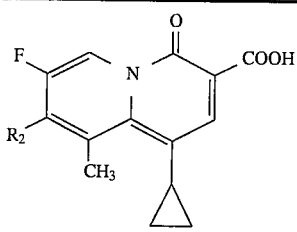 |
| 564 | 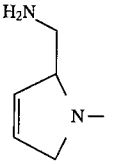 |

TABLE 13A-continued

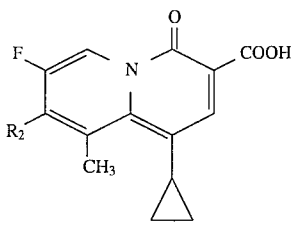

| Example # | R² |
|---|---|
| 565 | 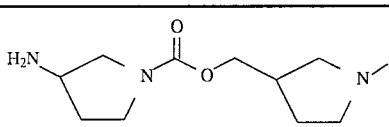 |

EXAMPLE 566

In Vitro Assay Of Antibacterial Activity

The in vitro antibacterial activity of the compounds of the present invention was demonstrated as follows: Minimum inhibitory concentrations (MICs) were determined by the agar dilution method, in which twelve petri dishes were prepared, each containing successive aqueous 2-fold dilutions of the test compounds mixed with 10 mL of sterilized Brain Heart Infusion (BHI) agar. Each plate was inoculated with 1:100 (or 1:10 for slow-growing strains, primarily Micrococcus and Streptococcus) dilutions of up to 32 different microorganisms, using a Steers replicatoro block calibrated to deliver approximately $10^4$ colony forming units (CFUs). The inoculated plates were incubated at from about 35° C. to about 37° C. for approximately 20–24 hours. In addition, a control plate using BHI agar containing no test compound was prepared and incubated at the beginning and at the end of each test. The quinolone antibacterial ciprofloxacin was used as a control ("Cntl").

After incubation, each petri dish was observed for the presence or absence of microorganism growth. The MIC was defined as the lowest concentration of test compound yielding no growth (a slight haze or sparsely isolated colonies at the inoculum spot) as compared to the growth control containing no test compound.

The results of the above tests, shown in Tables 14, 15 and 16 below, demonstrate that the compounds of the present invention are surprisingly effective in combating bacterial growth. Moreover, the 9-methyl quinolizinone compounds of the invention (in which A of formula (I) is $=CR^6-$ and $R^6$ is methyl) are shown to have excellent activity even against the ciprofloxacinresistant pathogen *Staphylococcus aureus* 1775, demonstrating the potential usefulness of these compounds in treating infections not susceptible to this widely-used agent.

TABLE 14

In Vitro Antibacterial Activity (MIC Values in µg/ml)

| Organism | Cntl | 1 | 2 | 62 | 64 | 65 | 157 |
|---|---|---|---|---|---|---|---|
| *Staphylococcus aureus* ATCC 6538P | 0.2 | 0.39 | 0.39 | 3.1 | 25 | 12.5 | 0.2 |
| *Staphylococcus aureus* A5177 | 0.39 | 0.78 | 0.78 | 12.5 | 50 | 25 | 0.39 |
| *Staphylococcus aureus* A-5278 | 0.39 | — | 0.78 | — | — | — | 0.39 |
| *Staphylococcus aureus* 642A | 0.39 | 0.78 | 0.78 | 6.2 | — | — | 0.39 |
| *Staphylococcus aureus* NCTC 10649 | 0.39 | 0.39 | 0.39 | 6.2 | — | — | 0.2 |
| *Staphylococcus aureus* CMX 553 | 0.78 | 0.78 | 0.78 | 12.5 | 50 | 50 | 0.39 |
| *Staphylococcus aureus* 1775 | >100 | — | 25 | — | — | — | 25 |
| *Staphylococcus epidermidis* 3519 | 0.39 | 0.78 | 0.78 | 12.5 | 50 | 25 | 0.39 |
| *Micrococcus luteus* ATCC 9341 | 1.56 | 50 | 50 | 25 | 25 | 25 | 3.1 |
| *Micrococcus luteus* ATCC 4698 | 0.78 | 25 | 25 | 12.5 | 25 | 25 | 1.56 |
| *Enterococcus faecium* ATCC 8043 | 0.39 | 25 | 25 | 50 | 100 | 50 | 1.56 |
| *Streptococcus bovis* A5169 | 1.56 | 25 | 25 | 25 | 25 | 100 | 3.1 |
| *Streptococcus agalactaciae* CMX 508 | 0.39 | 12.5 | 12.5 | 25 | 50 | 100 | 1.56 |
| *Streptococcus pyogenes* EES61 | 0.39 | 6.2 | 6.2 | 25 | 50 | 100 | 1.56 |
| *Streptococcus pyogenes* CONST | 0.78 | 6.2 | 6.2 | 25 | 50 | 50 | 1.56 |
| *Streptococcus pyogenes* 2548 INDUC | 0.39 | 3.1 | 3.1 | 25 | 50 | 50 | 0.39 |
| *Escherichia coli* JUHL | 0.01 | 0.39 | 0.39 | 3.1 | 6.2 | 12.5 | 0.02 |
| *Escherichia coli* SS | .005 | <.05 | 0.05 | 0.39 | 1.56 | 1.56 | 0.01 |
| *Escherichia coli* DC-2 | 0.2 | 12.5 | 12.5 | 25 | 100 | >100 | 0.39 |
| *Escherichia coli* H560 | 0.01 | — | 0.39 | 3.1 | 12.5 | 12.5 | 0.02 |
| *Escherichia coli* KNK 437 | 0.2 | 6.2 | 6.2 | 25 | 100 | 100 | 0.39 |
| *Enterobacter aerogenes* ATCC 13048 | 0.05 | 0.78 | 0.78 | 3.1 | 6.2 | 12.5 | 0.02 |
| *Klebsiella pneumoniae* ATCC 8045 | 0.02 | 0.2 | 0.2 | 3.1 | 6.2 | 6.2 | 0.02 |
| *Providencia stuartii* CMX 640 | 0.78 | 25 | 25 | 25 | >100 | >100 | 1.56 |
| *Pseudomonas aeruginosa* BMH 10 | 0.1 | 6.2 | 6.2 | 6.2 | 25 | 25 | 0.2 |
| *Pseudomonas aeruginosa* A5007 | 0.1 | 6.2 | 6.2 | 6.2 | 50 | 25 | 0.39 |
| *Pseudomonas aeruginosa* K799/WT | 0.1 | 3.1 | 3.1 | 6.2 | 25 | 25 | 0.2 |
| *Pseudomonas aeruginosa* K799/61 | 0.02 | 0.39 | 0.39 | 0.05 | 6.2 | 25 | 0.05 |
| *Pseudomonas aeruginosa* 5263 | 12.5 | — | — | — | — | — | 50 |
| *Pseudomonas aeruginosa* 2862 | 25 | — | — | — | — | — | 25 |
| *Pseudomonas cepacia* 2961 | 3.1 | 25 | 25 | 3.1 | 100 | 100 | 3.1 |
| *Acinetobacter calcoaceticus* CMX 669 | 0.39 | 0.78 | 0.78 | 0.78 | 50 | 25 | 0.2 |

TABLE 14-continued

| Organism | Example number | | | | |
|---|---|---|---|---|---|
| | 158 | 159 | 160 | 161 | 162 |
| S. aureus ATCC 6538P | 0.2 | 0.2 | 0.2 | 0.05 | 0.1 |
| S. aureus A5177 | 0.39 | 0.39 | 0.39 | 0.1 | 0.1 |
| S. aureus A-5278 | 0.78 | 0.2 | 0.2 | 0.1 | 0.1 |
| S. aureus 642A | 0.2 | 0.39 | 0.2 | 0.1 | 0.2 |
| S. aureus NCTC 10649 | 0.2 | 0.2 | 0.2 | 0.05 | 0.1 |
| S. aureus CMX 553 | 0.39 | 0.39 | 0.39 | 0.1 | 0.2 |
| S. aureus 1775 | 100 | >100 | 100 | 100 | >100 |
| S. epidermidis 3519 | 0.39 | 0.39 | 0.39 | 0.1 | 0.2 |
| M. luteus ATCC 9341 | 3.1 | 25 | 6.2 | 3.1 | 6.2 |
| M. luteus ATCC 4698 | 1.56 | 12.5 | 0.78 | 3.1 | 3.1 |
| E. faecium ATCC 8043 | 1.56 | 6.2 | 3.1 | 0.78 | 0.78 |
| S.s bovis A5169 | 6.2 | 12.5 | 6.2 | 1.56 | 1.56 |
| S. agalactaciae CMX 508 | 1.56 | 3.1 | 1.56 | 0.39 | 0.78 |
| S. pyrogenes EES61 | 1.56 | 3.1 | 1.56 | 0.39 | 0.39 |
| S. pyrogenes CONST | 1.56 | 3.1 | 1.56 | 0.39 | 0.39 |
| S. pyrogenes 2548 INDUC | 0.78 | 3.1 | 0.78 | 0.1 | 0.2 |
| E. coli JUHL | 0.02 | 0.39 | 0.39 | 0.02 | 0.02 |
| E. coli SS | 0.01 | 0.02 | .005 | .005 | .005 |
| E. coli DC-2 | 0.39 | 6.2 | 25 | 0.2 | 0.39 |
| E. coli H560 | 0.02 | 0.39 | 3.1 | 0.02 | 0.02 |
| E. coli KNK 437 | 0.39 | 6.2 | 25 | 0.2 | 0.39 |
| E. aerogenes ATCC 13048 | 0.1 | 0.78 | 12.5 | 0.05 | 0.05 |
| K. pneumoniae ATCC 8045 | 0.05 | 0.2 | 1.56 | 0.01 | 0.02 |
| P. stuartii CMX 640 | 3.1 | 25 | >100 | 1.56 | 1.56 |
| P. aeruginosa BMH 10 | 0.2 | 3.1 | 12.5 | 0.2 | 0.2 |
| P. aeruginosa A5007 | 0.2 | 6.2 | 25 | 0.2 | 0.39 |
| P. aeruginosa K799/WT | 0.2 | 3.1 | 12.5 | 0.2 | 0.39 |
| P. aeruginosa K799/61 | 0.05 | 0.39 | 3.1 | 0.05 | 0.05 |
| P. aeruginosa 5263 | 50 | >100 | >100 | 100 | 100 |
| P. aeruginosa 2862 | 50 | >100 | >100 | 100 | 100 |
| P. cepacia 2961 | 3.1 | 25 | >100 | 3.1 | 6.2 |
| A. calcoaceticus CMX 669 | 0.2 | 0.78 | 3.1 | 0.05 | 0.1 |

| Organism | Example number | | | |
|---|---|---|---|---|
| | 163 | 164 | 165 | 166 |
| S. aureus ATCC 6538P | 1.56 | 0.78 | 6.2 | 0.39 |
| S. aureus A5177 | 1.56 | 1.56 | 6.2 | 1.56 |
| S. aureus A-5278 | 1.56 | 1.56 | 6.2 | 1.56 |
| S. aureus 642A | 1.56 | 1.56 | 6.2 | 1.56 |
| S. aureus NCTC 10649 | 0.78 | 1.56 | 6.2 | 0.39 |
| S. aureus CMX 553 | 1.56 | 1.56 | 6.2 | 3.1 |
| S. aureus 1775 | 100 | 50 | >100 | >100 |
| S. epidermidis 3519 | 1.56 | 1.56 | 6.2 | 0.78 |
| M. luteus ATCC 9341 | 25 | 12.5 | >100 | 50 |
| M. luteus ATCC 4698 | 12.5 | 6.2 | >100 | 25 |
| E. faecium ATCC 8043 | 12.5 | 12.5 | >100 | 12.5 |
| S.s bovis A5169 | 50 | 12.5 | >100 | 25 |
| S. agalactaciae CMX 508 | 12.5 | 12.5 | >100 | 3.1 |
| S. pyrogenes EES61 | 12.5 | 12.5 | >100 | 1.56 |
| S. pyrogenes CONST | 12.5 | 12.5 | >100 | 1.56 |
| S. pyrogenes 2548 INDUC | 12.5 | 12.5 | >100 | 1.56 |
| E. coli JUHL | 0.2 | 0.05 | 3.1 | 0.78 |
| E. coli SS | 0.1 | 0.02 | 0.2 | 0.05 |
| E. coli DC-2 | 6.2 | 1.56 | >100 | 12.5 |
| E. coli H560 | 0.1 | 0.1 | 3.1 | 0.78 |
| E. coli KNK 437 | 3.1 | 1.56 | >100 | 6.2 |
| E. aerogenes ATCC 13048 | 0.39 | 0.05 | 3.1 | 3.1 |
| K. pneumoniae ATCC 8045 | 0.1 | 0.05 | 0.39 | 1.56 |
| P. stuartii CMX 640 | 50 | 12.5 | >100 | >100 |
| P. aeruginosa BMH 10 | 1.56 | 0.39 | 50 | 3.1 |
| P. aeruginosa A5007 | 3.1 | 0.39 | 25 | 6.2 |
| P. aeruginosa K799/WT | 3.1 | 0.39 | 25 | 6.2 |
| P. aeruginosa K799/61 | 1.56 | 0.1 | 3.1 | 0.39 |
| P. aeruginosa 5263 | 100 | 100 | | >100 |
| P. aeruginosa 2862 | >100 | 100 | | >100 |
| P. cepacia 2961 | 12.5 | 3.1 | 25 | >100 |
| A. calcoaceticus CMX 669 | 0.39 | 0.39 | 6.2 | 3.1 |

TABLE 14-continued

| | Example number | | | | | | |
|---|---|---|---|---|---|---|---|
| Organism | 167 | 168 | 169 | 170 | 171 | 172 | 173 |
| S. aureus ATCC 6538P | 0.78 | 0.78 | 0.1 | 0.05 | 0.1 | 50 | 1.56 |
| S. aureus A5177 | 3.1 | 3.1 | 0.2 | 0.1 | 0.1 | 100 | 6.2 |
| S. aureus A-5278 | 1.56 | 3.1 | 0.2 | 0.1 | 0.1 | 50 | 6.2 |
| S. aureus 642A | 3.1 | 3.1 | 0.39 | 0.1 | 0.2 | 100 | 12.5 |
| S. aureus NCTC 10649 | 0.78 | 0.78 | 0.2 | 0.05 | 0.1 | 50 | 1.56 |
| S. aureus CMX 553 | 6.2 | 6.2 | 0.39 | 0.2 | 0.2 | >100 | 12.5 |
| S. aureus 1775 | >100 | >100 | 25 | 100 | 50 | >100 | >100 |
| S. epidermidis 3519 | 3.1 | 3.1 | 0.39 | 0.2 | 0.2 | 50 | 6.2 |
| M. luteus ATCC 9341 | 50 | 50 | 3.1 | 12.5 | 3.1 | >100 | >100 |
| M. luteus ATCC 4698 | 50 | 50 | 0.39 | 1.56 | 0.78 | >100 | 100 |
| E. faecium ATCC 8043 | 12.5 | 12.5 | 1.56 | 0.78 | 0.78 | >100 | 50 |
| S.s bovis A5169 | 12.5 | 12.5 | 3.1 | 6.2 | 1.56 | >100 | 25 |
| S. agalactaciae CMX 508 | 6.2 | 6.2 | 0.78 | 0.78 | 0.78 | >100 | 12.5 |
| S. pyrogenes EES61 | 6.2 | 6.2 | 0.78 | 0.78 | 0.78 | >100 | 12.5 |
| S. pyrogenes CONST | 3.1 | 3.1 | 0.39 | 0.78 | 0.78 | >100 | 12.5 |
| S. pyrogenes 2548 INDUC | 1.56 | 1.56 | 0.39 | 0.39 | 0.39 | >100 | 6.2 |
| E. coli JUHL | 1.56 | 0.78 | 0.78 | — | 0.02 | 6.2 | 6.2 |
| E. coli SS | 0.05 | 0.05 | 0.005 | 0.001 | 0.001 | 0.39 | 0.1 |
| E. coli DC-2 | 25 | 25 | 12.5 | 3.1 | 0.78 | >100 | >100 |
| E. coli H560 | 1.56 | 0.78 | 0.78 | 0.1 | 0.02 | 6.2 | 3.1 |
| E. coli KNK 437 | 25 | 12.5 | 6.2 | 1.56 | 0.39 | >100 | 100 |
| E. aerogenes ATCC 13048 | 3.1 | 3.1 | 3.1 | 0.39 | 0.1 | 6.2 | 25 |
| K. pneumoniae ATCC 8045 | 3.1 | 3.1 | 0.39 | 0.05 | 0.01 | 3.1 | 3.1 |
| P. stuartii CMX 640 | 100 | 100 | 25 | 6.2 | 6.2 | >100 | >100 |
| P. aeruginosa BMH 10 | 12.5 | 3.1 | 3.1 | 0.78 | 0.2 | 50 | 50 |
| P. aeruginosa A5007 | 6.2 | 12.5 | 3.1 | 0.78 | 0.39 | 50 | 50 |
| P. aeruginosa K799/WT | 6.2 | 6.2 | 3.1 | 0.78 | 0.39 | 100 | 100 |
| P. aeruginosa K799/61 | 1.56 | 1.56 | 0.39 | 0.05 | 0.05 | 6.2 | 3.1 |
| P. aeruginosa 5263 | >100 | >100 | >100 | >100 | 50 | >100 | >100 |
| P. aeruginosa 2862 | >100 | >100 | >100 | >100 | 50 | >100 | >100 |
| P. cepacia 2961 | 100 | >100 | 25 | 6.2 | 6.2 | >100 | >100 |
| A. calcoaceticus CMX 669 | 12.5 | 12.5 | 3.1 | 0.2 | 0.05 | 25 | 25 |

TABLE 15

| | In Vitro Antibacterial Activity (MIC Values in µg/ml) | | | | | |
|---|---|---|---|---|---|---|
| Organisms | Ex. 253 | Ex. 254 | Ex. 255 | Ex. 256 | Ex. 257 | Ciprofloxacin |
| Staph. aureus ATCC 6538P | 0.01 | 0.002 | 0.01 | 0.05 | 0.01 | 0.2 |
| Staph. aureus A5177 | 0.01 | 0.005 | 0.02 | 0.1 | 0.01 | 0.39 |
| Staph. aureus 5278 | 0.01 | 0.005 | 0.02 | 0.1 | 0.01 | 0.39 |
| Staph. aureus 642A | 0.02 | 0.002 | 0.05 | 0.1 | 0.02 | 0.39 |
| Staph. aureus NCTC10649 | 0.01 | 0.002 | 0.02 | 0.05 | 0.02 | 0.39 |
| Staph. aureus CMX 553 | 0.02 | 0.01 | 0.02 | 0.1 | 0.02 | 0.78 |
| Staph. aureus 1775 Cipro.R. | 1.56 | 0.39 | 1.56 | 6.2 | 0.78 | >100 |
| Staph. epidermidis 3519 | 0.01 | 0.005 | 0.02 | 0.1 | 0.01 | 0.39 |
| M. luteus ATCC 9341 | 0.05 | 0.01 | 0.1 | 0.78 | 0.05 | 1.56 |
| M. luteus ATCC 4698 | 0.02 | 0.01 | 0.1 | 0.78 | 0.05 | 0.78 |
| Entero. faecium ATTC 8043 | 0.02 | 0.01 | 0.1 | 0.2 | 0.02 | 0.39 |
| Strep. bovis A5169 | 0.02 | 0.002 | 0.05 | 0.78 | 0.02 | 1.56 |
| Strep. agalactiae CMX 508 | 0.02 | 0.002 | 0.02 | 0.39 | 0.02 | 0.39 |
| Strep. pyogenes EES61 | 0.02 | 0.002 | 0.05 | 0.39 | 0.02 | 0.78 |
| Strep. pyogenes 930 CONST | 0.02 | 0.002 | 0.05 | 0.2 | 0.02 | 0.78 |
| Strep. pyogenes 2458 INDUC | 0.01 | 0.002 | 0.05 | 0.2 | 0.02 | 0.39 |
| Escherichia coli Juhl | 0.002 | 0.005 | 0.005 | 0.01 | 0.002 | 0.01 |
| E. coli SS | 0.0005 | 0.0005 | 0.0005 | 0.002 | 0.0005 | 0.005 |
| E. coli DC-2 | 0.02 | 0.05 | 0.1 | 0.2 | 0.02 | 0.2 |
| E. coli H560 | 0.002 | 0.002 | 0.01 | 0.02 | 0.002 | 0.01 |
| E. coli KNK 437 | 0.02 | 0.05 | 0.1 | 0.2 | 0.02 | 0.2 |
| Enter. aerogenes ATCC 13048 | 0.005 | 0.01 | 0.05 | 0.05 | 0.01 | 0.02 |
| Klebsiella pneumoniae ATCC 8045 | 0.002 | 0.005 | 0.005 | 0.01 | 0.002 | 0.02 |
| Providencia stuartii CMX 640 | 0.2 | 0.39 | 0.78 | 1.56 | 0.2 | 0.78 |
| Pseudomonas cepacia 2961 | 0.39 | 0.39 | 0.78 | 0.78 | 0.39 | 3.1 |
| P. aeruginosa BMH 10 | 0.05 | 0.05 | 0.2 | 0.2 | 0.02 | 0.1 |
| P. aeruginosa A5007 | 0.05 | 0.1 | 0.2 | 0.2 | 0.05 | 0.1 |
| P. aeruginosa K799/WT | 0.05 | 0.1 | 0.2 | 0.2 | 0.05 | 0.1 |
| P. aeruginosa K799/61 | 0.01 | 0.01 | 0.05 | 0.05 | 0.01 | 0.02 |
| P. aeruginosa 5263 | 0.78 | 1.56 | 3.1 | 12.5 | 0.39 | 12.5 |
| P. aeruginosa 2863 | 0.78 | 1.56 | 1.56 | 12.5 | 0.39 | 12.5 |
| Acinetobacter calcoaceticus CMX 669 | 0.01 | 0.05 | 0.01 | 0.1 | 0.02 | 0.39 |
| Myco. smegmatis ATCC 114 | 0.02 | 0.1 | 0.2 | 0.78 | 0.2 | 0.78 |

TABLE 15-continued

| | | | | | | |
|---|---|---|---|---|---|---|
| *Nocardia asteroides* ATCC 9970 | 0.2 | 0.1 | 0.2 | 0.39 | 0.2 | 12.5 |
| *Candida albicans* CCH 442 | >100 | >100 | >100 | >100 | >100 | >100 |

| Organisms | Ex. 258 | Ex. 259 | Ex. 260 | Ex. 261 | Ex. 262 | Ciprofloxacin |
|---|---|---|---|---|---|---|
| *Staph. aureus* ATCC 6538P | 0.1 | 0.05 | 0.05 | 0.05 | 0.05 | 0.2 |
| *Staph. aureus* A5177 | 0.1 | 0.1 | 0.1 | 0.05 | 0.05 | 0.39 |
| *Staph. aureus* 5278 | 0.1 | 0.1 | 0.1 | 0.05 | 0.05 | 0.39 |
| *Staph. aureus* 642A | 0.1 | 0.1 | 0.1 | 0.05 | 0.05 | 0.39 |
| *Staph. aureus* NCTC10649 | 0.1 | 0.1 | 0.05 | 0.05 | 0.05 | 0.39 |
| *Staph. aureus* CMX 553 | 0.2 | 0.2 | 0.1 | 0.05 | 0.1 | 0.78 |
| *Staph. aureus* 1775 Cipro.R. | 6.2 | 12.5 | 6.2 | 0.78 | 3.1 | >100 |
| *Staph. epidermidis* 3519 | 0.1 | 0.1 | 0.1 | 0.05 | 0.05 | 0.39 |
| *Entero. faecium* ATTC 8043 | 0.2 | 0.2 | 0.1 | 0.1 | 0.1 | 0.39 |
| *Strep. bovis* A5169 | 0.39 | 0.78 | 0.1 | 0.2 | 0.1 | 1.56 |
| *Strep. agalactiae* CMX 508 | 0.2 | 0.2 | 0.1 | 0.1 | 0.05 | 0.39 |
| *Strep. pyogenes* EES61 | 0.39 | 0.2 | 0.1 | 0.1 | 0.05 | 0.78 |
| *Strep. pyogenes* 930 CONST | 0.39 | 0.2 | 0.1 | 0.1 | 0.05 | 0.78 |
| *Strep. pyogenes* 2458 INDUC | 0.2 | 0.2 | 0.05 | 0.1 | 0.05 | 0.39 |
| *M. luteus* ATCC 9341 | 0.39 | 0.2 | 0.2 | 0.2 | 0.1 | 1.56 |
| *M. luteus* ATCC 4698 | 0.2 | 0.2 | 0.2 | 0.1 | 0.05 | 0.78 |
| *Escherichia coli* Juhl | 0.01 | 0.01 | 0.1 | 0.78 | 0.02 | 0.01 |
| *E. coli* SS | 0.005 | 0.001 | 0.02 | 0.05 | <0.005 | 0.005 |
| *E. coli* DC-2 | 0.2 | 0.2 | 1.56 | 100 | 0.2 | 0.2 |
| *E. coli* H560 | 0.01 | 0.01 | 0.2 | 0.39 | 0.01 | 0.01 |
| *E. coli* KNK 437 | 0.2 | 0.2 | 1.56 | 12.5 | 0.1 | 0.2 |
| *Enter. aerogenes* ATCC 13048 | 0.05 | 0.02 | 0.39 | 1.56 | 0.1 | 0.02 |
| *Klebsiella pneumoniae* ATCC 8045 | 0.01 | 0.01 | 0.2 | 0.39 | 0.05 | 0.02 |
| *Providencia stuartii* CMX 640 | 1.56 | 0.78 | 12.5 | 100 | 1.56 | 0.78 |
| *P. aeruginosa* BMH 10 | 0.2 | 0.2 | 1.56 | 50 | 0.2 | 0.1 |
| *P. aeruginosa* A5007 | 0.39 | 0.2 | 3.1 | 50 | 0.39 | 0.1 |
| *P. aeruginosa* K799/WT | 0.39 | 0.2 | 1.56 | 50 | 0.39 | 0.1 |
| *P. aeruginosa* K799/61 | 0.05 | 0.02 | 0.39 | 0.39 | 0.1 | 0.02 |
| *Pseudomonas cepacia* 2961 | 3.1 | 1.56 | 12.5 | 50 | 3.1 | 3.1 |
| *Acinetobacter calcoaceticus* CMX 669 | 0.05 | 0.1 | 0.78 | 0.39 | 0.2 | 0.39 |
| *P. aeruginosa* 5263 | 6.2 | 3.1 | 50 | >100 | 3.1 | 12.5 |
| *P. aeruginosa* 2863 | 6.2 | 3.1 | 25 | >100 | 3.1 | 12.5 |
| *Candida albicans* CCH 442 | >100 | >100 | >100 | >100 | >100 | >100 |
| *Myco. smegmatis* ATCC 114 | 0.78 | 0.2 | 1.56 | 50 | 1.56 | 0.78 |
| *Nocardia asteroides* ATCC 9970 | 12.5 | 1.56 | 1.56 | 50 | 0.78 | 12.5 |

| Organisms | Ex. 263 | Ex. 264 | Ex. 265 | Ex. 266 | Ex. 267 | Ciprofloxacin |
|---|---|---|---|---|---|---|
| *Staph. aureus* ATCC 6538P | 0.01 | 0.02 | 0.02 | 0.02 | 0.1 | 0.2 |
| *Staph. aureus* A5177 | 0.02 | 0.05 | 0.1 | 0.05 | 0.1 | 0.39 |
| *Staph. aureus* 5278 | 0.02 | 0.05 | 0.05 | 0.05 | 0.1 | 0.39 |
| *Staph. aureus* 642A | 0.02 | 0.1 | 0.1 | 0.1 | 0.2 | 0.39 |
| *Staph. aureus* NCTC10649 | 0.01 | 0.02 | 0.1 | 0.02 | 0.1 | 0.39 |
| *Staph. aureus* CMX 553 | 0.05 | 0.1 | 0.05 | 0.1 | 0.2 | 0.78 |
| *Staph. aureus* 1775 Cipro.R. | .39 | 3.1 | 0.78 | 0.39 | 6.2 | >100 |
| *Staph. epidermidis* 3519 | 0.02 | 0.05 | 0.1 | 0.05 | 0.1 | 0.39 |
| *Entero. faecium* ATTC 8043 | 0.05 | 0.1 | 0.1 | 0.2 | 0.39 | 0.39 |
| *Strep. bovis* A5169 | 0.05 | 0.1 | 0.2 | 0.2 | 0.78 | 1.56 |
| *Strep. agalactiae* CMX 508 | 0.02 | 0.02 | 0.05 | 0.1 | 0.39 | 0.39 |
| *Strep. pyogenes* EES61 | 0.02 | 0.02 | 0.05 | 0.2 | 0.39 | 0.78 |
| *Strep. pyogenes* 930 CONST | 0.02 | 0.05 | 0.1 | 0.2 | 0.78 | 0.78 |
| *Strep. pyogenes* 2458 INDUC | 0.01 | 0.05 | 0.1 | 0.2 | 0.78 | 0.39 |
| *M. luteus* ATCC 9341 | 0.05 | 0.2 | 0.1 | 0.1 | 0.39 | 1.56 |
| *M. luteus* ATCC 4698 | 0.05 | 0.1 | 0.1 | 0.1 | 0.39 | 0.78 |
| *Escherichia coli* Juhl | 0.02 | 0.02 | 0.78 | 0.1 | 0.02 | 0.01 |
| *E. coli* SS | 0.002 | 0.005 | 0.05 | 0.005 | 0.002 | 0.005 |
| *E. coli* DC-2 | 0.1 | 0.2 | 0.78 | 0.78 | 0.2 | 0.2 |
| *E. coli* H560 | 0.01 | 0.02 | 1.56 | 0.1 | 0.02 | 0.01 |
| *E. coli* KNK 437 | 0.1 | 0.39 | 6.2 | 0.78 | 0.2 | 0.2 |
| *Enter. aerogenes* ATCC 13048 | 0.05 | 0.1 | 1.56 | 0.2 | 0.1 | 0.02 |
| *Klebsiella pneumoniae* ATCC 8045 | 0.02 | 0.1 | 0.39 | 0.2 | 0.02 | 0.02 |
| *Providencia stuartii* CMX 640 | 0.78 | 3.1 | 12.5 | 25 | 3.1 | 0.78 |
| *P. aeruginosa* BMH 10 | 0.2 | 0.39 | 3.1 | 1.56 | 0.78 | 0.1 |
| *P. aeruginosa* A5007 | 0.2 | 0.39 | 6.2 | 1.56 | 1.56 | 0.1 |
| *P. aeruginosa* K799/WT | 0.2 | 0.39 | 6.2 | 1.56 | 0.78 | 0.1 |
| *P. aeruginosa* K799/61 | 0.05 | 0.1 | 0.78 | 0.2 | 0.1 | 0.02 |
| *Pseudomonas cepacia* 2961 | 0.78 | 3.1 | 6.2 | 3.1 | 3.1 | 3.1 |
| *Acinetobacter calcoaceticus* CMX 669 | 0.1 | 0.2 | 1.56 | 0.78 | 0.05 | 0.39 |
| *P. aeruginosa* 5263 | 3.1 | 6.2 | >100 | 50 | 25 | 12.5 |
| *P. aeruginosa* 2863 | 3.1 | 6.2 | >100 | 25 | 12.5 | 12.5 |
| *Candida albicans* CCH 442 | >100 | >100 | >100 | >100 | >100 | >100 |
| *Myco. smegmatis* ATCC 114 | 0.2 | 0.2 | 25 | 3.1 | 0.2 | 0.78 |

TABLE 15-continued

| | | | | | | |
|---|---|---|---|---|---|---|
| Nocardia asteroides ATCC 9970 | 0.2 | 3.1 | 12.5 | 1.56 | 6.2 | 12.5 |

| Organisms | Ex. 268 | Ex. 269 | Ex. 270 | Ex. 271 | Ex. 272 | Cipro-floxacin |
|---|---|---|---|---|---|---|
| Staph. aureus ATCC 6538P | 0.05 | 0.01 | 0.02 | 0.01 | 0.1 | 0.2 |
| Staph. aureus A5177 | 0.1 | 0.02 | 0.02 | 0.02 | 0.1 | 0.39 |
| Staph. aureus 5278 | 0.1 | 0.02 | 0.02 | 0.01 | 0.1 | 0.39 |
| Staph. aureus 642A | 0.1 | 0.05 | 0.02 | 0.01 | 0.1 | 0.39 |
| Staph. aureus NCTC10649 | 0.05 | 0.02 | 0.01 | 0.005 | 0.1 | 0.39 |
| Staph. aureus CMX 553 | 0.1 | 0.05 | 0.02 | 0.02 | 0.1 | 0.78 |
| Staph. aureus 1775 Cipro.R. | 6.2 | 0.78 | 0.39 | 0.2 | 1.56 | >100 |
| Staph. epidermidis 3519 | 0.1 | 0.05 | 0.02 | 0.02 | 0.1 | 0.39 |
| Entero. faecium ATTC 8043 | 0.1 | 0.1 | 0.1 | 0.05 | 0.39 | 0.39 |
| Strep. bovis A5169 | 0.1 | 0.05 | 0.2 | 0.05 | 0.78 | 1.56 |
| Strep. agalactiae CMX 508 | 0.1 | 0.05 | 0.1 | 0.05 | 0.39 | 0.39 |
| Strep. pyogenes EES61 | 0.1 | 0.05 | 0.1 | 0.05 | 0.39 | 0.78 |
| Strep. pyogenes 930 CONST | 0.1 | 0.05 | 0.2 | 0.05 | 0.39 | 0.78 |
| Strep. pyogenes 2458 INDUC | 0.05 | 0.02 | 0.2 | 0.05 | 0.39 | 0.39 |
| M. luteus ATCC 9341 | 0.2 | 0.1 | 0.2 | 0.02 | 0.39 | 1.56 |
| M. luteus ATCC 4698 | 0.1 | 0.1 | 0.05 | 0.02 | 0.39 | 0.78 |
| Escherichia coli Juhl | 0.01 | 0.01 | 0.1 | 0.02 | 0.02 | 0.01 |
| E. coli SS | 0.005 | 0.001 | 0.005 | 0.001 | 0.001 | 0.005 |
| E. coli DC-2 | 0.2 | 0.1 | 0.39 | 0.2 | 0.39 | 0.2 |
| E. coli H560 | 0.02 | 0.01 | 0.1 | 0.05 | 0.02 | 0.01 |
| E. coli KNK 437 | 0.2 | 0.1 | 0.39 | 0.2 | 0.39 | 0.2 |
| Enter. aerogenes ATCC 13048 | 0.05 | 0.05 | 0.39 | 0.02 | 0.01 | 0.02 |
| Klebsiella pneumoniae ATCC 8045 | 0.02 | 0.01 | 0.05 | 0.02 | 0.02 | 0.02 |
| Providencia stuartii CMX 640 | 1.56 | 0.78 | 1.56 | 0.2 | 1.56 | 0.78 |
| P. aeruginosa BMH 10 | 0.2 | 0.2 | 0.78 | 0.2 | 0.78 | 0.1 |
| P. aeruginosa A5007 | 0.39 | 0.39 | 1.56 | 0.2 | 0.78 | 0.1 |
| P. aeruginosa K799/WT | 0.39 | 0.2 | 0.78 | 0.2 | 0.78 | 0.1 |
| P. aeruginosa K799/61 | 0.05 | 0.05 | 0.1 | 0.02 | 0.02 | 0.02 |
| Pseudomonas cepacia 2961 | 3.1 | 1.56 | 3.1 | 0.1 | 1.56 | 3.1 |
| Acinetobacter calcoaceticus CMX 669 | 0.1 | 0.02 | 0.2 | 0.01 | 0.05 | 0.39 |
| P. aeruginosa 5263 | 3.1 | 3.1 | 50 | 6.2 | 12.5 | 12.5 |
| P. aeruginosa 2863 | 3.1 | 3.1 | 25 | 6.2 | 6.2 | 12.5 |
| Candida albicans CCH 442 | >100 | >100 | >100 | >100 | >100 | >100 |
| Myco. smegmatis ATCC 114 | 0.78 | 0.1 | 0.78 | 0.78 | 1.56 | 0.78 |
| Nocardia asteroides ATCC 9970 | 3.1 | 0.39 | 1.56 | 0.78 | 1.56 | 12.5 |

| Organisms | Ex. 273 | Ex. 274 | Ex. 275 | Ex. 276 | Ex. 277 | Cipro-floxacin |
|---|---|---|---|---|---|---|
| Staph. aureus ATCC 6538P | 0.2 | 0.1 | 0.05 | 0.02 | 0.01 | 0.2 |
| Staph. aureus A5177 | 0.2 | 0.2 | 0.05 | 0.05 | 0.02 | 0.39 |
| Staph. aureus 5278 | 0.2 | 0.2 | 0.05 | 0.02 | 0.02 | 0.39 |
| Staph. aureus 642A | 0.39 | 0.2 | 0.1 | 0.05 | 0.02 | 0.39 |
| Staph. aureus NCTC10649 | 0.2 | 0.1 | 0.05 | 0.02 | 0.02 | 0.39 |
| Staph. aureus CMX 553 | 0.39 | 0.39 | 0.1 | 0.05 | 0.05 | 0.78 |
| Staph. aureus 1775 Cipro.R. | 6.2 | 6.2 | 3.1 | 1.56 | 1.56 | >100 |
| Staph. epidermidis 3519 | 0.2 | 0.2 | 0.05 | 0.02 | 0.02 | 0.39 |
| Entero. faecium ATTC 8043 | 0.39 | 0.78 | 0.2 | 0.1 | 0.05 | 0.39 |
| Strep. bovis A5169 | 0.78 | 0.78 | 0.39 | 0.1 | 0.1 | 1.56 |
| Strep. agalactiae CMX 508 | 0.39 | 0.78 | 0.2 | 0.05 | 0.05 | 0.39 |
| Strep. pyogenes EES61 | 0.39 | 0.78 | 0.2 | 0.05 | 0.05 | 0.78 |
| Strep. pyogenes 930 CONST | 0.2 | 0.78 | 0.1 | 0.05 | 0.05 | 0.78 |
| Strep. pyogenes 2458 INDUC | 0.2 | 0.78 | 0.1 | 0.05 | 0.05 | 0.39 |
| M. luteus ATCC 9341 | 0.78 | 0.78 | 0.2 | 0.1 | 0.05 | 1.56 |
| M. luteus ATCC 4698 | 0.78 | 0.39 | 0.2 | 0.1 | 0.05 | 0.78 |
| Escherichia coli Juhl | 0.05 | 0.01 | 0.02 | 0.005 | 0.005 | 0.01 |
| E. coli SS | 0.005 | 0.01 | 0.005 | 0.002 | 0.0005 | 0.005 |
| E. coli DC-2 | 0.02 | 0.2 | 0.2 | 0.05 | 0.05 | 0.2 |
| E. coli H560 | 0.02 | 0.05 | 0.02 | 0.005 | 0.005 | 0.01 |
| E. coli KNK 437 | 0.39 | 0.2 | 0.2 | 0.05 | 0.05 | 0.2 |
| Enter. aerogenes ATCC 13048 | 0.1 | 0.02 | 0.05 | 0.02 | 0.01 | 0.02 |
| Klebsiella pneumoniae ATCC 8045 | 0.05 | 0.01 | 0.01 | 0.005 | 0.005 | 0.02 |
| Providencia stuartii CMX 640 | 3.1 | 3.1 | 1.56 | 0.39 | 0.2 | 0.78 |
| P. aeruginosa BMH 10 | 0.39 | 0.2 | 0.2 | 0.1 | 0.05 | 0.1 |
| P. aeruginosa A5007 | 0.39 | 0.39 | 0.39 | 0.2 | 0.05 | 0.1 |
| P. aeruginosa K799/WT | 0.39 | 0.39 | 0.2 | 0.1 | 0.05 | 0.1 |
| P. aeruginosa K799/61 | 0.1 | 0.05 | 0.05 | 0.02 | 0.01 | 0.02 |
| Pseudomonas cepacia 2961 | 6.2 | 3.1 | 3.1 | 1.56 | 0.78 | 3.1 |
| Acinetobacter calcoaceticus CMX 669 | 0.2 | 0.2 | 0.1 | 0.02 | 0.02 | 0.39 |
| P. aeruginosa 5263 | 12.5 | 12.5 | 6.2 | 1.56 | 1.56 | 12.5 |
| P. aeruginosa 2863 | 6.2 | 6.2 | 3.1 | 1.56 | 1.56 | 12.5 |
| Candida albicans CCH 442 | >100 | >100 | >100 | >100 | >100 | >100 |
| Myco. smegmatis ATCC 114 | 6.2 | 0.2 | 0.78 | 0.78 | 0.05 | 0.78 |
| Nocardia asteroides ATCC 9970 | 6.2 | 3.1 | 0.78 | 0.39 | 0.39 | 12.5 |

TABLE 15-continued

| Organisms | Ex. 278 | Ex. 279 | Ex. 280 | Ex. 281 | Ex. 282 | Ciprofloxacin |
|---|---|---|---|---|---|---|
| Staph. aureus ATCC 6538P | 0.39 | 3.1 | 0.39 | 0.39 | 0.78 | 0.2 |
| Staph. aureus A5177 | 0.39 | 25 | 0.78 | 0.39 | 3.1 | 0.39 |
| Staph. aureus 5278 | 0.39 | 12.5 | 0.78 | 0.39 | 3.1 | 0.39 |
| Staph. aureus 642A | 0.39 | 25 | 0.78 | 1.56 | 3.1 | 0.39 |
| Staph. aureus NCTC10649 | 0.39 | 25 | 0.78 | 0.39 | 1.56 | 0.39 |
| Staph. aureus CMX 553 | 0.78 | 12.5 | 0.78 | 0.39 | 3.1 | 0.78 |
| Staph. aureus 1775 Cipro.R. | 25 | >100 | >100 | 25 | 25 | >100 |
| Staph. epidermidis 3519 | 0.78 | 25 | 0.78 | 0.39 | 3.1 | 0.39 |
| Entero. faecium ATTC 8043 | 1.56 | 50 | 6.2 | 3.1 | 3.1 | 0.39 |
| Strep. bovis A5169 | 6.2 | 100 | 25 | 3.1 | 3.1 | 1.56 |
| Strep. agalactiae CMX 508 | 3.1 | 100 | 12.5 | 1.56 | 0.78 | 0.39 |
| Strep. pyogenes EES61 | 3.1 | 100 | 12.5 | 1.56 | 0.78 | 0.78 |
| Strep. pyogenes 930 CONST | 3.1 | 50 | 6.2 | 1.56 | 0.78 | 0.78 |
| Strep. pyogenes 2458 INDUC | 3.1 | 100 | 12.5 | 1.56 | 0.78 | 0.39 |
| M. luteus ATCC 9341 | 6.2 | 100 | 25 | | 6.2 | 1.56 |
| M. luteus ATCC 4698 | 3.1 | 50 | 12.5 | | 6.2 | 0.78 |
| Escherichia coli Juhl | 0.2 | 6.2 | 1.56 | 0.2 | 3.1 | 0.01 |
| E. coli SS | 0.01 | 0.78 | =<0.39 | 0.02 | 0.2 | 0.005 |
| E. coli DC-2 | 1.56 | 50 | 25 | 1.56 | 6.2 | 0.2 |
| E. coli H560 | 0.1 | 6.2 | 1.56 | 0.2 | 3.1 | 0.01 |
| E. coli KNK 437 | 0.78 | 25 | 12.5 | 3.1 | 6.2 | 0.2 |
| Enter. aerogenes ATCC 13048 | 0.2 | 6.2 | 3.1 | 0.39 | 6.2 | 0.02 |
| Klebsiella pneumoniae ATCC 8045 | 0.1 | 3.1 | =<0.39 | 0.2 | 3.1 | 0.02 |
| Providencia stuartii CMX 640 | 6.2 | 100 | 25 | 3.1 | 25 | 0.78 |
| P. aeruginosa BMH 10 | 1.56 | 25 | 6.2 | 1.56 | 6.2 | 0.1 |
| P. aeruginosa A5007 | 3.1 | 25 | 6.2 | 1.56 | 6.2 | 0.1 |
| P. aeruginosa K799/WT | 3.1 | 25 | 6.2 | 1.56 | 6.2 | 0.1 |
| P. aeruginosa K799/61 | 0.2 | 6.2 | =<0.39 | 0.39 | 3.1 | 0.02 |
| Pseudomonas cepacia 2961 | 6.2 | 100 | 6.2 | 3.1 | 25 | 3.1 |
| Acinetobacter calcoaceticus CMX 669 | 0.2 | 6.2 | 3.1 | 1.56 | 12.5 | 0.39 |
| P. aeruginosa 5263 | 50 | >100 | | 12.5 | 25 | 12.5 |
| P. aeruginosa 2863 | 25 | >100 | | 12.5 | 25 | 12.5 |
| Candida albicans CCH 442 | | | | | | >100 |
| Myco. smegmatis ATCC 114 | | | | | | 0.78 |
| Nocardia asteroides ATCC 9970 | | | | | | 12.5 |

| Organisms | Ex. 284 | Ex. 285 | Ex. 296 | Ciprofloxacin |
|---|---|---|---|---|
| Staph. aureus ATCC 6538P | 0.78 | 0.78 | 0.02 | 0.2 |
| Staph. aureus A5177 | 1.56 | 0.78 | 0.05 | 0.39 |
| Staph. aureus 5278 | 0.78 | 0.78 | 0.05 | 0.39 |
| Staph. aureus 642A | 1.56 | 0.78 | 0.05 | 0.39 |
| Staph. aureus NCTC10649 | 0.78 | 1.56 | 0.05 | 0.39 |
| Staph. aureus CMX 553 | 3.1 | 0.78 | 0.05 | 0.78 |
| Staph. aureus 1775 Cipro.R. | 25 | >100 | 3.1 | >100 |
| Staph. epidermidis 3519 | 1.56 | 1.56 | 0.05 | 0.39 |
| Entero. faecium ATTC 8043 | 3.1 | 3.1 | 0.1 | 0.39 |
| Strep. bovis A5169 | na | 25 | 0.1 | 1.56 |
| Strep. agalactiae CMX 508 | 3.1 | 12.5 | 0.05 | 0.39 |
| Strep. pyogenes EES61 | 3.1 | 12.5 | 0.05 | 0.78 |
| Strep. pyogenes 930 CONST | 12.5 | 12.5 | 0.05 | 0.78 |
| Strep. pyogenes 2458 INDUC | 6.2 | 12.5 | 0.05 | 0.39 |
| M. luteus ATCC 9341 | 12.5 | 50 | 0.1 | 1.56 |
| M. luteus ATCC 4698 | 6.2 | 12.5 | 0.1 | 0.78 |
| Escherichia coli Juhl | 1.56 | 0.39 | 0.01 | 0.01 |
| E. coli SS | 0.1 | 0.1 | 0.002 | 0.005 |
| E. coli DC-2 | 12.5 | 3.1 | 0.2 | 0.2 |
| E. coli H560 | 3.1 | 0.39 | 0.01 | 0.01 |
| E. coli KNK 437 | 12.5 | 3.1 | 0.05 | 0.2 |
| Enter. aerogenes ATCC 13048 | 3.1 | 0.39 | 0.5 | 0.02 |
| Klebsiella pneumoniae ATCC 8045 | 1.56 | 0.2 | 0.01 | 0.02 |
| Providencia stuartii CMX 640 | 12.5 | 12.5 | 3.1 | 0.78 |
| P. aeruginosa BMH 10 | 12.5 | 1.56 | 0.1 | 0.1 |
| P. aeruginosa A5007 | 12.5 | 1.56 | 0.39 | 0.1 |
| P. aeruginosa K799/WT | 12.5 | 1.56 | 0.39 | 0.1 |
| P. aeruginosa K799/61 | 1.56 | 0.39 | 0.1 | 0.02 |
| Pseudomonas cepacia 2961 | 12.5 | 25 | 0.78 | 3.1 |
| Acinetobacter calcoaceticus CMX 669 | 3.1 | 0.39 | 0.02 | 0.39 |
| P. aeruginosa 5263 | 50 | >100 | 3.1 | 12.5 |
| P. aeruginosa 2863 | 50 | >100 | 3.1 | 12.5 |
| Candida albicans CCH 442 | >100 | | >100 | >100 |
| Myco. smegmatis ATCC 114 | 25 | | 0.05 | 0.78 |
| Nocardia asteroides ATCC 9970 | 25 | | 3.1 | 12.5 |

TABLE 16

| In Vitro Antibacterial Activity (MIC Values in µg/ml) | | | | | | |
|---|---|---|---|---|---|---|
| Organisms | Ex. 298 | Ex. 299 | Ex. 300 | Ex. 301 | Ex. 302 | Cntl |
| *Staph. aureus* ATCC 6538P | 0.02 | 0.05 | 0.001 | 0.002 | 0.002 | 0.2 |
| *Staph. aureus* A5177 | 0.02 | 0.05 | 0.001 | 0.005 | 0.005 | 0.39 |
| *Staph. aureus* 5278 | 0.05 | 0.05 | 0.001 | 0.005 | 0.005 | 0.39 |
| *Staph. aureus* 642A | 0.1 | 0.05 | 0.001 | 0.01 | 0.01 | 0.39 |
| *Staph. aureus* NCTC 10649 | 0.02 | 0.05 | 0.001 | 0.002 | 0.002 | 0.39 |
| *Staph. aureus* CMX 553 | 0.1 | 0.1 | 0.002 | 0.01 | 0.1 | 0.78 |
| *Staph. aureus* 1775 Cipro. R. | 1.56 | 0.78 | 0.05 | 0.2 | 0.39 | >100 |
| *Staph. epidermidis* 3519 | 0.05 | 0.05 | 0.001 | 0.005 | 0.005 | 0.39 |
| *Entero. faecium* ATCC 8043 | 0.2 | 0.1 | 0.001 | 0.01 | 0.01 | 0.39 |
| *Strep. bovis* A5169 | 0.39 | 0.39 | 0.001 | 0.005 | 0.01 | 1.56 |
| *Strep. agalactiae* CMX 508 | 0.2 | 0.1 | 0.001 | 0.001 | 0.005 | 0.39 |
| *Strep. pyogenes* EES61 | 0.2 | 0.1 | 0.001 | 0.001 | 0.005 | 0.78 |
| *Strep. pyogenes* 930 CONST | 0.1 | 0.1 | 0.001 | 0.002 | 0.005 | 0.78 |
| *Strep. pyogenes* 2548 INDUC | 0.1 | 0.1 | 0.001 | 0.002 | 0.005 | 0.39 |
| *M. luteus* ATCC 9341 | 0.2 | 0.2 | 0.01 | 0.02 | 0.01 | 1.56 |
| *M. luteus* ATCC 4698 | 0.1 | 0.1 | 0.005 | 0.02 | 0.01 | 0.78 |
| *Escherichia coli* Juhl | 0.02 | 0.02 | 0.001 | 0.01 | 0.001 | 0.01 |
| *E. coli* SS | 0.002 | 0.005 | | | 0.0005 | 0.005 |
| *E. coli* DC-2 | 0.2 | 0.39 | 0.02 | 0.05 | 0.05 | 0.2 |
| *E. coli* H560 | 0.02 | 0.02 | 0.002 | 0.01 | 0.001 | 0.01 |
| *E. coli* KNK 437 | 0.2 | 0.2 | 0.02 | 0.1 | 0.1 | 0.2 |
| *Enter. aerogenes* ATCC 13048 | 0.1 | 0.1 | 0.01 | 0.02 | 0.01 | 0.02 |
| *Klebs. pneunoniae* ATCC 8045 | 0.05 | 0.02 | 0.005 | 0.01 | 0.001 | 0.02 |
| *Providencia stuartii* CMX 640 | 3.1 | 3.1 | 0.2 | 0.39 | 0.78 | 0.78 |
| *P. aeruginosa* BMH 10 | 0.39 | 0.39 | 0.02 | 0.05 | 0.1 | 0.1 |
| *P. aeruginosa* A5007 | 0.39 | 0.39 | 0.05 | 0.2 | 0.2 | 0.1 |
| *P. aeruginosa* K799/WT | 0.39 | 0.39 | 0.05 | 0.2 | 0.2 | 0.1 |
| *P. aeruginosa* K799/61 | 0.1 | 0.05 | 0.01 | 0.02 | 0.02 | 0.02 |
| *Pseudomonas cepacia* 2961 | 3.1 | 1.56 | 0.78 | 1.56 | 1.56 | 3.1 |
| *Acinetob. calcoaceticus* CMX 669 | 0.05 | 0.05 | 0.01 | 0.05 | 0.02 | 0.78 |
| *P. aeruginosa* 5263 | 12.5 | 12.5 | 0.78 | 1.56 | 3.1 | 12.5 |
| *P. aeruginosa* 2862 | 12.5 | 12.5 | 1.56 | 3.1 | 6.2 | 12.5 |
| *Candida albicans* CCH 442 | >100 | >100 | 50 | >100 | >100 | >100 |
| *Myco. smegmatis* ATCC 114 | 0.39 | 0.2 | 0.1 | 0.2 | 0.002 | 0.78 |
| *Nocardia asteroides* ATCC 9970 | 6.2 | 6.2 | 0.39 | 1.56 | 0.39 | 25 |
| Organisms | Ex. 303 | Ex. 304 | Ex. 305 | Ex. 306 | Ex. 307 | Cntl |
| *Staph. aureus* ATCC 6538P | 0.02 | 0.1 | 0.1 | 0.02 | 0.1 | 0.2 |
| *Staph. aureus* A5177 | 0.05 | 0.2 | 0.2 | 0.05 | 0.2 | 0.39 |
| *Staph. aureus* 5278 | 0.05 | 0.2 | 0.2 | 0.05 | 0.2 | 0.39 |
| *Staph. aureus* 642A | 0.05 | 0.2 | 0.2 | 0.05 | 0.2 | 0.39 |
| *Staph. aureus* NCTC 10649 | 0.02 | 0.1 | 0.1 | 0.02 | 0.1 | 0.39 |
| *Staph. aureus* CMX 553 | 0.05 | 0.39 | 0.39 | 0.05 | 0.39 | 0.78 |
| *Staph. aureus* 1775 Cipro. R. | 1.56 | 3.1 | 12.5 | 0.39 | 25 | >100 |
| *Staph. epidermidis* 3519 | 0.01 | 0.2 | 0.2 | 0.02 | 0.2 | 0.39 |
| *Entero. faecium* ATCC 8043 | 0.05 | 0.78 | 0.39 | 0.1 | 0.39 | 0.39 |
| *Strep. bovis* A5169 | 0.1 | 0.78 | 0.39 | 0.2 | 1.56 | 1.56 |
| *Strep. agalactiae* CMX 508 | 0.1 | 0.39 | 0.2 | 0.1 | 0.78 | 0.39 |
| *Strep. pyogenes* EES61 | 0.1 | 0.78 | 0.39 | 0.1 | 0.78 | 0.78 |
| *Strep. pyogenes* 930 CONST | 0.2 | 0.78 | 0.39 | 0.1 | 0.78 | 0.78 |
| *Strep. pyogenes* 2548 INDUC | 0.1 | 0.39 | 0.39 | 0.1 | 0.39 | 0.39 |
| *M. luteus* ATCC 9341 | 0.2 | 0.78 | 0.78 | 0.1 | 0.78 | 1.56 |
| *M. luteus* ATCC 4698 | 0.1 | 0.39 | 0.39 | 0.05 | 1.56 | 0.78 |
| *Escherichia coli* Juhl | 0.1 | 0.1 | 0.39 | 0.78 | 0.05 | 0.01 |
| *E. coli* SS | 0.02 | 0.005 | 0.01 | 0.05 | 0.02 | 0.005 |
| *E. coli* DC-2 | 1.56 | 0.78 | 1.56 | 3.1 | 0.39 | 0.2 |
| *E. coli* H560 | 0.05 | 0.1 | 0.39 | 0.39 | 0.1 | 0.01 |
| *E. coli* KNK 437 | 0.39 | 0.78 | 6.2 | 3.1 | 0.78 | 0.2 |
| *Enter. aerogenes* ATCC 13048 | 0.39 | 0.39 | 1.56 | 1.56 | 0.05 | 0.02 |
| *Klebs. pneunoniae* ATCC 8045 | 0.1 | 0.05 | 0.39 | 0.39 | 0.05 | 0.02 |
| *Providencia stuartii* CMX 640 | 0.78 | 12.5 | 50 | 12.5 | 3.1 | 0.78 |
| *P. aeruginosa* BMH 10 | 0.78 | 1.56 | 3.1 | 6.2 | 0.39 | 0.1 |
| *P. aeruginosa* A5007 | 1.56 | 3.1 | 3.1 | 6.2 | 0.39 | 0.1 |
| *P. aeruginosa* K799/WT | 3.1 | 3.1 | 3.1 | 6.2 | 0.39 | 0.1 |
| *P. aeruginosa* K799/61 | 0.05 | 0.39 | 0.78 | 0.39 | 0.05 | 0.02 |
| *Pseudomonas cepacia* 2961 | 0.78 | 12.5 | 12.5 | 3.1 | 6.2 | 3.1 |
| *Acinetob. calcoaceticus* CMX 669 | 0.1 | 0.39 | 3.1 | 1.56 | 0.78 | 0.78 |
| *P. aeruginosa* 5263 | 6.2 | 100 | >100 | >100 | 25 | 12.5 |
| *P. aeruginosa* 2862 | 50 | 100 | >100 | >100 | 25 | 12.5 |
| *Candida albicans* CCH 442 | >100 | >100 | >100 | >100 | >100 | >100 |
| *Myco. smegmatis* ATCC 114 | 0.78 | 0.78 | 0.78 | 0.39 | 0.78 | 0.78 |
| *Nocardia asteroides* ATCC 9970 | 0.78 | 12.5 | 25 | 6.2 | 25 | 25 |

TABLE 16-continued

In Vitro Antibacterial Activity (MIC Values in µg/ml)

| Organisms | Ex. 308 | Ex. 309 | Ex. 310 | Ex. 311 | Ex. 312 | Cntl |
|---|---|---|---|---|---|---|
| Staph. aureus ATCC 6538P | 0.002 | 0.005 | 0.005 | 0.002 | 0.01 | 0.2 |
| Staph. aureus A5177 | 0.002 | 0.005 | 0.005 | 0.002 | 0.02 | 0.39 |
| Staph. aureus 5278 | 0.002 | 0.005 | 0.005 | 0.002 | 0.02 | 0.39 |
| Staph. aureus 642A | 0.002 | 0.01 | 0.01 | 0.005 | 0.02 | 0.39 |
| Staph. aureus NCTC 10649 | 0.0005 | 0.005 | 0.005 | 0.002 | 0.01 | 0.39 |
| Staph. aureus CMX 553 | 0.002 | 0.01 | 0.01 | 0.005 | 0.02 | 0.78 |
| Staph. aureus 1775 Cipro. R. | 0.05 | 0.05 | 0.05 | 0.02 | 0.78 | >100 |
| Staph. epidermidis 3519 | 0.002 | 0.01 | 0.005 | 0.005 | 0.02 | 0.39 |
| Entero. faecium ATCC 8043 | 0.01 | 0.2 | 0.02 | 0.01 | 0.02 | 0.39 |
| Strep. bovis A5169 | 0.002 | 0.005 | 0.005 | 0.002 | 0.005 | 1.56 |
| Strep. agalactiae CMX 508 | 0.002 | 0.005 | 0.002 | 0.001 | 0.005 | 0.39 |
| Strep. pyogenes EES61 | 0.002 | 0.005 | 0.005 | 0.001 | 0.005 | 0.78 |
| Strep. pyogenes 930 CONST | 0.002 | 0.005 | 0.005 | 0.005 | 0.005 | 0.78 |
| Strep. pyogenes 2548 INDUC | 0.002 | 0.005 | 0.005 | 0.005 | 0.005 | 0.39 |
| M. luteus ATCC 9341 | 0.01 | 0.0050 | 0.02 | 0.01 | 0.1 | 1.56 |
| M. luteus ATCC 4698 | 0.01 | 0.02 | 0.01 | 0.01 | 0.05 | 0.78 |
| Escherichia coli Juhl | 0.01 | 0.05 | 0.01 | 0.01 | 0.05 | 0.01 |
| E. coli SS | 0.0005 | 0.0005 | 0.001 | 0.0005 | 0.002 | 0.005 |
| E. coli DC-2 | 0.02 | 0.01 | 0.02 | 0.02 | 0.2 | 0.2 |
| E. coli H560 | 0.005 | 0.02 | 0.02 | 0.01 | 0.05 | 0.01 |
| E. coli KNK 437 | 0.05 | 0.2 | 0.1 | 0.05 | 0.39 | 0.2 |
| Enter. aerogenes ATCC 13048 | 0.05 | 0.1 | 0.1 | 0.05 | 0.2 | 0.02 |
| Klebs. pneumoniae ATCC 8045 | 0.01 | 0.02 | 0.005 | 0.01 | 0.1 | 0.02 |
| Providencia stuartii CMX 640 | 0.39 | 0.78 | 0.78 | 0.39 | 3.1 | 0.78 |
| P. aeruginosa BMH 10 | 0.1 | 0.39 | 0.2 | 0.1 | 0.39 | 0.1 |
| P. aeruginosa A5007 | 0.2 | 0.39 | 0.39 | 0.2 | 0.39 | 0.1 |
| P. aeruginosa K799/WT | 0.2 | 0.39 | 0.39 | 0.2 | 0.39 | 0.1 |
| P. aeruginosa K799/61 | 0.05 | 0.1 | 0.1 | 0.05 | 0.05 | 0.02 |
| Pseudomonas cepacia 2961 | 1.56 | 3.1 | 1.56 | 1.56 | — | 3.1 |
| Acinetob. calcoaceticus CMX 669 | 0.005 | 0.05 | 0.1 | 0.005 | 0.39 | 0.78 |
| P. aeruginosa 5263 | 1.56 | 12.5 | 6.2 | 1.56 | 3.1 | 12.5 |
| P. aeruginosa 2862 | 3.1 | 25 | 6.2 | 6.2 | 6.2 | 12.5 |
| Candida albicans CCH 442 | 12.5 | 100 | 6.2 | 50 | >100 | >100 |
| Myco. smegmatis ATCC 114 | 0.02 | 0.01 | 0.1 | 0.01 | 0.1 | 0.78 |
| Nocardia asteroides ATCC 9970 | 0.2 | 0.39 | 0.2 | 0.39 | 6.2 | 25 |

| Organisms | Ex. 313 | Ex. 314 | Ex. 316 | Ex. 324 | Ex. 325 | Ex. 326 | Cntl |
|---|---|---|---|---|---|---|---|
| Staph. aureus ATCC 6538P | 0.005 | 0.005 | 0.005 | 0.02 | 0.01 | 0.05 | 0.2 |
| Staph. aureus A5177 | 0.005 | 0.005 | 0.005 | 0.05 | 0.01 | 0.1 | 0.39 |
| Staph. aureus 5278 | 0.005 | 0.005 | 0.005 | 0.05 | 0.02 | 0.1 | 0.39 |
| Staph. aureus 642A | 0.005 | 0.005 | 0.01 | 0.02 | 0.02 | 0.1 | 0.39 |
| Staph. aureus NCTC 10649 | 0.002 | 0.005 | 0.005 | 0.02 | 0.01 | 0.05 | 0.39 |
| Staph. aureus CMX 553 | 0.01 | 0.01 | 0.01 | 0.05 | 0.02 | 0.2 | 0.78 |
| Staph. aureus 1775 Cipro. R. | 0.1 | 0.05 | 0.1 | 1.56 | 0.78 | 25 | >100 |
| Staph. epidermidis 3519 | 0.01 | 0.005 | 0.005 | 0.05 | 0.02 | 0.1 | 0.39 |
| Entero. faecium ATCC 8043 | 0.02 | 0.01 | 0.01 | 0.2 | 0.02 | 0.1 | 0.39 |
| Strep. bovis A5169 | 0.005 | 0.002 | 0.002 | 0.39 | 0.02 | 0.39 | 1.56 |
| Strep. agalactiae CMX 508 | 0.002 | 0.002 | 0.002 | 0.2 | 0.02 | 0.1 | 0.39 |
| Strep. pyogenes EES61 | 0.002 | 0.002 | 0.002 | 0.2 | 0.02 | 0.2 | 0.78 |
| Strep. pyogenes 930 CONST | 0.005 | 0.005 | 0.002 | 0.2 | 0.02 | 0.2 | 0.78 |
| Strep. pyogenes 2548 INDUC | 0.005 | 0.005 | 0.002 | 0.2 | 0.02 | 0.2 | 0.39 |
| M. luteus ATCC 9341 | 0.02 | 0.01 | 0.01 | 0.2 | 0.05 | 0.39 | 1.56 |
| M. luteus ATCC 4698 | 0.01 | 0.01 | 0.01 | 0.2 | 0.1 | 0.39 | 0.78 |
| Escherichia coli Juhl | 0.01 | 0.01 | 0.01 | 0.05 | 0.02 | 0.05 | 0.01 |
| E. coli SS | 0.002 | 0.001 | 0.002 | 0.005 | 0.0005 | 0.0005 | 0.005 |
| E. coli DC-2 | 0.1 | 0.1 | 0.1 | 0.78 | 0.2 | 0.39 | 0.2 |
| E. coli H560 | 0.01 | 0.02 | 0.02 | 0.05 | 0.02 | 0.1 | 0.01 |
| E. coli KNK 437 | 0.1 | 0.2 | 0.1 | 0.39 | 0.1 | 0.39 | 0.2 |
| Enter. aerogenes ATCC 13048 | 0.05 | 0.05 | 0.05 | 0.2 | 0.05 | 0.39 | 0.02 |
| Klebs. pneumoniae ATCC 8045 | 0.01 | 0.01 | 0.01 | 0.05 | 0.01 | 0.01 | 0.02 |
| Providencia stuartii CMX 640 | 0.39 | 1.56 | 0.78 | 3.1 | 1.56 | 3.1 | 0.78 |
| P. aeruginosa BMH 10 | 0.2 | 0.39 | 0.39 | 0.78 | 0.2 | 0.78 | 0.1 |
| P. aeruginosa A5007 | 0.2 | 0.39 | 0.39 | 0.78 | 0.39 | 0.78 | 0.1 |
| P. aeruginosa K799/WT | 0.2 | 0.39 | 0.39 | 0.78 | 0.39 | 0.78 | 0.1 |
| P. aeruginosa K799/61 | 0.05 | 0.05 | 0.2 | 0.1 | 0.05 | 0.2 | 0.02 |
| Pseudomonas cepacia 2961 | 3.1 | 1.56 | 1.56 | 1.56 | 1.56 | 6.2 | 3.1 |
| Acinetob. calcoaceticus CMX 669 | 0.02 | 0.005 | 0.05 | 0.1 | 0.05 | 0.39 | 0.78 |
| P. aeruginosa 5263 | 3.1 | 12.5 | 6.2 | 100 | 50 | 25 | 12.5 |
| P. aeruginosa 2862 | 3.2 | 12.5 | 12.5 | 50 | 12.5 | 25 | 12.5 |
| Candida albicans CCH 442 | >100 | 50 | >100 | >100 | >100 | >100 | >100 |
| Myco. smegmatis ATCC 114 | 0.02 | 0.01 | 0.1 | 0.2 | 0.05 | 0.78 | 0.78 |
| Nocardia asteroides ATCC 9970 | 0.2 | 0.2 | 0.78 | 25 | 0.78 | 50 | 25 |

TABLE 16-continued

In Vitro Antibacterial Activity (MIC Values in µg/ml)

| Organisms | Ex. 327 | Ex. 328 | Ex. 329 | Ex. 330 | Ex. 331 | Cntl |
|---|---|---|---|---|---|---|
| Staph. aureus ATCC 6538P | 0.1 | 0.78 | 0.78 | 0.1 | 0.1 | 0.2 |
| Staph. aureus A5177 | 0.2 | 3.1 | 1.56 | 0.39 | 0.1 | 0.39 |
| Staph. aureus 5278 | 0.2 | 3.1 | 1.56 | 0.39 | 0.1 | 0.39 |
| Staph. aureus 642A | 0.39 | 3.1 | 1.56 | 0.2 | 0.1 | 0.39 |
| Staph. aureus NCTC 10649 | 0.1 | 0.78 | 1.56 | 0.2 | 0.1 | 0.39 |
| Staph. aureus CMX 553 | 0.39 | 6.2 | 1.56 | 0.39 | 0.2 | 0.78 |
| Staph. aureus 1775 Cipro. R. | 25 | >100 | 50 | 6.2 | 12.5 | >100 |
| Staph. epidermidis 3519 | 0.2 | 1.56 | 1.56 | 0.2 | 0.1 | 0.39 |
| Entero. faecium ATCC 8043 | 0.39 | 3.1 | 6.2 | 0.39 | 0.2 | 0.39 |
| Strep. bovis A5169 | 0.2 | 1.56 | 6.2 | | 0.78 | 1.56 |
| Strep. agalactiae CMX 508 | 0.2 | 1.56 | 3.1 | 1.56 | 0.39 | 0.39 |
| Strep. pyogenes EES61 | 0.2 | 1.56 | 3.1 | 1.56 | 0.39 | 0.78 |
| Strep. pyogenes 930 CONST | 0.2 | 1.56 | 3.1 | 0.78 | 0.2 | 0.78 |
| Strep. pyogenes 2548 INDUC | 0.2 | 1.56 | 1.56 | 0.78 | 0.2 | 0.39 |
| M. luteus ATCC 9341 | 0.78 | 12.5 | 25 | 1.56 | 0.78 | 1.56 |
| M. luteus ATCC 4698 | 0.78 | 12.5 | 6.2 | 1.56 | 0.78 | 0.78 |
| Escherichia coli Juhl | 0.1 | 0.39 | 0.2 | 0.39 | 0.01 | 0.01 |
| E. coli SS | 0.0005 | 0.02 | 0.01 | 0.02 | 0.002 | 0.005 |
| E. coli DC-2 | 0.78 | 12.5 | 3.1 | 3.1 | 0.2 | 0.2 |
| E. coli H560 | 0.1 | 0.78 | 0.1 | 0.78 | 0.02 | 0.01 |
| E. coli KNK 437 | 0.78 | 6.2 | 3.1 | 3.1 | 0.2 | 0.2 |
| Enter. aerogenes ATCC 13048 | 0.78 | 3.1 | 0.39 | 0.39 | 0.05 | 0.02 |
| Klebs. pneumoniae ATCC 8045 | 0.39 | 1.56 | 0.1 | 0.2 | 0.02 | 0.02 |
| Providencia stuartii CMX 640 | 12.5 | 50 | 12.5 | 12.5 | 0.78 | 0.78 |
| P. aeruginosa BMH 10 | 1.56 | 12.5 | 1.56 | 6.2 | 0.1 | 0.1 |
| P. aeruginosa A5007 | 1.56 | 12.5 | 1.56 | 6.2 | 0.2 | 0.1 |
| P. aeruginosa K799/WT | 1.56 | 12.5 | 1.56 | 6.2 | 0.2 | 0.1 |
| P. aeruginosa K799/61 | 0.2 | 1.56 | 0.39 | 0.2 | 0.05 | 0.02 |
| Pseudomonas cepacia 2961 | 25 | >100 | 25 | 3.1 | 1.56 | 3.1 |
| Acinetob. calcoaceticus CMX 669 | 1.56 | 6.2 | 0.78 | 3.1 | 0.2 | 0.78 |
| P. aeruginosa 5263 | 50 | >100 | 100 | >100 | 12.5 | 12.5 |
| P. aeruginosa 2862 | 50 | >100 | 100 | >100 | 12.5 | 12.5 |
| Candida albicans CCH 442 | >100 | >100 | >100 | >100 | >100 | >100 |
| Myco. smegmatis ATCC 114 | 1.56 | 1.56 | 1.56 | 25 | 0.1 | 0.78 |
| Nocardia asteroides ATCC 9970 | 50 | >100 | 50 | >100 | 12.5 | 25 |

| Organisms | Ex. 332 | Ex. 333 | Ex. 334 | Ex. 335 | Ex. 336 | Cntl |
|---|---|---|---|---|---|---|
| Staph. aureus ATCC 6538P | 0.1 | 0.01 | 0.02 | 0.78 | 0.005 | 0.2 |
| Staph. aureus A5177 | 0.2 | 0.01 | 0.02 | 1.56 | 0.005 | 0.39 |
| Staph. aureus 5278 | 0.2 | 0.01 | 0.02 | 3.1 | 0.01 | 0.39 |
| Staph. aureus 642A | 0.2 | 0.01 | 0.02 | 1.56 | 0.01 | 0.39 |
| Staph. aureus NCTC 10649 | 0.1 | 0.01 | 0.02 | 1.56 | 0.005 | 0.39 |
| Staph. aureus CMX 553 | 0.39 | 0.02 | 0.02 | 3.1 | 0.02 | 0.78 |
| Staph. aureus 1775 Cipro. R. | 6.2 | 0.78 | 0.78 | >100 | 0.39 | >100 |
| Staph. epidermidis 3519 | 0.2 | 0.01 | 0.02 | 1.56 | 0.01 | 0.39 |
| Entero. faecium ATCC 8043 | 0.39 | 0.05 | 0.05 | 3.1 | 0.02 | 0.39 |
| Strep. bovis A5169 | | 0.2 | 0.02 | 12.5 | 0.01 | 1.56 |
| Strep. agalactiae CMX 508 | 0.39 | 0.05 | 0.05 | 6.2 | 0.01 | 0.39 |
| Strep. pyogenes EES61 | 0.39 | 0.05 | 0.05 | 6.2 | 0.01 | 0.78 |
| Strep. pyogenes 930 CONST | 0.39 | 0.05 | 0.02 | 6.2 | 0.01 | 0.78 |
| Strep. pyogenes 2548 INDUC | 0.39 | 0.05 | 0.01 | 3.1 | 0.005 | 0.39 |
| M. luteus ATCC 9341 | 0.78 | 0.1 | 0.05 | 3.1 | 0.05 | 1.56 |
| M. luteus ATCC 4698 | 3.1 | 0.05 | 0.05 | 6.2 | 0.05 | 0.78 |
| Escherichia coli Juhl | 0.2 | 0.01 | 0.005 | 0.2 | 0.02 | 0.01 |
| E. coli SS | 0.02 | 0.001 | 0.001 | 0.02 | 0.001 | 0.005 |
| E. coli DC-2 | 1.56 | 0.1 | 0.05 | 1.56 | 0.1 | 0.2 |
| E. coli H560 | 0.2 | 0.05 | 0.01 | 0.2 | 0.01 | 0.01 |
| E. coli KNK 437 | 1.56 | 0.1 | 0.05 | 1.56 | 0.1 | 0.2 |
| Enter. aerogenes ATCC 13048 | 0.39 | 0.2 | 0.02 | 0.39 | 0.1 | 0.02 |
| Klebs. pneumoniae ATCC 8045 | 0.1 | 0.05 | 0.005 | 0.2 | 0.02 | 0.02 |
| Providencia stuartii CMX 640 | 3.1 | 0.39 | 0.78 | 6.2 | 0.78 | 0.78 |
| P. aeruginosa BMH 10 | 1.56 | 0.78 | 0.1 | 0.39 | 0.39 | 0.1 |
| P. aeruginosa A5007 | 1.56 | 0.39 | 0.1 | 0.78 | 0.39 | 0.1 |
| P. aeruginosa K799/WT | 1.56 | 0.39 | 0.1 | 0.78 | 0.39 | 0.1 |
| P. aeruginosa K799/61 | 0.39 | 0.05 | 0.05 | 0.2 | 0.05 | 0.02 |
| Pseudomonas cepacia 2961 | 6.2 | 1.56 | 0.39 | 6.2 | 6.2 | 3.1 |
| Acinetob. calcoaceticus CMX 669 | 0.39 | 0.2 | 0.01 | 3.1 | 0.05 | 0.78 |
| P. aeruginosa 5263 | 100 | 12.5 | 3.1 | 25 | 6.2 | 12.5 |
| P. aeruginosa 2862 | 50 | 12.5 | 1.56 | 50 | 12.5 | 12.5 |
| Candida albicans CCH 442 | >100 | >100 | >100 | >100 | >100 | >100 |
| Myco. smegmatis ATCC 114 | 50 | 0.39 | 1.56 | 25 | 0.02 | 0.78 |
| Nocardia asteroides ATCC 9970 | 50 | 12.5 | 1.56 | 100 | 0.78 | 25 |

TABLE 16-continued

| In Vitro Antibacterial Activity (MIC Values in µg/ml) | | | | | | |
|---|---|---|---|---|---|---|
| Organisms | Ex. 337 | Ex. 338 | Ex. 339 | Ex. 340 | Ex. 341 | Cntl |
| *Staph. aureus* ATCC 6538P | 0.005 | 0.02 | 0.1 | 0.01 | 0.005 | 0.2 |
| *Staph. aureus* A5177 | 0.01 | 0.05 | 0.2 | 0.02 | 0.005 | 0.39 |
| *Staph. aureus* 5278 | 0.01 | 0.02 | 0.2 | 0.02 | 0.005 | 0.39 |
| *Staph. aureus* 642A | 0.01 | 0.05 | 0.2 | 0.05 | 0.01 | 0.39 |
| *Staph. aureus* NCTC 10649 | 0.005 | 0.02 | 0.2 | 0.02 | 0.005 | 0.39 |
| *Staph. aureus* CMX 553 | 0.01 | 0.05 | 0.39 | 0.02 | 0.02 | 0.78 |
| *Staph. aureus* 1775 Cipro. R. | 0.2 | 0.78 | 6.2 | 0.2 | 0.39 | >100 |
| *Staph. epidermidis* 3519 | 0.01 | 0.05 | 0.2 | 0.02 | 0.01 | 0.39 |
| *Entero. faecium* ATCC 8043 | 0.01 | 0.1 | 0.2 | 0.05 | 0.02 | 0.39 |
| *Strep. bovis* A5169 | 0.002 | 0.05 | 0.39 | 0.05 | 0.01 | 1.56 |
| *Strep. agalactiae* CMX 508 | 0.005 | 0.05 | 0.2 | 0.02 | 0.01 | 0.39 |
| *Strep. pyogenes* EES61 | 0.002 | 0.05 | 0.2 | 0.05 | 0.02 | 0.78 |
| *Strep. pyogenes* 930 CONST | 0.002 | 0.05 | 0.2 | 0.05 | 0.02 | 0.78 |
| *Strep. pyogenes* 2548 INDUC | 0.002 | 0.05 | 0.2 | 0.05 | 0.01 | 0.39 |
| *M. luteus* ATCC 9341 | 0.05 | 0.2 | 0.39 | 0.2 | 0.05 | 1.56 |
| *M. luteus* ATCC 4698 | 0.01 | 0.1 | 0.2 | 0.05 | 0.05 | 0.78 |
| *Escherichia coli* Juhl | 0.005 | 0.02 | 0.02 | 0.05 | 0.02 | 0.01 |
| *E. coli* SS | 0.0005 | 0.002 | 0.002 | 0.005 | 0.0005 | 0.005 |
| *E. coli* DC-2 | 0.05 | 0.39 | 0.2 | 0.78 | 0.2 | 0.2 |
| *E. coli* H560 | 0.002 | 0.02 | 0.05 | 0.02 | 0.02 | 0.01 |
| *E. coli* KNK 437 | 0.1 | 0.2 | 0.2 | 0.78 | 0.1 | 0.2 |
| *Enter. aerogenes* ATCC 13048 | 0.01 | 0.1 | 0.1 | 0.78 | 0.1 | 0.02 |
| *Klebs. pneumoniae* ATCC 8045 | 0.005 | 0.05 | 0.05 | 0.05 | 0.02 | 0.02 |
| *Providencia stuartii* CMX 640 | 0.39 | 3.1 | 0.78 | 1.56 | 0.78 | 0.78 |
| *P. aeruginosa* BMH 10 | 0.1 | 0.78 | 0.2 | 1.56 | 0.2 | 0.1 |
| *P. aeruginosa* A5007 | 0.2 | 0.78 | 0.2 | 0.78 | 0.39 | 0.1 |
| *P. aeruginosa* K799/WT | 0.2 | 0.78 | 0.2 | 0.78 | 0.39 | 0.1 |
| *P. aeruginosa* K799/61 | 0.05 | 0.1 | 0.05 | 0.05 | 0.05 | 0.02 |
| *Pseudomonas cepacia* 2961 | 3.1 | 3.1 | 3.1 | 0.78 | 0.78 | 3.1 |
| *Acinetob. calcoaceticus* CMX 669 | 0.02 | 0.1 | 0.39 | 0.2 | 0.05 | 0.78 |
| *P. aeruginosa* 5263 | 3.1 | 25 | 6.2 | 12.5 | 3.1 | 12.5 |
| *P. aeruginosa* 2862 | 6.2 | 25 | 6.2 | 12.5 | 6.2 | 12.5 |
| *Candida albicans* CCH 442 | >100 | >100 | >100 | >100 | >100 | >100 |
| *Myco. smegmatis* ATCC 114 | 0.01 | 0.1 | 0.2 | 0.78 | 0.1 | 0.78 |
| *Nocardia asteroides* ATCC 9970 | 0.39 | 1.56 | 6.2 | 6.2 | 0.78 | 25 |
| Organisms | Ex. 342 | Ex. 343 | Ex. 344 | Ex. 345 | Ex. 346 | Cntl |
| *Staph. aureus* ATCC 6538P | 0.005 | 0.02 | 0.02 | 0.1 | 3.1 | 0.2 |
| *Staph. aureus* A5177 | 0.005 | 0.05 | 0.05 | 0.2 | 6.2 | 0.39 |
| *Staph. aureus* 5278 | 0.005 | 0.05 | 0.05 | 0.2 | 6.2 | 0.39 |
| *Staph. aureus* 642A | 0.01 | 0.05 | 0.05 | 0.2 | 12.5 | 0.39 |
| *Staph. aureus* NCTC 10649 | 0.005 | 0.02 | 0.02 | 0.2 | 3.1 | 0.39 |
| *Staph. aureus* CMX 553 | 0.01 | 0.05 | 0.05 | 0.39 | 12.5 | 0.78 |
| *Staph. aureus* 1775 Cipro. R. | 0.1 | 1.56 | 0.78 | 25 | >100 | >100 |
| *Staph. epidermidis* 3519 | 0.005 | 0.05 | 0.05 | 0.2 | 12.5 | 0.39 |
| *Entero. faecium* ATCC 8043 | 0.02 | 0.1 | 0.1 | 0.2 | 100 | 0.39 |
| *Strep. bovis* A5169 | 0.002 | 0.1 | 0.2 | 0.78 | 50 | 1.56 |
| *Strep. agalactiae* CMX 508 | 0.002 | 0.05 | 0.2 | 0.39 | 25 | 0.39 |
| *Strep. pyogenes* EES61 | 0.005 | 0.1 | 0.2 | 0.39 | 25 | 0.78 |
| *Strep. pyogenes* 930 CONST | 0.01 | 0.1 | 0.2 | 0.2 | 25 | 0.78 |
| *Strep. pyogenes* 2548 INDUC | 0.005 | 0.1 | 0.2 | 0.2 | 25 | 0.39 |
| *M. luteus* ATCC 9341 | 0.05 | 0.1 | 0.2 | 0.39 | 50 | 1.56 |
| *M. luteus* ATCC 4698 | 0.02 | 0.05 | 0.1 | 0.2 | 25 | 0.78 |
| *Escherichia coli* Juhl | 0.01 | 0.01 | 0.02 | 0.02 | 3.1 | 0.01 |
| *E. coli* SS | 0.0005 | 0.002 | 0.002 | 0.002 | 0.1 | 0.005 |
| *E. coli* DC-2 | 0.1 | 0.1 | 0.39 | 0.39 | 50 | 0.2 |
| *E. coli* H560 | 0.01 | 0.01 | 0.2 | 0.05 | 6.2 | 0.01 |
| *E. coli* KNK 437 | 0.2 | 0.1 | 0.2 | 0.39 | 12.5 | 0.2 |
| *Enter. aerogenes* ATCC 13048 | 0.1 | 0.02 | 0.05 | 0.1 | 12.5 | 0.02 |
| *Klebs. pneumoniae* ATCC 8045 | 0.02 | 0.01 | 0.02 | 0.05 | 1.56 | 0.02 |
| *Providencia stuartii* CMX 640 | 0.39 | 0.78 | 1.56 | 3.1 | >100 | 0.78 |
| *P. aeruginosa* BMH 10 | 0.2 | 0.2 | 0.39 | 0.39 | 25 | 0.1 |
| *P. aeruginosa* A5007 | 0.39 | 0.2 | 0.78 | 0.78 | 25 | 0.1 |
| *P. aeruginosa* K799/WT | 0.39 | 0.2 | 0.78 | 0.78 | 25 | 0.1 |
| *P. aeruginosa* K799/61 | 0.05 | 0.02 | 0.05 | 0.1 | 1.56 | 0.02 |
| *Pseudomonas cepacia* 2961 | 1.56 | 1.56 | 0.78 | 3.1 | >100 | 3.1 |
| *Acinetob. calcoaceticus* CMX 669 | 0.05 | 0.02 | 0.05 | 0.2 | 6.2 | 0.78 |
| *P. aeruginosa* 5263 | 3.1 | 3.1 | 12.5 | 12.5 | >100 | 12.5 |
| *P. aeruginosa* 2862 | 6.2 | 6.2 | 12.5 | 6.2 | >100 | 12.5 |
| *Candida albicans* CCH 442 | 50 | >100 | >100 | >100 | >100 | >100 |
| *Myco. smegmatis* ATCC 114 | 0.1 | 0.1 | 0.1 | 3.1 | 6.2 | 0.78 |
| *Nocardia asteroides* ATCC 9970 | 0.39 | 12.5 | 12.5 | 25 | 100 | 25 |

TABLE 16-continued

In Vitro Antibacterial Activity (MIC Values in μg/ml)

| Organisms | Ex. 348 | Ex. 349 | Ex. 350 | Ex. 351 | Ex. 352 | Cntl |
|---|---|---|---|---|---|---|
| Staph. aureus ATCC 6538P | 0.01 | 0.05 | 0.02 | 0.05 | 0.05 | 0.2 |
| Staph. aureus A5177 | 0.02 | 0.1 | 0.05 | 0.1 | 0.05 | 0.39 |
| Staph. aureus 5278 | 0.01 | 0.1 | 0.05 | 0.1 | 0.05 | 0.39 |
| Staph. aureus 642A | 0.02 | 0.1 | 0.05 | 0.1 | 0.05 | 0.39 |
| Staph. aureus NCTC 10649 | 0.01 | 0.05 | 0.05 | 0.05 | 0.05 | 0.39 |
| Staph. aureus CMX 553 | 0.02 | 0.1 | 0.05 | 0.1 | 0.05 | 0.78 |
| Staph. aureus 1775 Cipro. R. | 0.39 | 3.1 | 3.1 | 3.1 | 0.78 | >100 |
| Staph. epidermidis 3519 | 0.02 | 0.1 | 0.05 | 0.1 | 0.05 | 0.39 |
| Entero. faecium ATCC 8043 | 0.1 | 0.39 | 0.1 | 0.39 | 0.39 | 0.39 |
| Strep. bovis A5169 | 0.1 | 0.39 | 0.1 | 0.39 | 0.39 | 1.56 |
| Strep. agalactiae CMX 508 | 0.1 | 0.39 | 0.05 | 0.39 | 0.39 | 0.39 |
| Strep. pyogenes EES61 | 0.1 | 0.39 | 0.1 | 0.39 | 0.39 | 0.78 |
| Strep. pyogenes 930 CONST | 0.1 | 0.2 | 0.05 | 0.39 | 0.39 | 0.78 |
| Strep. pyogenes 2548 INDUC | 0.1 | 0.2 | 0.05 | 0.39 | 0.2 | 0.39 |
| M. luteus ATCC 9341 | 0.2 | 0.39 | 0.05 | 0.2 | 0.39 | 1.56 |
| M. luteus ATCC 4698 | 0.1 | 0.39 | 0.05 | 0.2 | 0.2 | 0.78 |
| Escherichia coli Juhl | 0.2 | 0.05 | 0.01 | 0.1 | 0.78 | 0.01 |
| E. coli SS | 0.01 | 0.005 | 0.005 | 0.005 | 0.02 | 0.005 |
| E. coli DC-2 | 1.56 | 0.78 | 0.1 | 0.78 | 6.2 | 0.2 |
| E. coli H560 | 0.2 | 0.1 | 0.01 | 0.1 | 0.39 | 0.01 |
| E. coli KNK 437 | 0.78 | 0.39 | 0.1 | 0.78 | 3.1 | 0.2 |
| Enter. aerogenes ATCC 13048 | 0.78 | 0.2 | 0.1 | 0.2 | 1.56 | 0.02 |
| Klebs. pneumoniae ATCC 8045 | 0.39 | 0.05 | 0.01 | 0.05 | 0.78 | 0.02 |
| Providencia stuartii CMX 640 | 3.1 | 3.1 | 1.56 | 3.1 | 6.2 | 0.78 |
| P. aeruginosa BMH 10 | 3.1 | 0.78 | 0.1 | 1.56 | 6.2 | 0.1 |
| P. aeruginosa A5007 | 3.1 | 1.56 | 0.2 | 1.56 | 6.2 | 0.1 |
| P. aeruginosa K799/WT | 1.56 | 1.56 | 0.2 | 1.56 | 3.1 | 0.1 |
| P. aeruginosa K799/61 | 0.2 | 0.2 | 0.05 | 0.2 | 0.39 | 0.02 |
| Pseudomonas cepacia 2961 | 6.2 | 3.1 | 3.1 | 3.1 | 6.2 | 3.1 |
| Acinetob. calcoaceticus CMX 669 | 0.39 | 0.1 | 0.05 | 0.39 | 0.78 | 0.78 |
| P. aeruginosa 5263 | 50 | 25 | 3.1 | 50 | >100 | 12.5 |
| P. aeruginosa 2862 | 25 | 25 | 3.1 | 25 | 100 | 12.5 |
| Candida albicans CCH 442 | >100 | >100 | >100 | >100 | >100 | >100 |
| Myco. smegmatis ATCC 114 | 0.39 | 0.2 | 0.05 | 0.2 | 0.78 | 0.78 |
| Nocardia asteroides ATCC 9970 | 3.1 | 12.5 | 3.1 | 25 | 25 | 25 |

| Organisms | Ex. 353 | Ex. 354 | Ex. 355 | Ex. 356 | 357 | Cntl |
|---|---|---|---|---|---|---|
| Staph. aureus ATCC 6538P | 0.1 | 0.01 | 0.02 | 0.02 | 0.02 | 0.2 |
| Staph. aureus A5177 | 0.2 | 0.05 | 0.02 | 0.05 | 0.05 | 0.39 |
| Staph. aureus 5278 | 0.2 | 0.05 | 0.02 | 0.05 | 0.05 | 0.39 |
| Staph. aureus 642A | 0.2 | 0.05 | 0.05 | 0.05 | 0.05 | 0.39 |
| Staph. aureus NCTC 10649 | 0.1 | 0.02 | 0.02 | 0.05 | 0.05 | 0.39 |
| Staph. aureus CMX 553 | 0.2 | 0.05 | 0.05 | 0.1 | 0.1 | 0.78 |
| Staph. aureus 1775 Cipro. R. | 6.2 | 0.39 | 3.1 | 1.56 | 3.1 | >100 |
| Staph. epidermidis 3519 | 0.2 | 0.05 | 0.05 | 0.05 | 0.05 | 0.39 |
| Entero. faecium ATCC 8043 | 0.39 | 0.1 | 0.05 | 0.1 | 0.2 | 0.39 |
| Strep. bovis A5169 | 0.39 | na | 0.05 | 0.1 | 0.2 | 1.56 |
| Strep. agalactiae CMX 508 | 0.39 | 0.1 | 0.05 | 0.1 | 0.1 | 0.39 |
| Strep. pyogenes EES61 | 0.39 | 0.1 | 0.05 | 0.1 | 0.2 | 0.78 |
| Strep. pyogenes 930 CONST | 0.39 | 0.2 | 0.05 | 0.1 | 0.2 | 0.78 |
| Strep. pyogenes 2548 INDUC | 0.2 | 0.2 | 0.05 | 0.05 | 0.2 | 0.39 |
| M. luteus ATCC 9341 | 0.39 | 0.39 | 0.1 | 0.1 | 0.2 | 1.56 |
| M. luteus ATCC 4698 | 0.39 | 0.2 | 0.1 | 0.1 | 0.2 | 0.78 |
| Escherichia coli Juhl | 0.05 | 0.78 | 0.02 | 0.01 | 0.1 | 0.01 |
| E. coli SS | 0.001 | 0.02 | 0.005 | 0.001 | 0.001 | 0.005 |
| E. coli DC-2 | 0.39 | 3.1 | 0.2 | 0.2 | 0.78 | 0.2 |
| E. coli H560 | 0.1 | 0.78 | 0.05 | 0.01 | 0.1 | 0.01 |
| E. coli KNK 437 | 0.78 | 3.1 | 0.2 | 0.1 | 0.78 | 0.2 |
| Enter. aerogenes ATCC 13048 | 0.2 | 3.1 | 0.1 | 0.05 | 0.39 | 0.02 |
| Klebs. pneumoniae ATCC 8045 | 0.05 | 0.78 | 0.05 | 0.01 | 0.1 | 0.02 |
| Providencia stuartii CMX 640 | 3.1 | 6.2 | 1.56 | 0.78 | 6.2 | 0.78 |
| P. aeruginosa BMH 10 | 0.39 | 6.2 | 0.39 | 0.2 | 1.56 | 0.1 |
| P. aeruginosa A5007 | 1.56 | 6.2 | 0.39 | 0.2 | 1.56 | 0.1 |
| P. aeruginosa K799/WT | 1.56 | 6.2 | 0.39 | 0.2 | 6.2 | 0.1 |
| P. aeruginosa K799/61 | 0.1 | 0.39 | 0.05 | 0.02 | 0.2 | 0.02 |
| Pseudomonas cepacia 2961 | 3.1 | 25 | 1.56 | 1.56 | 6.2 | 3.1 |
| Acinetob. calcoaceticus CMX 669 | 0.2 | 1.56 | 0.1 | 0.05 | 0.2 | 0.78 |
| P. aeruginosa 5263 | 25 | >100 | 6.2 | 3.1 | 50 | 12.5 |
| P. aeruginosa 2862 | 25 | >100 | 12.5 | 6.2 | 50 | 12.5 |
| Candida albicans CCH 442 | >100 | >100 | >100 | >100 | >100 | >100 |
| Myco. smegmatis ATCC 114 | 0.2 | 6.2 | 0.78 | 0.1 | 0.1 | 0.78 |
| Nocardia asteroides ATCC 9970 | 12.5 | >100 | 12.5 | 3.1 | 6.2 | 25 |

TABLE 16-continued

In Vitro Antibacterial Activity (MIC Values in µg/ml)

| Organisms | Ex. 358 | Ex. 359 | Ex. 360 | Ex. 361 | Ex. 362 | Cntl |
|---|---|---|---|---|---|---|
| Staph. aureus ATCC 6538P | 0.1 | 0.1 | 0.02 | 0.01 | 0.02 | 0.2 |
| Staph. aureus A5177 | 0.2 | 0.1 | 0.2 | 0.02 | 0.05 | 0.39 |
| Staph. aureus 5278 | 0.2 | 0.1 | 0.2 | 0.02 | 0.1 | 0.39 |
| Staph. aureus 642A | 0.2 | 0.1 | 0.2 | 0.02 | 0.05 | 0.39 |
| Staph. aureus NCTC 10649 | 0.2 | 0.1 | 0.1 | 0.02 | 0.05 | 0.39 |
| Staph. aureus CMX 553 | 0.39 | 0.2 | 0.39 | 0.05 | 0.1 | 0.78 |
| Staph. aureus 1775 Cipro. R. | 25 | 6.2 | 12.5 | 1.56 | 12.5 | >100 |
| Staph. epidermidis 3519 | 0.2 | 0.1 | 0.2 | 0.02 | 0.05 | 0.39 |
| Entero. faecium ATCC 8043 | 0.2 | 0.2 | 0.1 | 0.05 | 0.05 | 0.39 |
| Strep. bovis A5169 | 0.2 | 0.2 | 0.02 | 0.02 | 0.1 | 1.56 |
| Strep. agalactiae CMX 508 | 0.2 | 0.1 | 0.01 | 0.01 | 0.05 | 0.39 |
| Strep. pyogenes EES61 | 0.2 | 0.1 | 0.02 | 0.01 | 0.1 | 0.78 |
| Strep. pyogenes 930 CONST | 0.2 | 0.2 | 0.02 | 0.01 | 0.05 | 0.78 |
| Strep. pyogenes 2548 INDUC | 0.2 | 0.2 | 0.02 | 0.01 | 0.05 | 0.39 |
| M. luteus ATCC 9341 | 0.2 | 0.39 | 0.39 | 0.05 | 0.2 | 1.56 |
| M. luteus ATCC 4698 | 0.2 | 0.39 | 0.39 | 0.05 | 0.1 | 0.78 |
| Escherichia coli Juhl | 0.1 | 0.1 | 0.1 | 0.02 | 0.1 | 0.01 |
| E. coli SS | 0.005 | 0.002 | 0.005 | 0.002 | 0.005 | 0.005 |
| E. coli DC-2 | 0.78 | 0.78 | 0.78 | 0.2 | 0.78 | 0.2 |
| E. coli H560 | 0.2 | 0.1 | 0.2 | 0.05 | 0.1 | 0.01 |
| E. coli KNK 437 | 0.78 | 0.78 | 0.78 | 0.39 | 0.78 | 0.2 |
| Enter. aerogenes ATCC 13048 | 0.39 | 0.78 | 0.39 | 0.1 | 0.2 | 0.02 |
| Klebs. pneumoniae ATCC 8045 | 0.1 | 0.1 | 0.2 | 0.02 | 0.05 | 0.02 |
| Providencia stuartii CMX 640 | 3.1 | 12.5 | 6.2 | 3.1 | 6.2 | 0.78 |
| P. aeruginosa BMH 10 | 0.39 | 1.56 | 0.39 | 0.2 | 0.39 | 0.1 |
| P. aeruginosa A5007 | 0.39 | 3.1 | 0.78 | 0.78 | 0.78 | 0.1 |
| P. aeruginosa K799/WT | 0.78 | 1.56 | 0.39 | 0.78 | 0.78 | 0.1 |
| P. aeruginosa K799/61 | 0.05 | 0.39 | 0.1 | 0.1 | 0.05 | 0.02 |
| Pseudomonas cepacia 2961 | 12.5 | 12.5 | 12.5 | 3.1 | 6.2 | 3.1 |
| Acinetob. calcoaceticus CMX 669 | 3.1 | 0.78 | 3.1 | 0.1 | 0.78 | 0.78 |
| P. aeruginosa 5263 | 6.2 | 50 | 6.2 | 6.2 | 25 | 12.5 |
| P. aeruginosa 2862 | 12.5 | 100 | 12.5 | 6.2 | 25 | 12.5 |
| Candida albicans CCH 442 | 100 | >100 | >100 | >100 | >100 | >100 |
| Myco. smegmatis ATCC 114 | 0.2 | 0.39 | 0.78 | 1.56 | 0.05 | 0.78 |
| Nocardia asteroides ATCC 9970 | 6.2 | 25 | 25 | 0.78 | 3.1 | 25 |

| Organisms | Ex. 363 | Ex. 364 | Ex. 365 | Ex. 366 | Ex. 367 | Cntl |
|---|---|---|---|---|---|---|
| Staph. aureus ATCC 6538P | 0.01 | 0.05 | 0.01 | 0.1 | 0.05 | 0.2 |
| Staph. aureus A5177 | 0.02 | 0.1 | 0.02 | 0.1 | 0.1 | 0.39 |
| Staph. aureus 5278 | 0.02 | 0.1 | 0.02 | 0.1 | 0.1 | 0.39 |
| Staph. aureus 642A | 0.02 | 0.2 | 0.05 | 0.1 | 0.1 | 0.39 |
| Staph. aureus NCTC 10649 | 0.01 | 0.05 | 0.01 | 0.05 | 0.05 | 0.39 |
| Staph. aureus CMX 553 | 0.05 | 0.2 | 0.05 | 0.1 | 0.2 | 0.78 |
| Staph. aureus 1775 Cipro. R. | 1.56 | 3.1 | 1.56 | 1.56 | 3.1 | >100 |
| Staph. epidermidis 3519 | 0.05 | 0.1 | 0.02 | 0.1 | 0.1 | 0.39 |
| Entero. faecium ATCC 8043 | 0.05 | 0.39 | 0.05 | 0.2 | 0.39 | 0.39 |
| Strep. bovis A5169 | 0.05 | 0.78 | 0.05 | 0.2 | 0.39 | 1.56 |
| Strep. agalactiae CMX 508 | 0.05 | 0.39 | 0.02 | 0.05 | 0.39 | 0.39 |
| Strep. pyogenes EES61 | 0.05 | 0.39 | 0.02 | 0.2 | 0.39 | 0.78 |
| Strep. pyogenes 930 CONST | 0.05 | 0.39 | 0.05 | 0.2 | 0.39 | 0.78 |
| Strep. pyogenes 2548 INDUC | 0.02 | 0.39 | 0.02 | 0.2 | 0.39 | 0.39 |
| M. luteus ATCC 9341 | 0.1 | 0.39 | 0.1 | 0.39 | 0.39 | 1.56 |
| M. luteus ATCC 4698 | 0.1 | 0.2 | 0.1 | 0.2 | 0.39 | 0.78 |
| Escherichia coli Juhl | 0.05 | 0.78 | 0.02 | 0.05 | 0.39 | 0.01 |
| E. coli SS | 0.01 | 0.05 | 0.002 | 0.05 | 0.01 | 0.005 |
| E. coli DC-2 | 0.78 | 12.5 | 0.1 | 0.39 | 1.56 | 0.2 |
| E. coli H560 | 0.1 | 1.56 | 0.02 | 0.05 | 0.39 | 0.01 |
| E. coli KNK 437 | 0.39 | 6.2 | 0.2 | 0.39 | 3.1 | 0.2 |
| Enter. aerogenes ATCC 13048 | 0.39 | 3.1 | 0.05 | 0.2 | 0.78 | 0.02 |
| Klebs. pneumoniae ATCC 8045 | 0.1 | 1.56 | 0.1 | 0.05 | 0.39 | 0.02 |
| Providencia stuartii CMX 640 | 3.1 | 12.5 | 0.78 | 3.1 | 12.5 | 0.78 |
| P. aeruginosa BMH 10 | 0.39 | 12.5 | 0.2 | 0.78 | 3.1 | 0.1 |
| P. aeruginosa A5007 | 1.56 | 12.5 | 0.39 | 0.78 | 6.2 | 0.1 |
| P. aeruginosa K799/WT | 1.56 | 12.5 | 0.39 | 0.78 | 3.1 | 0.1 |
| P. aeruginosa K799/61 | 0.39 | 0.78 | 0.05 | 0.2 | 0.1 | 0.02 |
| Pseudomonas cepacia 2961 | 3.1 | 12.5 | 1.56 | 3.1 | 6.2 | 3.1 |
| Acinetob. calcoaceticus CMX 669 | 0.2 | 1.56 | 0.1 | 0.1 | 0.78 | 0.78 |
| P. aeruginosa 5263 | 12.5 | >100 | 6.2 | 12.5 | 100 | 12.5 |
| P. aeruginosa 2862 | 25 | >100 | 6.2 | 25 | >100 | 12.5 |
| Candida albicans CCH 442 | >100 | >100 | >100 | >100 | >100 | >100 |
| Myco. smegmatis ATCC 114 | 0.39 | 3.1 | 0.1 | 0.78 | 6.2 | 0.78 |
| Nocardia asteroides ATCC 9970 | 12.5 | 12.5 | 1.56 | 12.5 | 50 | 25 |

TABLE 16-continued

In Vitro Antibacterial Activity (MIC Values in µg/ml)

| Organisms | Ex. 368 | Ex. 369 | Ex. 370 | Ex. 371 | Ex. 372 | Cntl |
|---|---|---|---|---|---|---|
| *Staph. aureus* ATCC 6538P | 0.005 | 0.01 | 0.02 | 0.005 | 0.05 | 0.2 |
| *Staph. aureus* A5177 | 0.01 | 0.02 | 0.05 | 0.01 | 0.05 | 0.39 |
| *Staph. aureus* 5278 | 0.01 | 0.02 | 0.05 | 0.01 | 0.05 | 0.39 |
| *Staph. aureus* 642A | 0.01 | 0.05 | 0.1 | 0.01 | 0.1 | 0.39 |
| *Staph. aureus* NCTC 10649 | 0.005 | 0.01 | 0.05 | 0.005 | 0.05 | 0.39 |
| *Staph. aureus* CMX 553 | 0.01 | 0.05 | 0.1 | 0.01 | 0.1 | 0.78 |
| *Staph. aureus* 1775 Cipro. R. | 0.1 | 0.2 | 1.56 | 0.39 | 0.78 | >100 |
| *Staph. epidermidis* 3519 | 0.01 | 0.02 | 0.05 | 0.01 | 0.05 | 0.39 |
| *Entero. faecium* ATCC 8043 | 0.01 | 0.1 | 0.1 | 0.02 | 0.39 | 0.39 |
| *Strep. bovis* A5169 | 0.01 | 0.2 | 0.1 | 0.002 | 0.1 | 1.56 |
| *Strep. agalactiae* CMX 508 | 0.002 | 0.1 | 0.1 | 0.002 | 0.05 | 0.39 |
| *Strep. pyogenes* EES61 | 0.01 | 0.1 | 0.1 | 0.005 | 0.1 | 0.78 |
| *Strep. pyogenes* 930 CONST | 0.01 | 0.1 | 0.1 | 0.01 | 0.2 | 0.78 |
| *Strep. pyogenes* 2548 INDUC | 0.005 | 0.1 | 0.05 | 0.01 | 0.1 | 0.39 |
| *M. luteus* ATCC 9341 | 0.02 | 0.2 | 0.2 | 0.02 | 0.78 | 1.56 |
| *M. luteus* ATCC 4698 | 0.05 | 0.05 | 0.1 | 0.02 | 0.78 | 0.78 |
| *Escherichia coli* Juhl | 0.02 | 0.2 | 0.05 | 0.02 | 0.78 | 0.01 |
| *E. coli* SS | 0.002 | 0.01 | 0.002 | 0.002 | 0.01 | 0.005 |
| *E. coli* DC-2 | 0.1 | 1.56 | 0.39 | 0.1 | 1.56 | 0.2 |
| *E. coli* H560 | 0.01 | 0.2 | 0.05 | 0.01 | 0.39 | 0.01 |
| *E. coli* KNK 437 | 0.1 | 1.56 | 0.39 | 0.2 | 3.1 | 0.2 |
| *Enter. aerogenes* ATCC 13048 | 0.05 | 0.39 | 0.2 | 0.05 | 3.1 | 0.02 |
| *Klebs. pneumoniae* ATCC 8045 | 0.01 | 0.05 | 0.1 | 0.02 | 0.78 | 0.02 |
| *Providencia stuartii* CMX 640 | 0.78 | 3.1 | 3.1 | 0.78 | 12.5 | 0.78 |
| *P. aeruginosa* BMH 10 | 0.2 | 1.56 | 0.78 | 0.2 | 3.1 | 0.1 |
| *P. aeruginosa* A5007 | 0.39 | 1.56 | 0.78 | 0.39 | 12.5 | 0.1 |
| *P. aeruginosa* K799/WT | 0.39 | 1.56 | 0.78 | 0.39 | 12.5 | 0.1 |
| *P. aeruginosa* K799/61 | 0.05 | 0.05 | 0.1 | 0.05 | 0.78 | 0.02 |
| *Pseudomonas cepacia* 2961 | 1.56 | 0.78 | 6.2 | 1.56 | 25 | 3.1 |
| *Acinetob. calcoaceticus* CMX 669 | 0.01 | 0.1 | 0.05 | 0.05 | 0.78 | 0.78 |
| *P. aeruginosa* 5263 | 3.1 | 12.5 | 12.5 | 6.2 | >100 | 12.5 |
| *P. aeruginosa* 2862 | 6.2 | 50 | 25 | 6.2 | >100 | 12.5 |
| *Candida albicans* CCH 442 | >100 | >100 | >100 | >100 | 100 | >100 |
| *Myco. smegmatis* ATCC 114 | 0.01 | 0.2 | 0.2 | 0.02 | 3.1 | 0.78 |
| *Nocardia asteroides* ATCC 9970 | 0.78 | 12.5 | 12.5 | 0.2 | 25 | 25 |

| Organisms | Ex. 373 | Ex. 374 | Ex. 413 | Cntl |
|---|---|---|---|---|
| *Staph. aureus* ATCC 6538P | 0.05 | 0.02 | 0.002 | 0.2 |
| *Staph. aureus* A5177 | 0.1 | 0.02 | 0.005 | 0.39 |
| *Staph. aureus* 5278 | 0.1 | 0.02 | 0.005 | 0.39 |
| *Staph. aureus* 642A | 0.2 | 0.05 | 0.005 | 0.39 |
| *Staph. aureus* NCTC 10649 | 0.1 | 0.02 | 0.002 | 0.39 |
| *Staph. aureus* CMX 553 | 0.39 | 0.1 | 0.01 | 0.78 |
| *Staph. aureus* 1775 Cipro. R. | 6.2 | 0.78 | 0.05 | >100 |
| *Staph. epidermidis* 3519 | 0.1 | 0.05 | 0.005 | 0.39 |
| *Entero. faecium* ATCC 8043 | 0.2 | 0.1 | 0.005 | 0.39 |
| *Strep. bovis* A5169 | 0.1 | 0.1 | 0.002 | 1.56 |
| *Strep. agalactiae* CMX 508 | 0.1 | 0.1 | 0.001 | 0.39 |
| *Strep. pyogenes* EES61 | 0.1 | 0.1 | 0.002 | 0.78 |
| *Strep. pyogenes* 930 CONST | 0.2 | 0.1 | 0.002 | 0.78 |
| *Strep. pyogenes* 2548 INDUC | 0.1 | 0.1 | 0.002 | 0.39 |
| *M. luteus* ATCC 9341 | 0.39 | 0.2 | 0.02 | 1.56 |
| *M. luteus* ATCC 4698 | 0.39 | 0.2 | 0.02 | 0.78 |
| *Escherichia coli* Juhl | 0.39 | 0.2 | 0.02 | 0.01 |
| *E. coli* SS | 0.01 | 0.005 | 0.002 | 0.005 |
| *E. coli* DC-2 | 1.56 | 0.78 | 0.05 | 0.2 |
| *E. coli* H560 | 0.2 | 0.39 | 0.01 | 0.01 |
| *E. coli* KNK 437 | 1.56 | 0.05 | 0.1 | 0.2 |
| *Enter. aerogenes* ATCC 13048 | 0.78 | 6.2 | 0.02 | 0.02 |
| *Klebs. pneumoniae* ATCC 8045 | 0.39 | 1.56 | 0.01 | 0.02 |
| *Providencia stuartii* CMX 640 | 12.5 | 1.56 | 0.78 | 0.78 |
| *P. aeruginosa* BMH 10 | 3.1 | 3.1 | 0.2 | 0.1 |
| *P. aeruginosa* A5007 | 3.1 | 0.39 | 0.39 | 0.1 |
| *P. aeruginosa* K799/WT | 3.1 | 6.2 | 0.39 | 0.1 |
| *P. aeruginosa* K799/61 | 0.78 | 0.39 | 0.05 | 0.02 |
| *Pseudomonas cepacia* 2961 | 12.5 | 6.2 | 1.56 | 3.1 |
| *Acinetob. calcoaceticus* CMX 669 | 0.78 | 0.2 | 0.02 | 0.78 |
| *P. aeruginosa* 5263 | 50 | 100 | 6.2 | 12.5 |
| *P. aeruginosa* 2862 | 100 | 50 | 12.5 | 12.5 |
| *Candida albicans* CCH 442 | >100 | >100 | 100 | >100 |
| *Myco. smegmatis* ATCC 114 | 1.56 | 0.2 | 0.2 | 0.78 |
| *Nocardia asteroides* ATCC 9970 | 25 | 1.56 | 0.2 | 25 |

TABLE 16-continued

In Vitro Antibacterial Activity (MIC Values in µg/ml)

| Organisms | Ex. 414 | Ex. 415 | Ex. 416 | Ex. 417 | Ex. 418 | Cntl |
|---|---|---|---|---|---|---|
| *Staph. aureus* ATCC 6538P | 0.01 | 0.01 | 0.01 | 0.1 | 0.01 | 0.05 |
| *Staph. aureus* A5177 | 0.05 | 0.05 | 0.02 | 0.2 | 0.01 | 0.39 |
| *Staph. aureus* 5278 | 0.05 | 0.05 | 0.01 | 0.1 | 0.002 | 0.39 |
| *Staph. aureus* 642A | 0.05 | 0.05 | 0.02 | 0.1 | 0.01 | 0.39 |
| *Staph. aureus* NCTC 10649M | 0.05 | 0.02 | 0.01 | 0.1 | 0.01 | 0.39 |
| *Staph. aureus* CMX 553 | 0.1 | 0.1 | 0.02 | — | 0.002 | 0.78 |
| *Staph. aureus* 1775 Cipro. R. | 6.2 | 6.2 | 0.78 | 0.39 | 0.78 | >100 |
| *Staph. epidermidis* 3519 | 0.05 | 0.05 | 0.02 | — | 0.01 | 0.39 |
| *Entero. faecium* ATCC 8043 | 0.02 | 0.2 | 0.1 | 0.1 | 0.05 | 0.78 |
| *Strep. bovis* A5169 | 0.2 | 0.2 | 0.1 | 0.2 | 0.05 | 1.56 |
| *Strep. agalactiae* CMX 508 | 0.2 | 0.1 | 0.1 | 0.05 | 0.05 | 0.78 |
| *Strep. pyogenes* EES61 | 0.1 | 0.1 | 0.1 | 0.1 | 0.1 | 0.39 |
| *Strep. pyogenes* 930 CONST | 0.1 | 0.2 | 0.1 | 0.1 | 0.05 | 0.78 |
| *Strep. pyogenes* 2548 INDUC | 0.1 | 0.1 | 0.1 | 0.05 | 0.05 | 0.39 |
| *M. luteus* ATCC 9341 | 0.2 | 0.39 | 0.2 | 0.2 | 0.1 | 3.1 |
| *M. luteus* ATCC 4698 | 0.1 | 0.1 | 0.1 | 0.2 | 0.05 | 1.56 |
| *Escherichia coli* Juhl | 0.1 | 0.39 | 0.1 | 0.2 | 0.1 | 0.05 |
| *E. coli* SS | 0.005 | 0.005 | 0.005 | 0.2 | 0.005 | 0.005 |
| *E. coli* DC-2 | 1.56 | 3.1 | 0.78 | 1.56 | 1.56 | 0.2 |
| *E. coli* H560 | 0.2 | 0.39 | 0.2 | 0.39 | 0.1 | 0.01 |
| *E. coli* KNK 437 | 0.78 | 1.56 | 0.78 | 0.78 | 0.78 | 0.2 |
| *Enter. aerogenes* ATCC 13048 | 0.39 | 0.78 | 0.39 | 0.39 | 0.2 | 0.05 |
| *Klebs. pneunoniae* ATCC 8045 | 0.05 | 0.1 | 0.1 | 0.1 | 0.78 | 0.01 |
| *Providencia stuartii* CMX 640 | 3.1 | 6.2 | 1.56 | 3.1 | 1.56 | 0.78 |
| *P. aeruginosa* BMH 10 | 1.56 | 3.1 | 0.78 | 1.56 | 1.56 | 0.1 |
| *P. aeruginosa* A5007 | 1.56 | 3.1 | 1.56 | 1.56 | 0.78 | 0.2 |
| *P. aeruginosa* K799/WT | 1.56 | 3.1 | 1.56 | 6.2 | 0.78 | 0.1 |
| *P. aeruginosa* K799/61 | 0.1 | 0.2 | 0.1 | 0.2 | 0.1 | 0.02 |
| *Pseudomonas cepacia* 2961 | 3.1 | 6.2 | 0.78 | 1.56 | 0.78 | 3.1 |
| *Acinetob. calcoaceticus* CMX 669 | 0.39 | 0.78 | 0.2 | 0.39 | 0.1 | 0.39 |
| *P. aeruginosa* 5263 | 25 | 50 | 25 | 25 | 25 | 12.5 |
| *P. aeruginosa* 2862 | 50 | 50 | 25 | 25 | 25 | 12.5 |
| *Candida albicans* CCH 442 | >100 | >100 | >100 | >100 | >100 | >100 |
| *Myco. smegmatis* ATCC 114 | 0.1 | 0.2 | 0.39 | 0.39 | — | 1.56 |
| *Nocardia asteroides* ATCC 9970 | 6.2 | 12.5 | 6.2 | 6.2 | — | 25 |

| Organisms | Ex. 419 | Ex. 420 | Ex. 421 | Ex. 422 | Ex. 423 | Cntl |
|---|---|---|---|---|---|---|
| *Staph. aureus* ATCC 6538P | 0.39 | 0.01 | 0.05 | 0.005 | 0.01 | 0.05 |
| *Staph. aureus* A5177 | 0.78 | 0.02 | 0.05 | 0.01 | 0.02 | 0.39 |
| *Staph. aureus* 5278 | 0.78 | 0.01 | 0.05 | 0.005 | 0.02 | 0.39 |
| *Staph. aureus* 642A | 0.78 | 0.02 | 0.05 | 0.01 | 0.02 | 0.39 |
| *Staph. aureus* NCTC 10649M | 0.39 | 0.01 | 0.05 | 0.005 | 0.02 | 0.39 |
| *Staph. aureus* CMX 553 | 0.78 | 0.05 | 0.05 | 0.01 | 0.05 | 0.78 |
| *Staph. aureus* 1775 Cipro. R. | 100 | 0.39 | 0.78 | 0.39 | 0.78 | >100 |
| *Staph. epidermidis* 3519 | 0.78 | 0.02 | 0.05 | 0.01 | 0.02 | 0.39 |
| *Entero. faecium* ATCC 8043 | 3.1 | 0.1 | 0.05 | 0.05 | 0.1 | 0.78 |
| *Strep. bovis* A5169 | — | 0.05 | 0.1 | 0.05 | 0.2 | 1.56 |
| *Strep. agalactiae* CMX 508 | 3.1 | 0.05 | 0.05 | 0.02 | 0.1 | 0.78 |
| *Strep. pyogenes* EES61 | 3.1 | 0.05 | 0.05 | 0.02 | 0.1 | 0.39 |
| *Strep. pyogenes* 930 CONST | 3.1 | 0.05 | 0.05 | 0.05 | 0.1 | 0.78 |
| *Strep. pyogenes* 2548 INDUC | 1.56 | 0.02 | 0.05 | 0.01 | 0.05 | 0.39 |
| *M. luteus* ATCC 9341 | 3.1 | 0.1 | 0.2 | 0.05 | 0.2 | 3.1 |
| *M. luteus* ATCC 4698 | 3.1 | 0.1 | 0.2 | 0.02 | 0.1 | 1.56 |
| *Escherichia coli* Juhl | 0.1 | 0.005 | 0.05 | 0.02 | 0.02 | 0.05 |
| *E. coli* SS | 0.02 | 0.002 | 0.002 | 0.0005 | 0.005 | 0.005 |
| *E. coli* DC-2 | 0.78 | 0.05 | 0.78 | 0.1 | 0.2 | 0.2 |
| *E. coli* H560 | 0.1 | 0.005 | 0.05 | 0.01 | 0.02 | 0.01 |
| *E. coli* KNK 437 | 0.78 | 0.05 | 0.39 | 0.2 | 0.2 | 0.2 |
| *Enter. aerogenes* ATCC 13048 | 0.2 | 0.02 | 0.05 | 0.05 | 0.1 | 0.05 |
| *Klebs. pneunoniae* ATCC 8045 | 0.05 | 0.01 | 0.005 | 0.005 | 0.01 | 0.01 |
| *Providencia stuartii* CMX 640 | 3.1 | 0.39 | 1.56 | 0.39 | 0.39 | 0.78 |
| *P. aeruginosa* BMH 10 | 0.3 | 0.1 | 0.78 | 0.39 | 0.39 | 0.1 |
| *P. aeruginosa* A5007 | 0.78 | 0.2 | 0.78 | 0.39 | 0.39 | 0.2 |
| *P. aeruginosa* K799/WT | 0.78 | 0.2 | 0.78 | 0.78 | 0.39 | 0.1 |
| *P. aeruginosa* K799/61 | 0.1 | 0.02 | 0.05 | 0.02 | 0.05 | 0.02 |
| *Pseudomonas cepacia* 2961 | 6.2 | 0.78 | 3.1 | 0.78 | 0.78 | 3.1 |
| *Acinetob. calcoaceticus* CMX 669 | 0.78 | 0.02 | 0.05 | 0.02 | 0.05 | 0.39 |
| *P. aeruginosa* 5263 | 50 | 3.1 | 12.5 | 3.1 | 6.2 | 12.5 |
| *P. aeruginosa* 2862 | 50 | 3.1 | 12.5 | 3.1 | 6.2 | 12.5 |
| *Candida albicans* CCH 442 | >100 | >100 | >100 | >100 | >100 | >100 |
| *Myco. smegmatis* ATCC 114 | 0.39 | 0.02 | 0.1 | 0.1 | 0.1 | 1.56 |
| *Nocardia asteroides* ATCC 9970 | 50 | 3.1 | 3.1 | 0.78 | 6.2 | 25 |

TABLE 16-continued

In Vitro Antibacterial Activity (MIC Values in µg/ml)

| Organisms | Ex. 424 | Ex. 425 | Ex. 426 | Ex. 427 | Ex. 428 | Cntl |
|---|---|---|---|---|---|---|
| Staph. aureus ATCC 6538P | 0.01 | 0.005 | 0.02 | 0.005 | 0.002 | 0.05 |
| Staph. aureus A5177 | 0.01 | 0.01 | 0.02 | 0.01 | 0.01 | 0.39 |
| Staph. aureus 5278 | 0.01 | 0.01 | 0.02 | 0.01 | 0.01 | 0.39 |
| Staph. aureus 642A | 0.01 | 0.01 | 0.02 | 0.01 | 0.01 | 0.39 |
| Staph. aureus NCTC 10649M | 0.01 | 0.005 | 0.02 | 0.01 | 0.002 | 0.39 |
| Staph. aureus CMX 553 | 0.02 | 0.01 | 0.02 | 0.02 | 0.01 | 0.78 |
| Staph. aureus 1775 Cipro. R. | 0.39 | 0.39 | 1.56 | 0.39 | 0.39 | >100 |
| Staph. epidermidis 3519 | 0.01 | 0.01 | 0.2 | 0.02 | 0.01 | 0.39 |
| Entero. faecium ATCC 8043 | 0.02 | 0.05 | 0.2 | 0.05 | 0.05 | 0.78 |
| Strep. bovis A5169 | 0.02 | 0.1 | 0.2 | — | — | 1.56 |
| Strep. agalactiae CMX 508 | 0.02 | 0.05 | 0.1 | 0.02 | 0.01 | 0.78 |
| Strep. pyogenes EES61 | 0.02 | — | — | 0.02 | 0.01 | 0.39 |
| Strep. pyogenes 930 CONST | 0.02 | — | — | 0.02 | 0.02 | 0.78 |
| Strep. pyogenes 2548 INDUC | 0.02 | 0.05 | 0.2 | 0.01 | 0.01 | 0.39 |
| M. luteus ATCC 9341 | 0.05 | 0.1 | 0.2 | 0.05 | 0.05 | 3.1 |
| M. luteus ATCC 4698 | 0.05 | 0.02 | 0.2 | 0.05 | 0.05 | 1.56 |
| Escherichia coli Juhl | 0.02 | 0.02 | 0.1 | 0.01 | 0.01 | 0.05 |
| E. coli SS | 0.002 | 0.0005 | 0.005 | 0.0005 | 0.0005 | 0.005 |
| E. coli DC-2 | 0.1 | 0.2 | 0.78 | 0.1 | 0.1 | 0.2 |
| E. coli H560 | 0.02 | 0.05 | 0.1 | 0.01 | 0.01 | 0.01 |
| E. coli KNK 437 | 0.1 | 0.1 | 0.78 | 0.1 | 0.1 | 0.2 |
| Enter. aerogenes ATCC 13048 | 0.05 | 0.1 | 0.2 | 0.05 | 0.05 | 0.05 |
| Klebs. pneunoniae ATCC 8045 | 0.005 | 0.01 | 0.02 | 0.01 | 0.005 | 0.01 |
| Providencia stuartii CMX 640 | 0.78 | 0.39 | 0.78 | 0.78 | 0.39 | 0.78 |
| P. aeruginosa BMH 10 | 0.2 | 0.05 | 0.78 | 0.2 | 0.1 | 0.1 |
| P. aeruginosa A5007 | 0.39 | 0.39 | 0.78 | 0.39 | 0.39 | 0.2 |
| P. aeruginosa K799/WT | 0.39 | 0.39 | 0.78 | 0.39 | 0.39 | 0.1 |
| P. aeruginosa K799/61 | 0.05 | 0.02 | 0.1 | 0.05 | 0.05 | 0.02 |
| Pseudomonas cepacia 2961 | 1.56 | 0.39 | 0.78 | 0.78 | 1.56 | 3.1 |
| Acinetob. calcoaceticus CMX 669 | 0.02 | 0.02 | 0.2 | 0.01 | 0.02 | 0.39 |
| P. aeruginosa 5263 | 3.1 | 3.1 | 6.2 | 3.1 | 3.1 | 12.5 |
| P. aeruginosa 2862 | 3.1 | 3.1 | 25 | 6.2 | 3.1 | 12.5 |
| Candida albicans CCH 442 | >100 | >100 | >100 | >100 | >100 | >100 |
| Myco. smegmatis ATCC 114 | 0.1 | 0.05 | 0.2 | 0.2 | 0.2 | 1.56 |
| Nocardia asteroides ATCC 9970 | 3.1 | 3.1 | 6.2 | 0.78 | 1.56 | 25 |

| Organisms | Ex. 429 | Ex. 430 | Ex. 431 | Ex. 432 | Ex. 433 | Cntl |
|---|---|---|---|---|---|---|
| Staph. aureus ATCC 6538P | 0.01 | 0.05 | 0.1 | 0.1 | 0.01 | 0.05 |
| Staph. aureus A5177 | 0.01 | 0.1 | 0.1 | 0.1 | 0.02 | 0.39 |
| Staph. aureus 5278 | 0.05 | 0.05 | 0.1 | 0.1 | 0.02 | 0.39 |
| Staph. aureus 642A | 0.2 | 0.05 | 0.1 | 0.1 | 0.02 | 0.39 |
| Staph. aureus NCTC 10649M | 0.005 | 0.02 | 0.78 | 0.1 | 0.02 | 0.39 |
| Staph. aureus CMX 553 | 0.02 | 0.1 | 0.2 | 0.1 | 0.02 | 0.78 |
| Staph. aureus 1775 Cipro. R. | 0.39 | 0.78 | 6.2 | 12.5 | 1.56 | >100 |
| Staph. epidermidis 3519 | 0.05 | 0.1 | 0.1 | 0.1 | 0.02 | 0.39 |
| Entero. faecium ATCC 8043 | 0.1 | 0.39 | 0.78 | 1.56 | 0.2 | 0.78 |
| Strep. bovis A5169 | 0.2 | 0.39 | 0.78 | 6.2 | 0.78 | 1.56 |
| Strep. agalactiae CMX 508 | 0.1 | 0.2 | 0.78 | 1.56 | 0.1 | 0.78 |
| Strep. pyogenes EES61 | 0.2 | 0.2 | 0.78 | 1.56 | 0.2 | 0.39 |
| Strep. pyogenes 930 CONST | 0.2 | 0.2 | 0.78 | 1.56 | 0.2 | 0.78 |
| Strep. pyogenes 2548 INDUC | 0.1 | 0.2 | 0.78 | 1.56 | 0.2 | 0.39 |
| M. luteus ATCC 9341 | 0.2 | 0.39 | 1.56 | 3.1 | 0.2 | 3.1 |
| M. luteus ATCC 4698 | 0.02 | 0.39 | 0.39 | 1.56 | 0.02 | 1.56 |
| Escherichia coli Juhl | 0.2 | 0.78 | 0.78 | 1.56 | 0.02 | 0.05 |
| E. coli SS | 0.01 | 0.02 | 0.01 | 0.005 | 0.002 | 0.005 |
| E. coli DC-2 | 1.56 | 3.1 | 6.2 | 50 | 6.2 | 0.2 |
| E. coli H560 | 0.39 | 0.78 | 0.78 | 3.1 | 0.02 | 0.01 |
| E. coli KNK 437 | 1.56 | 3.1 | 6.2 | 25 | 1.56 | 0.2 |
| Enter. aerogenes ATCC 13048 | 0.78 | 1.56 | 3.1 | 6.2 | 1.56 | 0.05 |
| Klebs. pneunoniae ATCC 8045 | 0.2 | 0.39 | 0.78 | 12.5 | 3.1 | 0.01 |
| Providencia stuartii CMX 640 | 3.1 | 6.2 | 25 | 100 | 12.5 | 0.78 |
| P. aeruginosa BMH 10 | 3.1 | 3.1 | 12.5 | 50 | 3.1 | 0.1 |
| P. aeruginosa A5007 | 6.2 | 6.2 | 12.5 | 50 | 6.2 | 0.2 |
| P. aeruginosa K799/WT | 1.56 | 6.2 | 12.5 | 50 | 12.5 | 0.1 |
| P. aeruginosa K799/61 | 0.2 | 0.39 | 0.78 | 3.1 | 0.39 | 0.02 |
| Pseudomonas cepacia 2961 | 3.1 | 3.1 | 25 | 100 | 6.2 | 3.1 |
| Acinetob. calcoaceticus CMX 669 | 0.39 | 0.78 | 3.1 | 3.1 | 0.39 | 0.39 |
| P. aeruginosa 5263 | >100 | 100 | 100 | >100 | 100 | 12.5 |
| P. aeruginosa 2862 | >100 | 100 | 100 | >100 | 100 | 12.5 |
| Candida albicans CCH 442 | >100 | >100 | 100 | >100 | >100 | >100 |
| Myco. smegmatis ATCC 114 | 0.78 | 3.1 | 50 | — | — | 1.56 |
| Nocardia asteroides ATCC 9970 | 6.2 | 6.2 | 50 | — | — | 25 |

TABLE 16-continued

In Vitro Antibacterial Activity (MIC Values in µg/ml)

| Organisms | Ex. 434 | Ex. 435 | Ex. 436 | Ex. 437 | Ex. 438 | Cntl |
|---|---|---|---|---|---|---|
| Staph. aureus ATCC 6538P | 0.2 | 0.01 | 0.01 | 0.01 | 0.39 | 0.05 |
| Staph. aureus A5177 | 0.2 | 0.02 | 0.02 | 0.02 | 0.78 | 0.39 |
| Staph. aureus 5278 | 0.2 | 0.02 | 0.02 | 0.02 | 0.78 | 0.39 |
| Staph. aureus 642A | 0.2 | 0.02 | 0.02 | 0.02 | 0.78 | 0.39 |
| Staph. aureus NCTC 10649M | 0.2 | 0.02 | 0.01 | 0.02 | 0.39 | 0.39 |
| Staph. aureus CMX 553 | 0.2 | 0.02 | 0.02 | 0.02 | 1.56 | 0.78 |
| Staph. aureus 1775 Cipro. R. | 12.5 | 3.1 | 1.56 | 0.39 | 100 | >100 |
| Staph. epidermidis 3519 | 0.2 | 0.02 | 0.02 | 0.02 | 0.39 | 0.39 |
| Entero. faecium ATCC 8043 | 3.1 | 0.1 | 0.1 | 0.02 | 1.56 | 0.78 |
| Strep. bovis A5169 | 3.1 | — | — | — | 0.78 | 1.56 |
| Strep. agalactiae CMX 508 | 1.56 | 0.02 | 0.02 | 0.02 | 0.78 | 0.78 |
| Strep. pyogenes EES61 | 1.56 | 0.1 | 0.02 | 0.02 | 0.78 | 0.39 |
| Strep. pyogenes 930 CONST | 1.56 | 0.1 | 0.05 | 0.05 | 0.39 | 0.78 |
| Strep. pyogenes 2548 INDUC | 0.78 | 0.1 | 0.02 | 0.02 | 0.39 | 0.39 |
| M. luteus ATCC 9341 | 1.56 | 0.1 | 0.1 | 0.02 | 0.78 | 3.1 |
| M. luteus ATCC 4698 | 1.56 | 0.1 | 0.05 | 0.02 | 0.78 | 1.56 |
| Escherichia coli Juhl | 0.2 | 0.01 | 0.005 | 0.02 | 0.78 | 0.05 |
| E. coli SS | 0.02 | 0.0005 | 0.0005 | 0.0005 | 0.05 | 0.005 |
| E. coli DC-2 | 1.56 | 0.1 | 0.05 | 0.2 | 6.2 | 0.2 |
| E. coli H560 | 0.2 | 0.02 | 0.005 | 0.02 | 0.78 | 0.01 |
| E. coli KNK 437 | 0.78 | 0.2 | 0.05 | 0.2 | 6.2 | 0.2 |
| Enter. aerogenes ATCC 13048 | 0.39 | 0.05 | 0.02 | 0.05 | 3.1 | 0.05 |
| Klebs. pneunoniae ATCC 8045 | 0.1 | 0.005 | 0.005 | 0.005 | 0.39 | 0.01 |
| Providencia stuartii CMX 640 | 25 | 0.78 | 0.39 | 0.78 | 25 | 0.78 |
| P. aeruginosa BMH 10 | 1.56 | 0.2 | 0.1 | 0.39 | 0.78 | 0.1 |
| P. aeruginosa A5007 | 3.12 | 0.39 | 0.2 | 0.39 | 1.56 | 0.2 |
| P. aeruginosa K799/WT | 6.2 | 0.39 | 0.2 | 0.78 | 3.1 | 0.1 |
| P. aeruginosa K799/61 | 0.78 | 0.05 | 0.02 | 0.05 | 0.39 | 0.02 |
| Pseudomonas cepacia 2961 | 25 | 0.78 | 0.39 | 0.78 | 100 | 3.1 |
| Acinetob. calcoaceticus CMX 669 | 0.39 | 0.05 | 0.02 | 0.05 | 6.2 | 0.39 |
| P. aeruginosa 5263 | 100 | 6.2 | 3.1 | 6.2 | 25 | 12.5 |
| P. aeruginosa 2862 | 100 | 6.2 | 3.1 | 6.2 | 50 | 12.5 |
| Candida albicans CCH 442 | >100 | >100 | <100 | >100 | >100 | >100 |
| Myco. smegmatis ATCC 114 | 0.78 | 0.05 | 0.01 | 0.02 | 0.78 | 1.56 |
| Nocardia asteroides ATCC 9970 | 25 | 3.1 | 1.56 | 1.56 | 50 | 25 |

| Organisms | Ex. 439 | Ex. 440 | Ex. 441 | Ex. 442 | Ex. 443 | Cntl |
|---|---|---|---|---|---|---|
| Staph. aureus ATCC 6538P | 0.01 | 0.5 | 0.05 | 0.1 | 0.02 | 0.05 |
| Staph. aureus A5177 | 0.02 | 0.2 | 0.1 | 0.1 | 0.05 | 0.39 |
| Staph. aureus 5278 | 0.05 | 0.2 | 0.05 | 0.1 | 0.05 | 0.39 |
| Staph. aureus 642A | 0.05 | 0.2 | 0.05 | 0.1 | 0.05 | 0.39 |
| Staph. aureus NCTC 10649M | 0.01 | 0.05 | 0.05 | 0.1 | 0.02 | 0.39 |
| Staph. aureus CMX 553 | 0.1 | 0.39 | 0.1 | — | 0.05 | 0.78 |
| Staph. aureus 1775 Cipro. R. | 6.2 | 12.5 | 6.2 | 3.1 | 1.56 | >100 |
| Staph. epidermidis 3519 | 0.02 | 0.2 | 0.1 | — | 0.05 | 0.39 |
| Entero. faecium ATCC 8043 | 0.05 | 0.39 | 0.2 | 0.39 | 0.1 | 0.78 |
| Strep. bovis A5169 | 0.05 | 0.2 | 0.1 | 0.39 | 0.05 | 1.56 |
| Strep. agalactiae CMX 508 | 0.05 | 0.1 | 0.05 | 0.1 | 0.05 | 0.78 |
| Strep. pyogenes EES61 | 0.02 | 0.05 | 0.05 | 0.1 | 0.02 | 0.39 |
| Strep. pyogenes 930 CONST | 0.02 | 0.2 | 0.1 | 0.1 | 0.02 | 0.78 |
| Strep. pyogenes 2548 INDUC | 0.02 | 0.1 | 0.1 | 0.1 | 0.02 | 0.39 |
| M. luteus ATCC 9341 | 0.1 | 0.78 | 0.78 | 1.56 | 0.2 | 3.1 |
| M. luteus ATCC 4698 | 0.1 | 0.39 | 0.2 | 1.56 | 0.1 | 1.56 |
| Escherichia coli Juhl | 0.05 | 0.2 | 0.1 | 0.39 | 0.1 | 0.05 |
| E. coli SS | 0.005 | 0.01 | 0.01 | 0.39 | 0.005 | 0.005 |
| E. coli DC-2 | 0.39 | 1.56 | 0.78 | 3.1 | 0.39 | 0.2 |
| E. coli H560 | 0.1 | 0.39 | 0.1 | 0.39 | 0.05 | 0.01 |
| E. coli KNK 437 | 0.78 | 1.56 | 0.39 | 3.1 | 0.39 | 0.2 |
| Enter. aerogenes ATCC 13048 | 0.1 | 0.78 | 0.39 | 1.56 | 0.39 | 0.05 |
| Klebs. pneunoniae ATCC 8045 | 0.1 | 0.1 | 0.05 | 0.2 | 0.05 | 0.01 |
| Providencia stuartii CMX 640 | 3.1 | 12.5 | 3.1 | 6.2 | 1.56 | 0.78 |
| P. aeruginosa BMH 10 | 0.39 | 3.1 | 0.78 | 3.1 | 0.39 | 0.1 |
| P. aeruginosa A5007 | 0.78 | 6.2 | 1.56 | 6.2 | 0.78 | 0.2 |
| P. aeruginosa K799/WT | 0.78 | 6.2 | 3.1 | 12.5 | 0.78 | 0.1 |
| P. aeruginosa K799/61 | 0.1 | 0.39 | 0.2 | 1.56 | 0.1 | 0.02 |
| Pseudomonas cepacia 2961 | 3.1 | 12.5 | 6.2 | 6.2 | 3.1 | 3.1 |
| Acinetob. calcoaceticus CMX 669 | 0.78 | 0.78 | 0.39 | 0.39 | 0.1 | 0.39 |
| P. aeruginosa 5263 | 12.5 | 100 | 25 | <100 | 12.5 | 12.5 |
| P. aeruginosa 2862 | 12.5 | 100 | 25 | <100 | 12.5 | 12.5 |
| Candida albicans CCH 442 | <100 | <100 | <100 | <100 | <100 | >100 |
| Myco. smegmatis ATCC 114 | 0.1 | 0.39 | 0.2 | 0.39 | 0.05 | 1.56 |
| Nocardia asteroides ATCC 9970 | 6.2 | 6.2 | 25 | 12.5 | 1.56 | 25 |

TABLE 16-continued

In Vitro Antibacterial Activity (MIC Values in µg/ml)

| Organisms | Ex. 444 | Ex. 445 | Ex. 446 | Ex. 447 | Ex. 448 | Cntl |
|---|---|---|---|---|---|---|
| Staph. aureus ATCC 6538P | 0.02 | 0.05 | 0.39 | 0.1 | 0.01 | 0.05 |
| Staph. aureus A5177 | 0.05 | 0.1 | 0.78 | 0.2 | 0.02 | 0.39 |
| Staph. aureus 5278 | 0.02 | 0.1 | 0.78 | 0.2 | 0.02 | 0.39 |
| Staph. aureus 642A | 0.05 | 0.05 | 0.78 | 0.1 | 0.02 | 0.39 |
| Staph. aureus NCTC 10649M | 0.02 | 0.05 | 0.39 | 0.02 | 0.02 | 0.39 |
| Staph. aureus CMX 553 | 0.05 | 0.1 | 0.78 | 0.05 | 0.02 | 0.78 |
| Staph. aureus 1775 Cipro. R. | 0.39 | 6.2 | 50 | 0.78 | 0.78 | >100 |
| Staph. epidermidis 3519 | 0.05 | 0.1 | 0.78 | 0.05 | 0.02 | 0.39 |
| Entero. faecium ATCC 8043 | 0.05 | 0.1 | 3.1 | 0.39 | 0.1 | 0.78 |
| Strep. bovis A5169 | 0.05 | 0.1 | 1.56 | 0.39 | 0.2 | 1.56 |
| Strep. agalactiae CMX 508 | 0.05 | 0.1 | 0.78 | 0.39 | 0.05 | 0.78 |
| Strep. pyogenes EES61 | 0.05 | 0.1 | 0.78 | 0.2 | 0.05 | 0.39 |
| Strep. pyogenes 930 CONST | 0.05 | 0.1 | 1.56 | 0.39 | 0.1 | 0.78 |
| Strep. pyogenes 2548 INDUC | 0.05 | 0.05 | 1.56 | 0.2 | 0.1 | 0.39 |
| M. luteus ATCC 9341 | 0.2 | 0.2 | 12.5 | 0.39 | 0.2 | 3.1 |
| M. luteus ATCC 4698 | 0.05 | 0.2 | 3.1 | 0.2 | 0.1 | 1.56 |
| Escherichia coli Juhl | 0.02 | 0.02 | 6.2 | 0.39 | 0.05 | 0.05 |
| E. coli SS | 0.002 | 0.005 | 0.2 | 0.05 | 0.0005 | 0.005 |
| E. coli DC-2 | 0.39 | 0.2 | 100 | 3.1 | 0.39 | 0.2 |
| E. coli H560 | 0.02 | 0.05 | 12.5 | 0.39 | 0.05 | 0.01 |
| E. coli KNK 437 | 0.2 | 0.2 | 50 | 1.56 | 0.39 | 0.2 |
| Enter. aerogenes ATCC 13048 | 0.05 | 0.05 | 12.5 | 0.78 | 0.2 | 0.05 |
| Klebs. pneunoniae ATCC 8045 | 0.01 | 0.02 | 1.56 | 0.39 | 0.02 | 0.01 |
| Providencia stuartii CMX 640 | 0.78 | 0.78 | 100 | 3.1 | 1.56 | 0.78 |
| P. aeruginosa BMH 10 | 0.39 | 0.1 | 100 | 3.1 | 0.39 | 0.1 |
| P. aeruginosa A5007 | 0.39 | 0.2 | 100 | 3.1 | 0.78 | 0.2 |
| P. aeruginosa K799/WT | 0.39 | 0.2 | 50 | 3.1 | 0.78 | 0.1 |
| P. aeruginosa K799/61 | 0.1 | 0.05 | 1.56 | 0.39 | 0.1 | 0.02 |
| Pseudomonas cepacia 2961 | 1.56 | 3.1 | 6.2 | 3.1 | 1.56 | 3.1 |
| Acinetob. calcoaceticus CMX 669 | 0.05 | 0.2 | 3.1 | 0.39 | 0.1 | 0.39 |
| P. aeruginosa 5263 | 6.2 | 6.2 | >100 | >100 | 12.5 | 12.5 |
| P. aeruginosa 2862 | 6.2 | 6.2 | >100 | >100 | 12.5 | 12.5 |
| Candida albicans CCH 442 | >100 | >100 | >100 | >100 | 100 | >100 |
| Myco. smegmatis ATCC 114 | 0.2 | 0.39 | 6.2 | 6.2 | 0.39 | 1.56 |
| Nocardia asteroides ATCC 9970 | 3.1 | 25 | >100 | 25 | 12.5 | 25 |

| Organisms | Ex. 449 | Ex. 450 | Ex. 451 | Ex. 452 | Ex. 453 | Cntl |
|---|---|---|---|---|---|---|
| Staph. aureus ATCC 6538P | 0.002 | 0.005 | 0.02 | 0.05 | 0.02 | 0.05 |
| Staph. aureus A5177 | 0.005 | 0.01 | 0.02 | 0.05 | 0.02 | 0.39 |
| Staph. aureus 5278 | 0.005 | 0.01 | 0.02 | 0.1 | 0.02 | 0.39 |
| Staph. aureus 642A | 0.005 | 0.01 | 0.02 | 0.05 | 0.05 | 0.39 |
| Staph. aureus NCTC 10649M | 0.002 | 0.01 | 0.02 | 0.05 | 0.02 | 0.39 |
| Staph. aureus CMX 553 | 0.005 | 0.02 | 0.02 | 0.05 | 0.02 | 0.78 |
| Staph. aureus 1775 Cipro. R. | 0.1 | 0.39 | 0.39 | 1.56 | 0.78 | >100 |
| Staph. epidermidis 3519 | 0.005 | 0.02 | 0.02 | 0.1 | 0.1 | 0.39 |
| Entero. faecium ATCC 8043 | 0.02 | 0.1 | 0.1 | 0.2 | 0.1 | 0.78 |
| Strep. bovis A5169 | 0.01 | — | 0.2 | 0.2 | 0.2 | 1.56 |
| Strep. agalactiae CMX 508 | 0.002 | 0.1 | 0.1 | 0.1 | 0.05 | 0.78 |
| Strep. pyogenes EES61 | 0.002 | 0.1 | 0.1 | 0.1 | — | 0.39 |
| Strep. pyogenes 930 CONST | 0.002 | 0.1 | 0.05 | 0.2 | — | 0.78 |
| Strep. pyogenes 2548 INDUC | 0.002 | 0.02 | 0.05 | 0.2 | 0.1 | 0.39 |
| M. luteus ATCC 9341 | 0.05 | 0.1 | 0.1 | 0.2 | 0.2 | 3.1 |
| M. luteus ATCC 4698 | 0.02 | 0.05 | 0.1 | 0.2 | 0.2 | 1.56 |
| Escherichia coli Juhl | 0.02 | 0.02 | 0.1 | 0.1 | 0.5 | 0.05 |
| E. coli SS | 0.0005 | 0.0005 | 0.002 | 0.001 | 0.02 | 0.005 |
| E. coli DC-2 | 0.2 | 0.39 | 0.78 | 0.78 | 0.39 | 0.2 |
| E. coli H560 | 0.01 | 0.02 | 0.05 | 0.1 | 0.1 | 0.01 |
| E. coli KNK 437 | 0.2 | 0.2 | 1.56 | 0.78 | 0.39 | 0.2 |
| Enter. aerogenes ATCC 13048 | 0.1 | 0.1 | 0.1 | 0.2 | 0.2 | 0.05 |
| Klebs. pneunoniae ATCC 8045 | 0.01 | 0.02 | 0.02 | 1.56 | 0.05 | 0.01 |
| Providencia stuartii CMX 640 | 0.78 | 1.56 | 1.56 | 3.1 | 1.56 | 0.78 |
| P. aeruginosa BMH 10 | 0.39 | 0.39 | 0.78 | 0.78 | 0.39 | 0.1 |
| P. aeruginosa A5007 | 0.78 | 0.78 | 1.56 | 1.56 | 0.78 | 0.2 |
| P. aeruginosa K799/WT | 0.78 | 0.78 | 3.1 | 3.1 | 1.56 | 0.1 |
| P. aeruginosa K799/61 | 0.05 | 0.05 | 0.1 | 0.2 | 0.2 | 0.02 |
| Pseudomonas cepacia 2961 | 3.1 | 3.1 | 1.56 | 1.56 | 3.1 | 3.1 |
| Acinetob. calcoaceticus CMX 669 | 0.02 | 0.05 | 0.1 | 0.1 | 0.1 | 0.39 |
| P. aeruginosa 5263 | 12.5 | 12.5 | 25 | 25 | 12.5 | 12.5 |
| P. aeruginosa 2862 | 12.5 | 12.5 | 50 | 25 | 25 | 12.5 |
| Candida albicans CCH 442 | >100 | >100 | >100 | >100 | >100 | >100 |
| Myco. smegmatis ATCC 114 | 0.02 | 0.1 | 0.1 | 0.05 | 25 | 1.56 |
| Nocardia asteroides ATCC 9970 | 0.78 | 1.56 | 0.78 | 0.39 | 6.2 | 25 |

TABLE 16-continued

In Vitro Antibacterial Activity (MIC Values in µg/ml)

| Organisms | Ex. 454 | Ex. 455 | Ex. 456 | Ex. 457 | Ex. 458 | Cntl |
|---|---|---|---|---|---|---|
| Staph. aureus ATCC 6538P | 0.05 | 1.56 | 0.02 | 0.02 | 0.02 | 0.05 |
| Staph. aureus A5177 | 0.05 | 1.56 | 0.02 | 0.05 | 0.02 | 0.39 |
| Staph. aureus 5278 | 0.05 | 1.56 | 0.02 | 0.05 | 0.02 | 0.39 |
| Staph. aureus 642A | 0.05 | 1.56 | 0.02 | 0.02 | 0.02 | 0.39 |
| Staph. aureus NCTC 10649M | 0.05 | 1.56 | 0.02 | 0.05 | 0.02 | 0.39 |
| Staph. aureus CMX 553 | 0.1 | — | 0.02 | 0.1 | 0.02 | 0.78 |
| Staph. aureus 1775 Cipro. R. | 1.56 | >100 | 0.39 | 6.2 | 0.39 | >100 |
| Staph. epidermidis 3519 | 0.1 | — | 0.02 | 0.05 | 0.02 | 0.39 |
| Entero. faecium ATCC 8043 | 0.39 | 50 | 0.2 | 0.2 | 0.2 | 0.78 |
| Strep. bovis A5169 | 0.78 | >100 | 0.2 | 0.1 | 0.2 | 1.56 |
| Strep. agalactiae CMX 508 | 0.39 | 12.5 | 0.1 | 0.05 | 0.1 | 0.78 |
| Strep. pyogenes EES61 | — | 25 | 0.1 | 0.05 | 0.05 | 0.39 |
| Strep. pyogenes 930 CONST | — | 12.5 | 0.1 | 0.05 | 0.05 | 0.78 |
| Strep. pyogenes 2548 INDUC | 0.39 | 12.5 | 0.1 | 0.05 | 0.05 | 0.39 |
| M. luteus ATCC 9341 | 0.39 | >100 | 0.1 | 0.2 | 0.1 | 3.1 |
| M. luteus ATCC 4698 | 0.39 | >100 | 0.1 | 0.2 | 0.1 | 1.56 |
| Escherichia coli Juhl | 0.39 | 3.1 | 0.1 | 0.05 | 0.01 | 0.05 |
| E. coli SS | 0.02 | 3.1 | 0.01 | 0.001 | 0.0005 | 0.005 |
| E. coli DC-2 | 0.78 | >100 | 0.78 | 0.2 | 0.2 | 0.2 |
| E. coli H560 | 0.39 | 6.2 | 0.1 | 0.05 | 0.02 | 0.01 |
| E. coli KNK 437 | 12.5 | 100 | 0.39 | 0.2 | 0.2 | 0.2 |
| Enter. aerogenes ATCC 13048 | 1.56 | 6.2 | 0.39 | 0.1 | 0.1 | 0.05 |
| Klebs. pneunoniae ATCC 8045 | 0.1 | 1.56 | 0.1 | 0.39 | 0.39 | 0.01 |
| Providencia stuartii CMX 640 | 6.2 | >100 | 3.1 | 1.56 | 1.56 | 0.78 |
| P. aeruginosa BMH 10 | 3.1 | >100 | 1.56 | 0.2 | 0.2 | 0.1 |
| P. aeruginosa A5007 | 100 | >100 | 1.56 | 0.39 | 0.39 | 0.2 |
| P. aeruginosa K799/WT | 100 | >100 | 6.2 | 1.56 | 1.56 | 0.1 |
| P. aeruginosa K799/61 | 0.2 | 6.2 | 0.39 | 0.2 | 0.1 | 0.02 |
| Pseudomonas cepacia 2961 | 0.78 | 12.5 | 6.2 | 0.39 | 0.39 | 3.1 |
| Acinetob. calcoaceticus CMX 669 | 0.2 | 6.2 | 0.1 | 0.1 | 0.05 | 0.39 |
| P. aeruginosa 5263 | >100 | >100 | 25 | 6.2 | 12.5 | 12.5 |
| P. aeruginosa 2862 | >100 | >100 | 25 | 6.2 | 6.2 | 12.5 |
| Candida albicans CCH 442 | >100 | >100 | >100 | 50 | 25 | >100 |
| Myco. smegmatis ATCC 114 | 0.78 | 12.5 | 0.2 | — | — | 1.56 |
| Nocardia asteroides ATCC 9970 | >100 | 50 | 1.56 | — | — | 25 |

| Organisms | Ex. 459 | Ex. 460 | Ex. 461 | Ex. 462 | Ex. 463 | Cntl |
|---|---|---|---|---|---|---|
| Staph. aureus ATCC 6538P | 0.02 | 0.05 | 0.05 | 0.001 | 0.005 | 0.05 |
| Staph. aureus A5177 | 0.05 | 0.05 | 0.1 | 0.005 | 0.01 | 0.39 |
| Staph. aureus 5278 | 0.05 | 0.05 | 0.1 | 0.005 | 0.01 | 0.39 |
| Staph. aureus 642A | 0.05 | 0.05 | 0.1 | 0.005 | 0.01 | 0.39 |
| Staph. aureus NCTC 10649M | 0.05 | 0.05 | 0.1 | 0.002 | 0.005 | 0.39 |
| Staph. aureus CMX 553 | 0.05 | 0.05 | 0.1 | 0.005 | 0.01 | 0.78 |
| Staph. aureus 1775 Cipro. R. | 0.78 | 3.1 | 6.2 | 0.2 | 0.39 | >100 |
| Staph. epidermidis 3519 | 0.05 | 0.1 | 0.1 | 0.005 | 0.01 | 0.39 |
| Entero. faecium ATCC 8043 | 0.1 | 0.1 | 0.2 | 0.05 | 0.05 | 0.78 |
| Strep. bovis A5169 | 0.1 | 0.1 | 0.39 | 0.05 | 0.05 | 1.56 |
| Strep. agalactiae CMX 508 | 0.02 | 0.05 | 0.39 | 0.02 | 0.05 | 0.78 |
| Strep. pyogenes EES61 | — | — | — | 0.02 | 0.05 | 0.39 |
| Strep. pyogenes 930 CONST | — | — | — | 0.02 | 0.05 | 0.78 |
| Strep. pyogenes 2548 INDUC | 0.05 | 0.02 | 0.1 | 0.02 | 0.05 | 0.39 |
| M. luteus ATCC 9341 | 0.1 | 0.2 | 0.2 | 0.05 | 0.05 | 3.1 |
| M. luteus ATCC 4698 | 0.1 | 0.2 | 0.2 | 0.02 | 0.02 | 1.56 |
| Escherichia coli Juhl | 0.01 | 0.02 | 0.05 | 0.05 | 0.05 | 0.05 |
| E. coli SS | 0.002 | 0.001 | 0.02 | 0.0005 | 0.002 | 0.005 |
| E. coli DC-2 | 0.2 | 0.1 | 0.39 | 0.39 | 0.39 | 0.2 |
| E. coli H560 | 0.05 | 0.005 | 0.05 | 0.05 | 0.05 | 0.01 |
| E. coli KNK 437 | 0.2 | 0.1 | 0.39 | 0.39 | 0.2 | 0.2 |
| Enter. aerogenes ATCC 13048 | 0.1 | 0.05 | 0.05 | 0.1 | 0.1 | 0.05 |
| Klebs. pneunoniae ATCC 8045 | 0.01 | 0.01 | 0.02 | 0.02 | 0.02 | 0.01 |
| Providencia stuartii CMX 640 | 0.78 | 0.39 | 0.39 | 0.39 | 0.78 | 0.78 |
| P. aeruginosa BMH 10 | 0.39 | 0.1 | 0.39 | 0.39 | 0.39 | 0.1 |
| P. aeruginosa A5007 | 0.78 | 0.2 | 0.39 | 0.39 | 0.39 | 0.2 |
| P. aeruginosa K799/WT | 0.78 | 0.39 | 0.39 | 0.39 | 0.39 | 0.1 |
| P. aeruginosa K799/61 | 0.1 | 0.02 | 0.05 | 0.02 | 0.02 | 0.02 |
| Pseudomonas cepacia 2961 | 3.1 | 0.78 | 0.78 | 0.39 | 0.39 | 3.1 |
| Acinetob. calcoaceticus CMX 669 | 0.05 | 0.05 | 0.1 | 0.05 | 0.1 | 0.39 |
| P. aeruginosa 5263 | 6.2 | 3.1 | 6.2 | 3.1 | 6.2 | 12.5 |
| P. aeruginosa 2862 | 6.2 | 3.1 | 6.2 | 6.2 | 6.2 | 12.5 |
| Candida albicans CCH 442 | >100 | >100 | >100 | >100 | >100 | >100 |
| Myco. smegmatis ATCC 114 | 0.1 | 0.05 | 0.1 | 0.1 | 0.39 | 1.56 |
| Nocardia asteroides ATCC 9970 | 3.1 | 1.56 | 3.1 | 3.1 | 3.1 | 25 |

TABLE 16-continued

In Vitro Antibacterial Activity (MIC Values in µg/ml)

| Organisms | Ex. 464 | Ex. 465 | Ex. 466 | Ex. 467 | Ex. 469 | Cntl |
|---|---|---|---|---|---|---|
| Staph. aureus ATCC 6538P | 0.005 | 0.1 | 0.05 | 0.39 | 0.002 | 0.05 |
| Staph. aureus A5177 | 0.005 | 0.2 | 0.05 | 0.39 | 0.005 | 0.39 |
| Staph. aureus 5278 | 0.005 | 0.2 | 0.05 | 0.39 | 0.002 | 0.39 |
| Staph. aureus 642A | 0.005 | 0.2 | 0.1 | 0.39 | 0.005 | 0.39 |
| Staph. aureus NCTC 10649M | 0.005 | 0.2 | 0.05 | 0.39 | 0.002 | 0.39 |
| Staph. aureus CMX 553 | 0.005 | 0.2 | 0.1 | 0.39 | 0.005 | 0.78 |
| Staph. aureus 1775 Cipro. R. | 0.39 | 100 | 1.56 | 25 | 0.02 | >100 |
| Staph. epidermidis 3519 | 0.005 | 0.2 | 0.05 | 0.39 | 0.005 | 0.39 |
| Entero. faecium ATCC 8043 | 0.05 | 1.56 | 0.2 | 0.78 | 0.01 | 0.78 |
| Strep. bovis A5169 | 0.1 | 25 | — | — | 0.002 | 1.56 |
| Strep. agalactiae CMX 508 | 0.1 | 1.56 | 0.1 | 0.78 | 0.002 | 0.78 |
| Strep. pyogenes EES61 | 0.1 | 6.2 | 0.2 | 0.78 | 0.002 | 0.39 |
| Strep. pyogenes 930 CONST | 0.1 | 6.2 | 0.1 | 1.56 | 0.002 | 0.78 |
| Strep. pyogenes 2548 INDUC | 0.05 | 1.56 | 0.1 | 0.78 | 0.002 | 0.39 |
| M. luteus ATCC 9341 | 0.1 | 12.5 | 0.2 | 1.56 | 0.005 | 3.1 |
| M. luteus ATCC 4698 | 0.05 | 1.56 | 0.2 | 1.56 | 0.005 | 1.56 |
| Escherichia coli Juhl | 0.1 | 1.56 | 0.02 | 0.39 | 0.01 | 0.05 |
| E. coli SS | 0.0005 | 0.05 | 0.002 | 0.05 | 0.001 | 0.005 |
| E. coli DC-2 | 0.78 | 100 | 0.2 | 1.56 | 0.05 | 0.2 |
| E. coli H560 | 0.1 | 3.1 | 0.02 | 0.39 | 0.01 | 0.01 |
| E. coli KNK 437 | 0.39 | 50 | 0.2 | 1.56 | 0.1 | 0.2 |
| Enter. aerogenes ATCC 13048 | 0.1 | 6.2 | 0.1 | 0.78 | 0.05 | 0.05 |
| Klebs. pneunoniae ATCC 8045 | 0.05 | 0.78 | 0.02 | 0.2 | 0.005 | 0.01 |
| Providencia stuartii CMX 640 | 1.56 | 100 | 1.56 | 6.2 | 0.1 | 0.78 |
| P. aeruginosa BMH 10 | 0.78 | 100 | 0.2 | 1.56 | 0.1 | 0.1 |
| P. aeruginosa A5007 | 0.78 | 100 | 0.39 | 3.1 | 0.1 | 0.2 |
| P. aeruginosa K799/WT | 0.78 | 50 | 0.78 | 6.2 | 0.1 | 0.1 |
| P. aeruginosa K799/61 | 0.05 | 1.56 | 0.1 | 0.39 | 0.05 | 0.02 |
| Pseudomonas cepacia 2961 | 0.78 | 12.5 | 1.56 | 12.5 | 0.78 | 3.1 |
| Acinetob. calcoaceticus CMX 669 | 0.1 | 6.2 | 0.1 | 0.78 | 0.01 | 0.39 |
| P. aeruginosa 5263 | 50 | >100 | 6.2 | 50 | 1.56 | 12.5 |
| P. aeruginosa 2862 | 50 | >100 | 6.2 | 50 | 1.56 | 12.5 |
| Candida albicans CCH 442 | >100 | >100 | >100 | >100 | 25 | >100 |
| Myco. smegmatis ATCC 114 | 0.1 | 12.5 | 0.1 | 3.1 | 0.01 | 1.56 |
| Nocardia asteroides ATCC 9970 | 6.2 | 50 | 1.56 | 25 | 0.2 | 25 |

| Organisms | Ex. 469 | Ex. 470 | Ex. 471 | Ex. 472 | Cntl |
|---|---|---|---|---|---|
| Staph. aureus ATCC 6538P | 0.05 | 0.05 | 0.005 | 0.1 | 0.05 |
| Staph. aureus A5177 | 0.05 | 0.05 | 0.005 | 0.1 | 0.39 |
| Staph. aureus 5278 | 0.05 | 0.05 | 0.005 | 0.1 | 0.39 |
| Staph. aureus 642A | 0.05 | 0.05 | 0.01 | 0.1 | 0.39 |
| Staph. aureus NCTC 10649M | 0.05 | 0.05 | 0.005 | 0.1 | 0.39 |
| Staph. aureus CMX 553 | 0.1 | 0.1 | 0.05 | 0.2 | 0.78 |
| Staph. aureus 1775 Cipro. R. | 3.1 | 0.78 | 0.39 | 12.5 | >100 |
| Staph. epidermidis 3519 | 0.05 | 0.05 | 0.02 | 0.1 | 0.39 |
| Entero. faecium ATCC 8043 | 0.1 | 0.2 | 0.02 | 0.2 | 0.78 |
| Strep. bovis A5169 | 0.1 | 0.02 | 0.02 | — | 1.56 |
| Strep. agalactiae CMX 508 | 0.1 | 0.02 | 0.0005 | 0.2 | 0.78 |
| Strep. pyogenes EES61 | 0.1 | 0.02 | 0.0005 | 0.1 | 0.39 |
| Strep. pyogenes 930 CONST | 0.1 | 0.05 | 0.02 | 0.1 | 0.78 |
| Strep. pyogenes 2548 INDUC | 0.05 | 0.05 | 0.005 | 0.1 | 0.39 |
| M. luteus ATCC 9341 | 0.2 | 0.39 | 0.1 | 0.78 | 3.1 |
| M. luteus ATCC 4698 | 0.2 | 0.2 | 0.05 | 0.78 | 1.56 |
| Escherichia coli Juhl | 0.01 | 0.39 | 0.005 | 0.05 | 0.05 |
| E. coli SS | 0.005 | 0.02 | 0.0005 | 0.01 | 0.005 |
| E. coli DC-2 | 0.1 | 1.56 | 0.2 | 0.78 | 0.2 |
| E. coli H560 | 0.02 | 0.2 | 0.02 | 0.1 | 0.01 |
| E. coli KNK 437 | 0.1 | 1.56 | 0.1 | 0.78 | 0.2 |
| Enter. aerogenes ATCC 13048 | 0.05 | 0.78 | 0.05 | 0.2 | 0.05 |
| Klebs. pneunoniae ATCC 8045 | 0.005 | 0.1 | 0.005 | 0.05 | 0.01 |
| Providencia stuartii CMX 640 | 0.39 | 3.1 | 0.78 | 1.56 | 0.78 |
| P. aeruginosa BMH 10 | 0.1 | 1.56 | 0.2 | 0.39 | 0.1 |
| P. aeruginosa A5007 | 0.2 | 3.1 | 0.39 | 0.78 | 0.2 |
| P. aeruginosa K799/WT | 0.2 | 3.1 | 0.39 | 0.78 | 0.1 |
| P. aeruginosa K799/61 | 0.05 | 0.39 | 0.05 | 0.05 | 0.02 |
| Pseudomonas cepacia 2961 | 1.56 | 12.5 | 3.1 | 3.1 | 3.1 |
| Acinetob. calcoaceticus CMX 669 | 0.1 | 0.39 | 0.05 | 0.78 | 0.39 |
| P. aeruginosa 5263 | 3.1 | 50 | 6.2 | 25 | 12.5 |
| P. aeruginosa 2862 | 3.1 | 50 | 6.2 | 25 | 12.5 |
| Candida albicans CCH 442 | >100 | >100 | >100 | >100 | >100 |
| Myco. smegmatis ATCC 114 | 0.2 | 1.56 | 0.05 | 0.1 | 1.56 |
| Nocardia asteroides ATCC 9970 | 1.56 | 1.56 | 3.1 | 12.5 | 25 |

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound having the formula

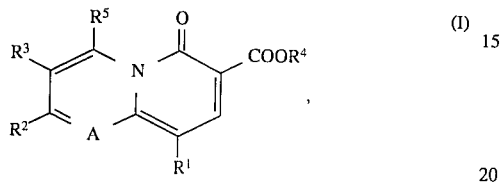

or a pharmaceutically acceptable salt, ester or amide thereof, wherein $R^1$ in formula (I) is selected from (a) loweralkyl, (b) loweralkenyl, (c) halo(loweralkyl), (d) loweralkoxy, (e) cycloalkyl of from three to eight carbon atoms, (f) phenyl, (g) substituted phenyl, (h) halo, (i) cyano, (j) nitro, (k) bicycloalkyl, (l) loweralkynyl, (m) loweralkoxycarbonyl, (n) nitrogen-containing aromatic heterocycle, selected from the group consisting of pyridine, pyrazine, pyrimidine, pyrrazole, imidazole, thiazole, oxazole, isoxazole, thiadiazole and oxadiazole, (o) halo-substituted nitrogen-containing aromatic heterocycle, where the nitrogen-containing aromatic heterocycle is as defined above, (p) a 4-, 5- or 6-membered cyclic ether, and (q) —$NR^7R^8$ where $R^7$ and $R^8$ are independently selected from the group consisting of hydrogen, loweralkyl and alkanoyl of from one to eight carbon atoms or, taken together with the nitrogen atom to which they are attached, $R^7$ and $R^8$ form a 5-, 6- or 7-membered heterocycle;

$R^2$ in formula (I) is selected from (a) halogen, (b) loweralkyl, (c) loweralkenyl, (d) cycloalkyl of from three to eight carbons, (e) cycloalkenyl of from four to eight carbons, (f) loweralkoxy, (g) aryloxy, (h) aryl(loweralkyl)oxy, (i) aryl(loweralkyl), (j) cycloalkyl(loweralkyl), (k) amino, (l) (loweralkyl)amino, (m) aryl(loweralkyl)amino, (n) hydroxy-substituted (loweralkyl)amino, (o) phenyl, (p) substituted phenyl, (q) bicyclic nitrogen-containing heterocycle, (r) nitrogen-containing aromatic heterocycle as defined above, (s) nitrogen-containing heterocycle having the formula

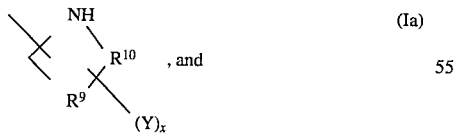

(t) non-nitrogen-containing heterocycle having the formula

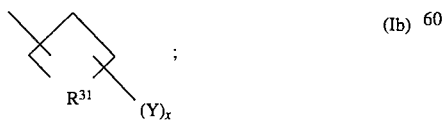

where x is zero, one, two or three;

$R^9$ is selected from the group consisting of (i) —$(CH_2)_m$- where m is one, two or three, and (ii) —$(CH_2)_nR^{13}(CH_2)_p$- where $R^{13}$ is selected from —S—, —O— and —NH—, $R^{10}$ is $CH_2$, or when $R^9$ is selected from option (i) may be O, S or N, n is one or two, and p is one or two; and $R^{31}$ is —$(CH_2)_qR^{32}$- where $R^{32}$ is selected from —S— and —O—, and q is one, two or three; and Y is independently selected at each occurrence from the group consisting, of:

(i) loweralkyl,
(ii) hydroxy,
(iii) halogen,
(iv) halo(loweralkyl),
(v) hydroxy-substituted loweralkyl,
(vi) loweralkenylamino,
(vii) loweralkylamino,
(viii) loweralkoxy,
(ix) (loweralkoxy)loweralkylamino,
(x) loweralkoxy(loweralkyl),
(xi) loweralkoxy(loweralkoxy)(loweralkyl),
(xii) hydroxy-substituted loweralkyl,
(xiii) imino,
(xiv) alkoxycarbonyl,
(xv) carbamoyl,
(xvi) aryl(loweralkyl),
(xvii) aminoxy
(xviii) amino(loweralkyl),
(xix) halo(loweralkyl)amino,
(xx) halo(loweralkyl)amino(loweralkyl),
(xxi) thioloweralkoxy(loweralkyl),
(xxii) aminothioloweralkoxy,
(xxiii) cycloalkyl of from three to six carbon atoms,
(xxiv) cycloalkyl(loweralkyl),
(xxv) cycloalkylamino,
(xxvi) phenyl,
(xxvii) substituted phenyl,
(xxviii) substituted phenyl(loweralkyl)
(xxix) nitrogen-containing aromatic heterocycle as defined above,
(xxx) —$NR^{11}R^{12}$ where $R^{11}$ and $R^{12}$ are independently selected from hydrogen and loweralkyl or, when one of $R^{11}$ and $R^{12}$ is hydrogen, the other is alkanoyl of from one to eight carbon atoms, an alpha-amino acid, or a polypeptide residue of from two to five amino acids, and
(xxxi) —$C(R^{21})(R^{22})NH_2$ where $R^{21}$ and $R^{22}$ are independently selected from among hydrogen, loweralkyl, hydroxy-substituted loweralkyl, amino(loweralkyl), loweralkoxy-(loweralkyl), thioloweralkoxy(loweralkyl), cycloalkyl of from three to six carbon atoms, and loweralkyl substituted with nitrogen-containing aromatic heterocycle as defined above or, taken together with the carbon atom to which they are attached, $R^{21}$ and $R^{22}$ form a ring structure selected from cycloalkyl of from three to six carbon atoms and nitrogen-containing heterocycle;

$R^3$ is selected from the group consisting of hydrogen, halogen and loweralkoxy;

$R^4$ is selected from the group consisting of hydrogen, loweralkyl, a pharmaceutically acceptable cation, and a prodrug ester group;

$R^5$ is selected from the group consisting of (a) hydrogen, (b) halogen, (c) hydroxy, (d) loweralkyl, (e) halo(loweralkyl), (f) loweralkoxy, and (g) —$NR^{13}R^{14}$ where $R^{13}$ and $R^{14}$ are independently selected from the group consisting of hydrogen, loweralkyl, hydroxy-substituted loweralkyl, loweralkoxy(loweralkyl), and alkanoyl of from one to eight carbon atoms; and A is =CR$^6$-, where R$^6$ is selected from the group consisting of (a) hydrogen, (b) halogen, (c) loweralkyl, (d) halo(loweralkyl), (e) hydroxy-substituted loweralkyl, (f) loweralkoxy(loweralkyl), (h) loweralkoxy, and (i) amino(loweralkyl); provided that, when R$^5$ is hydrogen and A is =CH—, R$^1$ is not unsubstituted phenyl.

2. A compound according to claim 1 wherein R$^6$ is selected from the group consisting of halogen, loweralkyl, halo(loweralkyl), hydroxy-substituted loweralkyl, loweralkoxy(loweralkyl), loweralkoxy, and amino(loweralkyl).

3. A compound according to claim 1 wherein R$^2$ is selected from the group consisting of bicyclic nitrogen-containing heterocycle and a nitrogen-containing heterocycle having the formula

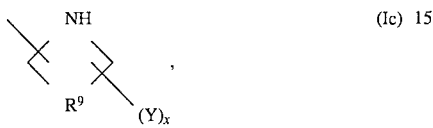

(Ic)

where R$^9$, Y and x are as previously defined.

4. A compound according to claim 3 wherein R$^2$ is selected from the group consisting of

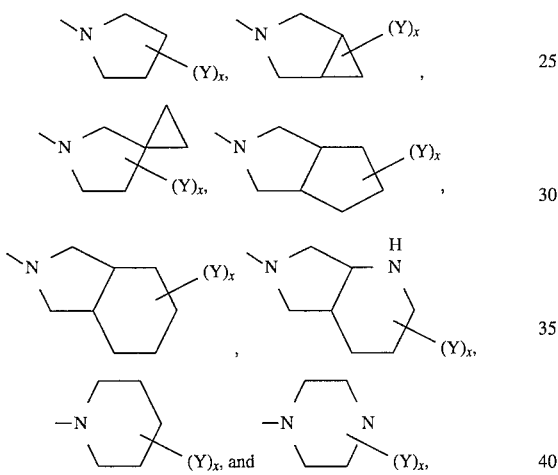

where Y and x are as previously defined.

5. A compound according to claim 4 wherein x is one or two and Y is selected from the group consisting of —NR$^{11}$R$^{12}$ and —C(R$^{21}$)(R$^{22}$)NH$_2$, where R$^{11}$, R$^{12}$, R$^{21}$ and R$^{22}$ are as previously defined.

6. A compound according to claim 2 wherein R$^6$ is methyl.

7. A compound according to claim 2 wherein R$^3$ is halogen.

8. A compound according to claim 7 wherein R$^5$ is selected from the group consisting of hydrogen, loweralkyl, halo(loweralkyl), and —NR$^{13}$R$^{14}$ where R$^{13}$ and R$^{14}$ are as previously defined.

9. A compound according to claim 8 wherein R$^1$ is selected from the group consisting of cycloalkyl of from three to eight carbon atoms and substituted phenyl.

10. A compound according to claim 9 wherein R$^6$ is selected from the group consisting of halogen, loweralkyl, and loweralkoxy.

11. A compound according to claim 10 wherein R$^3$ is halogen.

12. A compound according to claim 11 wherein R$^5$ is selected from the group consisting of hydrogen, loweralkyl, halo(loweralkyl), and —NR$^{13}$R$^{14}$ where R$^{13}$ and R$^{14}$ are as previously defined.

13. A compound according to claim 12 wherein R$^1$ is selected from the group consisting of cycloalkyl of from three to eight carbon atoms and substituted phenyl.

14. A compound according to claim 13 wherein R$^2$ is selected from the group consisting of bicyclic nitrogen-containing heterocycle and a nitrogen-containing heterocycle having the formula

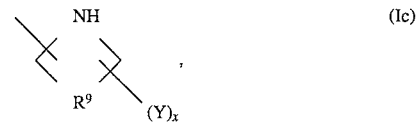

(Ic)

where R$^9$, Y and x are as previously defined.

15. A compound according to claim 14 wherein R$^2$ is selected from the group consisting of

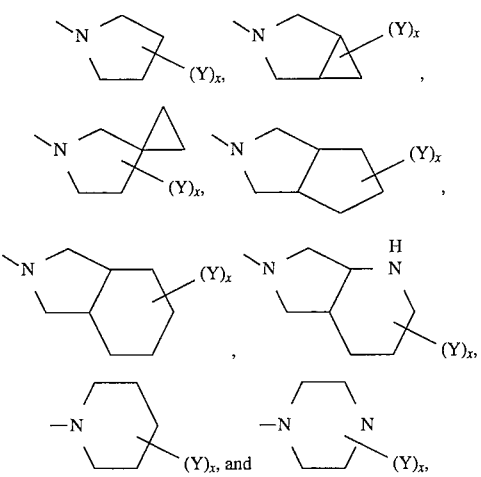

where Y and x are as previously defined.

16. A compound according to claim 15 wherein x is one or two and Y is selected from the group consisting of —NR$^{11}$R$^{12}$ and —C(R$^{21}$)(R$^{22}$)NH$_2$, where R$^{11}$, R$^{12}$, R$^{21}$ and R$^{22}$ are as previously defined.

17. A compound according to claim 1 having the formula

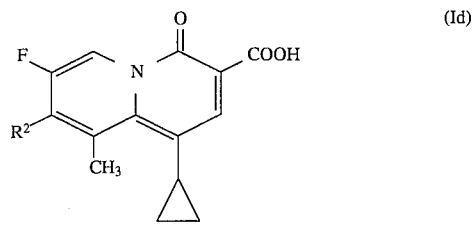

(Id)

or a pharmaceutically acceptable salt, ester or amide thereof, wherein

R$^2$ is selected from the group consisting of bicyclic nitrogen-containing heterocycle and a nitrogen-containing heterocycle having the formula

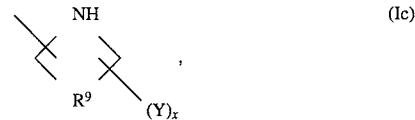

(Ic)

and where R$^4$, R$^9$, Y and x are as previously defined.

18. A compound according to claim 17 wherein R$^2$ is selected from the group consisting of

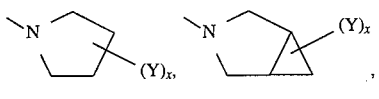

where Y and x are as previously defined.

19. A compound according to claim 18 wherein x is one or two and Y is selected from the group consisting of —NR$^{11}$R$^{12}$ and —C(R$^{21}$)(R$^{22}$)NH$_2$, where R$^{11}$, R$^{12}$, R$^{21}$ and R$^{22}$ are as previously defined.

20. A compound according to claim 1 selected from the group consisting of:

8-(3-aminopyrrolidin-1-yl)-1-ethyl-4H-quinolizine-4-one-3-carboxylic acid;

8-(3-amino-1-pyrrolidinyl)-1-cyclopropyl-7-fluoro-9-methyl-4-oxo-4H-quinolizine-3-carboxylic acid;

8-(3-(aminomethyl)pyrrolidinyl)-1-cyclopropyl-7-fluoro-9-methyl-4-oxo-4H-quinolizine-3-carboxylic acid;

8-(2S,4S-4-amino-2-methylpyrrolidinyl)-1-cyclopropyl-7-fluoro-9-methyl-4-oxo-4H-quinolizine-3-carboxylic acid;

8-(3-aminoazetidinyl)-1-cyclopropyl-7-fluoro-9-methyl-4-oxo-4H-quinolizine-3-carboxylic acid;

8-(3(S)-aminopyrrolidinyl)-1-cyclopropyl-7-fluoro-9-methyl-4-oxo-4H-quinolizine-3-carboxylic acid;

1-cyclopropyl-7-fluoro-9-methyl-4-oxo-8-(3-methyl-1-piperazinyl)-4H-quinolizine-3-carboxylic acid;

1-cyclopropyl-7-fluoro-9-methyl-4-oxo-8-piperazinyl-4H-quinolizine-3-carboxylic acid;

1-cyclopropyl-7-fluoro-9-methyl-8-(2-((N-methyl)aminemethyl)-4-morpholinyl)-4-oxo-4H- quinolizine-3-carboxylic acid;

1-cyclopropyl-7-fluoro-9-methyl-4-oxo-8-(1,2,3,4-tetrahydro-2-isoquinolinyl)-4H-quinolizine-3-carboxylic acid;

1-cyclopropyl-7-fluoro-9-methyl-4-oxo-8-(4-amino-1-piperdinyl)-4H-quinolizine-3-carboxylic acid;

1-cyclopropyl-7-fluoro-9-methyl-4-oxo-8-(3-amino-1-piperdinyl)-4H-quinolizine-3-carboxylic acid;

1-cyclopropyl-7-fluoro-9-methyl-4-oxo-8-(4-(aminomethyl)-1-piperdinyl)-4H-quinolizine-3-carboxylic acid;

1-cyclopropyl-7-fluoro-9-methyl-4-oxo-8-(5-amino-1,2,3,4-tetrahydro-2-isoquinolinyl)-4H-quinolizine-3-carboxylic acid;

1-cyclopropyl-7-fluoro-9-methyl-4-oxo-8-(4-(1-pyrrolyl)-1-piperidinyl)-4H-quinolizine-3-carboxylic acid;

1-cyclopropyl-8-(cis-3,5-dimethyl-1-piperazinyl)-7-fluoro-9-methyl-4-oxo-4H-quinolizine-3-carboxylic acid;

1-cyclopropyl-8-(2,7-diaza-7-bicyclo[3,3,0]octyl)-7-fluoro-9-methyl-4-oxo-4H-quinolizine-3-carboxylic acid;

1-cyclopropyl-8-(2,8-diaza-8-bicyclo[4,3,0]nonyl)-7-fluoro-9-methyl-4-oxo-4H-quinolizine-3-3-carboxylic acid;

1-cyclopropyl-7-fluoro-9-methyl-4-oxo-8-(3(S)-(1-pyrrolyl)-1-pyrrolidinyl)-4H-quinolizine-3-carboxylic acid;

1-cyclopropyl-7-fluoro-8-(3-hydroxy-1-pyrrolidinyl)-9-methyl-4-oxo-4H-quinolizine-3-carboxylic acid;

1-cyclopropyl-7-fluoro-8-(4-methyl-1-piperazinyl)-9-methyl-4-oxo-4H-quinolizine-3-carboxylic acid;

1-cyclopropyl-9-chloro-7-fluoro-8-(3-amino-1-pyrrolidinyl)-4-oxo-4H-quinolizine-3-carboxylic acid trifluoroacetic acid;

8-(3-amino-1-pyrrolidinyl)-1-cyclopropyl-7,9-difluoro-4-oxo-4H-quinolizine-3-carboxylic acid;

8-(3-amino-1-pyrrolidinyl)-1-cyclopropyl-7-fluoro-9-methoxy-4-oxo-4H-quinolizine-3-carboxylic acid.

1cyclopropyl-8-(2,7-diaza-7-bicyclo[3,3,0]oct-2-yl)-7-fluoro-9-methyl-4-oxo-4H-quinolizine-3-carboxylic acid;

1-cyclopropyl-8-(2,8-diaza-8-bicyclo[4,3,0]nonyl)-7-fluoro-9-methyl-4-oxo-4H-quinolizine-3-carboxylic acid;

1-cyclopropyl-7-fluoro-9-methyl-4-oxo-8-(3(S)-(1-pyrrolyl)-1-pyrrolidinyl)-4H-quinolizine-3-carboxylic acid;

1-cyclopropyl-7-fluoro-8-(3-hydroxy-1-pyrrolidinyl)-9-methyl-4-oxo-4H-quinolizine-3-carboxylic acid;

1-cyclopropyl-7-fluoro-8-(4-methyl-1-piperazinyl)-9-methyl-4-oxo-4H-quinolizine-3-carboxylic acid;

1-cyclopropyl-9-chloro-7-fluoro-8-(3-amino-1-pyrrolidinyl)-4-oxo-4H-quinolizine-3-carboxylic acid;

8-(3-amino-1-pyrrolidinyl)-1-cyclopropyl-7,9-difluoro-4-oxo-4H-quinolizine-3-carboxylic acid;

8-(3-amino-1-pyrrolidinyl)-1-cyclopropyl-7-fluoro-9-methoxy-4-oxo-4H-quinolizine-3-carboxylic acid;

1-cyclopropyl-7-fluoro-9-methyl-8-(3(S)-methylamino-1-pyrrolidinyl)-4-oxo-4H-quinolizine3-carboxylic acid;

1-cyclopropyl-7-fluoro-9-methyl-8-(3(S)-methylamino-1-pyrrolidinyl)-4-oxo-4H-quinolizine3-carboxylic acid;

1-cyclopropyl-7-fluoro-9-methyl-8-(3(R)-amino-1-pyrrolidinyl)-4-oxo-4H-quinolizine-3-carboxylic acid;

(3S)-9-fluoro-3-methyl-10-(4-methyl-1-piperazinyl)-2H,3H,6H-6-oxo-pyrano[2,3,4ij]quinolizine-5-carboxylic acid;

(R)-9-fluoro-3-methyl-10-(4-methyl-1-piperazinyl)-2H, 3H, 6H-6-oxo-pyrano[2,3,4-ij]quinolizine-5-carboxylic acid;

9-fluoro-10-(1-morpholinyl)-2H,3H,6H-6-oxo-pyrano[2,3,4-ij]quinolizine-5-carboxylic acid;

(3S)-10-(3-amino-1-pyrrolidinyl)-9-fluoro-3-methyl-2H,3H,6H-6-oxo-pyrano[2,3,4-ij]quinolizine-5-carboxylic acid;

3(S)-10-(3-aminomethyl-1-pyrrolidinyl)-9-fluoro-3-methyl-2H,3H,6H-6-oxo-pyrano[2,3,4-ij]quinolizine-5-carboxylic acid;

3(S)-10-((2S,4S)-4-amino-2-methyl-1-pyrrolidinyl)-9-fluoro-3-methyl-2H,3H,6H-6-oxo-pyrano-[2,3,4-ij]quinolizine-5-carboxylic acid;

3(S)-9-fluoro-10-(3-hydroxy-1-pyrrolidinyl)-3-methyl-2H,3H,6H-6-oxo-pyrano[2,3,4-ij]quinolizine-5-carboxylic acid;

9-fluoro-10-(4-methyl-1-piperazinyl)-2H,3H, 6H-6-oxo-pyrano[2,3,4-ij]quinolizine-3-carboxylic acid;

8-(2,4-dimethyl-1-piperazinyl)-1-cyclopropyl-7-fluoro-9-methyl-4-oxo-4H-quinolizine-3-carboxylic acid;

8-(3-(methylamino)-1-piperazinyl)-1-cyclopropyl-7-fluoro-9-methyl-4-oxo-4H-quinolizine-3-carboxylic acid;

8-(3-(methylamino)-1-morpholinyl)-1-cyclopropyl-7-fluoro-9-methyl-4-oxo-4H-quinolizine-3-carboxylic acid;

8-(3-(S)-(methylamino)-1-pyrrolidinyl)-1-cyclopropyl-7-fluoro-9-methyl-4-oxo-4H-quinolizine-3-carboxylic acid;

8-(3-(S)-(1-(methylamino)methyl)-1-pyrrolidinyl)-1-cyclopropyl-7-fluoro-9-methyl-4-oxo-4-H-quinolizine-3-carboxylic acid;

8-(3-(S)-(1-(ethylamino)methyl)-1-pyrrolidinyl)-1-cyclopropyl-7-fluoro-9-methyl-4-oxo-4H-quinolizine-3-carboxylic acid;

8-(octahydropyrrolo[3,4-c]pyrrol-1-yl)-1-cyclopropyl-7-fluoro-9-methyl-4-oxo-4H-quinolizine-3-carboxylic acid;

8-(octahydropyrrolo[3,4-c]pyridin-5-yl)-1-cyclopropyl-7-fluoro-9-methyl-4-oxo-4H-quinolizine-3-carboxylic acid;

8-(cis-4-amino-3-methylpyrrolidinyl)-1-cyclopropyl-7-fluoro-9-methyl-4-oxo-4H-quinolizine-3-carboxylic acid;

8-(trans-4-amino-3-methylpyrrolidinyl)-1-cyclopropyl-7-fluoro-9-methyl-4-oxo-4H-quinolizine-3-carboxylic acid;

8-(3-methyl-4-spirocyclopropylpyrrolidinyl)-1-cyclopropyl-7-fluoro-9-methyl-4-oxo-4H-quinolizine-3-carboxylic acid;

8-(2S,4S-4-amino-2-methylpyrrolidinyl)-1-cyclopropyl-7-fluoro-9-(fluoro)methyl-4-oxo-4H-quinolizine-3-carboxylic acid;

8-(3-dimethylaminopyrrolidinyl)-1-cyclopropyl-7-fluoro-9-methyl-4-oxo-4H-quinolizine-3carboxylic acid;

(3R)-8-(3-dimethylaminopyrrolidinyl)-1-cyclopropyl-7-fluoro-9-methyl-4-oxo-4H-quinolizine-3-carboxylic acid;

(3R, 1S)-8-(3-(1-aminoethyl)pyrrolidinyl)-1-cyclopropyl-7-fluoro-9-methyl-4-oxo-4H-quinolizine-3-carboxylic acid;

(3S,1R)-8-(3-(1-aminoethyl)pyrrolidinyl)-1-cyclopropyl-7-fluoro-9-methyl-4-oxo-4H-quinolizine-3-carboxylic acid;

(3R, 1R)-8-(3-(1-aminoethyl)pyrrolidinyl)-1-cyclopropyl-7-fluoro-9-methyl-4-oxo-4H-quinolizine-3-carboxylic acid;

1cyclopropyl-8-((R,S)-3-fluoropyrrolidine)7-fluoro-9-methyl-4-oxo-4H-quinolizine-3-carboxylic acid;

8-(4-(1-piperidyl)-1-piperidyl)-1-cyclopropyl-7-fluoro-9-methyl-4-oxo-4H-quinolizine-3-carboxylic acid;

8-(4-(1-piperidyl)-1-piperidyl)-1-cyclopropyl-7-fluoro-9-methyl-4-oxo-4H-quinolizine-3-carboxylic acid;

8-(4-(2-pyridyl)-1-piperazinyl)-1-cyclopropyl-7-fluoro-9-methyl-4-oxo-4H-quinolizine-3-carboxylic acid;

8-((2-amino)thioethoxy)-1-cyclopropyl-7-fluoro-9-methyl-4-oxo-4H-quinolizine-3-carboxylic acid;

(3R, 1S)-8-(3-(1-amino)propyl)pyrrolidinyl)-1-cyclopropyl-7-fluoro-9-methyl-4-oxo-4H-quinolizine-3-carboxylic acid;

(3R, 1S)-8-(3-(1-(N-methyl)amino)propyl)pyrrolidinyl)-1-cyclopropyl-7-fluoro-9-methyl-4oxo-4H-quinolizine-3-carboxylic acid;

(3R,1S)-8-(3-(1-amino-3-methylpropyl)pyrrolidinyl)-1-cyclopropyl-7-fluoro-9-methyl-4H-quinolizine-3-carboxylic acid;

8-(3-(1-aminocyclopropyl)pyrrolidinyl)-1-cyclopropyl-7-fluoro-9-methyl-4-oxo-4H- quinolizine-3-carboxylic acid;

(3R, 1S)-8-(3-(1-amino-2-hydroxyethyl)pyrrolidinyl)-1-cyclopropyl-7-fluoro-9-methyl-4-oxo-4H-quinolizine-3-carboxylic acid;

(8-(3-(1-amino-1-methylethyl)pyrrolidinyl)-1-cyclopropyl-7-fluoro-9-methyl-4-oxo-4H-quinolizine-3-carboxylic acid;

8-(3-(1-aminobutyl)pyrrolidinyl)-1-cyclopropyl-7-fluoro-9-methyl-4-oxo-4H-quinolizine-3-carboxylic acid;

1-cyclopropyl-7-fluoro-9-methyl-4-oxo-8-(trans-4-trifluoromethyl-3-aminopyrrolidinyl)-4H-quinolizine-3-carboxylic acid;

1-cyclopropyl-7-fluoro-9-methyl-4-oxo-8-(trans-4-trifluoromethyl-3- aminomethylpyrrolidinyl)-4H-quinolizine-3-carboxylic acid;

3(S)-1-cyclopropyl-7-fluoro-9-methyl-4-oxo-8-(3-(N-(S)-norvalylamino)pyrrolidinyl)-4H-quinolizine-3-carboxylic acid;

3(S)-1 -cyclopropyl-7-fluoro-9-methyl-4-oxo-8-(3-(N-(S)-alanylamino)pyrrolidinyl)-4H-quinolizine-3-carboxylic acid;

3(S)-1-cyclopropyl-7-fluoro-9-methyl-4-oxo-8-(3-(N-(S)-alanyl-(S)-alanylamino)pyrrolidinyl)-4H-quinolizine-3-carboxylic acid;

1-cyclopropyl-7-fluoro-6-methyl-4-oxo-8-(3-aminopyrrolidinyl)-4H-quinolizine-3-carboxylic acid;

1-cyclopropyl-7-fluoro-4H-8-(1-imidazolyl)-9-methyl-4-oxo-quinolizine-3-carboxylic acid;

8-(3-amino-1-pyrrolidinyl)-1-ethyl-7-fluoro-4H-4-oxo-9-methyl-quinolizine-3-carboxylic acid;

8-(3-amino-1-pyrrolidinyl)-1-cyclopropyl-9-ethyl-7-fluoro-4H-4-oxo-quinolizine-3-carboxylic acid;

1-cyclopropyl-7-fluoro-4H-9-methyl-4-oxo-8-(3-(1,2,3-triazol-1-yl)-1-pyrrolidinyl)-quinolizine-3-carboxylic acid;

1-cyclopropyl-7-fluoro-4H-9-methyl-4-oxo-8-(cis-3-amino-4-methyl-1-pyrrolidinyl)-quinolizine-3-carboxylic acid;

8-(2-aminoethyl)-1-cyclopropyl-7-fluoro-4H-9-methyl-4-oxo-quinolizine-3-carboxylic acid;

8-(3-(ethylaminomethyl)pyrrolidinyl)-1-cyclopropyl-7-fluoro-4H-9-methyl-4-oxo-quinolizine-3-carboxylic acid;

8-(3-(1-aminoethyl)pyrrolidinyl)-1-cyclopropyl-7-fluoro-4H-9-methyl-4-oxo-quinolizine-3-carboxylic acid;

1-cyclopropyl-7-fluoro-4H-9-methyl-8-(2-methyl-2-8-diaza-8-bicyclo[4,3,0]nonyl)-4-oxo-quinolizine-3-carboxylic acid;

1-cycloptopyl-7-fluoro-4H-8-((1S, 4S)-2,5-diaza-bicyclo[2,2,1]heptan-2-yl)-9-methyl-4-oxo-quinolizine-3-carboxylic acid;

1-cyclopropyl-7-fluoro-4H-9-methyl-4-oxo-8-(3-(2-pyridinyl)-1-pyrrolidinyl)-quinolizine-3-carboxylic acid;

8-((1R*,2S*,6R*)-2-amino-8-azabicyclo[4,3,0]nonan-8-yl))-1-cyclopropyl-7-fluoro-4H-9-methyl-4-oxo-quinolizine-3-carboxylic acid;

8-((1R *,2R *, 6R* )-2-amino-8-azabicyclo[4,3,0]nonan-8-yl))-1-cyclopropyl-7-fluoro-4H-9-methyl-4-oxo-quinolizine-3-carboxylic acid;

8-((1 a,5a,6a)-6-amino-3-azabicyclo[3,1,0]hexan-3-yl))-1-cyclopropyl-9-methyl-4-oxo-quinolizine-3-carboxylic acid;

8-(trans-3-amino-4-fluoro-1-pyrrolidinyl))-1-cyclopropyl-9-methyl-7-fluoro-4H-4-oxo-quinolizine-3-carboxylic acid;

1-cyclopropyl-7-fluoro-4H-8-(1-homopiperazinyl))-9-methyl-4-oxo-quinolizine-3-carboxylic acid;

7,9-difluoro-4H-8-(4-methylpiperazinyl)-4-oxo-1-phenyl-quinolizine-3-carboxylic acid;

8-(spiro-1,3-dioxacyclopentane[2,3]-1-piperidinyl)-1-cyclopropyl-7-fluoro-4H-9-methyl-4-oxo-quinolizine-3-carboxylic acid;

8-(3-amino-4-methoxypyrrolidinyl)-1-cyclopropyl-7-fluoro-4H-9-methyl-4-oxo-quinolizine-3-carboxylic acid;

8-(4-amino-4-methylpyrrolidinyl)-1-cyclopropyl-7-fluoro-4H-9-methyl-4-oxo-quinolizine-3-carboxylic acid;

8-(4-(2-hydroxyethyl)piperidinyl)-1-cyclopropyl-7-fluoro-4H-9-methyl-4-oxo-quinolizine-3-carboxylic acid;

8-(4-(methoxymethyl)piperidinyl)-1-cyclopropyl-7-fluoro-4H-9-methyl-4-oxo-quinolizine-3-carboxylic acid;

8-(3-amino-3-methylpiperidinyl)-1-cyclopropyl-7-fluoro-4H-9-methyl-4-oxo-quinolizine-3-carboxylic acid;

8-(3-pyrrolylpiperidinyl)-1-cyclopropyl-7-fluoro-4H-9-methyl-4-oxo-quinolizine-3-carboxylic acid;

8-(3-aminopiperidinyl)-1-cyclopropyl-7-fluoro-4H-9-methyl-4-oxo-quinolizine-3-carboxylic acid;

8-(3-amino-3-methylpyrrolidinyl)-1-cyclopropyl-7-fluoro-4H-9-methyl-4-oxo-quinolizine-3-carboxylic acid;

8-(3-amino-4-(1',3'-dioxolanyl)pyrrolidinyl)-1-cyclopropyl-7-fluoro-4H-9-methyl-4-oxo-quinolizine-3-carboxylic acid;

8-(3-amino-4-hydroxy-pyrrolidinyl)-1-cyclopropyl-7-fluoro-4H-9-methyl-4-oxo-quinolizine-3-carboxylic acid;

8-(4-(1-(N-ethylamino)methyl)piperidinyl)-1-cyclopropyl-7-fluoro-4H-9-methyl-4-oxo-quinolizine-3-carboxylic acid;

1-cyclopropyl-7-fluoro-8-(3-hydroxy-4-methylaminopyrrolidinyl)-4H-9-methyl-4-oxo-quinolizine-3-carboxylic acid;

8-(3-aminomethylpiperidinyl)-1-cyclopropyl-7-fluoro-4H-9-methyl-4-oxo-quinolizine -3-carboxylic acid;

8-(2-aminomethyl-4-morpholinyl)-1-cyclopropyl-7-fluoro-4H-9-methyl-4-oxo-quinolizine-3-carboxylic acid;

8-(3-(1-(methylamino)methypiperidinyl)-1-cyclopropyl-7-fluoro-4H-9-methyl-4-oxo-quinolizine-3-carboxylic acid;

8-(3-(methyl(methylenedioxy)methyl)piperidinyl)-1-cyclopropyl-7-fluoro-4H-9-methyl-4-oxo-quinolizine-3-carboxylic acid;

8-(3-(S)-aminopiperidinyl)-1-cyclopropyl-7-fluoro-4H-9-methyl-4-oxo-quinolizine-3-carboxylic acid;

8-(3-(S)-(N-ethyl-N-methylamino)piperidinyl)-1-cyclopropyl-7-fluoro-4H-9-methyl-4-oxo-quinolizine-3-carboxylic acid;

1-cyclopropyl-8-(4-(2'-(N-methylamino)methyl-1',3'-dioxolanyl)piperidinyl)-7-fluoro-9-methyl-4-oxo-4H-quinolizine-3-carboxylic acid;

1-cyclopropyl-8-(3-aza-6-amino-6-methylbicyclo[3,3,0]octan-1-yl)-7-fluoro-9-methyl-4-oxo-4H-quinolizine-3-carboxylic acid;

1-cyclopropyl-8-(3-fluoromethylpiperidinyl)-7-fluoro-9-methyl-4-oxo-4H-quinolizine;

1-cyclopropyl-8-(4-(N,N-dimethyl)aminopiperidinyl)-7-fluoro-9-methyl-4-oxo-4H-quinolizine-3-carboxylic acid;

1cyclopropyl-8-(6-amino-3-azabicyclo[3,3,0]octyl)-7-fluoro-9-methyl-4-oxo-4H-quinolizine-3-carboxylic acid;

1-cyclopropyl-8-((2-aza-4-(dimethylaminomethyl)bicyclo[4,3,0]non-2-yl)-7-fluoro-9-methyl-4-oxo-4H-quinolizine carboxylic acid;

1-cyclopropyl-8-(3-aza-6-(L-alanylamino)-6-methylbicyclo[3,3,0]octane)-7-fluoro-9-methyl-4-oxo-4H-quinolizine carboxylic acid;

(3R,1R)-8-(3-(1-(N-methyl)amino)propyl)pyrrolidinyl)-1-cyclopropyl-7-fluoro-9-methyl-4-oxo-4H-quinolizine-3-carboxylic acid;

(3R, 1S)-8-(3-(1-amino-2-methoxyethyl)pyrrolidinyl)-1-cyclopropyl-7-fluoro-9-methyl-4-oxo-4H-quinolizine-3-carboxylic acid;

8-(3-(S)-(acetylamino)pyrrolidinyl-1-cyclopropyl-7-fluoro-4H-9-methyl-4-oxo-quinolizine-3-carboxylic acid;

8-(3-carbamoylpiperidinyl)-1-cyclopropyl-7-fluoro-4H-9-methyl-4-oxo-quinolizine-3-carboxylic acid;

8-(3-hydroxypiperidinyl)-1-cyclopropyl-7-fluoro-4H-9-methyl-4-oxo-quinolizine-3-carboxylic acid;

8-(3-hydroxymethylpiperidinyl)-1-cyclopropyl-7-fluoro-4H-9-methyl-4-oxo-quinolizine-3-carboxylic acid;

8-(3-(R)-hydroxypiperidinyl)-1-cyclopropyl-7-fluoro-4H-9-methyl-4-oxo-quinolizine-3-carboxylic acid;

(3R)-9-fluoro-3-methyl-10-(piperazin-1-yl)-2H, 3H, 6H -6-oxo-pyrano[2,3,4-ij]acid;

1-cyclopropyl-8-(S,S-2,8-diaza-8-bicyclo[4,3,0]nonyl)-7-fluoro-4H-9-methyl-4-oxo-quinolizine-3-carboxylic acid;

1-cyclopropyl-8-(R,R-2,8-diaza-8-bicyclo[4,3,0]nonyl)-7-fluoro-4H-9-methyl-4-oxo-quinolizine-3-carboxylic acid;

1-cyclopropyl-8-(1-amino-3-aza-bicyclo[3,1,0]hexan-3-yl)-7-fluoro-4H-9-methyl-4-oxo-quinolizine-3-carboxylic acid;

8-(3-amino-3-fluoromethyl-1-pyrrolidinyl)-1-cyclopropyl-7-fluoro-4H-9-methyl-4-oxo-quinolizine-3-carboxylic acid;

8-(3-aminomethyl-3-fluoro-1-pyrrolidinyl)-1-cyclopropyl-7-fluoro-4H-9-methyl-4-oxo-quinolizine-3-carboxylic acid;

8-(3-(S)-hydroxy-1-pyrrolidinyl)-1-cyclopropyl-7-fluoro-4H-9-methyl-4-oxo-quinolizine-3-carboxylic acid;

8-(3-(R)-hydroxy-1-pyrrolidinyl)-1-cyclopropyl-7-fluoro-4H-9-methyl-4-oxo-quinolizine-3-carboxylic acid;

8-(1-amino-5-aza-spiro[2,4]heptan-5-yl-1-cyclopropyl-7-fluoro-4H-9-methyl-4-oxo-quinolizine-3-carboxylic acid Diastereomer A;

8-(1-amino-5-aza-spiro[2,4]heptan-5-yl)-1-cyclopropyl-7-fluoro-4H-9-methyl-4-oxo-quinolizine-3-carboxylic acid Diastereomer B;

8-(3-(1-amino-2,2,2-trifluoroethyl)pyrrolidinyl)-1-cyclopropyl-7-fluoro-4H-9-methyl-4-oxo-quinolizine-3-carboxylic acid;

8-(3-(S*)-(1-(S)-amino-2,2,2-trifluoroethyl)pyrrolidinyl)-1-cyclopropyl-7-fluoro-4H-9-methyl-4-oxo-quinolizine-3-carboxylic acid;

8-(3-aminoxypyrrolidinyl)-1-cyclopropyl-7-fluoro-4H-9-methyl-4-oxo-quinolizine-3-carboxylic acid;

8-(3-(R)-aminoxypyrrolidinyl)-1-cyclopropyl-7-fluoro-4H-9-methyl-4-oxo-quinolizine-3-carboxylic acid;

8-(3-(S)-aminoxypyrrolidinyl)-1-cyclopropyl-7-fluoro-4H-9-methyl-4-oxo-quinolizine-3-carboxylic acid;

8-(octahydropyrrolo[3,2-b]pyridin-1-yl)-1-cyclopropyl-7-fluoro-4H-9-methyl-4-oxo-quinolizine-3-carboxylic acid;

8-(trans-3-amino-4-fluoromethylpyrrodin-1-yl)-1-cyclopropyl-7-fluoro-4H-9-methyl-4-oxo-quinolizine-3-carboxylic acid;

8-(cis-3-amino-4-fluoromethylpyrrodin-1-yl)-1-cyclopropyl-7-fluoro-4H-9-methyl-4-oxo-quinolizine-3-carboxylic acid;

8-(8-amino-6-azaspiro[3,4]oct-6-yl)-1-cyclopropyl-7-fluoro-4H-9-methyl-4-oxo-quinolizine-3-carboxylic acid;

8-(2-aminomethyl-4-hydroxypyrrolidin-1-yl)-1-cyclopropyl-7-fluoro-4H-9-methyl-4-oxo-quinolizine-3-carboxylic acid;

8-(3-(R)-(aminomethyl)morpholin-1-yl)-1-cyclopropyl-7-fluoro-4H-9-methyl-4-oxo-quinolizine-3-carboxylic acid;

8-(3-(R)-(L-alanylamino)piperidinyl)-1-cyclopropyl-7-fluoro-4H-9-methyl-4-oxo-quinolizine-3-carboxylic acid;

8-(3-(5-aminooctahydroindol-1-yl)-1-cyclopropyl-7-fluoro-4H-9-methyl-4-oxo-quinolizine-3carboxylic acid;

8-(3-(2-piperidyl)piperidin-1-yl)-1-cyclopropyl-7-fluoro-4H-9-methyl-4-oxo-quinolizine-3-carboxylic acid;

8-(5-amino-decahydroisoquinolin-2-yl)-1-cyclopropyl-7-fluoro-4H-9-methyl-4-oxo-quinolizine-3-carboxylic acid;

8-(2,7-diazabicyclo[3,3,0]oct-7-yl)-1-cyclopropyl-7-fluoro-4H-9-methyl-4-oxo-quinolizine--3-carboxylic acid;

8-(3,7-diazabicyclo[3,3,0]oct-3-yl)-1-cyclopropyl-7-fluoro-4H-9-methyl-4-oxo-quinolizine-3-carboxylic acid;

8-(3-carboxypyrrolidin-1-yl)-1-cyclopropyl-7-fluoro-4H-9-methyl-4-oxo-quinolizine-3-carboxylic acid;

8-(3-(2,2,2-trifluoroethyl)aminopyrrolidin-1-yl)-1-cyclopropyl-7-fluoro-4H-9-methyl-4-oxo-quinolizine-3-carboxylic acid;

8-(3-(2-fluoroethyl)aminopyrrolidin-1-yl)-1-cyclopropyl-7-fluoro-4H-9-methyl-4-oxo-quinolizine-3-carboxylic acid;

8-(3-((2-fluoroethyl)aminomethyl)pyrrolidin-1-yl)-1-cyclopropyl-7-fluoro-4H-9-methyl-4-oxo-quinolizine-3-carboxylic acid;

8-(3-(S)-(2-fluoroethyl)aminopyrrolidin-1-yl)-1-cyclopropyl-7-fluoro-4H-9-methyl-4-oxo-quinolizine-3-carboxylic acid;

8-(3-(R)-(2-fluoroethyl)aminopyrrolidin-1-yl)-1-cyclopropyl-7-fluoro-4H-9-methyl-4-oxo-quinolizine-3-carboxylic acid;

-(3a-amino-octahydroisoindol-2-yl)-1-cyclopropyl-7-fluoro-4H-9-methyl-4-oxo-quinolizine-3-carboxylic acid;

8-(6-amino-2-aza-spiro[3,3]non-2-yl)-1-cyclopropyl-7-fluoro-4H-9-methyl-4-oxo-quinolizine-3-carboxylic acid (Isomer (I));

8-(3-amino-3-trifluoromethylpyrrolidin-1-yl)-1-cyclopropyl-7-fluoro-4H-9-methyl-4-oxo-quinolizine-3-carboxylic acid;

8-(3-(S)-hydroxymethylazetidin-1-yl)-1-cyclopropyl-7-fluoro-4H-9-methyl-4-oxo-quinolizine-3-carboxylic acid;

8-(3-aminomethyl-3-trifluoromethyl-pyrrolidin-1-yl)-1-cyclopropyl-7-fluoro-4H-9-methyl-4-oxo-quinolizine-3-carboxylic acid;

8-(octahydropyrrolo[3,4-c]pyrid-2-yl)-1-cyclopropyl-7-fluoro-4H-9-methyl-4-oxo-quinolizine-3-carboxylic acid;

8-(3-(cyclopropylamino)pyrrolidin-1-yl)-1-cyclopropyl-7-fluoro-4H-9-methyl-4-oxo-quinolizine-3-carboxylic acid;

8-(6-amino-2-aza-spiro[3,3]non-2-yl)-1-cyclopropyl-7-fluoro-4H-9-methyl-4-oxo-quinolizine-3-carboxylic acid (Isomer (II));

8-(2,7-diazabicyclo[3,3,0]oct-7-yl)-1-cyclopropyl-7-fluoro-4H-9-methyl-4-oxo-quinolizine-3-carboxylic acid Isomer A;

8-(2,7-diazabicyclo[3,3,0]oct-7-yl)-1-cyclopropyl-7-fluoro-4H-9-methyl-4-oxo-quinolizine-3-carboxylic acid Isomer B;

8-(3-(R)-(hydroxymethyl)pyrrolidin-1-yl)-1-cyclopropyl-7-fluoro-4H-9-methyl-4-oxo-quinolizine-3-carboxylic acid;

8-(3-(S)-(hydroxymethyl)pyrrolidin-1-yl)-1-cyclopropyl-7-fluoro-4H-9-methyl-4-oxo-quinolizine-3-carboxylic acid;

8-(2-(R)-(hydroxymethyl)pyrrolidin-1-yl)-1-cyclopropyl-7-fluoro-4H-9-methyl-4-oxo-quinolizine-3-carboxylic acid;

8-(2-(S)-(hydroxymethyl)pyrrolidin-1-yl)-1-cyclopropyl-7-fluoro-4H-9-methyl-4-oxo-quinolizine-3-carboxylic acid;

8-(2-(R)-aminomethyl-pyrrolidin-1-yl)-1-cyclopropyl-7-fluoro-4H-9-methyl-4-oxo-quinolizine-3-carboxylic acid;

8-(2-(S)-aminomethyl-pyrrolidin-1-yl)-1-cyclopropyl-7-fluoro-4H-9-methyl-4-oxo-quinolizine-3-carboxylic acid;

8-(3-(R)-(1-aminocyclopropyl)pyrrolidinyl)-1-cyclopropyl-7-fluoro-9-methyl-4-oxo-4H-quinolizine-3-carboxylic acid;

8-(3-(S)-(1-aminocyclopropyl)pyrrolidinyl)-1-cyclopropyl-7-fluoro-9-methyl-4-oxo-4H-quinolizine-3-carboxylic acid;

8-(3-(1-amino-1-cyclopropyl-methyl)pyrrolidinyl)-1-cyclopropyl-7-fluoro-9-methyl-4-oxo-4H-quinolizine-3-carboxylic acid;

8-(3-(R)-(pyrrolidin-2-(S)-yl)pyrrolidin-1-yl)-1-cyclopropyl-7-fluoro-9-methyl-4-oxo-4H-quinolizine-3-carboxylic acid;

8-(3-(aminomethyl)azetidin-1-yl)-1-cyclopropyl-7-fluoro-9-methyl-4-oxo-4H-quinolizine-3-carboxylic acid;

8-(3-amino-4-methyl-piperidin-1-yl)-1-cyclopropyl-7-fluoro-9-methyl-4-oxo-4H-quinolizine-3-carboxylic acid; and 8-(3-(7-amino-5-azaspiro[2,4]heptan-5-yl)-1-cyclopropyl-7-fluoro-9-methyl-4-oxo-4H-quinolizine-3-carboxylic acid;

and the pharmaceutically acceptable salts, esters and amides thereof.

21. A compound according to claim 20 selected from the group consisting of:

8-(3-(aminomethyl)pyrrolidinyl)-1-cyclopropyl-7-fluoro-9-methyl-4-oxo-4H-quinolizine-3-carboxylic acid;

8-(3(S)-amino-1-pyrrolidinyl)-1-cyclopropyl-7-fluoro-9-methyl-4-oxo-4H-quinolizine-3-carboxylic acid;

8-(3-amino-1-pyrrolidinyl)-1-cyclopropyl-7-fluoro-9-methyl-4-oxo-4H-quinolizine-3-carboxylic acid;

8(3R, 1S)-8-(3-(1-amino)propyl)pyrrolidinyl)-1-cyclopropyl-7-fluoro-9-methyl-4-oxo-4H-quinolizine-3-carboxylic acid;

8-(3-(1-aminobutyl)pyrrolidinyl)-1-cyclopropyl-7-fluoro-9-methyl-4-oxo-4H-quinolizine-3-carboxylic acid;

(3R, 1S)-8-(3-(1-amino-2-methoxyethyl)pyrrolidinyl)-1-cyclopropyl-7-fluoro-9-methyl-4oxo-4H-quinolizine-3-carboxylic acid;

1-cyclopropyl-7-fluoro-9-methyl-4-oxo-8-(4-amino-1-piperdinyl)-4H-quinolizine-3-carboxylic acid;

1-cyclopropyl-7-fluoro-9-methyl-4-oxo-8-(4-(aminomethyl)-1-piperdinyl)-4H-quinolizine-3-carboxylic acid;

1-cyclopropyl-7-fluoro-9-methyl-4-oxo-8-(3-amino-1-piperdinyl)-4H-quinolizine-3-carboxylic acid;

1-(3-(S)-aminopiperidinyl)-1-cyclopropyl-7-fluoro-4H-9-methyl-4-oxo-quinolizine-3-carboxylic acid;

1-cyclopropyl-8-(3-aza-6-amino-6-methylbicyclo[3,3,0]octan-1-yl)-7-fluoro-9-methyl-4-oxo-4H-quinolizine-3-carboxylic acid;

1-cyclopropyl-8-(6-amino-3-azabicyclo[3,3,0]octyl)-7-fluoro-9-methyl-4-oxo-4H-quinolizine-3-carboxylic acid;

8-((1R*,2S*, 6R*)-2-amino-8-azabicyclo[4,3,0]nonan-8-yl))-1-cycloptopyl-7-fluoro-9-methyl-4-oxo-quinolizine-3-carboxylic acid;

8-((1R*,2R*, 6R*)-2-amino-8-azabicyclo[4,3,0]nonan-8-yl))-1-cyclopropyl-7-fluoro-9-methyl-4-oxo-quinolizine-3-carboxylic acid;

8-(3-(1-aminoethyl)pyrrolidinyl)-1-cyclopropyl-7-fluoro-4H-9-methyl-4-oxo-quinolizine-3-carboxylic acid;

(8-(3-(1-amino-1-methylethyl)pyrrolidinyl)-1-cyclopropyl-7-fluoro-9-methyl-4-oxo-4H-quinolizine-3-carboxylic acid;

(3R, 1S)-8-(3-(1-(N-methyl)amino)propyl)pyrrolidinyl)-1-cyclopropyl-7-fluoro-9-methyl-4oxo-4H-quinolizine-3-carboxylic acid;

8-(3-aminopiperidinyl)-1-cyclopropyl-7-fluoro-4H-9-methyl-4-oxo-quinolizine-3-carboxylic acid;

8-(3-(1-aminocyclopropyl)pyrrolidinyl)-1-cyclopropyl-7-fluoro-9-methyl-4-oxo-4H-quinolizine-3-carboxylic acid;

(3S,1R)-8-(3-(1-aminoethyl)pyrrolidinyl)-1-cyclopropyl-7-fluoro-9-methyl-4-oxo-4H-quinolizine-3-carboxylic acid;

(3R, 1S)-8-(3-(1-aminoethyl)pyrrolidinyl)-1-cyclopropyl-7-fluoro-9-methyl-4-oxo-4H-quinolizine-3-carboxylic acid;

(3 R, 1R)-8-(3-(1-aminoethyl)pyrrolidinyl)-1-cycloptopyl-7-fluoro-9-methyl-4-oxo-4H-quinolizine-3-carboxylic acid;

1-cyclopropyl-8-(S,S-2,8-diaza-8-bicyclo[4,3,0]nonyl)-7-fluoro-4H-9-methyl-4-oxo-4H-quinolizine-3-carboxylic acid;

1-cyclopropyl-8-(R,R-2,8-diaza-8-bicyclo[4,3,0]nonyl)-7-fluoro-4H-9-methyl-4-oxo-quinolizine-3-carboxylic acid;

1-cyclopropyl-8-(1-amino-3-aza-bicyclo[3,1,0]hexan-3-yl)-7-fluoro-4H-9-methyl-4-oxo-quinolizine-3-carboxylic acid;

8-(3-amino-3-fluoromethyl-1-pyrrolidinyl)-1-cyclopropyl-7-fluoro-4H-9-methyl-4-oxo-quinolizine-3-carboxylic acid;

8-(trans-3-amino-4-fluoromethylpyrrodin-1-yl)-1-cyclopropyl-7-fluoro-4H-9-methyl-4-oxo-quinolizine-3-carboxylic acid;

8-(cis-3-amino-4-fluoromethylpyrrodin-1-yl)-1-cyclopropyl-7-fluoro-4H-9-methyl-4-oxo-quinolizine-3-carboxylic acid;

8-(3-(S)-(2-fluoroethyl)aminopyrrolidin-1-yl)-1-cyclopropyl-7-fluoro-4H-9-methyl-4-oxo-quinolizine-3-carboxylic acid;

8-(3-(R)-(2-fluoroethyl)aminopyrrolidin-1-yl)-1-cyclopropyl-7-fluoro-4H-9-methyl-4-oxo-quinolizine-3-carboxylic acid;

8-(3-(R)-(hydroxymethyl)pyrrolidin-1-yl)-1-cyclopropyl-7-fluoro-4H-9-methyl-4-oxo-quinolizine-3-carboxylic acid;

8-(2-(R)-aminomethyl-pyrrolidin-1-yl)-1-cyclopropyl-7-fluoro-4H-9-methyl-4-oxo-quinolizine-3-carboxylic acid;

8-(2-(R)-aminomethyl-pyrrolidin-1-yl)-1-cyclopropyl-7-fluoro-4H-9-methyl-4-oxo-quinolizine-3-carboxylic acid;

8-(3-amino-4-methyl-piperidin-1-yl)-1-cyclopropyl-7-fluoro-9-methyl-4-oxo-4H-quinolizine-3-carboxylic acid; and 8-(3-(7-amino-5-azaspiro[2,4]heptan-5-yl)-1-cyclopropyl-7-fluoro-9-methyl-4-oxo-4H-quinolizine-3-carboxylic acid;

and the pharmaceutically acceptable salts, esters and amides thereof.

22. A compound according to claim 20 selected from the group consisting of:

8-(3(S)-amino-1-pyrrolidinyl)-1-cyclopropyl-7-fluoro-9-methyl-4-oxo-4H-quinolizine-3-carboxylic acid;

8-(3-amino-1-pyrrolidinyl-1-cyclopropyl-7-fluoro-9-methyl-4-oxo-4H-quinolizine-3-carboxylic acid;

(3R, 1S)-8-(3-(1-amino-2-methoxyethyl)pyrrolidinyl)-1-cyclopropyl-7-fluoro-9-methyl-4-oxo-4H-quinolizine-3-carboxylic acid;

(8-(3-(1-amino-1-methylethyl)pyrrolidinyl)-1-cyclopropyl-7-fluoro-9-methyl-4-oxo-4H-quinolizine-3-carboxylic acid;

8-(3-(1-aminocyclopropyl)pyrrolidinyl)-1-cyclopropyl-7-fluoro-9-methyl-4-oxo-4H-quinolizine-3-carboxylic acid;

(3R, 1S)-8-(3-(1-aminoethyl)pyrrolidinyl)-1-cyclopropyl-7-fluoro-9-methyl-4-oxo-4H-quinolizine-3-carboxylic acid;

1-cyclopropyl-8-(S,S,2,8-diaza-8-bicyclo[4,3,0]nonyl)-7-fluoro-4H-9-methyl-4-oxo-quinolizine-3-carboxylic acid;

1-cyclopropyl-8-(R,R-2, 8-diaza-8-bicyclo[4,3,0]nonyl)-7-fluoro-4H-9-methyl-4oxo-quinolizine-3-carboxylic acid;

1-cyclopropyl-8-(1-amino-3-aza-bicyclo[3,1,0]hexan-3-yl)-7-fluoro-4H-9-methyl-4-oxo-quinolizine-3-carboxylic acid;

8-(3-amino-3-fluoromethyl-1-pyrrolidinyl)-1-cyclopropyl-7-fluoro-4H-9-methyl-4-oxo-quinolizine-3-carboxylic acid;

8-(trans-3-amino-4-fluoromethylpyrrodin-1-yl)-1-cyclopropyl-7-fluoro-4H-9-methyl-4-oxo-quinolizine-3-carboxylic acid;

8-(cis-3-amino-4-fluoromethylpyrrodin-1-yl)-1-cyclopropyl-7-fluoro-4H-9-methyl-4-oxo-quinolizine-3-carboxylic acid;

8-(3-(S)-(2-fluoroethyl)aminopyrrolidin-1-yl)-1-cyclopropyl-7-fluoro-4H-9-methyl-4-oxo-quinolizine-3-carboxylic acid;

8-(3-(R)-(2-fluoroethyl)aminopyrrolidin-1-yl)-1-cyclopropyl-7-fluoro-4H-9-methyl-4-oxo-quinolizine-3-carboxylic acid;

8-(3-(R)-(hydroxymethyl)pyrrolidin-1-yl)-1-cyclopropyl-7-fluoro-4H-9-methyl-4-oxo-quinolizine-3-carboxylic acid;

8-(2-(R)-aminomethyl-pyrrolidin-1-yl)-1-cyclopropyl-7-fluoro-4H-9-methyl-4-oxo-quinolizine-3-carboxylic acid; and (8-(3-amino-4-methyl-piperidin-1-yl)-1-cyclopropyl-7-fluoro-9-methyl-4-oxo-4H-quinolizine-3-carboxylic acid; and 8-(3-(7-amino-5-azaspiro[2,4]heptan-5-yl)-1 -cyclopropyl-7-fluoro-9-methyl-4-oxo-4H-quinolizine-3-carboxylic acid;

and the pharmaceutically acceptable salts, esters and amides thereof.

23. A pharmaceutical composition comprising a compound according to claim 1 in combination with a pharmaceutically acceptable carrier.

24. A pharmaceutical composition comprising a compound according to claim 6 in combination with a pharmaceutically acceptable carrier.

25. A pharmaceutical composition comprising a compound according to claim 20 in combination with a pharmaceutically acceptable carrier.

26. A pharmaceutical composition comprising a compound according to claim 23 in combination with a pharmaceutically acceptable carrier.

27. A method of treating a bacterial infection in a human or veterinary patient, comprising administering to the patient a therapeutically effective amount of a compound according to claim 1.

28. A method of treating a bacterial infection in a human or veterinary patient, comprising administering to the patient a therapeutically effective amount of a compound according to claim 6.

29. A method of treating a bacterial infection in a human or veterinary patient, comprising administering to the patient a therapeutically effective amount of a compound according to claim 20.

30. A method of treating a bacterial infection in a human or veterinary patient, comprising administering to the patient a therapeutically effective amount of a compound according to claim 23.

31. A synthetic intermediate selected from the group consisting of:

4-t-butoxy-3-chloro-2,5,6-trifluoropyridine;

4-t-butoxy-2,3,6-trifluoropyridine;

4-t-butoxy-2,3,6-trifluoro-5-methylpyridine;

4-t-butoxy-2,5-difluoro-3-methylpyridine;

2-(4-t-butoxy-5-fluoro-3- methyl-2-pyridinyl)cyclopropaneacetonitrile;

2-(4-chloro-5-fluoro-3-methyl-2-pyridinyl)cyclopropaneacetonitrile;

2-(4-chloro-5-fluoro-3-methyl-2-pyridinyl)cyclopropaneacetic acid;

ethyl 2-(4-chloro-5-fluoro-3-methyl-2-pyridinyl)cyclopropaneacetate;

2-(4-chloro-5-fluoro-3-methyl-2-pyridinyl)cyclopropaneacetaldehyde;

2-(4-chloro-5-fluoro-3-methyl-2-pyridinyl)cyclopropaneethanol;

2-(2-(4-chloro-5-fluoro-3-methyl-2-pyridinyl)-2-cyclopropylethylidinyl)-1,3-propanedicarboxylic acid, diethyl ester; and 8-chloro-1-cyclopropyl-7-fluoro-9-methyl-4-oxo-4h-quinolizine-3-carboxylic acid ethyl ester.

* * * * *